(12) United States Patent
Nakamoto et al.

(10) Patent No.: US 7,932,272 B2
(45) Date of Patent: Apr. 26, 2011

(54) ANTIFUNGAL AGENT CONTAINING HETEROCYCLIC COMPOUND

(75) Inventors: Kazutaka Nakamoto, Tsukuba (JP); Itaru Tsukada, Tsukuba (JP); Keigo Tanaka, Tsukuba (JP); Masayuki Matsukura, Tsukuba (JP); Toru Haneda, Kamisu (JP); Satoshi Inoue, Tsukuba (JP); Norihiro Ueda, Tsukuba (JP); Shinya Abe, Tsukuba (JP); Katsura Hata, Tsukuba (JP); Naoaki Watanabe, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 1033 days.

(21) Appl. No.: 10/573,890

(22) PCT Filed: Sep. 27, 2004

(86) PCT No.: PCT/JP2004/014063
§ 371 (c)(1),
(2), (4) Date: Mar. 29, 2006

(87) PCT Pub. No.: WO2005/033079
PCT Pub. Date: Apr. 14, 2005

(65) Prior Publication Data
US 2007/0105943 A1 May 10, 2007

(30) Foreign Application Priority Data

Sep. 30, 2003 (JP) .................................. 2003-342273
Mar. 10, 2004 (JP) .................................. 2004-068186

(51) Int. Cl.
*A61K 31/4436* (2006.01)
*C07D 409/12* (2006.01)
(52) U.S. Cl. .................. 514/336; 546/280.4; 546/281.4
(58) Field of Classification Search ............... 546/280.4, 546/281.4; 514/336
See application file for complete search history.

(56) References Cited

U.S. PATENT DOCUMENTS

| | | | |
|---|---|---|---|
| 4,576,956 A | 3/1986 | Makisumi et al. | |
| 4,720,493 A | 1/1988 | Kawakita et al. | |
| 4,785,010 A | 11/1988 | Zoller et al. | |
| 5,034,393 A | 7/1991 | Hackler et al. | |
| 5,296,484 A | 3/1994 | Coghlan et al. | |
| 5,350,749 A | 9/1994 | Hackler et al. | |
| 5,371,086 A | 12/1994 | Takemoto et al. | |
| 5,691,136 A | 11/1997 | Lupski et al. | |
| 5,691,336 A | 11/1997 | Dorn et al. | |
| 5,710,171 A | 1/1998 | Dinsmore et al. | |
| 5,747,518 A * | 5/1998 | Yoshikawa et al. | 514/403 |
| 5,852,042 A | 12/1998 | Jakobi et al. | |
| 5,945,431 A | 8/1999 | Jin et al. | |
| 6,022,884 A | 2/2000 | Mantlo et al. | |
| 6,080,767 A | 6/2000 | Klein et al. | |
| 6,174,905 B1 | 1/2001 | Suzuki et al. | |
| 6,235,728 B1 | 5/2001 | Golik et al. | |
| 6,313,127 B1 | 11/2001 | Waterson et al. | |
| 6,380,218 B1 * | 4/2002 | Marfat et al. | 514/326 |
| 6,414,013 B1 * | 7/2002 | Fancelli et al. | 514/438 |
| 6,596,718 B1 | 7/2003 | Flohr et al. | |
| 6,630,495 B1 | 10/2003 | Cooke et al. | |
| 7,179,804 B2 | 2/2007 | Amegadzie et al. | |
| 7,179,822 B2 | 2/2007 | Bunker et al. | |
| 7,687,525 B2 | 3/2010 | Suzuki et al. | |
| 7,691,882 B2 | 4/2010 | Tanaka et al. | |
| 7,754,726 B2 | 7/2010 | Lang et al. | |
| 2002/0111495 A1 | 8/2002 | Magee et al. | |
| 2003/0045554 A1 | 3/2003 | Sankaranarayanan | |
| 2003/0114491 A1 | 6/2003 | Kim et al. | |
| 2003/0191158 A1 | 10/2003 | Magee | |
| 2004/0038239 A1 | 2/2004 | Tsukahara et al. | |
| 2004/0044040 A1 | 3/2004 | Neubert et al. | |
| 2004/0152730 A1 | 8/2004 | Farina et al. | |
| 2004/0198773 A1 | 10/2004 | Hart et al. | |
| 2005/0119229 A1 | 6/2005 | Ammermann et al. | |
| 2006/0264419 A1 | 11/2006 | Schiemann et al. | |
| 2006/0270637 A1 | 11/2006 | Gravestock et al. | |
| 2007/0060619 A1 | 3/2007 | Burns et al. | |
| 2007/0105904 A1 | 5/2007 | Tanaka et al. | |

(Continued)

FOREIGN PATENT DOCUMENTS

DE 19727117 A1 1/1999

(Continued)

OTHER PUBLICATIONS

Vippagunta et al., "Crystalline solids", Advanced Drug Reviews, 48 (2001), 3-26.*
Guillory, "Generation of Polymorphs, etc.," in Brittain ed., Polymorphism in Pharmaceutical Solids, 95, Marcel Dekker, NY, 1999, 1-2, 183-226.*
Accession No. 2020895193, Chemcats (Jul. 9, 2007).
Accession No. 2036647688, Chemcats (Jun. 1, 2007).
Accession No. 2021278791, Chemcats (Feb. 7, 2006).
Accession No. 2025887145, Chemcats (Jan. 1, 2007).

(Continued)

*Primary Examiner* — Patricia L Morris
(74) *Attorney, Agent, or Firm* — Birch, Stewart, Kolasch & Birch, LLP

(57) ABSTRACT

The present invention provides an antifungal agent represented by the formula:

(II)

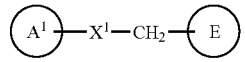

[wherein $A^1$ represents a 3-pyridyl group which may have a substituent, a quinolyl group which may have a substituent, or the like; $X^1$ represents a group represented by the formula —NH—C(=O)—, a group represented by the formula —C(=O)—NH—, or the like; E represents a furyl group, a thienyl group, a pyrrolyl group, a phenyl group, a pyridyl group, a tetrazolyl group, a thiazolyl group or a pyrazolyl group; with the proviso that $A^1$ may have 1 to 3 substituents, and E has one or two substituents].

17 Claims, No Drawings

U.S. PATENT DOCUMENTS

| | | |
|---|---|---|
| 2007/0105943 A1 | 5/2007 | Nakamoto et al. |
| 2007/0167493 A1 | 7/2007 | Sankaranarayanan |
| 2008/0090846 A1 | 4/2008 | Bridger et al. |

FOREIGN PATENT DOCUMENTS

| | | |
|---|---|---|
| EP | 0 124 154 | 11/1984 |
| EP | 0124067 A1 | 11/1984 |
| EP | 0274867 A2 | 7/1988 |
| EP | 0 326 328 A2 | 8/1989 |
| EP | 0414386 A1 | 2/1991 |
| EP | 0533130 A1 | 9/1992 |
| EP | 0976744 A1 | 2/2000 |
| EP | 1 216 980 A1 | 6/2002 |
| EP | 1217000 A1 | 6/2002 |
| EP | 1229034 A1 | 8/2002 |
| EP | 1275301 A1 | 1/2003 |
| EP | 1275653 A1 | 1/2003 |
| EP | 1 369 420 A1 | 12/2003 |
| EP | 1 669 348 A1 | 6/2006 |
| EP | 1 782 811 A1 | 5/2007 |
| JP | 54-2325 A | 1/1979 |
| JP | 59-073575 | 4/1984 |
| JP | 59-73575 A | 4/1984 |
| JP | 59-206353 A | 11/1984 |
| JP | 61-148178 A | 7/1986 |
| JP | 64-3162 A | 1/1989 |
| JP | 1-246264 A | 10/1989 |
| JP | 3-66689 A | 3/1991 |
| JP | 3-161470 A | 7/1991 |
| JP | 52-94935 | 11/1993 |
| JP | 7-25853 A | 1/1995 |
| JP | 8-175993 | 7/1996 |
| JP | 10-505600 A | 6/1998 |
| JP | 2000-504336 A | 4/2000 |
| JP | 2000-178243 A | 6/2000 |
| JP | 2001-522834 A | 11/2001 |
| JP | 2001-527083 | 12/2001 |
| JP | 2002-275159 A | 9/2002 |
| JP | 2002-284766 A | 10/2002 |
| JP | 2003-506466 A | 2/2003 |
| JP | 2004-529154 A | 9/2004 |
| JP | 2005-033079 A | 2/2005 |
| JP | 2005-526751 | 9/2005 |
| JP | 2006-519247 | 8/2006 |
| WO | WO-86/03203 A1 | 6/1986 |
| WO | WO-93/12084 A1 | 6/1993 |
| WO | WO-96/09294 A1 | 3/1996 |
| WO | WO-97/27852 A1 | 8/1997 |
| WO | WO-97/28128 A1 | 8/1997 |
| WO | WO-98/25883 A1 | 6/1998 |
| WO | WO-98/50029 A1 | 11/1998 |
| WO | WO-99/24404 A1 | 5/1999 |
| WO | WO-99/50247 A1 | 7/1999 |
| WO | WO-99/48492 A1 | 9/1999 |
| WO | WO-00/07991 A1 | 2/2000 |
| WO | WO-00/51998 A1 | 9/2000 |
| WO | WO-00/62778 A1 | 10/2000 |
| WO | WO-00/73283 A1 | 12/2000 |
| WO | WO-01/11966 A1 | 2/2001 |
| WO | WO-01/21584 A1 | 3/2001 |
| WO | WO-01/25181 A1 | 4/2001 |
| WO | WO 01/26652 A1 | 4/2001 |
| WO | WO-01/27096 A1 | 4/2001 |
| WO | WO-01/51456 A2 | 7/2001 |
| WO | WO-01/53274 A1 | 7/2001 |
| WO | WO-01/74779 A1 | 10/2001 |
| WO | WO-02/00651 A2 | 1/2002 |
| WO | WO-02/04626 A1 | 1/2002 |
| WO | WO-02/06275 A1 | 1/2002 |
| WO | WO-02/22583 A2 | 3/2002 |
| WO | WO-02/060875 A1 | 8/2002 |
| WO | WO-02/060896 A1 | 8/2002 |
| WO | WO-02/060898 A1 | 8/2002 |
| WO | WO-02/083645 A1 | 10/2002 |
| WO | WO-02/085897 A1 | 10/2002 |
| WO | WO 03/006628 A2 | 1/2003 |
| WO | WO-03/027095 A1 | 4/2003 |
| WO | WO-03/031435 A1 | 4/2003 |
| WO | 03/045920 A1 | 6/2003 |
| WO | WO-03/045385 A1 | 6/2003 |
| WO | WO-03/059903 A2 | 7/2003 |
| WO | 03/068747 A1 | 8/2003 |
| WO | WO-03/068232 A1 | 8/2003 |
| WO | WO-03/068235 A1 | 8/2003 |
| WO | WO 03-091226 | 11/2003 |
| WO | WO 03-091227 | 11/2003 |
| WO | WO-2004/000813 A1 | 12/2003 |
| WO | WO 2004-014366 | 2/2004 |
| WO | WO-2004/014370 A2 | 2/2004 |
| WO | WO-2004/029027 A1 | 4/2004 |
| WO | WO-2004/033432 A1 | 4/2004 |
| WO | WO-2004/048567 A2 | 6/2004 |
| WO | WO-2004/052280 A2 | 6/2004 |
| WO | WO-2004/089931 A1 | 10/2004 |
| WO | WO-2005/033079 A | 2/2005 |
| WO | WO-2006/016548 A1 | 2/2006 |
| WO | WO-2006/106711 A1 | 10/2006 |
| WO | WO-2007/052615 A1 | 5/2007 |
| WO | WO 2009/081970 A1 | 7/2009 |
| WO | WO 2009-084621 | 7/2009 |

OTHER PUBLICATIONS

Ikizler et al., Indian J. Pharm. Sci., vol. 61, No. 5, pp. 271-274 (1999).
Satyanarayana et al., Bollettino Chimico Farmaceutico., vol. 140, No. 4, pp. 228-232 (2001).
Okawa, Tomohiro et al., Synthesis, 1998, No. 10, pp. 1467 to 1475.
Shinkai et al., J. Med. Chem., vol. 31, pp. 2092-2097, (1988).
Okawa et al., Synthesis, pp. 1467-1475, (1998).
Ohshima et al., J. Med. Chem., vol. 35, pp. 3402-3413, (1992).
Chan, L., et al., Database Crossfire Beilstein: Beilstein Institute Zur Foerderung Der Chemischen Wissenschaften; XP-002512523; Database accession No. 8422493 (1999).
Okawa T., et al., "Pyrido [2, 3-d] pyrimidine derivatives. Synthesis via intermolecular aza-Wittig reaction/heterocyclization and the crystal structure", Database CA [Online] Chemical Abstract Service; XP002512524; Database accession No. 677971 (1998).
Kajino M., et al., "Preparation and formulation of quinazoline derivatives as allergy inhibitors", Database CA [Online], Chemical Abstract Service; XP002512525 Database accession No. 216905 (1999).
Piechaczek J., et al., "Monoamine oxidase inhibitors. VII. Derivatives of quinolinecarboxylic acids", Database CA [Online], Chemical Abstract Service; XP002512526 Database accession No. 75701 (1966).
Modena T., et al., "Plant growth regulating activities of 2-[2-(arylamino)-2-oxoethyl] benzoic acids", Database CA [Online], Chemical Abstract Service; XP002512527 Database accession No. 597690 (1993).
Gardner et al., Nature, vol. 419, pp. 498-511, (2002).
Naik et al., J. of Biological Chemistry, vol. 278, No. 3, pp. 2036-2042, (2003).
Lo et al., "Development of highly selective and sensitive probes for hydrogen peroxide," Communications, Chem Comm, The Royal Society of Chemistry, 2003, pp. 2728-2729.
European Search Report issued Jul. 19, 2010, in corresponding European Patent Application No. 06730370.1.
Pernak, J. et al., "Synthesis and antimicrobial activities of new pyridinium and benzimidazolium chlorides," Eur. J. Med. Chem., vol. 36 (2001) pp. 313-320.
Pregnolato, M. et al., "3H-[1,2]Dithiolo[3,4-b]pyridine-3-thione and its derivatives Synthesis and antimicrobial activity," Il Farmaco, vol. 55, (2000) pp. 669-679.
Chandran et al., "Synthesis of 8-Aminoquinolines: Part II—8-Guidance Derivatives," Journal of Scientific & Industrial Reserarch (1952), 11B, pp. 129-132.
Office Action issued May 4, 2001, in copending U.S. Appl. No. 11/658,901.
Chang et al., "Synthesis and Structure-Activity Relationships of Quaternary Ammonium Cephalosporins with 3-Pyrazolylpyridinium Derivatives," Bioorganic & Medicinal Chemistry Letters (2000) vol. 10, No. 11, pp. 1211-1214.

Connors et al., "Prodrugs in medicine," Overview, Biologicals & Immunologicals, Exp. Opin. Ther. Patents, vol. 5, No. 9, 1995, pp. 873-885.

Office Action from co-pending U.S. Appl. No. 11/589,128, mailed May 7, 2009.

Hata, "New Approaches to Antifungal Drugs for the Treatment of Fungal and Protozoal Infections, Ravuconazole and Beyond: New Targets and Pre-clinical Strategies," The SMI's 12th Annual Conference, Superbugs and Superdrugs, Mar. 18, 2010, Crowne Plaza London—St. James, 44 pages.

International Search Report dated May 20, 2008 for corresponding International Application No. PCT/JP2008/057851.

Ishikawa et al., "TAK-599, a Novel N-Phosphono Type Prodrug of Anti-MRSA Cephalosporin T-91825: Synthesis, Physicochemical and Pharmacological Properties," Bioorganic & Medicinal Chemistry, vol. 11, pp. 2427-2437, (2003).

Lukevics et al., "Synthesis and cytotoxicity of silyl- and carbonyl-substituted isoxazoles," Chemistry of Heterocyclic Compounds (2000) vol. 36, No. 10, pp. 1226-1231.

Plate et al., "Synthesis and Muscarinic Activities of 3-(Pyrazolyl)-1,2,5,6-tetrahydropyridine Derivatives," Bioorganic & Medicinal Chemistry Letters (1996) vol. 4, No. 2, pp. 227-237.

Supplementary European Search Report dated Feb. 6, 2009 for corresponding European Application No. 04788159.4.

Vrzheschch et al., "Supercooperativity in platelet aggregation: Substituted pyridyl isoxazoles, a new class of supercooperative platelet aggregation inhibitors," FEBS Letters (1994) vol. 351, No. 2, pp. 168-170.

European Search Report issued Jul. 29, 2010, in corresponding European Patent Application No. 05768893.9.

English translation of JP-A-07-25853, published Jan. 27, 1995.

Notice of Reasons for Rejection mailed Aug. 6, 2010, in corresponding Japanese Patent Application No. 2005-514417 (with English translation).

Database Chemcats [Online] Chemical Abstracts Service, Columbus, Ohio, US; XP002600785 Database accession No. 2059288788 *Order No. (ON): 6700755* & Chembridge Corporation: "ChemBridge Screening Library" Jun. 9, 2010, ChemBridge Corporation, San Diego (USA).

Database Chemcats [Online] Chemical Abstracts Service, Columbus, Ohio, US; XP002600787 Database accession No. 2084604173 *Order No. (ON): STK143803 & Vitas-M: "Vitas-M Screening Collection" Jul. 13, 2010, Vitas-M, Hodynski Blv. 15, Moskow, (RU).

Database Registry [Online] Chemical Abstracts Service, Columbus, Ohio, US; Jul. 16, 2002, XP002600783 Database accession No. 438574-99-3(RN).

Database Registry [Online] Chemical Abstracts Service, Columbus, Ohio, US; Jun. 18, 2002, XP002600784 Database accession No. 431922-54-2(RN)*abstract*.

Database Registry [Online] Chemical Abstracts Service, Columbus, Ohio, US; Oct. 18, 2004, XP002600786 Database accession No. 764713-41-9(RN)*abstract*.

Extended European Search Report dated Oct. 11, 2010, issued in corresponding European Patent Application No. 07828273.8.

Office Action issued Oct. 13, 2010, in copending U.S. Appl. No. 11/658,901.

* cited by examiner

SEQUENCE LISTING

<160> NUMBER OF SEQ ID NOS: 8

<210> SEQ ID NO 1
<211> LENGTH: 33
<212> TYPE: DNA
<213> ORGANISM: Artificial Sequence
<220> FEATURE:
<223> OTHER INFORMATION: an artificially synthesized primer sequence

<400> SEQUENCE: 1
cccggatcct gtttgcagca tgagacttgc ata                33

<210> SEQ ID NO 2
<211> LENGTH: 42
<212> TYPE: DNA
<213> ORGANISM: Artificial Sequence
<220> FEATURE:
<223> OTHER INFORMATION: an artificially synthesized primer sequence

<400> SEQUENCE: 2
cccgcggccc cttccaattc gaaaaccttc cccagagcag cc       42

<210> SEQ ID NO 3
<211> LENGTH: 32
<212> TYPE: DNA
<213> ORGANISM: Artificial Sequence
<220> FEATURE:
<223> OTHER INFORMATION: an artificially synthesized primer sequence

<400> SEQUENCE: 3
ggttcgaagc cgcaaaaaca gaacaacaaa tt                 32

<210> SEQ ID NO 4
<211> LENGTH: 32
<212> TYPE: DNA
<213> ORGANISM: Artificial Sequence
<220> FEATURE:
<223> OTHER INFORMATION: an artificially synthesized primer sequence

<400> SEQUENCE: 4
ggtctagatt gcagtttttc aagaatgcgc ca                 32

<210> SEQ ID NO 5
<211> LENGTH: 33
<212> TYPE: DNA
<213> ORGANISM: Artificial Sequence
<220> FEATURE:
<223> OTHER INFORMATION: an artificially synthesized primer sequence

<400> SEQUENCE: 5
ccctctagaa ctgacggtca aatccaagct act                33

<210> SEQ ID NO 6
<211> LENGTH: 32
<212> TYPE: DNA
<213> ORGANISM: Artificial Sequence
<220> FEATURE:
<223> OTHER INFORMATION: an airtificially synthesized primer sequence

```
<400> SEQUENCE: 6
ggaagctttt ataacaacat agcggcagca ga                                32

<210> SEQ ID NO 7
<211> LENGTH: 48
<212> TYPE: DNA
<213> ORGANISM: Artificial Sequence
<220> FEATURE:
<223> OTHER INFORMATION: an artificially synthesized primer sequence

<400> SEQUENCE: 7
cccgcggccg cttgatagta agcttgcttg ggccgcatca tgtaatta              48

<210> SEQ ID NO 8
<211> LENGTH: 33
<212> TYPE: DNA
<213> ORGANISM: Artificial Sequence
<220> FEATURE:
<223> OTHER INFORMATION: an artificially synthesized primer sequence

<400> SEQUENCE: 8
cccggtacca aattaaagcc ttcgagcctc cca                              33
```

ANTIFUNGAL AGENT CONTAINING HETEROCYCLIC COMPOUND

TECHNICAL FIELD

The present invention relates to a novel antifungal agent containing a heterocyclic compound.

BACKGROUND ART

In recent years, managements of opportunistic infections have become more and more significant more than ever because of an increase in the number of elderly people and immunocompromised patients as a result of advanced chemotherapies or the like. As demonstrated by the fact that opportunistic infections are occurring one after another by different weakly avirulent bacteria, it is shown that the problem of infectious disease will not ends as long as there are underlying diseases that diminish the immune functions of patients. Consequently, new strategies for infectious diseases control, including the problem of resistant bacteria, will be one of the important issues in the soon-to-come aged society.

In the field of antifungal agents, heretofore, for instance, amphotericine B which is based on a polyene skeleton, fluconazole, itraconazole and voriconazole which are based on an azole skeleton, or the like, have been developed for the treatment of deep seated mycoses. Among pre-existing drugs already available commercially are many agents having similar mechanism of action, and currently, the appearance of azole-resistant fungi or the like has been problems.

In recent years, as a 1,3-β-glucan synthetase inhibitor with a novel mechanism, naturally occurring compound-derived cyclic hexapeptides caspofungin and micafungin or the like, have been developed; however, from the fact that these agents only exist in injectable form, they are not yet sufficient practically as antifungal agents.

Since there have been the situations that the pre-existing antifungal agents are insufficient for treatment of the deep seated mycoses, there is a demand and need for development of agents which are based on a novel mechanism and are of high safety.

As the prior art related to antifungal agents based on such a novel mechanism, Patent Document 1 describes heterocyclic compounds which demonstrates effects against the onset, progress, and persistence of infections by inhibiting the expression of cell wall proteins, inhibiting the cell wall assembly and also adhesion onto cells, and preventing pathogens from showing pathogenicity, with the process which transports GPI (Glycosylphosphatidylinositol)-anchored proteins to the cell wall being inhibited. However, groups of the compounds disclosed in Patent Document 1 have 2-benzyl pyridine moieties as the common structure, clearly differing structurally from compounds according to the present invention. In addition, the groups of the compounds disclosed in Patent Document 1 bear the problem that, although these compounds demonstrate activities in vitro, they are easily metabolized inside the body, or the like.

Meanwhile, there are Patent Documents 2 through 8 as the prior art that disclose structurally most similar compounds to the heterocyclic compound (I) according to the present invention. Patent Document 2 discloses N-(4-pyridyl)carboxamide derivatives having the effects as pesticides, in particular as insecticides, acaricides and nematicides. Patent Documents 3 through 6 disclose 2-aryloxy nicotinamide derivatives having phosphodiesterase 4 (PDE4) inhibitory action. Patent Document 7 discloses 6-(arylamino)nicotinamide derivatives having cannabinoid receptor modulation action and Patent Document 8 discloses 6-(aryloxy)nicotinamide derivatives having $Na^+/Ca^{2+}$ exchanger inhibitory action. However, Patent Documents 2 through 8 do not disclose the compounds according to the present invention. In addition, Patent Documents 2 through 8 do not describe that the compounds disclosed in these documents exhibit antifungal and antimalarial actions for *Candida, Aspergillus, Cryptococcus* or the like which are general fungal strains in human mycosis at all.

[Patent Document 1] International Publication No. WO 02/04626 pamphlet;
[Patent Document 2] U.S. Pat. No. 5,852,042 Specification;
[Patent Document 3] European Patent Application No. 1229034 specification;
[Patent Document 4] International Publication No. WO 02/060875 pamphlet;
[Patent Document 5] International Publication No. WO 02/060896 pamphlet;
[Patent Document 6] International Publication No. WO 03/068232 pamphlet;
[Patent Document 7] International Publication No. WO 2004/029027 pamphlet; and
[Patent Document 8] International Publication No. WO 2004/000813 pamphlet.

DISCLOSURE OF THE INVENTION

It is an object of the present invention to 1) provide an antifungal agent which has excellent antifungal action not found in the antifungal agents in the prior art, and which is also excellent in terms of property, safety and metabolic stability, and 2) provide an excellent antimalarial agent.

In view of the aforementioned circumstances, the present inventors have intensively studied to attain the above object. As a result, the present inventions have succeeded in synthesizing novel heterocycle-containing compounds represented by the following formula (I):

which has the chemical structural characteristics of a heterocyclic group A and a heterocyclic group or a phenyl group E being bonded through a linker X, and have discovered that these compounds have excellent antifungal action, so as to arrive at the present invention.

That is to say, the present invention provides:
[1]: an antifungal agent comprising a compound represented by the formula (I), or a salt or a hydrate thereof:

[wherein A represents a 5- to 10-membered heterocyclic group containing at least one nitrogen atom;

X represents a group represented by the formula —NH—C(=Y)—(CH$_2$)$_n$—, a group represented by the formula —C(=Y)—NH—(CH$_2$)$_n$—, a group represented by the formula —C(=Z)—(CH$_2$)$_n$—, a group represented by the formula —CH$_2$—NH—(CH$_2$)$_n$—, a group represented by the formula —NH—CH$_2$—(CH$_2$)$_n$— or a group represented by the formula —Z—CH$_2$—(CH$_2$)$_n$—;

Y represents an oxygen atom, a sulfur atom or $NR^Y$ (wherein $R^Y$ represents a $C_{1-6}$ alkoxy group or a cyano group);

Z represents an oxygen atom or a sulfur atom;

n represents an integer from 0 to 3;

E represents a furyl group, a thienyl group, a pyrrolyl group, a pyridyl group, a tetrazolyl group, a thiazolyl group, a pyrazolyl group or a phenyl group;

with the proviso that A may contain 1 to 3 substituents selected from the following substituent groups a-1 and a-2, and that E has one or two substituents selected from the following substituent groups a-1 and a-2;

<Substituent Group a-1>

Substituent group a-1 represents the group consisting of: a halogen atom, a hydroxyl group, a mercapto group, a cyano group, a carboxyl group, an amino group, a carbamoyl group, a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a 5- to 10-membered heterocyclic group, a $C_{3-8}$ cycloalkyl $C_{1-6}$ alkyl group, a $C_{3-8}$ cycloalkylidene $C_{1-6}$ alkyl group, a $C_{6-10}$ aryl $C_{1-6}$ alkyl group, a 5- to 10-membered heterocyclic $C_{1-6}$ alkyl group, a $C_{1-6}$ alkoxy group, a $C_{2-6}$ alkenyloxy group, a $C_{2-6}$ alkynyloxy group, a $C_{3-8}$ cycloalkoxy group, a $C_{6-10}$ aryloxy group, a $C_{3-8}$ cycloalkyl $C_{1-6}$ alkoxy group, a $C_{6-10}$ aryl $C_{1-6}$ alkoxy group, a 5- to 10-membered heterocyclic $C_{1-6}$ alkoxy group, a $C_{1-6}$ alkylthio group, a $C_{2-6}$ alkenylthio group, a $C_{2-6}$ alkynylthio group, a $C_{3-8}$ cycloalkylthio group, a $C_{6-10}$ arylthio group, a $C_{3-8}$ cycloalkyl $C_{1-6}$ alkylthio group, a $C_{6-10}$ aryl $C_{1-6}$ alkylthio group, a 5- to 10-membered heterocyclic $C_{1-6}$ alkylthio group, a mono-$C_{1-6}$ alkylamino group, a mono-$C_{2-6}$ alkenylamino group, a mono-$C_{2-6}$ alkynylamino group, a mono-$C_{3-8}$ cycloalkylamino group, a mono-$C_{6-10}$ arylamino group, a mono-$C_{3-8}$ cycloalkyl $C_{1-6}$ alkylamino group, a mono-$C_{6-10}$ aryl $C_{1-6}$ alkylamino group, a mono-5- to 10-membered heterocyclic $C_{1-6}$ alkylamino group, a di-$C_{1-6}$ alkylamino group, a N—$C_{2-6}$ alkenyl-N—$C_{1-6}$ alkylamino group, a N—$C_{2-6}$ alkynyl-N—$C_{1-6}$ alkylamino group, a N—$C_{3-8}$ cycloalkyl-N—$C_{1-6}$ alkylamino group, a N—$C_{6-10}$ aryl-N—$C_{1-6}$ alkylamino group, a N—$C_{3-8}$ cycloalkyl $C_{1-6}$ alkyl-N—$C_{1-6}$ alkylamino group, a N—$C_{6-10}$ aryl $C_{1-6}$ alkyl-N—$C_{1-6}$ alkylamino group, a N-5- to 10-membered heterocyclic $C_{1-6}$ alkyl-N—$C_{1-6}$ alkylamino group, a $C_{1-6}$ alkylcarbonyl group, a $C_{1-6}$ alkoxycarbonyl group, a $C_{1-6}$ alkylsulfonyl group, a group represented by the formula —C(=N—$R^{a1}$)$R^{a2}$ (wherein $R^{a1}$ represents a hydroxyl group or a $C_{1-6}$ alkoxy group; $R^{a2}$ represents a $C_{1-6}$ alkyl group), a $C_{6-10}$ aryloxy $C_{1-6}$ alkyl group and a 5- to 10-membered heterocycle oxy $C_{1-6}$ alkyl group;

<Substituent Group a-2>

Substituent Group a-2 represents the group consisting of: a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a 5- to 10-membered heterocyclic group, a $C_{3-8}$ cycloalkyl $C_{1-6}$ alkyl group, a $C_{6-10}$ aryl $C_{1-6}$ alkyl group, a 5- to 10-membered heterocyclic $C_{1-6}$ alkyl group, a $C_{1-6}$ alkoxy group, a $C_{2-6}$ alkenyloxy group, a $C_{2-6}$ alkynyloxy group, a $C_{3-8}$ cycloalkoxy group, a $C_{6-10}$ aryloxy group, a $C_{3-8}$ cycloalkyl $C_{1-6}$ alkoxy group, a $C_{6-10}$ aryl $C_{1-6}$ alkoxy group, a 5- to 10-membered heterocyclic $C_{1-6}$ alkoxy group, a $C_{1-6}$ alkylthio group, a $C_{2-6}$ alkenylthio group, a $C_{2-6}$ alkynylthio group, a $C_{3-8}$ cycloalkylthio group, a $C_{6-10}$ arylthio group, a $C_{3-8}$ cycloalkyl $C_{1-6}$ alkylthio group, a $C_{6-10}$ aryl $C_{1-6}$ alkylthio group, a 5- to 10-membered heterocyclic $C_{1-6}$ alkylthio group, a mono-$C_{1-6}$ alkylamino group, a mono-$C_{2-6}$ alkenylamino group, a mono-$C_{2-6}$ alkynylamino group, a mono-$C_{3-8}$ cycloalkylamino group, a mono-$C_{6-10}$ arylamino group, a mono-$C_{3-8}$ cycloalkyl $C_{1-6}$ alkylamino group, a mono-$C_{6-10}$ aryl $C_{1-6}$ alkylamino group, a mono-5- to 10-membered heterocyclic $C_{1-6}$ alkylamino group, a di-$C_{1-6}$ alkylamino group, a N—$C_{2-6}$ alkenyl-N—$C_{1-6}$ alkylamino group, a N—$C_{2-6}$ alkynyl-N—$C_{1-6}$ alkylamino group, a N—$C_{3-8}$ cycloalkyl-N—$C_{1-6}$ alkylamino group, a N—$C_{6-10}$ aryl-N—$C_{1-6}$ alkylamino group, a N—$C_{3-8}$ cycloalkyl $C_{1-6}$ alkyl-N—$C_{1-6}$ alkylamino group, a N—$C_{6-10}$ aryl $C_{1-6}$ alkyl-N—$C_{1-6}$ alkylamino group, a N-5- to 10-membered heterocyclic $C_{1-6}$ alkyl-N—$C_{1-6}$ alkylamino group, a $C_{6-10}$ aryloxy-$C_{1-6}$ alkyl group and a 5- to 10-membered heterocycle oxy $C_{1-6}$ alkyl group;

with the proviso that each group described in the substituent group a-2 has 1 to 3 substituents selected from the following substituent group b;

<Substituent Group b>

Substituent group b represents the group consisting of: a halogen atom, a hydroxyl group, a mercapto group, a cyano group, a carboxyl group, an amino group, a carbamoyl group, a nitro group, a $C_{1-6}$ alkyl group, a $C_{3-8}$ cycloalkyl group, a $C_{6-10}$ aryl group, a 5- to 10-membered heterocyclic group, a $C_{1-6}$ alkoxy group, a $C_{6-10}$ aryloxy group, a 5- to 10-membered heterocycle oxy group, a $C_{1-6}$ alkylcarbonyl group, a $C_{1-6}$ alkoxycarbonyl group, a $C_{1-6}$ alkylsulfonyl group, a trifluoromethyl group, a trifluoromethoxy group, a mono-$C_{1-6}$ alkylamino group, a di-$C_{1-6}$ alkylamino group, a mono-$C_{6-10}$ arylamino group which may have one amino group or aminosulfonyl group and a N—$C_{6-10}$ aryl $C_{1-6}$ alkyl-N—$C_{1-6}$ alkylamino group which may have one amino group];

[2]: the antifungal agent according to item [1], wherein X represents a group represented by the formula —NH—C(=Y)—$CH_2$—, a group represented by the formula —C(=Y)—NH—$CH_2$—, a group represented by the formula —$CH_2$—NH— or a group represented by the formula —NH—$CH_2$— (wherein Y has the same meaning as defined above);

[3]: a compound represented by the formula (I-a), or a salt or a hydrate thereof:

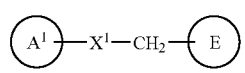

(I-a)

[wherein $A^1$ represents a 3-pyridyl group, a pyrazinyl group, a pyrimidinyl group, a pyrazolyl group, a quinolyl group, an isoquinolyl group, a naphthyidinyl group, a quinoxalinyl group, a cinnolinyl group, a quinazolinyl group, an imidazopyridyl group, a benzothiazolyl group, a benzoxazolyl group, a benzimidazolyl group, an indolyl group, a pyrrolopyridyl group, a thienopyridyl group, a furopyridyl group, a 2,3-dihydro-1H-pyrrolo[2,3-b]-pyridin-5-yl group or a benzothiadiazolyl group;

$X^1$ represents a group represented by the formula —NH—C(=$Y^1$)— or a group represented by the formula —C(=$Y^1$)—NH—;

$Y^1$ represents an oxygen atom, a sulfur atom or $NR^{Y1}$ (wherein $R^{Y1}$ represents a $C_{1-6}$ alkoxy group or a cyano group);

E represents a furyl group, a thienyl group, a pyrrolyl group, a pyridyl group, a tetrazolyl group, a thiazolyl group, a pyrazolyl group or a phenyl group;

with the proviso that $A^1$ may contain 1 to 3 substituents selected from the substituent groups a-1 and a-2 as defined above, and that E has 1 or 2 substituents selected from the substituent groups a-1 and a-2 defined above]
[with the proviso that (1) a compound in which E represents a group represented by the formula:

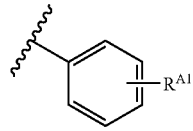

(wherein $R^{41}$ represents a phenyl group having a halogen atom, a methoxy group, an ethoxy group, a $C_{1-6}$ alkoxycarbonyl group or a carboxyl group), (2) A Compound in which E Represents a Group Represented by the Formula:

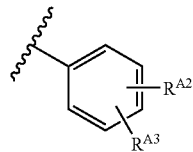

(wherein $R^{42}$ represents a halogen atom or a methoxy group; $R^{43}$ represents a $C_{1-6}$ alkyl group having a carboxyl group, a $C_{3-8}$ cycloalkyl group having a carboxyl group or a phenyl group having a carboxyl group), (3) A Compound in which $A^1$ Represents a Group Represented by the Formula:

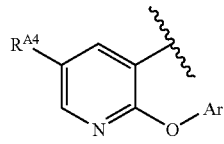

(wherein $R^{44}$ represents a hydrogen atom or a halogen atom; Ar represents a phenyl group which may have a substituent) and $X^1$ represents a group represented by the formula —C(=O)—NH—, (4) A Compound in which $A^1$ Represents a Group Represented by the Formula:

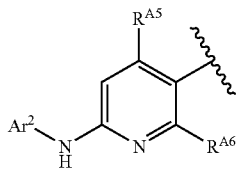

(wherein $R^{45}$ represents a hydrogen atom, a $C_{1-6}$ alkyl group or a trifluoromethyl group; $R^{46}$ represents a hydrogen atom or a trifluoromethyl group; $Ar^2$ represents a phenyl group that may have a substituent) and $X^1$ represents a group represented by the formula —C(=O)—NH— and (5) A Compound in which $A^1$ Represents a Group Represented by the Formula:

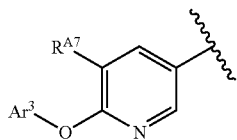

(wherein $R^{47}$ represents a hydrogen atom, a halogen atom or a $C_{1-6}$ alkyl group; $Ar^3$ represents a phenyl group which may have a substituent) and $X^1$ represents a group represented by the formula —C(=O)—NH— or a group represented by the formula —NH—C(=O)— are excluded];

[4]: the compound according to item [3], or the salt or the hydrate thereof, wherein $A^1$ represents a 3-pyridyl group, a quinolyl group, a naphthyidinyl group, a quinoxalinyl group, an imidazopyridyl group, a benzothiazolyl group, a pyrrolopyridyl group, a thienopyridyl group or a furopyridyl group (with the proviso that $A^1$ may have 1 to 3 substituents selected from the substituent groups a-1 and a-2 defined above);

[5]: the compound according to item [3], or the salt or the hydrate thereof, wherein $A^1$ represents a 3-pyridyl group (with the proviso that $A^1$ may have 1 to 3 substituents selected from the following substituent groups c-1 and c-2);

<Substituent Group c-1>

Substituent group c-1 represents the group consisting of: a halogen atom, an amino group, a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a 5- to 10-membered heterocyclic group, a $C_{3-8}$ cycloalkyl $C_{1-6}$ alkyl group, a $C_{6-10}$ aryl $C_{1-6}$ alkyl group, a 5- to 10-membered heterocyclic $C_{1-6}$ alkyl group, a $C_{1-6}$ alkoxy group, a $C_{2-6}$ alkenyloxy group, a $C_{2-6}$ alkynyloxy group, a $C_{3-8}$ cycloalkyl $C_{1-6}$ alkoxy group, a $C_{6-10}$ aryl $C_{1-6}$ alkoxy group, a 5- to 10-membered heterocyclic $C_{1-6}$ alkoxy group, a mono-$C_{1-6}$ alkylamino group, a mono-$C_{2-6}$ alkenylamino group, a mono-$C_{2-6}$ alkynylamino group, a mono-$C_{3-8}$ cycloalkylamino group, a mono-$C_{6-10}$ arylamino group, a mono-$C_{3-8}$ cycloalkyl $C_{1-6}$ alkylamino group, a mono-$C_{6-10}$ aryl $C_{1-6}$ alkylamino group, a mono-5- to 10-membered heterocyclic $C_{1-6}$ alkylamino group, a $C_{1-6}$ alkylcarbonyl group and a group represented by the formula —C(=N—OH)$R^{a2}$ (wherein $R^{a2}$ has the same meaning as defined above);

<Substituent Group c-2>

Substituent group c-2 represents the group consisting of: a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a 5- to 10-membered heterocyclic group, a $C_{3-8}$ cycloalkyl $C_{1-6}$ alkyl group, a $C_{6-10}$ aryl $C_{1-6}$ alkyl group, a 5- to 10-membered heterocyclic $C_{1-6}$ alkyl group, a $C_{1-6}$ alkoxy group, a $C_{2-6}$ alkenyloxy group, a $C_{2-6}$ alkynyloxy group, a $C_{3-8}$ cycloalkyl $C_{1-6}$ alkoxy group, $C_{6-10}$ aryl $C_{1-6}$ alkoxy group, a 5- to 10-membered heterocyclic $C_{1-6}$ alkoxy group, a mono-$C_{1-6}$ alkylamino group, a mono-$C_{2-6}$ alkenylamino group, a mono-$C_{2-6}$ alkynylamino group, a mono-$C_{3-8}$ cycloalkylamino group, a mono-$C_{6-10}$ arylamino group, a mono-$C_{3-8}$ cycloalkyl $C_{1-6}$ alkylamino group, a mono-$C_{6-10}$ aryl $C_{1-6}$ alkylamino group and a mono-5- to 10-membered heterocyclic $C_{1-6}$ alkylamino group;

with the proviso that each group described in substituent group c-2 has 1 to 3 substituents selected from the following substituent group d;

<Substituent Group d>

Substituent group d represents the group consisting of: a halogen atom, a hydroxyl group, a carboxyl group, an amino group, a carbamoyl group, a $C_{1-6}$ alkoxy group, a mono-$C_{1-6}$ alkylamino group, a di-$C_{1-6}$ alkylamino group, a mono-$C_{6-10}$ arylamino group that may have one amino group or aminosulfonyl group, a N—$C_{6-10}$ aryl $C_{1-6}$ alkyl-N—$C_{1-6}$ alkylamino group which may have one amino group, a cyano group, a $C_{6-10}$ aryl group, a 5- to 10-membered heterocyclic group and a $C_{1-6}$ alkoxycarbonyl group.

[6]: the compound according to item [3], or the salt or the hydrate thereof, wherein $A^1$ represents a group represented by the formula:

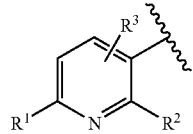

[wherein $R^1$, $R^2$ and $R^3$ may be the same as or different from each other and represent a substituent selected from the substituent groups c-1 and c-2 defined above];

[7]: the compound according to item [3], or the salt or the hydrate thereof, wherein $A^1$ represents a group represented by the formula:

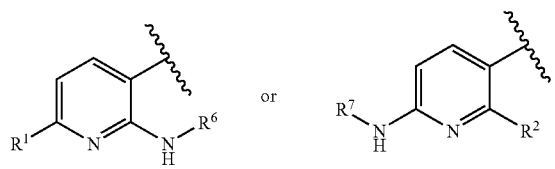

[wherein $R^1$ and $R^2$ have the same meanings as defined above, respectively; $R^6$ and $R^7$ may be the same or different from each other and represent a hydrogen atom, a $C_{1-6}$ alkyl group, a $C_{3-8}$ cycloalkyl group or a group represented by the formula —$CHR^8$—$(CH_2)_{n1}$—$R^9$ (wherein $R^8$ represents a hydrogen atom, a carboxyl group or a $C_{1-6}$ alkoxycarbonyl group; $R^9$ represents a hydroxyl group, a carboxyl group, a carbamoyl group, a $C_{3-8}$ cycloalkyl group, a furyl group, a thienyl group, a pyrrolyl group, a pyridyl group, a triazolyl group, a tetrahydrofuryl group, a $C_{1-6}$ alkoxy group, a $C_{1-6}$ alkoxycarbonyl group, a mono-$C_{1-6}$ alkylamino group, a di-$C_{1-6}$ alkylamino group, a phenyl group which may have 1 to 3 substituents selected from the substituent group d defined above, a mono-$C_{6-10}$ arylamino group which may have one amino group or an N—$C_{6-10}$ aryl $C_{1-6}$ alkyl-N—$C_{1-6}$ alkylamino group which may have one amino group; n1 represents an integer from 0 to 3)];

[8]: the compound according to item [3], or the salt or the hydrate thereof, wherein $A^1$ represents a group represented by the formula:

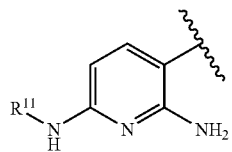

(wherein $R^{11}$ represents a hydrogen atom or a group represented by the formula —$CHR^{12}$—$(CH_2)_{n2}$—$R^{13}$ (wherein $R^{12}$ represents a hydrogen atom or a carboxyl group; $R^{13}$ represents a carboxyl group or a phenyl group which may have 1 to 3 substituents selected from the substituent group d defined above; n2 represents an integer from 0 to 3));

[9]: the compound according to item [3], or the salt or the hydrate thereof, wherein $A^1$ represents a group represented by the formula:

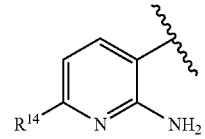

(wherein $R^{14}$ represents a $C_{1-6}$ alkyl group having one $C_{1-6}$ alkoxy group);

[10]: the compound according to item [3], or the salt or the hydrate thereof, wherein $A^1$ represents a 6-quinolyl group, a [1,5]naphthylidin-2-yl group, a 6-quinoxalinyl group, an imidazo[1,2-a]pyridin-6-yl group, a benzothiazol-6-yl group, a 1H-pyrrolo[2,3-b]pyridin-5-yl group, a pyrrolo[3,2-b]pyridin-1-yl group, a thieno[2,3-b]pyridin-5-yl group, a thieno[3,2-b]pyridin-6-yl group or a furo[3,2-b]pyridin-6-yl group (with the proviso that $A^1$ may have 1 to 3 substituents selected from the substituent groups c-1 and c-2 defined above);

[11]: the compound according to item [3], or the salt or the hydrate thereof, wherein $A^1$ represents a 6-quinolyl group, a [1,5]naphthylidin-2-yl group, a 6-quinoxalinyl group, an imidazo[1,2-a]pyridin-6-yl group, a benzothiazol-6-yl group, a pyrrolo[3,2-b]pyridin-1-yl group, a 1H-pyrrolo[2,3-b]pyridin-5-yl group which may have one amino group, a thieno[2,3-b]pyridin-5-yl group which may have one amino group, a thieno[3,2-b]pyridin-6-yl group which may have one amino group or furo[3,2-b]pyridin-6-yl group which may have one amino group.

[12]: the compound according to item [3], or the salt or the hydrate thereof, wherein $A^1$ represents a 6-quinolyl group;

[13]: the compound according to item [3], or the salt or the hydrate thereof, wherein $A^1$ represents a [1,5]naphthylidin-2-yl group;

[14]: the compound according to item [3], or the salt or the hydrate thereof, wherein $A^1$ represents an imidazo[1,2-a]pyridin-6-yl group;

[15]: the compound according to item [3], or the salt or the hydrate thereof, wherein $A^1$ represents a benzothiazol-6-yl group;

[16]: the compound according to item [3], or the salt or the hydrate thereof, wherein $A^1$ represents a 3-pyridyl group, a pyrazinyl group, a pyrimidinyl group, a quinolyl group, an isoquinolyl group, a naphthyldinyl group, a quinoxalinyl group, a cinnolinyl group, a quinazolinyl group, an imidazopyridyl group, a benzothiazolyl group, a benzoxazolyl group, a benzimidazolyl group, an indolyl group, a pyrrolopyridyl group, a thienopyridyl group, a furopyridyl group, a 2,3-dihydro-1H-pyrrolo[2,3-b]pyridin-5-yl group or a benzothiadiazolyl group (with the proviso that $A^1$ may have 1 to 3 substituents selected from the substituent groups a-1 and a-2 defined above);

[17]: the compound according to item [3], or the salt or the hydrate thereof, wherein $A^1$ represents a 3-pyridyl group, a pyrazinyl group, a pyrimidinyl group, a quinolyl group, an isoquinolyl group, a naphthyldinyl group, a quinoxalinyl group, a cinnolinyl group, a quinazolinyl group, an imidazopyridyl group, a benzothiazolyl group, a benzoxazolyl group, a benzimidazolyl group, an indolyl group, a pyrrolopyridyl group, a thienopyridyl group, a furopyridyl group, a 2,3-dihydro-1H-pyrrolo[2,3-b]pyridin-5-yl group or a benzothiadiazolyl group (with the proviso that $A^1$ may have 1 to 3 substituents selected from the substituent groups c-1 and c-2 defined above);

[18]: the compound according to item [3], or the salt or the hydrate thereof, wherein $A^1$ represents a 3-pyridyl group, a pyrazinyl group, a pyrimidinyl group, a quinolyl group, an isoquinolyl group, a naphthyldinyl group, a quinoxalinyl group, a cinnolinyl group, a quinazolinyl group, an imidazopyridyl group, a benzothiazolyl group, a benzoxazolyl group, a benzimidazolyl group, an indolyl group, a pyrrolopyridyl group, a thienopyridyl group, a furopyridyl group, a 2,3-dihydro-1H-pyrrolo[2,3-b]pyridin-5-yl group or a benzothiadiazolyl group (with the proviso that $A^1$ may have 1 to 3 substituents selected from the following substituent groups c'-1 and c'-2);

<Substituent Group c'-1>

Substituent group c'-1 represents the group consisting of: an amino group, a $C_{1-6}$ alkyl group and a mono-$C_{1-6}$ alkylamino group; and <Substituent Group c'-2>

Substituent group c'-2 represents the group consisting of: a $C_{1-6}$ alkyl group and a mono-$C_{1-6}$ alkylamino group;

with the proviso that each group described in substituent group c'-2 has 1 to 3 substituents selected from the following substituent group d';

<Substituent Group d'>

Substituent group d' represents the group consisting of: a halogen atom, a hydroxyl group, a cyano group, a carboxyl group and a $C_{1-6}$ alkoxy group.

[19]: the compound according to any one of items [3] to [18], or the salt or the hydrate thereof, wherein $X^1$ represents a group represented by the formula —C(=O)—NH— or a group represented by the formula —NH—C(=O)—;

[20]: the compound according to any one of items [3] to [18], or the salt or the hydrate thereof, wherein $X^1$ represents a group represented by the formula —C(=O)—NH—;

[21]: the compound according to any one of items [3] to [20], or the salt or the hydrate thereof, wherein E represents a furyl group, a thienyl group, a pyrrolyl group, a phenyl group or pyridyl group (with the proviso that E has 1 or 2 substituents selected from the substituent groups a-1 and a-2 defined above);

[22]: the compound according to any one of items [3] to [20], or the salt or the hydrate thereof, wherein E represents a furyl group, a thienyl group, a pyrrolyl group, a phenyl group or pyridyl group (with the proviso that E has 1 or 2 substituents selected from the following substituent groups e-1 and e-2);

<Substituent Group e-1>

Substituent group e-1 represents the group consisting of: a halogen atom, a hydroxyl group, a $C_{1-6}$ alkyl group, a $C_{2-6}$ alkenyl group, a $C_{2-6}$ alkynyl group, a $C_{6-10}$ aryl group, a $C_{3-8}$ cycloalkyl $C_{1-6}$ alkyl group, a $C_{3-8}$ cycloalkylidene $C_{1-6}$ alkyl group, a $C_{6-10}$ aryl $C_{1-6}$ alkyl group, 5- to 10-membered heterocyclic $C_{1-6}$ alkyl group, a $C_{1-6}$ alkoxy group, a $C_{2-6}$ alkenyloxy group, a $C_{2-6}$ alkynyloxy group, a $C_{6-10}$ aryloxy group, a $C_{3-8}$ cycloalkyl $C_{1-6}$ alkoxy group, a $C_{6-10}$ aryl $C_{1-6}$ alkoxy group, a 5- to 10-membered heterocyclic $C_{1-6}$ alkoxy group, a $C_{6-10}$ arylthio group, a $C_{6-10}$ aryl $C_{1-6}$ alkylthio group, a mono-$C_{6-10}$ arylamino group, a mono-$C_{6-10}$ aryl $C_{1-6}$ alkylamino group, a N—$C_{6-10}$ aryl-N—$C_{1-6}$ alkylamino group, a N—$C_{6-10}$ aryl $C_{1-6}$ alkyl-N—$C_{1-6}$ alkylamino group, a $C_{6-10}$ aryloxy $C_{1-6}$ alkyl group and a 5- to 10-membered heterocycle oxy $C_{1-6}$ alkyl group;

<Substituent Group e-2>

Substituent group e-2 represents the group consisting of: a $C_{1-6}$ alkyl group, a $C_{2-6}$ alkenyl group, a $C_{2-6}$ alkynyl group, a $C_{6-10}$ aryl group, a $C_{3-8}$ cycloalkyl $C_{1-6}$ alkyl group, a $C_{6-10}$ aryl $C_{1-6}$ alkyl group, a 5- to 10-membered heterocyclic $C_{1-6}$ alkyl group, a $C_{1-6}$ alkoxy group, a $C_{2-6}$ alkenyloxy group, a $C_{2-6}$ alkynyloxy group, a $C_{6-10}$ aryloxy group, a $C_{3-8}$ cycloalkyl $C_{1-6}$ alkoxy group, a $C_{6-10}$ aryl $C_{1-6}$ alkoxy group, 5- to 10-membered heterocycle-$C_{1-6}$ alkoxy group, a $C_{6-10}$ arylthio group, a $C_{6-10}$ aryl $C_{1-6}$ alkylthio group, a mono-$C_{6-10}$ arylamino group, a mono-$C_{6-10}$ aryl $C_{1-6}$ alkylamino group, a N—$C_{6-10}$ aryl-N—$C_{1-6}$ alkylamino group, a N—$C_{6-10}$ aryl $C_{1-6}$ alkyl-N—$C_{1-6}$ alkylamino group, a $C_{6-10}$ aryloxy $C_{1-6}$ alkyl group and a 5- to 10-membered heterocycle oxy $C_{1-6}$ alkyl group;

with the proviso that each group described in substituent group e-2 has 1 to 3 substituents selected from the following substituent group f;

<Substituent Group f>

Substituent group f represents the group consisting of: a halogen atom, a hydroxyl group, a cyano group, an amino group, a nitro group, a $C_{3-8}$ cycloalkyl group, a $C_{1-6}$ alkoxy group, a $C_{6-10}$ aryloxy group, a 5- to 10-membered heterocycle oxy group, a $C_{1-6}$ alkylcarbonyl group, a $C_{1-6}$ alkoxycarbonyl group, a $C_{1-6}$ alkylsulfonyl group, a mono-$C_{6-10}$ arylamino group, a trifluoromethyl group, a trifluoromethoxy group and a $C_{1-6}$ alkyl group;

[23]: the compound according to any one of items [3] to [20], or the salt or the hydrate thereof, wherein E represents a furyl group, a thienyl group, a pyrrolyl group, a phenyl group or a pyridyl group (with the proviso that E has one substituent selected from the following substituent groups g-1 and g-2);

<Substituent Group g-1>

Substituent group g-1 represents the group consisting of: a $C_{3-8}$ cycloalkyl $C_{1-6}$ alkyl group, a phenyl $C_{1-6}$ alkyl group, a furyl $C_{1-6}$ alkyl group, a thienyl $C_{1-6}$ alkyl group, a benzofuryl $C_{1-6}$ alkyl group, a benzothienyl $C_{1-6}$ alkyl group, a $C_{1-6}$ alkoxy group, a phenoxy group, a $C_{3-8}$ cycloalkyl $C_{1-6}$ alkoxy group, a phenyl $C_{1-6}$ alkoxy group, a furyl $C_{1-6}$ alkoxy group, a thienyl $C_{1-6}$ alkoxy group, a pyridyl $C_{1-6}$ alkoxy group, a phenoxy $C_{1-6}$ alkyl group and a pyridyloxy $C_{1-6}$ alkyl group;

<Substituent Group g-2>

Substituent group g-2 represents the group consisting of: a $C_{3-8}$ cycloalkyl $C_{1-6}$ alkyl group, a phenyl $C_{1-6}$ alkyl group, a furyl $C_{1-6}$ alkyl group, a thienyl $C_{1-6}$ alkyl group, a benzofuryl $C_{1-6}$ alkyl group, a benzothienyl $C_{1-6}$ alkyl group, a $C_{1-6}$ alkoxy group, a phenoxy group, a $C_{3-8}$ cycloalkyl $C_{1-6}$ alkoxy group, a phenyl $C_{1-6}$ alkoxy group, a furyl $C_{1-6}$ alkoxy group, a thienyl $C_{1-6}$ alkoxy group, a pyridyl $C_{1-6}$ alkoxy group, a phenoxy $C_{1-6}$ alkyl group and a pyridyloxy $C_{1-6}$ alkyl group;

with the proviso that each group described in substituent group g-2 has 1 to 3 substituents selected from the following substituent group h;

<Substituent Group h>

Substituent group h represents the group consisting of: a halogen atom, a hydroxyl group, a cyano group and a $C_{1-6}$ alkyl group;

[24]: the compound according to any one of items [31 to [20], or the salt or the hydrate thereof, wherein E represents a 2-furyl group, a 2-thienyl group, a 3-pyrrolyl group, a phenyl group, a 2-pyridyl group or 3-pyridyl group (with the proviso that E has one substituent selected from the substituent groups g-1 and g-2 defined above);

[25]: the compound according to item [3], or the salt or the hydrate thereof, wherein $X^1$ represents a group represented by the formula —C(=O)—NH—, and $A^1$ represents a group represented by the formula:

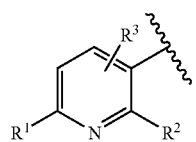

(wherein $R^1$, $R^2$ and $R^3$ have the same meanings as defined above, respectively), and E represents a 2-furyl group, a 2-thienyl group, a 3-pyrrolyl group, a phenyl group, a 2-pyridyl group or a 3-pyridyl group (with the proviso that E has one substituent selected from the substituent group g-1 or g-2 defined above).

[26]: the compound according to item [25], or the salt or the hydrate thereof, wherein $A^1$ represents a group represented by the formula:

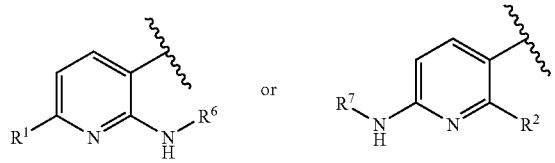

(wherein $R^1$, $R^2$, $R^6$ and $R^7$ have the same meanings as defined above, respectively);

[27]: the compound according to item [25], or the salt or the hydrate thereof, wherein $A^1$ represents a group represented by the formula:

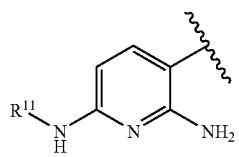

(wherein $R^{11}$ has the same meaning as defined above);

[28]: the compound according to item [25], or the salt or the hydrate thereof, wherein $A^1$ represents a group represented by the formula:

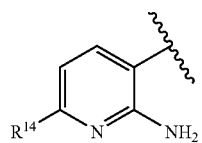

(wherein $R^{14}$ has the same meaning as defined above);

[29]: the compound according to item [3], or the salt or the hydrate thereof, wherein $X^1$ represents a group represented by the formula —C(=O)—NH—, $A^1$ represents a 6-quinolyl group, a [1,5]naphthylidin-2-yl group, a 6-quinoxalinyl group, an imidazo[1,2-a]pyridinyl group, a benzothiazol-6-yl group, a pyrrolo[3,2-b]pyridin-1-yl group, a 1H-pyrrolo[2,3-b]pyridin-5-yl group which may have one amino group, a thieno[2,3-b]pyridin-5-yl group which may have one amino group, a thieno[3,2-b]pyridin-6-yl group which may have one amino group or a furo[3,2-b]pyridin-6-yl group which may have one amino group, and E represents a 2-furyl group, a 2-thienyl group, a 3-pyrrolyl group, a phenyl group or a 2-pyridyl group (with the proviso that E has a substituent selected from the substituent group g-1 or g-2 defined above);

[30]: the compound according to item [29], or the salt or the hydrate thereof, wherein $A^1$ represents a 6-quinolyl group;

[31]: the compound according to item [29], or the salt or the hydrate thereof, wherein $A^1$ represents a [1,5]naphthylidin-2-yl group;

[32]: the compound according to item [29], or the salt or the hydrate thereof, wherein $A^1$ represents an imidazo[1,2-a]pyridin-6-yl group;

[33]: the compound according to item [29], or the salt or the hydrate thereof, wherein $A^1$ represents a benzothiazol-6-yl group;

[34]: A compound represented by the formula (I-b), or a salt or a hydrate thereof:

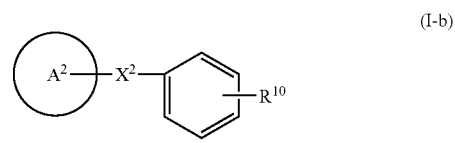

(I-b)

[wherein $A^2$ represents a 6-quinolyl group, a 4-quinazolinyl group or a pyrido[2,3-d]pyrimidin-4-yl group which may have an amino group;

$X^2$ represents a group represented by the formula —O—CH$_2$—, a group represented by the formula —S—CH$_2$—, a group represented by the formula —C(=O)—CH$_2$—, a group represented by the formula —NH—CH$_2$— or a group represented by the formula —CH$_2$—NH—;

$R^{10}$ represents a $C_{1-6}$ alkyl group, a $C_{6-10}$ aryloxy group or a $C_{6-10}$ aryl $C_{1-6}$ alkoxy group];

[35]: the compound according to item [34], or the salt or the hydrate thereof, wherein $X^2$ represents a group represented by the formula —NH—CH$_2$— or a group represented by the formula —CH$_2$—NH—;

[36]: a pharmaceutical composition comprising the compound according to item [3] or [34], or the salt or the hydrate thereof;

[37]: an antifungal agent comprising, as an active ingredient, the compound according to item [3] or [34], or the salt or the hydrate thereof;

[38]: a method for prevention or treatment of fungal infection comprising administering a pharmacologically effective amount of the compound according to item [3] or [34], or the salt or the hydrate thereof;

[39]: a use of the compound according to item [3] or [34], or the salt or the hydrate thereof, for manufacture of an antifungal agent;

[40]: a method for prevention or treatment of fungal infection comprising administering a pharmacologically effective amount of the antifungal agent according to item [1].

BEST MODE FOR CARRYING OUT THE INVENTION

The present invention is explained below in more detail by reference to the symbols and the terms used herein being defined and the following examples.

Herein, a structural formula of a compound sometimes represents a certain isomer for convenience of description. However, compounds according to the present invention may include all possible isomers, such as structurally possible geometric isomers, optical isomers generated due to the presence of asymmetric carbons, stereoisomers, tautomers, and mixtures of isomers, and are not limited to formulae being used for the convenience of description, and may be either of two isomers of a mixture of both isomers. Thus, the compounds according to the present invention may be either optically active compounds having an asymmetric carbon atom in their molecules or their racemates, and are not restricted to either of them but include both. Furthermore, the compounds according to the present invention may exhibit crystalline polymorphism, but likewise are not restricted to any one of these, but may be in any one of these crystal forms or exist as a mixture of two or more crystal forms. The compounds according to the present invention also include both anhydrous and hydrated forms.

In addition, compounds resulting from compounds according to the present invention that undergo in vivo metabolism such as oxidation, reduction, hydrolysis and conjugation (so-called metabolites), and compounds that undergo in vivo metabolism such as oxidation, reduction, hydrolysis and conjugation and generates compounds according to the present invention (so-called prodrugs) are also encompassed by the scope of the present invention.

The term "$C_{1-6}$ alkyl group" used in the present specification means a linear or branched chain alkyl group containing 1 to 6 carbon atoms, which is a monovalent group derived by removal of any one of the hydrogen atoms from an aliphatic hydrocarbon containing 1 to 6 carbons. Specifically, examples of "$C_{1-6}$ alkyl group" include a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a neopentyl group, a 1-methylbutyl group, a 2-methylbutyl group, a 1,1-dimethylpropyl group, a 1,2-dimethylpropyl group, a n-hexyl group, an iso-hexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group or the like, and preferably, a methyl group, an ethyl group, a n-propyl group, an iso-propyl group, a n-butyl group, an iso-butyl group, a sec-butyl group, a tert-butyl group or the like.

The term "$C_{2-6}$ alkenyl group" used in the present specification means a linear or branched chain alkenyl group containing 2 to 6 carbon atoms, which may contain 1 to 2 double-bonds. Specifically, examples of "$C_{2-6}$ alkenyl group" include an ethenyl group, a 1-propenyl group, a 2-propenyl group, a 1-butenyl group, a 2-butenyl group, a 3-butenyl group, a 2-methyl-1-propenyl group, a pentenyl group, a 3-methyl-2-butenyl group, a hexenyl group, a hexane dienyl group or the like, and preferably an ethenyl group, a 1-propenyl group, a 2-propenyl group, a 1-butenyl group, a 2-butenyl group, a 3-butenyl group, a 2-methyl-1-propenyl group, a 3-methyl-2-butenyl group or the like.

The term "$C_{2-6}$ alkynyl group" used in the present specification means a linear or branched chain alkynyl group containing 2 to 6 carbon atoms, which may contain 1 to 2 triple-bonds. Specifically, examples of "$C_{2-6}$ alkynyl group" include an ethynyl group, a 1-propynyl group, a 2-propynyl group, a 1-butynyl group, a 2-butynyl group, a 3-butynyl group, a pentynyl group, a hexynyl group, a hexane diynyl group or the like, and preferably, an ethynyl group, a 1-propynyl group, a 2-propynyl group, a 1-butynyl group, a 2-butynyl group, a 3-butynyl group or the like.

The term "$C_{3-8}$ cycloalkyl group" used in the present specification means a cyclic aliphatic hydrocarbon group containing 3 to 8 carbon atoms. Specifically, examples of "$C_{3-8}$ cycloalkyl group" include a cyclopropyl group, a cyclobutyl group, a cyclopentyl group, a cyclohexyl group, a cycloheptyl group, a cyclooctyl group or the like, and preferably, a cyclopropyl group, a cyclobutyl group, a cyclopentyl group, a cyclohexyl group or the like.

The term "$C_{1-6}$ alkoxy group" used in the present specification means a group in which an oxygen atom is bonded to terminus of the "$C_{1-6}$ alkyl group" defined above. Specifically, examples of "$C_{1-6}$ alkoxy group" include a methoxy group, an ethoxy group, a n-propoxy group, an iso-propoxy group, a n-butoxy group, an iso-butoxy group, a sec-butoxy group, a tert-butoxy group, a n-pentyloxy group, an iso-pentyloxy group, a sec-pentyloxy group, a neopentyloxy group, a 1-methylbutoxy group, a 2-methylbutoxy group, a 1,1-dimethylpropoxy group, a 1,2-dimethylpropoxy group, a n-hexyloxy group, an iso-hexyloxy group, a 1-methylpentyloxy group, a 2-methylpentyloxy group, a 3-methylpentyloxy group, a 1,1-dimethylbutoxy group, a 1,2-dimethylbutoxy group, a 2,2-dimethylbutoxy group, a 1,3-dimethylbutoxy group, a 2,3-dimethylbutoxy group, a 3,3-dimethylbutoxy group, a 1-ethylbutoxy group, a 2-ethylbutoxy group, a 1,1,2-trimethylpropoxy group, a 1,2,2-trimethylpropoxy group, a 1-ethyl-1-methylpropoxy group, a 1-ethyl-2-methylpropoxy group or the like and preferably, a methoxy group, an ethoxy group, a n-propoxy group, an iso-propoxy group, a n-butoxy group, an iso-butoxy group, a sec-butoxy group, a tert-butoxy group and the like.

The term "$C_{1-6}$ alkylthio group" used in the present specification means a group in which a sulfur atom is bonded to terminus of the "$C_{1-6}$ alkyl group" defined above. Specifically, examples of "$C_{1-6}$ alkylthio group" include a methylthio group, an ethylthio group, a n-propylthio group, an iso-propylthio group, a n-butylthio group, an iso-butylthio group, a sec-butylthio group, a tert-butylthio group, a n-pentylthio group, an iso-pentylthio group, a sec-pentylthio group, a neopentylthio group, a 1-methylbutylthio group, a 2-methylbutylthio group, a 1,1-dimethylpropylthio group, a 1,2-dimethylpropylthio group, a n-hexylthio group, an iso-hexylthio group, a 1-methylpentylthio group, a 2-methylpentylthio group, a 3-methylpentylthio group, a 1,1-dimethylbutylthio group, a 1,2-dimethylbutylthio group, a 2,2-dimethylbutylthio group, a 1,3-dimethylbutylthio group, a 2,3-dimethylbutylthio group, a 3,3-dimethylbutylthio group, a 1-ethylbutylthio group, a 2-ethylbutylthio group, a 1,1,2-trimethylpropylthio group, a 1,2,2-trimethylpropylthio group, a 1-ethyl-1-methylpropylthio group, a 1-ethyl-2-methylpropylthio group or the like, and preferably, a methylthio group, an ethylthio group, a n-propylthio group, an iso-propylthio group, a n-butylthio group, an iso-butylthio group, a sec-butylthio group, a tert-butylthio group or the like.

The term "$C_{1-6}$ alkylcarbonyl group" used in the present specification means a group in which a carbonyl group is bonded to terminus of the "$C_{1-6}$ alkyl group" defined above. Specifically, examples of "$C_{1-6}$ alkylcarbonyl group" include a methylcarbonyl group, an ethylcarbonyl group, a n-propylcarbonyl group, an iso-propylcarbonyl group or the like.

The term "$C_{1-6}$ alkoxycarbonyl group" used in the present specification means a group in which a carbonyl group is bonded to terminus of the "$C_{1-6}$ alkoxy group" defined above. Specifically, examples of "$C_{1-6}$ alkoxycarbonyl group" include a methoxycarbonyl group, an ethoxycarbonyl group, a n-propoxycarbonyl group, an iso-propoxycarbonyl group or the like.

The term "$C_{1-6}$ alkylsulfonyl group" used in the present specification means a group in which a sulfonyl group is bonded to terminus of the "$C_{1-6}$ alkyl group" defined above. Specifically, examples of "$C_{1-6}$ alkylsulfonyl group" include a methylsulfonyl group, an ethylsulfonyl group, a n-propylsulfonyl group, an iso-propylsulfonyl group or the like.

The term "$C_{2-6}$ alkenyloxy group" used in the present specification means a group in which an oxygen atom is bonded to terminus of the "$C_{2-6}$ alkenyl group" defined above. Specifically, examples of "$C_{2-6}$ alkenyloxy group" include an ethenyloxy group, a 1-propenyloxy group, a 2-propenyloxy group, a 1-butenyloxy group, a 2-butenyloxy group, a 3-butenyloxy group, a 2-methyl-1-propenyloxy group, a pentenyloxy group, a 3-methyl-2-butenyloxy group, a hexenyloxy group, a hexane dienyloxy group or the like, and preferably, an ethenyloxy group, a 1-propenyloxy group, a 2-propenyloxy group, a 1-butenyloxy group, a 2-butenyloxy group, a 3-butenyloxy group, a 2-methyl-1-propenyloxy group, a 3-methyl-2-butenyloxy group or the like.

The term "$C_{2-6}$ alkenylthio group" used in the present specification means a group in which a sulfur atom is bonded to terminus of the "$C_{2-6}$ alkenyl group" defined above. Specifically, examples of "$C_{2-6}$ alkenylthio group" include an ethenylthio group, a 1-propenylthio group, a 2-propenylthio group, a 1-butenylthio group, a 2-butenylthio group, a 3-butenylthio group, a 2-methyl-1-propenylthio group, a pentenylthio group, a 3-methyl-2-butenylthio group, a hexenylthio group, a hexane dienylthio group or the like, and preferably, an ethenylthio group, a 1-propenylthio group, a 2-propenylthio group, a 1-butenylthio group, a 2-butenylthio group, a 3-butenylthio group, a 2-methyl-1-propenylthio group, a 3-methyl-2-butenylthio group or the like.

The term "$C_{2-6}$ alkynyloxy group" used in the present specification means a group in which an oxygen atom is bonded to terminus of the "$C_{2-6}$ alkynyl group" defined above. Specifically, examples of "$C_{2-6}$ alkynyloxy group" include an ethynyloxy group, a 1-propynyloxy group, a 2-propynyloxy group, a 1-butynyloxy group, a 2-butynyloxy group, a 3-butynyloxy group, a pentynyloxy group, a hexynyloxy group, a hexane diynyloxy group or the like, and preferably, an ethynyloxy group, a 1-propynyloxy group, a 2-propynyloxy group, a 1-butynyloxy group, a 2-butynyloxy group, a 3-butynyloxy group or the like.

The term "$C_{2-6}$ alkynylthio group" used in the present specification means a group in which a sulfur atom is bonded to terminus of the "$C_{2-6}$ alkynyl group" defined above. Specifically, examples of "$C_{2-6}$ alkynylthio group" include an ethynylthio group, a 1-propynylthio group, a 2-propynylthio group, a 1-butynylthio group, a 2-butynylthio group, a 3-butynylthio group, a pentynylthio group, a hexynylthio group, a hexane diynylthio group or the like, and preferably, an ethynylthio group, a 1-propynylthio group, a 2-propynylthio group, a 1-butynylthio group, a 2-butynylthio group, a 3-butynylthio group or the like.

The term "$C_{3-8}$ cycloalkoxy group" used in the present specification means a group in which an oxygen atom is bonded to terminus of the "$C_{3-8}$ cycloalkyl group" defined above. Specifically, examples of "$C_{3-8}$ cycloalkoxy group" include a cyclopropoxy group, a cyclobutoxy group, a cyclopentyloxy group, a cyclohexyloxy group, a cycloheptyloxy group, a cyclooctyloxy group or the like, and preferably, a cyclopropoxy group, a cyclobutoxy group, a cyclopentyloxy group, a cyclohexyloxy group or the like.

The term "$C_{3-8}$ cycloalkylthio group" used in the present specification means a group in which a sulfur atom is bonded to terminus of the "$C_{3-8}$ cycloalkyl group" defined above. Specifically, examples of "$C_{3-8}$ cycloalkylthio group" include a cyclopropylthio group, a cyclobutylthio group, a cyclopentylthio group, a cyclohexylthio group, a cycloheptylthio group, a cyclooctylthio group or the like, and preferably, a cyclopropylthio group, a cyclobutylthio group, a cyclopentylthio group, a cyclohexylthio group or the like.

The term "$C_{3-8}$ cycloalkyl $C_{1-6}$ alkyl group" used in the present specification means a group in which any hydrogen atom within the "$C_{1-6}$ alkyl group" defined above is substituted by the "$C_{3-8}$ cycloalkyl group" defined above. Specifically, examples of "$C_{3-8}$ cycloalkyl $C_{1-6}$ alkyl group" include a cyclopropylmethyl group, a cyclobutylmethyl group, a cyclopentylmethyl group, a cyclohexylmethyl group, a cyclopropylethyl group, a cyclobutylethyl group, a cyclopentylethyl group, a cyclohexylethyl group or the like.

The term "$C_{3-8}$ cycloalkyl $C_{1-6}$ alkoxy group" used in the present specification means a group in which any hydrogen atom within the "$C_{1-6}$ alkoxy group" defined above is substituted by the "$C_{3-8}$ cycloalkyl group" defined above. Specifically, examples of "$C_{3-8}$ cycloalkyl $C_{1-6}$ alkoxy group" include a cyclopropylmethoxy group, a cyclobutylmethoxy group, a cyclopentylmethoxy group, a cyclohexylmethoxy group, a cyclopropylethoxy group, a cyclobutylethoxy group, a cyclopentylethoxy group, a cyclohexylethoxy group or the like.

The term "$C_{3-8}$ cycloalkyl $C_{1-6}$ alkylthio group" used in the present specification means a group in which any hydrogen atom within the "$C_{1-6}$ alkylthio group" defined above is substituted by the "$C_{3-8}$ cycloalkyl group" defined above. Specifically, examples of "$C_{3-8}$ cycloalkyl $C_{1-6}$ alkylthio group" include a cyclopropylmethylthio group, a cyclobutylmethylthio group, a cyclopentylmethylthio group, a cyclohexylmethylthio group, a cyclopropylethylthio group, a cyclobutylethylthio group, a cyclopentylethylthio group, a cyclohexylethylthio group or the like.

The term "$C_{3-8}$ cycloalkylidene $C_{1-6}$ alkyl group" used in the present specification means a group in which any carbon atom of a saturated cyclic aliphatic hydrocarbon containing 3 to 8 carbon atoms and the "$C_{1-6}$ alkyl group" defined above are bonded through a double-bond. Specifically, examples of "$C_{3-8}$ cycloalkylidene $C_{1-6}$ alkyl group" include a cyclopropylidene methyl group, a cyclobutylidene methyl group, a cyclopentilydene methyl group, a cyclohexylidene methyl group, a cyclopropylidene ethyl group, a cyclobutylidene ethyl group, a cyclopentylidene ethyl group, a cyclohexylidene ethyl group or the like.

The term "$C_{6-10}$ aryl group" used in the present specification means an aromatic cyclic hydrocarbon group containing 6 to 10 carbon atoms. Specifically, examples of "$C_{6-10}$ aryl group" include a phenyl group, a 1-naphthyl group, a 2-naphthyl group, an indenyl group, an azulenyl group, a heptalenyl group or the like, and preferably, a phenyl group, a 1-naphthyl group, a 2-naphthyl group or the like.

The term "$C_{6-10}$ aryloxy group" used in the present specification means a group in which an oxygen atom is bonded to terminus of the "$C_{6-10}$ aryl group" defined above. Specifically, examples of "$C_{6-10}$ aryloxy group" include a phenoxy group, a 1-naphthyloxy group, a 2-naphthyloxy group, an indenyloxy group, an azulenyloxy group, a heptalenyloxy group or the like, and preferably, a phenoxy group, a 1-naphthyloxy group, a 2-naphthyloxy group or the like.

The term "$C_{6-10}$ arylthio group" used in the present specification means a group in which a sulphur atom is bonded to terminus of the "$C_{6-10}$ aryl group" defined above. Specifically, examples of "$C_{6-10}$ arylthio group" include a phenylthio group, a 1-naphthylthio group, a 2-naphthylthio group, an indenylthio group, an azulenylthio group, a heptalenylthio group or the like, and preferably, a phenylthio group, a 1-naphthylthio group, a 2-naphthylthio group or the like.

The term "$C_{6-10}$ aryl $C_{1-6}$ alkyl group" used in the present specification means a group in which any hydrogen atom within the "$C_{1-6}$ alkyl group" defined above is substituted by the "$C_{6-10}$ aryl group" defined above. Specifically, examples of "$C_{6-10}$ aryl $C_{1-6}$ alkyl group" include a benzyl group, a 1-naphthylmethyl group, a 2-naphthylmethyl group, a phenethyl group, a 1-naphthylethyl group, a 2-naphthylethyl group, a 3phenyl-1-propyl group or the like.

The term "phenyl $C_{1-6}$ alkyl group" used in the present specification means a group in which any hydrogen atom within the "$C_{1-6}$ alkyl group" defined above is substituted by a phenyl group. Specifically, examples of "phenyl $C_{1-6}$ alkyl group" include a benzyl group, a phenethyl group, a 3-phenyl-1-propyl group or the like.

The term "$C_{6-10}$ aryl $C_{1-6}$ alkoxy group" used in the present specification means a group in which any hydrogen atom within the "$C_{1-6}$ alkoxy group" defined above is substituted by the "$C_{6-10}$ aryl group" defined above. Specifically, examples of "$C_{6-10}$ aryl $C_{1-6}$ alkoxy group" include a benzyloxy group, a 1-naphthylmethoxy group, a 2-naphthylmethoxy group, a phenethyloxy group, a 1-naphthylethoxy group, a 2-naphthylethoxy group, a 3-phenyl-1-propoxy group or the like.

The term "phenyl $C_{1-6}$ alkoxy group" used in the present specification means a group in which any hydrogen atom within the "$C_{1-6}$ alkoxy group" defined above is substituted by a phenyl group. Specifically, examples of "phenyl $C_{1-6}$ alkoxy group" include a benzyloxy group, a phenethyloxy group, a 3-phenyl-1-propoxy group or the like.

The term "$C_{6-10}$ aryl $C_{1-6}$ alkylthio group" used in the present specification means a group in which any hydrogen atom within the "$C_{1-6}$ alkylthio group" defined above is substituted by the "$C_{6-10}$ aryl group" defined above. Specifically, examples of "$C_{6-10}$ aryl $C_{1-6}$ alkylthio group" include a benzylthio group, a phenethylthio group, a 3phenyl-1-propylthio group or the like.

The term "mono-$C_{1-6}$ alkylamino group" used in the present specification means a group in which one hydrogen atom within an amino group is substituted by the "$C_{1-6}$ alkyl group" defined above. Specifically, examples of "mono-$C_{1-6}$ alkylamino group" include a methylamino group, an ethylamino group, a n-propylamino group, an iso-propylamino group, a n-butylamino group, an iso-butylamino group, a sec-butylamino group, a tert-butylamino group, a n-pentylamino group, an iso-pentylamino group, a sec-pentylamino group, a neopentylamino group, a 1-methylbutylamino group, a 2-methylbutylamino group, a 1,1-dimethylpropylamino group, a 1,2-dimethylpropylamino group, a n-hexylamino group, an iso-hexylamino group, a 1-methylpentylamino group, a 2-methylpentylamino group, a 3-methylpentylamino group, a 1,1-dimethylbutylamino group, a 1,2-dimethylbutylamino group, a 2,2-dimethylbutylamino group, a 1,3-dimethylbutylamino group, a 2,3-dimethylbutylamino group, a 3,3-dimethylbutylamino group, a 1-ethylbutylamino group, a 2-ethylbutylamino group, a 1,1,2-trimethylpropylamino group, a 1,2,2-trimethylpropylamino group, a 1-ethyl-1-methylpropylamino group, a 1-ethyl-2-methylpropylamino group or the like, and preferably, a methylamino group, an ethylamino group, a n-propylamino group, an iso-propylamino group, a n-butylamino group, an iso-butylamino group, a sec-butylamino group, a tert-butylamino group or the like.

The term "mono-$C_{2-6}$ alkenylamino group" used in the present specification means a group in which one hydrogen atom within an amino group is substituted by the "$C_{2-6}$ alkenyl group" defined above. Specifically, examples of "mono-$C_{2-6}$ alkenylamino group" include an ethenylamino group, a 1-propenylamino group, a 2-propenylamino group, a 1-butenylamino group, a 2-butenylamino group, a 3-butenylamino group, a 2-methyl-1-propenylamino group, a pentenylamino group, a 3methyl-2-butenylamino group, a hexenylamino group, a hexane dienylamino group or the like, and preferably, an ethenylamino group, a 1-propenylamino group, a 2-propenylamino group, a 1-butenylamino group, a 2-butenylamino group, a 3-butenylamino group, a 2-methyl-1-propenylamino group, a 3-methyl-2-butenylamino group or the like.

The term "mono-$C_{2-6}$ alkynylamino group" used in the present specification means a group in which one hydrogen atom within an amino group is substituted by the "$C_{2-6}$ alkynyl group" defined above. Specifically, examples of "mono-$C_{2-6}$ alkynylamino group" include an ethynylamino group, a 1-propynylamino group, a 2-propynylamino group, a 1-butynylamino group, a 2-butynylamino group, a 3-butynylamino group, a pentynylamino group, a hexynylamino group, a hexane diynylamino group or the like, and preferably, an ethynylamino group, a 1-propynylamino group, a 2-propynylamino group, a 1-butynylamino group, a 2-butynylamino group, a 3-butynylamino group or the like.

The term "mono-$C_{3-8}$ cycloalkylamino group" used in the present specification means a group in which one hydrogen atom within an amino group is substituted by the "$C_{3-8}$ cydoalkyl group" defined above. Specifically, examples of "mono-$C_{3-8}$ cycloalkylamino group" include a cyclopropylamino group, a cyclobutylamino group, a cyclopentylamino group, a cyclohexylamino group, a cycloheptylamino group, a cyclooctylamino group or the like, and preferably, a cyclopropylamino group, a cyclobutylamino group, a cyclopentylamino group, a cyclohexylamino group or the like.

The term "mono-$C_{6-10}$ arylamino group" used in the present specification means a group in which one hydrogen atom within an amino group is substituted by the "$C_{6-10}$ aryl group" defined above. Specifically, examples of "mono-$C_{6-10}$ arylamino group" include a phenylamino group, a 1-naphthylamino group, a 2-naphthylamino group, an indenylamino group, an azulenylamino group, a heptalenylamino group or the like, and preferably, a phenylamino group, a 1-naphthylamino group, a 2-naphthylamino group or the like.

The term "mono-$C_{3-8}$ cycloalkyl $C_{1-6}$ alkylamino group" used in the present specification means a group in which one hydrogen atom within an amino group is substituted by the "$C_{3-8}$ cycloalkyl $C_{1-6}$ alkyl group" defined above. Specifically, examples of "mono-$C_{3-8}$ cycloalkyl $C_{1-6}$ alkylamino group" include a cyclopropylmethylamino group, a cyclobutylmethylamino group, a cyclopentylmethylamino group, a cyclohexylmethylamino group, a cyclopropylethylamino group, a cyclobutylethylamino group, a cyclopentylethylamino group, a cyclohexylethylamino group or the like.

The term "mono-$C_{6-10}$ aryl $C_{1-6}$ alkylamino group" used in the present specification means a group in which one hydrogen atom within an amino group is substituted by the "$C_{6-10}$ aryl $C_{1-6}$ alkyl group" defined above. Specifically, examples of "mono-$C_{6-10}$ aryl $C_{1-6}$ alkylamino group" include a benzyl amino group, a 1-naphthylmethylamino group, a 2-naphthylmethylamino group, a phenethylamino group, a 1-naphthylethylamino group, a 2-naphthylethylamino group or the like.

The term "di-$C_{1-6}$ alkylamino group" used in the present specification means a group in which two hydrogen atoms within an amino group are substituted by the identical to or different from the "$C_{1-6}$ alkyl groups" defined above. Specifically, examples of "di-$C_{1-6}$ alkylamino group" include a N,N-dimethylamino group, a N,N-diethylamino group, a N,N-din-propylamino group, a N,N-di-iso-propylamino group, a N,N-di-n-butylamino group, a N,N-di-iso-butylamino group, a N,N-di-sec-butylamino group, a N,N-di-tert-butylamino group, a N-ethyl-N-methylamino group, a N-n-propyl-N-methylamino group, a N-iso-propyl-N-methylamino group, a N-n-butyl-N-methylamino group, a N-iso-butyl-N-methylamino group, a N-sec-butyl-N-methylamino group, a N-tert-butyl-N-methylamino group or the like, and preferably, a N,N-dimethylamino group, a N,N-diethylamino group, a N-ethyl-N-methylamino group or the like.

The term "N—$C_{2-6}$ alkenyl-N—$C_{1-6}$ alkylamino group" used in the present specification means a group in which one of the hydrogen atoms within an amino group is substituted by the "$C_{2-6}$ alkenyl group" defined above, and the other hydrogen atom is substituted by the "$C_{1-6}$ alkyl group" defined above. Specifically, examples of "N—$C_{2-6}$ alkenyl-N—$C_{1-6}$ alkylamino group" include a N-ethenyl-N-methylamino group, a N-1-propenyl-N-methylamino group, a N-2-propenyl-N-methylamino group, a N-1-butenyl-N-methylamino group, a N-2-butenyl-N-methylamino group, a N-3-butenyl-N-methylamino group, a N-2-methyl-1-propenyl-N-methylamino group, a N-pentenyl-N-methylamino group, a N-3-methyl-2-butenyl-N-methylamino group, a N-hexenyl-N-methylamino group, a N-hexanedienyl-N-methylamino group or the like, and preferably, a N-ethenyl-N-methylamino group, a N-1-propenyl-N-methylamino group, a N-2-propenyl-N-methylamino group, a N-1-butenyl-N-methylamino group, a N-2-butenyl-N-methylamino group, a N-3-butenyl-N-methylamino group, a N-2-methyl-1-propenyl-N-methylamino group, a N-3-methyl-2-butenyl-N-methylamino a group or the like.

The term "N—$C_{2-6}$ alkynyl-N—$C_{1-6}$ alkylamino group" used in the present specification means a group in which one of the hydrogen atoms within an amino group is substituted by the "$C_{2-6}$ alkynyl group" defined above, and the other hydrogen atom is substituted by the "$C_{1-6}$ alkyl group" defined above. Specifically, examples of "N—$C_{2-6}$ alkynyl-N—$C_{1-6}$ alkylamino group" include a N-ethynyl-N-methylamino group, a N-1-propynyl-N-methylamino group, a N-2-propynyl-N-methylamino group, a N-1-butynyl-N-methylamino group, a N-2-butynyl-N-methylamino group, a N-3-butynyl-N-methylamino group, a N-pentynyl-N-methylamino group, a N-hexynyl-N-methylamino group, a N-hexanediynyl-N-methylamino group or the like, and preferably, a N-ethynyl-N-methylamino group, a N-1-propynyl-N-methylamino group, a N-2-propynyl-N-methylamino group, a N-1-butynyl-N-methylamino group, a N-2-butynyl-N-methylamino group, a N-3-butynyl-N-methylamino group or the like.

The term "N—$C_{3-8}$ cycloalkyl-N—$C_{1-6}$ alkylamino group" used in the present specification means a group in which one of the hydrogen atoms within an amino group is substituted by the "$C_{3-8}$ cycloalkyl group" defined above, and the other hydrogen atom is substituted by the "$C_{1-6}$ alkyl group" defined above. Specifically, examples of "N—$C_{3-8}$ cycloalkyl-N—$C_{1-6}$ alkylamino group" include a N-cyclopropyl-N-methylamino group, a N-cyclobutyl-N-methylamino group, a N-cyclopentyl-N-methylamino group, a N-cyclohexyl-N-methylamino group, a N-cycloheptyl-N-methylamino group, a N-cyclooctyl-N-methylamino group or the like, and preferably, a N-cyclopropyl-N-methylamino group, a N-cyclobutyl-N-methylamino group, a N-cyclopentyl-N-methylamino group, a N-cyclohexyl-N-methylamino group or the like.

The term "N—$C_{6-10}$ aryl-N—$C_{1-6}$ alkylamino group" used in the present specification means a group in which one of the hydrogen atoms within an amino group is substituted by the "$C_{6-10}$ aryl group" defined above, and the other hydrogen atom is substituted by the "$C_{1-6}$ alkyl group" defined above. Specifically, examples of "N—$C_{6-10}$ aryl-N—$C_{1-6}$ alkylamino group" include a N-phenyl-N-methylamino group, a N-1-naphthyl-N-methylamino group, a N-2-naphthyl-N-methylamino group, a N-indenyl-N-methylamino group, a N-azulenyl-N-methylamino group, a N-heptalenyl-N-methylamino group or the like, and preferably, a N-phenyl-N-methylamino group, a N-1-naphthyl-N-methylamino group, a N-2-naphthyl-N-methylamino group or the like.

The term "N—$C_{3-8}$ cycloalkyl $C_{1-6}$ alkyl-N—$C_{1-6}$ alkylamino group" used in the present specification means a group in which one of the hydrogen atoms within an amino group is substituted by the "$C_{3-8}$ cycloalkyl $C_{1-6}$ alkyl group" defined above, and the other hydrogen atom is substituted by the "$C_{1-6}$ alkyl group" defined above. Specifically, examples of "N—$C_{3-8}$ cycloalkyl $C_{1-6}$ alkyl-N—$C_{1-6}$ alkylamino group" include a N-cyclopropylmethyl-N-methylamino group, a N-cyclobutylmethyl-N-methylamino group, a N-cyclopentylmethyl-N-methylamino group, a N-cyclohexylmethyl-N-methylamino group, a N-cyclopropylethyl-N-amino group, a N-cyclobutylethyl-N-methylamino group, a N-cyclopentylethyl-N-methylamino group, a N-cyclohexylethyl-N-methylamino group or the like.

The term "N—$C_{6-10}$ aryl $C_{1-6}$ alkyl-N—$C_{1-6}$ alkylamino group" used in the present specification means a group in which one of the hydrogen atoms within an amino group is substituted by the "$C_{6-10}$ aryl $C_{1-6}$ alkyl group" defined above, and the other hydrogen atom is substituted by the "$C_{1-6}$ alkyl group" defined above. Specifically, examples of "N—$C_{6-10}$ aryl $C_{1-6}$ alkyl-N—$C_{1-6}$ alkylamino group" include a N-benzyl-N-methylamino group, a N-1-naphthylmethyl-N-methylamino group, a N-2-naphthylmethyl-N-methylamino group, a N-phenethyl-N-methylamino group, a N-1-naphthylethyl-N-methylamino group, a N-2-naphthylethyl-N-methylamino group or the like.

The term "halogen atom" used in the present specification refers to a fluorine atom, a chlorine atom, a bromine atom or an iodine atom, and preferably, a fluorine atom, a chlorine atom or a bromine atom.

The term "heteroatom" used in the present specification refers to a nitrogen atom, a sulfur atom or an oxygen atom.

The term "5- to 10-membered heterocyclic group" used in the present specification means a monovalent group derived by removal of any one hydrogen atom from the ring of an aromatic or a non-aromatic that has one or a plurality of heteroatoms among the atoms constituting the ring, the number of atoms constituting the ring being 5 to 10. Specifically, examples of aromatic "5- to 10-membered heterocyclic group" include a furyl group (for instance, a 2-furyl group, a 3-furyl group or the like), a thienyl group (for instance, a 2-thienyl group, a 3-thienyl group or the like), a pyrrolyl group (for instance, a 1-pyrrolyl group, a 2-pyrrolyl group, a 3-pyrrolyl group or the like), a pyridyl group (for instance, a 2-pyridyl group, a 3-pyridyl group, a 4-pyridyl group or the like), a pyrazinyl group, a pyridazinyl group (for instance, a 3-pyridazinyl group, a 4-pyridazinyl group or the like), a pyrimidinyl group (for instance, a 2-pyrimidinyl group, a 4-pyrimidinyl group, a 5-pyrimidinyl group or the like), a triazolyl group (for instance, a 1,2,3-triazolyl group, a 1,2,4-triazolyl group or the like), a tetrazolyl group (for instance, a 1H-tetrazolyl group, a 2H-tetrazolyl group or the like), a thiazolyl group (for instance, a 2-thiazolyl group, a 4-thiazolyl group, a 5-thiazolyl group or the like), a pyrazolyl group (for instance, a 3-pyrazolyl group, a 4-pyrazolyl group or the like), an oxazolyl group (for instance, a 2-oxazolyl group, 4-oxazolyl group, a 5-oxazolyl group or the like), an isooxazolyl group (for instance, a 3-isooxazolyl group, a 4-isooxazolyl group, a 5-isooxazolyl group or the like), an isothiazolyl group (for instance, a 3-isothiazolyl group, a 4-isothiazolyl group, a 5-isothiazolyl group or the like), a quinolyl group (for instance, a 5-quinolyl group, a 6-quinolyl group, a 7-quinolyl group, a 8-quinolyl group or the like), an isoquinolyl group (for instance, a 5-isoquinolyl group, a 6-isoquinolyl group, a 7-isoquinolyl group, a 8-isoquinolyl group or the like), a naphthyidinyl group (for instance, a [1,5]naphthylidin-2-yl group, a [1,5]naphthylidin-3-yl group, a [1,8]naphthylidin-2-yl group, a [1,8]naphthylidin-3-yl group or the like), a quinoxalinyl group (for instance, a 5-quinoxalinyl group, a 6-quinoxalinyl group, a 7-quinoxalinyl group, a 8-quinoxalinyl group or the like), a cinnolinyl group (for instance, a 5-cinnolinyl group, a 6-cinnolinyl group, a 7-cinnolinyl group, a 8-cinnolinyl group or the like), a quinazolinyl group (for instance, a 4quinazolinyl group, a 5-quinazolinyl group, a 6-quinazolinyl group, a 7-quinazolinyl group, a 8-quinazolinyl group or the like), an imidazopyridyl group (for instance, an imidazo[1,2-a]pyridin-6-yl group or the like), a benzothiazolyl group (for instance, a benzothiazol-4-yl group, a benzothiazol-5-yl group, a benzothiazol-6-yl group, a benzothiazol-7-yl group or the like), a benzoxazolyl group (for instance, a benzoxazol-4-yl group, a benzoxazol-5-yl group, a benzoxazol-6-yl group, a benzoxazol-7-yl group or the like), a benzimidazolyl group (for instance, a benzimidazol-4-yl group, a benzimidazol-5-yl group, a benzimidazol-6-yl group, a benzimidazol-7-yl group or the like), an indolyl group (for instance, an indol-4-yl group, an indol-5-yl group, an indol-6-yl group, an indol-7-yl group or the like), a pyrrolopyridyl group (for instance, a 1H-pyrrolo[2,3-b]pyridin-5-yl group, a pyrrolo[3,2-b]pyridin-1-yl group or the like), a thienopyridyl group (for instance, a thieno[2,3-b]pyridin-5-yl group, a thieno[3,2-b]pyridin-6-yl group or the like), a furopyridyl group (for instance, a furo[2,3-b]pyridin-5-yl group, a furo[3,2-b]pyridin-6-yl group or the like), a 2,3-dihydro-1H-pyrrolo[2,3-b]pyridin-5-yl group, a benzothiadiazolyl group (for instance, a benzo[1,2,5]thiadiazol-5-yl group or the like), a benzoxadiazolyl group (for instance, a benzo[1,2,5]oxadiazol-5-yl group or the like), a pyridopyrimidinyl group (for instance, a pyrido[2,3-d]pyrimidin-4-yl group or the like), a benzofuryl group (for instance, a benzofuran-4-yl group, a benzofuran-5-yl group, a benzofuran-6-yl group, a benzofuran-7-yl group or the like), a benzothienyl group (for instance, a benzothiophen-4-yl group, a benzothiophen-5-yl group, a benzothiophen-6-yl group, a benzothiophen-7-yl group or the like), a benzo[1,3]dioxol group (for instance, a benzo[1,3]dioxol-5-yl group or the like) or the like. Specifically, examples of non-aromatic "5-10 membered heterocyclic group" include a pyrrolidinyl group, a piperidinyl group, a homopiperidinyl group, a piperazinyl group, a homopiperazinyl group, a morpholinyl group, a thiomorpholinyl group, a tetrahydrofuryl group, a tetrahydropyanyl group or the like.

The term "5- to 10-membered heterocyclic group containing at least one nitrogen atom" means a monovalent group derived by removal of one hydrogen atom from any position on the ring of an aromatic or a non-aromatic having from 1 to a plurality of heteroatoms among the atoms constituting the ring, and having at least one nitrogen atom, the number of atoms constituting the ring being 5 to 10. Specifically, examples of "5- to 10-membered heterocyclic group containing at least one nitrogen atom" include a pyrrolyl group, a pyridyl group, a pyrazinyl group, a pyridazinyl group, a pyrimidinyl group, a tetrazolyl group, a thiazolyl group, a pyrazolyl group, an oxazolyl group, an isooxazolyl group, an isothiazolyl group, a quinolyl group, an isoquinolyl group, a naphthyidinyl group, a quinoxalinyl group, a cinnolinyl group, a quinazolinyl group, an imidazopyridyl group, a benzothiazolyl group, a benzoxazolyl group, a benzimidazolyl group, an indolyl group, a pyrrolopyridyl group, a thienopyridyl group, a furopyridyl group, a 2,3-dihydro-1H-pyrrolo[2,3-b]pyridin-5-yl group, a benzothiadiazolyl group, a benzoxadiazolyl group, a pyridopyrimidinyl group or the like.

The term "5- to 10-membered heterocyclic $C_{1-6}$ alkyl group" used in the present specification means a group in which any hydrogen atom within the "$C_{1-6}$ alkyl group" defined above is substituted by the "5- to 10-membered heterocyclic group" defined above. Specifically, examples of "5- to 10-membered heterocyclic $C_{1-6}$ alkyl group" include a furylmethyl group, a thienylmethyl group, a pyrrolylmethyl group, a pyridylmethyl group, a triazolylmethyl group, a tetrazolylmethyl group, a thiazolylmethyl group, a pyrazolylmethyl group, an oxazolylmethyl group, a benzo[1,3]dioxol methyl group, a tetrahydrofurylmethyl group, a furylethyl group, a thienylethyl group, a pyrrolylethyl group, a pyridylethyl group, a triazolylethyl group, a tetrazolylethyl group, a thiazolylethyl group, a pyrazolylethyl group, an oxazolylethyl group, a benzo[1,3]dioxol ethyl group, a tetrahydrofurylethyl group or the like.

The term "furyl $C_{1-6}$ alkyl group" used in the present specification means a group in which any hydrogen atom within the "$C_{1-6}$ alkyl group" defined above is substituted by a furyl group. Specifically, examples of "furyl $C_{1-6}$ alkyl group" include a furylmethyl group, a furylethyl group or the like.

The term "thienyl $C_{1-6}$ alkyl group" used in the present specification means a group in which any hydrogen atom within the "$C_{1-6}$ alkyl group" defined above is substituted by a thienyl group. Specifically, examples of "thienyl $C_{1-6}$ alkyl group" include a thienylmethyl group, a thienylethyl group or the like.

The term "benzofuryl $C_{1-6}$ alkyl group" used in the present specification means a group in which any hydrogen atom within the "$C_{1-6}$ alkyl group" defined above is substituted by a benzofuryl group. Specifically, examples of "benzofuryl $C_{1-6}$ alkyl group" include a benzofurylmethyl group, a benzofurylethyl group or the like.

The term "benzothienyl $C_{1-6}$ alkyl group" used in the present specification means a group in which any hydrogen atom within the "$C_{1-6}$ alkyl group" defined above is substituted by a benzothienyl group. Specifically, examples of "benzothienyl $C_{1-6}$ alkyl group" include a benzothienylmethyl group, a benzothienylethyl group or the like.

The term "5- to 10-membered heterocycle oxy group" used in the present specification means a group in which an oxygen atom is bonded to terminus of the "5-10 membered heterocyclic group" defined above. Specifically, examples of "5- and 10-membered heterocycle oxy group" include a furyloxy group, a thienyloxy group, a pyrrolyloxy group, a pyridyloxy group, a triazolyloxy group, a tetrazolyloxy group, a thiazolyloxy group, a pyrazolyloxy group, an oxazolyloxy group, a benzo[1,3]dioxol oxy group, a tetrahydrofuryloxy group or the like.

The term "5- to 10-membered heterocyclic $C_{1-6}$ alkoxy group" used in the present specification means a group in which any hydrogen atom within the "$C_{1-6}$ alkoxy group" defined above is substituted by the "5- to 10-membered heterocyclic group" defined above. Specifically, examples of "5- to 10-membered heterocyclic $C_{1-6}$ alkoxy group" include a furylmethoxy group, a thienylmethoxy group, a pyrrolylmethoxy group, a pyridylmethoxy group, a triazolylmethoxy group, a tetrazolylmethoxy group, a thiazolylmethoxy group, a pyrazolylmethoxy group, an oxazolylmethoxy group, a benzo[1,3]dioxol methoxy group, a tetrahydrofurylmethoxy group, a furylethoxy group, a thienylethoxy group, a pyrrolylethoxy group, a pyridylethoxy group, a triazolylethoxy group, a tetrazolylethoxy group, a thiazolylethoxy group, a pyrazolylethoxy group, an oxazolylethoxy group, a benzo[1,3]dioxol ethoxy group, a tetrahydrofurylethoxy group or the like.

The term "furyl $C_{1-6}$ alkoxy group" used in the present specification means a group in which any hydrogen atom within the "$C_{1-6}$ alkoxy group" defined above is substituted by a furyl group. Specifically, examples of "furyl $C_{1-6}$ alkoxy group" include a furylmethoxy group, a furylethoxy group or the like.

The term "thienyl $C_{1-6}$ alkoxy group" used in the present specification means a group in which any hydrogen atom within the "$C_{1-6}$ alkoxy group" defined above is substituted by a thienyl group. Specifically, examples of "thienyl $C_{1-6}$ alkoxy group" include a thienylmethoxy group, a thienylethoxy group or the like.

The term "pyridyl $C_{1-6}$ alkoxy group" used in the present specification means a group in which any hydrogen atom within the "$C_{1-6}$ alkoxy group" defined above is substituted by a pyridyl group. Specifically, examples of "pyridyl $C_{1-6}$ alkoxy group" include a pyridylmethoxy group, a pyridylethoxy group or the like.

The term "5- to 10-membered heterocyclic $C_{1-6}$ alkylthio group" used in the present specification means a group in which any hydrogen atom within the "$C_{1-6}$ alkylthio group" defined above is substituted by the "5- to 10-membered heterocyclic group" defined above. Specifically, examples of "5- to 10-membered heterocyclic $C_{1-6}$ alkylthio group" include a furylmethylthio group, a thienylmethylthio group, a pyrrolylmethylthio group, a pyridylmethylthio group, a triazolylmethylthio group, a tetrazolylmethylthio group, a thiazolylmethylthio group, a pyrazolylmethylthio group, an oxazolylmethylthio group, a benzo[1,3]dioxol methylthio group, a tetrahydrofurylmethylthio group, a furylethylthio group, a thienylethylthio group, a pyrrolylethylthio group, a pyridylethylthio group, a triazolylethylthio group, a tetrazolylethylthio group, a thiazolylethylthio group, a pyrazolylethylthio group, an oxazolylethylthio group, a benzo[1,3]dioxol ethylthio group, a tetrahydrofurylethylthio group or the like.

The term "mono-5- to 10-membered heterocyclic $C_{1-6}$ alkylamino group" used in the present specification means a group in which one hydrogen atom within an amino group is substituted by the "5- to 10-membered heterocyclic $C_{1-6}$ alkyl group" defined above. Specifically, examples of "mono-5 to 10-membered heterocyclic $C_{1-6}$ alkylamino group" include a furylmethylamino group, a thienylmethylamino group, a pyrrolylmethylamino group, a pyridylmethylamino group, a triazolylmethylamino group, a tetrazolylmethylamino group, a thiazolylmethylamino group, a pyrazolylmethylamino group, an oxazolylmethylamino group, a tetrahydrofurylmethylamino group, a furylethylamino group, a thienylethylamino group, a pyrrolylethylamino group, a pyridylethylamino group, a triazolylethylamino group, a tetrazolylethylamino group, a thiazolylethylamino group, a pyrazolylethylamino group, an oxazolylethylamino group, a tetrahydrofurylethylamino group, a triazolyl-1-propylamino group or the like.

The term "N-5 to 10-membered heterocyclic $C_{1-6}$ alkyl-N—$C_{1-6}$ alkylamino group" used in the present specification means a group in which one of the hydrogen atoms within an amino group is substituted by the "5- to 10-membered heterocyclic $C_{1-6}$ alkyl group" defined above and the other hydrogen atom is substituted by the "$C_{1-6}$ alkyl group" defined above. Specifically, examples of "N-5- to 10-membered heterocyclic $C_{1-6}$ alkyl-N—$C_{1-6}$ alkylamino group" include a N-furylmethyl-N-methylamino group, a N-thienylmethyl-N-methylamino group, a N-pyrrolylmethyl-N-methylamino group, a N-pyridylmethyl-N-methylamino group, a N-triazolylmethyl-N-methylamino group, a N-tetrazolylmethyl-N-methylamino group, a N-thiazolylmethyl-N-methylamino group, a N-pyrazolylmethyl-N-methylamino group, a N-oxazolylmethyl-N-methylamino group, a N-tetrahydrofurylmethyl-N-methylamino group, a N-furylethyl-N-methylamino group, a N-thienylethyl-N-methylamino group, a N-pyrrolylethyl-N-methylamino group, a N-pyridylethyl-N-methylamino group, a N-triazolylethyl-N-methylamino group, a N-tetrazolylethyl-N-methylamino group, a N-thiazolylethyl-N-methylamino group, a N-pyrazolylethyl-N-methylamino group, a N-oxazolylethyl-N-methylamino group, a N-tetrahydrofurylethyl-N-methylamino group or the like.

The term "$C_{6-10}$ aryloxy $C_{1-6}$ alkyl group" used in the present specification means a group in which any hydrogen atom within the "$C_{1-6}$ alkyl group" defined above is substituted by the "$C_{6-10}$ aryloxy group" defined above. Specifically, examples of "$C_{6-10}$ aryloxy $C_{1-6}$ alkyl group" include a phenoxymethyl group, a 1-naphthyloxymethyl group, a 2-naphthyloxymethyl group, an indenyloxymethyl group, an azulenyloxymethyl group, a heptalenyloxymethyl group or the like, and preferably, a phenoxymethyl group, a 1-naphthyloxymethyl group, a 2-naphthyloxymethyl group or the like.

The term "phenoxy $C_{1-6}$ alkyl group" used in the present specification means a group in which any hydrogen atom within the "$C_{1-6}$ alkyl group" defined above is substituted by a phenoxy group. Specifically, examples of "phenoxy $C_{1-6}$ alkyl group" include a phenoxymethyl group or the like.

The term "5- to 10-membered heterocycle oxy $C_{1-6}$ alkyl group" used in the present specification means a group in which any hydrogen atom within the "$C_{1-6}$ alkyl group" defined above is substituted by the "5- to 10-membered heterocycle oxy group". Specifically, examples of "5- to 10-membered heterocycle oxy $C_{1-6}$ alkyl group" include a furyloxymethyl group, a thienyloxymethyl group, a pyrrolyloxymethyl group, a pyridyloxymethyl group, a triazolyloxymethyl group, a tetrazolyloxymethyl group, a thiazolyloxymethyl group, a pyrazolyloxymethyl group, an oxazolyloxymethyl group, a benzo[1,3]dioxol oxymethyl group, a tetrahydrofuryloxymethyl group or the like, and preferably, a furyloxymethyl group, a thienyloxymethyl group, a pyrrolyloxymethyl group, a pyridyloxymethyl group or the like.

The term "pyridyloxy $C_{1-6}$ alkyl group" used in the present specification means a group in which any hydrogen atom within the "$C_{1-6}$ alkyl group" defined above is substituted by a pyridyl group. Specifically, examples of "pyridyloxy $C_{1-6}$ alkyl group" include a pyridyloxymethyl group or the like.

The term "which may have a substituent" used in the present specification means that a group may have from one to a plurality of substituents combined at replaceable positions arbitrarily.

The term "having a substituent" used in the present specification refers to having from one to a plurality of substituents combined at replaceable positions arbitrarily.

The term "A" used in the present specification means a 5- to 10-membered heterocyclic group containing at least one nitrogen atom (with the proviso that A may have 1 to 3 substituents selected from the substituent group a-1 or a-2 defined above). Preferable examples of "A" include an aromatic 5 to 10-membered heterocyclic group containing at least one nitrogen atom, such as, a 3-pyridyl group, a pyrazinyl group, a pyrimidinyl group, a pyrazolyl group, a quinolyl group, an isoquinolyl group, a naphthyidinyl group, a quinoxalinyl group, a cinnolinyl group, a quinazolinyl group, an imidazopyridyl group, a benzothiazolyl group, a benzoxazolyl group, a benzimidazolyl group, an indolyl group, a 1H-pyrrolopyridyl group, a thienopyridyl group, a furopyridyl group, a 2,3-dihydro-1H-pyrrolo[2,3-b]pyridin-5-yl group, a benzothiadiazolyl group or a pyrido[2,3-d]pyrimidinyl group (with the proviso that each above-mentioned group may have 1 to 3 substituents selected from the substituent groups a-1 and a-2 defined above).

The term "X" used in the present specification means a group represented by the formula —NH—C(=Y)—(CH$_2$)$_n$—, a group represented by the formula —C(=Y)—NH—(CH$_2$)$_n$—, a group represented by the formula —C(=Z)—(CH$_2$)$_n$—, a group represented by the formula —CH$_2$—NH—(CH$_2$)$_n$—, a group represented by the formula —NH—CH$_2$—(CH$_2$)$_n$— or a group represented by the formula —Z—CH$_2$—(CH$_2$)$_n$— (wherein Y, Z and n have the same meanings as defined above, respectively). Preferable examples of "X" include a group represented by the formula —NH—C(=Y)—CH$_2$—, a group represented by the formula —C(=Y)—NH—CH$_2$—, a group represented by the formula —CH$_2$—NH— or a group represented by the formula —NH—CH$_2$— (wherein Y has the same meaning as defined above).

The term "A$^1$" used in the present specification means a 3-pyridyl group, a pyrazinyl group, a pyrimidinyl group, a pyrazolyl group, a quinotyl group, an isoquinolyl group, a naphthyidinyl group, a quinoxalinyl group, a cinnolinyl group, a quinazolinyl group, an imidazopyridyl group, a benzothiazolyl group, a benzoxazolyl group, a benzimidazolyl group, an indolyl group, a pyrrolopyridyl group, a thienopyridyl group, a furopyridyl group, a 2,3-dihydro-1H-pyrrolo[2,3-b]pyridin-5-yl group or a benzothiadiazolyl group (with the proviso that each above-mentioned group may have 1 to 3 substituents selected from the substituent groups a-1 and a-2 defined above). Preferable examples of "A$^1$" include a 3-pyridyl group, a quinolyl group, a naphthyidinyl group, a quinoxalinyl group, an imidazopyridyl group, a benzothiazolyl group, a pyrrolopyridyl group, a thienopyridyl group or a furopyridyl group (with the proviso that each above-mentioned group may have 1 to 3 substituents selected from the substituent groups a-1 and a-2 defined above), more preferably, a 3-pyridyl group, a 6-quinolyl group, a [1,5]naphthylidin-2-yl group, a 6-quinoxalinyl group, an imidazo[1,2-a]pyridin-6-yl group, a benzothiazol-6-yl group, a 1H-pyrrolo[2,3-b]pyridin-5-yl group, a pyrrolo[3,2-b]pyridin-1-yl group, a thieno[2,3-b]pyridin-5-yl group, a thieno[3,2-b]pyridin-6-yl group or a furo[3,2-b]pyridin-6-yl group (with the proviso that each above-mentioned group may have 1 to 3 substituents selected from the substituent groups c-1 and c-2 defined above), still more preferably, group represented by the formula:

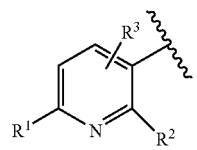

(wherein R$^1$, R$^2$, R$^3$, R$^4$ and R$^5$ have the same meanings as defined above, respectively), a 6-quinolyl group, a [1,5]naphthylidin-2-yl group, a 6-quinoxalinyl group, an imidazo[1,2-a]pyridin-6-yl group, a benzothiazol-6-yl group, a pyrrolo[3,2-b]pyridin-1-yl group, a 1H-pyrrolo[2,3-b]pyridin-5-yl group which may have one amino group, a thieno[2,3-b]pyridin-5-yl group which may have one amino group, a thieno[3,2-b]pyridin-6-yl group which may have one amino group or a furo[3,2-b]pyridin-6-yl group which may have one amino group, and particularly preferably, a group represented by the formula:

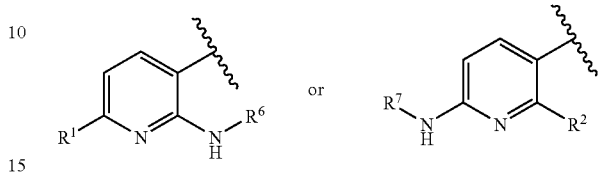

(wherein R$^1$, R$^2$, R$^6$ and R$^7$ have the same meanings as defined above, respectively), a 6-quinolyl group, a [1,5]naphthylidin-2-yl group, an imidazo[1,2-a]pyridin-6-yl group or a benzothiazol-6-yl group, most preferably 1) a group represented by the formula:

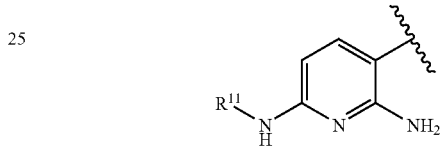

(wherein R$^{11}$ has the same meaning as defined above) or 2) group represented by the formula:

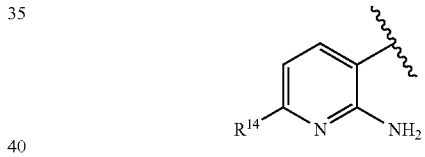

(wherein R$^{14}$ has the same meaning as defined above), a 6-quinolyl group, a [1,5]naphthylidin-2-yl group or an imidazo[1,2-a]pyridin-6-yl group.

In addition, preferable examples of "A$^1$" include a 3-pyridyl group, a pyrazinyl group, a pyrimidinyl group, a quinolyl group, an isoquinolyl group, a naphthyidinyl group, a quinoxalinyl group, a cinnolinyl group, a quinazolinyl group, an imidazopyridyl group, a benzothiazolyl group, a benzoxazolyl group, a benzimidazolyl group, an indolyl group, a pyrrolopyridyl group, a thienopyridyl group, a furopyridyl group, a 2,3-dihydro-1H-pyrrolo[2,3-b]pyridin-5-yl group or a benzothiadiazolyl group (with the proviso that A$^1$ may have 1 to 3 substituents selected from the substituent groups a-1 and a-2 defined above), more preferably, a 3-pyridyl group, a pyrazinyl group, a pyrimidinyl group, a quinolyl group, an isoquinolyl group, a naphthyidinyl group, a quinoxalinyl group, a cinnolinyl group, a quinazolinyl group, an imidazopyridyl group, a benzothiazolyl group, a benzoxazolyl group, a benzimidazolyl group, an indolyl group, a pyrrolopyridyl group, a thienopyridyl group, a furopyridyl group, a 2,3-dihydro-1H-pyrrolo[2,3-b]pyridin-5-yl group or a benzothiadiazolyl group (with the proviso that A$^1$ may have 1 to 3 substituents selected from the substituent groups c-1 and c-2 defined above), still more preferably, a 3-pyridyl group, a pyrazinyl group, a pyrimidinyl group, a quinolyl group, an isoquinolyl group, a naphthyldinyl group, a quinoxalinyl group, a cinnolinyl group, a quinazolinyl group, an imidazopyridyl group, a benzothiazolyl group, a benzoxazolyl group, a benzimidazolyl group, an indolyl group, a pyrrolopyridyl group, a thienopyridyl group, a furopyridyl group, a 2,3-dihydro-1H-pyrrolo[2,3-b]pyridin-5-yl group or a benzothiadiazolyl group (with the proviso that $A^1$ may have 1 to 3 substituents selected from the substituent groups c'-1 and c'-2 defined above).

Preferable examples of "a group represented by the formula —C(=N—$R^{a1}$) $R^{a2}$" (wherein $R^{a1}$ and $R^{a2}$ have the same meanings as defined above, respectively) used in the present specification includes a group represented by the formula —C(=N—OH)$R^{a2}$ (wherein $R^{a2}$ has the same meaning as defined above), and more preferably, a group represented by the formula —C(=N—OH)$CH_3$.

The term "$X^1$" used in the present specification means a group represented by the formula —NH—C(=O)—, a group represented by the formula —C(=O)—NH—, a group represented by the formula —NH—C(=S)—, a group represented by the formula —C(=S)—NH—, a group represented by the formula —NH—C(=$NR^{Y1}$)— or a group represented by the formula —C(=$R^{Y1}$)—NH— (wherein $R^{Y1}$ has the same meaning as defined above). Preferable examples of "$X^1$" include a group represented by —C(=O)—NH— or a group represented by the formula —NH—C(=O)—, more preferably a group represented by —C(=O)—NH—.

The term "E" used in the present specification refers to a furyl group, a thienyl group, a pyrrolyl group, a phenyl group, a pyridyl group, a tetrazolyl group, a thiazolyl group or a pyrazolyl group (with the proviso that each above-mentioned group has 1 or 2 substituents selected from the substituent groups a-1 and a-2 defined above). Preferable examples of "E" include a furyl group, a thienyl group, a pyrrolyl group, a phenyl group or a pyridyl group (with the proviso that each above-mentioned group has 1 or 2 substituents selected from the substituent groups a-1 and a-2 defined above), more preferably, a furyl group, a thienyl group, a pyrrolyl group, a phenyl group or a pyridyl group (with the proviso that each above-mentioned group has 1 or 2 substituents selected from the substituent groups e-1 and e-2 defined above), still more preferably, a furyl group, a thienyl group, a pyrrolyl group, a phenyl group or a pyridyl group (with the proviso that each above-mentioned group has one substituent selected from the substituent groups g-1 and g-2 defined above), particularly preferably, a 2-furyl group, a 2-thienyl group, a 3-pyrrolyl group, a phenyl group, a 2-pyridyl group or a 3-pyridyl group (with the proviso that each above-mentioned group has one substituent selected from the substituent groups g-1 and g-2 defined above).

Examples of compound (I-a) include compounds in which the "$X^1$" defined above, the "$A^1$" defined above and the "E" defined above are combined arbitrarily; it is preferable that the compound (1-a) be the compounds in which $X^1$ represents a group represented by the formula —C(=O)—NH— or a group represented by the formula —NH—C(=O)—, (1) $A^1$ represents a 3-pyridyl group and E represents a furyl group;
(2) $A^1$ represents a 3-pyridyl group and E represents a thienyl group;
(3) $A^1$ represents a 3-pyridyl group and E represents a pyrrolyl group;
(4) $A^1$ represents a 3-pyridyl group and E represents a phenyl group;
(5) $A^1$ represents a 3-pyridyl group and E represents a pyridyl group;
(6) $A^1$ represents a quinolyl group and E represents a furyl group;
(7) $A^1$ represents a quinolyl group and E represents a thienyl group;
(8) $A^1$ represents a quinolyl group and E represents a pyrrolyl group;
(9) $A^1$ represents a quinolyl group and E represents a phenyl group;
(10) $A^1$ represents a quinolyl group and E represents a pyridyl group;
(11) $A^1$ represents a naphthyidinyl group and E represents a furyl group;
(12) $A^1$ represents a naphthyldinyl group and E represents a thienyl group;
(13) $A^1$ represents a naphthyidinyl group and E represents a pyrrolyl group;
(14) $A^1$ represents a naphthyldinyl group and E represents a phenyl group;
(15) $A^1$ represents a naphthyldinyl group and E represents a pyridyl group;
(16) $A^1$ represents a quinoxalinyl group and E represents a furyl group;
(17) $A^1$ represents a quinoxalinyl group and E represents a thienyl group;
(18) $A^1$ represents a quinoxalinyl group and E represents a pyrrolyl group;
(19) $A^1$ represents a quinoxalinyl group and E represents a phenyl group;
(20) $A^1$ represents a quinoxalinyl group and E represents a pyridyl group;
(21) $A^1$ represents an imidazopyridyl group and E represents a furyl group;
(22) $A^1$ represents an imidazopyridyl group and E represents a thienyl group;
(23) $A^1$ represents an imidazopyridyl group and E represents a pyrrolyl group;
(24) $A^1$ represents an imidazopyridyl group and E represents a phenyl group;
(25) $A^1$ represents an imidazopyridyl group and E represents a pyridyl group;
(26) $A^1$ represents a benzothiazolyl group and E represents a furyl group;
(27) $A^1$ represents a benzothiazolyl group and E represents a thienyl group;
(28) $A^1$ represents a benzothiazolyl group and E represents a pyrrolyl group;
(29) $A^1$ represents a benzothiazolyl group and E represents a phenyl group;
(30) $A^1$ represents a benzothiazolyl group and E represents a pyridyl group;
(31) $A^1$ represents a 1H-pyrrolopyridyl group and E represents a furyl group;
(32) $A^1$ represents a 1H-pyrrolopyridyl group and E represents a thienyl group;
(33) $A^1$ represents a 1H-pyrrolopyridyl group and E represents a pyrrolyl group;
(34) $A^1$ represents a 1H-pyrrolopyridyl group and E represents a phenyl group;
(35) $A^1$ represents a 1H-pyrrolopyridyl group and E represents a pyridyl group;
(36) $A^1$ represents a thienopyridyl group and E represents a furyl group;
(37) $A^1$ represents a thienopyridyl group and E represents a thienyl group;
(38) $A^1$ represents a thienopyridyl group and E represents a pyrrolyl group;
(39) $A^1$ represents a thienopyridyl group and E represents a phenyl group;

(40) $A^1$ represents a thienopyridyl group and E represents a pyridyl group;
(41) $A^1$ represents a furopyridyl group and E represents a furyl group;
(42) $A^1$ represents a furopyridyl group and E represents a thienyl group;
(43) $A^1$ represents a furopyridyl group and E represents a pyrrolyl group;
(44) $A^1$ represents a furopyridyl group and E represents a phenyl group or
(45) $A^1$ represents a furopyridyl group and E represents a pyridyl group (with the proviso that $A^1$ may contain 1 to 3 substituents selected from the substituent groups a-1 and a-2 defined above, and E has 1 or 2 substituents selected from the substituent group a-1 and a-2 defined above), more preferably, compounds in which $X^1$ represents a group represented by the formula —C(=O)—NH—,
(1) $A^1$ represents a 3-pyridyl group and E represents a furyl group;
(2) $A^1$ represents a 3-pyridyl group and E represents a thienyl group;
(3) $A^1$ represents a 3-pyridyl group and E represents a pyrrolyl group;
(4) $A^1$ represents a 3-pyridyl group and E represents a phenyl group;
(5) $A^1$ represents a 3-pyridyl group and E represents a pyridyl group;
(6) $A^1$ represents a 6-quinolyl group and E represents a furyl group;
(7) $A^1$ represents a 6-quinolyl group and E represents a thienyl group;
(8) $A^1$ represents a 6-quinolyl group and E represents a pyrrolyl group;
(9) $A^1$ represents a 6-quinolyl group and E represents a phenyl group;
(10) $A^1$ represents a 6-quinolyl group and E represents a pyridyl group;
(11) $A^1$ represents a [1,5]naphthylidin-2-yl group and E represents a furyl group;
(12) $A^1$ represents a [1,5]naphthylidin-2-yl group and E represents a thienyl group;
(13) $A^1$ represents a [1,5]naphthylidin-2-yl group and E represents a pyrrolyl group;
(14) $A^1$ represents a [1,5]naphthylidin-2-yl group and E represents a phenyl group;
(15) $A^1$ represents a [1,5]naphthylidin-2-yl group and E represents a pyridyl group;
(16) $A^1$ represents an imidazo[1,2-a]pyridin-6-yl group and E represents a furyl group;
(17) $A^1$ represents an imidazo[1,2-a]pyridin-6-yl group and E represents a thienyl group;
(18) $A^1$ represents an imidazo[1,2-a]pyridine-6-yl group and E represents a pyrrolyl group;
(19) $A^1$ represents an imidazo[1,2-a]pyridin-6-yl group and E represents a phenyl group;
(20) $A^1$ represents an imidazo[1,2-a]pyridin-6-yl group and E represents a pyridyl group;
(21) $A^1$ represents a benzothiazol-6-yl group and E represents a furyl group;
(22) $A^1$ represents a benzothiazol-6-yl group and E represents a thienyl group;
(23) $A^1$ represents a benzothiazol-6-yl group and E represents a pyrrolyl group;
(24) $A^1$ represents a benzothiazol-6-yl group and E represents a phenyl group or
(25) A' represents a benzothiazol-6-yl group and E represents a pyridyl group (with the proviso that $A^1$ may contain 1 to 3 substituents selected from the substituent groups c-1 and c-2 defined above, and E has 1 or 2 substituents selected from the substituent groups e-1 and e-2 defined above), still more preferably, compounds in which $X^1$ represents a group represented by the formula —C(=O)—NH—,
(1) $A^1$ represents a 3-pyridyl group and E represents a 2-furyl group;
(2) $A^1$ represents a 3-pyridyl group and E represents a 2-thienyl group;
(3) $A^1$ represents a 3-pyridyl group and E represents a 3-pyrrolyl group;
(4) $A^1$ represents a 3-pyridyl group and E represents a phenyl group;
(5) $A^1$ represents a 3-pyridyl group and E represents a 2-pyridyl group;
(6) $A^1$ represents a 3-pyridyl group and E represents a 3-pyridyl group;
(7) $A^1$ represents a 6-quinolyl group and E represents a 2-furyl group;
(8) $A^1$ represents a 6-quinolyl group and E represents a 2-thienyl group;
(9) $A^1$ represents a 6-quinolyl group and E represents a 3-pyrrolyl group;
(10) $A^1$ represents a 6-quinolyl group and E represents a phenyl group;
(11) $A^1$ represents a 6-quinolyl group and E represents a 2-pyridyl group;
(12) $A^1$ represents a 6-quinolyl group and E represents a 3-pyridyl group;
(13) $A^1$ represents a [1,5]naphthylidin-2-yl group and E represents a 2-furyl group;
(14) $A^1$ represents a [1,5]naphthylidin-2-yl group and E represents a 2-thienyl group;
(15) $A^1$ represents a [1,5]naphthylidin-2-yl group and E represents a 3-pyrrolyl group;
(16) $A^1$ represents a [1,5]naphthylidin-2-yl group and E represents a phenyl group;
(17) $A^1$ represents a [1,5]naphthylidin-2-yl group and E represents a 2-pyridyl group;
(18) $A^1$ represents a [1,5]naphthylidin-2-yl group and E represents a 3-pyridyl group;
(19) $A^1$ represents an imidazo[1,2-a]pyridin-6-yl group and E represents a 2-furyl group;
(20) $A^1$ represents an imidazo[1,2-a]pyridin-6-yl group and E represents a 2-thienyl group;
(21) $A^1$ represents an imidazo[1,2-a]pyridin-6-yl group and E represents a 3-pyrrolyl group;
(22) $A^1$ represents an imidazo[1,2-a]pyridin-6-yl group and E represents a phenyl group;
(23) $A^1$ represents an imidazo[1,2-a]pyridin-6-yl group and E represents a 2-pyridyl group;
(24) $A^1$ represents an imidazo[1,2-a]pyridin-6-yl group and E represents a 3-pyridyl group;
(25) $A^1$ represents a benzothiazol-6-yl group and E represents a 2-furyl group;
(26) $A^1$ represents a benzothiazol-6-yl group and E represents a 2-thienyl group;
(27) $A^1$ represents a benzothiazol-6-yl group and E represents a 3-pyrrolyl group;
(28) $A^1$ represents a benzothiazol-6-yl group and E represents a phenyl group;
(29) $A^1$ represents a benzothiazol-6-yl group and E represents a 2-pyridyl group or
(29) $A^1$ represents a benzothiazol-6-yl group and E represents a 3-pyridyl group (with the proviso that $A^1$ may contain 1 to 3 substituents selected from the substituent groups c-1 and c-2 defined above, and E has one substituent selected from the substituent group g-1 and g-2 defined above).

Examples of compound (I-b) include compounds in which the "$X^2$" defined above, the "$A^2$" defined above and "$R^{10}$" defined above are combined arbitrarily, preferably, (1) compounds in which $X^2$ represents a group represented by the formula —O—CH$_2$—, $A^2$ represents a 6-quinolyl group and $R^{10}$ represents a $C_{6-10}$ aryl $C_{1-6}$ alkoxy group;

(2) compounds in which $X^2$ represents a group represented by the formula —S—CH$_2$—, $A^2$ represents a 6-quinolyl group and $R^{10}$ represents a $C_{6-10}$ aryl $C_{1-6}$ alkoxy group;

(3) compounds in which $X^2$ represents a group represented by the formula —C(=O)—CH$_2$—, $A^2$ represents a 6-quinolyl group and $R^{10}$ represents a $C_{6-10}$ aryloxy group;

(4) compounds in which $X^2$ represents a group represented by the formula —C(=O)—CH$_2$—, $A^2$ represents a 6-quinolyl group and $R^{10}$ represents a $C_{6-10}$ aryl $C_{1-6}$ alkoxy group;

(5) compounds in which $X^2$ represents a group represented by the formula —NH—CH$_2$—, $A^2$ represents a 6-quinolyl group and $R^{10}$ represents a $C_{6-10}$ aryl $C_{1-6}$ alkoxy group;

(6) compounds in which $X^2$ represents a group represented by the formula —CH$_2$—NH—, $A^2$ represents a 6-quinolyl group and $R^{10}$ represents a $C_{6-10}$ aryl $C_{1-6}$ alkoxy group;

(7) compounds in which $X^2$ represents a group represented by the formula —NH—CH$_2$—, $A^2$ represents a 4-quinazolinyl group and $R^{10}$ represents a $C_{1-6}$ alkyl group;

(8) compounds in which $X^2$ represents a group represented by the formula —NH—CH$_2$—, $A^2$ represents a 4-quinazolinyl group and $R^{10}$ represents a $C_{6-10}$ aryl $C_{1-6}$ alkoxy group or (9) compounds in which $X^2$ represents a group represented by the formula —NH—CH$_2$—, $A^2$ represents a pyrido[2,3-d]pyrimidin-4-yl group which may have an amino group and $R^{10}$ represents a $C_{6-10}$ aryl $C_{1-6}$ alkoxy group, more preferably, (1) compounds in which $X^2$ represents a group represented by the formula —NH—CH$_2$—, $A^2$ represents a 6-quinolyl group and $R^{10}$ represents a $C_{6-10}$ aryl $C_{1-6}$ alkoxy group;

(2) compounds in which $X^2$ represents a group represented by the formula —CH$_2$—NH—, $A^2$ represents a 6-quinolyl group and $R^{10}$ represents a $C_{6-10}$ aryl $C_{1-6}$ alkoxy group;

(3) compounds in which $X^2$ represents a group represented by the formula —NH—CH$_2$—, $A^2$ represents a 4-quinazolinyl group and $R^{10}$ represents a $C_{1-6}$ alkyl group;

(4) compounds in which $X^2$ represents a group represented by the formula —NH—CH$_2$—, $A^2$ represents a 4-quinazolinyl group and $R^{10}$ represents a $C_{6-10}$ aryl $C_{1-6}$ alkoxy group or (5) compounds in which $X^2$ represents a group represented by the formula —NH—CH$_2$—, $A^2$ represents a pyrido[2,3-d]pyrimidin-4-yl group which may have an amino group and $R^{10}$ represents a $C_{6-10}$ aryl $C_{1-6}$ alkoxy group.

Examples of the term "salt" used in the present specification include a salt with an inorganic acid, a salt with an organic acid, a salt with an inorganic base, a salt with an organic base, a salt with an acidic or basic amino acid or the like. Among these salts, it is preferable that a salt used herein be a pharmaceutically acceptable.

Preferable examples of the salt with the inorganic acid include salts with hydrochloric acid, hydrobromic acid, sulfuric acid, nitric acid, phosphoric acid or the like. Preferable examples of the salt with the organic acid include salts with acetic acid, succinic acid, fumaric acid, maleic acid, tartaric acid, citric acid, lactic acid, stearic acid, benzoic acid, methanesulfonic acid, ethanesulfonic acid, p-toluenesulfonic acid or the like.

Preferable examples of the salt with the inorganic base include alkaline metal salts such as sodium salt and potassium salt, alkaline earth metal salts such as calcium salt and magnesium salt, aluminum salt, ammonium salt or the like. Preferable examples of the salt with the organic base include salts with diethyl amine, diethanolamine, meglumine, N,N-dibenzyl ethylenediamine or the like.

Preferable examples of the salt with the acidic amino acid include salts with aspartic acid, glutamic acid or the like. Preferable examples of the salt with the basic amino acid include salts with arginine, lysine, ornithine or the like.

The term "antifungal agent" used in the present specification refers to a preventive agent or a therapeutic agent for fungal infection.

The compounds according to the present invention, or salts or hydrates thereof, can be formulated into tablets, powders, fine granules, granules, coated tablets, capsulates, syrups, troches, inhalants, suppositories, injections, ointments, eye ointments, tapes, eye drops, nose drops, ear drops, cataplasms, lotions or the like, by the conventional methods. Such formulation can be achieved by using typical diluents, binders, lubricants, colorants, flavorants, and, as necessary, stabilizers, emulsifiers, absorbefacients, surfactants, pH modulators, preservatives, antioxidants or the like, and materials commonly used as ingredients of pharmaceutical preparations according to the conventional methods. For example, an oral preparation can be produced by combining a compound according to the present invention or a pharmaceutically acceptable salt thereof with a diluent, and if required, a binder, a disintegrating agent, a lubricant, a colorant, a flavorant or the like, and formulating the mixture into powders, fine granules, granules, tablets, coated tablets, capsules or the like according to the conventional methods. Examples of the materials include animal and vegetable oils such as soya bean oil, beef tallow, and synthetic glyceride; hydrocarbons such as liquid paraffin, squalane, and solid paraffin; ester oils such as octyldodecyl myristate and iso-propyl myristate; higher alcohols such as cetostearyl alcohol and behenyl alcohol; silicone resins; silicone oils; surfactants such as polyoxyethylene fatty acids ester, sorbitan fatty acid ester, polyoxyethylene sorbitan fatty acid ester, polyoxyethylene hydrogenated castor oil, and polyoxyethylene polyoxypropylene block copolymer; water-soluble polymers such as hydroxyethyl cellulose, polyacrylic acid, carboxyvinyl polymer, polyethylene glycol, polyvinylpyrrolidone, and methytl cellulose; lower alcohols such as ethanol and isopropanol; polyhydric alcohols such as glycerol, propylene glycol, dipropylene glycol, and sorbitol; sugars such as glucose and sucrose; inorganic powder such as anhydrous silicic acid, magnesium aluminum silicate, and aluminum silicate; and pure water. Examples of the diluents include lactose, corn starch, white sugar, glucose, mannitol, sorbitol, crystalline cellulose, silicon dioxide or the like. Examples of the binders include polyvinyl alcohol, polyvinyl ether, methylcellulose, ethylcellulose, gum Arabic, tragacanth, gelatin, shellac, hydroxypropyl methylcellulose, hydroxypropyl cellulose, polyvinylpyrrolidone, polypropylene glycol-polyoxyethylene block co-polymer, and meglumine or the like. Examples of disintegrating agents include starch, agar, gelatin powder, crystalline cellulose, calcium carbonate, sodium hydrogencarbonate, calcium citrate, dextrin, pectin, calcium carboxymethyl cellulose or the like. Examples of lubricants include magnesium stearate, talc, polyethylene glycol, silica, hydrogenated vegetable oil or the like. Examples of colorants include those pharmaceutically acceptable. Examples of flavorants include cocoa powder, peppermint camphor, aromatic powder peppermint oil, Borneo camphor, cinnamon powder or the like. Tablets and granules may be coated with sugar, or if required, other appropriate coatings can be made. Solutions, such as syrups or injectable preparations, to be administered can be formulated by combining a compound according to the present invention or a pharmaceutically acceptable salt thereof with a pH modulator, a solubilizing agent, an isotonizing agent or the like, and if required, with an auxiliary solubilizing agent, a stabilizer or the like, according to the conventional methods. Methods for manufacturing an external preparations are not limited and such preparations can be manufactured by the conventional methods. Specifically, various materials typically used for manufacturing pharmaceuticals, quasi drugs, cosmetics or the like can be used as base materials for the external formulation. More specifically, examples of base materials to be used include animal and vegetable oils, minerals oils, ester oils, wax, higher alcohols, fatty acids, silicone oil, surfactants, phospholipids, alcohols, polyhydric alcohols, water-soluble polymers, clay minerals, pure water or the like. Furthermore, external preparations of the present invention can contain, as required, pH modulators, antioxidants, chelating agents, antibacterial/antifungal agents, colorants, odoriferous substances or the like. But this does not limit the type of base materials that are to be used in the external preparations of the present invention. If required, the preparation may contain differentiation inducers, blood flow improving agents, antimicrobial agents, antiphologistics, cell activators, vitamins, amino acids, humectants, keratolytic agents or the like. The amount of the base materials listed above is adjusted within a concentration range used for producing typical external preparations.

When administering a compound according to the present invention or a salt thereof, or a hydrate thereof, the forms of the compounds are not limited in particular, and the compound can be given orally or parenterally by the conventional method. For instance, the compound can be administered as a dosage form such as tablets, powders, granules, capsules, syrups, troches, inhalants, suppositories, injections, ointments, eye ointments, tapes, eye drops, nasal drops, ear drops, cataplasms and lotions.

Dose of a pharmaceutical of the present invention can be selected appropriately according to symptom severity, age, sex, body weight, forms of administration, type of salts, specific type of disease or the like.

The does varies remarkably depending on the patient's disease, symptom severity, age and sex, drug susceptibility or the like. An oral preparation of the present invention can be generally administered once or several time at a dose of from 1 to 10000 mg/adult/day, preferably from 10 to 2000 mg/adult/day. An injection of the present invention can be generally administered at a dose of from 0.1 to 10000 mg/adult/day, preferably from 1 to 2000 mg/adult/day.

The method for preparing compounds according to the present invention represented by Formula (I) (hereinafter referred to as compound (I)) will be described. The compounds according to the present invention can be prepared by the conventional organic synthesis methods. For instance, among the compounds (I), the compounds represented by the following Formula (1a), Formula (2a), Formula (3a), Formula (3b), Formula (3c), Formula (3d) and Formula (3e) (hereinafter referred to as compound (1a), compound (2a), compound (3a), compound (3b), compound (3c), compound (3d) and compound (3e), respectively) can be prepared by the methods described in the following [Preparation Method 1] to [Preparation Method 3] or the like. In addition, conversion of substituents on A and E of compound (I) according to the present invention can be accomplished by the methods described in the following [Preparation Method 4-1] to [Preparation Method 4-5] or the like.

[General Synthesis Method]
[Preparation Method 1] Representative Preparation Method for Compound (1a)

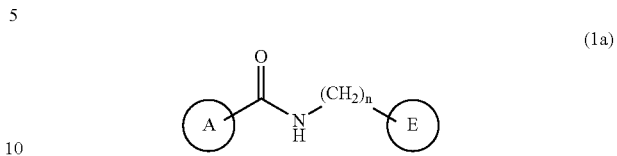

[wherein each symbol has the same meaning as defined above.]
[Preparation Method 1-1] Amidation

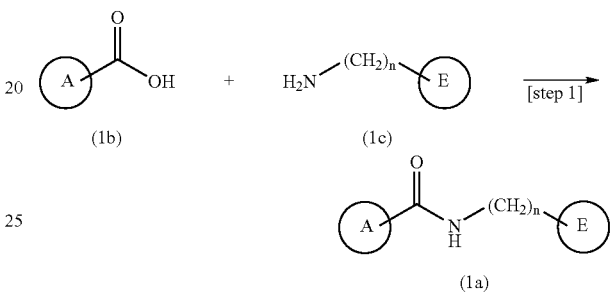

[wherein each symbol has the same meaning as defined above.]

Compound (1b) which is a commercially available product can be used, or compound (1b) can also be prepared from a commercially available product by the well known method. In addition, compound (1b) can also be prepared by the methods described in the preparation examples among the following examples.

Compound (1c) which is a commercially available product can be used, or compound (1c) can also be prepared from a commercially available product by the well known method. In addition, compound (1c) can also be prepared by the method described in the preparation examples among the following examples or [Preparation Method 1-2-1], or the like.

[Step 1]

This step is a step wherein compound (1b) and compound (1c) are condensed in a solvent using a condensing agent to obtain compound (1a). The solvent used is not limited in particular. Examples of the solvent in this step include halogenated hydrocarbons such as dichloromethane and chloroform; sulfoxides such as dimethylsulfoxide; esters such as ethyl acetate; ethers such as tetrahydrofuran and 1,4-dioxane; amides such as N,N-dimethylformamide, and N,N-dimethylacetamide. Examples of the condensing agent include Bop (1H-1,2,3-benzotriazole-1-yloxy(tri(dimethylamino))phosphonium hexafluorophosphate), WSC (1-ethyl-3-(3-dimethylaminopropyl)carbodiimide hydrochloride), DCC (N,N-dicyclohexylcarbodiimide), CDI (carbonyldiimidazole), diethylphosphoryl cyanide or the like. Compound (1c) can be used in amounts of 1 equivalent to 1.5 equivalents based on compound (1b). The condensing agent can be used in amounts of 1 equivalent to 1.5 equivalents based on compound (1b). In addition, it is adequate to add from 1 equivalent to excess amount of an organic base, for instance, triethylamine or the like, as necessary. The reaction temperature is from room temperature to 80° C., and the reaction time is from 10 minutes to 30 hours.

Furthermore, compound (1a) can also be prepared from compound (1b) and compound (1c) by the method described in the other method (1), (2) or (3) below.

Other method (1): Compound (1a) can be obtained by converting compound (1b) into an acid chloride, then, reacting the acid chloride and compound (1c). The step for obtaining the acid chloride is carried out by reacting from 1 equivalent to excess amount of acid chloride synthesis reagent based on compound (1b), without solvent or in the presence of a solvent such as, dichloromethane, benzene, toluene or the like. Catalytic amounts of N,N-dimethylformamide may be added in the reaction system. Examples of the acid chloride synthesis reagent include, for instance, thionyl chloride, oxalyl chloride, phosphorus trichloride, phosphorus pentachloride or the like. The reaction temperature is from room temperature to reflux temperature, and the reaction time is from 10 minutes to 24 hours.

The step for condensing the acid chloride and compound (1c) is carried out by reacting the acid chloride and compound (1c) in a solvent such as, for instance, dichloromethane, tetrahydrofuran, N,N-dimethylformamide or the like, in the presence of 1 equivalent to 3 equivalents of base based on the acid chloride. Examples of the base include, for instance, an organic base such as triethylamine, pyridine and the like or an inorganic base such as potassium carbonate, cesium carbonate or the like. Compound (1c) is used in the amounts of 1 equivalent to 1.5 equivalents based on the acid chloride. The reaction time is from 10 minutes to 24 hours, and the reaction temperature is from 0° C. to reflux temperature.

Other method (2): Compound (1a) can be obtained by converting compound (1b) into mixed acid anhydride, then, reacting the mixed acid anhydride with compound (1c). The step for obtaining the mixed acid anhydride is carried out by reacting compound (1b) and, for instance, chloroformates such as ethyl chloroformate or the like, in the presence of a base such as, for instance, triethylamine or the like. Chloroformates and base are used in the amounts of 1 equivalent to 2 equivalents based on compound (1b). The reaction time is from 10 minutes to 5 hours. The reaction temperature is from 0° C. to room temperature.

The step for condensing the mixed acid anhydride and compound (1c) is carried out by reacting the mixed acid anhydride and compound (1c) in a solvent such as, for instance, dichloromethane, tetrahydrofuran, N,N-dimethylformamide or the like. Compound (1c) is used in the amounts of 1 equivalent to 1.5 equivalents based on the mixed acid anhydride. The reaction time is from 10 minutes to 24 hours, and the reaction temperature is from 0° C. to 50° C.

Other method (3): Compound (1a) can be obtained by converting compound (1b) into an active ester, then, reacting the active ester and compound (1c). The step for obtaining the active ester is carried out by reacting compound (1b) and an active ester synthesis reagent in a solvent such as, for instance, 1,4-dioxane, tetrahydrofuran or the like, in the presence of a condensing agent such as, for instance, DCC or the like. Examples of the active ester synthesis reagent include, for instance, N-hydroxysuccinimide or the like. The active ester synthesis reagent and the condensing agent are used in the amounts of 1 equivalent to 1.5 equivalents based on compound (1b). The reaction temperature is from 0° C. to room temperature. The reaction time is from 2 hours to 24 hours.

The step for condensing the active ester and compound (1c) is carried out by reacting the active ester and compound (1c) in a solvent such as, for instance, dichloromethane, tetrahydrofuran, N,N-dimethylformamide or the like. Compound (1c) is used in the amounts of 1 equivalent to 1.5 equivalents based on the active ester. The reaction temperature is from 0° C. to 50° C., and the reaction time is from 10 minutes to 24 hours.

Note that, after [Step 1], a substituent on A and E of compound (1a) can be converted using a well known method. Furthermore, a substituent on A of compound (1a) can also be converted using a method described in [Preparation Method 4-1] or [Preparation Method 4-4], and a substituent on E of compound (1a) can also be converted using a method described in [Preparation Method 4-2], [Preparation Method 4-3], [Preparation Method 4-5] or the like.

[Preparation Method 1-2-1] Preparation Method for Compound (1c)

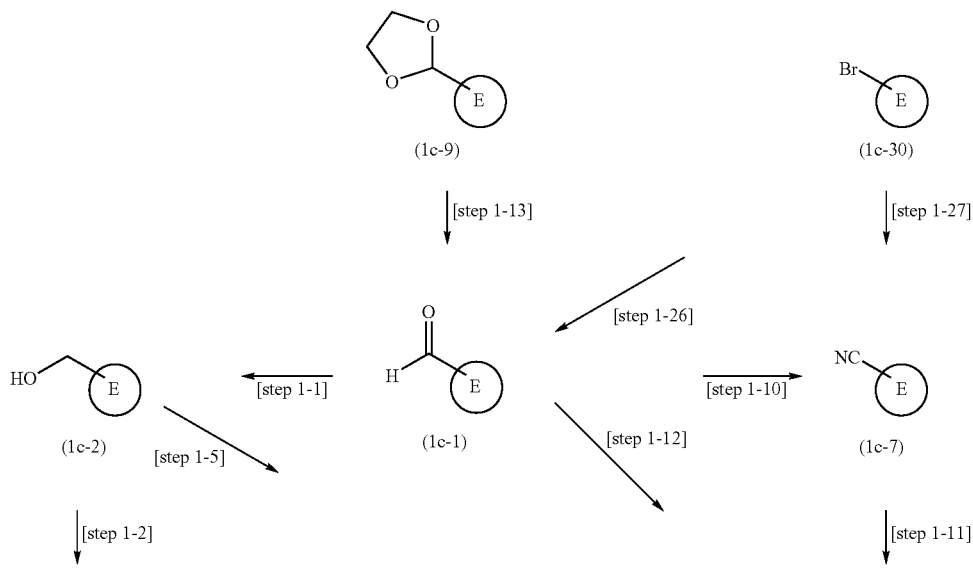

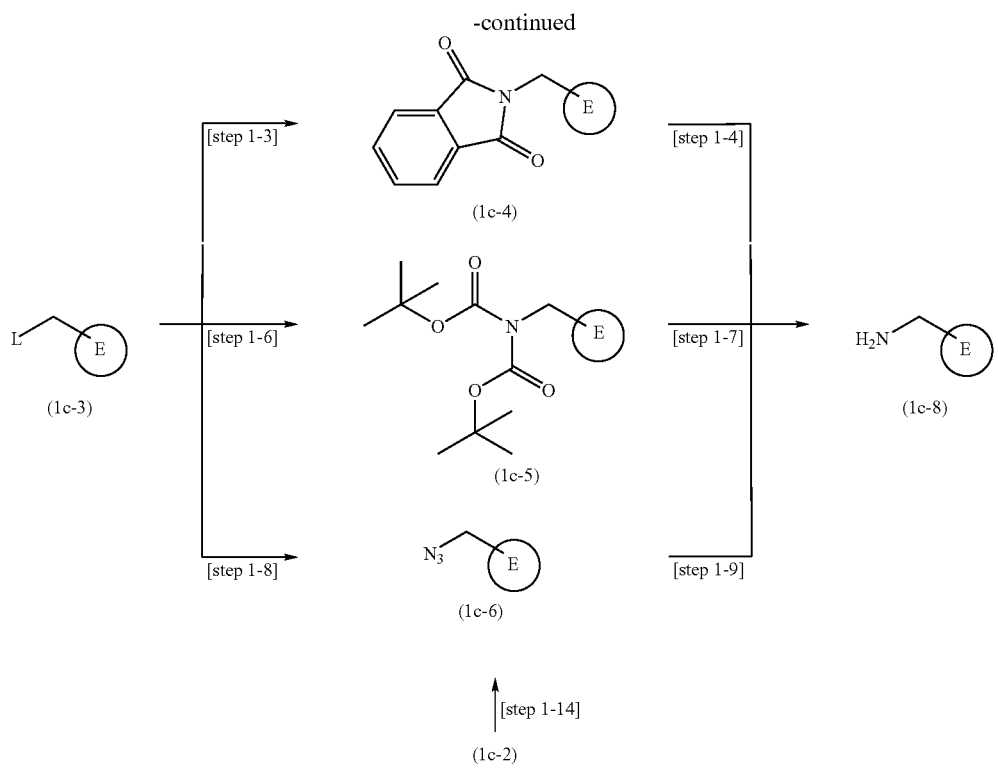

[wherein E has the same meaning as defined above; L represents a leaving group such as a halogen atom, a methanesulfonyloxy group or a p-toluenesulfonyloxy group]

For each compound in the above step figure, a commercially available product can be used as is, or it can also be prepared from a commercially available product by a well known method. In addition, it can be prepared using the method described in the preparation examples among the examples and in [Preparation Method 1-2-2] to [Preparation Method 1-2-6]. Further, each compound in the above step figure can also be prepared by converting a substituent on E using the method described in [Preparation Method 4-2] to [Preparation Method 4-5] or the like.

[Step 1-1]

The present step is a step wherein compound (1c-1) is reduced to obtain compound (1c-2). Examples of the reducing agent include, for instance, sodium borohydride, lithium borohydride, lithium aluminum hydride or the like. Examples of the solvent include alcohols such as, for instance, methanol, ethanol or the like, and ethers such as, for instance, tetrahydrofuran, diethyl ether or the like. The reducing agent is used in the amounts of 1 equivalent to 10 equivalents based on compound (1c-1). The reaction temperature is from 0° C. to reflux temperature, and the reaction time is from 5 minutes to 24 hours.

[Step 1-2]

The present step is a step wherein a hydroxyl group of compound (1c-2) is converted into a leaving group to obtain compound (1c-3).

When L represents a methanesulfonyloxy group or p-toluenesulfonyloxy group, compound (1c-3) can be obtained by reacting compound (1c-2) and methanesulfonyl chloride or p-toluenesulfonyl chloride in a solvent such as, for instance, dichloromethane or the like, in the presence of an organic base such as, for instance, triethylamine or the like. The organic base is used in the amounts of 2 equivalents to 6 equivalents based on compound (1c-2). Methanesulfonyl chloride or p-toluenesulfonyl chloride is used in the amounts of 1 equivalent to 3 equivalents based on compound (1c-2). The reaction temperature is from 0° C. to room temperature, and the reaction time is from 10 minutes to 24 hours.

When L represents a chlorine atom, compound (1c-3) can be obtained by action of a chlorination reagent such as, for instance, thionyl chloride, oxalyl chloride or the like on compound (1c-2). The chlorination reagent is used in the amounts of 1 equivalent to excess amount based on compound (1c-2). The reaction temperature is from 0° C. to room temperature, and the reaction time is from 10 minutes to 24 hours.

[Step 1-3]

The present step is a step wherein compound (1c-3) and phthalimide potassium salt are reacted to obtain compound (1c-4). Compound (1c-4) can be obtained by reacting compound (1c-3) and phthalimide potassium salt in a solvent such as, for instance, N,N-dimethylformamide or the like. Phthalimide is used in the amounts of 1 equivalent to 2 equivalents based on compound (1c-3). The reaction temperature is from room temperature to 160° C. The reaction time is from 10 minutes to 48 hours.

[Step 1-4]

The present step is a step for obtaining compound (1c-8) from compound (1c-4). Compound (1c-8) can be obtained by adding from 1 equivalent to excess amount of hydrazine hydrate based on compound (1c-4) in a solvent such as, for instance, ethanol or the like. The reaction temperature is from 80° C. to reflux temperature, and the reaction time is from 10 minutes to 24 hours.

[Step 1-5]

The present step is a step wherein compound (1c-2) and phthalimide are reacted to obtain compound (1c-4). Compound (1c-4) can be obtained by reacting compound (1c-2), phthalimide, triphenylphosphine and diethyl azodicarboxylate or diisopropyl azodicarboxylate, in a solvent such as, for instance, dichloromethane, tetrahydrofuran or the like. Phthalimide, triphenylphosphine and diethyl azodicarboxylate or diisopropyl azodicarboxylate are used in the amounts of 1 equivalent to 2 equivalents based on compound (1c-2). The reaction temperature is from −20° C. to 80° C., and the reaction time is from 5 minutes to 48 hours.

[Step 1-6]

The present step is a step wherein compound (1c-3) and an amine protected with a tert-butoxycarbonyl group are reacted to obtain compound (1c-5). Compound (1c-5) can be obtained by reacting compound (1c-3) and the amine protected with the tert-butoxycarbonyl group in a solvent such as, for instance, N,N-dimethylformamide or the like, in the presence of a base such as, for instance, sodium hydride or the like. The base is used in the amounts of 1 equivalent to 2 equivalents based on compound (1c-3). The amine protected with the tert-butoxycarbonyl group is used in the amounts of 1 equivalent to 2 equivalents based on compound (1c-3). The reaction temperature is from room temperature to 80° C., and the reaction time is from 1 hour to 24 hours.

[Step 1-7]

The present step is a step wherein the tert-butoxycarbonyl group of compound (1c-5) is deprotected to obtain compound (1c-8). Compound (1c-8) can be obtained by deprotecting the tert-butoxycarbonyl group of compound (1c-5) without a solvent or in a solvent such as, for instance, dichloromethane or the like, in the presence of an acid such as trifluoroacetic acid or the like in the amounts of 2 equivalents to excess amount based on compound (1c-5). The reaction temperature is from 0° C. to 60° C., and the reaction time is from 10 minutes to 24 hours.

[Step 1-8]

The present step is a step wherein the leaving group of compound (1c-3) is converted into an azide group to obtain compound (1c-6). Compound (1c-6) can be obtained by reacting compound (1c-3) and an azidation reagent such as, for instance, sodium azide, potassium azide or the like in a solvent such as, for instance, N,N-dimethylformamide or the like. The azidation reagent is used in the amounts of 1 equivalent to 5 equivalents based on compound (1c-3). The reaction temperature is from room temperature to 80° C., and the reaction time is from 10 minutes to 48 hours.

[Step 1-9]

The present step is a step wherein the azide group of compound (1c-6) is reduced to obtain compound (1c-8). Compound (1c-8) can be obtained by carrying out catalytic hydrogenation using Lindlar catalyst in a solvent such as, for instance, ethanol or the like. Lindlar catalyst is used in catalytic amount to excess amount based on compound (1c-6). The reaction temperature is from room temperature to 80° C., the reaction time is from 30 minutes to 36 hours, and the reaction pressure is from 1 atm to 4 atm.

As other method, compound (1c-8) can be obtained by action of triphenylphosphine in a solvent such as, for instance, dichloromethane, tetrahydrofuran or the like. Triphenylphosphine is used in the amounts of 1.0 equivalent to 2.0 equivalents based on compound (1c-6).

[Step 1-10]

The present step is a step wherein a formyl group of compound (1c-1) is converted into a cyano group to obtain compound (1c-7). Compound (1c-7) can be obtained by reacting 1 equivalent to 3 equivalents of hydroxyamine hydrochloride based on compound (1c-1) in a solvent such as, for instance, ethanol or the like, to obtain an oxime, then, carrying out dehydration reaction by the action of CDI on the oxime. CDI is used in the amounts of 1 equivalent to 5 equivalents based on the oxime. The reaction temperature is from room temperature to reflux temperature, and the reaction time is from 30 minutes to 24 hours.

[Step 1-11]

The present step is a step wherein a cyano group of compound (1c-7) is reduced to obtain compound (1c-8). Compound (1c-8) can be obtained either by carrying out a reduction reaction using a reducing agent such as, for instance, lithium aluminum hydride, diisobutylaluminum hydride or the like, or, by carrying out catalytic hydrogenation under hydrogen atmosphere using a catalyst such as, for instance, Raney nickel, palladium-carbon or the like. The solvent used is not limited, however, when carrying out reduction reaction using the reducing agent, ethers such as, for instance, tetrahydrofuran, diethyl ether or the like, hydrocarbons such as, for instance, toluene or the like, are used. When carrying out catalytic hydrogenation, alcohols such as, for instance, methanol, ethanol, propanol or the like are used. The reducing agent is used in the amounts of 1 equivalent to 10 equivalents based on compound (1c-7). The reaction temperature is from room temperature to 80° C., and the reaction time is from 10 minutes to 24 hours. The reaction pressure when carrying out catalytic hydrogenation is from 1 atm to 4 atm.

[Step 1-12]

The present step is a step for obtaining compound (1c-8) from compound (1c-1). Compound (1c-8) can be obtained by carrying out catalytic hydrogenation using a catalyst such as Raney nickel or the like, in a solvent containing ammonia, under hydrogen atmosphere. Examples of the solvent include, but are not limited to, alcohols such as methanol, ethanol, propanol or the like. The reaction temperature is from room temperature to 80° C., the reaction time is from 1 hour to 36 hour, and the reaction pressure is from 1 atm to 4 atm.

[Step 1-13]

The present step is a step wherein an acetal group on compound (1c-9) is deprotected to obtain compound (1c-1). Compound (1c-1) can be obtained by dissolving compound (1c-9) in an organic solvent, and by action of an aqueous solution of acid such as, for instance, hydrochloric acid, sulfuric acid, citric acid or the like. Examples of the solvent include, but are not limited to, for instance, methanol, ethanol, acetonitrile, tetrahydrofuran or the like. The reaction temperature is from room temperature to 60° C., and the reaction time is from 5 minutes to 24 hours.

[Step 1-14]

The present step is a step wherein an hydroxyl group of compound (1c-2) is converted into an azide group to obtain compound (1c-6). Compound (1c-6) can be obtained by reacting compound (1c-2) and diphenylphosphoryl azide in a solvent such as, for instance, benzene, toluene or the like, in the presence of an organic base such as, for instance, 1,8-diazabicyclo[5,4,0]undec-7-ene. The organic base is used in the amounts of 1 equivalent to 1.5 equivalents based on compound (1c-2). Diphenylphosphoryl azide is used in the amounts of 1 equivalent to 1.5 equivalents based on compound (1c-2). The reaction temperature is from room temperature to 80° C., and the reaction time is from 10 minutes to 48 hours.

[Step 1-26]

The present step is a step wherein compound (1c-30) is formylated to obtain compound (1c-1). Compound (1c-1) can be obtained by action of 1 equivalent to 1.5 equivalents of a strong base based on compound (1c-30) for anionization, then, reacting a formylation agent. Examples of the solvent include, for instance, tetrahydrofuran, diethyl ether or the like. Examples of the strong base include, for instance, n-butyl lithium or the like. Examples of the formylation agent include, for instance, N,N-dimethylformamide, N-formyl-morpholine or the like. The formylation agent is used in the amounts of 1 equivalent to 2 equivalents based on compound (1c-30). The reaction temperature is from −80° C. to room temperature, and the reaction time is from 5 minutes to 12 hours.

[Step 1-27]

The present step is a step wherein compound (1c-30) is cyanated to obtain compound (1c-7). Compound (1c-7) can be obtained by reacting compound (1c-30) and zinc cyanide in a solvent such as, for instance, N,N-dimethylformamide, N-methylpyrrolidinone or the like, under nitrogen atmosphere, in the presence of a catalyst. Examples of the catalyst include, for instance, tetrakis(triphenylphosphine)palladium (0) or the like. Zinc cyanide is used in the amounts of 1 equivalent to 2 equivalents based on compound (1c-30). The catalyst is used in the amounts of 0.01 equivalents to 0.1 equivalents based on compound (1c-30). The reaction temperature is from 50° C. to reflux temperature, and the reaction time is from 5 minutes to 24 hours.

Other method: Compound (1c-7) can be obtained by reacting compound (1c-30) and copper cyanide in a solvent such as, for instance, N,N-dimethylformamide and N-methylpyrrolidinone, under nitrogen atmosphere. Copper cyanide is used in the amounts of 1 equivalent to excess amount based on compound (1c-30). The reaction temperature is from 50° C. to reflux temperature, and the reaction time is from 10 minutes to 72 hours.

[Preparation Method 1-2-2] Preparation Method for Compound (1c-11), which is Compound (1c-1)

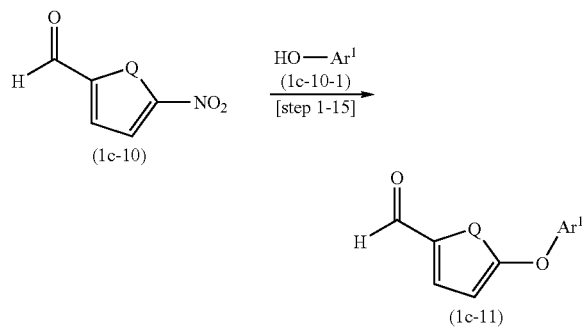

[wherein Q represents an oxygen atom or a sulfur atom; $Ar^1$ represents a $C_{6-10}$ aryl group that may have 1 or 2 substituents selected from the following substituent group i or an aromatic 5-10 membered heterocyclic group that may have 1 to 3 substituents selected from the following substituent group i.

Substituent group i: a halogen atom, a cyano group, an amino group, a carbamoyl group, a $C_{1-6}$ alkyl group, a $C_{3-8}$ cycloalkyl group, a $C_{1-6}$ alkoxy group, a $C_{1-6}$ alkylcarbonyl group, a $C_{1-6}$ alkoxy-carbonyl group, a $C_{1-6}$ alkylsulfonyl group, a mono-$C_{6-10}$ arylamino group, a trifluoromethyl group and a trifluoromethoxy group]

Compound (1c-10) which is a commercially available product can be used as is. Compound (1c-10-1) which is a commercially available product can be used as is, or it can also be prepared from a commercially available product by a well known method.

[Step 1-15]

The present step is a step wherein compound (1c-10) and compound (1c-10-1) are reacted to obtain compound (1c-11). Compound (1c-11) can be obtained by reacting compound (1c-10) and compound (1c-10-1) in a solvent such as, for instance, N,N-dimethylformamide, dimethylsulfoxide or the like, in the presence of a base such as, for instance, sodium hydride, potassium carbonate, cesium carbonate or the like. Compound (1c-10-1) is used in the amounts of 1 equivalent to 2 equivalents based on compound (1c-10). The base is used in the amounts of 1 equivalent to 2 equivalents based on compound (1c-10). The reaction temperature is from 0° C. to 80° C., and the reaction time is from 5 minutes to 1 hour.

[Preparation Method 1-2-3] Preparation Method for Compound (1c-13), which is Compound (1c-1)

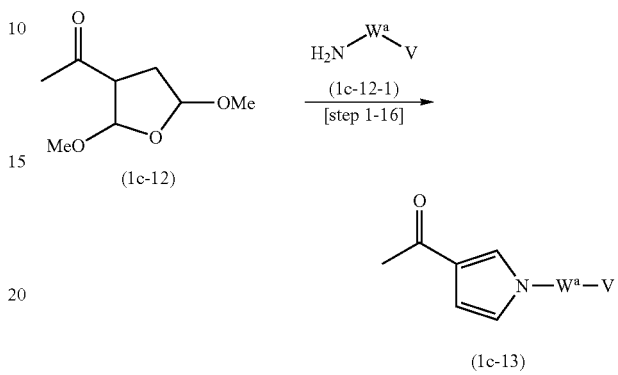

[wherein V represents a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a 5- to 10-membered heterocyclic group, a $C_{3-8}$ cycloalkyl $C_{1-6}$ alkyl group, a $C_{6-10}$ aryl $C_{1-6}$ alkyl group or a 5- to 10-membered heterocycle $C_{1-6}$ alkyl group; $W^a$ represents a single bond or an oxygen atom]

Compound (1c-12) which is a commercially available product can be used as is. Compound (1c-12-1) which is a commercially available product can be used as is, or it can also be prepared from a commercially available product by a well known method.

[Step 1-16]

The present step is a step wherein compound (1c-12) and compound (1c-12-1) are reacted to obtain compound (1c-13). Examples of the solvent include, for instance, acetic acid or the like. Compound (1c-12-1) is used in the amount of 1 equivalent based on compound (1c-12). The reaction temperature is from 50° C. to 110° C., and the reaction time is from 5 minutes to 1 hour.

[Preparation Method 1-2-4] Preparation Method for Compound (1c-15), which is Compound (1c-7)

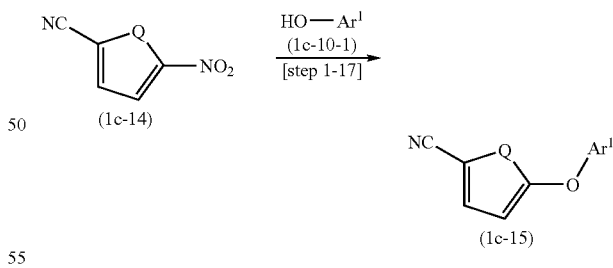

[wherein Q and $Ar^1$ have the same meanings as defined above.]

Compound (1c-14) which is a commercially available product can be used as is. Compound (1c-10-1) which is a commercially available product can be used as is, or it can also be prepared from a commercially available product by a well known method.

[Step 1-17]

The present step is a step wherein compound (1c-14) and compound (1c-10-1) are reacted to obtain compound (1c-15). Compound (1c-15) can be obtained by reacting compound (1c-14) and compound (1c-10-1) in a solvent such as, for instance, N,N-dimethylformamide, dimethylsulfoxide or the like, in the presence of a base such as, for instance, sodium hydride, potassium carbonate, cesium carbonate or the like. Compound (1c-10-1) is used in the amounts of 1 equivalent to 2 equivalents based on compound (1c-14). The base is used in the amounts of 2 equivalent to 3 equivalents based on compound (1c-14). The reaction temperature is from room temperature to 80° C., and the reaction time is from 1 hour to 72 hours.

[Preparation Method 1-2-5] Preparation Method for Compound (1c-17), Compound (1c-19), Compound (1c-21), Compound (1c-23) and Compound (1c-25), which are Compound (1c-7)

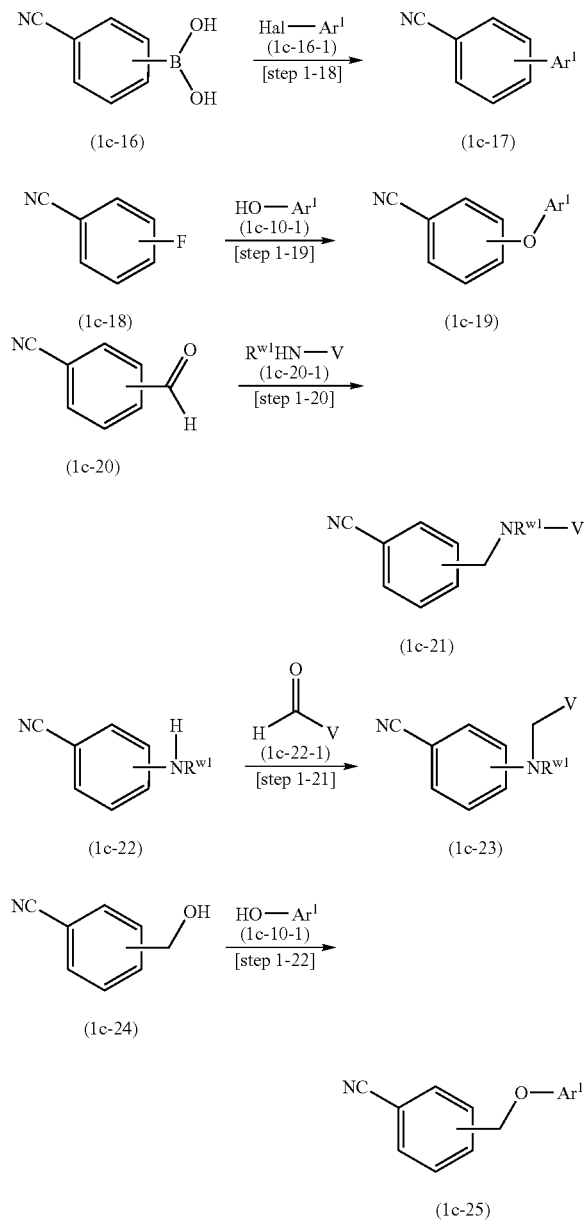

[wherein V and Ar¹ have the same meanings as defined above; $R^{w1}$ represents a hydrogen atom or a $C_{1-6}$ alkyl group; Hal represents a chlorine atom, a bromine atom or an iodine atom.]

Compound (1c-16), compound (1c-18), compound (1c-20), compound (1c-22), compound (1c-24), compound (1c-16-1), compound (1c-10-1), compound (1c-20-1) and compound (1c-22-1) which are commercially available products can be used as is, or they can also be prepared from commercially available products by a 10 well known method.

[Step 1-18]

The present step is a step wherein compound (1c-16) and compound (1c-16-1) are subjected to a coupling reaction to obtain compound (1c-17). Compound (1c-17) can be obtained by reacting compound (1c-16) and compound (1c-16-1) in a solvent such as, for instance, tetrahydrofuran, 1,4-dioxane, methanol, ethanol, toluene, N,N-dimethylformamide or the like, in the presence of a base such as, for instance, potassium carbonate, cesium carbonate, potassium phosphate or the like, and a catalyst such as, for instance, palladium(II)acetate, tetrakis(triphenylphosphine)palladium(0), dichlorobis(triphenylphosphine)palladium(II), tris(dibenzylideneacetone)dipalladium(0), dichloro(1,1'-bis(diphenylphosphino)ferrocene)nickel(II) or the like. The base is used in the amounts of 1.5 equivalents to excess amount based on compound (1c-16). The catalyst is used in the amounts of 0.05 equivalents to 0.3 equivalents based on compound (1c-16).

[Step 1-19]

The present step is a step wherein compound (1c-18) and compound (1c-10-1) are reacted to obtain compound (1c-19). Compound (1c-19) can be obtained by reacting compound (1c-18) and compound (1c-10-1) in a solvent such as dimethylsulfoxide or the like, in the presence of a base such as potassium tert-butoxide or the like. The base is used in the amounts of 1 equivalent to excess amount based on compound (1c-18). The reaction temperature is from 80° C. to 220° C., and the reaction time is from 30 minutes to 48 hours.

[Step 1-20]

The present step is a step wherein compound (1c-20) and compound (1c-20-1) are reacted to carry out reductive amination and to obtain compound (1c-21). Compound (1c-21) can be obtained by reacting compound (1c-20) and compound (1c-20-1) in a solvent such as, for instance, tetrahydrofuran, methanol, ethanol or the like, in the presence of a reducing agent such as, for instance, lithium aluminum hydride, sodium borohydride, sodium cyanoborohydride, triacetoxy sodium borohydride or the like, and acetic acid. The reducing agent is used in the amounts of 1 equivalent to 2 equivalents based on compound (1c-20). The reaction temperature is from room temperature to 60° C., and the reaction time is from 10 minutes to 24 hours.

[Step 1-21]

The present step is a step wherein compound (1c-22) and compound (1c-22-1) are reacted to carry out reductive amination and to obtain compound (1c-23). Compound (1c-23) can be prepared by a method similar to Step 1-20].

[Step 1-22]

The present step is a step wherein compound (1c-24) and compound (1c-10-1) are reacted to obtain compound (1c-25). Compound (1c-25) can be obtained by reacting compound (1c-24) and compound (1c-10-1) in a solvent such as, for instance, dimethylsulfoxide or the like, and in the presence of a base such as, for instance, potassium carbonate, cesium carbonate or the like. The base is used in the amounts of 1 equivalent to 3 equivalents based on compound (1c-24). The reaction temperature is from room temperature to 80° C., and the reaction time is from 10 minutes to 24 hours.

[Preparation Method 1-2-6] Preparation Method for Compound (1c-27), which is Compound (1c-9), and Compound (1c-29), which is Compound (1c-1)

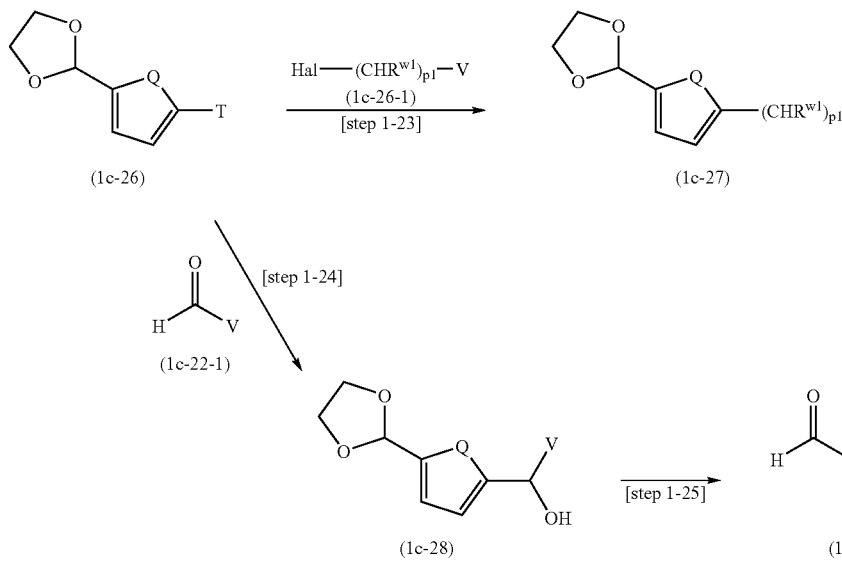

(wherein $R^{w1}$, V, Q and Hal have the same meanings as defined above; p1 is an integer of 1 or 2; T represents a hydrogen atom when Q represents an oxygen atom, and a bromine atom when Q represents a sulfur atom.)

Compound (1c-26) which is a commercially available product can be used as is. Compound (1c-26-1) and compound (1c-22-1) which are commercially available products can be used as is, or they can also be prepared from commercially available products by a well known method.

[Step 1-23]

The present step is a step wherein compound (1c-26) and compound (1c-26-1) are reacted to obtain compound (1c-27). Compound (1c-27) can be obtained by action of 1 equivalent of a strong base based on compound (1c-26) for anionization, then, reacting with compound (1c-26-1). Examples of the solvent include, for instance, tetrahydrofuran, diethyl ether or the like. Examples of the strong base include, for instance, n-butyl lithium or the like. The reaction temperature is from −80° C. to room temperature.

[Step 1-24]

The present step is a step wherein compound (1c-26) and compound (1c-22-1) are reacted to obtain compound (1c-28). Compound (1c-28) can be obtained by action of 1 equivalent of a strong base based on compound (1c-26) for anionization, then, reacting with compound (1c-22-1). Examples of the solvent include, for instance, tetrahydrofuran, diethyl ether or the like. Examples of the strong base include, for instance, n-butyl lithium or the like. In addition, 0.1 equivalent to 1 equivalent of copper(I) iodide or copper(I) bromide based on compound (1c-26) may be added in the reaction system. The reaction temperature is from −80° C. to room temperature.

[Step 1-25]

The present step is a step wherein elimination of a hydroxyl group and deprotection of an acetal group of compound (1c-28) are carried out simultaneously to obtain compound (1c-29). When compound (1c-28) is treated with trimethylsilyliodide, elimination of the hydroxyl group and deprotection of the acetal group occur simultaneously, to give compound (1c-29). Trimethylsilyliodide is used in the amounts of 2 equivalents to 6 equivalents based on compound (1c-28). In additiori, trimethylsilyliodide may be prepared from trimethylsilyl chloride and sodium iodide in the reaction solution and used as is. Examples of the solvent include, for instance, acetonitrile or the like. The reaction temperature is from 0° C. to 60° C., and the reaction time is from 5 minutes to 6 hours.

Other method: Compound (1c-29) can be obtained by converting the hydroxyl group of compound (1c-28) into the acetyl group, then, eliminating the acetyl group, and carrying out deprotection of an acetal group. Conversion of the hydroxyl group into the acetyl group can be carried out by using an acetylating reagent such as, for instance, acetic anhydride, acetyl chloride or the like. A base such as, for instance, N,N-dimethylaminopyridine, triethylamine, pyridine or the like, in the amounts of 1 equivalent to excess amount based on compound (1c-28) may be added in the reaction system. Examples of the solvent include, for instance, dichloromethane, ethyl acetate, N,N-dimethylformamide or the like. In addition, pyridine, which is added as a base, may be used directly as a solvent. An acetylating reagent is used in the amounts of 1 equivalent to excess amount based on compound (1c-28). The reaction temperature is from 0° C. to 60° C., and the reaction time is from 1 hour to 36 hours. Elimination of the acetyl group can be carried out, for instance, under hydrogen atmosphere, in a solvent such as, for instance, ethanol, methanol or the like, and using a catalyst such as for instance, palladium-carbon, Raney nickel or the like. The reaction temperature is from room temperature to 80° C., and the reaction time is from 5 hours to 36 hours. Deprotection of the acetal group can be carried out by an analogous method to [Step 1-13].

[Preparation Method 2] Representative Preparation Method for Compound (2a)

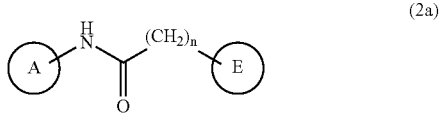

(2a)

[wherein each symbol has the same meaning as defined above.]
[Preparation Method 2-1] Amidation

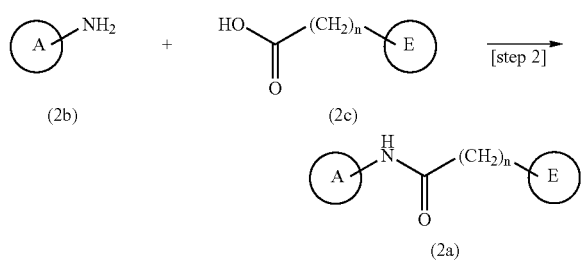

[where each symbol has the same meaning as defined above.]

Compound (2b) which is a commercially available product can be used as is, or it can also be prepared from a commercially available product by a well known method. In addition, it can also be prepared using a method described in the preparation examples among the examples.

Compound (2c) which is a commercially available product can be used as is, or it can also be prepared from a commercially available product by a well known method. In addition, it can also be prepared by a method described in the preparation examples among the examples or [Preparation Method 2-2-1] or the like.

[Step 2]

Compound (2a) is obtained by condensing compound (2b) and compound (2c) in a solvent using a condensing agent. Compound (2a) can be prepared by an analogous method to [Step 1].

[Preparation Method 2-2-1] Preparation Method for Compound (2c-2), which is Compound (2c), and Compound (2c-5), which is Compound (2c)

2 equivalents of sodium chlorite and 1 equivalent to 2 equivalents of sodium dihydrogenphosphate based on compound (2c-1). The reaction temperature is the room temperature, and the reaction time is from 10 minutes to 2 hours.

In addition, compound (2c-2) can also be prepared compound (2c-1) by a method described in the following other method (1), (2) or (3).

Other method (1): Compound (2c-2) can be obtained by dissolving compound (2c-1) in a mixed solvent of tert-butanol and water (preferable mixing ratio being tert-butanol:water=10:1 to 2:1), and reacting with 1 equivalent to 2 equivalents of potassium permanganate and 1 equivalent to 2 equivalents of potassium dihydrogenphosphate based on compound (2c-1). The reaction temperature is room temperature, and the reaction time is from 10 minutes to 2 hours.

Other method (2): Compound (2c-2) can be obtained by dissolving compound (2c-1) in a sodium hydroxide aqueous solution and ethanol, and reacting with 1.5 equivalents to 2 equivalents of silver nitrate based on compound (2c-1). The reaction temperature is from 0C to room temperature, and the reaction time is from 5 minutes to 24 hours.

Other method (3): Compound (2c-2) can also be obtained by dissolving compound (2c-1) in methanol and N,N-dimethylformamide, and reacting with 1.0 equivalent to 1.5 equivalents of pyridinium dichromate (PDC) based on compound (2c-1). The reaction temperature is from −10° C. to 40° C., and the reaction time is from 10 minutes to 24 hours.

[Step 2-2]

The present step is a step wherein compound (2c-1) is extended by one carbon to obtain compound (2c-3). Compound (2c-3) can be obtained in a solvent such as, for instance, tetrahydrofuran, 1,4-dioxane or the like, at 10° C. to room temperature, by reacting 2 equivalents to 10 equivalents of methoxymethyl triphenylphosphonium chloride and 2 equivalents to 10 equivalents of base (for instance, potassium

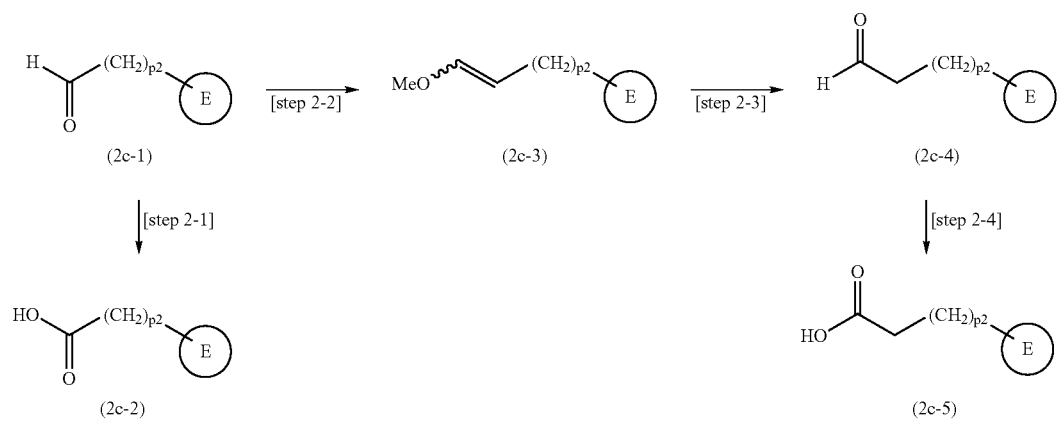

[wherein E has the same meaning as defined above; p2 represents an integer from 0 to 2.]

Compound (2c-1) which is a commercially available product can be used as is, or it can also be prepared from a commercially available product by a well known method.

[Step 2-1]

The present step is a step wherein compound (2c-1) is oxidized to obtain compound (2c-2). Compound (2c-2) can be obtained by dissolving compound (2c-1) in a mixed solvent of tert-butanol and water (preferable mixing ratio being tert-butanol:water=10:1 to 2:1), and reacting with 3 equivalents to 10 equivalents of 2-methyl-2-butene, 1 equivalent to tert-butoxide) based on compound (2c-1) for 30 minutes to 2 hours, then adding compound (2c-1) to this reaction solution, and reacting at room temperature to reflux temperature for 30 minutes to 4 hours.

[Step 2-3]

The present step is a step wherein compound (2c-3) is hydrolyzed to obtain compound (2c-4). Compound (2c-4) can be obtained by dissolving compound (2c-3) in a solvent such as, for instance, hydrous methanol, hydrous 1,4-dioxane or the like, adding an acid such as, for instance, hydrochloric acid, p-toluenesulfonic acid or the like, and reacting at 80° C. to reflux temperature for 10 minutes to 16 hours.

[Step 2-4]

The present step is a step wherein compound (2c-4) is oxidized to obtain compound (2c-5). Compound (2c-5) can be prepared by an analogous method to [Step 2-1].

[Preparation Method 2-2-2] Preparation Method for Compound (2c-7), which is Compound (2c)

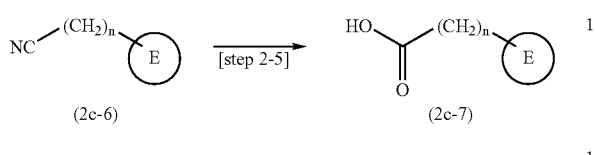

[wherein E and n have the same meanings as defined above.]

Compound (2c-6) which is a commercially available product can be used as is, or it can also be prepared from a commercially available product by a well known method.

[Step 2-5]

The present step is a step wherein compound (2c-6) is hydrolyzed to obtain compound (2c-7). Compound (2c-7) can be obtained in an aqueous solution of acid such as, for instance, hydrochloric acid and sulfuric acid or the like, or, in an aqueous solution of alkali such as, for instance, sodium hydroxide, potassium hydroxide or the like, by hydrolyzing compound (2c-6). The reaction temperature is from room temperature to reflux temperature, and the reaction time is from 10 minutes to 10 hours.

[Preparation Method 3] Representative Preparation Method for Compound (3a), Compound (3b), Compound (3c), Compound (3d) and Compound (3e)

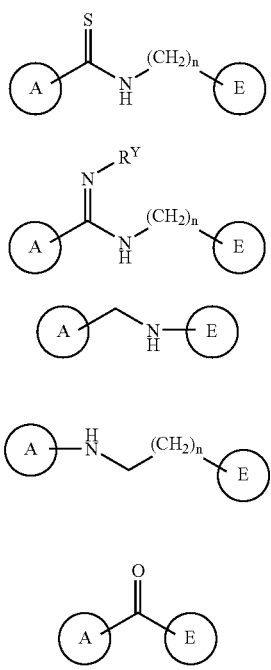

[wherein each symbol has the same meaning as defined above.]

[Preparation Method 3-1] Representative Preparation Method for Compound (3a) and Compound (3b)

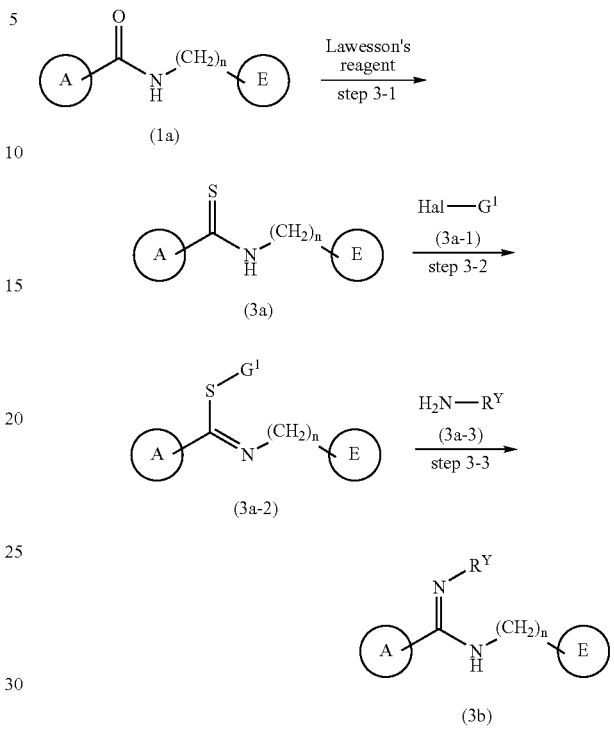

[wherein A, $R^Y$, n, E and Hal have the same meanings as defined above; $G^1$ represent a $C_{1-6}$ alkyl group that may be substituted with a $C_{6-10}$ aryl group.]

[Step 3-1]

The present process is a process wherein compound (1a) is converted into thioamide to obtain compound (3a). Compound (3a) can be obtained by reacting compound (1a) and 2,4-bis(4-methoxyphenyl)-1,3-dithia-2,4-diphosphetane-2,4-disulfide (Lawesson's reagent). Examples of the solvent include, for instance, tetrahydrofuran, toluene or the like. Lawesson's reagent is used in the amounts of 1 equivalent to 5 equivalents based on compound (1a). The reaction temperature is from room temperature to reflux temperature, and the reaction time is from 10 minutes to 48 hours.

[Step 3-2]

The present step is a step wherein compound (3a) is converted into thioimidate to obtain compound (3a-2). Compound (3a-2) can be obtained by reacting compound (3a) and compound (3a-1). Examples of the solvent include, for instance, acetonitrile, tetrahydrofuran, toluene or the like. For compound (3a-1), preferably, alkylating agents such as, for instance, iodomethane, benzyl bromide, (bromomethyl)naphthalene or the like can be used. Compound (3a-1) is used in the amounts of 1 equivalent to 10 equivalents based on compound (3a). The reaction temperature is from room temperature to reflux temperature, and the reaction time is from 10 minutes to 48 hours.

[Step 3-3]

The present step is a step wherein compound (3a-2) is converted into amidine to obtain compound (3b). Compound (3b) can be obtained by reacting compound (3a-2) and compound (3a-3). Examples of the solvent include, for instance, methanol, ethanol, N,N-dimethylformamide, N-methylpyrrolidinone or the like. Examples of compound (3a-3) include, preferably, alkoxy amines such as, for instance, methoxylamine, benzyloxy amine, cyanamide or the like. Compound (3a-3) is used in the amounts of 1 equivalent to 10 equivalents based on compound (3a-2). The reaction temperature is from room temperature to reflux temperature, and the reaction time is from 10 minutes to 48 hours.

[Preparation Method 3-2] Representative Preparation Method for Compound (3c)

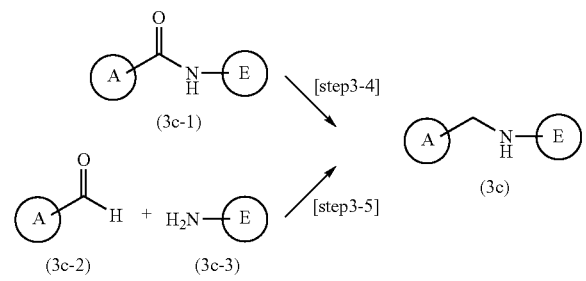

[wherein each symbol has the same meaning as defined above.]

Compound (3c-1) can be prepared using the method described in [Preparation Method 1-1]. Compound (3c-2) and compound (3c-3) which are commercially available products can be used as is, or they can also be prepared from commercially available products by a well known method.

[Step 3-4]

The present step is a step wherein compound (3c-1) is reduced to obtain compound (3c). Compound (3c) can be obtained by reacting compound (3c-1) in a solvent such as, for instance, tetrahydrofuran or the like, in the presence of a reducing agent such as, for instance, lithium aluminum hydride or the like. The reducing agent is used in the amounts of 1 equivalent to 5 equivalents based on compound (3c-1). The reaction temperature is from room temperature to reflux temperature, and the reaction time is from 1 hour to 24 hours.

[step 3-5]

The present step is a step wherein compound (3c-2) and compound (3c-3) are reacted to carry out reductive amination and obtain compound (3c). Compound (3c) can be prepared by an analogous method to [Step 1-20].

[Preparation Method 3-3] Representative Preparation Method for Compound (3d)

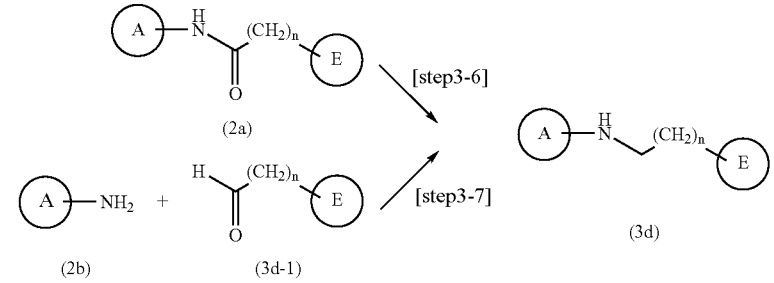

[wherein each symbol has the same meaning as defined above.]

Compound (3d-1) which is a commercially available product can be used as is, or it can also be prepared from a commercially available product by a well known method.

[Step 3-6]

The present step is a step wherein compound (2a) is reduced to obtain compound (3d). Compound (3d) can be prepared by an analogous method to [Step 34].

[Step 3-7]

The present step is a step wherein compound (2b) and compound (3d-1) are reacted to carry out reductive amination and obtain compound (3d). Compound (3d) can be prepared by an analogous method to [Step 1-20].

[Preparation Method 3-3-1] Preparation Method for Compound (3d-3), which is compound (3d)

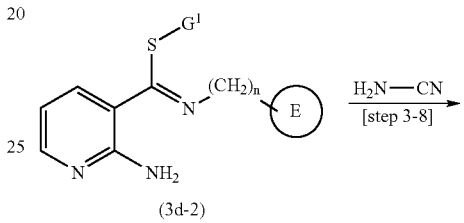

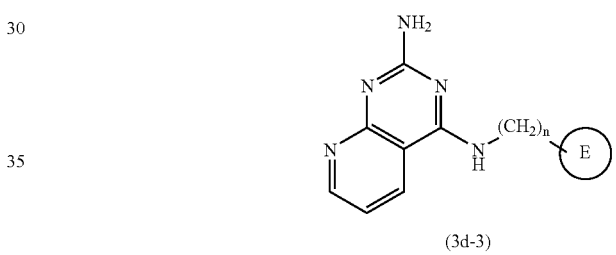

[wherein each symbol has the same meaning as defined above.]

[Step 3-8]

The present step is a step wherein compound (3d-2) and cyanamide are reacted to obtain compound (3d-3). Examples of the solvent include, for instance, N,N-dimethylformamide, N-methylpyrrolidinone or the like. Cyanamide is used in the amounts of 2 equivalent to 5 equivalents based on compound (3d-2). The reaction temperature is from room temperature to reflux temperature, and the reaction time is from 10 minutes to 48 hours.

[Preparation Method 3-4] Representative Preparation Method for Compound (3e)

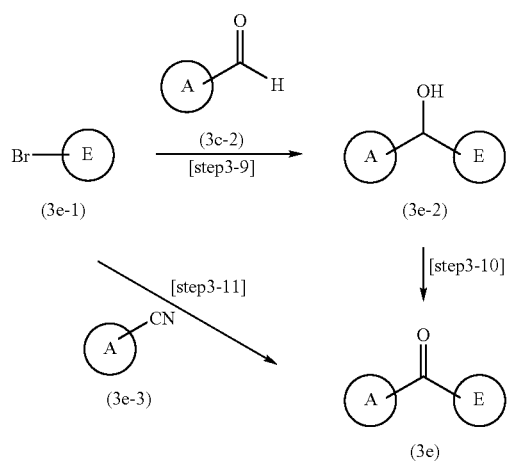

[wherein each symbol has the same meaning as defined above.]

Compound (3e-1), compound (3c-2) and compound (3e-3) which are commercially available products can be used as is, or they can also be prepared from commercially available products by a well known method.

[Step 3-9]

The present step is a step wherein compound (3e-1) is converted into Grignard reagent, then, the Grignard reagent and compound (3c-2) are reacted to obtain compound (3e-2). Compound (3e-2) can be obtained by preparing the Grignard reagent of compound (3e-1) in a solvent such as, for instance, tetrahydrofuran or the like, in the presence of metallic magnesium and an initiator such as, for instance, dibromoethane or the like, and reacting the Grignard reagent and compound (3c-2). Metallic magnesium is used in the amounts of 1 equivalent to 1.2 equivalents based on compound (3e-1). The initiator is used in catalytic amounts based on compound (3e-1). The reaction temperature is from 0C to reflux temperature, and the reaction time is from 10 minutes to 24 hours.

[Step 3-10]

The present step is a step wherein a hydroxyl group of compound (3e-2) is oxidized to obtain compound (3e). Compound (3e) can be obtained by reacting compound (3e-2) in a solvent such as, for instance, chloroform, acetone or the like, in the presence of an oxidizing agent such as, for instance, manganese dioxide or the like. The oxidizing agent is used in the amounts of 2 equivalents to 10 equivalents based on compound (3e-2). The reaction temperature is from room temperature to reflux temperature, and the reaction time is from 10 minutes to 24 hours.

[Step 3-11]

The present step is a step wherein compound (3e-1) is converted into Grignard reagent, then, the Grignard reagent and compound (3e-3) are reacted, and hydrolysis is carried out to obtain compound (3e). Compound (3e) can be obtained by preparing the Grignard reagent of compound (3e-1) in a solvent such as, for instance, tetrahydrofuran or the like, in the presence of metallic magnesium and an initiator such as, for instance, dibromoethane or the like, reacting the Grignard reagent and compound (3c-2), and hydrolyzing in the presence of acid. Metallic magnesium is used in the amounts of 1 equivalent to 1.2 equivalents based on compound (3e-1). The initiator is used in catalytic amounts based on compound (3e-1). The reaction temperature is from 0° C. to reflux temperature, and the reaction time is from 10 minutes to 24 hours.

[Preparation Method 4-1] Conversion of Substituent on A in Compound (I) (with the Proviso that A Represents an Aromatic 5- and 10-Membered Heterocyclic Group Containing at Least 1 Nitrogen Atom)—1

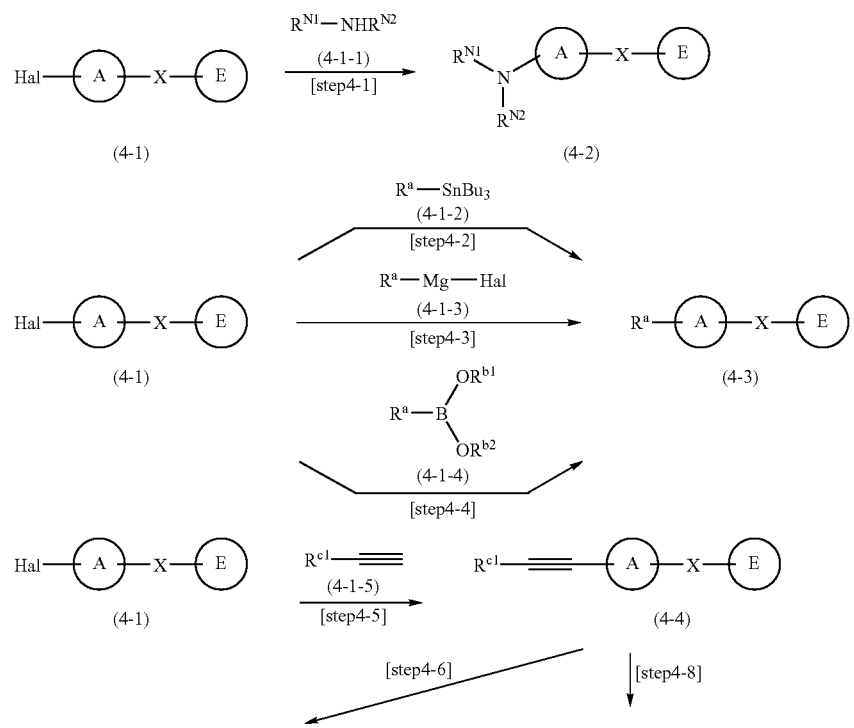

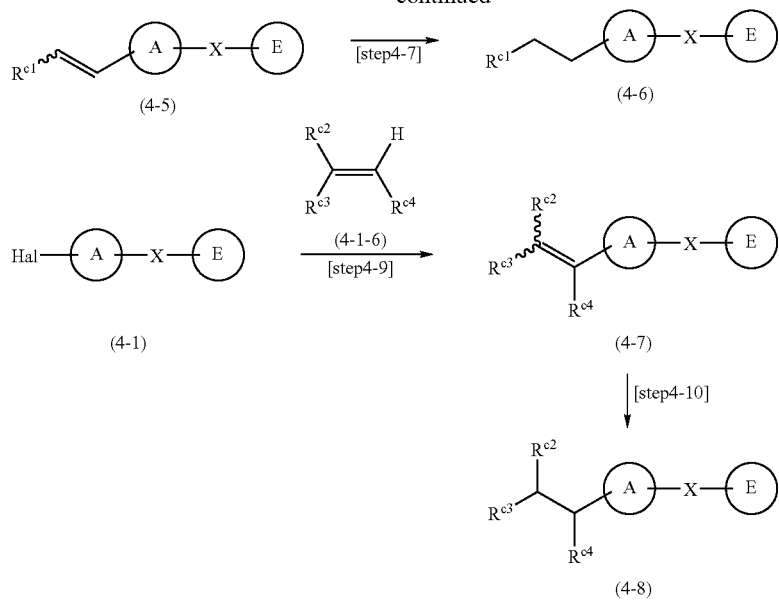

[wherein A, X (with the proviso that the case where X represents a group represented by the formula —CH$_2$—NH—(CH$_2$)$_n$— or a group represented by the formula —NH—CH$_2$—(CH$_2$)$_n$— are excluded; n represents an integer from 0 to 3),E and Hal have the same meanings as defined above; R$^{N1}$ represents a C$_{1-6}$ alkyl group, a C$_{2-6}$ alkenyl group or a C$_{2-6}$ alkynyl group; R$^{N2}$ represents a hydrogen atom or a C$_{1-6}$ alkyl group; R$^a$ represents a C$_{2-6}$ alkenyl group, a C$_{6-10}$ aryl group or an aromatic 5- and 10-membered heterocyclic group; R$^{b1}$ and R$^{b2}$ may be the same or different from each other, and represent a hydrogen atom or a C$_{1-6}$ alkyl group, or form a cyclic boric acid ester together; R$^{c1}$, R$^{c2}$, R$^{c3}$ and R$^{c4}$ may be the same or different from each other, and represent a hydrogen atom, a C$_{1-6}$ alkyl group, a C$_{2-6}$ alkenyl group, a C$_{2-6}$ alkynyl group, a C$_{3-8}$ cycloalkyl group, a C$_{6-10}$ aryl group or a 5- to 10-membered heterocyclic group.]

Compound (4-1-1), compound (4-1-2), compound (4-1-3), compound (4-1-4), compound (4-1-5) and compound (4-1-6) which are commercially available products can be used as is, or they can also be prepared from commercially available products by a well known method.

[Step 4-1]

The present step is a step wherein compound (4-1) and compound (4-1-1) are reacted to obtain compound (4-2). Examples of the solvent include, for instance, dimethylsulfoxide, tetrahydrofuran, toluene, acetonitrile, N,N-dimethylformamide or the like. In addition, the reaction can also be carried out without the solvent. The reaction is preferably carried out in a sealed tube; the reaction time is from 1 hour to 60 hours, and the reaction temperature is from 50° C. to 200° C. Note that, an organic base such as, for instance, N,N-diisopropylethylamine, triethylamine, pyridine, 1,8-diazabicyclo[5,4,0]undec-7-ene, inorganic base such as, for instance, potassium carbonate, sodium carbonate, can be added in the amounts of 2 equivalents to excess amount based on compound (4-1).

[Step 4-2]

The present step is a step wherein compound (4-1) and compound (4-1-2) are reacted to obtain compound (4-3). Compound (4-3) can be obtained by reacting compound (4-1) and compound (4-1-2) in the presence of a catalyst. Examples of the catalyst include tetrakis(triphenylphosphine)palladium (0), dichlorobis(triphenylphosphine)palladium(II) or the like. Examples of the solvent include, toluene, 1,4-dioxane, xylene or the like. Compound (4-1-2) is used in the amounts of 2 equivalent to 3 equivalents based on compound (4-1). The catalyst is used in the amounts of 0.05 equivalents to 0.3 equivalents based on compound (4-1). The reaction temperature is from 100° C. to 140° C., and the reaction time is from 1 hour to 24 hours.

[Step 4-3]

The present step is a step wherein compound (4-1) and compound (4-1-3) are reacted to obtain compound (4-3). Compound (4-3) can be obtained by reacting compound (4-1) and compound (4-1-3) in the presence of a catalyst. Examples of the catalyst include, for instance, dichloro(1,1'-bis(diphenylphosphino)propane)nickel(II), dichloro(1,1'-bis(diphenylphosphino)ferrocene) nickel (II), tetrakis(triphenylphosphine)palladium(0) or the like. Examples of the solvent include, for instance, tetrahydrofuran, 1,4-dioxane or the like. Compound (4-1-3) is used in the amounts of 3 equivalents to excess amount based on compound (4-1). The catalyst is used in the amounts of 0.05 equivalents to 0.3 equivalents based on compound (4-1). The reaction temperature is from 0° C. to reflux temperature, and the reaction time is from 5 minutes to 24 hours.

[Step 4-4]

The present step is a step wherein compound (4-1) and compound (4-1-4) are reacted to obtain compound (4-3). Compound (4-3) can be obtained by reacting compound (4-1) and compound (4-1-4) in the presence of a catalyst and a base. Examples of the catalyst include, for instance, palladium(II) acetate, tetrakis(triphenylphosphine)palladium (0), dichlorobis(triphenylphosphine)palladium (II), tris(dibenzylideneacetone) dipalladium(0) or the like. To obtain satisfactory results, a phosphorus ligand (for instance, triphenylphosphine, tri-tert-butylphosphine or the like) may be added in the amounts of 0.25 equivalents to 1.5 equivalents based on compound (4-1). Examples of the basic include, for instance, potassium carbonate, sodium carbonate, cesium carbonate, potassium fluoride, cesium fluoride, potassium phosphate, sodium hydroxide, barium hydroxide, potassium hydroxide or the like. The present reaction is preferably carried out under an inert gas atmosphere such as, for instance, nitrogen gas and argon gas. Examples of the solvent include, for instance, tetrahydrofuran, 1,4-dioxane, methanol, ethanol, toluene, water or the like. Depending on the reagent used, quaternary ammonium salt such as tetrabutylammonium bromide can be added. The catalyst is used in the amounts of 0.05 equivalents to 0.3 equivalents based on compound (4-1). The base is used in the amounts of 2 equivalents to excess amount based on compound (4-1). The reaction temperature is from room temperature to reflux temperature, and the reaction time is from 30 minutes to 24 hours.

[Step 4-5]

The present step is a step wherein compound (4-1) and compound (4-1-5) are reacted to obtain compound (4-4). Compound (4-4) can be obtained by reacting compound (4-1) and compound (4-1-5) in the presence of a catalyst and a base. Examples of the catalyst include, for instance, palladium(II) acetate, tetrakis(triphenylphosphine) palladium(0), dichlorobis(triphenylphosphine)palladium (II), tris(dibenzylideneacetone) dipalladium (0) or the like. Examples of the base include, for instance, triethylamine, N,N-diisopropylethylamine, pyridine or the like. Examples of the solvent include, for instance, tetrahydrofuran, acetonitrile, 1,4-dioxane, N,N-dimethylformamide, N-methylpyrrolidinone, dimethylsulfoxide, toluene or the like. In addition, to obtain satisfactory results, 0.1 equivalents to 0.3 equivalents of copper (I) iodide or tetrabutylammonium fluoride may be added based on compound (4-1). Compound (4-1-5) is used in the amounts of 1 equivalent to 5 equivalents based on compound (4-1). The catalyst is used in the amounts of 0.05 equivalents to 0.3 equivalents based on compound (4-1). The base is used in the amounts of 2 equivalents to 5 equivalents based on compound (4-1). The reaction temperature is from room temperature to 150° C., and the reaction time is from 30 minutes to 24 hours.

[Step 4-6]

The present step is a step wherein a triple bond in compound (4-4) is reduced into a double bond to obtain compound (4-5). Compound (4-5) can be obtained using a catalyst such as, for instance, Lindlar catalyst, palladium-barium sulfate or the like, in a solvent such as, for instance, tetrahydrofuran, ethyl acetate, acetonitrile, methanol, ethanol or the like, under hydrogen atmosphere. The preferable solvent is ethyl acetate. To obtain satisfactory results, 0.1 equivalents to 1 equivalents of quinoline may be added based on compound (4-4). The catalyst is used in catalytic amount to excess amount based on compound (4-4). The reaction temperature is room temperature, the reaction time is from 15 minutes to 24 hours, and reaction pressure is from 1 atm to 4 atm.

[Step 4-7]

The present step is a step wherein compound (4-5) is reduced to obtain compound (4-6). Compound (4-6) can be obtained using a catalyst such as, for instance, palladium-carbon, Raney nickel, platinum dioxide or the like, in a solvent such as, for instance, tetrahydrofuran, ethyl acetate, acetonitrile, methanol, ethanol or the like, under hydrogen atmosphere. The catalyst is used in catalytic amount to excess amount based on compound (4-5). The reaction temperature is room temperature, the reaction time is from 5 minutes to 24 hours, and the reaction pressure is from 1 atm to 4 atm.

[Step 4-8]

The present step is a step wherein compound (4-4) is reduced to obtain compound (4-6). Compound (4-6) can be prepared by an analogous method to [Step 4-7].

[Step 4-9]

The present step is a step wherein compound (4-1) and compound (4-1-6) are reacted to obtain compound (4-7). Compound (4-7) can be obtained by reacting compound (4-1) and compound (4-1-6) in the presence of a catalyst and a base. Examples of the catalyst include, for instance, palladium(II) acetate, tetrakis(triphenylphosphine) palladium(0), dichlorobis(triphenylphosphine)palladium (II), tris(dibenzylideneacetone)dipalladium (0) or the like. Examples of the base include, for instance, triethylamine, N,N-diisopropylethylamine, N,N-dicyclohexylmethylamine or the like. Examples of the solvent include, for instance, acetonitrile, tetrahydrofuran, 1,4-dioxane, benzene, toluene, xylene, N,N-dimethylformamide, N-methylpyrrolidinone or the like. In addition, to obtain satisfactory results, 0.25 equivalents to 1.5 equivalents of a phosphorus ligand (for instance, triphenylphosphine, tri-tert-butylphosphine, 2-(di-tert-butylphosphino)biphenyl or the like) may be added based on compound (4-1). Compound (4-1-6) is used in the amounts of 1 equivalent to 4 equivalents based on compound (4-1). The catalyst is used in the amounts of 0.05 equivalents to 0.3 equivalents based on compound (4-1). The base is used in the amounts of 2 equivalents to 5 equivalents based on compound (4-1). The reaction temperature is from room temperature to 150° C., the reaction time is from 5 minutes to 24 hours.

[Step 4-10]

The present step is a step wherein compound (4-7) is reduced to obtain compound (4-8). Compound (4-8) can be prepared by an analogous method to [Step 4-7].

[Preparation Method 4-2] Conversion of Substituent on E in Compound (1)—1

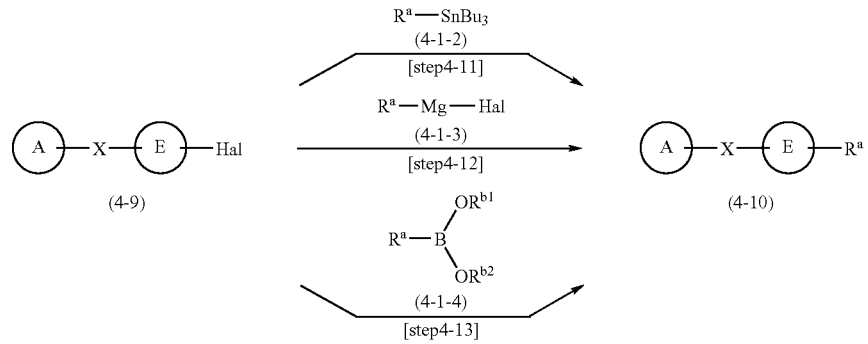

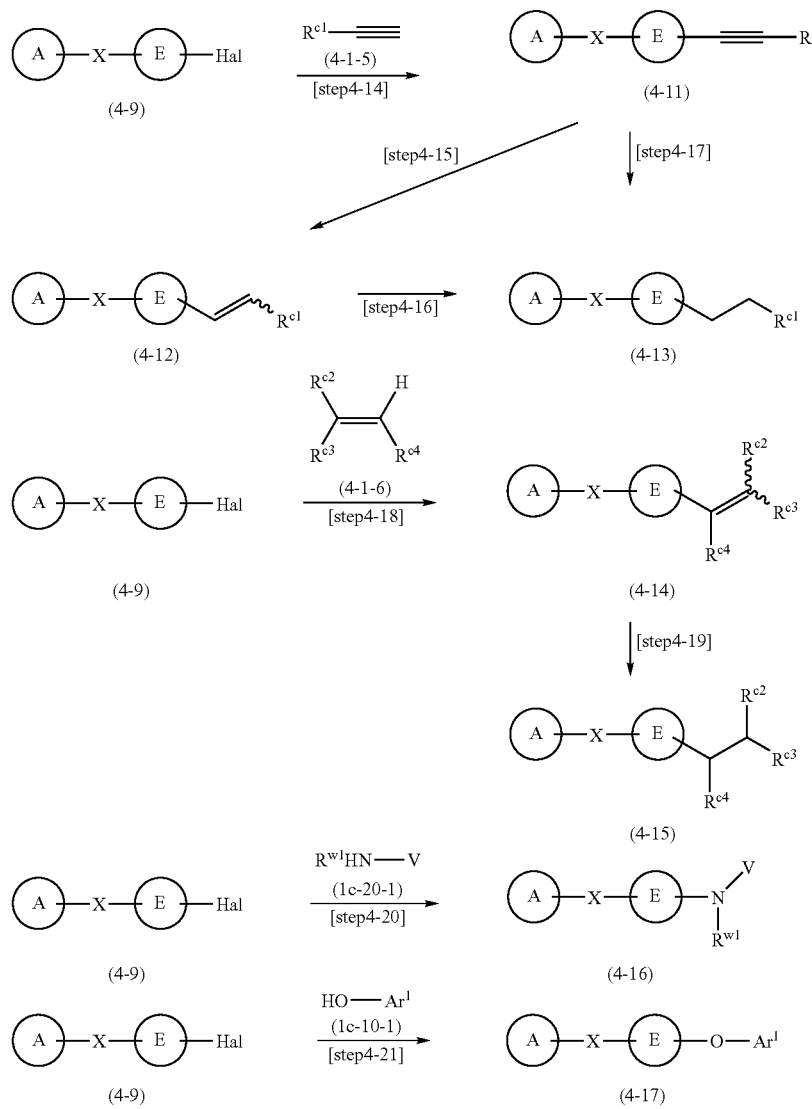

[wherein A, X (with the proviso that the case where X represents a group represented by the formula —CH$_2$—NH—(CH$_2$)$_n$— or a group represented by the formula —NH—CH$_2$—(CH$_2$)$_n$— are excluded; n represents an integer from 0 to 3), E, Hal, R$^a$, R$^{b1}$, R$^{b2}$, R$^{c1}$, R$^{c2}$, R$^{c3}$, C$^{c4}$, R$^{w1}$, V and Ar$^1$ have the same meanings as defined above.]

Compound (4-1-2), compound (4-1-3), compound (4-1-4), compound (4-1-5), compound (4-1-6), compound (1c-20-1) and compound (1c-10-1) which are commercially available products can be used as is, or they can also be prepared from commercially available products by a well known method.

[Step 4-11]

The present step is a step wherein compound (4-9) and compound (4-1-2) are reacted to obtain compound (4-10). Compound (4-10) can be prepared by an analogous method to [Step 4-2].

[Step 4-12]

The present step is a step wherein compound (4-9) and compound (4-1-3) are reacted to obtain compound (4-10). Compound (4-10) can be prepared by an analogous method to [Step 4-3].

[Step 4-13]

The present step is a step wherein compound (4-9) and compound (4-1-4) are reacted to obtain compound (4-10). Compound (4-10) can be prepared by an analogous method to [Step 4-4].

[Step 4-14]

The present step is a step wherein compound (4-9) and compound (4-1-5) are reacted to obtain compound (4-11). Compound (4-11) can be prepared by an analogous method to [Step 4-5].

[Step 4-15]

The present step is a step wherein a triple bond of compound (4-11) is reduced into a double bond to obtain compound (4-12). Compound (4-12) can be prepared by an analogous method to [Step 4-6].

[Step 4-16]

The present step is a step wherein compound (4-12) is reduced to obtain compound (4-13). Compound (4-13) can be prepared by an analogous method to [Step 4-7].

[Step 4-17]

The present step is a step wherein compound (4-11) is reduced to obtain compound (4-13). Compound (4-13) can be prepared by an analogous method to [Step 4-8].

[Step 4-18]

The present step is a step wherein compound (4-9) and compound (4-1-6) are reacted to obtain compound (4-14). Compound (4-14) can be prepared by an analogous method to [Step 4-9].

[Step 4-19]

The present step is a step wherein compound (4-14) is reduced to obtain compound (4-15). Compound (4-15) can be prepared by an analogous method to [Step 4-10].

[Step 4-20]

The present step is a step wherein compound (4-9) and compound (1c-20-1) are reacted to obtain compound (4-16). Compound (4-16) can be obtained by reacting compound (4-9) and compound (1c-20-1) in a solvent such as, for instance, tetrahydrofuran, benzene, toluene, xylene or the like, in the presence of a catalyst such as for instance, tris(dibenzylideneacetone)dipalladium(0), dichloro(1,1'-bis(diphenylphosphino)ferrocene)palladium(II), palladium(II) acetate, a phosphorus ligand such as, for instance, 2,2-bis(diphenylphosphino)-1,1'-binaphthyl, and a base such as, for instance, sodium tert-butoxide. Compound (1c-20-1) is used in the amounts of 1 equivalent to 3 equivalents based on compound (4-9). Catalyst is used in the amounts of 0.05 equivalents to 0.3 equivalents based on compound (4-9). The base is used in the amounts of 1.5 equivalent to excess amount based on compound (4-9). The phosphorus ligand is used in the amounts of 0.25 equivalents to 1.5 equivalents based on compound (4-9). The reaction temperature is 50° C. to reflux temperature, and the reaction time is from 1 hour to 48 hours.

[Step 4-21]

The present step is a step wherein compound (4-9) and compound (1c-10-1) are reacted to obtain compound (4-17). Compound (4-17) can be obtained by reacting compound (4-9) and compound (1c-10-1) in a solvent such as, for instance, tetrahydrofuran, toluene or the like, in the presence of a catalyst such as, for instance, copper(I) chloride, copper (I) iodide or the like, and a base such as, for instance, potassium carbonate, cesium carbonate, potassium phosphate, pyridine or the like. Compound (1c-10-1) is used in the amounts of 1 equivalent to 3 equivalents based on compound (4-9). Catalyst is used in the amounts of 0.5 equivalents to 3 equivalents based on compound (4-9). The base is used in the amounts of 2 equivalents to 10 equivalents based on compound (4-9). The reaction temperature is 50° C. to reflux temperature, and the reaction time is from 1 hour to 48 hours.

Other Method for [Step 4-20] and [Step 4-21]

When E represent a furyl group or a thienyl group, compound (4-16) or compound (4-17) can be obtained respectively by reacting compound (4-9) and compound (1c-20-1) or compound (1c-10-1) in a solvent such as, for instance, dimethylsulfoxide, N-methylpyrrolidone or the like, in the presence of a catalyst such as, for instance, copper(I) chloride or the like, a base such as, for instance, cesium carbonate and 2,2,6,6-tetramethyl-3,5-heptanedione. Compound (1c-20-1) or compound (1c-10-1) is used in the amounts of 1 equivalent to 3 equivalents based on compound (4-9). The catalyst is used in the amounts of 0.5 equivalents to 3 equivalents based on compound (4-9). The base is used in the amounts of 2 equivalents to 10 equivalents based on compound (4-9). The reaction temperature is 80° C. to reflux temperature, and the reaction time is from 1 hour to 24 hours.

[Preparation Method 4-3] Conversion of Substituent on E in Compound (I)-2

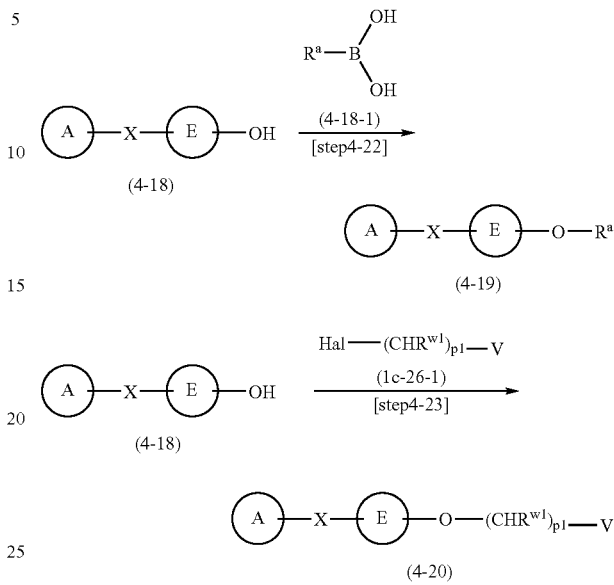

[wherein A, X (with the proviso that the cases where X represents a group represented by the formula —$CH_2$—NH—$(CH_2)_n$— or a group represented by the formula —NH—$CH_2$—$(CH_2)_n$— are excluded; n represents an integer from 0 to 3), E, $R^a$, Hal, $R^{w1}$, p1 and V have the same meanings as defined above.]

Compound (4-18-1) and compound (1c-26-1) which are commercially available products can be used as is, or they can also be prepared from commercially available products by a well known method.

[Step 4-22]

The present step is a step wherein compound (4-18) and compound (4-18-1) are reacted to obtain compound (4-19). Compound (4-19) can be obtained by reacting compound (4-18) and compound (4-18-1) in the presence of a catalyst and a base. Examples of the catalyst include a cuprous catalyst such as, for instance, copper (II) acetate. Examples of the base include, for instance, triethylamine, N,N-diisopropylethylamine or the like. Examples of the solvent include, for instance, dichloromethane, tetrahydrofuran, toluene or the like. It is preferable to use dichloromethane. The present reaction is preferably carried out in the presence of oxygen. To obtain satisfactory results, molecular sieves 4A may be added. Compound (4-18-1) is used in the amounts of 1 equivalent to 4 equivalents based on compound (4-18). The catalyst is used in the amounts of 0.1 equivalents to 0.3 equivalents based on compound (4-18). The base is used in the amounts of 2 equivalents to excess amount based on compound (4-18). The reaction temperature is from room temperature to 50° C., the reaction time is from 24 hours to 5 days.

[Step 4-23]

The present step is a step wherein compound (4-18) and compound (1c-26-1) are reacted to obtain compound (4-20). Compound (4-20) can be obtained by reacting compound (4-18) and compound (1c-26-1) in a solvent such as, for instance, N,N-dimethylformamide, N-methylpyrrolidinone, tetrahydrofuran or the like, in the presence of a base such as, for instance, potassium carbonate, cesium carbonate, sodium hydride or the like. To obtain satisfactory results, a catalytic amount of sodium iodide or potassium iodide may be added. The reaction temperature is from room temperature to 160° C., and the reaction time is from 10 minutes to 48 hours.

Another method is based on the technique that uses the Mitsunobu reaction. Compound (4-20) can be obtained by reacting compound (4-18), compound (1c-26-1), triphenylphosphine and diethyl azodicarboxylate or diisopropyl azodicarboxylate in a solvent such as, for instance, dichloromethane, tetrahydrofuran or the like. Compound (1c-26-1) is used in the amounts of 1 equivalent to 1.5 equivalents based on compound (4-18). Triphenylphosphine is used in the amounts of 1 equivalent to 1.5 equivalents based on compound (4-18). Diethyl azodicarboxylate or diisopropyl azodicarboxylate is used in the amounts of 1 equivalent to 1.5 equivalents based on compound (4-18). The reaction temperature is from room temperature to reflux temperature, and the reaction time is from 5 minutes to 24 hours.

[Preparation Method 4-4] Conversion of Substituent on A in Compound (I) (with the Proviso that A Represents an Aromatic 5- to 10-Membered Heterocyclic Group Containing at Least 1 Nitrogen Atom)-2

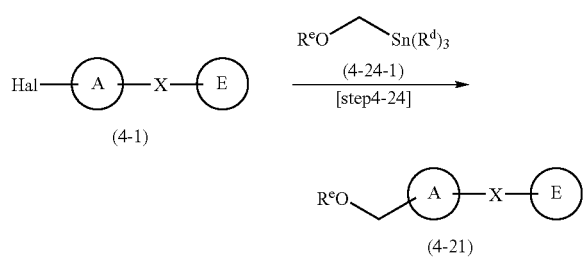

[wherein A, X (with the proviso that the cases where X represents a group represented by the formula —$CH_2$—NH—$(CH_2)_n$— or a group represented by the formula —NH—$CH_2$—$(CH_2)_n$— are excluded; n represents an integer from 0 to 3), E and Hal have the same meanings as defined above; $R^d$ and $R^e$ are the same or different from each other, and represent $C_{1-6}$ alkyl groups.]

[Step 4-24]

The present step is a step wherein compound (4-1) and compound (4-24-1) are reacted to obtain compound (4-21). The present reaction is preferably carried out under an inert gas atmosphere; the solvent for use varies depending on the starting materials and reagents used; for instance, N-methylpyrrolidinone, 1,4-dioxane or the like can be used. Examples of the catalyst include, for instance, palladium(II) acetate, tetrakis(triphenylphosphine)palladium(0), dichlorobis(triphenylphosphine)palladium(II) or tris(dibenzylideneacetone)dipalladium(0) or the like. To obtain satisfactory results, of phosphorus ligand, preferably, for instance, triphenylphosphine, tri-tert-butylphosphine, diphenylphosphino ferrocene or the like may be added. Compound (4-24-1) is used in the amounts of 1 equivalent to 10 equivalents based on compound (4-1). The catalyst is used in the amounts of 0.001 equivalents to 0.2 equivalents based on compound (4-1). The phosphorus ligand is used in the amounts of 0.001 equivalents to 0.4 equivalents based on compound (4-1). The reaction temperature is from room temperature to reflux temperature, and the reaction time is from 10 minutes to 24 hours.

[Preparation Method 4-5] Conversion of Substituent on E in Compound (I)-3

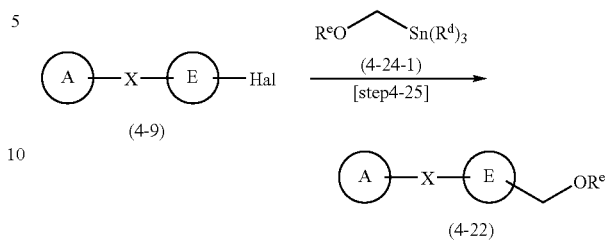

[wherein A, X (with the proviso that the cases where X represents a group represented by the formula —$CH_2$—NH—$(CH_2)_n$— or a group represented by the formula —NH—$CH_2$—$(CH_2)_n$— are excluded; n represents an integer from 0 to 3), E, Hal, $R^d$ and $R^e$ have the same meanings as defined above.]

[Step 4-25]

The present step is a step wherein compound (4-9) and compound (4-24-1) are reacted to obtain compound (4-22). Compound (4-22) can be prepared by an analogous method to [Step 4-24].

(Preparation Method for Compound (4-24-1))

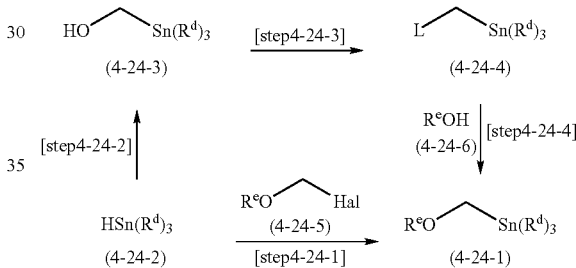

[wherein L, $R^d$ and $R^e$ have the same meanings as defined above.]

Compound (4-24-2), compound (4-24-5) and compound (4-24-6) which are commercially available products can be used as is, or they can also be prepared from commercially available products by a well known method.

[Step 4-24-1]

The present step is a step wherein compound (4-24-2) and compound (4-24-5) are reacted to obtain compound (4-24-1). Compound (4-24-1) can be obtained in a solvent such as, for instance, tetrahydrofuran, by abstracting a hydrogen atom from compound (4-24-2) with a strong base such as for instance, lithium diisopropyl amide, and then reacting with compound (4-24-5). Examples of compound (4-24-5) include, for instance, chloromethyl ethyl ether, chloromethyl benzyl ether or the like. The strong base is used in the amounts of 1 equivalent to 2 equivalents based on compound (4-24-2). Compound (4-24-5) is used in the amounts of 1 equivalent to 2 equivalents based on compound (4-24-2). The reaction temperature is from −78° C. to reflux temperature, and the reaction time is from 1 hour to 24 hours.

[Step 4-24-2]

The present step is a step wherein compound (4-24-2) and a formaldehyde equivalent are reacted to obtain compound (4-24-3). Compound (4-24-3) can be obtained in a solvent such as, for instance, tetrahydrofuran, by abstracting an hydrogen atom from compound (4-24-2) with a base such as, for instance, lithium diisopropyl amide, and then reacting with paraformaldehyde. The strong base is used in the amounts of 1 equivalent to 2 equivalents based on compound (4-24-2). The formaldehyde equivalent is used in the amounts of 1 equivalent to 2 equivalents based on compound (4-24-2). The reaction temperature is −78° C. to reflux temperature, and the reaction time is from 1 hour to 24 hours.

[Step 4-24-3]

The present step is a step wherein a hydroxyl group of compound (4-24-3) is converted into a leaving group to obtain compound (4-24-4).

When L represents a methane sulfonyloxy group, a p-toluenesulfonyloxy group, or the like, compound (4-24-4) can be obtained in a solvent such as, for instance, dichloromethane, by reacting compound (4-24-3) and a sulfonyl halide such as methane sulfonyl chloride or p-toluenesulfonyl chloride, in the presence of an organic base such as, for instance, triethylamine. The organic base is used in the amounts of 1 equivalent to 3 equivalents based on compound (4-24-3). The sulfonyl halide is used in the amounts of 1 equivalent to 2 equivalents based on compound (4-24-3). The reaction temperature is from 0° C. to reflux temperature, and the reaction time is from 10 minutes to 24 hours.

When L represents a bromine atom or an iodine atom, compound (4-24-4) can be obtained in a solvent such as, for instance, dichloromethane, by action of a halogenation agent such as, for instance, carbon tetrabromide, N-bromosuccinimide or N-iodosuccinimide on compound (4-24-3), in the presence of triphenylphosphine. Triphenylphosphine is used in the amounts of 1 equivalent to 2 equivalents with based on compound (4-24-3). The halogenation agent is used in the amounts of 1 equivalent to 2 equivalents with respect to compound (4-24-3). The reaction temperature is from 0° C. to room temperature, and the reaction time is from 10 minutes to 24 hours.

[Step 4-24-4]

The present step is a process wherein compound (4-24-4) and compound (4-24-6) are reacted to obtain compound (4-24-1). Compound (4-24-1) can be obtained in a solvent such as for instance, N,N-dimethylformamide, abstracting a hydrogen atom from compound (4-24-4) using a base such as, for instance, sodium hydride, and reacting with compound (4-24-6). Compound (4-24-6) is used in the amounts of 1 equivalent to 10 equivalents based on compound (4-24-4). The base is used in the amounts of 1 equivalent to 10 equivalents based on compound (4-24-4). The reaction temperature is from 0° C. to reflux temperature, and the reaction time is from 10 minutes to 24 hours.

EXAMPLES

The compounds according to the present invention can be prepared by a method described in, for instance, the following Preparation Examples and Examples. With the proviso that these are illustrative, and that the compounds according to the present invention is not to be limited in any way to the following specific examples.

Preparation Example A-1

2-Amino-6-chloro-nicotinic Acid

To liquid ammonia (approximately 20 mL) was added 2,6-dichloro-nicotinic acid (0.38 g, 2 mmol) and copper(I) iodide (720 mg, 3.8 mmol) at −78° C. in a sealed tube, and the solution was heated for 25 hours (the temperature of the oil bath was 115° C.). The temperature of the oil bath was raised to 125° C., which was further heated for 14 hours 30 minutes. The reaction mixture was allowed to room temperature, and ammonia was evaporated. Methanol was added, insoluble matter was removed by filtration, and the filtrate was concentrated to obtain the title compound (0.25 g, 1.45 mmol, 72%) as a solid.

$^1$H-NMR Spectrum (DMSO-$d_6$) δ(ppm): 6.63 (1H, d, J=8.0 Hz), 7.55 (2H, brs), 8.02 (1H, d, J=8.0 Hz).

Preparation Example A-2

2-Amino-nicotinic acid methyl ester

2-Amino-nicotinic acid (10.0 g, 72.4 mmol) was dissolved in a mixed solution of methanol (200 mL) and sulfuric acid (10 mL), and the solution was stirred under reflux for 35 hours. A saturated aqueous solution of sodium bicarbonate was added to the reaction solution at 0° C., which was extracted with ethyl acetate, the organic layer was washed with brine and dried over anhydrous magnesium sulfate. The solvent was evaporated in vacuo, the residue was purified by NH silica gel column chromatography to obtain the title compound (5.26 g, 34.6 mmol, 48%) as a white solid.

$^1$H-NMR Spectrum (CDCl$_3$) δ(ppm): 3.89 (3H, s), 6.63 (1H, ddd, J=1.1, 4.8, 7.7 Hz), 8.13 (1H, dd, J=1.6, 7.7 Hz), 8.22 (1H, dd, J=1.8, 4.8 Hz).

Preparation Example A-3

2-Amino-5-nitro-nicotinic acid methyl ester

2-Amino-nicotinic acid methyl ester (1.00 g, 6.57 mmol) described in Preparation Example A-2 was dissolved at 0° C. in a mixed solution of nitric acid (0.7 mL) and sulfuric acid (2.6 mL), which was stirred at 0° C. for 40 minute and at room temperature for 19 hours, then, further stirred at 70° C. for 4 hours. A saturated aqueous solution of sodium bicarbonate was added to the reaction solution at 0° C., which was extracted with ethyl acetate and tetrahydrofuran, the organic layer was washed with brine and dried over anhydrous magnesium sulfate. The solvent was evaporated in vacuo. Methanol was added to the residue, the precipitated solid was filtered to obtain the title compound (459 mg, 2.33 mmol, 35%) as a white solid.

$^1$H-NMR Spectrum (DMSO-$d_6$) δ(ppm): 3.86 (3H, s), 8.14 (1H, brs), 8.62 (1H, brs), 8.68 (1H, d, J=2.7 Hz), 9.04 (1H, d, J=2.9 Hz).

Preparation Example A-4

2-Amino-6-chloronicotinic Acid

Tris(2-(2-methoxyethoxy)ethyl)amine (3.0 mL, 9.4 mmol) was added to a mixture of 2,6-dichloronicotinic acid (40 g (90% purity), 0.19 mol), acetamide (80 g, 1.4 mol), potassium carbonate (78 g, 0.56 mol), copper(I) chloride (0.93 g, 9.4 mmol) and xylene (80 mL), which was stirred overnight at 145° C. After cooling, copper(I) chloride (0.46 g, 4.6 mmol) was added to the reaction solution, which was stirred overnight at 145° C. After cooling the reaction solution to 105° C., water (100 mL) was added, the solution was stirred for 1 hour at the same temperature, and cooled down to room temperature. 5N hydrochloric acid (150 mL) was added, the solution was neutralized with a citric acid aqueous solution, then, ethyl acetate was added, and the solution was filtered through Celite pad. The organic layer was washed with brine, then, the solvent was evaporated in vacuo. The residue was purified by silica gel column chromatography (ethyl acetate), recrystallization by the ethyl acetate-hexane was carried out to obtain the title compound (1.4 g, 8.3 mmol, 4.5%) as white crystal.

$^1$H-NMR Spectrum (DMSO-$d_6$) δ(ppm): 6.61 (1H, d, J=8.1 Hz), 7.53 (2H, brs), 8.01 (1H, d, J=8.1 Hz).

Preparation Example A-5

2-Amino-6-(2-hydroxy-ethoxy)-nicotinic Acid

To ethyleneglycol (0.50 mL) was added sodium hydride (70 mg, 1.7 mmol, 60% in oil), catalytic amount of copper(I) iodide and 2-amino-6-chloronicotinic acid (30 mg, 0.17 mmol), which was stirred for 3 hours at 110° C., then, further stirred overnight at 80° C. After cooling, water, diethyl ether and aqueous ammonia was added to the reaction solution, which was then partitioned, the aqueous layer was neutralized with citric acid, then, extracted with dichloromethane. The organic layer was washed with brine, then dried over anhydrous magnesium sulfate. The solvent was evaporated in vacuo to obtain the title compound (14 mg).

Preparation Example A-6

2-Amino-6-ethoxy-nicotinic Acid

The title compound (35mg) was obtained from ethanol (0.50 mL) and 2-amino-6-chloro-nicotinic acid (30 mg, 0.17 mmol) according to an analogous method to Preparation Example A-5.

Preparation Example A-7

2-Amino-6-isopropoxy-nicotinic Acid

The title compound (60 mg) was obtained from isopropanol (0.50 mL) and 2-amino-6-chloro-nicotinic acid (30 mg, 0.17 mmol) according to an analogous method to Preparation Example A-5.

Preparation Example A-8

2-Amino-6-chloro-nicotinic acid methyl ester

To methanol (50 mL) were added concentrated sulfuric acid (25 mL) and 2-amino-6-chloro-nicotinic acid (4.3 g, 25 mmol) described in Preparation Example A-1 (or A-4) on an ice bath, which was stirred at 70° C. for 5 hours. After cooling, an aqueous solution of sodium bicarbonate (90 g) was added to neutralize. The resulting solid was filtered to obtain the title compound (3.2 g, 17 mmol, 68%) as a light brown solid.

$^1$H-NMR Spectrum (CDCl$_3$) δ(ppm): 3.88 (3H, s), 6.62 (1H, d, J=8.2 Hz), 8.05 (1H, d, J=8.1 Hz).

Preparation Example A-9

Tributyl-methoxymethyl-stannane

To a mixture of diisopropylamine (9.4 mL, 67 mmol) and tetrahydrofuran (150 mL) was added n-butyl lithium (2.4M n-hexane solution, 25 mL, 61 mmol) dropwise at −78° C., which was stirred for 30 minutes at the same temperature. Tributyltin hydride (16 mL, 61 mmol) was added dropwise at the same temperature, the solution was then stirred for 30 minutes on ice. The reaction solution was brought to −78° C., chloromethyl methyl ether (4.6 mL, 61 mmol) was added dropwise thereto, the solution was then gradually warmed to room temperature. Water (100 mL) was added to the reaction solution, which was then extracted with diethyl ether (300 mL). The organic layer was washed with brine, then, evaporated in vacuo. The residue was purified by neutral silica gel column chromatography (heptane/ethyl acetate=30/1), and the title compound (18 g, 0.52 mmol, 86%) was obtained as a colorless oil.

$^1$H-NMR Spectrum (CDCl$_3$) δ(ppm): 0.88-0.93 (15H, m), 1.26-1.35 (6H, m), 1.47-1.55 (6H, m), 3.30 (3H, s), 3.71 (2H, t, J=6.8 Hz).

Preparation Example A-10

2-Amino-6-methoxymethyl-nicotinic acid methyl ester

A mixture of 2-amino-6-chloro-nicotinic acid methyl ester described in Preparation Example A-8 (1.4 g, 7.6 mmol), tributyl-methoxymethyl-stannane (3.1 g, 9.1 mmol) described in Preparation Example A-9, tetrakis(triphenylphosphine)palladium (440 mg, 0.38 mmol) and N-methylpyrrolidinone (20 mL) was stirred at 130° C. for 3.5 hours. The reaction solution was allowed to cool, an aqueous solution of potassium fluoride and ethyl acetate were added thereto on an ice bath, followed by filtering through Celite pad. The organic layer was washed with brine, then, evaporated in vacuo. The residue was purified by silica gel column chromatography (heptane/ethyl acetate=2/1), and the title compound (0.93 g, 4.7 mmol, 63%) was obtained as a light brown oil.

$^1$H-NMR Spectrum (CDCl$_3$) δ(ppm): 3.47 (3H, s), 3.88 (3H, s), 4.41 (2H, s), 6.74 (1H, d, J=7.9 Hz), 8.14 (1H, d, J=7.9 Hz).

Preparation Example A-11

2-Amino-6-methoxymethyl-nicotinic Acid

Lithium hydroxide monohydrate (1.2 g, 29 mmol) was added to a mixture of 2-amino-6-methoxymethyl-nicotinic acid methyl ester described in Preparation Example A-10 (2.9 g, 15 mmol), tetrahydrofuran (30 mL), methanol (7.5 mL), and water (7.5 mL), which was then stirred overnight at room temperature. Acetic acid (1.7 mL, 29 mmol) was added to the reaction solution and the solvent was evaporated in vacuo. After filtration using silica gel (methanol/ethyl acetate=1/3) and the solvent was evaporated in vacuo, the residue was washed with water, and the title compound (2.1 g, 12 mmol, 80%) was obtained as a pale yellow solid.

$^1$H-NMR Spectrum (DMSO-$d_6$) δ(ppm): 3.32 (3H, s), 4.29 (2H, s), 6.61 (1H, d, J=7.9 Hz), 7.16 (2H, br s), 8.02 (1H, d, J=7.9 Hz).

Preparation Example A-12

2-(2-Cyanoethyl)-3.3-diaminopropenoic acid ethyl ester (1-Ethoxyformimidoyl) 1-acetic acid ethyl ester hydrochloride (50 g, 0.26 mol) was suspended in an ammonia-ethanol solution (300 mL; prepared by saturating ethanol with ammonia gas at room temperature), which was then stirred at room temperature for 4 hours. After the reaction was completed, the precipitated salt was removed by filtration, and the filtrate was concentrated in vacuo at room temperature to reach ⅓ of the amount. Hydrochloric acid-methanol (130 mL; hydrochloric acid content:7.5%) was added to this filtrate, the solution was then concentrated under a reduced pressure to obtain 3,3-diamino-acrylic acid ethyl ester hydrochloride (40 g, 0.24 mol, 92%) as a solid.

The resulting 3,3-diamino-acrylic acid ethyl ester hydrochloride (2.2 g, 13.2 mmol) was suspended in tetrahydrofuran (40 mL), triethylamine (2 mL, 14.3 mmol) and acrylonitrile (1.2 mL, 19.3 mmol) were added thereto, and the solution was refluxed for 6 hours. After the reaction was completed, the resulting triethylamine hydrochloride was filtered, and the filtrate was concentrated to obtain the title compound (0.6 g, 3.3 mmol, 25%).

$^1$H-NMR Spectrum (CDCl$_3$) δ(ppm): 1.26 (3H, t, J=7.2 Hz), 2.42-2.49 (2H, m), 2.50-2.57 (2H, m), 4.12 (2H, q, J=7.2 Hz), 4.22 (2H, brs), 6.45 (2H, brs).

Preparation Example A-13

2.6-Diamino-4.5-dihydronicotinic acid ethyl ester

A solution of 2-(2-cyanoethyl) 3,3-diaminopropenoic acid ethyl ester described in Preparation Example A-12 (0.55 g, 3 mmol) in tetrahydrofuran (7 mL) was added dropwise to a suspension of sodium hydride (208 mg, 5.2 mmol, 60% in oil) in tetrahydrofuran (7 mL), and the solution was stirred for 19 hours 20 minutes under reflux. After the reaction was completed, the reaction solution was poured into an ice water, which was then extracted with ethyl acetate. The organic layer was dried over anhydrous magnesium sulfate, then, concentrated to obtain the title compound as a crude product (0.188 g, 1 mmol, 34%).

$^1$H-NMR Spectrum (CDCl$_3$) δ(ppm):1.27 (3H, t, J=7.2 Hz), 2.28-2.34 (2H, m), 2.46-2.52 (2H, m), 4.14 (2H, q, J=7.2 Hz).

Preparation Example A-14

2.6-Diamino-nicotinic acid ethyl ester

To a solution of 2,6-diamino-4,5-dihydronicotinic acid ethyl ester described in Preparation Example A-13 (4.5 g, 24.6 mmol) in tetrahydrofuran (300 mL) was added 2,3-Dichloro-5,6-dicyano-1,4-benzoquinone (5.6 g, 24.7 mmol), which was then stirred for 40 minutes at room temperature. The residue obtained by concentrating the reaction solution was then purified by NH silica gel column chromatography (ethyl acetate) to obtain a solid of the target compound. This solid was washed with hexane and dried to obtain the title compound (3.1 g, 17.1 mmol, 69.5%).

$^1$H-NMR Spectrum (CDCl$_3$) δ(ppm): 1.35 (3H, t, J=7.2 Hz), 4.27 (2H, q, J=7.2 Hz), 4.60 (2H, brs), 5.82 (1H, d, J=8.4 Hz), 7.90 (1H, d, J=8.4 Hz).

Preparation Example A-15

2,6-Diamino-nicotinic Acid 2,6-Diamino-nicotinic acid ethyl ester described in Preparation Example A-14 (2 g, 11 mmol) was dissolved in ethanol (15 mL), an aqueous solution of 1N sodium hydroxide (15 mL) was added thereto, followed by stirring for 2 hours under reflux. The reaction solution was allowed to room temperature, ethanol was then removed by evaporation, the residue was cooled on an ice bath, then neutralized with 1N hydrochloric acid. The precipitated solid was collected by filtration, washed with water, then, dried to obtain the title compound (1.72 g, 11 mmol, quantitatively).

$^1$H-NMR Spectrum (DMSO-d$_6$) δ(ppm): 5.70 (1H, d, J=8.4 Hz), 6.31 (2H, brs), 6.58-7.12 (1H, brs), 7.62 (1H, d, J=8.4 Hz).

Preparation Example A-16

2-Amino-6-vinyl-nicotinic acid methyl ester

2-Amino-6-chloro-nicotinic acid methyl ester (2.95 g, 15.8 mmol), vinyl tri-n-butyltin (5.01 g, 15.8 mmol) and tetrakis (triphenylphosphine)palladium(0) (1.83 g, 1.58 mmol) were suspended in xylene (15 mL), and heated for 1 hour at 130° C. The reaction mixture was allowed to room temperature, water and ethyl acetate were added thereto, this mixture was filtered through Celite pad, then, the filtrate thereof was partitioned. The organic layer was separated, the solvent was evaporated in vacuo, and the residue was purified by silica gel column chromatography to obtain the title compound (1.87 g, 10.5 mmol, 66%) as a white solid.

$^1$H-NMR Spectrum (DMSO-d$_6$) δ(ppm): 3.81 (3H, s), 5.54 (1H, dd, J=1.6, 10.4 Hz), 6.24 (1H, dd, J=1.6, 17.2 Hz), 6.65 (1H, dd, J=10.4, 17.2 Hz), 6.76 (1H, d, J=8.0 Hz), 7.16 (1H, brs), 8.04 (1H, d, J=8.0 Hz).

Preparation Example A-17

2-Amino-6-(2-cyanoethyl)-nicotinic acid methyl ester

To a solution of 2-amino-6-vinyl-nicotinic acid methyl ester (760 mg, 4.26 mmol) in tetrahydrofuran (76 mL) was added a solution of diethyl aluminum cyanide in toluene (12.8 mL, 12.8 mmol) dropwise under sodium chloride—an ice bath cooling, at an internal temperature of −5° C. or below, then, the solution was gradually allowed to room temperature and stirred overnight. The reaction solution was partitioned into an aqueous solution of saturated ammonium chloride and ethyl acetate. This organic layer was separated, washed with brine and dried over anhydrous magnesium sulfate. The solvent was evaporated in vacuo, the residue was purified by silica gel column chromatography, and the title compound (180 mg, 0.878 mmol, 21%) was obtained as a yellow oil.

$^1$H-NMR Spectrum (CDCl$_3$) δ(ppm): 2.80 (2H, t, J=7.2 Hz), 2.97 (2H, t, J=7.2 Hz), 3.88 (3H, s), 6.53 (1H, d, J=8.0 Hz) 8.07 (1H, d, J=8.0 Hz).

Preparation Example A-18

2-Amino-6-(2-cyanoethyl)-nicotinic Acid

To a solvent mixture of 2N-sodium hydroxide aqueous solution (5 mL) and methanol (5 mL) was added 2-amino-6-(2-cyanoethyl)-nicotinic acid methyl ester (90 mg, 0.439 mmol), and the solution was stirred for 18 hours at room temperature. This mixed solution was neutralized with 5N-hydrochloric acid, then, extracted with ethyl acetate. This organic layer was dried over anhydrous magnesium sulfate, then, the solvent was evaporated in vacuo, and the title compound (68 mg, 0.355 mmol, 81%) was obtained as a yellowish brown solid.

$^1$H-NMR Spectrum (DMSO-d$_6$) δ(ppm): 2.86 (4H, bs), 6.54 (1H, d, J=8.0 Hz), 7.18 (2H, bs), 7.98 (1H, d, J=8.0 Hz).

Preparation Example A-19

2-Amino-6-(2-ethoxy-vinyl)-nicotinic acid methyl ester

To a solution of ethyl ethynyl ether (3.6 g, 25.7 mmol) in tetrahydrofuran (10 mL) was added catechol borane (3.08 g, 25.7 mmol) on an ice bath. Immediately, the cold bath was removed, the reaction mixture was allowed to room temperature, and then, the solution was stirred for 1.5 hours under reflux. This reaction mixture was allowed to room temperature. To this mixture solution were added 2-amino-6-chloro-nicotinic acid methyl ester (1.6 g, 8.57 mmol), sodium hydroxide powder (1.13 g, 28.3 mmol), tetrakis(triphenylphosphine)palladium(0) (0.99 g, 0.857 mmol) and dioxane (20 mL), which was then stirred for 2 hours under reflux. The reaction mixture was allowed to room temperature, and partitioned into water and ethyl acetate. The organic layer was separated, the solvent was evaporated in vacuo, the residue was purified by silica gel column chromatography, and the title compound (1.30 g, 5.85 mmol, 68%) was obtained as a brown solid.

$^1$H-NMR Spectrum (DMSO-d$_6$) δ(ppm): 1.27 (3H, t, J=7.2 Hz), 3.77 (3H, s), 3.95 (2H, q, J=7.2 Hz), 5.75 (1H, d, J=12.8 Hz), 6.49 (1H, d, J=8.4 Hz), 7.02 (2H, brs), 7.63 (1H, d, J=12.8 Hz), 7.89 (1H, d, J=8.4 Hz).

Preparation Example A-20

2-Amino-6-(2-hydroxy-ethyl)-nicotinic acid methyl ester

2-Amino-6-(2-ethoxy-vinyl)-nicotinic acid methyl ester (1.07 g, 4.81 mmol) was dissolved in 5N-hydrochloric acid (25 mL), ethanol (20 mL) and tetrahydrofuran (5 mL), and the solution was stirred for 3 hours under reflux. This reaction mixture was allowed to room temperature, and neutralized with a aqueous solution of saturated sodium bicarbonate, then, sodium borohydride (1 g, 26.5 mmol) was added to this reaction mixture, which was then stirred for 20 minutes at room temperature. Ethyl acetate was added thereto, followed by filtrating through Celite pad. This filtrate was partitioned. This organic layer was separated, the solvent was evaporated in vacuo, the residue was purified by silica gel column chromatography, and the title compound (350 mg, 1.92 mmol, 40%) was obtained as a brown oil.

$^1$H-NMR Spectrum (DMSO-d$_6$) δ(ppm): 2.72 (2H, t, J=6.8 Hz), 3.71 (2H, q, J=6.8 Hz), 3.79 (3H, s), 4.66 (1H, t, J=6.8 Hz), 6.53 (1H, d, J=8.0 Hz), 7.12 (2H, brs), 7.95 (1H, d, J=8.0 Hz).

Preparation Example A-21

2-Amino-6-(2-fluoro-ethyl)-nicotinic acid methyl ester

A solution of (bis(2-methoxyethyl)amino)sulfur trifluoride (2.39 g, 10.8 mmol) in dichloromethane (30 mL) was cooled with a dry ice-methanol bath, and 2-amino-6-(2-hydroxyethyl)-nicotinic acid methyl ester (50 mg, 0.255 mmol) was added thereto dropwise. After dropwise addition the cold bath was immediately removed, and the solution was gradually allowed to room temperature. Water and ethyl acetate were added to the reaction solution, which was then partitioned. The organic layer was separated, the solvent was evaporated in vacuo, the residue was purified by silica gel column chromatography, and the title compound (4 mg, 0.020 mmol, 7.9%) was obtained as a white solid.

$^1$H-NMR Spectrum (DMSO-d$_6$) δ(ppm): 2.97 (2H, td, J=6.0, 26.0 Hz), 3.80 (3H, s), 4.77 (2H, td, J=6.0, 47.2 Hz), 6.58 (1H, d, J=8.0 Hz), 7.16 (2H, bs), 8.00 (1H, d, J=8.0 Hz).

Preparation Example A-22

2-Amino-6-(2-fluoro-ethyl)-nicotinic Acid

2-Amino-6-(2-fluoro-ethyl)-nicotinic acid methyl ester (77 mg, 0.387 mmol) was dissolved in an aqueous solution of 2N sodium hydroxide (5 mL) and methanol (5 mL), and the solution was stirred for 20 minutes at room temperature. This mixture solution was neutralized with 5N hydrochloric acid, then, extracted with ethyl acetate. The organic layer was separated, the solvent was evaporated in vacuo, and the title compound (64 mg, 0.348 mmol, 90%/65% purity) was obtained as a white solid.

$^1$H-NMR Spectrum (DMSO-d$_6$) δ(ppm): 2.97 (2H, td, J=6.0, 26.0 Hz), 4.77 (2H, td, J=6.0, 47.2 Hz), 6.57 (1H, d, J=8.0 Hz), 7.98 (1H, d, J=8.0 Hz).

Preparation Example A-23

Tributyl-ethoxymethyl-stannane

The title compound (2.8 g, 8.0 mmol, 67%) was obtained as a colorless oil from chloromethyl ethyl ether (1.1 mL, 12 mmol) according to an analogous method to Preparation Example A-9.

$^1$H-NMR Spectrum (CDCl$_3$) δ(ppm): 0.87-0.92 (15H, m), 1.16 (3H, t, J=7.0 Hz), 1.26-1.35 (6H, m), 1.43-1.55 (6H, m), 3.36 (2H, q, J=7.0 Hz), 3.74 (2H, t, J=6.5 Hz).

Preparation Example A-24

2-Amino-6-ethoxymethyl-nicotinic acid methyl ester

The title compound (0.35 g, 1.7 mmol, 39%) was obtained as a pale yellow solid from tributyl-ethoxymethyl-stannane (2.0 g, 6.3 mmol) described in Preparation Example A-23 and 2-amino-6-chloro-nicotinic acid methyl ester described in Preparation Example A-8 (0.80 g, 4.3 mmol) according to an analogous method to Preparation Example A-10.

$^1$H-NMR Spectrum (CDCl$_3$) δ(ppm):1.28 (3H, t, J=7.0 Hz), 3.61 (2H, q, J=7.0 Hz), 3.88 (3H, s), 4.45 (2H, s), 6.41 (2H, br s), 6.78 (1H, d, J=7.9Hz), 8.13 (1H, d, J=8.10 Hz).

Preparation Example A-25

2-Amino-6-ethoxymethyl-nicotinic Acid

The title compound (180 mg, 0.92 mmol, 57%) was obtained as a pale yellow solid from 2-amino-6-ethoxymethyl-nicotinic acid methyl ester (330 mg, 1.6 mmol) described in Preparation Example A-24 according to an analogous method to Preparation Example A-11.

$^1$H-NMR Spectrum (DMSO-d$_6$) δ(ppm):1.15 (3H, t, J=7.1 Hz), 3.51 (2H, q, J=7.0 Hz), 4.33 (2H, s), 6.64 (1H, d, J=7.9 Hz), 8.02 (1H, d, J=7.9 Hz).

Preparation Example A-26

Tributyl-isopropoxymethyl-stannane

To a mixture of isopropanol (2 mL) and tetrahydrofuran (2 mL) was added sodium hydride (66%, 58 mg, 1.6 mmol) on an ice bath, then, the solution was stirred for 20 minutes at room temperature. To the reaction solution was added a solution of tributyl-iodomethyl-stannane (230 mg, 0.53 mmol), synthesized according to the document (Synthetic Communications, Vol. 24, No. 8, pp. 1117-1120), in tetrahydrofuran (1 mL) dropwise on an ice bath, then, N,N-dimethylformamide (0.5 mL) was added thereto, followed by stirring overnight at room temperature. The reaction solution was partitioned into water (20 mL) and diethyl ether (50 mL). The organic layer was separated, washed with brine, and then, evaporated in vacuo. The residue was purified by neutral silica gel column chromatography (heptane:ethyl acetate=30:1), and the title compound (63 mg, 0.17 mmol, 32%) was obtained as a colorless oil.

$^1$H-NMR Spectrum (CDCl$_3$) δ(ppm): 0.87-0.91 (15H, m), 1.11 (6H, d, J=6.0 Hz), 1.26-1.35 (6H, m), 1.47-1.53 (6H, m), 3.28-3.31 (1H, m), 3.69 (2H, t, J=7.6 Hz).

Preparation Example A-27

Butoxymethyl-tributyl-stannane

The title compound (220 mg, 0.58 mmol, 99%) was obtained as a colorless oil from tributyl-iodomethyl-stannane (250 mg, 0.58 mmol) according to an analogous method to Preparation Example A-26.

$^1$H-NMR Spectrum (CDCl$_3$) δ(ppm): 0.87-0.93 (18H, m), 1.26-1.38 (8H, m), 1.47-1.55 (8H, m), 3.30 (2H, t, J=6.5 Hz), 3.73 (2H, t, J=6.5 Hz).

Preparation Example A-28

Tributyl-propoxymethyl-stannane

The title compound (230 mg, 0.63 mmol, 97%) was obtained as a colorless oil from tributyl-iodomethyl-stannane (280 mg, 0.65 mmol) according to an analogous method to Preparation Example A-26.

$^1$H-NMR Spectrum (CDCl$_3$) δ(ppm): 0.87-0.91 (18H, m), 1.26-1.35 (6H, m), 1.47-1.58 (8H, m), 3.27 (2H, t, J=6.5 Hz), 3.73 (2H, t, J=6.5 Hz).

Preparation Example A+-1

Sodium 4-(((2-Aminopyridine-3-carbonyl)-amino)-methyl)-phenolate

To a solution of 4-hydroxybenzaldehyde (10 g, 81.9 mmol) in methanol (45 mL) was added Raney nickel (3 g) and 7N aqueous ammonia solution (45 mL), and the solution was stirred under hydrogen atmosphere (1 atm) at room temperature for 21 hours. The reaction solution was filtered through Celite pad to remove the catalyst, the filtrate was concentrated, and 4-aminomethyl-phenol (10 g, quantitatively) was obtained as a pale green solid.

Then, a solution of 2-aminonicotinic acid (3.0 g, 21.7 mmol) in N,N-dimethylformamide (30 mL) was cooled with an ice water, 1-hydroxybenzotriazole (3.51 g, 26 mmol), (3-dimethylaminopropyl)-ethyl-carbodiimide (4.04 g, 26 mmol) and a solution of the resulting 4-aminomethyl-phenol (3.0 g, 21.7 mmol) in N,N-dimethylformamide (20 mL) were added, and the solution was stirred for 18 hours at this temperature. The reaction solution was partitioned into brine, the organic layer was dried over anhydrous magnesium sulfate, and the solvent was evaporated. The residue was dissolved in ethyl acetate, filtration was carried out using NH silica gel, and the filtrate was concentrated. The residue was dissolved in methanol (90 mL), 1N sodium hydroxide (17.8 mL, 17.8 mmol) was added thereto, followed by stirring at room temperature for an hour and a half. The reaction solution was concentrated in vacuo, and the title compound (5.66 g) was obtained as a pale yellow solid.

Preparation Example A+-2

(6-Amino-5-((5-(3-fluoro-phenoxy)-thiophene-2-ylmethyl)-carbamoyl)-pyridine-2-yl)-carbamic acid tert-butyl ester To a solution of 6-amino-nicotinic acid (270 mg, 2.0 mmol) and C-(5-(3-fluorophenoxy)thiophen-2-yl)methylamine (400 mg, 1.8 mmol) in N,N-dimethylformamide (10 mL) were added benzotriazole-1-yl-tris(dimethylamino)phosphonium hexafluorophosphate (870 mg, 2.0 mmol) and triethylamine (0.50 mL, 3.6 mmol), and the solution was stirred for 30 minutes at 60° C. Water and ethyl acetate were added to the reaction solution, which was then partitioned, and the organic layer was washed twice with water. Silica gel was added to the organic layer, the solvent was evaporated in vacuo for adsorption, purification was carried out with NH silica gel column chromatography (ethyl acetate, then ethyl acetate:methanol=10:1), and 6-amino-N-(5-(3-fluoro-phenoxy)-thiophen-2-yl)-methylnicotinamide (270 mg, 0.79 mmol, 43.9%) was obtained.

To the resulting 6-amino-N-(5-(3-fluoro-phenoxy)-thiophen-2-yl)-methylnicotinamide (270 mg, 0.79 mmol) were added di-tert-butyldicarbonate (210 mg, 0.94 mmol) and tert-butyl alcohol (15 mL), and the solution was stirred for 16.5 hours at room temperature. NH silica gel was added to the reaction solution, solvent was evaporated in vacuo for adsorption, purification was carried out by NH silica gel column chromatography (hexane:ethyl acetate=4:1 then 1:1), and the title compound (250 mg, 0.54 mmol, 68.3%) was obtained as a white solid.

$^1$H-NMR Spectrum (DMSO-d$_6$) δ(ppm):1.46 (9H, s), 4.52 (2H, d, J=5.6 Hz), 6.55-6.59 (1H, m), 6.78-6.82 (1H, m), 6.88-7.00 (4H, m), 7.36-7.44 (1H, m), 7.85 (1H, d, J=8.8 Hz), 8.15 (1H, d, J=8.8 Hz), 8.70 (1H, s), 9.14 (1H, t, J=5.6 Hz), 10.1 (1H, s).

Preparation Example A+-3

(6-Amino-5-((5-(3-fluoro-phenoxy)-thiophen-2-ylmethyl)-carbamoyl)-pyridin-2-yl)-methyl-carbamic acid tert-butyl ester To a solution of (6-amino-5-((5-(3-fluoro-phenoxy)-thiophen-2-ylmethyl)-carbamoyl)-pyridine-2-yl)-carbamic acid tert-butyl ester described in Preparation Example A+-2 (125 mg, 0.27 mmol) and methyl iodide (43 mg, 0.29 mmol) in N,N-dimethylformamide (5 mL) was added sodium hydride (12 mg, 0.29 mmol, 60% in oil) on an ice bath, and the solution was stirred for 1 hour at room temperature. NH silica gel was added to the reaction solution, the solvent was evaporated in vacuo for adsorption, purification was carried out by NH silica gel column chromatography (hexane:ethyl acetate=4:1 then 2:1), and the title compound (87 mg, 0.19 mmol, 70.5%) was obtained as a colorless oil.

$^1$H-NMR Spectrum (DMSO-d$_6$) δ(ppm):1.46 (9H, s), 3.31 (3H, s), 4.53 (2H, d, J=5.6 Hz), 6.57 (1H, d, J=3.6 Hz), 6.81 (1H, d, J=3.6 Hz), 6.86-7.00 (3H, m), 7.36-7.44 (1H, m), 7.76

(1H, d, J=8.8 Hz), 8.14 (1H, dd, J=2.0, 8.8 Hz), 8.80 (1H, d, J=2.0 Hz), 9.22 (1H, t, J=5.6 Hz).

Preparation Example A+-4

(6-Amino-5-((5-benzyl-thiophen-2-ylmethyl)-carbamoyl)-pyridine-2-yl)-carbamoylmethyl-carbamic acid tert-butyl ester To a solution of 6-aminonicotinic acid (340 mg, 2.4 mmol) and C-(5-benzyl-thiophen-2-yl)-methylamine described in Preparation Example 42 (450 mg, 2.2 mmol) in N,N-dimethylformamide (5 mL) were added benzotriazol-1-yl-tris(dimethylamino)phosphonium hexafluorophosphate (1.1 g, 2.4 mmol) and triethylamine(0.62 mL, 4.4 mmol), and the solution was stirred at 60° C. for 1 hour. Water and ethyl acetate were added to the reaction solution, which was then partitioned, and the organic layer was washed twice with water. Silica gel was added to the organic layer, the solvent was evaporated in vacuo adsorption, purification was carried out by NH silica gel column chromatography (hexane:ethyl acetate=1:1, then ethyl acetate, then ethyl acetate:methanol=10:1), and 6-amino-N-(5-benzyl-thiophen-2-ylmethyl)-nicotinamide (210 mg, 0.65 mmol, 29.5%) was obtained.

Then, according to an analogous method to Preparation Example A+-2, from the resulting 6-amino-N-(5-benzyl-thiophen-2-ylmethyl)-nicotinamide (210 mg, 0.65 mmol), (5-((5-benzyl-thiophen-2-ylmethyl)-carbamoyl)-pyridin-2-yl)-carbamic acid tert-butyl ester (120 mg, 0.28 mmol, 43.0%) was obtained as a colorless oil.

To a solution of this oil (60 mg, 0.14 mmol) in N,N-dimethylformamide (5 mL) were added sodium hydride (6.8 mg, 0.14 mmol, 60% in oil) and bromoacetamide (23 mg, 0.16 mmol), and the solution was stirred for 25 hours room temperature. Water and ethyl acetate were added to the reaction solution, which was then partitioned, the organic layer was evaporated in vacuo, the residue was purified by NH silica gel column chromatography (hexane:ethyl acetate=1:1, then ethyl acetate, then ethyl acetate:methanol=20:1), and the title compound (23 mg, 0.047 mmol, 33.5%) was obtained as a colorless oil.

$^1$H-NMR Spectrum (DMSO-$d_6$) δ(ppm):1.43 (9H, s), 4.04 (2H, s), 4.49-4.54 (4H, m), 6.69 (1H, d, J=3.6 Hz), 6.79 (1H, d, J=3.6 Hz), 6.94 (1H, s), 7.16-7.30 (5H, m), 7.38 (1H, s), 7.87 (1H, d, J=8.8 Hz), 8.10-8.16 (1H, m), 8.68-8.73 (1H, m), 9.13 (1H, t, J=5.6 Hz).

Preparation Example A+-5

6-Chloro-N-(1-(3-fluoro-benzyl)-1H-pyrrol-3-ylmethyl)-nicotinamide 6-chloro-nicotinic acid (100 mg, 0.58 mmol), triethylamine (0.194 mL, 1.39 mmol) and benzotriazol-1-yloxytris (dimethylamino)phosphonium hexafluorophosphate (308 mg, 0.696 mmol) were dissolved in N,N-dimethylformamide (3 mL), C-(1-(3-fluoro-benzyl)-1H-pyrrol-3-yl)-methylamine (142 mg, 0.695 mmol) described in Preparation Example 59 was added, and the solution was stirred for 15 hours 10 minutes at room temperature. After the reaction was completed, the reaction solution was poured into brine, and the solution was extracted with ethyl acetate. The organic layer was dried over anhydrous magnesium sulfate, then the solution was concentrated, the resulting residue was purified by NH silica gel column chromatography (ethyl acetate:hexane=1:1), and the title compound (0.14 g, 0.39 mmol, 67%) was obtained.

$^1$H-NMR Spectrum (CDCl$_3$) δ(ppm): 4.42 (2H, d, J=4.8 Hz), 5.02 (2H, s), 5.99-6.09 (1H, m), 6.16-6.18 (1H, m), 6.56 (1H, d, J=8.0 Hz), 6.57 (1H, brs), 6.64-6.68 (2H, m), 6.78-6.83 (1H, m), 6.91-6.94 (1H, m), 6.96-7.02 (1H, m), 7.27-7.33 (1H, m), 7.49 (1H, d, J=8.0 Hz).

Preparation Example A+-6

2-(Ethoxymethyl-amino)-N-(5-phenoxy-thiophen-2-ylmethyl)-nicotinamide

To a solution of 2-aminonicotinic acid (3245 mg, 23.49 mmol) in N,N-dimethylformamide (200 mL) were added C-(5-phenoxy-thiophen-2-yl)methylamine (5305 mg, 25.84 mmol) described in Preparation Example 24, benzotriazol-1-yloxytris(dimethylamino)phosphonium hexafluorophosphate (12.49 g, 28.19 mmol) and triethylamine (7.86 mL, 56.38 mmol), and the solution was stirred for 2 days at room temperature. Water was added to the reaction mixture, which was then extracted with ethyl acetate, the organic layer was sequentially washed with an aqueous solution of saturated sodium bicarbonate, water, then brine, the solvent was evaporated in vacuo, and 2-amino-N-(5-phenoxy-thiophen-2-ylmethyl)-nicotinamide (4999 mg, 15.36 mmol, 65%) was obtained as crude product.

To a solution of the resulting 2-amino-N-(5-phenoxy-thiophen-2-ylmethyl)-nicotinamide (602 mg, 1.85 mmol) in ethanol (40 mL) were added 5,5-dimethylhydantoin (260 mg, 2.04 mmol), 37% formic acid aqueous solution (3.00 mL, 23.6 mmol), and the solution was stirred under reflux for 1 hour. Water was added to the reaction mixture, which was then extracted with ethyl acetate, the organic layer was sequentially washed with water and brine, dried over anhydrous sodium sulfate, and then, evaporated in vacuo. The resulting residue was purified by silica gel chromatography (hexane-ethyl acetate), and the title compound (430 mg, 1.12 mmol, 61%) was obtained.

$^1$H-NMR Spectrum (DMSO-$d_6$) δ(ppm):1.03 (3H, t, J=6.8 Hz), 3.41 (2H, q, J=6.8 Hz), 4.48 (2H, d, J=5.6 Hz), 4.90 (2H, d, J=7.2 Hz), 6.49 (1H, d, J=3.6 Hz), 6.68 (1H, dd, J=4.8, 7.6 Hz), 6.77 (1H, d, J=3.6 Hz), 7.06-7.14 (3H, m), 7.33-7.38 (2H, m), 7.94 (1H, dd, J=1.6, 7.6 Hz), 8.19 (1H, dd, J=1.6, 4.8 Hz), 8.91 (1H, t, J=7.2 Hz), 9.16-9.20 (1H, m).

Preparation Example A+-7

2-Chloro-N-(5-phenoxy-thiophen-2-ylmethyl)-nicotinamide

To a solution of 2-chloro nicotinic acid (1182 mg, 7.50 mmol) in N,N-dimethylformamide (3 mL) were added C-(5-phenoxy-thiophen-2-yl)methylamine described in Preparation Example 24 (1693 mg, 8.25 mmol), benzotriazol-1-yloxy tris(dimethylamino)phosphonium hexafluorophosphate (3987 mg, 9.0 mmol) and triethylamine (2.5 mL, 18.0 mmol), and the solution was stirred at 60° C. for 2 days. Water was added to the reaction mixture, which was then extracted with ethyl acetate, and then concentrated. The residue was purified by silica gel column chromatography, and the title compound (1181 mg, 3.43 mmol, 46%) was obtained.

$^1$H-NMR Spectrum (DMSO-$d_6$) δ(ppm): 4.51 (2H, d, J=5.2 Hz), 6.52 (1H, d, J=3.6 Hz), 6.80 (1H, d, J=3.6 Hz), 7.07-7.16 (3H, m), 7.30-7.45 (2H, m), 7.47 (1H, dd, J=4.8, 7.6 Hz), 7.87 (1H, dd, J=1.6, 7.6 Hz), 8.46 (1H, dd, J=1.6, 4.8 Hz), 9.20 (1H, t, J=5.2 Hz).

Preparation Example A+-8

N-(4-Benzyloxy-benzyl)-6-(ethoxymethyl-amino)-nicotinamide

To a solution of 6-aminonicotinic acid (130 mg, 0.941 mmol) and 4-benzyloxy-benzylamine (201 mg, 0.941 mmol) described in Preparation Example 1 in N,N-dimethylformamide (5 mL), was added benzotriazol-1-yl-tris(dimethylamino)phosphonium hexafluorophosphate (624 mg, 1.41 mmol) and triethylamine (394 µl, 2.82 mmol), and the solution was stirred for 40 minutes at 80° C. Water and ethyl acetate were added to the reaction solution, which was then partitioned, and the organic layer was washed twice with water. The solvent was evaporated in vacuo, ethyl acetate was added to the residue, a white insoluble matter was collected by filtration, and 6-amino-N-(4-benzyloxy-benzyl)-nicotinamide (202 mg, 0.606 mmol, 64%) was obtained.

To a solution of the resulting 6-amino-N-(4-benzyloxy-benzyl)-nicotinamide (200 mg, 0.556 mmol) in ethanol (10 mL) were added 5,5-dimethylimidazophospho-2,4-dione (85 mg, 0.66 mmol) and 37% formaldehyde aqueous solution (1 mL), and the solution was stirred for 1 hour under reflux. Water and ethyl acetate were added to the reaction solution, which was then partitioned, and the organic layer was washed twice. NH silica gel was added to the organic layer, the solvent was evaporated in vacuo for adsorption, purification was carried out by NH silica gel column chromatography (ethyl acetate), and the title compound (95 mg, 0.243 mmol, 40%) was obtained as a white solid.

$^1$H-NMR Spectrum (CDCl$_3$) δ(ppm):1.20 (3H, t, J=7.0 Hz), 3.55 (2H, q, J=7.0 Hz), 4.56 (2H, d, J=5.5 Hz), 4.84 (2H, s), 5.07 (2H, s), 5.68 (1H, brs), 6.14 (1H, brs), 6.62 (1H, d, J=8.8 Hz), 6.96 (2H, d, J=8.8 Hz), 7.22-7.35 (4H, m), 7.27-7.44 (3H, m), 7.93 (1H, dd, J=2.4, 8.8 Hz), 8.54 (1H, d, J=2.4 Hz).

Preparation Example A+-9

2-Amino-5-nitro-N-(5-phenoxy-thiophen-2-ylmethyl)-nicotinamide

2-Amino-5-nitro-nicotinic acid methyl ester (48.4 mg, 0.245 mmol) described in Preparation Example A-3 and lithium hydroxide monohydrate (10.3 mg, 0.245 mmol) were dissolved in a solvent mixture of tetrahydrofuran (1 mL), methanol (0.1 mL) and water (0.1 mL), and the solution was stirred for 17 hours at room temperature. The solvent was evaporated in vacuo, and 2-amino-5-nitro-nicotinic acid was obtained as a lithium salt.

Then, the resulting lithium salt of 2-amino-5-nitro-nicotinic acid, C-(5-phenoxy-thiophen-2-yl)-methylamine (60 mg, 0.29 mmol), benzotriazol-1-yl-tris(dimethylamino) phosphonium hexafluorophosphate (162 mg, 0.367 mmol) and triethylamine (103 µl, 0.735 mmol) were dissolved in N,N-dimethylformamide (2.0 mL), and the solution was stirred for 6 hours at room temperature. Water was added to the reaction solution, which was then extracted with ethyl acetate, and the organic layer was washed with water and brine. The solvent was evaporated in vacuo, the residue was purified by silica gel column chromatography (hexane:ethyl acetate=1:1), and the title compound (87 mg, 0.24 mmol, 96%) was obtained as a pale yellow solid.

$^1$H-NMR Spectrum (DMSO-d$_6$) δ(ppm): 4.49 (2H, d, J=5.5 Hz), 6.50 (1H, d, J=3.7 Hz), 6.80 (1H, d, J=3.1 Hz), 7.08 (2H, d, J=7.7 Hz), 7.13 (1H, t, J=7.5 Hz), 7.37 (2H, t, J=7.5 Hz), 8.76 (1H, d, J=2.2 Hz), 8.96 (1H, d, J=1.7 Hz), 9.51 (1H, t, J=5.5 Hz).

Preparation Example A+-10

2,5-Diamino-N-(5-phenoxy-thiophen-2-ylmethyl)-nicotinamide

2-Amino-5-nitro-N-(5-phenoxy-thiophen-2-ylmethyl)-nicotinamide (74 mg, 0.20 mmol) described in Preparation Example A+-9, an iron powder (56 mg, 1.0 mmol) and ammonium chloride (21 mg, 0.40 mmol) were suspended in a solvent mixture of ethanol (2 mL) and water (0.5 mL), the solution was stirred at 60° C. for 3 hours, then, it was stirred at 90° C. for 6 hours. The reaction solution was cooled to room temperature, then, it was filtered through Celite pad. The filtrate was evaporated in vacuo, the residue was purified by reverse phase high performance liquid chromatography (acetonitrile-water:mobile phase (containing 0.1% trifluoroacetic acid) was used), and the title compound (54.4 mg) was obtained as a trifluoroacetic acid salt.

MS m/e (ESI) 341.26(MH$^+$)

Preparation Example A+-11

2-Amino-6-chloro-N-(5-phenoxy-thiophen-2-ylmethyl)-nicotinamide

2-Amino-6-chloro-nicotinic acid (400 mg, 2.31 mmol) described in Preparation Example A-1 was dissolved in N,N-dimethylformamide (10 mL), triethylamine (0.78 mL, 5.6 mmol), benzotriazol-1-yloxytris(dimethylamino)phosphonium hexafluorophosphate (1.23 g, 2.8 mmol) and C-(5-phenoxy-thiophen-2-yl)-methylamine (572 mg, 2.8 mmol) described in Preparation Example 35 were added thereto, and the solution was stirred for 13 hours 30 minutes at room temperature. After the reaction was completed, the reaction solution was poured into brine, and the solution was extracted with ethyl acetate. The organic layer was dried over anhydrous magnesium sulfate, then concentrated, the resulting residue was purified by silica gel column chromatography (ethyl acetate:hexane=1:1), and the title compound (380 mg, 1.05 mmol, 46%) was obtained.

$^1$H-NMR Spectrum (DMSO-d$_6$) δ(ppm): 4.47 (2H, d, J=6.0 Hz), 6.50 (1H, d, J=4.0 Hz), 6.64 (1H, d, J=8.0 Hz), 6.78 (1H, d, J=4.0 Hz), 7.07-7.17 (3H, m), 7.36-7.41 (2H, m), 7.53 (2H, brs), 7.93 (1H, d, J=8.0 Hz), 9.11 (1H, t, J=6.0 Hz).

Preparation Example A+-12

2-Amino-6-(2-amino-ethylamino)-N-(5-phenoxy-thiophen-2-ylmethyl)-nicotinamide

2-Amino-6-chloro-N-(5-phenoxy-thiophen-2-ylmethyl)-nicotinamide (150 mg, 0.417 mmol) described in Preparation Example A+-11, ethane-1,2-diamine (418 µl, 6.25 mmol) were dissolved in a mixture solution of dimethylsulfoxide (2 mL) and N,N-diisopropylethylamine (1 mL), and the solution was stirred at 120° C. for 15 hours. The reaction solution was cooled to room temperature, water was added, then extracted with ethyl acetate and tetrahydrofuran, the organic layer was washed with brine and dried over anhydrous magnesium sulfate. The solvent was evaporated in vacuo, tetrahydrofuran and NH silica gel were added to the residue, the solvent was evaporated in vacuo adsorption, purification was carried out by NH silica gel column chromatography (ethyl acetate:

methanol=10:1), and the title compound (95 mg, 0.25 mmol, 59%) was obtained as a white solid.

$^1$H-NMR Spectrum (DMSO-d$_6$) δ(ppm): 2.64 (2H, t, J=6.4 Hz), 3.16-3.22 (2H, m), 4.41 (2H, d, J=5.7 Hz), 5.70 (1H, d, J=8.6 Hz), 6.48 (1H, d, J=3.8 Hz), 6.67 (1H, brs), 6.72 (1H, d, J=3.8 Hz), 7.02 (2H, s), 7.08 (2H, d, J=8.6 Hz), 7.14 (1H, t, J=7.32 Hz), 7.38 (2H, dd, J=7.3, 8.6 Hz), 7.59 (1H, d, J=8.6 Hz), 8.38 (1H, t, J=5.7 Hz).

Preparation Example A+-13

2-Amino-6-(2-(4-nitro-phenylamino)-ethylamino)-N-(5-phenoxy-thiophen-2-ylmethyl)-nicotinamide 2-Amino-6-(2-amino-ethylamino)-N-(5-phenoxy-thiophen-2-ylmethyl)-nicotinamide (25 mg, 65 µmol) described in Preparation Example A+-12, 4-fluoronitrobenzene (7.6 µl, 71 µmol) and N,N-diisopropylethylamine (22.7 µl, 130 µmol) were dissolved in dimethylsulfoxide (0.5 mL), the solution was stirred for 3.5 hours at room temperature, and then, the solution was stirred for 15.5 hours at 70° C. The reaction solution was cooled to room temperature, water was added, the solution was extracted with ethyl acetate, the organic layer was washed with brine and dried over anhydrous magnesium sulfate. The solvent was evaporated in vacuo, residue was purified by reverse phase high performance liquid chromatography (mobile phase:acetonitrile-water (containing 0.1% trifluoroacetic acid) was used), and the title compound (23 mg) was obtained as a trifluoroacetic acid salt.

MS m/e (ESI) 505.37(MH$^+$)

Preparation Example A+-14

2-Amino-6-(1-ethoxyvinyl)-N-(5-phenoxy-thiophen-2-ylmethyl)-nicotinamide

1-Ethoxyvinyl(tri-n-butyl)tin (0.47 mL, 1.4 mmol) was added to a mixture of 2-amino-6-chloro-N-(5-phenoxy-thiophen-2-ylmethyl)-nicotinamide (170 mg, 0.46 mmol) described in Preparation Example A+-11, tetrakis(triphenylphosphine)palladium(0) (54 mg, 0.046 mmol) and xylene (5 mL), and the solution was stirred for 2.5 hours at 130° C. After cooling, water and ethyl acetate were added to the reaction solution for extraction, and the solution was washed with brine. The solvent was evaporated in vacuo, then, the residue was purified by NH silica gel column chromatography (hexane:ethyl acetate=2:1), and the title compound (150 mg, 0.38 mmol, 82%) was obtained as a pale yellow solid.

$^1$H-NMR Spectrum (DMSO-d$_6$) δ(ppm):1.42 (3H, t, J=7.0 Hz), 3.93 (2H, q, J=7.0 Hz), 4.35 (1H, d, J=1.8 Hz), 4.65 (2H, d, J=5.3 Hz), 5.37 (1H, d, J=1.8 Hz), 6.30-6.32 (3H, m), 6.39 (1H, d, J=3.7 Hz), 6.74 (1H, d, J=3.8 Hz), 7.00 (1H, d, J=8.1 Hz), 7.08-7.13 (3H, m), 7.30-7.35 (2H, m), 7.59 (1H, d, J=8.1 Hz).

Preparation Example A+-15

2-Amino-N-(5-phenoxy-thiophen-2-ylmethyl)-6-tributylstanyl-nicotinamide

To a mixture of 2-amino-6-chloro-N-(5-phenoxy-thiophen-2-ylmethyl)-nicotinamide (1.1 g, 3.0 mmol) described in Preparation Example A+-11, tetrakis(triphenylphosphine)palladium(0) (170 mg, 0.15 mmol) and xylene (5 mL) was added bis(tri n-butyl tin) (9.1 mL, 18 mmol), and the solution was stirred at 135° C. for 2 hours. After cooling, the reaction solution was directly purified by neutral silica gel column chromatography (hexane:ethyl acetate=3:1), then, the resulting crude product was washed with hexane cooled to 0° C. to obtain the title compound (600 mg, 0.98 mmol, 33%) as a colorless oil.

$^1$H-NMR Spectrum (CDCl$_3$) δ(ppm): 0.86-0.90 (9H, m), 1.05-1.09 (6H, m), 1.27-1.36 (6H, m), 1.50-1.58 (6H, m), 4.64 (1H, d, J=5.5 Hz), 6.26-6.30 (4H, m), 6.38 (1H, d, J=3.8 Hz), 6.73-6.74 (2H, m), 7.08-7.12 (3H, m), 7.31-7.36 (3H, m).

Preparation Example A+-16

2-Amino-5-iodo-N-(5-phenoxy-thiophene-2-ylmethyl)-nicotinamide

2-Amino-N-(5-phenoxy-thiophen-2-ylmethyl)-nicotinamide (250 mg, 0.768 mmol) obtained from 2-aminonicotinic acid and C-(5-phenoxy-thiophen-2-yl)methylamine described in Preparation Example 24 according to an analogous method to Preparation Example A+-5, and N-iodosuccinimide (190 mg, 0.845 mmol) were dissolved in tetrahydrofuran (5 mL), and the solution was stirred for 16 hours at room temperature. An aqueous solution of saturated sodium bicarbonate was added to the reaction solution at 0° C., which was then extracted with ethyl acetate, the organic layer was washed with brine and dried over anhydrous magnesium sulfate. The solvent was evaporated in vacuo, residue was purified by NH silica gel column chromatography (hexane:ethyl acetate=1:1), and title compound (45 mg, 0.10 mmol, 13%) was obtained as a pale yellow solid.

$^1$H-NMR Spectrum (DMSO-d$_6$) δ(ppm) 4.45 (2H, d, J=5.7 Hz), 6.49 (1H, d, J=3.7 Hz), 6.77 (1H, d, J=3.8 Hz), 7.08 (2H, d, J=7.7 Hz), 7.13 (1H, t, J=7.3 Hz), 7.23 (2H, s), 7.37 (2H, t, J=7.3 Hz), 8.15 (1H, d, J=2.2 Hz), 8.21 (1H, d, J=1.8 Hz), 9.13 (1H, d, J=5.7 Hz).

Preparation Example A+-17

2-Amino-N-(3-hydroxybenzyl)-nicotinamide

The title compound (0.63 g, 2.6 mmol, 53%) was obtained as a white solid from 3-aminomethylphenol (0.60 g, 4.9 mmol) described in Preparation Example 130 and 2-aminonicotinic acid (0.67 g, 4.9 mmol) according to an analogous method to Preparation Example Q+-1.

$^1$H-NMR Spectrum (DMSO-d$_6$) δ(ppm): 4.34 (2H, d, J=5.9 Hz), 6.56-6.61 (2H, m), 6.69-6.71 (2H, m), 7.06-7.10 (3H, m), 7.93 (1H, dd, J=1.8, 7.8 Hz), 8.06 (1H, dd, J=1.8, 4.8 Hz), 8.91 (1H, t, J=6.0 Hz), 9.30 (1H, s).

Preparation Example A+-18

2-Amino-N-(4-benzyloxy-benzyl)-6-chloro-nicotinamide

The title compound (0.43 g, 1.2 mmol, 28%) was obtained as a white solid from 14-benzyloxy-benzylamine (0.90 g, 4.2 mmol) described in Preparation Example and 2-amino-6-chloro-nicotinic acid (1.5 g, 8.4 mmol) described in Preparation Example A-1 (or A-4) according to an analogous method to Preparation Example Q+-1.

$^1$H-NMR Spectrum (DMSO-d$_6$) δ(ppm): 4.33 (2H, d, J=5.7 Hz), 5.06 (2H, s), 6.61 (1H, d, J=8.1 Hz), 6.94 (2H, d, J=8.6 Hz), 7.20 (2H, d, J=8.4 Hz), 7.28-7.31 (1H, m), 7.34-

Preparation Example A+-19

5-Bromo-thiophene-2-carbaldehyde oxime

To a mixture of 2-bromo-5-formylthiophene (2.5 mL, 21 mmol) and pyridine (25 mL) was added hydroxylamine hydrochloride (2.2 g, 32 mmol) on an ice bath, then, the solution was stirred overnight at room temperature. This reaction mixture was concentrated in vacuo, then, partitioned with water (50 mL), ethyl acetate (50 mL) then 1N hydrochloric acid solution (50 mL). The organic layer was separated, sequentially washed with an aqueous solution of saturated sodium bicarbonate and brine, and then, dried over anhydrous magnesium sulfate. The solvent was evaporated in vacuo, the residue was washed with heptane-ethyl acetate (30:1), and the title compound (4.3 g, 21 mmol, 98%) was obtained as a light brown solid.

$^1$H-NMR Spectrum (CDCl$_3$) δ(ppm): 7.07 (1H, d, J=4.0 Hz), 7.11 (1H, d, J=4.0 Hz), 7.62 (1H, s), 8.35 (1H, br s).

Preparation Example A+-20

5-Bromo-thiophene-2-carbonitrile

To a mixture of 5-bromo-thiophene-2-carbaldehyde oxime described in Preparation Example A+-19 (1.3 g, 6.2 mmol) and tetrahydrofuran (15 mL) were acetic acid (1.4 mL, 25 mmol) and acetic anhydride (1.5 mL, 15 mmol) at room temperature, then, stirred at 50° C. for 2 hours, and further stirred at 70° C. for 8 hours. After cooling this reaction mixture, the solution was concentrated in vacuo. The residue was purified by NH-silica gel column chromatography (heptane:ethyl acetate=8:1), and the title compound (1.0 g, 5.4 mmol, 88%) was obtained as a colorless solid.

$^1$H-NMR Spectrum (CDCl$_3$) δ(ppm): 7.11 (1H, d, J=4.0 Hz), 7.40 (1H, d, J=4.0 Hz).

Preparation Example A+-21

C-(5-Bromo-thiophen-2-yl)-methylamine

To a mixture of lithium aluminum hydride (1.6 g, 41 mmol) and tetrahydrofuran (45 mL) was aluminum chloride (6.1 g, 46 mmol) on an ice bath, then, the solution was stirred for 1 hour at room temperature. The reaction solution was cooled to −20° C., a solution of 5-bromo-thiophene-2-carbonitrile described in Preparation Example A+-20 (4.3 g, 25 mmol) in tetrahydrofuran (5 mL) was added dropwise at the same temperature. After stirring at 2° C. for 20 minutes, the reaction solution was cooled to −10° C., and while maintaining the internal temperature at 0° C. or lower, tetrahydrofuran (300 mL) and 28% aqueous ammonia solution (5 mL) were added thereto. Anhydrous magnesium sulfate was added to the reaction solution, which was then filtered using a filter paper, and then, concentrated in vacuo. The residue was purified by NH-silica gel column chromatography (ethyl acetate), and the title compound (840 mg, 4.4 mmol, 85%) was obtained as a colorless oil.

$^1$H-NMR Spectrum (CDCl$_3$) δ(ppm): 3.99 (2H, s), 6.67 (1H, d, J=3.7 Hz), 6.88 (1H, d, J=3.7 Hz).

Preparation Example A+-22

2-Amino-N-(5-bromo-thiophen-2-ylmethyl)-6-methoxymethyl-nicotinamide

To a solution of C-(5-bromo-thiophen-2-yl)-methylamine (250 mg, 1.3 mmol) in N,N-dimethylformamide (5 mL) were added tiethylamine (0.54 mL, 3.9 mmol), 2-amino-6-methoxymethyl-nicotinic acid (240 mg, 1.3 mmol) described in Preparation Example A-11, and benzotriazol-1-yloxytris(dimethylamino)phosphonium hexafluorophosphate (690 mg, 1.6 mmol) sequentially on an ice bath, then, the solution was stirred for 2 days at room temperature. The reaction solution was partitioned in water and ethyl acetate. The organic layer was separated, the solvent was evaporated in vacuo. The residue was purified by silica gel column chromatography (heptane:ethyl acetate=4:1), and the title compound (370 mg, 1.0 mmol, 79%) was obtained as a white solid.

$^1$H-NMR Spectrum (CDCl$_3$) δ(ppm): 3.46 (3H, s), 4.40 (2H, s), 4.67 (2H, d, J=5.7 Hz), 6.33 (1H, br s), 6.38 (2H, br s), 6.71 (1H, d, J=7.9 Hz), 6.79 (1H, d, J=3.7 Hz), 6.91 (1H, d, J=3.9 Hz), 7.59 (1H, d, J=7.9 Hz).

Preparation Example A+-23

2-Amino-N-(4-bromo-benzyl)-6-methoxymethyl-nicotinamide

The title compound (1.9 g, 5.4 mmol, 86%) was obtained as a pale yellow solid from 2-amino-6-methoxymethyl-nicotinic acid (1.2 g, 6.3 mmol) described in Preparation Example A-11 and 4-bromobenzylamine hydrochloride (1.5 g, 6.9 mmol) according to an analogous method to Preparation Example A+-22.

$^1$H-NMR Spectrum (CDCl$_3$) δ(ppm): 4.46 (3H, s), 4.40 (2H, s), 4.55 (2H, d, J=5.7 Hz), 6.30 (1H, br s), 6.39 (2H, br s), 6.70 (1H, d, J=7.9 Hz), 7.22 (2H, d, J=8.2 Hz), J=8.4 Hz), 7.60 (1H, d, J=7.9 Hz).

Preparation Example A+-24

2-Amino-N-(4-((Z)-2-ethoxy-vinyl)-benzyl)-6-methoxymethyl-nicotinamide

A mixture of (2-ethoxy-vinyl)-tributyl-stannane (37 mg, 0.10 mmol) synthesized according to WO02/018368, 2-amino-N-(4-bromo-benzyl)-6-methoxymethyl-nicotinamide (30 mg, 0.086 mmol) described in Preparation Example A+-23, tri-o-tolylphosphine (6.5 mg, 0.021 mmol), palladium acetate (0.96 mg, 0.0043 mmol), tetrabutylammonium chloride (24 mg, 0.086 mmol) and N-methylpyrrolidinone (1 mL) was stirred at 125° C. for 1 hour. The reaction solution was allowed to cool, an aqueous solution of potassium fluoride was added on an ice bath, the solution was filtered through Celite pad. The filtrate was partitioned with ethyl acetate. The organic layer was separated, washed with brine, then, evaporated in vacuo. The residue was purified by silica gel column chromatography (heptane:ethyl acetate=1:2), and the title compound (12 mg, 0.035 mmol, 35%) was obtained as a colorless solid.

$^1$H-NMR Spectrum (CDCl$_3$) δ(ppm):1.36 (3H, d, J=7.1 Hz), 3.45 (3H, s), 3.99 (2H, q, J=7.1 Hz), 4.39 (2H, s), 4.55 (2H, d, J=5.5 Hz), 5.21 (1H, d, J=7.0 Hz), 6.21-6.23 (2H, m), 6.40 (2H, br s), 6.68 (1H, d, J=7.9 Hz), 7.26 (2H, d, J=8.3 Hz), 7.57-7.59 (3H, m).

(First line continuing from previous page:)
7.38 (2H, m), 7.41 (2H, d, J=7.5 Hz), 7.49 (2H, brs), 7.95 (1H, d, J=8.1 Hz), 8.92-8.95 (1H, m).

Preparation Example A+-25

2-Amino-6-methoxymethyl-N-(3-hydroxybenzyl)-nicotinamide

2-Amino-6-methoxymethylcotinic acid (500 mg, 2.74 mmol), 3-hydroxybenzylamine (405 mg, 3.29 mmol), benzotriazol-1-yloxytris(dimethylamino)phosphonium hexafluorophosphate (1.33 mg, 3.01 mmol) and triethylamine (555 mg, 5.48 mmol) were added to dimethylsulfoxide (20 mL), and the solution was stirred for 15 minutes at 60° C. Water and ethyl acetate were added to the reaction mixture, which was then partitioned. The aqueous layer was extracted once with ethyl acetate, the ethyl acetate layers were combined and the solvent was evaporated in vacuo. The residue was purified by silica gel column chromatography (hexane:ethyl acetate=1:1, then ethyl acetate). The resulting residue was purified by NH silica gel column chromatography (ethyl acetate). The resulting residue was solidified from hexane-ethyl acetate, and the title compound (490 mg, 1.71 mmol, 62.2%) was obtained as a pale yellow solid.

$^1$H-NMR Spectrum (DMSO-$d_6$) δ(ppm): 3.34 (3H, s), 4.30 (2H, s), 4.35 (2H, d, J=6.0 Hz), 6.61 (2H, d, J=8.0 Hz), 6.70 (1H, s), 6.71 (1H, d, J=8.0 Hz), 7.10 (1H, dd, J=8.0, 8.0 Hz), 7.13 (2H, brs), 7.99 (1H, d, J=8.0 Hz), 8.91 (1H, t, J=6.0 Hz), 9.31 (1H, s).

Preparation Example A+-26

2-Amino-6-methoxymethyl-N-(4-hydroxybenzyl)-nicotinamide

The title compound (506 mg, 1.76 mmol, 64.3%) was obtained as a pale yellow solid from 2-amino-6-methoxymethylcotinic acid (500 mg, 2.74 mmol) and 4-hydroxybenzylamine (506 mg, 4.11 mmol) according to an analogous method to Preparation Example A+-25.

$^1$H-NMR Spectrum (DMSO-$d_6$) δ(ppm): 3.34 (3H, s), 4.29 (2H, s), 4.30 (2H, d, J=6.0), 6.59 (1H, d, J=7.6 Hz), 6.70 (2H, d, J=7.4 Hz), 7.10 (2H, d, J=7.4 Hz), 7.12 (2H, brs), 7.95 (1H, d, J=7.6 Hz), 8.84 (1H, t, J=6.0 Hz), 9.27 (1H, s).

Preparation Example AA-1

3,5-Diamino-pyrazine-2-carboxylic acid methyl ester

To a solution of 3,5-diamino-6-chloro-pyrazine-2-carboxylic acid methyl ester (8.00 g, 39.5 mmol) in tetrahydrofuran (150 mL) were added tetrakis(triphenylphosphine)palladium(0) (2.28 g, 1.98 mmol), formic acid (2.24 mL, 59.3 mmol) and triethylamine (16.5 mL, 119 mmol) at 0° C. under nitrogen atmosphere, then, the solution was stirred at 125° C. for 12 hours. The reaction solution was cooled to room temperature, and a solid precipitated. This solid was collected by filtration, and the title compound (10.7 g, quantitatively) was obtained as a crude product of a white solid.

$^1$H-NMR Spectrum (DMSO-$d_6$) δ(ppm): 3.70 (3H, s), 6.95 (2H, brs), 7.21 (1H, s).

Preparation Example M-2

3.5-Diamino-pyrazine-2-carboxylic Acid

Lithium hydroxide monohydrate (2.50 g, 59.5 mmol) was added to 3,5-diamino-pyrazine-2-carboxylic acid methyl ester (10.0 g, 59.5 mmol) described in Preparation Example AA-1 in a mixture solvent of tetrahydrofuran (100 mL), methanol (10 mL) and water (10 mL) at room temperature. The solution was stirred at room temperature for 17 hours, then, an aqueous solution of 5N sodium hydroxide (15 mL) was added thereto, followed by further stirring for 4.5 hours under reflux. The reaction solution was cooled to room temperature, and partitioned in 5N hydrochloric acid solution and ethyl acetate. The organic layer was separated, washed with brine, and then, dried over anhydrous magnesium sulfate. The organic layer was filtered, then, the solvent was evaporated in vacuo, and the title compound (3.34 g, 36%) was obtained as a crude product of a white solid.

$^1$H-NMR Spectrum (DMSO-$d_6$) δ(ppm): 6.93 (2H, brs), 7.20 (1H, s).

Preparation Example B-1

4-Amino-5-hydroxy-carbonyl-2-n-propylamino-pyrimidine

4-Amino-2-chloro-5-cyano-pyrimidine (300 mg, 1.94 mmol) and n-propyl amine (5 g, 84.6 mmol) were mixed and stirred for 10 minutes at 60° C. The reaction solution was directly purified by silica gel column chromatography, and a 2-propylamino compound (300 mg, 1.69 mmol, 101%) was obtained as a brown solid. This solid was suspended in concentrated sulfuric acid (3 mL) and water (3 mL), and the solution was stirred for 1.5 hours at 130° C. This mixture was alkalinized with an aqueous solution of saturated sodium bicarbonate, then, the aqueous layer was washed with ethyl acetate. Then, this aqueous layer was neutralized with citric acid, and extracted with a mixture solvent of acetate-methanol. This organic layer was separated, then, the solvent was evaporated, and the title compound (44 mg, 0.224 mmol, 12%) was obtained as a white solid.

$^1$H-NMR Spectrum (DMSO-$d_6$) δ(ppm): 0.87 (3H, t, J=7.2 Hz), 1.49 (2H, qt, J=7.2, 7.2 Hz), 3.18 (2H, q, J=7.2 Hz), 6.98 (2H, bs), 8.14 (1H, bs), 8.35 (1H, s).

Preparation Example C-1

Potassium Salt of 2-Cyano-3-hydroxy-acrylic acid ethyl ester

To a solution of potassium ethoxide (9.8 g, 116 mmol) in ethanol (180 mL) were added a solution of cyano ethyl acetate ester (13.2 g, 117 mmol) and formic acid ethyl ester (30 g, 405 mmol) in ethanol (20 mL), and the solution was stirred for 2 hours under reflux. The reaction solution was allowed to room temperature, the precipitated solid was collected by filtration and dried, and the title compound (18 g, 100 mmol, 85%) was obtained.

$^1$H-NMR Spectrum (DMSO-$d_6$) δ(ppm):1.13 (3H, t, J=7.2 Hz), 3.96 (2H, q, J=7.2 Hz), 9.18 (1H, s).

Preparation Example C-2

1-(Pyrrolidino)-2-(2-carbethoxy-2-cyanoethylene) cyclopentene

Potassium salt of 2-cyano-3-hydroxy-acrylic acid ethyl ester described in Preparation Example C-1 (18 g, 0.1 mol) was dissolved in dichloromethane (80 mL), phosphorus pentachloride (20.9 g, 0.1 mol) was added, and the solution was stirred for 2 hours under reflux. After the reaction was completed, the residue obtained by evaporating dichloromethane was subjected to distillation in vacuo, and ethyl(chloromethylene)cyanoacetate (9.5 g, 56 mmol) was obtained.

To a solution of 1-pyrrolidinocyclopentene (10.2 g, 74 mmol) and triethylamine (10 mL, 72 mmol) in dichloromethane (200 mL) was added a solution of the resulting ethyl(chloromethylene)cyanoacetate (9.5 g, 56 mmol) in dichloromethane (20 mL) dropwise while stirring at from −20° C. to −25° C. The solution was stirred at room temperature for 50 minutes, water (20 mL) was added thereto, followed by further stirring for 5 minutes. The reaction mixture was partitioned, the organic layer was dried over anhydrous magnesium sulfate, then concentrated, and the title compound (6 g, 23 mmol, 23%) was obtained.

$^1$H-NMR Spectrum (DMSO-$d_6$) δ(ppm):1.19 (3H, t, J=7.2 Hz), 1.76-1.86 (2H, m), 1.86-2.04 (4H, m), 2.73 (2H, t, J=7.6 Hz), 2.88 (2H, t, J=7.2 Hz), 3.60-3.71 (4H, m), 4.09 (2H, q, J=7.2 Hz), 7.97 (1H, brs).

Preparation Example C-3

1-Amino-2-(2-carbethoxy-2-cyanoethylene)cyclopentene 1-(Pyrrolidino)-2-(2-carbethoxy-2-cyanoethylene)cyclopentene (6 g, 23 mmol) described in Preparation Example C-2 was dissolved in ethanol saturated with ammonia (75 mL; was saturated at room temperature using ammonia gas), and the solution was stirred for 19 hours at room temperature. The reaction solution was concentrated and the title compound (4.8 g, 23 mmol, quantitatively) was obtained.

$^1$H-NMR Spectrum (DMSO-$d_6$) δ(ppm):1.21 (3H, t, J=7.2 Hz), 1.74-1.83 (2H, m), 2.48-2.54 (2H, m), 2.72-2.78 (2H, m), 4.12 (2H, q, J=7.2 Hz), 8.09-8.47 (1H, brs).

Preparation Example C-4

2-Amino-6,7-dihydro-5H-cyclopenta[b]pyridine-3-carboxylic acid ethyl ester

1-Amino-2-(2-carboethoxy-2-cyanoethylene)cyclopentene (0.8 g, 3.9 mmol) described in Preparation Example C-3 was dissolved in ethanol (27 mL), sodium ethoxide (0.12 g, 1.8 mmol) was added thereto, followed by stirring for 16 hours under reflux. The reaction mixture was allowed to room temperature, poured into brine, and the solution was extracted with ethyl acetate. The organic layer was dried over anhydrous magnesium sulfate, then, the residue obtained by concentration was purified by silica gel column chromatography (ethyl acetate:hexane=1:2), and the title compound (0.63 g, 3.1 mmol, 79%) was obtained.

$^1$H-NMR Spectrum (CDCl$_3$) δ(ppm): 1.38 (3H, t, J=7.2 Hz), 2.04-2.13 (2H, m), 2.79-2.88 (4H, m), 4.32 (2H, q, J=7.2 Hz), 6.16-6.32 (2H, brs), 7.96 (1H, s).

Preparation Example C-5

2-Amino-6,7-dihydro-5H-cyclopenta[b]pyridine-3-carboxylic Acid

2-Amino-6,7-dihydro-5H-cyclopenta[b]pyridine-3-carboxylic acid ethyl ester (0.2 g, 0.97 mmol) described in Preparation Example C-4 was dissolved in ethanol (15 mL), an aqueous solution of 1N sodium hydroxide (7.5 mL) was added thereto, followed by heating at 100° C. for 30 minutes. The reaction solution was allowed to room temperature, then cooled on an ice bath, and neutralized with 1N hydrochloric acid. The precipitated solid was collected by filtration, rinsed with water, then dried, and the title compound (143 mg, 0.8 mmol, 83%) was obtained.

$^1$H-NMR Spectrum (DMSO-$d_6$) δ(ppm):1.94-2.03 (2H, m), 2.71-2.76 (4H, m), 7.84 (1H, s).

Preparation Example D-1

[1,5]Naphthylidine-2-carboxylic Acid

5-Amino-2-chloro pyridine (10 g, 0.078 mol) and oxalacetic acid diethyl ester (14.7 g, 0.078 mol) were stirred at 90° C. for 7 hours. The reaction solution was allowed to room temperature, ethyl acetate was added thereto, the precipitated yellow solid was removed by filtration, and the filtrate was concentrated. The residue was purified by silica gel column chromatography (hexane:ethyl acetate), and 2-(6-chloro-pyridin-3-ylamino)-buto-2-enedioic acid diethyl ester (4.8 g, 21%) was obtained as a yellow oil.

The resulting 2-(6-chloro-pyridin-3-ylamino)-buto-2-enedioic acid diethyl ester (4.8 g, 16.1 mmol) was added to Dowtherm A (Dowtherm A; trademark) (300 mL), and the solution was stirred at 210° C. for 5 hours. The reaction solution was allowed to room temperature, hexane was added thereto, the precipitated solid was collected, washed with hexane, then, dried in vacuo to obtain 6-chloro-4-hydroxy-[1,5]naphthylidine-2-carboxylic acid ethyl ester (1.38 g, 34%) as a pale brown solid.

To the resulting 6-chloro-4-hydroxy-[1,5]naphthylidine-2-carboxylic acid ethyl ester (502 mg, 1.99 mmol) was added thionyl chloride (10 mL), and the solution was stirred for 7 hours under reflux. Excess thionyl chloride was evaporated in vacuo, 4,6-dichloro-[1,5]naphthylidine-2-carboxylic acid ethyl ester (522 mg, 97%) was obtained as a pale brown solid. Under nitrogen atmosphere, a portion of the resulting solid (200 mg, 0.738 mmol) was dissolved in dimethylsulfoxide (30 mL), tetrakis(triphenylphosphine)palladium(0) (171 mg, 0.148 mmol) and formic acid sodium (251 mg, 3.69 mmol) were added thereto, followed by stirring at 100° C. for 4 hours. The reaction solution was allowed to room temperature, ethyl acetate and water were added for partitioning, the organic layer was washed with water and dried over anhydrous magnesium sulfate. The solvent was evaporated, then, the residue was purified by silica gel column chromatography (hexane:ethyl acetate), and [1,5]naphthylidine-2-carboxylic acid ethyl ester (49 mg, 33%) was obtained as a colorless solid.

The resulting solid was dissolved in methanol (1.0 mL), an aqueous solution of 1N sodium hydroxide (0.3 mL) was added thereto, followed by stirring at room temperature for 30 minutes. Water was added to the reaction solution, the pH was adjusted from 3 to 4 using 1N hydrochloric acid, the solution was extracted with ethyl acetate, dried over anhydrous magnesium sulfate, and the solvent was evaporated to obtain the title compound (29 mg, 69%) as a white solid.

Preparation Example E-1

Quinoline-6-carboxylic acid cyanomethyl-amide

To a solution of quinoline-6-carboxylic acid (500 mg, 2.9 mmol) and amino acetonitrile hydrochloride (320 mg, 3.4 mmol) in N,N-dimethylformamide (10 mL) were added benzotriazol-1-yl-tris(dimethylamino)phosphonium hexafluorophosphate (1.5 g, 3.48 mmol) and triethylamine (1.2 mL, 8.7 mmol), and the solution was stirred at 60° C. for 10 minutes. Ethyl acetate and water was added to the reaction solution, which was then partitioned, the organic layer was washed twice with water. Silica gel was added to the organic layer, the solvent was evaporated in vacuo for adsorption, purified by NH silica gel column chromatography (ethyl acetate), and the title compound (420 mg, 2.0 mmol, 68.9%) was obtained as a light brown solid.

$^1$H-NMR Spectrum (DMSO-d$_6$) δ(ppm): 4.43 (2H, d, J=5.6 Hz), 7.65 (1H, dd, J=4.0, 8.4 Hz), 8.14 (1H, d, J=8.8 Hz), 8.18-8.22 (1H, m), 8.30-8.35 (1H, m), 8.58 (1H, d, J=1.2 Hz), 9.02-9.05 (1H, m), 9.49 (1H, t, J=5.6 Hz).

Preparation Example E+-1

Quinoline-6-carboxylic acid 4-hydroxybenzylamide

Trifluoroacetic acid (5 mL) and thioanisole (3 drops) were added to quinoline-6-carboxylic acid 4-benzyloxybenzylamide (2.67 g, 7.25 mmol) synthesized in Example E-8, the solution was stirred at room temperature for 14 hours, followed by stirring at 50° C. for 4 hours, lastly, and the solution was stirred at 70° C. for 3 hours. The reaction solution was allowed to room temperature, then, was neutralized with an aqueous solution of saturated sodium bicarbonate, extracted with ethyl acetate and dried over anhydrous magnesium sulfate. The solvent was evaporated, the residue was purified by NH silica gel column chromatography (ethyl acetate), and the title compound (433 mg, 22%) was obtained as a colorless solid.

Preparation Example E+-2

Quinoline-6-carboxylic acid(5-bromo-furan-2-ylmethyl)-amide

The title compound (1.0 g, 3.0 mmol, 75.5%) was obtained as a white solid from C-(5-bromo-furan-2-yl)-methylamine (700 mg, 4.0 mmol) and quinoline-6-carboxylic acid (700 mg, 4.0 mmol) according to an analogous method to Example Q-6.

$^1$H-NMR Spectrum (DMSO-d$_6$) δ(ppm): 4.49 (2H, d, J=5.6 Hz), 6.38-6.41 (1H, m), 6.50 (1H, d, J=3.6Hz), 7.60 (1H, dd, J=4.0, 8.4Hz), 8.06 (1H, d, J=8.8Hz), 8.17 (1H, dd, J=2.0, 8.8 Hz), 8.44-8.48 (1H, m), 8.52 (1H, d, J=2.0 Hz), 8.97 (1H, dd, J=1.6, 4.0 Hz), 9.23 (1H, t, J=5.6 Hz).

Preparation Example E+-3

Quinoline-6-carboxylic acid 4-benzylamino-benzylamide

4-Benzylamino-benzonitrile (472 mg, 2.27 mmol) described in Preparation Example 89 was dissolved at 0° C. in tetrahydrofuran (20 mL), and lithium aluminum hydride (430 mg, 11.3 mmol) was added thereto. The solution was stirred overnight at room temperature, then, at 0° C., water (430 μl), an aqueous solution of 5N sodium hydroxide (430 μl) and water (1.29 mL) were sequentially added to the solution. The reaction solution was filtered through Celite pad, the solvent was then evaporated in vacuo, (4-aminomethyl-phenyl)-benzylamine (475 mg, 2.24 mmol, 99%) was obtained as an oil.

The resulting (4-aminomethyl-phenyl)-benzylamine (162 mg, 0.763 mmol), quinoline-6-carboxylic acid (132 mg, 0.736 mmol), benzotriazol-1-yl-tris(dimethylamino)phosphonium hexafluorophosphate (506 mg, 1.14 mmol) and triethylamine (319 μl, 2.29 mmol) were dissolved in N,N-dimethylformamide (4.0 mL), and the solution was stirred for 2 hours at room temperature. Water was added to the reaction solution, which was then extracted with ethyl acetate, the organic layer was washed with water and brine and dried over anhydrous magnesium sulfate. The solvent was evaporated in vacuo, the residue was purified by NH silica gel column chromatography (hexane:ethyl acetate=1:1), and the title compound (224 mg, 0.610 mmol, 80%) was obtained as a white solid.

$^1$H-NMR Spectrum (DMSO-d$_6$) δ(ppm): 4.23 (2H, d, J=6.0 Hz), 4.33 (2H, d, J=6.0 Hz), 6.18 (1H, t, J=6.1 Hz), 6.51 (2H, d, J=8.6 Hz), 7.03 (2H, d, J=8.6 Hz), 7.18 (1H, t, J=7.0 Hz), 7.25-7.34 (4H, m), 7.58 (1H, dd, J=4.1, 8.3 Hz), 8.04 (1H, d, J=8.8 Hz), 8.16 (1H, dd, J=1.8, 9.0 Hz), 8.43 (1H, d, J=7.0 Hz), 8.49 (1H, d, J=2.0 Hz), 8.95 (1H, dd, J=1.8, 5.0 Hz), 9.04 (1H, t, J=5.5 Hz).

Preparation Example E+-4

Quinoline-6-carboxylic acid 3-hydroxybenzylamide

Thioanisole (1.7 mL, 14 mmol) was added to a mixture of quinoline-6-carboxylic acid 3-benzyloxybenzylamide (1.3 g, 3.6 mmol) and trifluoroacetic acid(8 mL) on an ice bath, and the solution was stirred for 4 hours at room temperature. The solvent was evaporated in vacuo, then water, an aqueous solution of saturated sodium bicarbonate, ethyl acetate and tetrahydrofuran were added to the residue for extraction, the organic layer was washed with brine, then, dried over anhydrous magnesium sulfate. The solvent was evaporated in vacuo, recrystallized from ethyl acetate-methanol, and the title compound (0.64 g, 2.3 mmol, 64%) was obtained as a white crystal.

$^1$H-NMR Spectrum (DMSO-d$_6$) δ(ppm): 4.45 (2H, d, J=5.9 Hz), 6.60-6.63 (1H, m), 6.75-6.77 (2H, m), 7.10 (1H, t, J=8.1 Hz), 7.60 (1H, dd, J=4.2, 8.2 Hz), 8.07 (1H, d, J=8.8 Hz), 8.20 (1H, dd, J=2.0, 8.8 Hz), 8.45-8.47 (1H, m), 8.54 (1H, d, J=1.8 Hz), 8.97 (1H, dd, J=1.7, 4.2 Hz), 9.23 (1H, t, J=5.8 Hz), 9.33 (1H, s).

Preparation Example E+-5

Quinoline-6-carboxylic acid 4-phenylethynyl-benzylamide

Quinoline-6-carboxylic acid 4-bromobenzylamide(1.3 g, 68%) was obtained from quinoline-6-carboxylic acid (1.0 g, 5.8 mmol) and 4-bromobenzylamine hydrochloride (1.3 g, 5.8 mmol) according to an analogous method to Preparation Example A+-5 (with the proviso that reaction was carried out at 80° C.).

N,N-diisopropylethylamine (0.31 mL, 1.8 mmol) was added to a mixture of the resulting quinoline-6-carboxylic acid 4-bromobenzylamide (200 mg, 0.59 mmol) ethynylbenzene(0.077 mL, 0.70 mmol), copper(I)iodide (catalytic amount), tetrakis(triphenylphosphine)palladium(0) (68 mg, 0.059 mmol) and N-methylpyrrolidinone (4 mL), and the solution was stirred at 100° C. for 30 minutes, and at 120° C. for 50 minutes. After cooling, water, ethyl acetate, tetrahydrofuran and 29% aqueous ammonia solution were added to the reaction mixture for extraction, the organic layer was washed with brine, then, the solvent was evaporated in vacuo. The residue was purified by silica gel column chromatography (hexane:ethyl acetate=1:4), then, the resulting crudely purified product was washed with diethyl ether to obtain the title compound (50 mg, 0.14 mmol, 24%) as a white solid.

$^1$H-NMR Spectrum (DMSO-d$_6$) δ(ppm): 4.57 (2H, d, J=5.7 Hz), 7.39-7.41 (5H, m), 7.52 (4H, d, J=6.8 Hz), 7.60 (1H, dd, J=3.8, 8.1 Hz), 8.08 (1H, d, J=8.6 Hz), 8.21 (1H, d, J=8.8 Hz), 8.47 (1H, d, J=7.9 Hz), 8.56 (1H, s), 8.97 (1H, d, J=4.0 Hz), 9.33 (1H, brs).

Preparation Example E+-6

Quinoline-6-carboxylic acid 4-[1,3]dioxolan-2-yl-benzylamide

The title compound (1.31 g, 3.92 mmol, 77%) was obtained as a white solid from 4-[1,3]dioxolan-2-yl-benzylamine described in Preparation Example 120 (970 mg, 5.60 mmol) and quinoline-6-carboxylic acid (913 mg, 5.09 mmol) according to an analogous method to Preparation Example Q+-1.

$^1$H-NMR Spectrum (DMSO-$d_6$) δ(ppm): 3.90-4.02 (4H, m), 4.54 (2H, d, J=5.9 Hz), 5.69 (1H, s), 7.35-7.40 (4H, m), 7.60 (1H, dd, J=4.2, 8.2 Hz), 8.07 (1H, d, J=9.0 Hz), 8.2 (1H, dd, J=1.9, 9.0 Hz), 8.46 (1H, d, J=8.1 Hz), 8.54 (1H, d, J=1.5 Hz), 8.97 (1H, dd, J=1.7, 4.2 Hz), 9.29 (1H, t, J=5.7 Hz).

Preparation Example E+-7

Quinoline-5 6-carboxylic acid 4-formyl-benzylamide

Quinoline-6-carboxylic acid 4-[1,3]dioxolan-2-yl-benzylamide described in Preparation Example E+-6 (1.30 g, 3.89 mmol) was dissolved in a mixture solution of tetrahydrofuran (20 mL), water (10 mL) and sulfuric acid (3 mL), the solution was stirred for 2 hours under reflux. An aqueous solution of saturated sodium bicarbonate was added to the reaction solution at 0° C., the solution was extracted with ethyl acetate and tetrahydrofuran. The organic layer was washed with brine, dried over anhydrous magnesium sulfate, and the solvent was evaporated in vacuo. Ethyl acetate was added to the residue, the precipitated solid was filtered, and the title compound (700 mg, 2.41 mmol, 62%) was obtained as a white solid.

$^1$H-NMR Spectrum (DMSO-$d_6$) δ(ppm): 4.63 (2H, d, J=5.7 Hz), 7.57 (2H, d, J=7.9 Hz), 7.61 (1H, t, J=4.1 Hz), 7.88 (2H, dd, J=1.8, 8.4 Hz), 8.09 (1H, d, J=8.8 Hz), 8.21 (1H, dd, J=2.0, 8.8 Hz), 8.48 (1H, d, J=7.9 Hz), 8.56 (1H, d, J=1.5 Hz), 8.98 (1H, dd, J=1.8, 4.2 Hz), 9.39 (1H, t, J=6.0 Hz), 9.97 (1H, s).

Preparation Example E+-8

Quinoline-6-carboxylic acid 3-bromobenzylamide

The title compound (1.4 g, 4.0 mmol, 70%) was obtained as a white solid from 3-bromobenzylamine hydrochloride (1.3 g, 5.8 mmol) and quinoline-6-carboxylic acid (1.0 g, 5.8 mmol) according to an analogous method to Preparation Example Q+-1.

$^1$H-NMR Spectrum (CDCl$_3$) δ(ppm): 4.68 (2H, d, J=5.7 Hz), 6.75 (1H, brs), 7.23 (1H, t, J=7.8 Hz), 7.31-7.34 (1H, m), 7.43-7.45 (1H, m), 7.47 (1H, dd, J=4.2, 8.2 Hz), 7.53-7.54 (1H, m), 8.07 (1H, dd, J=2.0, 8.8 Hz), 8.16 (1H, d, J=8.8 Hz), 8.22-8.24 (1H, m), 8.34 (1H, d, J=1.8 Hz), 8.99 (1H, dd, J=1.8, 4.2 Hz).

Preparation Example E+-9

Quinoline-6-carboxylic acid 4-bromobenzylamide

The title compound (1.3 g, 3.9 mmol, 68%) was obtained as a white solid from 4-bromobenzylamine hydrochloride (1.3 g, 5.8 mmol) and quinoline-6-carboxylic acid (1.0 g, 5.8 mmol) according to an analogous method to Preparation Example Q+-1.

$^1$H-NMR Spectrum (CDCl$_3$) δ(ppm): 4.67 (2H, d, J=5.9 Hz), 6.63 (1H, brs), 7.26-7.29 (2H, m), 7.47-7.51 (3H, m), 8.06 (1H, dd, J=2.0, 8.8 Hz), 8.16 (1H, d, J=8.8 Hz), 8.22-8.25 (1H, m), 8.33 (1H, d, J=2.0 Hz), 8.99 (1H, dd, J=1.7, 4.2 Hz).

Preparation Example E+-10

Quinoline-6-carbothioic acid 4-benzyloxy-benzylamide

To a solution of 6-quinoline carboxylic acid (100 mg, 0.577 mmol) in tetrahydrofuran (50 mL) was added N,N'-dicyclohexylcarbodiimide (1.90 g, 11.7 mmol), and the solution was stirred for 1 hour at room temperature. Then, a solution of 4-benzyloxybenzylamine described in Preparation Example 1 (2.49 g, 11.7 mmol) in tetrahydrofuran was added thereto, followed by stirring overnight at room temperature. The solvent was evaporated, the residue was purified by NH silica gel column chromatography (hexane:ethyl acetate), and quinoline-6-carboxylic acid 4-benzyloxy-benzylamide (4.31 g, quantitatively) was obtained as a white solid.

A mixture of the resulting quinoline-6-carboxylic acid 4-benzyloxy-benzylamide (310 mg, 0.84 mmol), 2,4-bis(4-methoxyphenyl)-1,3-dithia-2,4-diphosphetane-2,4-disulphide (Lawesson's reagent) (1.4 g, 3.4 mmol) and tetrahydrofuran (10 mL) was refluxed for 1 hour. After cooling, the solvent was evaporated in vacuo, dichloromethane was added to the residue, which was purified by NH silica gel column chromatography (hexane:ethyl acetate=1:1), and the title compound (55 mg, 0.14 mmol, 17%) was obtained as a pale yellow solid.

$^1$H-NMR Spectrum (DMSO-$d_6$) δ(ppm): 4.93 (2H, d, J=4.6 Hz), 5.09 (2H, s), 6.99 (2H, d, J=8.8 Hz), 7.26-7.44 (7H, m), 7.58 (1H, dd, J=4.2, 8.2 Hz), 8.01 (1H, d, J=9.0 Hz), 8.13 (1H, dd, J=2.1, 8.9 Hz), 8.29 (1H, d, J=1.8 Hz), 8.46 (1H, d, J=8.2 Hz), 8.94 (1H, dd, J=1.6, 4.2 Hz), 10.9 (1H, brs).

Preparation Example F-1

3-Acetyl-4-amino-benzoic acid methyl ester

To a solution of 4-amino-3-iodo-benzoic acid methyl ester (11.30 g, 40.77 mmol) in toluene (300 mL) were added tributyl(1-ethoxyvinyl)tin (16.5 mL, 48.9 mmol) and tetrakis(triphenylphosphine)palladium(0) (9422 mg, 8.154 mmol) under nitrogen atmosphere, and the solution was stirred at 105° C. for 7 hours. After cooling to room temperature, water was added, the mixture was extracted with ethyl acetate-tetrahydrofuran, the organic layer was washed with water, and then, evaporated. The residue was dissolved in 280 mL of tetrahydrofuran, 2N hydrochloric acid (80 mL) was added thereto, followed by stirring for 3 hours at room temperature. The reaction mixture was cooled on an ice bath, an aqueous solution of 2N sodium hydroxide (80 mL) was added, an aqueous solution of saturated sodium bicarbonate was further added, and the solution was extracted with ethyl acetate. An aqueous solution of 10% potassium fluoride was added to the organic layer, and the solution was stirred for 3 hours at room temperature. The organic layer was separated, washed with brine, then evaporated, the residue was purified by silica gel column chromatography (hexane-ethyl acetate), and title compound (6.42 g, 33.2 mmol, 81.4%) was obtained.

$^1$H-NMR Spectrum (CDCl$_3$) δ(ppm): 2.64 (3H, s), 3.89 (3H, s), 6.63 (1H, d, J=8.8 Hz), 7.91 (1H, dd, J=2.0, 8.8 Hz), 8.47 (1H, d, J=2.0 Hz).

Preparation Example F-2

4-Oxo-1,4-dihydro-cinnoline-6-carboxylic acid methyl ester

To a solution of 3-acetyl-4-amino-benzoic acid methyl ester (2063 mg, 10.68 mmol) in acetic acid (39 mL) was added sulfuric acid (6.5 mL) on an ice bath, then, an aqueous solution (6.5 mL) of sodium nitrite (922 mg, 13.35 mmol) was added thereto, followed by stirring on the ice for 1 hour, and at room temperature for 2 days. The reaction mixture was concentrated until it reached half of the amount, water was added, then an aqueous solution of 2N sodium hydroxide was added on an ice bath to adjust the pH to 5. The insoluble matter was separated by filtration, then, the filtrate was extracted with ethyl acetate, the organic layer was dried over sodium sulfate and then evaporated. Diethyl ether was added to the resulting residue for solidification, the resulting solid was washed with diethyl ether, and 365 mg of the title compound (1.78 mmol, 16.6%) was obtained.

$^1$H-NMR Spectrum (DMSO-$d_6$) δ(ppm): 3.88 (3H, s), 7.66 (1H, d, J=8.8 Hz), 7.82 (1H, s), 8.24 (1H, d, J=8.8 Hz), 8.58 (1H, s), 13.7 (1H, brs).

Preparation Example F-3

4-Chloro-cinnoline-6-carboxylic acid methyl ester

Thionyl chloride (5 mL, 68.5 mmol) and N,N-dimethylformamide (3 drops) were added to 4-oxo-1,4-dihydro-cinnoline-6-carboxylic acid methyl ester (212 mg, 1.04 mol), and the solution was stirred for 1.15 hours under reflux. Toluene was added to the reaction mixture, which was then evaporated in vacuo. Ethyl acetate was added to the residue the organic layer was washed with an ice water, dried over anhydrous magnesium sulfate, then, evaporated in vacuo, and the title compound (192 mg, 0.862 mmol, 82.9%) was obtained. This was used in the next reaction without purification.

$^1$H-NMR Spectrum (DMSO-$d_6$) δ(ppm): 3.97 (3H, s), 8.43 (1H, d, J=8.8 Hz), 8.66 (1H, d, J=8.8 Hz), 8.72 (1H, s), 9.73 (1H, s).

Preparation Example F-4

Cinnoline-6-carboxylic acid methyl ester

To a solution of 4-chloro-cinnoline-6-carboxylic acid methyl ester (192 mg, 0.863 mmol) in dimethylsulfoxide (30 mL) were added sodium formate (70 mg, 1.04 mmol), tetrakis(triphenylphosphine)palladium(0) (198 mg, 0.702 mmol) and N,N-diisopropylethylamine (0.21 mL, 1.21 mmol), and the mixture was stirred for 1.5 hours at 90° C. After cooling to room temperature, water was added, ethyl acetate extraction was carried out, the organic layer was washed with water and brine, then, after drying over anhydrous sodium sulfate, the organic layer was evaporated. The resulting solid was washed with diethyl ether, then, purified by silica gel column chromatography (hexane-ethyl acetate), and the title compound (16 mg, 0.089 mmol, 10%) was obtained.

$^1$H-NMR Spectrum (CDCl$_3$) δ(ppm): 4.03 (3H, s), 7.97 (1H, dd, J=0.8, 6.0 Hz), 8.42 (1H, J=0.8, 8.0 Hz), 8.59-8.63 (2H, m), 9.43 (1H, dd, J=0.8, 6.0 Hz).

Preparation Example G-1

Isoguinoline-6-carboxylic Acid

A solution prepared by adding (4-bromobenzylydene)-(2,2-diethoxyethyl) amine (synthesized from 4-bromobenzaldehyde, according to the method described in J. Org. Chem., vol. 48, 3344-3346 (1983)) (51.4 g, 0.189 mmol) to an ice-cold concentrated sulfuric acid (20 g) was added to a solution prepared by adding diphosphorus pentoxide (40 g) to an ice-cold concentrated sulfuric acid (360 g), and the solution was stirred at 160° C. for 2 hours. The reaction solution was gradually cooled to 0° C., the solution was filtered through Celite pad, the filtrate was neutralized with sodium carbonate. This solution was further filtrated through Celite pad, this filtrate was extracted with ethyl acetate and dried over anhydrous magnesium sulfate. The solvent was evaporated, and the residue was purified by silica gel column chromatography (hexane:ethyl acetate), and 6-bromoisoquinoline (482 mg, 1.2%) was obtained as an orange oil.

Next, to a solution of 6-bromoisoquinoline (382 mg, 1.84 mmol) in N,N-dimethylformamide (3.8 mL) were added zinc cyanide (431 mg, 3.67 mmol) and tetrakis(triphenylphosphine)palladium(0) (42 mg, 0.0367 mmol) under nitrogen atmosphere, and the mixture was stirred at 100° C. for 1 hour. Tetrakis(triphenylphosphine)palladium(0) (42 mg, 0.0367 mmol) was further added, and the mixture was stirred for 2.5 hours at 100° C. The reaction mixture was allowed to room temperature, ethyl acetate and water were added for extraction, the organic layer was washed with water and dried over anhydrous magnesium sulfate. The residue was purified by silica gel column chromatography (hexane:ethyl acetate), and isoquinoline-6-carbonitrile (234 mg, 83%) was obtained as a yellow solid.

Lastly, isoquinoline-6-carbonitrile (51 mg, 0.331 mmol) was dissolved in diethyleneglycol (1.0 mL), potassium hydroxide (9 mg, 0.166 mmol) was added thereto, followed by stirring at 160° C. for 3 hours. The reaction mixture was allowed to room temperature, neutralized using hydrochloric acid, extracted with ethyl acetate, dried over anhydrous magnesium sulfate, then, the solvent was evaporated. Water was added to the residue, the precipitated solid was collected, washed with water, dried in vacuo, so as to obtain the title compound (12 mg, 21%) as a yellow solid.

Preparation Example H-1

4-Chloro-quinazoline-6-carboxylic acid ethyl ester

The title compound (380 mg, 1.61 mmol, 88%) was obtained from 4-oxo-dihydroquinazoline-6-carboxylic acid ethyl ester (396 mg, 1.81 mmol) according to an analogous method to Preparation Example F-3.

$^1$H-NMR Spectrum (DMSO-$d_6$) δ(ppm):1.34 (3H, t, J=7.2 Hz), 4.35 (2H, q, J=7.2 Hz), 7.78 (1H, d, J=8.4 Hz), 8.29 (1H, dd, J=2.0, 8.4 Hz), 8.37 (1H, s), 8.64 (1H, d, J=2.0 Hz).

Preparation Example H-2

Quinazoline-6-carboxylic acid ethyl ester

The title compound (79 mg, 0.39 mmol, 24%) was obtained from 4-chloro-quinazoline-6-carboxylic acid ethyl ester (380 mg, 1.61 mmol) according to an analogous method to Preparation Example F-4.

$^1$H-NMR Spectrum (CDCl$_3$) δ(ppm):1.47 (3H, t, J=7.6 Hz), 4.48 (2H, t, J=7.6 Hz), 8.11 (1H, d, J=8.8 Hz), 8.53 (1H, dd, J=2.0, 8.8 Hz), 8.71 (1H, d, J=2.0 Hz), 9.42 (1H, s), 9.52 (1H, s).

Preparation Example H-3

Quinazoline-6-carboxylic Acid

To a solution of quinazoline-6-carboxylic acid ethyl ester (79 mg, 0.391 mmol) in ethanol (4 mL) was added an aqueous solution of 1N sodium hydroxide (4 mL), and the solution was stirred for 1 hour at room temperature. 1N Hydrochloric acid was added to the reaction mixture to adjust the pH to 4, and the solution was evaporated in vacuo. Ethanol was added to the residue, and the organic layer was concentrated. The residue was dissolved in an ethyl acetate-tetrahydrofuran mixture solvent, dried over anhydrous magnesium sulfate, then, evaporated in vacuo, and quinazoline-6-carboxylic acid (15 mg, 0.086 mmol, 22%) was obtained. This was used in the next reaction without purification.

$^1$H-NMR Spectrum (DMSO-d6) δ(ppm) 8.09 (1H, d, J=8.8 Hz), 8.44 (1H, dd, J=2.0, 8.8 Hz), 8.83 (1H, d, J=2.0 Hz), 9.39 (1H, s), 9.79 (1H, s).

Preparation Example I-1

Quinoxaline-6-carboxylic Acid

To a solution of quinoxaline-6-carboxylic acid methyl ester (2084 mg, 11.07 mmol) in ethanol (25 mL) was added an aqueous solution of 1N sodium hydroxide (25 mL), and the solution was stirred for 4 hours under reflux. 1N Hydrochloric acid was added to the reaction mixture to adjust the pH to 4, then, the precipitated solid was collected by filtration, washed with water and isopropanol, then dried to obtain the title compound (1477 mg, 8.479 mmol, 76.6%) as a solid.

$^1$H-NMR Spectrum (DMSO-d$_6$) δ(ppm): 8.18 (1H, d, J=8.4 Hz), 8.29 (1H, dd, J=8.4, 1.2 Hz), 8.61 (1H, d, J=1.2 Hz), 9.00-9.07 (2H, m).

Preparation Example J-1

2.2-Dimethyl-N-pyridin-2-yl-propionamide

2-Aminopyridine (3.1 g, 33 mmol) and triethylamine(6.9 mL, 49 mmol) was dissolved in dichloromethane (40 mL), 2,2-dimethylpropionyl chloride (4.5 mL, 36 mmol) was added on an ice bath, and the solution was stirred for 2 hours at the same temperature. Water was added thereto for extraction, the organic layer was sequentially washed with an aqueous solution of saturated sodium bicarbonate and brine, then, dried over anhydrous magnesium sulfate. The solvent was evaporated in vacuo, and the title compound (6.0 g, 34 mmol, 102%) was obtained as a white solid.

$^1$H-NMR Spectrum (CDCl$_3$) δ(ppm):1.27 (9H, s), 7.03 (1H, ddd, J=1.1, 4.9, 7.3 Hz), 7.68-7.72 (1H, m), 8.02 (1H, s), 8.23-8.27 (2H, m).

Preparation Example J-2

N-(3-formylpyridin-2-yl)-2.2-dimethylpropionamide

To a mixture solution of tert-butyl lithium (1.5M pentane solution, 10 mL, 15 mmol) and diethyl ether (50 mL) was added a solution of 2,2-dimethyl-N-pyridin-2-yl-propionamide described in Preparation Example J-1 (900 mg, 5.0 mmol) in diethyl ether (10 mL) dropwise at −78° C., and the solution was stirred for 90 minutes at the same temperature. At the same temperature, morpholine-4-carbaldehyde (1.0 mL, 10 mmol) was added dropwise, and the solution was warmed gradually to room temperature. Water and tetrahydrofuran were added to the reaction mixture for extraction, the organic layer was washed with brine, then, the solvent was evaporated in vacuo. The residue was purified by silica gel column chromatography (hexane:ethyl acetate=1:4), and the title compound (880 mg, 4.3 mmol, 85%) was obtained as a white solid.

$^1$H-NMR Spectrum (CDCl$_3$) δ(ppm):1.38 (9H, s), 7.21 (1H, dd, J=4.9, 7.6 Hz), 8.05 (1H, dd, J=2.0, 7.5 Hz), 8.69 (1H, dd, J=2.0, 4.9 Hz), 9.94 (1H, s), 10.9 (1H, brs).

Preparation Example J-3

(2-Aminopyridin-3-yl)-methanol

A mixture solution of N-(3-formylpyridin-2-yl)-2,2-dimethylpropionamide described in Preparation Example J-2 (500 mg, 2.4 mmol) and an aqueous solution of 5N sodium hydroxide (7 mL) was refluxed for 90 minutes. After cooling, ethyl acetate and tetrahydrofuran were added for extraction, the organic layer was washed with brine, then, the solvent was evaporated in vacuo. The residue was purified by silica gel column chromatography (methanol:ethyl acetate=1:5), and the title compound (160 mg, 1.2 mmol, 53%) was obtained as a pale yellow solid.

$^1$H-NMR Spectrum (DMSO-d$_6$) δ(ppm): 4.31 (2H, s), 5.13 (1H, brs), 5.62 (2H, s), 6.51 (1H, dd, J=5.0, 7.3 Hz), 7.34-7.36 (1H, m), 7.81-7.82 (1H, m).

Preparation Example J-4

2-Aminopyridine-3-carbaldehyde

To a mixture of (2-aminopyridin-3-yl)-methanol described in Preparation Example J-3 (130 mg, 1.1 mmol) and dichloromethane (10 mL) was added manganese dioxide (1.3 g, 15 mmol) at room temperature, and the solution was stirred overnight. The reaction solution was filtered through Celite pad, then, the solvent was evaporated in vacuo, and the title compound (108 mg, 0.88 mmol, 83%) was obtained as a white solid.

$^1$H-NMR Spectrum (CDCl$_3$) δ(ppm): 6.75 (1H, dd, J=4.9, 7.5 Hz), 7.83 (1H, dd, J=1.9, 7.5 Hz), 8.23 (1H, dd, J=1.9, 4.9 Hz), 9.86 (1H, s).

Preparation Example J-5

2-Hydroxy-[1.8]naphthylidine-3-carboxylic acid ethyl ester

To a mixture of 2-aminopyridine-3-carbaldehyde described in Preparation Example J-4 (8.0 mg, 0.066 mmol) and ethanol (2 mL) were added diethylmalonate (0.50 mL, 3.3 mmol) and piperidine (0.20 mL, 2.0 mmol), and the solution was stirred overnight at 70° C. The solvent was evaporated in vacuo, the residue was purified by silica gel column chromatography (methanol:ethyl acetate=1:10), and the title compound (9.2 mg, 0.042 mmol, 64%) was obtained as a white solid.

$^1$H-NMR Spectrum (CDCl$_3$) δ(ppm):1.43 (3H, t, J=7.1 Hz), 4.45 (2H, q, J=7.1 Hz), 7.28 (1H, dd, J=4.9, 7.8 Hz), 8.04 (1H, dd, J=1.7, 7.9 Hz), 8.48 (1H, s), 8.87-8.88 (1H, m), 12.16 (1H, brs).

Preparation Example J-6

2-Trifluoromethane sulfonyloxy-[1,8]naphthylidine-3-carboxylic acid ethyl ester

To a mixture of 2-hydroxy-[1,8]naphthylidine-3-carboxylic acid ethyl ester described in Preparation Example J-5 (95 mg, 0.44 mmol), dichloromethane(4 mL) and N,N-dimethylformamide (0.5 mL) were added N-phenyl-bis(trifluoromethanesulfonimide) (230 mg, 0.65 mmol), triethylamine (0.18 mL, 1.3 mmol) and catalytic amount of 4-(dimethylamino)pyridine, and the solution was stirred for 2.5 hours at room temperature. The solvent was evaporated in vacuo, the residue was purified by silica gel column chromatography (hexane:ethyl acetate=1:1), and the title compound (22 mg, 0.063 mmol, 14%) was obtained as a white solid.

$^1$H-NMR Spectrum (CDCl$_3$) δ(ppm):1.49 (3H, t, J=7.1 Hz), 4.54 (2H, q, J=7.1 Hz), 7.69 (1H, dd, J=4.3, 8.2 Hz), 8.41 (1H, dd, J=2.0, 8.4 Hz), 9.09 (1H, s), 9.28 (1H, dd, J=2.0, 4.2 Hz).

Preparation Example J-7

[1,8]Naphthylidine-3-carboxylic acid ethyl ester

To a mixture of 2-trifluoromethanesulfonyloxy-[1,8]naphthylidine-3-carboxylic acid ethyl ester described in Preparation Example J-6 (22 mg, 0.063 mmol), tetrakis(triphenylphosphine)palladium(0) (7.3 mg, 0.0063 mmol), and 1-methyl-2-pyrrolidinone (1.5 mL) were added N,N-diisopropylethylamine (0.033 mL, 0.19 mmol) and formic acid (0.0036 mL, 0.094 mmol), and the solution was stirred for 45 minutes at 100° C. After cooling, filtration was carried out using NH silica gel, and the filtrate was evaporated in vacuo. Water, ethyl acetate and tetrahydrofuran were added to the residue for extraction, the organic layer was washed with brine, the solvent was then evaporated in vacuo. The residue was purified by silica gel column chromatography (ethyl acetate), and the title compound (8.1 mg, 0.040 mmol, 64%) was obtained as a white solid.

$^1$H-NMR Spectrum (CDCl$_3$) δ(ppm):1.49 (3H, t, J=7.1 Hz), 4.51 (2H, q, J=7.1 Hz), 7.61 (1H, dd, J=4.3, 8.2 Hz), 8.34 (1H, dd, J=2.0, 8.2 Hz), 8.91 (1H, d, J=2.2 Hz), 9.25 (1H, dd, J=2.0, 4.2 Hz), 9.69 (1H, d, J=2.4 Hz).

Preparation Example K-1

2-Methyl-benzoxazole-6-carboxylic acid methyl ester

To a solution of 4-amino-3-hydroxy-benzoic acid methyl ester (2085 mg, 12.47 mmmol) in xylene (200 mL) were added acetyl chloride (1.06 mL, 14.96 mmol), pyridinium p-toluenesulfonate (940 mg, 3.74 mmol) and triethylamine (2.09 mL, 14.96 mmol), and the solution was stirred for 8.5 hours under reflux. Ethyl acetate was added to the reaction mixture, which was then washed with water, dried over anhydrous magnesium sulfate, then, evaporated in vacuo, the resulting residue was purified by silica gel chromatography (hexane-ethyl acetate), and the title compound (1917 mg, 10.02 mmol, 80.4%) was obtained.

$^1$H-NMR Spectrum (CDCl$_3$) δ(ppm): 2.69 (3H, s), 3.96 (3H, s), 7.68 (1H, d, J=8.4 Hz), 8.05 (1H, dd, J=1.2, 8.4 Hz), 8.17 (1H, d, J=1.2 Hz).

Preparation Example K-2

2-Methyl-benzoxazole-6-carboxylic Acid

To a solution of 2-methyl-benzoxazole-6-carboxylic acid methyl ester (301 mg, 1.57 mmol) in ethanol (10 mL) was added an aqueous solution of 2N sodium hydroxide (10 mL), and the mixture was stirred for 2 hours at room temperature. 2N Hydrochloric acid was added to the reaction mixture to adjust the pH to 4, and the solution was extracted with ethyl acetate. The organic layer was washed with brine, dried over anhydrous sodium sulfate, then, evaporated in vacuo, and the title compound (270 mg, 1.52 mmol, 97%) was obtained. This was used in the next reaction without purification.

$^1$H-NMR Spectrum (DMSO-d$_6$) δ(ppm): 2.64 (3H, s), 7.73 (1H, d, J=8.0 Hz), 7.93 (1H, dd, J=1.2, 8.0 Hz), 8.15 (1H, d, J=1.2 Hz).

Preparation Example O-1

2,3-Dihydro-1H-pyrrolo[2,3-b]pyridine-5-carbonitrile

1H-Pyrrolo[2,3-b]pyridine (1.0 g, 8.46 mmol) and 10% palladium-carbon (500 mg) were dissolved in a mixture of formic acid (10 mL) and triethylamine (10 mL), and the solution was stirred at 70° C. for 17 hours. To this reaction mixture was further added 10% palladium-carbon (270 mg), and the mixture was stirred at 70° C. for 2 hours. The reaction mixture was cooled to room temperature, then an aqueous solution of 5N sodium hydroxide was added thereto, the solution was extracted with ethyl acetate and tetrahydrofuran, and the organic layer was dried over anhydrous magnesium sulfate. The solvent was evaporated in vacuo, the residue was purified by silica gel column chromatography (ethyl acetate: methanol=10:1), and 2,3-dihydro-1H-pyrrolo[2,3-b]pyridine (614 mg, 5.11 mmol, 60%) was obtained as a pale yellow solid.

The resulting 2,3-dihydro-1H-pyrrolo[2,3-b]pyridine (614 mg, 5.11 mmol) and N-bromosuccinimide (1.09 g, 6.13 mmol) were dissolved in N,N-dimethylformamide (12 mL), and the solution was stirred for 2.5 hours at room temperature. An aqueous solution of saturated sodium bicarbonate was added to the reaction solution at 0° C., which was then extracted with ethyl acetate, the organic layer was washed with brine and dried over anhydrous magnesium sulfate. The solvent was evaporated in vacuo, the residue was purified by NH silica gel column chromatography (hexane:ethyl acetate=3:1), and 5-bromo-2,3-dihydro-1H-pyrrolo[2,3-b]pyridine (370 mg, 1.86 mmol, 36%) was obtained as a white solid.

The resulting 5-bromo-2,3-dihydro-1H-pyrrolo[2,3-b]pyridine (345 mg, 1.73 mmol), zinc cyanide (305 mg, 2.60 mmol) and tetrakis(triphenylphosphine)palladium(0) (200 mg, 0.173 mmol) were dissolved in dimethylsulfoxide (7 mL), and the solution was stirred at 120° C. for 4 hours under nitrogen atmosphere. The reaction solution was cooled to room temperature, water and ethyl acetate were added to the reaction solution, the organic layer was separated, the organic layer was washed with brine and dried over anhydrous magnesium sulfate. The solvent was evaporated in vacuo, the residue was purified by silica gel column chromatography (ethyl acetate), and the title compound (167 mg, 1.15 mmol, 66%) was obtained as a light brown solid.

$^1$H-NMR Spectrum (DMSO-d$_6$) δ(ppm): 3.01 (2H, t, J=8.6 Hz), 3.58 (2H, t, J=8.6 Hz), 7.46 (1H, s), 7.63 (1H, s), 8.10 (1H, s).

Preparation Example O-2

2.3-Dihydro-1H-pyrrolo[2,3-b]pyridine-5-carboxylic Acid

The title compound (259 mg, quantitatively) was obtained as a white solid from 2,3-dihydro-1H-pyrrolo[2,3-b]pyridine-5-carbonitrile described in Preparation Example O-1 (167 mg, 1.15 mmol) according to an analogous method to Preparation Example T-6.

¹H-NMR Spectrum (DMSO-d₆) δ(ppm): 3.00 (2H, t, J=8.6 Hz), 3.56 (2H, t, J=8.6 Hz), 7.25 (1H, s), 7.59 (1H, s), 8.30 (1H, s).

Preparation Example P-1

6-Oxo-1,6-dihydro-pyridine-3-carboxylic acid ethyl ester

To a suspension of 6-hydroxy-nicotinic acid (5.00 g, 35.9 mmol) in ethanol (60 mL) was added 1N hydrochloric acid (20 mL), which was then stirred at 110° C. for 3 hours. The reaction solution was cooled to 0° C., then, an aqueous solution of saturated sodium bicarbonate was added, the solution was extracted with ethyl acetate and tetrahydrofuran, and the organic layer was dried over anhydrous magnesium sulfate. The solvent was evaporated in vacuo, the residue was purified by silica gel column chromatography (ethyl acetate), and the title compound (3.90 g, 23.3 mmol, 65%) was obtained as a white solid.
¹H-NMR Spectrum (DMSO-d₆) δ(ppm):1.27 (3H, t, J=7.1 Hz), 4.23 (2H, q, J=7.1 Hz), 6.36 (1H, d, J=9.7 Hz), 7.79 (1H, dd, J=2.6, 9.7 Hz), 8.03 (1H, d, J=2.6 Hz).

Preparation Example P-2

5-Iodo-6-oxo-1,6-dihydro-pyridine-3-carboxylic acid ethyl ester

The title compound (2.82 g, 9.62 mmol, 80%) was obtained as a white solid from 6-oxo-1,6-dihydro-pyridine-3-carboxylic acid ethyl ester described in Preparation Example P-1 (2.00 g, 12.0 mmol) according to an analogous method to Preparation Example A+-16.
¹H-NMR Spectrum (DMSO-d₆) δ(ppm):1.28 (3H, t, J=7.1 Hz), 4.23 (2H, q, J=7.1 Hz), 8.09 (1H, s), 8.36 (1H, d, J=2.4 Hz).

Preparation Example P-3

6-Oxo-5-trimethylsilanylethynyl-1,6-dihydro-pyridine-3-carboxylic acid ethyl ester 5-Iodine-6-oxo-1,6-dihydro-pyridine-3-carboxylic acid ethyl ester described in Preparation Example P-2 (1.00 g, 3.41 mmol), trimethylsilylacetylene (626 μl, 4.43 mmol), palladium(II) acetate (7.66 mg, 34 μmol), triphenylphosphine (17.9 mg, 68 μmol), copper(I)iodide (13 mg, 68 μmol) and butylamine (674 μl, 6.82 mmol) were suspended in tetrahydrofuran (6 mL), and the mixture was stirred at 40° C. for 16 hours under nitrogen atmosphere. The reaction mixture was cooled to room temperature, then, water was added thereto, the solution was extracted with ethyl acetate, and the organic layer was washed with brine. The organic layer was dried over anhydrous magnesium sulfate, then, the solvent was evaporated in vacuo, the residue was purified by silica gel column chromatography (hexane:ethyl acetate=1:1), and the title compound (551 mg, 2.09 mmol, 61%) was obtained as a light brown solid.
¹H-NMR Spectrum (DMSO-d₆) δ(ppm): 0.22 (9H, s), 1.27 (3H, t, J=7.1 Hz), 4.23 (2H, q, J=7.1 Hz), 7.91 (1H, d, J=2.4 Hz), 8.07 (1H, d, J=2.4 Hz).

Preparation Example P-4

Furo[2,3-b]pyridine-5-carboxylic acid ethyl ester

6Oxo-5-trimethylsilanylethynyl-1,6-dihydro-pyridine-3-carboxylic acid ethyl ester described in Preparation Example P-3 (545 mg, 2.07 mmol) and copper(I)iodide (5.9 mg, 31 μmol) were suspended in ethanol (7 mL) and triethylamine (3 mL), and the mixture was stirred at 75° C. for 20 hours. The reaction mixture was cooled to room temperature, then, potassium carbonate (572 mg, 4.14 mmol) was added to the reaction mixture, which was further stirred at 75° C. for 5 hours. The reaction mixture was cooled to 0° C., then, water was added, the precipitated solid was filtered, and the title compound (303 mg) was obtained as a brown solid. In addition, ethyl acetate was added to the mother liquor for extraction, the organic layer was washed with brine, then, dried over anhydrous magnesium sulfate, the solvent was evaporated in vacuo, the residue was purified by silica gel column chromatography (hexane:ethyl acetate=1:1), and the title compound (33 mg, 0.17 mmol) was obtained as a white solid.
¹H-NMR Spectrum (DMSO-d₆) δ(ppm):1.36 (3H, t, J=7.1 Hz), 4.38 (2H, q, J=7.1 Hz), 7.16 (1H, d, J=2.4 Hz), 8.25 (1H, d, J=2.2 Hz), 8.69 (1H, d, J=1.8 Hz), 8.87 (1H, d, J=2.0 Hz).

Preparation Example Q+-1

Imidazo[1,2-a]pyridine-6-carboxylic acid (5-(3-fluorophenoxy)thiophene-2-ylmethyl) amide To a solution of imidazo[1,2-a]pyridine-6-carboxylic acid (87 mg, 0.54 mmol) and C-(5-(3-fluorophenoxy)thiophen-2-yl)methylamine (120 mg, 0.54 mmol) in N,N-dimethylformamide (5 mL) were added benzotriazol-1-yl-tris(dimethylamino)phosphonium hexafluorophosphate (240 mg, 0.54 mmol) and triethylamine(0.15 mL, 1.08 mmol), and the solution was stirred for 40 minutes at 80° C. Water and ethyl acetate were added to the reaction mixture for extraction, and the organic layer was washed twice with water. Silica gel was added to the organic layer, solvent was evaporated in vacuo for adsorption, purification was carried out by silica gel column chromatography (hexane:ethyl acetate=1:1, then ethyl acetate), and the title compound (90 mg, 0.25 mmol, 45.4%) was obtained as a light brown oil.
¹H-NMR Spectrum (DMSO-d₆) δ(ppm): 4.55 (2H, d, J=5.6 Hz), 6.58 (1H, d, J=4.0 Hz), 6.83 (1H, d, J=4.0 Hz), 6.90-7.00 (3H, m), 7.40 (1H, ddd, J=8.0, 8.0, 8.0 Hz), 7.57-7.66 (3H, m), 8.04 (1H, s), 9.12 (1H, d, J=0.8 Hz), 9.20 (1H, t, J=5.6 Hz).

Preparation Example R-1

2,6-Diamino-5-iodo-nicotinic acid ethyl ester

To a solution of 2,6-diamino-nicotinic acid ethyl ester described in Preparation Example A-14 (1.4 g, 7.7 mmol) in N,N-dimethylformamide (15 mL) was added N-iodosuccinimide (2.09 g, 9.3 mmol), and the solution was stirred for 1 hour at room temperature. The reaction mixture was poured into an aqueous solution of saturated sodium thiosulfate pentahydrate, and the solution was extracted with ethyl acetate. The organic layer was washed with brine, dried over anhydrous magnesium sulfate, and then evaporated. The resulting residue was purified by silica gel column chromatography (ethyl acetate:hexane=1:1) and the title compound (0.84 g, 2.7 mmol, 35.5%) was obtained.
¹H-NMR Spectrum (CDCl₃) δ(ppm):1.36 (3H, t, J=7.2 Hz), 4.27 (2H, q, J=7.2 Hz), 5.10 (2H, brs), 8.23 (1H, s).

Preparation Example R-2

6-Amino-1H-pyrrolo[2,3-b]pyridine-5-carboxylic acid ethyl ester

Catechol borane (2.7 mL, 1M tetrahydrofuran solution, 2.7 mmol) was added dropwise to ethoxyacetylene (0.7 mL, 40% hexane solution, 2.83 mmol) on an ice bath, and the mixture was stirred for 1 hour at room temperature. The mixture was further heated at 70° C. and stirred for 2 hours, and allowed to room temperature. A solution of 2,6-diamino-5-iodo-nicotinic acid ethyl ester described in Preparation Example R-1 (415 mg, 1.35 mmol) in tetrahydrofuran (5.5 mL), tetrakis(triphenylphosphine)palladium(0) (48 mg, 0.042 mmol) and sodium hydroxide (160 mg, 4 mmol, powder) were added thereto, followed by stirring for 7 hours 30 minutes under reflux. The reaction mixture was allowed to room temperature, 2N hydrochloric acid (4.7 mL, 9.4 mmol) was added thereto, followed by stirring for 60 hours at room temperature. After the reaction was completed, the reaction mixture was evaporated, and extracted using diethyl ether. The aqueous layer was fractionated, neutralized on an ice bath with an aqueous solution of 5N sodium hydroxide, then, was extracted with ethyl acetate. The organic layer was dried over anhydrous magnesium sulfate, then evaporated, the resulting residue was purified by silica gel column chromatography (ethyl acetate:hexane=2:1), and the title compound (97 mg, 0.47 mmol, 35%) was obtained.

$^1$H-NMR Spectrum (CDCl$_3$) δ(ppm): 1.41 (3H, t, J=7.2 Hz), 4.36 (2H, q, J=7.2 Hz), 6.28-6.42 (3H, m), 6.99-7.02 (1H, m), 8.49 (1H, s), 9.19 (1H, brs).

Preparation Example R-3

2,3-Dihydro-1H-pyrrolo[2,3-b]pyridine

1H-Pyrrolo[2,3-b]pyridine (1.00 g, 8.46 mmol) and 10% palladium-carbon (500 mg) were dissolved in a mixture of formic acid (10 mL) and triethylamine (10 mL), and the mixture was stirred at 70° C. for 87 hours. To this reaction mixture was further added 10% palladium-carbon (400 mg), and the solution was stirred for 9.5 hours at 70° C. The reaction mixture was cooled to room temperature, an aqueous solution of 5N sodium hydroxide was added thereto, the solution was extracted with ethyl acetate and tetrahydrofuran, and the organic layer was dried over anhydrous magnesium sulfate. The solvent was evaporated in vacuo, the residue was purified by silica gel column chromatography (ethyl acetate:methanol=10:1), and the title compound (219 mg, 1.82 mmol, 22%) was obtained as a pale yellow solid.

$^1$H-NMR Spectrum (DMSO-d$_6$) δ(ppm) 2.94 (2H, t, J=8.4 Hz), 3.43 (2H, t, J=8.4 Hz), 6.27 (1H, s), 6.39 (1H, dd, J=5.3, 7.0 Hz), 7.22 (1H, d, J=7.0 Hz), 7.66 (1H, d, J=4.9 Hz).

Preparation Example R4

5-Bromo-2,3-dihydro-1H-pyrrolo[2,3-b]pyridine 2,3-Dihydro-1H-pyrrolo[2,3-b]pyridine described in Preparation Example R-3 (15 mg, 0.13 mmol) and N-bromosuccinimide (24 mg, 0.14 mmol) were dissolved in N,N-dimethylformamide (0.5 mL), and the solution was stirred for 15 hours at room temperature. An aqueous solution of saturated sodium bicarbonate was added to the reaction solution at 0+ C., which was then extracted with ethyl acetate, the organic layer was washed with brine and dried over anhydrous magnesium sulfate. The solvent was evaporated in vacuo, the residue was purified by silica gel column chromatography (hexane:ethyl acetate=5:1), and the title compound (12 mg, 60 μmol, 48%) was obtained as a white solid.

$^1$H-NMR Spectrum (DMSO-d$_6$) δ(ppm): 2.98 (2H, t, J=8.8 Hz), 3.48 (2H, t, J=8.8 Hz), 6.60 (1H, s), 7.37 (1H, d, J=1.1 Hz), 7.71 (1H, d, J=2.4 Hz).

Preparation Example R-5

5-Bromo-1H-pyrrolo[2,3-b]pyridine

5-Bromo-2,3-dihydro-1H-pyrrolo[2,3-b]pyridine (600 mg, 3.01 mmol) and 2,3-dichloro-5,6-dicyano-1,4-benzoquinone described in Preparation Example R-4 (753 mg, 3.31 mmol) was dissolved in toluene (15 mL), and the solution was refluxed for 40 minutes under nitrogen atmosphere. The reaction solution was cooled to room temperature, water and ethyl acetate were added thereto, the organic layer was partitioned, the organic layer was washed with brine and dried over anhydrous magnesium sulfate. The solvent was evaporated in vacuo, the residue was purified by silica gel column chromatography (hexane:ethyl acetate=5:1), and the title compound (260 mg, 1.32 mmol, 44%) was obtained as a white solid.

$^1$H-NMR Spectrum (DMSO-d$_6$) δ(ppm): 6.40-6.48 (1H, m), 7.50-7.60 (1H, m), 8.20 (1H, s), 8.30 (1H, s), 11.9 (1H, s).

Preparation Example R-6

1H-Pyrrolo[2,3-b]pyridine-5-carbonitrile

5-Bromo-1H-pyrrolo[2,3-b]pyridine described in Preparation Example R-5 (90 mg, 0.46 mmol), zinc cyanide (80 mg, 0.69 mmol) and tetrakis(triphenylphosphine)palladium(0) (53 mg, 46 μmol) were dissolved in N-methyl-2-pyrrolidinone (2 mL), and the mixture was stirred for 4.5 hours at 110° C. under nitrogen atmosphere. The reaction mixture was cooled to room temperature, water and ethyl acetate were added to the reaction mixture, the organic layer was partitioned, the organic layer was washed with brine and dried over anhydrous magnesium sulfate. The solvent was evaporated in vacuo, the residue was purified by silica gel column chromatography (hexane:ethyl acetate=5:1), and the title compound (48 mg, 0.34 mmol, 73%) was obtained as a white solid.

$^1$H-NMR Spectrum (DMSO-d$_6$) δ(ppm): 6.55-6.68 (1H, m), 7.65-7.78 (1H, m), 8.52 (1H, s), 8.60 (1H, s), 12.3 (1H, brs).

Preparation Example R-7

1H-Pyrrolo[2,3-b]pyridine-5-carboxylic Acid

The title compound (47 mg, 0.29 mmol, 88%) was obtained as a white solid from 1H-pyrrolo[2,3-b]pyridine-5-carbonitrile described in Preparation Example R-6 (47 mg, 0.33 mmol) according to an analogous method to Preparation Example T-6.

$^1$H-NMR Spectrum (DMSO-$d_6$) δ(ppm): 6.57-6.63 (1H, m), 7.55-7.62 (1H, m), 8.51 (1H, s), 8.79 (1H, s), 12.0 (1H, s),12.7 (1H, brs).

Preparation Example S-1

3-Amino-2-bromopyridine

2-Bromo-3-nitropyridine (3 g, 15 mmol) was dissolved in a mixture solution of tetrahydrofuran (15 mL) and water (5 mL), then iron powder (1 g, 18 mmol) and ammonium chloride (2 g, 37 mmol) were added thereto, followed by stirring at from 60° C. to 70° C. for 5 hours. After the reaction was completed, the reaction mixture was filtered through Celite pad, brine was added, and the solution was extracted with ethyl acetate. The organic layer was dried over anhydrous magnesium sulfate, then evaporated, the resulting residue was purified by silica gel column chromatography (ethyl acetate:hexane=1:4), and the title compound (2.69, 15 mmol, quantitatively) was obtained.

$^1$H-NMR Spectrum (DMSO-$d_6$) δ(ppm): 5.47 (2H, brs), 7.07-7.09 (2H, m), 7.54 (1H, dd, J=2.0, 3.6 Hz).

Preparation Example S-2

(2-Bromo-pyridin-3-yl)carbamic acid ethyl ester

3-Amino-2-bromopyridine described in Preparation Example S-1 (1.4 g, 8.1 mmol) was dissolved in pyridine (10 mL), ethyl chloroformate (0.93 mL, 9.7 mmol) was added dropwise on an ice bath, and the solution was stirred for 2 hours at room temperature. After the reaction was completed, the reaction solution was poured into brine, and the solution was extracted with ethyl acetate. The organic layer was dried over anhydrous magnesium sulfate, then evaporated, the resulting residue was purified by silica gel column chromatography (ethyl acetate:hexane=1:4), and the title compound (0.56 g, 2.3 mmol, 28%) was obtained.

$^1$H-NMR Spectrum (DMSO-$d_6$) δ(ppm):1.22 (3H, t, J=7.2 Hz), 4.12 (2H, q, J=7.2 Hz), 7.43 (1H, dd, J=4.8, 8.0 Hz), 7.92 (1H, dd, J=1.6, 8.0 Hz), 8.17 (1H, dd, J=1.6, 4.8 Hz), 9.10 (1H, brs).

Preparation Example S-3

(2-Trimethylsilanylethynyl-pyridin-3-yl)carbamic acid ethyl ester

A mixture of (2-bromo-pyridin-3-yl)carbamic acid ethyl ester described in Preparation Example S-2 (395 mg, 1.6 mmol), dichlorobis(triphenylphosphine)palladium(II) (20 mg, 0.028 mmol), triethylamine (0.25 mL, 1.8 mmol), copper (I)iodide (10 mg, 0.05 mmol) and trimethylsilylacetylene (0.131 mL, 2.4 mmol) was placed in a sealed tube, and heated at 100° C. for 4 hours. After the reaction was completed, the reaction mixture was poured into water, which was then extracted with ethyl acetate. The organic layer was dried over anhydrous magnesium sulfate, then evaporated, the resulting residue was purified by silica gel column chromatography (ethyl acetate:hexane=1:2), and the title compound (0.42 g, 1.6 mmol, quantitatively) was obtained.

$^1$H-NMR Spectrum (DMSO-$d_6$) δ(ppm): 0.24 (9H, s), 1.21 (3H, t, J=7.2 Hz), 4.12 (2H, q, J=7.2 Hz), 7.38 (1H, dd, J=4.8, 8.4 Hz), 7.88-7.96 (1H, m), 8.29 (1H, dd, J=1.6, 4.8 Hz), 8.82 (1H, brs).

Preparation Example S-4

1H-Pyrrolo[3,2-b]pyridine (2-Trimethylsilanylethynyl-pyridin-3-yl)carbamic acid ethyl ester described in Preparation Example S-3 (0.42 g, 1.6 mmol) was dissolved in ethanol (8 mL), sodium ethoxide (204 mg, 3 mmol) was added thereto, followed by stirring for 1 hour under reflux. After the reaction was completed, the reaction mixture was poured into brine, and the solution was extracted with ethyl acetate. The organic layer was dried over anhydrous magnesium sulfate, then evaporated, the resulting solid was washed with solvent (diethylether:hexane=1:2), and the title compound (0.12 g, 1 mmol, 63.5%) was obtained.

$^1$H-NMR Spectrum (DMSO-$d_6$) δ(ppm): 6.50-6.54 (1H, m), 7.06 (1H, dd, J=4.8, 8.4 Hz), 7.58-7.62 (1H, m), 7.72-7.76 (1H, m), 8.26-8.30 (1H, m), 11.2 (1H, brs).

Preparation Example T-1

3-Dichloromethyl-2-nitro-thiophene

To a solution of potassium tert-butoxide (23.0 mL, 1.0M tetrahydrofuran solution, 23.2 mmol) in N,N-dimethyl formamide (20 mL) were added a mixture solution of 2-nitrothiophene (1.00 g, 7.74 mmol) in chloroform (682 μl, 8.51 mmol) and N,N-dimethylformamide (2 mL) dropwise at −78° C., the solution was stirred for 5 minutes, and then, methanol and acetic acid were added at 0° C. Brine was added to the reaction solution, which was then extracted with ethyl acetate. The solvent was evaporated in vacuo, the residue was purified by silica gel column chromatography (hexane:ethyl acetate=20:1), and the title compound (1.54 g, 7.26 mmol, 94%) was obtained as a light brown solid.

$^1$H-NMR Spectrum (CDCl$_3$) δ(ppm): 7.54 (1H, d, J=5.7 Hz), 7.57 (1H, d, J=5.7 Hz), 7.64 (1H, s).

Preparation Example T-2

2-nitro-thiophene-3-carbaldehyde

3-Dichloromethyl-2-nitro-thiophene described in Preparation Example T-1 (1.54 g, 7.26 mmol) was dissolved in formic acid (10 mL), and the solution was refluxed for 24 hours under nitrogen atmosphere. An aqueous solution of 5N sodium hydroxide was added to the reaction solution at 0° C., which was then extracted with ethyl acetate, the organic layer was washed with brine and dried over anhydrous magnesium sulfate. The solvent was evaporated in vacuo, the residue was purified by silica gel column chromatography (hexane:ethyl acetate=10:1), and the title compound (472 mg, 3.00 mmol, 41%) was obtained as a light brown solid.

$^1$H-NMR Spectrum (CDCl$_3$) δ(ppm): 7.49 (1H, d, J=5.5 Hz), 7.54 (1H, d, J=5.7 Hz), 10.62 (1H, s).

Preparation Example T-3

2-(2-Nitro-thiophen-3-yl)-[1,3]dioxolane

2-Nitro-thiophene-3-carbaldehyde described in Preparation Example T-2 (367 mg, 2.33 mmol), ethane-1,2-diol (651 μl, 11.7 mmol) and toluene-4-sulfonic acid monohydrate (40 mg, 0.233 mmol) were dissolved in toluene (8 mL), and the solution was stirred for 2.5 hours under reflux. An aqueous solution of saturated sodium bicarbonate was added to the reaction solution at 0° C., which was then extracted with ethyl acetate, the organic layer was washed with brine, and the organic layer was dried over anhydrous magnesium sulfate. The solvent was evaporated in vacuo, the residue was purified by NH silica gel column chromatography (hexane:ethyl acetate=5:1), and the title compound (304 mg, 1.51 mmol, 65%) was obtained as a white solid.

$^1$H-NMR Spectrum (CDCl$_3$) δ(ppm): 4.07-4.15 (4H, m), 6.51 (1H, s), 7.25 (1H, d, J=5.5 Hz), 7.45 (1H, d, J=5.5 Hz).

Preparation Example T-4

2-Amino-thiophene-3-carbaldehyde 2-(2-Nitro-thiophen-3-yl)-[1,3]dioxolane described in Preparation Example T-3 (150 mg, 0.746 mmol), iron powder (208 mg, 3.73 mmol) and ammonium chloride (80 mg, 1.49 mmol) were suspended in a mixture solvent of ethanol (3 mL) and water (0.75 mL), and the mixture was stirred at 90° C. for 5 hours. The reaction mixture was cooled to room temperature, then, filtered through Celite pad. The filtrate was evaporated in vacuo, the residue was purified by silica gel column chromatography (hexane:ethyl acetate=5:1), and the title compound (38 mg, 0.30 mmol, 40%) was obtained as a red oily substance.

$^1$H-NMR Spectrum (CDCl$_3$) δ(ppm): 6.19 (1H, d, J=5.7 Hz), 6.67 (2H, brs), 6.90 (1H, d, J=5.7 Hz), 9.69 (1H, s).

Preparation Example T-5

6-Amino-thieno[2,3-b]pyridine-5-carbonitrile

2-Amino-thiophene-3-carbaldehyde described in Preparation Example T-4 (38 mg, 0.30 mmol) and malononitrile (20 mg, 0.30 mmol) were dissolved in ethanol (1 mL) to which piperidine (several drops) had been added, and the solution was stirred for 1 hour under reflux. The reaction solution was cooled to room temperature, and the solvent was evaporated in vacuo. The residue was purified by NH silica gel column chromatography (hexane:ethyl acetate=10:1), and the title compound (50 mg, 0.29 mmol, 96%) was obtained as a white solid.

$^1$H-NMR Spectrum (DMSO-d$_6$) δ(ppm): 7.00 (2H, s), 7.18 (1H, d, J=6.0 Hz), 7.42 (1H, d, J=6.0 Hz), 8.40 (1H, s).

Preparation Example T6

6Amino-thieno[2,3-b]pyridine-5-carboxylic Acid

6-Amino-thieno[2,3-b]pyridine-5-carbonitrile described in Preparation Example T-5 (104 mg, 0.594 mmol) was dissolved in a mixture solution of water (1.5 mL) and sulfuric acid (1.5 mL), and the solution was stirred for 3 hours under reflux. An aqueous solution of 5N sodium hydroxide was added to the reaction solution at 0° C., to neutralize the solution. The precipitated solid was filtered, and title compound (65 mg, 0.33 mmol, 56%) was obtained as a pale yellow solid.

$^1$H-NMR Spectrum (DMSO-d$_6$) δ(ppm): 7.19 (1H, d, J=5.9 Hz), 7.25 (1H, d, J=6.0 Hz), 8.48 (1H, s).

Preparation Example T-7

6Amino-thieno[2,3-b]pyridine-5-carboxylic acid methyl ester

6-Amino-thieno[2,3-b]pyridine-5-carboxylic acid (44 mg, 0.23 mmol) was dissolved in a mixture solution of methanol (1 mL) and sulfuric acid (0.5 mL), and the solution was stirred for 24 hours under reflux. An aqueous solution of saturated sodium bicarbonate was added to the reaction solution at 0° C., which was then extracted with ethyl acetate, the organic layer was washed with brine and dried over anhydrous magnesium sulfate. The solvent was evaporated in vacuo, the residue was purified by NH silica gel column chromatography (hexane:ethyl acetate=2:1), and the title compound (34 mg, 0.16 mmol, 72%) was obtained as a white solid.

$^1$H-NMR Spectrum (CDCl$_3$) δ(ppm): 3.93 (3H, s), 7.09 (1H, d, J=6.0 Hz), 7.11 (1H, d, J=6.0 Hz), 8.54 (1H, s).

Preparation Example T-8

6-Oxo-6,7-dihydro-thieno[2,3-b]pyridine-5-carboxylic acid methyl ester

6-Amino-thieno[2,3-b]pyridine-5-carboxylic acid methyl ester described in Preparation Example T-7 (10 mg, 48 μmol) and sodium nitrite (10 mg, 144 μmol) were dissolved in phosphinic acid (0.5 mL), and the solution was stirred at 0° C. for 1 hour. An aqueous solution of saturated sodium bicarbonate was added to the reaction solution at 0° C., which was then extracted with ethyl acetate, and the organic layer was dried over anhydrous magnesium sulfate. The solvent was evaporated in vacuo, the residue was purified by silica gel column chromatography (hexane:ethyl acetate=1:1), and the title compound (10 mg, 48 μmol, quantitatively) was obtained as a white solid.

$^1$H-NMR Spectrum (CDCl$_3$) δ(ppm): 4.03 (3H, s), 7.21 (1H, d, J=5.9 Hz), 7.34 (1H, d, J=6.0 Hz), 8.61 (1H, s), 11.4 (1H, s).

Preparation Example T-9

6trifluoromethanesulfonyloxy-thieno[2,3-b]pyridine-5-carboxylic acid methyl ester 6Oxo-6,7-dihydro-thieno[2,3-b]pyridine-5-carboxylic acid methyl ester described in Preparation Example T-8 (9 mg, 43 μmol), N-phenyltrifluoromethanesulfonimide (23 mg, 65, mol) and dimethyl-pyridin-4yl-amine (catalytic amount) were dissolved in dichloromethane (0.5 mL), and the solution was stirred for 18.5 hours at room temperature. Water was added to the reaction solution, which was then extracted with ethyl acetate, the organic layer was washed with brine and dried over anhydrous magnesium sulfate. The solvent was evaporated in vacuo, the residue was purified by NH silica gel column chromatography (hexane:ethyl acetate=3:1), and the title compound (10 mg, 29 μmol, 68%) was obtained as a white solid.

$^1$H-NMR Spectrum (CDCl$_3$) δ(ppm): 4.03 (3H, s), 7.43 (1H, d, J=5.9 Hz), 7.73 (1H, d, J=5.9 Hz), 8.87 (1H, s).

Preparation Example T-10

Thieno[2,3-b]pyridine-5-carboxylic acid methyl ester

6-Trifluoromethanesulfonyloxy-thieno[2,3-b]pyridine-5-carboxylic acid methyl ester described in Preparation Example T-9 (10 mg, 29 μmol), tetrakis(triphenylphosphine)palladium(0) (3.4 mg, 2.9 μmol), formic acid (1.7 μl, 44 μmol) and N,N-diisopropylethylamine (15 μl, 87 μmol) were dissolved in 1-methyl-2-pyrrolidone (0.5 mL), and the mixture was stirred for 1.5 hours at 100° C. The reaction mixture was cooled to room temperature, water and ethyl acetate were added, the organic layer was partitioned, the organic layer was washed with brine and dried over anhydrous magnesium sulfate. The solvent was evaporated in vacuo, the residue was purified by NH silica gel column chromatography (hexane:ethyl acetate=5:1), and the title compound (7 mg, quantitatively) was obtained as a white solid.

$^1$H-NMR Spectrum (CDCl$_3$) δ(ppm): 3.99 (3H, s), 7.36 (1H, d, J=6.4 Hz), 7.62 (1H, d, J=6.0 Hz), 8.70 (1H, d, J=1.6 Hz), 9.17 (1H, d, J=2.0 Hz).

Preparation Example U-1

Thiophen-3-yl-carbamic acid tert-butyl ester

Thiophene-3-carboxylic acid (2.50 g, 19.5 mmol), diphenylphosphoryl azide (4.62 mL, 21.5 mmol), triethylamine (3.26 mL, 23.4 mmol) were dissolved in tert-butanol (50 mL), and the solution was stirred for 3.5 hours under reflux. Water was added to the reaction solution at 0° C., which was then extracted with ethyl acetate, the organic layer was washed with brine and dried over anhydrous magnesium sulfate. The solvent was evaporated in vacuo, the residue was purified by NH silica gel column chromatography (hexane:ethyl acetate=10:1), and the title compound (3.33 g, 16.7 mmol, 86%) was obtained as a white solid.

$^1$H-NMR Spectrum (DMSO-d$_6$) δ(ppm):1.46 (9H, s), 6.97 (1H, d, J=5.2 Hz), 7.16 (1H, s), 7.38 (1H, m), 9.61 (1H, s).

Preparation Example U-2

(2-Formyl-thiophen-3-yl)-carbamic acid tert-butyl ester

Thiophen-3-yl-carbamic acid tert-butyl ester described in Preparation Example U-1 (1.00 g, 5.02 mmol) was dissolved in tetrahydrofuran (20 mL), to which n-butyl lithium (2.47M hexane solution, 4.47 mL, 11.0 mmol) was added at −78° C., and the mixture was stirred at −78° C. for 1 hour. N,N-dimethylformamide (466 μl, 6.02 mmol) was added to the reaction mixture at −78° C., and the solution was stirred for 1 hour at room temperature. Water was added to the reaction solution, which was then extracted with ethyl acetate, the organic layer was washed with brine and dried over anhydrous magnesium sulfate. The solvent was evaporated in vacuo, the residue was purified by silica gel column chromatography (hexane:ethyl acetate=10:1), and the title compound (1.14 g, quantitatively) was obtained as a colorless oil.

$^1$H-NMR Spectrum (DMSO-d$_6$) δ(ppm):1.50 (9H, s), 7.60 (1H, d, J=5.3 Hz), 8.02 (1H, d, J=5.3 Hz), 9.94 (1H, s), 10.1 (1H, s).

Preparation Example U-3

5-Amino-thieno[3,2-b]pyridine-6-carbonitrile (2-Formyl-thiophen-3-yl)-carbamic acid tert-butyl ester described in Preparation Example U-2 (500 mg, 2.20 mmol) and malononitrile (153 mg, 2.31 mmol) were dissolved in a solution of ethanol (10 mL) to which piperidine (catalytic amount) had been added, and the mixture was stirred for 1 hour under reflux. The reaction mixture was cooled to room temperature, the precipitated solid was filtered, and title compound (215 mg, 1.23 mmol, 56%) was obtained as a white solid.

$^1$H-NMR Spectrum (DMSO-d$_6$) δ(ppm): 6.76 (2H, s), 7.22 (1H, dd, J=0.73, 5.5 Hz), 8.22 (1H, d, J=5.5 Hz), 8.64 (1H, s).

Preparation Example U-4

5-Amino-thieno[3,2-]pyridine-6-carboxylic Acid

The title compound (200 mg) was obtained as a white solid from 5-amino-thieno[3,2-b]pyridine-6-carbonitrile described in Preparation Example U-3 (208 mg, 1.19 mmol) according to an analogous method to Preparation Example T-6.

$^1$H-NMR Spectrum (DMSO-d$_6$) δ(ppm): 7.27 (1H, dd, J=0.73, 5.5 Hz), 8.28 (1H, d, J=5.5 Hz), 8.92 (1H, s).

Preparation Example U+-1

5-Oxo-4,5-dihydro-thieno[3,2-b]pyridine-6-carboxylic acid (5-phenoxy-thiophen-2-ylmethyl)-amide The title compound (17 mg, 44 μmol, 46%) was obtained as a white solid from 5-amino-thieno[3,2-b]pyridine-6-carboxylic acid(5-phenoxy-thiophen-2-ylmethyl)-amide described in Preparation Example U4 (37 mg, 97 μmol) according to an analogous method to Preparation Example T-8.

$^1$H-NMR Spectrum (DMSO-d$_6$) δ(ppm): 4.59 (2H, d, J=5.9 Hz), 6.49 (1H, d, J=3.8 Hz), 6.79 (1H, d, J=3.7 Hz), 7.07-7.15 (4H, m), 7.37 (2H, t, J=7.7Hz), 8.15 (1H, d, J=5.5 Hz), 8.94 (1H, s), 10.3 (1H, m), 13.0 (1H, s).

Preparation Example U+-2. Trifluoromethanesulfonic acid 6((5-phenoxy-thiophen-2-ylmethyl)-carbamoyl)-thieno[3,2-b]pyridin-5-yl ester The title compound (11 mg, 21 μmol, 68%) was obtained as a white solid from 5-oxo-4,5-dihydro-thieno[3,2-b]pyridine-carboxylic acid (5-phenoxy-thiophen-2-ylmethyl)-amide described in Preparation Example U+-1 (12 mg, 31 μmol) according to an analogous method to Preparation Example T-9 (with the proviso that N,N-dimethylformamide was used instead of dichloromethane).

$^1$H-NMR Spectrum (DMSO-d$_6$) δ(ppm): 4.53 (2H, d, J=5.5 Hz), 6.53 (1H, d, J=3.8 Hz), 6.83 (1H, d, J=4.4 Hz), 7.09 (2H, d, J=8.6 Hz), 7.13 (1H, t, J=7.7 Hz), 7.37 (2H, t, J=7.7 Hz), 7.65 (1H, d, J=5.5 Hz), 8.50 (1H, d, J=5.7 Hz), 8.97 (1H, s), 9.39-9.44 (1H, m).

Preparation Example W-1

Dithiocarbonic acid O-ethyl ester S-quinolin-6-yl ester

To a solution of quinolin-6-yl amine (2.88 g, 20 mmol) and HBF$_4$ aqueous solution (48% W/W, 11 mL) in tetrahydrofuran (100 mL) was added 3-methyl-1-nitrosooxy-butane (10.7 mL, 60 mmol) dropwise under nitrogen atmosphere at from −10° C. to −15° C., then, the mixture was stirred for 1 hour. At from −10° C. to −15° C., diethyl ether (200 mL) was added dropwise, the precipitated solid was collected by filtration, washed with diethyl ether, dried, and quinolin-6-diazonium tetrafluoroborate (6.85 g) was obtained as a yellow-red solid.

Next, to a solution of potassium O-ethyl dithiocarbonate (802 mg, 5 mmol), water (20 mL) and diethyl ether (30 mL) was added quinolin-6-diazonium tetrafluoroborate (665 mg, 2 mmol) dropwise on an ice bath, then, the solution was stirred for 18 hours. To this reaction mixture was added water (100 mL), then the solution was extracted with diethyl ether (50 mL), and washed with brine (150 mL). The organic layer was dried over anhydrous magnesium sulfate, filtered, then, evaporation in vacuo was carried out, and a residue of red oil (0.462 g) was obtained. This residue in the amount of 0.2 g was purified by thin layer silica gel chromatography (hexane:ethyl acetate=1:1), and the title compound (50 mg, 0.2 mmol) was obtained as a pale yellow oil.

$^1$H-NMR Spectrum (Acetone-d$_6$) δ(ppm):1.31 (3H, t, J=7.2 Hz), 4.66 (2H, q, J=7.2 Hz), 7.60 (1H, dd, J=8.4, 4.4 Hz), 7.86 (1H, m), 8.13 (1H, d, J=8.8 Hz), 8.18 (1H, m), 8.41 (1H, m), 9.01 (1H, m).

MS m/e (ESI) 360(MH$^+$)

Preparation Example X-1

4-Chloro-quinazoline

Phosphorus oxychloride (64 mL, 687 mmol) and phosphorus pentachloride (14.89 g, 71.50 mmol) were added to 4-hydroxyquinazoline (7.94 g, 52.3 mmol), and the solution was stirred for 20 minutes under reflux. The reaction mixture was evaporated in vacuo, and the residue was dissolved in chloroform. The chloroform solution was poured on an ice bath, concentrated aqueous ammonia was added to adjust the pH to 10, then, the solution was partitioned. The aqueous layer was extracted with chloroform, and the combined chloroform layers were washed with water. The organic layer was dried over anhydrous magnesium sulfate, then, evaporated in vacuo, and the title compound (8.03 g, 48.8 mmol, 93%) was obtained. This was used in the next reaction without purification.

$^1$H-NMR Spectrum (DMSO-d$_6$) δ(ppm): 7.64 (1H, dd, J=7.2, 8.0 Hz), 7.81 (1H, d, J=8.0 Hz), 7.93 (1H, ddd, J=0.8, 7.2, 8.0 Hz), 8.16 (1H, dd, J=0.8, 8.0 Hz), 8.86 (1H, brs).

Preparation Example Z-1

Quinoline-6-carbaldehyde n-Butyl lithium (19.2 mL; 1.5M hexane solution) was added dropwise to a solution of 6-bromoquinoline (5 g, 24.0 mmol) in diethyl ether (20 mL) that had been cooled to −70° C. under nitrogen atmosphere, a solution of N,N-dimethylformamide (3.7 mL, 48.0 mmol) in diethyl ether was further added, and the solution was stirred at −70° C. for 2 hours. The reaction solution was allowed to room temperature, then, an aqueous solution of saturated ammonium chloride was added, the solution was extracted with ethyl acetate and dried over anhydrous magnesium sulfate. The solvent was evaporated, the residue was purified by silica gel column chromatography (hexane:ethyl acetate), and the title compound (320 mg, 8.5%) was obtained as a yellow oil.

$^1$H-NMR Spectrum (CDCl$_3$) δ(ppm): 7.52-7.56 (1H, m), 8.21-8.22 (2H, m), 8.33-8.36 (1H, m), 8.37 (1H, s), 9.06-9.07 (1H, m), 10.2 (1H, s).

Preparation Example Z-2

4-Bromo-1-butyl-2-methylbenzene

Aluminum chloride (38.9 g, 0.292 mol) was portionwise added to a solution of 3-bromotoluene (25 g, 0.146 mol) and n-butyryl chloride (22.9 mL, 0.129 mol) in carbon disulfide (100 mL) that had been cooled with an ice water, and the solution was stirred for 18 hours while gradually allowing to room temperature. The reaction solution was poured into a mixture solution of an ice water (120 mL) and concentrated hydrochloric acid (10 mL), and the solution was stirred for 10 minutes. Then, the solution was extracted with hexane, washed with water and an aqueous solution of saturated sodium bicarbonate and dried over anhydrous magnesium sulfate. The solvent was evaporated, the residue was purified by silica gel column chromatography (hexane:ethyl acetate), and 1-(4bromo-2-methyl-1-phenyl)-butane-1-one (7.77 g, 22%) was obtained as a pale yellow oil. To a solution of the resulting compound in diethyleneglycol (40 mL), were added hydrazine monohydrate (4.52 g, 90.2 mmol) and potassium hydroxide (4.16 g, 74.1 mmol), then the solution was stirred at 80° C. for 2 hours, and further stirred at 160° C. overnight. The reaction solution was allowed to room temperature, hexane and water were added for partitioning, the organic layer was washed with water, and then, dried over anhydrous magnesium sulfate. The solvent was evaporated, then, the residue was purified by silica gel column chromatography (hexane:ethyl acetate), and the title compound (5.01 g, 69%) was obtained as a colorless oil.

$^1$H-NMR Spectrum (CDCl$_3$) δ(ppm): 0.90 (3H, t, J=0.2 Hz), 1.32-1.36 (2H, m), 1.51-1.55 (2H, m), 2.27 (3H, s), 2.52 (2H, t, J=7.6 Hz), 6.98 (1H, d, J=8.0 Hz), 7.23 (1H, dd, J=2.0 Hz, 8.0 Hz), 7.26-7.27 (1H, m).

Preparation Example Z+-1

(4-Butyl-3-methyl-phenyl)-quinolin-6-yl-metanol

Magnesium (83 mg, 3.40 mmol), 4-bromo-1-butyl-2-methylbenzene (722 mg, 3.18 mmol) and, as an initiator, catalytic amount of 1,2-dibromoethane were added to tetrahydrofuran (2.5 mL) under nitrogen atmosphere, and the mixture was stirred for 10 minutes under reflux. This mixture was cooled to 0° C., a solution of quinoline-6-carbaldehyde (100 mg, 6.36 mmol) in tetrahydrofuran (12 mL) was added thereto, followed by stirring for 1 hour at this temperature. An aqueous solution of saturated ammonium chloride was added to the reaction mixture, which was extracted with chloroform and dried over anhydrous magnesium sulfate. The solvent was evaporated, the residue was purified by silica gel column chromatography (hexane:ethyl acetate), and the title compound (152 mg, 78%) was obtained as a yellow solid.

$^1$H-NMR Spectrum (CDCl$_3$) δ(ppm): 0.93 (3H, t, J=7.2 Hz), 1.34-1.43 (2H, m), 1.49-1.57 (2H, m), 1.64 (1H, brs), 2.28 (3H, s), 2.57 (2H, t, J=8.0 Hz), 5.97 (1H, brs), 7.10-7.17 (3H, m), 7.38-7.42 (1H, m), 7.66-7.68 (1H,m), 7.93 (1H, s), 8.03-8.05 (1H, m), 8.16-8.18 (1H, m), 8.87-8.88 (1H, m).

Preparation Example Z+-2

Quinoline-6-carboxylic acid (4-benzyloxy phenyl)-amide

To a solution of 6-quinolinecarboxylic acid (500 mg, 2.89 mmol) and 4-benzyloxyphenylamine (681 mg, 2.89 mmol) in dichloromethane (25 mL) were added benzotriazol-1-yloxytris(dimethylamino)phosphonium hexafluorophosphate (1.53 g, 3.47 mmol) and triethylamine (0.96 mL, 6.94 mmol), and the solution was stirred overnight at room temperature. The solvent was evaporated, the residue was purified by NH silica gel column chromatography (hexane:ethyl acetate), and the title compound (194 mg, 19%) was obtained as a white solid.

$^1$H-NMR Spectrum (CDCl$_3$) δ(ppm): 5.11 (2H, s), 7.00-7.02 (2H, m), 7.32-7.45 (5H, m), 7.48-7.51 (1H, m), 7.57-7.59 (2H, m), 7.86 (1H, brs), 8.11-8.14 (1H, m), 8.19-8.21 (1H, m), 8.26-8.28 (1H, m), 8.38-8.39 (1H, m), 9.00-9.01 (1H, m).

Preparation Example Z+-3

4-Benzyloxy-N-quinolin-6-yl-benzamide

To a solution of 6-aminoquinoline (500 mg, 3.47 mmol) and 4-benzyloxybenzoic acid (792 mg, 3.47 mmol) in dichloromethane (25 mL) were added benzotriazol-1-yloxytris (dimethylamino)phosphonium hexafluorophosphate (1.84 g, 4.16 mmol) and triethylamine (0.58 mL, 4.16 mmol), and the solution was stirred overnight at room temperature. The solvent was evaporated, the residue was purified by NH silica gel column chromatography (hexane:ethyl acetate), and the title compound (218 mg, 18%) was obtained as a white solid.

$^1$H-NMR Spectrum (CDCl$_3$) δ(ppm): 5.16 (2H, s), 7.08-7.10 (2H, m), 7.36-7.47 (6H, m), 7.65-7.68 (1H, m), 7.89-7.91 (2H, m), 7.97 (1H, brs), 8.08-8.10 (1H, m), 8.15-8.17 (1H, m), 8.49-8.50 (1H, m), 8.84-8.86 (1H, m).

Preparation Example 1

4-Benzyloxybenzylamine

Potassium phthalimide (20 g, 0.108 mol) was added to a solution obtained by dissolving 4-benzyloxybenzyl chloride (25 g, 0.107 mol) in N,N-dimethylformamide (75 mL), and the solution was stirred for 3 hours under reflux. The reaction solution was allowed to room temperature, then, ethyl acetate and water were added for partitioning, the organic layer was washed with water and dried over anhydrous magnesium sulfate. The solvent was evaporated, and 2-(4-benzyloxybenzyl)-isoindol-1,3-dione (37 g, quantitatively) was obtained as a pale brown solid.

Next, to a solution of the resulting 2-(4benzyloxybenzyl)-isoindol-1,3-dione (37 g, 0.107 mol) in ethanol (1 L) was added hydrazine monohydrate (8.04 g, 0.161 mol), and the solution was stirred for 8 hours under reflux. The reaction solution was allowed to room temperature, then, water was added, and ethanol was evaporated in vacuo. Ethyl acetate and water were added to the residue for partitioning, the organic layer was washed with water, an aqueous solution of 2N sodium hydroxide and water, in this order, and dried over anhydrous magnesium sulfate. The solvent was evaporated, the residue was purified by NH silica gel column chromatography (hexane:ethyl acetate=2:1; hereinafter, the NH silica gel used was manufactured by Fuji Silysia), and the title compound (15 g, 64%) was obtained as a white solid.

Preparation Example 2

3-Benzyloxybenzylamine

To a solution of 3-benzyloxybenzyl alcohol (3.0 g, 14.0 mmol) in dichloromethane (30 mL) was added methanesulfonyl chloride (1.39 mL, 16.8 mmol) and triethylamine (2.34 mL, 16.8 mmol) on an ice bath, and the solution was stirred overnight. The reaction solution was diluted with dichloromethane, washed with aqueous solution of 5% sodium bicarbonate, and then, dried over anhydrous magnesium sulfate. The solvent was evaporated, then, the residue was purified by silica gel column chromatography (hexane:ethyl acetate=10:1), and 1-benzyloxy-3-chloromethyl-benzene (2.2 g, 67%) was obtained as a colorless oil.

Next, to a solution of iminodicarboxylic acid di-tert-butyl ester (2.12 g, 8.76 mmol) in N,N-dimethylformamide (13 mL) was added sodium hydride (0.39 g, 9.86 mmol, 60% in oil), the solution was stirred at 60° C. for 6 hours, 1-benzyloxy-3-chloromethyl-benzene (1.0 g, 4.30 mmol) was added, and the solution was further stirred at 60° C. for 4 hours. The reaction solution was allowed to room temperature, then, dichloromethane and water were added for partitioning, and the organic layer was dried over anhydrous magnesium sulfate. The solvent was evaporated, then, the residue was purified by silica gel column chromatography (hexane:ethyl acetate=10:1), and (3-benzyloxybenzyl)iminodicarboxylic acid di-tert-butyl ester (691 mg, 39%) was obtained as a pale yellow oil.

Lastly, (3-benzyloxybenzyl)iminodicarboxylic acid di-tert-butyl ester (691 mg, 1.67 mmol) was cooled on an ice bath, trifluoroacetic acid (3 mL) was added, and the solution was stirred for 30 minutes. An aqueous solution of saturated sodium bicarbonate was added to the reaction solution, which was then extracted with ethyl acetate and dried over anhydrous magnesium sulfate. The solvent was evaporated, and the title compound (292 mg, 82%) was obtained as a white waxy solid. This was used in the next reaction without further purification.

Preparation Example 3

4-Phenoxybenzylamine

A solution of sodium borohydride (2.20 g, 58.3 mmol) and concentrated sulfuric acid in diethyl ether (1.6 mL) was added to a solution of 4-phenoxybenzoic acid (5.0 g, 23.3 mmol) in tetrahydrofuran (20 mL) that had been cooled on an ice bath, and the solution was stirred for 4 hours at room temperature. The reaction solution was cooled on an ice bath, methanol was added, then, the solution was allowed to room temperature and stirred for 30 minutes. This reaction solution was cooled again, ethyl acetate and an aqueous solution of 2N sodium hydroxide were added for partitioning, the organic layer was washed with 10% sodium chloride water, dried over anhydrous magnesium sulfate, and the solvent was evaporated to obtain 4-phenoxybenzyl alcohol (4.669, quantitatively) as a colorless solid. This 4-phenoxybenzyl alcohol was used to carry out an analogous reaction to Preparation Example 2, and the title compound (886 mg) was obtained as a pale brown solid.

Preparation Example 4

3-Phenoxybenzylamine

The title compound was obtained as a pale brown solid from 3-phenoxybenzyl alcohol according to a similar method to Preparation Example 2.

Preparation Example 5

C-Biphenyl-3-yl-methylamine

To a solution of 3-cyanophenylboronic acid (1.0 g, 6.81 mmol) and bromobenzene (1.07 g, 6.81 mmol) in N,N-dimethylformamide (100 mL) were added tetrakis(triphenylphosphine)palladium(0) (0.393 g, 0.341 mmol) and cesium carbonate (2.77 g, 8.51 mmol) under nitrogen atmosphere, and the mixture was stirred for 4 hours under reflux. The reaction mixture was allowed to room temperature, ethyl acetate and water were added for partitioning, the organic layer was washed with water and dried over anhydrous magnesium sulfate. The solvent was evaporated, the residue was purified by silica gel column chromatography (hexane:ethyl acetate=10:1), and biphenyl-3-carbonitrile (821 mg, 67%) was obtained as a yellow solid.

Next, a solution of the resulting biphenyl-3-carbonitrile (821 mg, 4.58 mmol) in tetrahydrofuran (5 mL) was added to a solution of lithium aluminum hydride (0.435 g, 11.5 mmol) in tetrahydrofuran (5 mL) that had been cooled on an ice bath, and the solution was stirred for 6 hours at room temperature. The reaction solution was cooled on an ice bath, a mixture solution of methanol and water (9:1) was added thereto, an aqueous solution of saturated ammonium chloride was further added, filtration was carried out through Celite pad and insoluble matter was removed. The filtrate was partitioned, the organic layer was dried over anhydrous magnesium sulfate, and the title compound (527 mg, 63%) was obtained as a brown oil. This was used in the next reaction without further purification.

Preparation Example 6

4-(3-Fluorobenzyloxy)-benzylamine

To a solution of 4-cyanophenol (3.0 g, 25.2 mmol) and 3-fluorobenzyl bromide (3.1 mL, 25.2 mmol) in N,N-dimethylformamide (30 mL) was added potassium carbonate (8.71 g, 63.0 mmol), and the mixture was stirred for 1 hour at room temperature. Ethyl acetate and water were added to the reaction mixture, which was then partitioned, the organic layer was washed with water, then, dried over anhydrous magnesium sulfate, and the solvent was evaporated to obtain 4-(3-fluorobenzyloxy)-benzonitrile (5.31 g, 93%) as a colorless solid.

Next, to a solution of lithium aluminum hydride (1.25 g, 133.0 mmol) in tetrahydrofuran (15 mL) was added a solution of 4-(3-fluorobenzyloxy)-benzonitrile (218 mg, 0.615 mmol) in tetrahydrofuran (12 mL) on an ice bath, and the solution was stirred at room temperature for 19 hours. A mixture solvent of methanol and water (9:1) was added to the reaction solution, an aqueous solution of saturated ammonium chloride was further added, and the solution was stirred on an ice bath for 30 minutes. This solution was filtered through Celite pad, and insoluble matter was removed. The filtrate was partitioned, and the organic layer was dried over anhydrous magnesium sulfate. The solvent was evaporated, and the title compound (1.33 g, 44%) was obtained as a yellow solid. This was used in the next reaction without further purification.

Preparation Example 7

C-(4Phenoxy-pyridin-2-yl)-methylamine

To a solution of 4-phenoxypyridine (3.0 g, 17.5 mmol) in dichloromethane (500 mL) was added 3-chloro-perbenzoic acid (5.18 g, 21.0 mmol) on an ice bath, and the solution was stirred for 22 hours. An aqueous solution of saturated sodium thiosulfate and an aqueous solution of saturated sodium bicarbonate were added to the reaction solution, the solution was stirred at room temperature for 10 minutes, then, the organic layer was separated, washed with brine and dried over anhydrous magnesium sulfate. The solvent was evaporated, and 4-phenoxy-pyridine N-oxide (3.3 g, quantitatively) was obtained as a pale yellow solid.

The resulting solid (3.3 g, 17.6 mmol) was dissolved in acetonitrile (18 mL), trimethylsilyl cyanide (6.6 mL, 52.8 mmol) and triethylamine (4.9 mL, 35.2 mmol) were added, and the solution was stirred for 5 hours under reflux. The solvent was evaporated, the residue was purified by silica gel column chromatography (hexane:ethyl acetate=4:1), and 4-phenoxy-pyridine-2-carbonitrile (2.5 g, 73%) was obtained as a pale yellow solid.

Next, to a solution of lithium aluminum hydride (725 mg, 19.1 mmol) in tetrahydrofuran (6.0 mL) was portionwise added a solution of the resulting 4-phenoxy-pyridine-2-carbonitrile (1.5 g, 7.65 mmol) in tetrahydrofuran (3 mL) on an ice bath, and the solution was stirred at room temperature for 15 hours. A mixture solvent of methanol and water (9:1) was added to the reaction solution, an aqueous solution of saturated ammonium chloride was further added, the solution was extracted with ethyl acetate, dried over anhydrous magnesium sulfate, then, the solvent was evaporated to obtain the title compound (730 mg, 48%) as a pale brown oil. This was used in the next reaction without further purification.

Preparation Example 8

3-(4-Fluorophenoxy)-benzylamine

The title compound (790 mg, quantitatively) was obtained as a pale yellow solid from 3-(4fluorophenoxy)benzyl bromide (944 mg, 3.36 mmol) according to a similar technique to Preparation Example 1.

Preparation Example 9

3-(4-Methoxyphenoxy)benzylamine

To a solution of 3-(4-methoxyphenoxy)benzaldehyde (5.0 g, 21.9 mmol) in methanol (35 mL) was added a solution of sodium borohydride (0.86 g, 22.8 mmol) in an aqueous solution of 2N sodium hydroxide (2.5 mL), and the mixture was stirred at room temperature for 30 minutes. Water was added to the reaction mixture, which was neutralized with acetic acid, then, extracted with ethyl acetate, washed with brine, then, dried over anhydrous magnesium sulfate, and the solvent was evaporated to obtain (3-(4-methoxy-phenoxy)-phenyl)-metanol (5.3 g, quantitatively) as a colorless oil.

To a solution of the obtained (3-(4-methoxy-phenoxy)-phenyl)-metanol (2.0 g, 8.73 mmol) in dichloromethane (20 mL) was added methanesulfonyl chloride (0.81 mL, 10.5 mmol) and triethylamine (1.46 mL, 10.5 mmol) on an ice bath, and the solution was stirred for 19 hours. The reaction solution was diluted with dichloromethane, washed with an aqueous solution of 5% sodium bicarbonate, dried over anhydrous magnesium sulfate, and the solvent was evaporated to obtain methanesulfonic acid 3-(4-methoxy-phenoxy)benzyl ester (2.49, 89%) as a pale brown oil.

Next, the title compound (859 mg, 89%) was obtained as a pale yellow solid from the resulting methanesulfonic acid 3-(4-methoxy-phenoxy)benzyl ester (2.4 g, 7.78 mmol) according to a similar technique to Preparation Example 1.

Preparation Example 10

3-(3-Trifluoromethyl-phenoxy)-benzylamine

The title compound (2.63 g) was obtained as a brown oil from 3-(3-(trifluoromethyl)phenoxy)benzaldehyde (5.01 g, 18.8 mmol) according to an analogous method to Preparation Example 9.

Preparation Example 11

3-(3-Fluoro-phenoxy)-benzylamine

To a solution of 3-fluoro-phenol (500 mg, 4.46 mmol) and 3-fluoro-benzonitrile (540 mg, 4.46 mmol) in dimethylsulfoxide (1.0 mL) was added potassium tert-butoxide (500 mg, 4.46 mmol), and the solution was stirred at 140° C. for 3 hours. The reaction solution was allowed to room temperature, ethyl acetate and water were added for partitioning, the organic layer was washed with water and dried over anhydrous magnesium sulfate. The solvent was evaporated, the residue was purified by silica gel column chromatography (hexane:ethyl acetate=4:1), and 3-(3-fluoro-phenoxy)-benzonitrile (313 mg, 33%) was obtained as a yellow solid.

Next, to a solution of lithium aluminum hydride (139 mg, 3.68 mmol) in tetrahydrofuran (3.0 mL) was added a solution of the resulting 3-(3-fluoro-phenoxy)-benzonitrile (313 mg, 1.47 mmol) in tetrahydrofuran (1 mL) on an ice bath, and the solution was stirred at room temperature for 18 hours. A mixture solvent of methanol and water (9:1) was added to the reaction solution, an aqueous solution of saturated ammonium chloride was further added thereto, followed by stirring at room temperature for 10 minutes, then, extracted with ethyl acetate, dried over anhydrous magnesium sulfate, then, the solvent was evaporated to obtain the title compound (285 mg, 89%) as a yellow oil.

Preparation Example 12

4-(Furan-2-ylmethoxy)-benzylamine

To a solution of 4-cyanophenol (2.0 g, 16.8 mmol) in dichloromethane (20 mL) were added triphenyl phosphine (6.6 g, 25.2 mmol), furfuryl alcohol (1.65 g, 16.8 mmol) and diethyl azodicarboxylate (3.97 mL, 25.2 mmol) on an ice bath, and the solution was stirred at room temperature for 16 hours. The reaction solution was directly purified by silica gel column chromatography (hexane:ethyl acetate), the obtained crudely purified product was further purified by NH silica gel column chromatography (hexane:ethyl acetate), 4-furan-2-ylmethoxy)-benzonitrile (106 mg, 3%) was obtained as a pale yellow solid.

Next, to a solution of lithium aluminum hydride (50 mg, 1.33 mmol) in tetrahydrofuran (1.0 mL) was added a solution of the resulting 4-furan-2-ylmethoxy)-benzonitrile (106 mg, 0.532 mmol) in tetrahydrofuran (1 mL) on an ice bath, and the solution was stirred at room temperature for 4 hours. A mixture solvent of methanol and water (9:1) was added to the reaction solution, an aqueous solution of saturated ammonium chloride was further added, the solution was extracted with ethyl acetate, dried over anhydrous magnesium sulfate, then, the solvent was evaporated to obtain the title compound (76 mg, 70%) as a yellow solid.

Preparation Example 13

4-(Thiophen-2-ylmethoxy)-benzylamine

To a solution of 2-thiophenemethanol (2.0 g, 17.5 mmol) in dichloromethane (20 mL) were added methanesulfonyl chloride (1.63 mL, 21.0 mmol) and triethylamine (2.93 mL, 21.0 mmol) on an ice bath, and the solution was stirred for 13 hours. The reaction solution was diluted with dichloromethane, washed with an aqueous solution of 5% sodium bicarbonate, dried over anhydrous magnesium sulfate, and the solvent was evaporated to obtain methanesulfonic acid 2-thiophen-2-ylmethyl ester (2.4 g) as a brown oil.

Next, to a solution of the resulting methanesulfonic acid 2-thiophen-2-ylmethyl ester (2.4 g, 12.6 mmol) and p-cyanophenol (1.50 g, 12.6 mmol) in N,N-dimethylformamide (25 mL) was added potassium carbonate (4.35 g, 32.5 mmol), and the solution was stirred at room temperature for 13 hours. Ethyl acetate and water were added to the reaction solution, which was then separated, the organic layer was washed with water and dried over anhydrous magnesium sulfate. The solvent was evaporated, the residue was purified by NH silica gel column chromatography (hexane:ethyl acetate=4:1), and 4-(thiophen-2-ylmethoxy)-benzonitrile (1.88 g) was obtained as a white solid.

In addition, to a solution of lithium aluminum hydride (220 mg, 5.80 mmol) in tetrahydrofuran (2.5 mL) was added a solution of the resulting 4-(thiophene-2-ylmethoxy)-benzonitrile (500 mg, 2.32 mmol) in tetrahydrofuran (1 mL) on an ice bath, and the solution was stirred at room temperature for 4 hours. A mixture solvent of methanol and water (9:1) was added to the reaction solution, an aqueous solution of saturated ammonium chloride was further added, the solution was extracted with ethyl acetate, dried over anhydrous magnesium sulfate, then, the solvent was evaporated to obtain the title compound (415 mg, 82%) as a colorless solid.

Preparation Example 14

4-(Thiophen-3-ylmethyl)-benzylamine

The title compound (419 mg) was obtained as a pale brown solid from 3-thiophenemethanol according to an analogous method to Preparation Example 13.

Preparation Example 15

4-((S)-1-Phenyl-ethoxy)-benzylamine

To a solution of 4-bromobenzonitrile (500 mg, 2.75 mmol) and S-(−)-α-phenylethylalcohol (403 mg, 3.30 mmol) in toluene (5 mL) were added sodium hydride (220 mg, 5.49 mmol; 60% in oil), tris(dibenzylideneacetone)dipalladium(0) (38 mg, 0.0413 mmol) and 2,2-bis(di-p-tolylphosphino)-1,1-binaphthyl (67 mg, 0.099 mmol), and the solution was stirred at 70° C. for 4 hours. The reaction solution was allowed to room temperature, ethyl acetate and water were added for partitioning, the organic layer was washed with water and dried over anhydrous magnesium sulfate. The solvent was evaporated, the residue was purified by silica gel column chromatography (hexane:ethyl acetate), and 4-(1-phenyl-ethoxy)-benzonitrile (159 mg, 26%) was obtained as a colorless oil.

Next, to a solution of lithium aluminum hydride (68 mg, 1.78 mmol) in tetrahydrofuran (5.0 mL) was added a solution of the resulting 4-(1-phenyl-ethoxy)-benzonitrile (159 mg, 0.712 mmol) in tetrahydrofuran (1 mL) on an ice bath, which was stirred under reflux for 2 hours. The reaction solution was allowed to room temperature, a mixture solvent of methanol and water (9:1) was added, an aqueous solution of saturated ammonium chloride was further added, then, ethyl acetate and water were added for partitioning, the organic layer was dried over anhydrous magnesium sulfate, then, the solvent was evaporated to obtain the title compound (172 mg, quantitatively) as a yellow oily substance.

Preparation Example 16

C-(6-Phenoxy-pyridin-2-yl)-methylamine

To a solution of 2,6dibromopyridine (20 g, 84.4 mmol) and phenol (7.94 g, 84.4 mmol) in dimethylsulfoxide (200 mL) was added potassium tert-butoxide (9.47 g, 84.4 mmol), and the solution was stirred at 160° C. for 7 hours. The reaction solution was allowed to room temperature, ethyl acetate and water were added for partitioning, the organic layer was washed with water and dried over anhydrous magnesium sulfate. The solvent was evaporated, the residue was purified by silica gel column chromatography (hexane:ethyl acetate=10:1), and 2-bromo-6-phenoxy-pyridine (19.6, 93%) was obtained as a yellow solid.

Next, to a solution of the resulting 2-bromo-phenoxy-pyridine (1.0 g, 4.0 mmol) in N,N-dimethylformamide (30 mL) were added zinc cyanide (940 mg, 8.0 mmol) and tetrakis(triphenylphosphine)palladium(0) (924 mg, 0.8 mmol) under nitrogen atmosphere, and the mixture was stirred at 100° C. for 1 hour. The reaction mixture was allowed to room temperature, ethyl acetate and water were added for partitioning, the organic layer was washed with water and dried over anhydrous magnesium sulfate. The solvent was evaporated, the residue was purified by silica gel column chromatography (hexane:ethyl acetate=10:1), and 6-phenoxy-pyridine-2-carbonitrile (524 mg, 67%) was obtained as a white solid.

10% Palladium-carbon (50 mg) was added to a solution of the resulting 6-phenoxy-pyridine-2-carbonitrile (100 mg, 0.51 mmol) in methanol (5.0 mL), the mixture was stirred at room temperature for 24 hours under hydrogen atmosphere (1 atm). The catalyst was removed by filtration, and the filtrate was concentrated to obtain the title compound (65 mg, 64%) as a colorless oil.

Preparation Example 17

C-(5-(3-bromophenoxy)-thiophen-2-yl)-methylamine

To a solution of 5-nitrothiophene-2-carbonitrile (1.79 g, 11.6 mmol) and 3-bromophenol (2.00 g, 11.6 mmol) in dimethylsulfoxide (22 mL) was added potassium carbonate (1.76 g, 12.8 mmol), and the solution was stirred at 70° C. for 3 hours. The reaction solution was allowed to room temperature, ethyl acetate and water were added for partitioning, the organic layer was washed with brine and dried over anhydrous magnesium sulfate. The solvent was evaporated, the residue was purified by silica gel column chromatography (hexane:ethyl acetate=10:1), and 5-(3-bromophenoxy)-thiophene-2-carbonitrile (2.00 g, 62%) was obtained as a yellow oil.

Next, to a solution of lithium aluminum hydride (204 mg, 5.39 mmol) in tetrahydrofuran (10 mL) was added a solution of the resulting 5-(3-bromophenoxy)-thiophene-2carbonitrile (1.01 g, 3.59 mmol) in tetrahydrofuran (10 mL), and the solution was stirred at room temperature for 2 hours. Then, lithium aluminum hydride (68 mg, 1.80 mmol) was added, and the solution was further stirred at room temperature for 1 hour. Water was added to the reaction solution, which was then extracted with ethyl acetate, dried over anhydrous magnesium sulfate, and the solvent was evaporated to obtain a mixture of the title compound and debrominated compound (740 mg) as a pale brown oil. As this mixture cannot be purified, it was used in the next reaction without purification.

Preparation Example 18

C-(5-(3-Benzyloxy-phenoxy)-thiophen-2-yl)-methylamine

To a solution of resorcinol (10 g, 90.8 mmol) in N,N-dimethylformamide (100 mL) was added potassium carbonate (12.6 g, 90.8 mmol) and benzyl bromide (10.8 mL, 90.8 mmol), and the mixture was stirred at 60° C. for 2 hours. The reaction mixture was allowed to room temperature, ethyl acetate and water were added for partitioning, the organic layer was washed with water and dried over anhydrous magnesium sulfate. The solvent was evaporated, then, the residue was purified by silica gel column chromatography (hexane:ethyl acetate), and 3-benzyloxy-phenol (6.0 g, 33%) was obtained as a pale brown oil.

To a solution of the resulting 3-benzyloxy-phenol (2.6 g, 13.0 mmol) and a 5-nitrothiophene-2-carbonitrile (2.0 g, 13.0 mmol) in dimethylsulfoxide (25 mL) was added potassium carbonate (1.98 g, 14.0 mmol), and the solution was stirred at 70° C. for 3 hours. The reaction solution was allowed to room temperature, ethyl acetate and water were added for partitioning, the organic layer was washed with water and dried over anhydrous magnesium sulfate. The solvent was evaporated, the residue was purified by silica gel column chromatography (hexane:ethyl acetate=10:1), and 5-(3-benzyloxy-phenoxy)-thiophene-2-carbonitrile (110 mg, 2.8%) was obtained as a pale brown solid.

Next, to a solution of lithium aluminum hydride (27 mg, 0.716 mmol) in tetrahydrofuran (2.0 mL) was added a solution of 5-(3-benzyloxy-phenoxy)-thiophene-2-carbonitrile obtained above (110 mg, 0.358 mmol) in tetrahydrofuran (1 mL), and the solution was stirred at room temperature for 3 hours. Water was added to the reaction solution, which was then extracted with ethyl acetate, dried over anhydrous magnesium sulfate, and the solvent was evaporated to obtain the title compound (80 mg, 72%) as a red solid. This compound was used in the next reaction without purification.

Preparation Example 19

(4-Aminomethylphenyl)-benzyl-amine

To a mixture of sodium tert-butoxide (7.44 g, 77.4 mmol), tris(dibenzylideneacetone)dipalladium(0) (0.38 g, 0.415 mmol) and rac-2,2-bis(diphenylphosphino)-1,1-binaphthyl (0.172 g, 0.277 mmol) was added a solution of 4-bromobenzonitrile (10 g, 55.3 mmol) and benzylamine (11.8 g, 0.11 mol) in toluene (100 mL) under nitrogen atmosphere, and the solution was stirred at 80° C. for 5 hours. The reaction solution was allowed to room temperature, then, filtrated through Celite pad to remove insoluble matter, and the filtrate was concentrated. The residue was purified by silica gel column chromatography (hexane:ethyl acetate), and 4-benzyl aminobenzonitrile (11.1 g, 96%) was obtained as a yellow solid.

Next, to a solution of lithium aluminum hydride (911 mg, 24.0 mmol) in tetrahydrofuran (60 mL) was added a solution of the resulting 4-benzyl amino-benzonitrile (2.0 g, 9.61 mmol) in tetrahydrofuran (5 mL), and the solution was stirred at room temperature for 3 hours. Water was added to the reaction solution, which was then extracted with ethyl acetate, dried over anhydrous magnesium sulfate, and the solvent was evaporated to obtain the title compound (2.0 g, quantitatively) as an orange oil. This compound was used in the next reaction without purification.

Preparation Example 20

(4-Aminomethyl-phenyl)-phenyl-amine

To a mixture of sodium tert-butoxide (7.44 g, 77.4 mmol), tris(dibenzylideneacetone)dipalladium(0) (0.38 g, 0.415 mmol) and rac-2,2-bis(diphenylphosphino)-1,1-binaphthyl (0.172 g, 0.277 mmol) was added a solution of 4bromobenzonitrile (10 g, 55.3 mmol) and benzylamine (6.5 mL, 0.11 mol) in toluene (100 mL) under nitrogen atmosphere, and the solution was stirred at 80° C. for 5 hours. The reaction mixture was allowed to room temperature, then, filtered through Celite pad to remove insoluble matter, and the filtrate was concentrated. The residue was purified by silica gel column chromatography (hexane:ethyl acetate), and 4-phenylamino-benzonitrile (6.7 g, 63%) was obtained as a yellow solid.

Next, to a solution of lithium aluminum hydride (1.17 g, 30.9 mmol) in tetrahydrofuran (60 mL) was added a solution of the obtained 4-phenylamino-benzonitrile (2.0 g, 10.3 mmol) in tetrahydrofuran (5 mL), and the solution was stirred at room temperature for 22 hours. Water was added to the reaction solution, which was then extracted with ethyl acetate, dried over anhydrous magnesium sulfate, and the solvent was evaporated to obtain the title compound (2.0 g, 98%) as an orange oil. This compound was used in the next reaction without purification.

Preparation Example 21

(4-Aminomethyl-benzyl)-phenylamine

To a solution of 4-cyanobenzaldehyde (10 g, 76.3 mmol) and aniline (4.48 mL, 76.3 mmol) in tetrahydrofuran (370 mL) were added acetic acid (21.9 mL, 0.383 mol) and triacetoxy sodium borohydride (32.3 g, 0.153 mol), and the solution was stirred at room temperature for 1 hour. Ethyl acetate and water were added to the reaction solution, which was then partitioned, the organic layer was washed with water and dried over anhydrous magnesium sulfate. The solvent was evaporated, the residue was purified by silica gel column chromatography (hexane:ethyl acetate), and 4-phenylaminomethyl-benzonitrile) (5.1 g, 320%) was obtained as a pale yellow solid.

Next, to a solution of lithium aluminum hydride (0.91 g, 24 mmol) in tetrahydrofuran (60 mL) was added a solution of the resulting 4-phenylaminomethyl-benzonitrile (2.0 g, 9.61 mmol) in tetrahydrofuran (5 mL), and the solution was stirred at room temperature for 2 hours. Water was added to the reaction solution, which was then extracted with ethyl acetate, dried over anhydrous magnesium sulfate, and the solvent was evaporated to obtain the title compound (1.98 g, 97%) as a yellow oil. This compound was used in the next reaction without purification.

Preparation Example 22

5-(3-Fluorophenoxy)thiophene-2-carbonitrile

5-Nitrothiophene-2-carbonitrile (2 g, 13 mmol), 3-fluorophenol (1.75 g, 15.6 mmol) and potassium carbonate (3.6 g, 26 mmol) were suspended in dimethylsulfoxide (15 mL), and the mixture was stirred at room temperature for 16 hours. Water and ethyl acetate were added for partitioning, silica gel was added to the organic layer, and the solvent was evaporated in vacuo for adsorption. Purification was carried out by silica gel column chromatography (hexane:ethyl acetate=10:1), and the title compound (670 mg, 3.1 mmol, 23.5%) was obtained as an oil.

$^1$H-NMR Spectrum (DMSO-$d_6$) δ(ppm): 6.83 (1H, d, J=4.0 Hz), 7.08-7.26 (2H, m), 7.18-7.24 (1H, m), 7.49 (1H, ddd, J=8.0, 8.0, 8.0 Hz), 7.81 (1H, d, J=4.0 Hz).

Preparation Example 23

C-(5-(3-Fluorophenoxy)thiophen-2-yl)methylamine

To a solution of 5-(3-fluorophenoxy)thiophene-2-carbonitrile described in Preparation Example 22 (670 mg, 3 mmol) in tetrahydrofuran (30 mL) was added lithium aluminum hydride (460 mg, 12 mmol), and the solution was stirred at room temperature for 16 hours. Water and ethyl acetate were added to the reaction solution, which was then partitioned, the organic layer was filtered with NH silica gel, the filtrate was evaporated in vacuo, and the title compound (570 mg, 2.42 mmol, 80.7%) was obtained as a brown oil.

$^1$H-NMR Spectrum (DMSO-$d_6$) δ(ppm): 2.08 (2H, brs), 3.80 (2H, s), 6.54 (1H, d, J=3.6 Hz), 6.66-6.70 (1H, m), 6.88-6.99 (3H, m), 7.39 (1H, ddd, J=8.0, 8.0, 8.0 Hz).

Preparation Example 24

C-(5Phenoxy thiophen-2-yl)methylamine

5-Nitrothiophene-2-carbonitrile (0.80 g, 5.2 mmol), phenol (1.0 g, 10.4 mmol) and potassium carbonate (2.2 g, 15.6 mmol) were suspended in dimethylsulfoxide (30 mL), and the mixture was stirred at room temperature for 15.5 hours. Water and ethyl acetate were added for partitioning, and the organic layer was washed three times with water. NH silica gel was added to the organic layer, the solvent was evaporated in vacuo for adsorption, purification was carried out by NH silica gel column chromatography (hexane:ethyl acetate=8:1), and 5-phenoxythiophene-2-carbonitrile (720 mg, 3.6 mmol, 69.2%) was obtained as a colorless oil.

To a solution of this oil in tetrahydrofuran (40 mL) was added lithium aluminum hydride (540 mg, 14.4 mmol), and the mixture was stirred for 30 minutes at room temperature. Water and ethyl acetate were added to the reaction mixture, which was then partitioned, silica gel was added to the organic layer, the solvent was evaporated in vacuo for adsorption, purification was carried out by silica gel column chromatography (ethyl acetate, then ethyl acetate:methanol=4:1), and the title compound (570 mg, 2.8 mmol, 77.2%) was obtained as a light brown oil.

$^1$H-NMR Spectrum (DMSO-$d_6$) δ(ppm): 2.34 (2H, brs), 3.78-3.82 (2H, m), 6.47 (1H, d, J=4.0 Hz), 6.65-6.68 (1H, m), 7.04-7.14 (3H, m), 7.34-7.40 (2H, m).

Preparation Example 25

5-Phenoxy thiophene-2-carbonitrile

5-Nitro-thiophene-2-carbonitrile(1.5 g, 9.7 mmol), phenol (1.8 g, 19.4 mmol) and potassium carbonate(4.0 g, 29.1 mmol) were suspended in dimethylsulfoxide (20 mL), and the mixture was stirred for 50 minutes at 60° C., followed by further stirring overnight at room temperature. Water and ethyl acetate were added to the reaction mixture, which was then partitioned, the organic layer was washed 4 times with water, then, NH silica gel was added to the organic layer, the solvent was evaporated in vacuo for adsorption, purification was carried out by NH silica gel column chromatography (hexane, then hexane:ethyl acetate=20:1, then 10:1), and the title compound (1.4 g, 7.0 mmol, 72.1%) was obtained as a pale yellow oil.

$^1$H-NMR Spectrum (DMSO-$d_6$) δ(ppm): 6.75 (1H, d, J=4.0 Hz), 7.23-7.31 (3H, m), 7.42-7.49 (2H, m), 7.78 (1H, d, J=4.0 Hz).

Preparation Example 26

C-(5-Phenoxy thiophen-2-yl)methylamine

To a solution of 5-phenoxythiophene-2-carbonitrile described in Preparation Example 25 (1.4 g, 7.0 mmol) in tetrahydrofuran (30 mL) was added lithium aluminum hydride (1.1 g, 28 mmol), and the solution was stirred at room temperature for 25 minutes. Water and ethyl acetate were added to the reaction solution, this mixed solution was filtered through Celite pad, furthermore, the organic layer was partitioned. The solvent was evaporated in vacuo, and the title compound (1.29 g, 6.3 mmol, 89.9%) was obtained as a brown oil.

$^1$H-NMR Spectrum (DMSO-$d_6$) δ(ppm):1.92 (2H, brs), 3.74-3.80 (2H, m), 6.46 (1H, d, J=3.6 Hz), 6.62-6.66 (1H, m), 7.02-7.14 (3H, m), 7.32-7.39 (2H, m).

Preparation Example 27

5-(4-Fluorophenoxy)thiophene-2-carbonitrile

5-Nitrothiophene-2-carbonitrile (2.0 g, 13 mmol), 4-fluorophenol (2.9 g, 26 mmol) and potassium carbonate (5.4 g, 39 mmol) were suspended in dimethylsulfoxide (30 mL), and the mixture was stirred for 30 minutes at 60° C. Water and ethyl acetate were added to the reaction mixture, which was then separated, the organic layer was washed with water twice, then, NH silica gel was added to the organic layer, the solvent was evaporated in vacuo for adsorption, purification was carried out by NH silica gel column chromatography (hexane: ethyl acetate=20:1), and the title compound (3.7 g, containing 4-fluorophenol) was obtained as a brown oil.
$^1$H-NMR Spectrum (DMSO-d$_6$) δ(ppm): 6.68-6.76 (2H, m), 7.26-7.38 (3H, m), 7.74-7.80 (1H, m).

Preparation Example 28

C-(5-(4-Fluorophenoxy)thiophen-2-yl)methylamine

To a solution of 5-(4-fluorophenoxy)thiophene-2-carbonitrile described in Preparation Example 27 (containing 4-fluorophenol) (3.7 g) in tetrahydrofuran (40 mL) was added lithium aluminum hydride (1.3 g, 34 mmol), and the solution was stirred at room temperature for 30 minutes. Water and ethyl acetate were added to the reaction solution, which was then partitioned, the solvent was evaporated in vacuo, the residue was purified by silica gel column chromatography (ethyl acetate, then ethyl acetate:methanol=4:1), and the title compound (1.2 g, 5.4 mmol) was obtained as a brown oil.
$^1$H-NMR Spectrum (DMSO-d$_6$) δ(ppm) 2.00 (2H, brs), 3.75-3.80 (2H, m), 6.44-6.48 (1H, m), 6.62-6.67 (1H, m), 7.08-7.14 (2H, m), 7.16-7.24 (2H, m).

Preparation Example 29

5-m-Tolyloxy-thiophene-2-carbonitrile

The title compound (960 mg, 4.47 mmol, 68.7%) was obtained as a yellow oil from 5-nitro-thiophene-2-carbonitrile (1.0 g, 6.5 mmol) and 3-methylphenol (1.4 g, 13 mmol) according to an analogous method to Preparation Example 27.
$^1$H-NMR Spectrum (DMSO-d$_6$) δ(ppm): 2.31 (3H, s), 6.73 (1H, dd, J=0.8, 4.0 Hz), 7.03-7.06 (1H, m), 7.07-7.12 (2H, m), 7.33 (1H, dd, J=8.0, 8.0Hz), 7.77 (1H, dd, J=0.8, 4.0 Hz).

Preparation Example 30

C-(5-m-Tolyloxy-thiophen-2-yl)-methylamine

The title compound (900 mg, 4.10 mmol, 91.7%) was obtained as a reddish brown oil from 5-m-tolyloxy thiophene-2-carbonitrile described in Preparation Example 29 (960 mg, 4.47 mmol) according to an analogous method to Preparation Example 28.
$^1$H-NMR Spectrum (DMSO-d$_6$) δ(ppm): 2.03 (2H, brs), 2.34 (3H, s), 3.85 (2H, s), 6.51-6.54 (1H, m), 6.71-6.74 (1H, m), 6.90-7.03 (3H, m), 7.31 (1H, dd, J=8.0, 8.0 Hz).

Preparation Example 31

5-p-Tolyloxy-thiophene-2-carbonitrile

The title compound (1.0 g, 4.65 mmol, 71.5%) was obtained as a yellow oil from 5-nitro-thiophene-2-carbonitrile (1.0 g, 6.5 mmol) and 4-methylphenol (1.4 g, 13 mmol) according to an analogous method to Preparation Example 27.
$^1$H-NMR Spectrum (DMSO-d$_6$) δ(ppm): 2.30 (3H, s), 6.69-6.71 (1H, m), 7.15-7.18 (2H, m), 6.24-6.28 (2H, m), 7.15-7.78 (1H, m).

Preparation Example 32

C-(5-p-Tolyloxy thiophen-2-yl)methylamine

The title compound (780 mg, 3.56 mmol, 76.5%) was obtained as a reddish brown oil from 5-p-tolyloxy thiophene-2-carbonitrile described in Preparation Example 31 (1.0 g, 4.65 mmol) according to an analogous method to Preparation Example 28.
$^1$H-NMR Spectrum (DMSO-d$_6$) δ(ppm): 2.06 (2H, br), 2.22 (3H, s), 3.76 (2H, s), 6.41 (1H, d, J=3.6 Hz), 6.62 (1H, d, J=3.6 Hz), 6.90-6.98 (2H, m), 7.15-7.18 (2H, m).

Preparation Example 33

2-(4-(3-Fluoro-phenoxy)-thiophen-2-yl)-[1.31dioxolane 2-(4-Bromo-thiophen-2-yl)-[1,3]dioxolane (1.0 g, 4.3 mmol), 3-fluorophenol (0.95 g, 8.6 mmol), 2,2,6,6-tetramethyl-3,5-heptanedione (0.078 g, 0.43 mmol), copper(I) chloride (0.21 g, 2.7 mmol) and cesium carbonate (2.8 g, 8.6 mmol) were suspended in N-methylpyrrolidone (10 mL) under a nitrogen stream, and the mixture was stirred for 4.5 hours at 120° C. To this suspension was added 2,2,6,6-tetramethyl-3,5-heptanedione (0.12 g, 0.65 mmol), and the solution was further stirred for 8 hours at 140° C. The reaction mixture was filtered through Celite pad, then, water and ethyl acetate were added for partitioning, and the organic layer was washed with water twice. NH silica gel was added to the organic layer, the solvent was evaporated in vacuo for adsorption to NH silica gel, purification was carried out by NH silica gel column chromatography (hexane, then hexane:ethyl acetate=30: 1), and the title compound (280 mg, 1.05 mmol, 24.4%) was obtained as a colorless oil.
$^1$H-NMR Spectrum (DMSO-d$_6$) δ(ppm): 3.88-3.96 (2H, m), 3.96-4.04 (2H, m), 5.98 (1H, s), 6.82-6.88 (2H, m), 6.91-6.97 (1H, m), 7.04-7.05 (1H, m), 7.09 (1H, d, J=2.0 Hz), 7.35-7.42 (1H, m).

Preparation Example 34

4-(3-Fluorophenoxy)thiophene-2-carbaldehyde

To a solution of 2-(4-(3-fluoro-phenoxy)-thiophen-2-yl)-[1,3]dioxolane described in Preparation Example 33 (280 mg, 1.05 mmol) in methanol (10 mL) was added citric acid aqueous solution (10 mL), and the solution was stirred at room temperature for 30 minutes. The reaction solution was neutralized with an aqueous solution of sodium bicarbonate, the solution was extracted with ethyl acetate, the organic layer was dried over anhydrous sodium sulfate, the solvent was evaporated in vacuo, and the title compound (210 mg, 0.95 mmol, 90%) was obtained as a colorless oil.
$^1$H-NMR Spectrum (DMSO-d$_6$) δ(ppm): 6.88-7.03 (3H, m), 7.38-7.46 (1H, m), 7.67 (1H, d, J=1.6 Hz), 7.88 (1H, d, J=1.6 Hz), 9.86 (1H, s).

Preparation Example 35

(C-(4-(3-Fluorophenoxy)thiophen-2-yl)methylamine 4-(3-Fluorophenoxy)thiophene-2-carbaldehyde described in Preparation Example 34 (210 mg, 0.95 mmol) was dissolved in 7N ammonia/methanol (30 mL), Raney nickel (500 mg) was added thereto, followed by stirring for 19 hours under hydrogen atmosphere at room temperature. The reaction mixture was filtered through Celite pad, Raney nickel was removed, silica gel was added to the filtrate, then, the solvent was evaporated in vacuo, for adsorption on silica gel, purification by silica gel chromatography (ethyl acetate, then ethyl acetate:methanol=4:1) was carried out, and the title compound (70 mg, 0.32 mmol) was obtained as a pale yellow oil.

$^1$H-NMR Spectrum (DMSO-$d_6$) δ(ppm): 2.11 (2H, brs), 3.82 (2H, s), 6.75 (1H, s), 6.80-6.95 (4H, m), 7.33-7.41 (1H, m).

Preparation Example 36

2-(5-(4-Fluoro-benzyl)-thiophen-2-yl)-[1,3]dioxolane n-Butyl lithium (2.6N hexane solution, 3.3 mL, 8.47 mmol) was added dropwise to a solution of 2-(5-bromo-thiophen-2-yl)-[1,3]dioxolane (1.8 g, 7.7 mmol) in tetrahydrofuran (20 mL) that had been cooled to from −75° to −70° C., and the solution was stirred for 30 minutes. 4-Fluorobenzyl bromide (1.1 mL, 8.47 mmol) was added dropwise to this reaction solution while keeping it at −70° C. or less. After completion of dropwise addition, the reaction solution was gradually allowed to room temperature. Water and ethyl acetate were added to the reaction solution, which was then partitioned, silica gel was added to the organic layer, which was then evaporated in vacuo for adsorption, purification by silica gel column chromatography (hexane, then hexane:ethyl acetate=20:1, then 10:1) was carried out, and the title compound (560 mg, 2.04 mmol, 26.4%) was obtained as a brown oil.

$^1$H-NMR Spectrum (DMSO-$d_6$) δ(ppm): 3.84-3.98 (4H, m), 4.08 (2H, s), 5.90 (1H, s), 6.75-6.78 (1H, m), 7.00 (1H, d, J=3.6 Hz), 7.08-7.15 (2H, m), 7.25-7.30 (2H, m).

Preparation Example 37

5-(4-Fluoro-benzyl)-thiophene-2-carbaldehyde

To a solution of 2-(5-(4-fluoro-benzyl)-thiophen-2-yl)-[1,3]dioxolane described in Preparation Example 36 (560 mg, 2.04 mmol) in methanol (20 mL) was added citric acid aqueous solution (20 mL), and the solution was stirred at room temperature for 30 minutes. Ethyl acetate and water were added to the reaction solution, which was then partitioned, the organic layer was washed with water twice, dried over anhydrous sodium sulfate, the solvent was evaporated in vacuo, and title compound (460 mg, 2.09 mmol) was obtained as a brown oil.

$^1$H-NMR Spectrum (DMSO-$d_6$) δ(ppm): 4.22 (2H, s), 7.08-7.18 (3H, m), 7.29-7.36 (2H, m), 7.83-7.87 (1H, m), 9.79 (1H, s).

Preparation Example 38

C-(5-(4-Fluorobenzyl)thiophen-2-yl)methylamine 7N ammonia/methanol (30 mL) and Raney nickel (500 mg) were added to 5-(4-fluorobenzyl)thiophene-2-carbaldehyde described in Preparation Example 37 (460 mg, 2.09 mmol), and the mixture was stirred for 14 hours under hydrogen atmosphere at room temperature. The catalyst was removed by filtering through Celite pad, then, purification by silica gel column chromatography (ethyl acetate, then ethyl acetate:methanol=4:1) was carried out, and the title compound (70 mg, 0.316 mol, 15.1%) was obtained as an oil.

$^1$H-NMR Spectrum (DMSO-$d_6$) δ(ppm): 2.20 (2H, brs), 3.78 (2H, s), 4.03 (2H, s), 6.58-6.80 (2H, m), 7.00-7.38 (4H, m).

Preparation Example 39

5-Benzyl-furan-2-carbaldehyde n-Butyl lithium (2.44N hexane solution, 15 mL, 39.6 mmol) was added dropwise to a solution of 2-furan-2-yl-[1,3]dioxolane (5 g, 36 mmol) in tetrahydrofuran (30 mL) that had been cooled to from −75° C. to −70° C., and the solution was stirred for 1 hour. Benzyl bromide (4.7 mL, 39.6 mmol) was added dropwise to this solution at from −75° C. to −70° C. After completion of dropwise addition, the cold bath was removed, and the solution was gradually allowed to room temperature. Water and ethyl acetate were added to the reaction mixture for partitioning, silica gel was added to the organic layer, which was then evaporated in vacuo to adsorb the reaction mixture, purification by silica gel column chromatography (hexane:ethyl acetate=50:1, then 6:1) was carried out, and 2-(5-benzyl-4-furan-2-yl)-[1,3]dioxolane (3.8 g, 16.5 mmol, 45.9%) was obtained as a yellow oil.

The resulting 2-(5-benzyl-furan-2-yl)-[1,3]dioxolane (3.8 g, 16.5 mmol) was suspended in a mixture solution of methanol (15 mL), tetrahydrofuran (10 mL) and 2N hydrochloric acid (15 mL), and the solution was stirred at room temperature for 2 hours. Ethyl acetate and an aqueous solution of sodium bicarbonate were added to the reaction solution, which was then partitioned, the organic layer was washed with water twice and dried over anhydrous sodium sulfate. The solvent was evaporated, and the title compound (2.5 g, 13 mmol) was obtained as a brown oil.

$^1$H-NMR Spectrum (DMSO-$d_6$) δ(ppm): 4.09 (2H, s), 6.45-6.48 (1H, m), 7.20-7.35 (5H, m), 7.45 (1H, d, J=3.6 Hz), 9.46 (1H, s).

Preparation Example 40

2-(5-Benzyl-thiophen-2-yl)-[1.3]dioxolane

The title compound (520 mg, 2.1 mmol, 41.4%) was obtained as a colorless oil from benzyl bromide according to an analogous method to Preparation Example 36.

$^1$H-NMR Spectrum (DMSO-$d_6$) δ(ppm): 3.84-3.90 (2H, m), 3.90-3.98 (2H, m), 4.08 (2H, s), 5.90 (1H, s), 6.75-6.78 (1H, m), 7.00 (1H, d, J=3.6 Hz), 7.18-7.32 (5H, m).

Preparation Example 41

5-Benzyl-thiophene-2-carbaldehyde

The title compound (containing impurity, 460 mg) was obtained as a colorless oil from 2-(5-benzyl-thiophen-2-yl)-[1,3]dioxolane described in Preparation Example 40 (520 mg, 2.1 mmol) according to an analogous method to Preparation Example 37.

$^1$H-NMR Spectrum (DMSO-$d_6$) δ(ppm): 4.22 (2H, s), 7.11 (1H, d, J=3.6 Hz), 7.20-7.34 (5H, m), 7.85 (1H, d, J=3.6 Hz), 9.79 (1H, s).

Preparation Example 42

C-(5-benzyl-thiophen-2-yl)-methylamine

The title compound (270 mg) was obtained as a brown oil from 5-benzyl-thiophene-2-carbaldehyde described in Preparation Example 41 (containing impurity, 460 mg, 2.27 mmol) according to an analogous method to Preparation Example 38.

$^1$H-NMR Spectrum (DMSO-d$_6$) δ(ppm): 1.85 (2H, brs), 3.75 (2H, s), 4.01 (2H, s), 6.65-6.72 (2H, m), 7.15-7.30 (5H, m).

Preparation Example 43

2-(5-(3-Chloro-benzyl)-thiophen-2-yl)-[1.3]-dioxolane n-Butyl lithium (2.6N hexane solution, 15.6 mL, 39 mmol) was added dropwise to a solution of 2-(5bromo-thiophen-2-yl)-[1,3]dioxolane (7.0 g, 30 mmol) in tetrahydrofuran (40 mL) at from −75° to −68° C., and the solution was stirred for 20 minutes. 3-Chlorobenzyl bromide (4.3 mL, 33 mmol) was added dropwise to this reaction solution at from −75° C. to −68° C., and the solution was stirred for 20 minutes. The cold bath was removed, and the reaction solution was gradually allowed to room temperature. Water and ethyl acetate were added to the reaction solution, which was then partitioned, the solvent was evaporated, the residue was purified by NH silica gel column chromatography (hexane:ethyl acetate=20:1), and the title compound (1.6 g, 5.7 mmol, 19.0%) was obtained as a yellow oil.

$^1$H-NMR Spectrum (DMSO-d$_6$) δ(ppm): 3.82-4.00 (4H, m), 4.11 (2H, s), 5.91 (1H, s), 6.78-6.80 (1H, m), 7.01 (1H, d, J=3.6 Hz), 7.19-7.36 (4H, m).

Preparation Example 44

5-(3-Chloro-benzyl)-thiophene-2-carbaldehyde

To a solution of 2-(5-(3-chloro-benzyl)-thiophen-2-yl)-[1,3]dioxolane described in Preparation Example 43 (1.6 g, 5.7 mmol) in methanol (20 mL) was added citric acid aqueous solution (20 mL), and the solution was stirred at room temperature for 20 minutes. An aqueous solution of sodium bicarbonate and ethyl acetate were added to the reaction solution, which was then partitioned, the organic layer was washed with water twice and dried over anhydrous magnesium sulfate. The solvent was evaporated, and the title compound (1.2 g, 5.08 mmol, 89.2%) was obtained as a yellow oil.

$^1$H-NMR Spectrum (DMSO-d$_6$) δ(ppm): 4.25 (2H, s), 7.12-7.15 (1H, m), 7.24-7.40 (4H, m), 7.86 (1H, d, J=3.6 Hz), 9.80 (1H, s).

Preparation Example 45

C-(5-(3-Chloro-benzyl)-thiophen-2-yl)-methylamine

To a solution of 5-(3-chloro-benzyl)thiophene-2-carbaldehyde described in Preparation Example 44 (1.2 g, 5.08 mmol) in 7N ammonia/methanol (40 mL) was added Raney nickel (2 g), and the solution was stirred at room temperature for 17 hours under hydrogen atmosphere. The reaction solution was filtered through Celite pad, the catalyst was removed, then, this filtrate was evaporated in vacuo, the residue was purified by silica gel column chromatography (ethyl acetate, then ethyl acetate:methanol=5:1), and the title compound (740 mg, 3.12 mmol, 61.4%) was obtained as a brown oil.

$^1$H-NMR Spectrum (DMSO-d$_6$) δ(ppm) :1.94 (2H, brs), 3.76 (2H, s), 4.06 (2H, s), 6.69-6.72 (2H, m), 7.18-7.34 (4H, m).

Preparation Example 46

5-(4-Chloro-phenoxy)-furan-2-carbaldehyde

To a solution of 4-chlorophenol (4.4 g, 33.6 mmol) in dimethylsulfoxide (30 mL) was added sodium hydride (1.34 g, 33.6 mmol, 60% in oil), and the solution was stirred at room temperature for 10 minutes. 5-Nitrofuran-2-carbaldehyde (4.0 g, 28 mmol) was added to this reaction solution, and the solution was stirred at room temperature for 5 minutes. Water and ethyl acetate were added to the reaction solution, which was then partitioned, and the organic layer was washed with water 6 times. The solvent was evaporated in vacuo, the residue was purified by silica gel column chromatography (hexane, then hexane:ethyl acetate=10:1, then 4:1), and the title compound (3.3 g, 14.9 mmol, 53.0%) was obtained as a yellow oil.

$^1$H-NMR Spectrum (DMSO-d$_6$) δ(ppm): 5.89-5.93 (1H, m), 7.30-7.36 (2H, m), 7.50-7.60 (3H, m), 9.35-9.38 (1H, m).

Preparation Example 47

C-(5-(4-Chloro-phenoxy)-furan-2-yl)-methylamine

The title compound (200 mg, 0.90 mmol, 8.7%) was obtained as a brown oil from 5-(4-chloro-phenoxy)-furan-2-carbaldehyde described in Preparation Example 46 (2.3 g, 10.3 mmol) according to an analogous method to Preparation Example 38.

$^1$H-NMR Spectrum (DMSO-d$_6$) δ(ppm): 3.56 (2H, s), 5.73 (1H, d, J=3.2Hz), 6.18 (1H, d, J=3.2 Hz), 7.03-7.08 (2H, m), 7.40-7.45 (2H, m).

Preparation Example 48

5-Phenoxy-furan-2-carbaldehyde

The title compound (2.3 g, 12.2 mmol, 43.5%) was obtained as a light brown oil from phenol (3.2 g, 33.6 mmol) and 5-nitro-furan-2-carbaldehyde (4.0 g, 28 mmol) according to an analogous method to Preparation Example 46.

$^1$H-NMR Spectrum (DMSO-d$_6$) δ(ppm): 5.85 (1H, d, J=4.0 Hz), 7.25-7.33 (3H, m), 7.45-7.50 (2H, m), 7.57 (1H, d, J=4.0 Hz), 9.34 (1H, s).

Preparation Example 49

C-(5-Phenoxy-furan-2-yl)-methylamine

The title compound (250 mg, 1.32 mmol, 24.9%) was obtained as a yellow oil from 5-phenoxy-furan-2-carbaldehyde described in Preparation Example 48 (1.0 g, 5.3 mmol) according to an analogous method to Preparation Example 38. $^1$H-NMR Spectrum (DMSO-d$_6$) δ(ppm): 1.98 (2H, brs), 3.56 (2H, s), 5.67 (1H, d, J=3.2 Hz), 6.16-6.18 (1H, m), 6.99-7.04 (2H, m), 7.10-7.16 (1H, m), 7.34-7.40 (2H, m).

Preparation Example 50

5-(3-Fluoro-phenoxy)-furan-2-carbaldehyde

The title compound (1.5 g, 7.3 mmol, 52.1%) was obtained as a yellow oil from 3-fluorophenol (1.9 g, 16.8 mmol) and 5-nitro-furan-2-carbaldehyde (2.0 g, 14 mmol) according to an analogous method to Preparation Example 46.

¹H-NMR Spectrum (DMSO-d₆) δ(ppm): 5.97-6.00 (1H, m), 7.10-7.20 (2H, m), 7.24-7.30 (1H, m), 7.48-7.55 (1H, m), 7.59 (1H, d, J=3.6 Hz) 9.37 (1H, s).

Preparation Example 51

(5-(3-Fluoro-phenoxy)-furan-2-yl)-methanol

To a solution of 5-(3-fluoro-phenoxy)-furan-2-carbaldehyde described in Preparation Example 50 (1.5 g, 7.3 mmol) in tetrahydrofuran (20 mL) was added sodium borohydride (280 mg, 7.3 mmol), and the solution was stirred at room temperature for 1 hour. Water and ethyl acetate were added to the reaction solution, which was then partitioned, the organic layer was washed with water twice, and the organic layer was filtered through a glass filter lined with silica gel. The solvent was evaporated in vacuo, and the title compound (1.5 g, 7.2 mmol) was obtained as a pale yellow oil.

¹H-NMR Spectrum (DMSO-d₆) δ(ppm): 4.29 (2H, d, J=6.0 Hz), 5.17 (1H, t, J=6.0 Hz), 5.78-5.82 (1H, m), 6.78-6.82 (1H, m), 6.85-6.95 (2H, m), 6.98-7.04 (1H, m), 7.40-7.46 (1H, m).

Preparation Example 52

2-(5-(3-Fluoro-benzyl)-thiophen-2-yl)-[1,3]dioxolane n-Butyl lithium (2.44N hexane solution, 6.4 mL, 16.9 mmol) was added dropwise to a solution of 2-(5-bromo-thiophen-2-yl)-[1,3]dioxolane (3.0 g, 13 mmol) in tetrahydrofuran (30 mL) at from −75° C. to −69° C., and the solution was stirred for 17 minutes. 3-Fluorobenzyl bromide (1.7 mL, 14.3 mmol) was added dropwise to this reaction solution at from −75° C. to −69° C. After dropwise addition was completed, the reaction solution was gradually allowed to room temperature. Water and ethyl acetate were added to the reaction solution, which was then partitioned, the organic layer was concentrated in vacuo, the residue was purified by silica gel column chromatography (hexane:ethyl acetate=20:1), and the title compound (478 mg, 1.81 mmol, 13.9%) was obtained as a brown oil.

¹H-NMR Spectrum (DMSO-d₆) δ(ppm): 3.82-4.00 (4H, m), 4.13 (2H, s), 5.91 (1H, s), 6.78-6.80 (1H, m), 7.00-7.10 (4H, m), 7.30-7.37 (1H, m).

Preparation Example 53

5-(3-Fluorobenzyl)-thiophene-2-carbaldehyde

An aqueous solution of saturated citric acid (20 mL) was added to a solution of 2-(5-(3-fluoro-benzyl)thiophen-2-yl)-[1,3]dioxolane described in Preparation Example 52 (670 mg, 2.53 mmol) in methanol (20 mL), and the solution was stirred at room temperature for 30 minutes. Water and ethyl acetate were added to the reaction solution, which was then partitioned, and the organic layer was dried over anhydrous magnesium sulfate. The solvent was evaporated in vacuo, and the title compound (485 mg, 2.2 mmol, 87.0%) was obtained as a brown oil.

¹H-NMR Spectrum (DMSO-d₆) δ(ppm): 4.25 (2H, s), 7.03-7.18 (4H, m), 7.30-7.40 (1H, m), 7.86 (1H, dd, J=1.6, 3.6 Hz), 9.80 (1H, d, J=1.6 Hz).

Preparation Example 54

2-(5 (3-Chloro-benzyl)-furan-2-yl)-[1,3]dioxolane

The title compound (1.34 g, 5.07 mmol, 14.1%) was obtained as a yellow oil from 2-furan-2-yl-[1,3]dioxolane (5.0 g, 36 mol) and 3-chlorobenzyl bromide (5.2 mL, 39.6 mmol) according to an analogous method to Preparation Example 36. ¹H-NMR Spectrum (DMSO-d₆) δ(ppm): 3.84-4.02 (6H, m), 5.76 (1H, s), 6.10-6.12 (1H, m), 6.41 (1H, d, J=3.2 Hz), 7.16-7.20 (1H, m), 7.26-7.36 (3H, m).

Preparation Example 55

5-(3-Chloro-benzyl)furan-2-carbaldehyde

The title compound (1.03 g, 4.68 mmol, 82.1%) was obtained as a yellow oil from 2-(5-(3-chloro-benzyl)-furan-2-yl)-[1,3]dioxolane described in Preparation Example 54 (1.34 g, 5.07 mmol) according to an analogous method to Preparation Example 37.

¹H-NMR Spectrum (DMSO-d₆) δ(ppm): 4.11 (2H, s), 6.48-6.51 (1H, m), 7.20-7.24 (1H, m), 7.28-7.37 (3H, m), 7.46 (1H, d, J=3.2 Hz), 9.46-9.49 (1H, m).

Preparation Example 56

C-(5-(3-Chloro-benzyl)-furan-2-yl)-methylamine

The title compound (690 mg, 3.12 mmol, 66.6%) was obtained as a yellow oil from 5-(3-Chlorobenzyl)-furan-2-carbaldehyde described in Preparation Example 55 (1.03 g, 4.68 mmol) according to an analogous method to Preparation Example 38.

¹H-NMR Spectrum (DMSO-d₆) δ(ppm): 1.90 (2H, brs), 3.57 (2H, s), 3.92 (2H, s), 6.01 (1H, d, J=2.8 Hz), 6.07 (1H, d, J=2.8 Hz), 7.16-7.20 (1H, m), 7.24-7.34 (3H, m).

Preparation Example 57

1-Benzyl-1H-pyrrole-3-carbaldehyde

Benzylamine (540 mg, 5.00 mmol) and acetic acid (10 mL) were added to 2,5-dimethoxy-tetrahydrofuran-3-carbaldehyde (1 g, 6.25 mmol), and the solution was stirred for 20 minutes at 90° C. Water and ethyl acetate were added to the reaction solution, which was then partitioned, the organic layer was washed with an aqueous solution 2N sodium hydroxide once and with water twice, filtered with a glass filter lined with silica gel, the filtrate was evaporated in vacuo, and title compound (800 mg, 4.3 mmol, 68.8%) was obtained as a brown oil.

¹H-NMR Spectrum (DMSO-d₆) δ(ppm): 5.18 (2H, s), 6.46 (1H, dd, J=2.0, 2.0 Hz), 6.97 (1H, dd, J=2.0, 2.0 Hz), 7.24-7.37 (5H, m), 7.71 (1H, dd, J=2.0, 2.0 Hz), 9.63 (1H, s).

Preparation Example 58

1-(3-Fluorobenzyl)-1H-pyrrole-3-carbaldehyde

The title compound (2.33 g, 11.4 mmol, 71.7%) was obtained as an oil from 2,5-dimethoxy-tetrahydrofuran-3-carbaldehyde (2.6 g, 16 mmol) and 3-fluorobenzylamine (2.0 g, 16 mmol) according to an analogous method to Preparation Example 57.

¹H-NMR Spectrum (DMSO-d₆) δ(ppm): 5.20 (2H, s), 6.44-6.48 (1H, m), 6.98-7.02 (1H, m), 7.07-7.17 (3H, m), 7.36-7.42 (1H, m), 7.74 (1H, d, J=1.6 Hz), 9.63 (1H, s).

Preparation Example 59

C-(1-(3-Fluoro-benzyl)-1H-pyrrol-3-yl)-methylamine

7N Ammonia/methanol (40 mL) and Raney nickel (2 g) were added to 1-(3-fluoro-benzyl)-1H-pyrrole-3-carbaldehyde described in Preparation Example 58 (1.0 g, 4.9 mmol), and the solution was stirred for 18 hours under hydrogen atmosphere at room temperature. The catalyst was removed by filtering through Celite pad, then, NH silica gel was added to the filtrate, the solvent was evaporated in vacuo for adsorption, purification by NH silica gel column chromatography (hexane:ethyl acetate=2:1, then 1:1, then ethyl acetate) was carried out, and the title compound (530 mg, 2.5 mmol, 53.0%) was obtained as a brown oil.

$^1$H-NMR Spectrum (DMSO-$d_6$) δ(ppm): 3.50 (2H, s), 5.01 (2H, s), 5.95 (1H, d, J=2.0 Hz), 6.64 (1H, d, J=1.2 Hz), 6.69-6.74 (1H, m), 6.92-7.10 (3H, m), 7.32-7.38 (1H, m).

Preparation Example 60

1-Benzo[1,3]dioxol-5-ylmethyl-1H-pyrrole-3-carbaldehyde

The title compound (2.0 g, 8.7 mmol, 69.8%) was obtained as a brown oil from 2,5-dimethoxy-tetrahydrofuran-3-carbaldehyde (2.0 g, 12.5 mmol) and C-benzo[1,3]dioxol-5-ylmethylamine) (1.9 g, 12.5 mmol) according to an analogous method to Preparation Example 57.

$^1$H-NMR Spectrum (DMSO-$d_6$) δ(ppm): 5.04 (2H, s), 5.97 (2H, s), 6.42-6.45 (1H, m), 6.80-7.00 (4H, m), 7.69-7.72 (1H, m), 9.61 (1H, s).

Preparation Example 61

C-(1-benzo[1,3]dioxol-5-ylmethyl-1H-pyrrol-3-yl)-methylamine

The title compound (1.5 g, 6.5 mmol, 74.7%) was obtained as a light green oil from 1-benzo[1,3]dioxol-5-ylmethyl-1H-pyrrole-3-carbaldehyde described in Preparation Example 60 (2.0 g, 8.7 mmol) according to an analogous method to Preparation Example 59.

$^1$H-NMR Spectrum (DMSO-$d_6$) δ(ppm): 1.37 (2H, brs), 3.48 (2H, brs), 4.87 (2H, s), 5.90 (1H, s), 5.95 (2H, s), 6.60 (1H, s), 6.66-6.72 (2H, m), 6.75 (1H, s), 6.83 (1H, d, J=7.6 Hz).

Preparation Example 62

1-Phenethyl-1H-pyrrol-3-carbaldehyde

The title compound (840 mg, 4.2 mmol, 84%) was obtained as a brown oil from 2,5-dimethoxy-tetrahydrofuran-3-carbaldehyde (1.0 g, 6.25 mmol) and phenethyl amine (600 mg, 5.0 mmol) according to an analogous method to Preparation Example 57.

$^1$H-NMR Spectrum (DMSO-$d_6$) δ(ppm): 3.03 (2H, t, J=7.2 Hz), 4.19 (2H, t, J=7.2 Hz), 6.38-6.42 (1H, m), 6.37-6.82 (1H, m), 7.15-7.30 (5H, m), 7.54-7.60 (1H, m), 9.57 (1H, s).

Preparation Example 63

1-Benzyloxy-1H-pyrrole-3-carbaldehyde

The title compound (500 mg, 2.5 mmol, 13.1%) was obtained as a yellow oil from 2,5-dimethoxy-tetrahydrofuran-3-carbaldehyde (3.0 g, 19 mmol) and O-benzyl hydroxylamine (2.3 g, 19 mmol) according to an analogous method to Preparation Example 57.

$^1$H-NMR Spectrum (DMSO-$d_6$) δ(ppm): 5.24 (2H, s), 6.35-6.48 (1H, m), 7.05-7.08 (1H, m), 7.28-7.43 (5H, m), 7.74-7.77 (1H, m), 9.55 (1H, s).

Preparation Example 64

(1-Benzyloxy-1H-pyrrol-3-yl)-methanol

To a solution of 1-benzyloxy-1H-pyrrole-3-carbaldehyde described in Preparation Example 63 (500 mg, 2.5 mmol) in tetrahydrofuran (10 mL) was added lithium aluminum hydride (75 mg, 1.97 mmol), and the solution was stirred at room temperature for 10 minutes. Water and ethyl acetate were added to the reaction solution, which was then partitioned, silica gel was added to the organic layer, the solvent was evaporated in vacuo for adsorption, purification by silica gel column chromatography (hexane:ethyl acetate=2:1) was carried out, and the title compound (168 mg, 0.828 mmol, 33.1%) was obtained as a colorless oil.

$^1$H-NMR Spectrum (DMSO-$d_6$) δ(ppm): 4.22 (2H, d, J=5.6 Hz), 4.60 (1H, t, J=5.6 Hz), 5.10 (2H, s), 5.78-5.81 (1H, m), 6.75-6.78 (1H, m), 6.78-6.81 (1H, m), 7.37-7.42 (5H, m).

Preparation Example 65

(5-[1,3]Dioxolan-2-yl-thiophen-2-yl)-(5-methyl-thiophen-2-yl)-methanol n-Butyl lithium (2.44N hexane solution, 7.4 mL, 17.9 mmol) was added dropwise to a solution of 2-(5-bromo-thiophen-2-yl)-[1,3]dioxolane (4.0 g, 17 mmol) in tetrahydrofuran (50 mL) at from −75° C. to −70° C., and the solution was stirred for 10 minutes. 5-Methylthiophene-2-carbaldehyde (2.4 g, 18.7 mmol) was further added dropwise to the reaction solution at from −75° C. to −70° C. After dropwise addition was completed, the reaction solution was gradually allowed to room temperature. Water and ethyl acetate were added to the reaction mixture, which was then partitioned, and the solvent was evaporated. The residue was purified by NH silica gel column chromatography (hexane:ethyl acetate=4:1, then 2:1), and the title compound (2.0 g, 7.09 mmol, 41.7%) was obtained as a brown oil.

$^1$H-NMR Spectrum (DMSO-$d_6$) δ(ppm): 2.38 (3H, s), 3.88-4.04 (4H, m), 5.95 (1H, s), 6.04-6.08 (1H, m), 6.43-6.46 (1H, m), 6.60-6.63 (1H, m), 6.75 (1H, d, J=3.6 Hz), 6.83 (1H, d, J=3.6 Hz), 7.02 (1H, d, J=3.6 Hz).

Preparation Example 66

5-(5-Methyl-thiophen-2-ylmethyl)-thiophene-2-carbaldehyde

Sodium iodide (6.4 g, 42.6 mmol) and trimethylsilyl chloride (4.6 g, 42.6 mmol) were suspended in acetonitrile (100 mL) on an ice bath, and (5-[1,3]dioxolane-2-ylthiophen-2-yl)-(5-methyl-thiophen-2-yl)-methanol described in Preparation Example 65 (2.0 g, 7.09 mmol) was added dropwise. After dropwise addition was completed, the reaction solution was gradually allowed to room temperature. A solution obtained by dissolving an aqueous solution of 2N sodium hydroxide (10.6 mL) and sodium thiosulfate pentahydrate (530 mg, 2.13 mmol) in water (5 mL) was added to the reaction solution that had been cooled on an ice bath, and the solution was stirred. Water and ethyl acetate were added to the reaction solution, which was then partitioned, and the organic layer was concetrated in vacuo. The residue was purified by silica gel column chromatography (hexane:ethyl acetate=20:1), and the title compound (790 mg, 3.56 mmol, 50.2%) was obtained as a brown oil.

¹H-NMR Spectrum (DMSO-d₆) δ(ppm): 2.38 (3H, s), 4.38 (2H, s), 6.62-6.67 (1H, m), 6.76-6.80 (1H, m), 7.12-7.16 (1H, m), 7.85-7.90 (1H, m), 9.83 (1H, s).

Preparation Example 67

(5-(5-Methyl-thiophen-2-ylmethyl)-thiophen-2-yl)-methanol

To a solution of 5-(5-methyl-thiophen-2-ylmethyl)-thiophene-2-carbaldehyde described in Preparation Example 66 (790 mg, 3.56 mmol) in tetrahydrofuran (5 mL) was added lithium aluminum hydride (41 mg, 1.06 mmol), and the mixture was stirred at room temperature for 10 minutes. Water and ethyl acetate were added to the reaction mixture, which was then partitioned, the organic layer was filtered with a glass filter lined with silica gel, the filtrate was evaporated in vacuo, and the title compound (640 mg, 2.86 mmol, 80.3%) was obtained as a light brown oil.

¹H-NMR Spectrum (DMSO-d₆) δ(ppm): 2.36 (3H, s), 4.20 (2H, s), 4.52 (2H, d, J=6.0 Hz), 5.33 (1H, t, J=6.0 Hz), 6.56-6.63 (1H, m), 6.66-6.76 (3H, m).

Preparation Example 68

(5-[1,3]Dioxolan-2-yl-thiophen-2-yl)-(5-methyl-furan-2-yl)-methanol

The title compound (4.2 g, 16 mmol) was obtained as a reddish brown oil from 2-(5-bromo-thiophen-2-yl)-[1,3]dioxolane (4.0 g, 17 mmol) and 5-methyl-furan-2-carbaldehyde (1.9 g, 17 mmol) according to an analogous method to Preparation Examples 65.

¹H-NMR Spectrum (DMSO-d₆) δ(ppm): 2.22 (3H, s), 3.89-3.96 (2H, m), 3.98-4.06 (2H, m), 5.83 (1H, d, J=4.8 Hz), 5.96-6.02 (2H, m), 6.11-6.13 (1H, m), 6.22-6.24 (1H, m), 6.82-6.84 (1H, m), 7.02-7.05 (1H, m).

Preparation Example 69

5-(5-Methyl-furan-2-ylmethyl)-thiophene-2-carbaldehyde

The title compound (400 mg, 1.9 mmol, 11.8%) was obtained as a brown oil from 5-[1,3]dioxolan-2-yl-thiophen-2-yl)-(5-methyl-furan-2-yl)-methanol described in Preparation Example 68 (4.2 g, 16 mmol) according to an analogous method to Preparation Example 66.

¹H-NMR Spectrum (DMSO-d₆) δ(ppm): 2.21 (3H, s), 4.24 (2H, s), 5.98-6.02 (1H, m), 6.12-6.14 (1H, m), 7.13 (1H, d, J=3.6 H), 7.89 (1H, d, J=3.6 Hz), 9.82 (1H, s).

Preparation Example 70

(5-(5-Methyl-furan-2-ylmethyl)-thiophen-2-yl)-methanol

The title compound (210 mg, 1.0 mmol, 52.6%) was obtained as a brown oil from 5-(5-methyl-furan-2-ylmethyl)-thiophene-2-carbaldehyde described in Preparation Example 69 (400 mg, 1.9 mmol) according to an analogous method to Preparation Example 67.

¹H-NMR Spectrum (DMSO-d₆) δ(ppm): 2.20 (3H, s), 4.05 (2H, s), 4.53 (2H, d, J=5.6 Hz), 5.33 (1H, t, J=5.6 Hz), 5.94-5.98 (1H, m), 6.02 (1H, d, J=2.8 Hz), 6.70-6.77 (2H, m).

Preparation Example 71

Benzofuran-2-yl-(5-[1,3]dioxolan-2-yl-thiophen-2-yl)-methanol

The title compound (7.2 g, 23.8 mmol, 91.5%) was obtained as a yellow oil from 2-(5-bromo-thiophen-2-yl)-[1,3]dioxolane (6.0 g, 26 mmol) and benzofuran-2-carbaldehyde (3.8 g, 26 mmol) according to an analogous method to Preparation Example 65.

¹H-NMR Spectrum (DMSO-d₆) δ(ppm): 3.88-4.06 (4H, m), 5.98 (1H, s), 6.08-6.11 (1H, m), 6.59 (1H, d, J=5.2 Hz), 6.78 (1H, s), 6.95 (1H, d, 3.6 Hz), 7.07 (1H, d, J=3.6 Hz), 7.20-7.30 (2H, m), 7.52 (1H, d, J=8.0 Hz), 7.61 (1H, d, J=7.2 Hz).

Preparation Example 72

(5-Benzofuran-2-ylmethyl-thiophene)-methanol (Benzofuran-2-ylmethyl)-thiophene-2-carbaldehyde (1.3 g, 5.4 mmol, 54.5%) was obtained as a brown oil from benzofuran-2-yl-(5-[1,3]dioxolan-2-yl-thiophen-2-yl)-methanol described in Preparation Example 71 (3.0 g, 9.9 mmol) according to an analogous method to Preparation Example 66, Using this oil (1.2 g) according to an analogous method to Preparation Example 67, the title compound (900 mg, 3.7 mmol, 68.5%) was obtained as a brown oil.

¹H-NMR Spectrum (DMSO-d₆) δ(ppm): 4.32 (2H, s), 4.55 (2H, d, J=5.6 Hz), 5.36 (1H, t, J=5.6 Hz), 6.67 (1H, s), 6.80 (1H, d, J=3.2 Hz), 6.83 (1H, d, J=3.2 Hz), 7.17-7.27 (2H, m), 7.50 (1H, d, J=8.0 Hz), 7.56 (1H, d, J=7.2 Hz).

Preparation Example 73

1-Phenyl-1H-pyrrole-3-carbaldehyde

The title compound (1.2, 7.0 mmol, 70%) was obtained as a brown oil from 2,5-dimethoxy-tetrahydrofuran-3-carbaldehyde (2.0 g, 12.5 mmol) and aniline (930 mg, 10 mmol) according to an analogous method to Preparation Example 57.

¹H-NMR Spectrum (DMSO-d₆) δ(ppm): 6.67-6.70 (1H, m), 7.32-7.39 (1H, m), 7.48-7.55 (3H, m), 7.65-7.70 (2H, m), 8.22-8.26 (1H, m), 9.77 (1H, s).

Preparation Example 74

C-(1-Phenyl-1H-pyrrol-3-yl)-methylamine

The title compound (580 mg, 3.37 mmol, 48.1%) was obtained as a light green oil from 1-phenyl-1H-pyrrole-3-carbaldehyde described in Preparation Example 73 (1.2 g, 7.0 mmol) according to an analogous method to Preparation Example 59.

¹H-NMR Spectrum (DMSOd₆) δ(ppm): 3.58 (2H, s), 6.19-6.22 (1H, m), 7.16-7.22 (2H, m), 7.24-7.28 (1H, m), 7.38-7.44 (2H, m), 7.47-7.52 (2H, m).

Preparation Example 75

(3-Phenoxy-benzyl)-carbamic acid phenyl ester

To a solution of phenyl chloroformate (0.29 mL, 2.3 mmol) in tetrahydrofuran (10 mL) were added 3-phenoxybenzylamine described in Preparation Example 4 (0.5 g, 2.5 mmol) and triethylamine (0.35 mL, 2.5 mmol) dropwise on an ice bath, and then, the solution was stirred at room temperature for 4 hours. The reaction solution was poured into brine, the solution was extracted with ethyl acetate and concentrated, and the title compound (0.7 g, 2.2 mmol, 88%) was obtained.

$^1$H-NMR Spectrum (DMSO-$d_6$) δ(ppm): 4.24 (2H, d, J=6.0 Hz), 6.87-7.49 (14H, m), 8.29 (1H, t, J=6.0 Hz).

Preparation Example 76

5-(2.4-Difluorophenoxy)-furan-2-carbaldehyde

To a solution of 2,4-difluorophenol (6.54 mL, 68.0 mmol) in dimethylsulfoxide (70 mL) was sodium hydride (4534 mg, 68.0 mmol, 60% in oil), which was then stirred for 40 minutes. 5-Nitro-2-furaldehyde (8000 mg, 56.7 mmol) was added to the reaction solution, and the solution was stirred at room temperature for 2 hours. Water was added to the reaction mixture, which was then extracted with ethyl acetate. The organic layer was washed with water and brine, dried over anhydrous magnesium sulfate, and then, concentrated in vacuo. The resulting residue was purified by silica gel chromatography (hexane:ethyl acetate), and the title compound (4134 mg, 18.44 mmol, 33%) was obtained.

$^1$H-NMR Spectrum (CDCl3) δ(ppm): 5.54 (1H, d, J=3.6 Hz), 6.90-7.03 (2H, m), 7.21 (1H, d, J=3.6 Hz), 7.24-7.31 (1H, m), 9.40 (1H, s).

Preparation Example 77

C-(5-(2,4-Difluoro-phenoxy)-furan-2-yl)-methylamine

To a solution of 5-(2,4-difluoro-phenoxy)-furan-2-carbaldehyde (2060 mg, 9.19 mmol) in 7N ammonia/methanol solution (100 mL) was added Raney nickel (5.9 g), and the mixture was stirred for 24 hours at room temperature under hydrogen atmosphere. The reaction mixture was filtered through Celite pad, and the filtrate was concentrated in vacuo. The residue was purified by NH silica gel column chromatography (hexane:ethyl acetate), and the title compound (1814 mg, 88.06 mmol, 87.7%) was obtained as a yellow oil.

$^1$H-NMR Spectrum (DMSO-$d_6$) δ(ppm): 1.70 (2H, brs), 3.55 (2H, s), 5.55 (1H, d, J=3.2 Hz), 6.13 (1H, d, J=3.2 Hz), 7.05-7.22 (1H, m), 7.21-7.28 (1H, m), 7.43-7.50 (1H, m).

Preparation Example 78

5-(2,5-Difluoro-phenoxy)-furan-2-carbaldehyde

To a solution of 2,5-difluorophenol (3360 mg, 25.83 mmol) in N,N-dimethylformamide (60 mL) was sodium hydride (1032 mg, 25.83 mmol, 60% in oil), which was then stirred for 1 hour. 5-Bromo-2-furaldehyde (3826 mg, 21.52 mmol) was added to the reaction solution, and the solution was stirred at 60° C. for 12 hours. Water was added to the reaction mixture, which was then extracted with ethyl acetate. The organic layer was washed with water and brine, dried over anhydrous magnesium sulfate, and then, concentrated in vacuo. The resulting residue was purified by silica gel chromatography (hexane-ethyl acetate), and the title compound (1104 mg, 4.92 mmol, 22.9%) was obtained.

$^1$H-NMR Spectrum (CDCl3) δ(ppm): 5.67 (1H, d, J=3.6 Hz), 6.93-7.04 (2H, m), 7.15-7.22 (1H, m), 7.24 (1H, d, J=3.6 Hz), 9.43 (1H, s).

Preparation Example 79

C-(5-(2.5-Difluoro-phenoxy)-furan-2-yl)-methylamine

The title compound (2353 mg, 10.50 mmol, 97%) was obtained from 5-(2,5-difluoro-phenoxy)-furan-2-carbaldehyde (2402 mg, 11.65 mmol) according to an analogous method to Preparation Example 77.

$^1$H-NMR Spectrum (DMSO-$d_6$) δ(ppm): 1.72 (2H, brs), 3.56 (2H, s), 5.71 (1H, d, J=3.2 Hz), 6.17 (1H, d, J=3.2 Hz), 7.01-7.12 (2H, m), 7.41-7.50 (1H, m).

Preparation Example 80

2-Benzyloxy-thiophene

To a solution of benzyl alcohol (3.45 mL, 33.3 mmol) in 1,2-dimethoxyethane (80 mL) was added n-butyl lithium (2.6M hexane solution, 13.5 mL, 33.3 mmol) dropwise, which was then stirred for 10 minutes. Copper(I) chloride (5210 mg, 49.45 mmol) was added thereto, followed by stirring for 10 minutes on an ice bath, then, it was stirred for 2.5 hours at room temperature. 2-Iodothiophene (4995 mg, 23.78 mmol) and pyridine 320 mL were further added, and the solution was stirred for 13 hours under reflux. Ethyl acetate was added to the reaction mixture, which was sequentially washed with 1N hydrochloric acid, an aqueous solution of sodium hydrogen sulfate and brine, dried over anhydrous magnesium sulfate, and then, concentrated in vacuo. The resulting residue was purified by silica gel chromatography (hexane-ethyl acetate), and the title compound (420 mg, 2.21 mmol, 9.5%) was obtained.

$^1$H-NMR Spectrum (CDCl3) δ(ppm): 5.08 (2H, s), 6.28 (1H, dd, J=1.6, 4.0 Hz), 6.57 (1H, dd, J=1.6, 5.6 Hz), 6.71 (1H, dd, J=4.0, 5.6 Hz), 7.30-7.47 (5H, m).

Preparation Example 81

5-Benzyloxy-thiophene-2-carbonitrile

To a solution of 2-benzyloxy-thiophene (184 mg, 0.967 mmol) in diethyl ether (4 mL) was added n-butyl lithium (2.47M hexane solution, 0.47 mL, 1.16 mmol) at −78° C. under nitrogen atmosphere, then, the solution was stirred for 1.5 hours on an ice bath. The solution was cooled again to −78° C., N,N-dimethylformamide (487 μl, 4.84 mmol) was added, and the solution was stirred for 45 minutes while warming to room temperature. An aqueous solution of saturated ammonium chloride was added to the reaction mixture, which was then extracted with ethyl acetate. The organic layer was washed with brine, dried over anhydrous magnesium sulfate, then, filtered with silica gel, the filtrate was concentrated in vacuo, and 5-benzyloxy-thiophene-2-carbaldehyde (171 mg) was obtained.

The resulting 5-benzyloxy-thiophene-2-carbaldehyde (171 mg) was dissolved in N,N-dimethylformamide (4 mL), pyridine (82 μl, 1.02 mmol) and hydroxylamine hydrochloride (65 mg, 0.94 mmol) were added thereto, followed by stirring for 30 minutes at 60° C., then, cooled on an ice bath. 1,1'-Carbonyldiimidazole (635 mg, 3.92 mmol) was added, the solution was warmed again to 60° C. and stirred for 35 minutes, triethylamine (272 μl, 1.96 mmol) was added, and the solution was further stirred for 30 minutes. The reaction mixture was cooled to room temperature, water was added, and the solution was extracted with ethyl acetate. The organic layer was sequentially washed with an aqueous solution of oxalic acid, an aqueous solution of saturated sodium bicarbonate and brine, dried over anhydrous sodium sulfate, and then, concentrated in vacuo. The resulting residue was purified by silica gel chromatography (hexane-ethyl acetate), and the title compound (30 mg, 0.14 mmol, 14%) was obtained.

$^1$H-NMR Spectrum (CDCl3) δ(ppm): 5.15 (2H, s), 6.28 (1H, d, J=4.0 Hz), 7.32 (1H, d, J=4.0 Hz), 7.38-7.48 (5H, m).

Preparation Example 82

2-(5-(3-Fluoro-benzyl)-furan-2-yl)-[1,3]dioxolane n-Butyl lithium (2.66M hexane solution, 25.5 mL, 67.88 mmol) was added dropwise to a solution of 2-(1,3-dioxolan-2-yl)furan (8272 mg, 59.03 mmol) in tetrahydrofuran (160 mL) that had been cooled to −78° C. solution under nitrogen atmosphere, which was then stirred for 10 minutes. To this solution was added a solution of 3-fluorobenzyl bromide (14.50 g, 76.73 mmol) in tetrahydrofuran (60 mL) dropwise, which was then stirred for 1 hour at −78° C., and for 1.25 hours at room temperature. An aqueous solution of saturated ammonium chloride was added to the reaction mixture, which was extracted with diethyl ether. The organic layer was washed with brine, dried over anhydrous sodium sulfate, and then, concentrated in vacuo. The obtained residue was purified by silica gel chromatography (hexane-ethyl acetate), and a mixture of the title compound and 2-(1,3-dioxolane-2-yl)furan (8033 mg), which is the starting material, was obtained.

Preparation Example 83

5-(3-Fluoro-benzyl)-furan-2-carbaldehyde

To a solution of a mixture of 2-(5-(3-fluoro-benzyl)-furan-2-yl)-[1,3]dioxolane and 2-(1,3-dioxolan-2-yl)furan (8033 mg) in methanol (80 mL) was added an aqueous solution of oxalic acid (22 g, 115 mmol) (80 mL), and the solution was stirred at room temperature for 1 hour. Water was added to the reaction mixture, which extracted with diethyl ether, the organic layer was sequentially washed with an aqueous solution of saturated sodium bicarbonate, water and brine, dried over anhydrous sodium sulfate, and then, concentrated in vacuo. The resulting residue was purified by silica gel chromatography (hexane-ethyl acetate), and the title compound (4084 mg, 20.0 mmol, 34%) was obtained.

$^1$H-NMR Spectrum (CDCl3) δ(ppm): 4.07 (2H, s), 6.23 (1H, d, J=4.0 Hz), 6.90-7.10 (3H, m), 7.18 (1H, d, J=4.0 Hz), 7.25-7.37 (1H, m), 9.56 (1H, s).

Preparation Example 84

C-(5-(3-Fluoro-benzyl)-furan-2-yl)-methylamine

The title compound (4104 mg, 20.0 mmol, 100%) was obtained from 5-(3-fluoro-benzyl)-furan-2-carbaldehyde (4084 mg, 20.0 mmol) according to an analogous method to Preparation Example 77.

$^1$H-NMR Spectrum (DMSO-d$_6$) δ(ppm): 1.60 (2H, brs), 3.31 (2H, s), 3.93 (2H, s), 5.97-6.11 (2H, m), 6.82-7.15 (3H, m), 7.20-7.41 (1H, m).

Preparation Example 85

2-(3-[1,2,3]Triazol-2-yl-propyl)-isoindol-1,3-dione

To a solution of 1H-1,2,3-triazole (2000 mg, 28.96 mmol) in N,N-dimethylformamide (60 mL) was added sodium hydride (1159 mg, 28.96 mmol, 60% in oil), which was stirred for 30 minutes. N-(3-Bromopropyl)phthalimide (7057 mg, 26.32 mmol) and potassium iodide (431 mg, 2.63 mmol) were added thereto, and the solution was stirred for 3 hours at 70°. Water was added to the reaction mixture, which was then extracted with ethyl acetate. The organic layer was washed with water and brine, dried over anhydrous magnesium sulfate, and then, concentrated in vacuo. The resulting residue was purified by silica gel chromatography (dichloromethane-ethyl acetate), and the title compound (3526 mg, 13.75 mmol, 47%) was obtained.

$^1$H-NMR Spectrum (DMSO-d$_6$) δ(ppm): 2.19-2.28 (2H, m), 3.65 (2H, t, J=6.8 Hz), 4.51 (2H, t, J=6.8 Hz), 7.74 (2H, s), 7.80-7.89 (4H, m).

Preparation Example 86

3-[1,2,3]Triazol-2-yl-propyl amine

To a mixture solution of 2-(3-[1,2,3]triazol-2-yl-propyl)-isoindol-1,3-dione (1782 mg, 6.95 mmol) in methanol-tetrahydrofuran (5:4, 27 mL) was added hydrazine monohydrate (371 μl, 7.65 mmol), and the solution was stirred for 5 days at room temperature. Methanol (8 mL) was added thereto, followed by further stirring for 3.25 hours under reflux. The reaction mixture was filtered, and the filtrate was concentrated. The resulting residue was dissolved in tetrahydrofuran, adsorbed onto NH silica gel, purified by NH silica gel chromatography (ethyl acetate-methanol), and the title compound (491 mg, 1.36 mmol, 19.6%) was obtained.

$^1$H-NMR Spectrum (DMSO-d$_6$) δ(ppm): 1.85-1.93 (2H, m), 2.46-2.51 (2H, m), 4.42-4.52 (2H, m), 7.75 (2H, s).

Preparation Example 87

3-Benzyl amino-benzonitrile

3-Bromo-benzonitrile (500 mg, 2.75 mmol), benzylamine (360 μl, 3.30 mmol), 2,2-bis(diphenylphosphino)-1,1'-binaphthyl (8.6 mg, 14 μmol), tris(dibenzylideneacetone)dipalladium(0) (19 mg, 21 μmol) and sodium tert-butoxide (370 mg, 3.85 mmol) were suspended in toluene (10 mL), and the mixture was stirred at 80° C. for 22 hours under nitrogen atmosphere. The reaction mixture was filtered through Celite pad, then, the filtrate was evaporated in vacuo, the residue was purified by NH silica gel column chromatography (hexane: ethyl acetate=15:1), and the title compound (331 mg, 1.59 mmol, 58%) was obtained as a pale yellow oil.

$^1$H-NMR Spectrum (CDCl$_3$) δ(ppm): 4.33 (2H, m), 4.34 (1H, s), 6.79-6.83 (2H, m), 6.97 (1H, dt, J=1.2, 7.7 Hz), 7.22 (1H, t, J=8.1 Hz), 7.29-7.39 (5H, m).

Preparation Example 88

4-Phenylamino-benzonitrile

The title compound (460 mg, 2.37 mmol, 86%) was obtained as a white solid from 4bromo-benzonitrile (500 mg, 2.75 mmol) and phenylamine (300 μl, 3.30 mmol) according to an analogous method to Preparation Example 87.

$^1$H-NMR Spectrum (CDCl$_3$) δ(ppm) 6.04 (1H, s), 6.97 (2H, d, J=8.8 Hz), 7.12 (1H, t, J=7.3 Hz), 7.17 (2H, d, J=7.7 Hz), 7.36 (2H, t, J=7.5 Hz), 7.48 (2H, d, J=8.8 Hz).

Preparation Example 89

4-Benzylamino-benzonitrile

The title compound (472 mg, 2.27 mmol, 83%) was obtained as a pale yellow solid from 4-bromo-benzonitrile (500 mg, 2.75 mmol) and benzylamine (360 μl, 3.30 mmol) according to an analogous method to Preparation Example 87.

$^1$H-NMR Spectrum (CDCl$_3$) δ(ppm): 4.38 (2H, d, J=5.5 Hz), 4.58 (1H, s), 6.59 (2H, d, J=8.8 Hz), 7.29-7.39 (5H, m), 7.42 (2H, d, J=8.8 Hz).

Preparation Example 90

2-(3-Bromo-phenyl)-[1.3]dioxolane

3-Bromobenzaldehyde (4.00 g, 21.6 mmol), ethane-1,2-diol (6.03 mL, 108 mmol) and toluene-4-sulfonic acid monohydrate (186 mg, 1.08 mmol) were dissolved in toluene (80 mL), and the solution was stirred under reflux for 4 hours. An aqueous solution of saturated sodium bicarbonate was added to the reaction solution at 0° C., which was then extracted with ethyl acetate, the organic layer was washed with brine, and the organic layer was dried over anhydrous magnesium sulfate. The solvent was evaporated in vacuo, the residue was purified by NH silica gel column chromatography (hexane:ethyl acetate=20:1), and the title compound (4.79 g, 20.9 mmol, 97%) was obtained as a colorless oil.

$^1$H-NMR Spectrum (CDCl$_3$) δ(ppm): 4.02-4.05 (2H, m), 4.07-4.13 (2H, m), 5.79 (1H, s), 7.23-7.27 (1H, m), 7.40 (1H, d, J=7.7 Hz), 7.49 (1H, dt, J=1.1, 7.1 Hz), 7.64 (1H, s).

Preparation Example 91

2-(3-Phenylsulfanyl-phenyl)-[1,3]dioxolane 2-(3-Bromo-phenyl)-[1,3]dioxolane described in Preparation Example 90 (515 mg, 2.25 mmol) was dissolved in tetrahydrofuran (10 mL) under nitrogen atmosphere, n-butyl lithium (2.47M hexane solution, 1.64 mL, 4.05 mmol) was added at −78° C., the solution was stirred for 15 minutes, then, diphenyldisulphide (540 mg, 2.48 mmol) was added thereto, followed by stirring for 3 hours. The reaction solution was cooled to 0° C., water was added, the solution was extracted with ethyl acetate, the organic layer was washed with brine and dried over anhydrous magnesium sulfate. The solvent was evaporated in vacuo, the residue was purified by silica gel column chromatography (hexane:ethyl acetate=20:1), and the title compound (402 mg, 1.56 mmol, 69%) was obtained as a colorless oil.

$^1$H-NMR Spectrum (CDCl$_3$) δ(ppm): 4.01-4.06 (2H, m), 4.09-4.14 (2H, m), 5.76 (1H, s), 7.22-7.39 (8H, m), 7.48 (1H, s).

Preparation Example 92

3-Phenylsulfanyl-benzaldehyde 2-(3-Phenylsulfanyl-phenyl)-[1,3]dioxolane described in Preparation Example 91 (396 mg, 1.53 mmol) was dissolved in a mixture solution of ethanol (5 mL), water (5 mL), tetrahydrofuran (5 mL) and sulfuric acid (1 mL), and the solution was stirred for 2.5 hours under reflux. The reaction solution was cooled to 0° C., an aqueous solution of saturated sodium bicarbonate was added thereto, the solution was extracted with ethyl acetate, the organic layer was washed with brine and dried over anhydrous magnesium sulfate. The solvent was evaporated in vacuo, the residue was purified by silica gel column chromatography (hexane:ethyl acetate=20:1), and the title compound (323 mg, 1.51 mmol, 98%) was obtained as a colorless oil.

$^1$H-NMR Spectrum (CDCl$_3$) δ(ppm): 7.31-7.39 (3H, m), 7.41-7.50 (3H, m), 7.52 (1H, d, J=7.9 Hz), 7.71 (1H, d, J=7.3 Hz), 7.76 (1H, s), 9.94 (1H, s).

Preparation Example 93

(3-Phenylsulfanyl-phenyl)-methanol

3-Phenylsulfanyl-benzaldehyde described in Preparation Example 92 (321 mg, 1.49 mmol) was dissolved in ethanol (6 mL), sodium borohydride (113 mg, 2.98 mmol) was added thereto at 0° C., followed by stirring at room temperature for 3 hours. Water was added to the reaction solution, which was then extracted with ethyl acetate, the organic layer was washed with brine and dried over anhydrous magnesium sulfate. The solvent was evaporated in vacuo, the residue was purified by silica gel column chromatography (hexane:ethyl acetate=5:1), and the title compound (220 mg, 1.02 mmol, 68%) was obtained as a colorless oil.

$^1$H-NMR Spectrum (CDCl$_3$) δ(ppm): 3.73 (2H, s), 4.66 (1H, s), 7.18-7.37 (9H, m).

Preparation Example 94

2-(3-Phenylsulfanyl-benzyl)-isoindol-1,3-dione (3-Phenylsulfanyl-phenyl)-methanol described in Preparation Example 93 (212 mg, 0.980 mmol), phthalimide (144 mg, 0.980 mmol), diethylazodicarboxylate (170 μl, 1.08 mmol) and triphenylphosphine (308 mg, 1.18 mmol) were dissolved in tetrahydrofuran (4 mL), and the solution was stirred overnight at room temperature. Water was added to the reaction solution, which was then extracted with ethyl acetate, the organic layer was washed with brine and dried over anhydrous magnesium sulfate. The solvent was evaporated in vacuo, the residue was purified by silica gel column chromatography (hexane:ethyl acetate=10:1), and the title compound (124 mg, 0.359 mmol, 37%) was obtained as a solid.

$^1$H-NMR Spectrum (CDCl$_3$) δ(ppm): 4.80 (2H, s), 7.17-7.36 (9H, m), 7.73 (2H, dd, J=2.9, 5.3 Hz), 7.86 (2H, dd, J=2.9, 5.3 Hz).

Preparation Example 95

3-Phenylsulfanyl-benzylamine 2-(3-Phenylsulfanyl-benzyl)-isoindole-1,3-dione described in Preparation Example 94 (123 mg, 0.356 mmol) was dissolved in ethanol (3 mL), hydrazine monohydrate (518 μl, 10.7 mmol) was added at 0° C., and the solution was stirred under reflux for 2 hours. Water was added to the reaction solution at 0° C., which was then extracted with ethyl acetate, the organic layer was washed with brine and dried over anhydrous magnesium sulfate. The solvent was evaporated in vacuo, the residue was purified by NH silica gel column chromatography (ethyl acetate), and the title compound (75 mg, 0.35 mmol, 98%) was obtained as a colorless oil.

$^1$H-NMR Spectrum (CDCl$_3$) δ(ppm): 3.83 (2H, s), 7.19-7.36 (9H, m).

Preparation Example 96

2-(4-Bromo-phenyl)-[1,3]dioxolane

4-Bromo-benzaldehyde (4.00 g, 21.6 mmol), ethane-1,2-diol (6.03 mL, 108 mmol) and toluene-4-sulfonic acid monohydrate (186 mg, 1.08 mmol) were dissolved in toluene (80 mL), and the solution was stirred under reflux for 4 hours. An aqueous solution of saturated sodium bicarbonate was added to the reaction solution at 0° C., which was then extracted with ethyl acetate, the organic layer was washed with brine, and the organic layer was dried over anhydrous magnesium sulfate. The solvent was evaporated in vacuo, the residue was purified by NH silica gel column chromatography (hexane: ethyl acetate=20:1), and the title compound (4.66 g, 20.3 mmol, 94%) was obtained as a colorless oil.

$^1$H-NMR Spectrum (CDCl$_3$) δ(ppm): 4.01-4.05 (2H, m), 4.07-4.13 (2H, m), 5.77 (1H, s), 7.35 (2H, d, J=8.2 Hz), 7.51 (2H, d, J=8.4 Hz).

Preparation Example 97

2-(4-Benzylsulfanyl-phenyl)-[1,3]dioxolane

The title compound (568 mg, 2.09 mmol, 48%) was obtained as a solid from 2-(4bromo-phenyl)-[1,3]dioxolane described in Preparation Example 96 (1.00 g, 4.37 mmol) and benzyl disulphide (1.18 g, 4.81 mmol) according to an analogous method to Preparation Example 91.

$^1$H-NMR Spectrum (CDCl$_3$) δ(ppm): 4.02-4.04 (2H, m), 4.10-4.13 (2H, m), 4.13 (2H, s), 5.76 (1H, s), 7.23-7.27 (1H, m), 7.28-7.32 (6H, m), 7.37 (2H, d, J=8.2Hz).

Preparation Example 98

4-Benzylsulfanyl-benzaldehyde

The title compound (462 mg, 2.02 mmol, 97%) was obtained as a white solid from 2-(4-benzyl sulfanyl-phenyl)-[1,3]dioxolane described in Preparation Example 97 (568 mg, 2.09 mmol) according to an analogous method to Preparation Example 92.

$^1$H-NMR Spectrum (CDCl$_3$) δ(ppm): 4.24 (2H, s), 7.26-7.40 (7H, m), 7.75 (2H, d, J=8.6 Hz), 9.92 (1H, s).

Preparation Example 99

(4-Benzylsulfanyl-phenyl)-methanol

The title compound (406 mg, 1.76 mmol, 87%) was obtained as a white solid from 4-benzylsulfanyl-benzaldehyde described in Preparation Example 98 (462 mg, 2.02 mmol) according to an analogous method to Preparation Example 93.

$^1$H-NMR Spectrum (CDCl$_3$) δ(ppm): 4.11 (2H, s), 4.65 (2H, d, J=4.4 Hz), 7.20-7.35 (8H, m), 7.37 (1H, d, J=4.4 Hz).

Preparation Example 100

2-(4-Benzylsulfanyl-benzyl)-isoindol-1,3-dione

The title compound (563 mg, 1.57 mmol, 89%) was obtained as a white solid from (4benzylsulfanyl)-methanol described in Preparation Example 99 (406 mg, 1.76 mmol) according to an analogous method to Preparation Example 94.

$^1$H-NMR Spectrum (CDCl$_3$) δ(ppm): 4.09 (2H, s), 4.79 (2H, s), 7.20-7.35 (5H, m), 7.24 (2H, d, J=8.2 Hz), 7.32 (2H, d, J=8.1 Hz), 7.71 (2H, dd, J=2.9, 5.3 Hz), 7.84 (2H, dd, J=2.9, 5.3 Hz).

Preparation Example 101

4-Benzylsulfanyl-benzylamine

The title compound (260 mg, 1.13 mmol, 72%) was obtained as a white solid from 2-(4-benzylsulfanyl-benzyl)-isoindol-1,3-dione described in Preparation Example 100 (563 mg, 1.57 mmol) according to an analogous method to Preparation Example 95.

$^1$H-NMR Spectrum (CDCl$_3$) δ(ppm): 3.83 (2H, s), 4.10 (2H, s), 7.20 (2H, d, J=8.6 Hz), 7.19-7.32 (7H, m).

Preparation Example 102

(5-Phenylaminomethyl-furan-2-yl)-methanol

Acetic acid 5-formyl-furan-2-ylmethyl ester (2.00 g, 11.9 mmol), aniline (1.63 mL, 17.9 mmol) and triacetoxy sodium borohydride (5.04 g, 23.8 mmol) were suspended in a mixture solution of tetrahydrofuran (40 mL) and acetic acid (1 mL) at 0° C., and the mixture was stirred at room temperature for 7 hours. An aqueous solution of saturated sodium bicarbonate was added to the reaction solution at 0° C., which was then extracted with ethyl acetate and tetrahydrofuran, the organic layer was washed with brine and dried over anhydrous magnesium sulfate. The solvent was evaporated in vacuo, the residue was purified by silica gel column chromatography (hexane:ethyl acetate=1:1), and a mixture of acetic acid 5-phenylaminomethyl-furan-2-ylmethyl ester and aniline (2.91 g) was obtained as a pale yellow oil.

Then, the resulting mixture of acetic acid 5-phenylaminomethyl-furan-2-ylmethyl ester and aniline (2.91 g) as well as potassium carbonate (3.28 g, 23.7 mmol) were suspended in methanol (60 mL), and the solution was stirred overnight at room temperature. The reaction solution was evaporated in vacuo, water and ethyl acetate were added to the residue, the organic layer was partitioned, washed with brine and dried over anhydrous magnesium sulfate. The solvent was evaporated in vacuo, the residue was purified by NH silica gel column chromatography (hexane:ethyl acetate=1:1), and the title compound (1.99 g, 9.79 mmol, 82%) was obtained as a colorless oil.

$^1$H-NMR Spectrum (CDCl$_3$) δ(ppm): 4.04 (1H, brs), 4.31 (2H, s), 4.59 (2H, d, J=5.9 Hz), 6.19 (1H, d, J=3.1 Hz), 6.23 (1H, d, J=3.1 Hz), 6.68 (2H, d, J=7.5 Hz), 6.75 (1H, t, J=7.3 Hz), 7.19 (2H, t, J=7.3 Hz).

Preparation Example 103

2-(5-phenylaminomethyl-furan-2-ylmethyl)-isoindol-1,3-dione

The title compound (603 mg, 1.81 mmol, 23%) was obtained as a pale yellow solid from (5-phenylaminomethyl-furan-2-yl)-methanol described in Preparation Example 102 (1.58 g, 7.77 mmol) according to an analogous method to Preparation Example 94.

$^1$H-NMR Spectrum (CDCl$_3$) δ(ppm): 4.25 (2H, s), 4.82 (2H, s), 6.14 (1H, d, J=3.1 Hz), 6.28 (1H, d, J=3.1 Hz), 6.63 (2H, d, J=7.5 Hz), 6.70 (1H, t, J=7.3 Hz), 7.14 (2H, t, J=7.3 Hz), 7.72 (2H, dd, J=3.1, 5.3 Hz), 7.87 (2H, dd, J=3.1, 5.3 Hz).

Preparation Example 104

(5-Aminomethyl-furan-2-ylmethyl)-phenyl-amine

The title compound (92 mg, 0.46 mmol, 60%) was obtained as a pale yellow oil from 2-(5-phenylaminomethylfuran-2-ylmethyl)-isoindol-1,3-dione described in Preparation Example 103 (251 mg, 0.755 mmol) according to an analogous method to Preparation Example 95.

$^1$H-NMR Spectrum (CDCl$_3$) δ(ppm): 3.79 (2H, s), 4.28 (2H, s), 6.06 (1H, d, J=3.1 Hz), 6.15 (1H, d, J=3.1 Hz), 6.68 (2H, d, J=7.7 Hz), 6.74 (1H, t, J=7.3 Hz), 7.19 (2H, t, J=7.3 Hz).

Preparation Example 105

(2-(5-[1,3]Dioxolan-2-yl-furan-2-yl)-ethyl)-phenylamine

5-[1,3]Dioxolan-2-yl-furan-2-carbaldehyde (2.03 g, 12.1 mmol), trimethylsulfonium bromide (1.90 g, 12.1 mmol) and potassium hydroxide (779 mg, 13.9 mmol) were suspended in acetonitrile (75 mL), and the solution was stirred overnight at room temperature. Water was added to the reaction solution, which was then extracted with ethyl acetate, the organic layer was washed with brine and dried over anhydrous magnesium sulfate. The solvent was evaporated in vacuo, 2-(5-oxiranyl-furan-2-yl)-[1,3]dioxolane (2.25 g) was obtained as a pale yellow oil.

The resulting 2-(5-oxiranyl-furan-2-yl)-[1,3]dioxolane (2.25 g) and silica gel (5.00 g) were suspended in ethyl acetate (40 mL), and the solution was stirred for 6.5 hours at room temperature. The reaction solution was filtered, then, the filtrate was evaporated in vacuo, and (5-[1,3]dioxolan-2-yl-furan-2-yl)-acetaldehyde (1.57 g) was obtained as a yellow oil.

Next, the resulting (5-[1,3]dioxolan-2-yl-furan-2-yl)-acetaldehyde (1.57 g), aniline (0.94 mL, 10.3 mmol) and triacetoxy sodium borohydride (3.76 g, 17.2 mmol) were suspended in a mixture solution of tetrahydrofuran (30 mL) and acetic acid (1 mL) at 0° C., and the mixture was stirred at room temperature for 19 hours. An aqueous solution of saturated sodium bicarbonate was added to the reaction mixture at 0° C., which was then extracted with ethyl acetate, the organic layer was washed with brine and dried over anhydrous magnesium sulfate. The solvent was evaporated in vacuo, the residue was purified by silica gel column chromatography (hexane:ethyl acetate=5:1), and the title compound (453 mg, 1.75 mmol, 14%) was obtained as a brown oil.

$^1$H-NMR Spectrum (CDCl$_3$) δ(ppm): 2.95 (2H, t, J=6.8 Hz), 3.43 (2H, t, J=6.8 Hz), 3.99-4.06 (2H, m), 4.10-4.15 (2H, m), 5.88 (1H, s), 6.06 (1H, d, J=3.3 Hz), 6.37 (1H, d, J=3.1 Hz), 6.62 (2H, dd, J=1.1, 8.6 Hz), 6.71 (1H, tt, J=1.1, 7.3 Hz), 7.18 (2H, dd, J=7.3, 8.6 Hz).

Preparation Example 106

5-(2-Phenylamino-ethyl)-furan-2-carbaldehyde

The title compound (314 mg, 1.46 mmol) was obtained as a light brown oil from (2-(5-[1,3]dioxolan-2-yl-furan-2-yl)-ethyl)-phenylamine described in Preparation Example 105 (453 mg, 1.75 mmol) according to an analogous method to Preparation Example 44.

$^1$H-NMR Spectrum (CDCl$_3$) δ(ppm): 3.05 (2H, t, J=6.8 Hz), 3.53 (2H, t, J=6.8 Hz), 6.33 (1H, d, J=3.5 Hz), 6.62 (2H, dd, J=1.1, 8.6 Hz), 6.73 (1H, t, J=7.3 Hz), 7.17-7.21 (3H, m), 9.55 (1H, s).

Preparation Example 107

(2-(5-Aminomethyl-furan-2-yl)-ethyl)-phenylamine

The title compound (117 mg, 0.541 mmol, 78%) was obtained as a pale yellow oil from 5-(2-phenylamino-ethyl)-furan-2-carbaldehyde described in Preparation Example 106 (150 mg, 0.697 mmol) according to an analogous method to Preparation Example 45.

$^1$H-NMR Spectrum (CDCl$_3$) δ(ppm): 2.92 (2H, t, J=6.8 Hz), 3.41 (2H, t, J=6.8 Hz), 3.78 (2H, s), 6.00 (1H, d, J=3.1 Hz), 6.04 (1H, d, J=2.9 Hz), 6.62 (2H, dd, J=1.1, 8.6 Hz), 6.71 (1H, t, J=7.3 Hz), 7.18 (2H, dd, J=7.3, 8.6 Hz).

Preparation Example 108

2-(4-Bromo-thiophen-2-yl)-[1,3]dioxolane

4-Bromo-thiophene-2-carbaldehyde (9.24 g, 48.4 mmol), ethane-1,2-diol (13.5 mL, 242 mmol), toluene-4-sulfonic acid monohydrate (416 mg, 2.42 mmol) were dissolved in toluene (100 mL), and the solution was stirred for 1.5 hours under reflux. An aqueous solution of saturated sodium bicarbonate was added to the reaction solution at 0° C., which was then extracted with ethyl acetate, the organic layer was washed with brine and dried over anhydrous magnesium sulfate. The solvent was evaporated in vacuo, the residue was purified by NH silica gel column chromatography (hexane:ethyl acetate=20:1), and the title compound (11.8 g, quantitatively) was obtained as a white solid.

$^1$H-NMR Spectrum (CDCl$_3$) δ(ppm): 4.02-4.04 (2H, m), 4.09-4.11 (2H, m), 6.07 (1H, s), 7.08 (1H, dd, J=0.73, 1.5 Hz), 7.22 (1H, d, J=1.5 Hz).

Preparation Method 109

2-(4-Phenoxy-thiophen-2-yl)-[1.3]dioxolane

The title compound (5.40 g, 21.7 mmol, 73%) was obtained as a pale yellow oil from 2-(4-bromo-thiophen-2-yl)-[1,3]dioxolane described in Preparation Example 108 (6.96 g, 29.6 mmol) and phenol (6.60 g, 71.0 mmol) according to an analogous method to Preparation Example 33.

$^1$H-NMR Spectrum (CDCl$_3$) δ(ppm): 4.00-4.04 (2H, m), 4.12-4.17 (2H, m), 6.04 (1H, s), 6.60 (1H, d, J=1.7 Hz), 6.94 (1H, d, J=1.7 Hz), 7.04 (2H, dd, J=1.1, 8.6 Hz), 7.09 (1H, tt, J=1.1, 7.3 Hz), 7.32 (2H, dd, J=7.3, 8.6 Hz).

Preparation Example 110

4-Phenoxy-thiophene-2-carbaldehyde

The title compound (183 mg, 0.896 mmol, 44%) was obtained as a colorless oil from 2-(4-phenoxy-thiophen-2-yl)-[1,3]dioxolane described in Preparation Example 109 (500 mg, 2.01 mmol) according to an analogous method to Preparation Example 34.

$^1$H-NMR Spectrum (CDCl$_3$) δ(ppm): 7.04 (1H, dd, J=1.3, 1.6 Hz), 7.07 (2H, dd, J=1.1, 8.8 Hz), 7.16 (1H, tt, J=1.1, 7.3 Hz), 7.35 (2H, dd, J=7.3, 8.6 Hz), 7.51 (1H, d, J=1.7 Hz), 9.84 (1H, s).

Preparation Example 111

C-(4-Phenoxy-thiophen-2-yl)-methylamine

The title compound (94 mg, 0.458 mmol, 51%) was obtained as a pale yellow oil from 4-phenoxy-thiophene-2-carbaldehyde described in Preparation Example 110 (183 mg, 0.896 mmol) according to an analogous method to Preparation Example 35.

¹H-NMR Spectrum (CDCl₃) δ(ppm): 3.99 (2H, s), 6.46 (1H, d, J=1.7 Hz), 6.69-6.70 (1H, m), 7.05 (2H, dd, J=1.1, 7.7 Hz), 7.09 (1H, t, J=7.5 Hz), 7.33 (2H, dd, J=7.5, 8.6 Hz).

Preparation Example 112

5-Oxo-2,5-dihydro-isoxazole-4-carboxylic acid ethyl ester

2-Ethoxymethylene-malonic acid diethyl ester (5.00 g, 23.1 mmol), hydroxylamine hydrochloride (4.01 g, 57.8 mmol) and triethylamine (8.06 mL, 57.8 mmol) were dissolved in ethanol (100 mL), the solution was stirred at room temperature for 17 hours, then, the solution was stirred for 4.5 hours under reflux. The reaction solution was cooled to room temperature, water was added, and 1N hydrochloric acid was added until a salt precipitated. The precipitated salt was collected by filtration, and a hydrochloride salt of the title compound (2.39 g, 15.2 mmol, 66%) was obtained as a white solid.
¹H-NMR Spectrum (CDCl₃) δ(ppm): 1.19 (3H, t, J=7.1 Hz), 4.08 (2H, q, J=7.1 Hz), 4.90 (1H, brs), 8.51 (1H, d, J=6.8 Hz).

Preparation Example 113

5-Oxo-2-phenoxy thiocarbonyl-2,5-dihydro-isoxazole-4-carboxylic acid ethyl ester 5-Oxo-2,5-dihydro-isoxazole-4-carboxylic acid ethyl ester described in Preparation Example 112 (1.00 g, 5.17 mmol), phenyl chlorothionoformate (786 µl, 5.69 mmol) and pyridine (919 µl, 11.4 mmol) were dissolved at 0° C. in toluene (20 mL), and the solution was stirred at room temperature for 17 hours under nitrogen atmosphere. Water was added to the reaction solution at 0° C., which was then extracted with ethyl acetate, and the organic layer was washed with brine. The solvent was evaporated in vacuo, the residue was purified by silica gel column chromatography (hexane:ethyl acetate=1:1), and the title compound (1.66 g, 5.66 mmol, quantitatively) was obtained as a pale yellow solid.
¹H-NMR Spectrum (CDCl₃) δ(ppm): 1.39 (3H, t, J=7.1 Hz), 4.39 (2H, q, J=7.1 Hz), 7.16 (2H, dd, J=1.3, 8.6 Hz), 7.38 (1H, t, J=7.1 Hz), 7.49 (2H, dd, J=7.1, 8.8 Hz), 9.30 (1H, s).

Preparation Example 114

2-Phenoxy-thiazole-5-carboxylic acid ethyl ester

5-Oxo-2-phenoxythiocarbonyl-2,5-dihydro-isoxazole-4-carboxylic acid ethyl ester described in Preparation Example 113 (500 mg, 2.01 mmol) was dissolved in acetone (500 mL), and the solution was irradiated with light (300 nm) for 30 minutes at room temperature. The reaction solution was evaporated in vacuo, the residue was purified by silica gel column chromatography (hexane:ethyl acetate=2:1), and the title compound (384 mg, 1.54 mmol, 90%) was obtained as a pale yellow oil.
¹H-NMR Spectrum (CDCl₃) δ(ppm): 1.35 (3H, t, J=7.1 Hz), 4.33 (2H, q, J=7.1 Hz), 7.26-7.35 (3H, m), 7.47 (2H, dd, J=7.5, 8.4 Hz), 7.90 (1H, s).

Preparation Example 115

(2-Phenoxy-thiazol-5-yl)-methanol

2-Phenoxy-thiazole-5-carboxylic acid ethyl ester described in Preparation Example 114 (384 mg, 1.54 mmol) was dissolved in tetrahydrofuran (5 mL), and lithium aluminum hydride (292 mg, 7.70 mmol) was added at 0° C. The solution was stirred at room temperature for 1 hour, then, at 0° C., water (292 µl), an aqueous solution of 5N sodium hydroxide (292 µl) and water (876 µl) were sequentially added thereto. The reaction solution was filtered through Celite pad, then, the filtrate was evaporated in vacuo, the residue was purified by silica gel column chromatography (hexane:ethyl acetate=1:4), and the title compound (270 mg, 1.30 mmol, 85%) was obtained as a white solid.
¹H-NMR Spectrum (CDCl₃) δ(ppm): 4.73 (2H, d, J=5.9 Hz), 7.13 (1H, s), 7.25-7.29 (3H, m), 7.41-7.45 (2H, m).

Preparation Example 116

2-(2-Phenoxy-thiazol-5-ylmethyl)-isoindol-1,3-dione

The title compound (131 mg, 0.389 mmol, 30%) was obtained as a colorless oil from (2-phenoxy-thiazole-5-yl)-methanol described in Preparation Example 115 (270 mg, 1.30 mmol) according to an analogous method to Preparation Example 94.
¹H-NMR Spectrum (CDCl₃) δ(ppm): 4.89 (2H, s), 7.21-7.28 (4H, m), 7.40 (2H, t, J=8.0 Hz), 7.73 (2H, dd, J=3.1, 5.3 Hz), 7.86 (2H, dd, J=2.9, 5.5 Hz).

Preparation Example 117

C-(2-Phenoxy-thiazol-5-yl)-methylamine

The title compound (63 mg, 0.31 mmol, 78%) was obtained as a colorless oil from 2-(2-phenoxy-thiazol-5-ylmethyl)-isoindol-1,3-dione described in Preparation Example 116 (131 mg, 0.389 mmol) according to an analogous method to Preparation Example 95.
¹H-NMR Spectrum (CDCl₃) δ(ppm): 3.95 (2H, s), 7.03 (1H, t, J=1.1 Hz), 7.25-7.28 (3H, m), 7.39-7.43 (2H, m).

Preparation Example 118

4-Benzyloxy-2-fluoro-benzonitrile

To a solution of 4-hydroxy-2-fluoro-benzonitrile (1.0 g, 7.3 mmol) in N,N-dimethylformamide (15 mL) was added potassium carbonate (2.09, 15 mmol) and benzyl bromide (0.87 mL, 7.3 mmol), and the solution was stirred at room temperature for 5 hours. Water and ethyl acetate were added to the reaction solution, which was then extracted, washed with brine, then, the solvent was evaporated in vacuo. The residue was purified by silica gel column chromatography (hexane:ethyl acetate=5:1), and the title compound (1.5 g, 6.7 mmol, 92%) was obtained as a white solid.
¹H-NMR Spectrum (CDCl₃) δ(ppm): 5.11 (2H, s), 6.78 (1H, dd, J=2.4, 11.0 Hz), 6.83 (1H, ddd, J=0.6, 2.4, 8.8 Hz), 7.37-7.43 (5H, m), 7.52 (1H, dd, J=7.5, 8.6 Hz).

Preparation Example 119

4-[1,3]Dioxolane-2-yl-benzonitrile

4-Formyl-benzonitrile (3.00 g, 22.9 mmol), ethane-1,2-diol (6.38 mL, 115 mmol) and toluene-4-sulfonic acid monohydrate (197 mg, 1.15 mmol) were dissolved in toluene (60 mL), and the solution was stirred under reflux for 10 hours. An aqueous solution of saturated sodium bicarbonate was added to the reaction solution at 0° C., which was then extracted with ethyl acetate, the organic layer was washed with brine, and the organic layer was dried over anhydrous magnesium sulfate. The solvent was evaporated in vacuo, the residue was purified by NH silica gel column chromatography (hexane:ethyl acetate=10:1), and the title compound (3.78 g, 21.6 mmol, 94%) was obtained as a white solid.

$^1$H-NMR Spectrum (CDCl$_3$) δ(ppm): 4.04-4.13 (4H, m), 5.85 (1H, s), 7.59 (2H, d, J=8.1 Hz), 7.68 (2H, d, J=8.4 Hz).

Preparation Example 120

4-[1,3]Dioxolan-2-yl-benzylamine

4-[1,3]Dioxolan-2-yl-benzonitrile described in Preparation Example 119 (3.78 g, 21.6 mmol) was dissolved in tetrahydrofuran (76 mL), lithium aluminum hydride (4.09 g, 108 mmol) was added at 0° C., and the solution was stirred overnight at room temperature. Water (4.09 mL), an aqueous solution of 5N sodium hydroxide (4.09 mL) and water (12.3 mL) were sequentially added to the reaction solution. The reaction solution was filtered through Celite pad, then, the filtrate was evaporated in vacuo, and the title compound (3.92 g, quantitatively) was obtained as a pale yellow oil.

$^1$H-NMR Spectrum (CDCl$_3$) δ(ppm): 3.89 (2H, s), 4.03-4.16 (4H, m), 5.81 (1H, s), 7.34 (2H, d, J=7.9 Hz), 7.46 (2H, d, J=8.1 Hz).

Preparation Example 121

5-(3-Chloro-phenoxy)-thiophene-2-carbonitrile

5-Nitro-thiophene-2-carbonitrile (5.00 g, 32.5 mmol), 3-chloro-phenol (6.90 mL, 65.0 mmol) and potassium carbonate (13.4 g, 97.5 mmol) were suspended in dimethylsulfoxide (50 mL), and the mixture was stirred at 60° C. for 4 hours. Water was added to the reaction mixture at 0° C., which was then extracted with ethyl acetate, the organic layer was washed with water twice, and further washed with brine. The organic layer was dried over anhydrous magnesium sulfate. The solvent was evaporated in vacuo, the residue was purified by NH silica gel silica gel column chromatography (hexane:ethyl acetate=20:1), and the title compound (5.56 g, 23.6 mmol, 73%) was obtained as a pale yellow oil.

$^1$H-NMR Spectrum (CDCl$_3$) δ(ppm): 6.49 (1H, d, J=4.2 Hz), 7.04 (1H, ddd, J=0.92, 2.4, 8.2 Hz), 7.15 (1H, t, J=2.2 Hz), 7.22 (1H, ddd, J=0.92, 2.0, 8.1 Hz), 7.33 (1H, t, J=8.2 Hz), 7.4 (1H, d, J=4.2 Hz).

Preparation Example 122

2-(5-(2-Fluoro-benzyl)-thiophen-2-yl)-[1,3]dioxolane

The title compound (4.33 g, 16.4 mmol, 54%) was obtained as a pale yellow oil from 2-(5-bromo-thiophen-2-yl)-[1,3]dioxolane (8.00 g, 30.4 mmol) and 1-bromo methyl-2-fluorobenzene (4.48 mL, 36.5 mmol) according to an analogous method to Preparation Example 36.

$^1$H-NMR Spectrum (CDCl$_3$) δ(ppm): 3.97-4.03 (2H, m), 4.06-4.13 (2H, m), 4.14 (2H, s), 6.01 (1H, s), 6.71 (1H, d, J=3.7 Hz), 6.98 (1H, d, J=3.9 Hz), 7.01-7.08 (2H, m), 7.19-7.23 (2H, m).

Preparation Example 123

5-(2-Fluoro-benzyl)-thiophene-2-carbaldehyde 2-(5-(2-Fluoro-benzyl)-thiophen-2-yl)-[1,3]dioxolane described in Preparation Example 122 (4.33 g, 16.4 mmol) was dissolved in a mixture solvent of methanol (40 mL) and water (10 mL), 1N hydrochloric acid (20 mL) was added thereto, followed by stirring at room temperature for 1 hour. An aqueous solution of saturated sodium bicarbonate was added to the reaction solution at 0° C., which was then extracted with ethyl acetate, the organic layer was washed with brine and dried over anhydrous magnesium sulfate. The solvent was evaporated in vacuo, the residue was purified by silica gel column chromatography (hexane:ethyl acetate=10:1), and the title compound (3.54 g, 16.1 mmol, 98%) was obtained as a light yellow oil.

$^1$H-NMR Spectrum (CDCl$_3$) δ(ppm): 4.22 (2H, s), 6.94 (1H, d, J=3.8 Hz), 7.05-7.13 (2H, m), 7.21-7.28 (2H, m), 7.60 (1H, d, J=3.8 Hz), 9.81 (1H, s).

Preparation Example 124

(5-(2-fluoro-benzyl)-thiophene-2-yl)-methanol 5-(2-Fluoro-benzyl)-thiophene-2-carbaldehyde described in Preparation Example 123 (2.81 g, 12.7 mmol) was dissolved in ethanol (40 mL), sodium borohydride (964 mg, 25.4 mmol) was added at 0° C., and the solution was stirred at room temperature for 1 hour. Water was added to the reaction solution at 0° C., which was then extracted with ethyl acetate, the organic layer was washed with brine and dried over anhydrous magnesium sulfate. The solvent was evaporated in vacuo, the residue was purified by silica gel column chromatography (hexane:ethyl acetate=5:1), and the title compound (2.10 g, 9.45 mmol, 74%) was obtained as a colorless oil.

$^1$H-NMR Spectrum (CDCl$_3$) δ(ppm): 4.14 (2H, s), 4.73 (2H, s), 6.69 (1H, d, J=3.5 Hz), 6.82 (1H, d, J=3.7 Hz), 7.02-7.10 (2H, m), 7.19-7.26 (2H, m).

Preparation Example 125

2-(5-(2-fluoro-benzyl)-thiophen-2-ylmethyl)-isoindol-1,3-dione

The title compound (1.49 g, 4.24 mmol, 45%) was obtained as a pale yellow solid from (5-(2-fluoro-benzyl)-thiophen-2-yl)-methanol described in Preparation Example 124 (2.10 g, 9.44 mmol) according to an analogous method to Preparation Example 94.

$^1$H-NMR Spectrum (CDCl$_3$) δ(ppm): 4.08 (2H, s), 4.92 (2H, s), 6.63 (1H, d, J=3.5 Hz), 6.94 (1H, d, J=3.5 Hz), 6.99-7.08 (2H, m), 7.12-7.23 (2H, m), 7.70 (2H, dd, J=3.1, 5.5 Hz), 7.84 (2H, dd, J=3.1, 5.5 Hz).

Preparation Example 126

C-(5-(2-Fluoro-benzyl)thiophen-2-yl)-methylamine

The title compound (901 mg, 4.07 mmol, 96%) was obtained as a pale yellow oil from 2-(5-(2-fluoro-benzyl)-thiophen-2-ylmethyl)-isoindol-1,3-dione described in Preparation Example 125 (1.49 g, 4.24 mmol) according to an analogous method to Preparation Example 95.

$^1$H-NMR Spectrum (CDCl$_3$) δ(ppm): 3.95 (2H, s), 4.12 (2H, s), 6.65 (1H, d, J=3.5 Hz), 6.71 (1H, d, J=3.5 Hz), 7.01-7.09 (2H, m), 7.18-7.25 (2H, m).

Preparation Example 127

(5-Bromo-4-phenoxy-thiophen-2-yl)-methanol 2-(4-Phenoxy-thiophen-2-yl)-[1,3]dioxolane described in Preparation Example 109 (4.88 g, 19.7 mmol) and N-bromosuccinimide (3.85 g, 21.7 mmol) were dissolved in tetrahydrofuran (100 mL), and the solution was stirred for 4.5 hours at room temperature. An aqueous solution of saturated sodium bicarbonate was added to the reaction solution at 0° C., which was then extracted with ethyl acetate, the organic layer was washed with brine and dried over anhydrous magnesium sulfate. The solvent was evaporated in vacuo, and the residue was silica gel-filtered to obtain 2-(5-bromo-4-phenoxy-thiophen-2-yl)-[1,3]dioxolane (5.48 g) as a pale yellow oil.

Then, 5-bromo-4-phenoxy-thiophene-2-carbaldehyde (3.11 g) was obtained as a colorless oil from 2-(5-bromo-4-phenoxy-thiophen-2-yl)-[1,3]dioxolane (5.48 g) according to an analogous method to Preparation Example 34.

Then, the title compound (2.76 g, 9.68 mmol, 88%) was obtained as a colorless oil from 5-bromo-4-phenoxy-thiophene-2-carbaldehyde (3.11 g, 11.0 mmol) according to an analogous method to Preparation Example 93.

$^1$H-NMR Spectrum (CDCl$_3$) δ(ppm): 4.70 (2H, s), 6.62 (1H, s), 6.98 (2H, dd, J=1.1, 8.8 Hz), 7.09 (1H, tt, J=1.1, 7.5 Hz), 7.29-7.34 (2H, m).

Preparation Example 128

2-(5-Bromo-4-phenoxy-thiophen-2-ylmethyl)-isoindol-1,3-dione

The title compound (2.66 g, 6.42 mmol, 68%) was obtained as a white solid from (5-bromo-4-phenoxy-thiophen-2-yl)-methanol described in Preparation Example 127 (2.71 g, 9.50 mmol) according to an analogous method to Preparation Example 94.

$^1$H-NMR Spectrum (CDCl$_3$) δ(ppm): 4.86 (2H, s), 6.76 (1H, s), 6.95 (2H, dd, J=1.1, 8.8 Hz), 7.08 (1H, t, J=7.5 Hz), 7.30 (2H, dd, J=7.3, 8.8 Hz), 7.70-7.76 (2H, m), 7.83-7.88 (2H, m).

Preparation Example 129

C-(5-Bromo-4-phenoxy-thiophen-2-yl)-methylamine

The title compound (1.62 g, 5.70 mmol, 89%) was obtained as a colorless oil from 2-(5-bromo-4-phenoxy-thiophen-2-ylmethyl)-isoindole-1,3-diene described in Preparation Example 128 (2.66 g, 6.42 mmol) according to an analogous method to Preparation Example 95.

$^1$H-NMR Spectrum (CDCl$_3$) δ(ppm): 3.94 (2H, s), 6.53 (1H, t, J=1.1 Hz), 6.97 (2H, dd, J=1.1, 8.6 Hz), 7.08 (1H, tt, J=1.1, 7.5 Hz), 7.31 (2H, dd, J=7.5, 8.8 Hz).

Preparation Example 130

3-Aminomethylphenol

The title compound (2.9 g, 24 mmol, 97%) was obtained as a white solid from 3-hydroxybenzaldehyde (3.0 g, 24 mmol) according to an analogous method to Preparation Example 38.

$^1$H-NMR Spectrum (DMSO-d$_6$) δ(ppm): 3.60 (2H, s), 6.55 (1H, d, J=7.5 Hz), 6.68-6.70 (2H, m), 7.03-7.07 (1H, m).

Preparation Example 131

1-Quinolin-6-yl-ethanone

6-Bromoquinoline (4.4 g, 21.3 mmol), 1-ethoxyvinyl (tri-n-butyl)tin (10 g, 27.69 mmol) and dichlorobis(triphenylphosphine)palladium(II) (1.2 g, 1.7 mmol) were dissolved in toluene (120 mL) under nitrogen atmosphere, and the solution was stirred at 80° C. for 7 hours. At room temperature, 5M hydrochloric acid (30 mL) and tetrahydrofuran (150 mL) were added to the reaction solution, which was then stirred for 15 hours. The reaction solution was poured into an aqueous solution of saturated sodium bicarbonate containing finely ground ice (200 mL), the solution was adjusted to pH 8-9, and filtered through Celite pad. The filtrate was extracted with ethyl acetate twice, washed with brine twice, dried over anhydrous magnesium sulfate, and then, filtered. The organic layer was evaporated in vacuo, then, residue of reddish brown oil (16.8 g) was obtained. Ethyl acetate (20 mL) was added thereto, which was dissolved, then, silica gel (80 mL) was added, the solvent was evaporated in vacuo for adsorption, purification was carried out by silica gel column chromatography (hexane:ethyl acetate=95:5, then hexane:ethyl acetate=60:40), and a yellow solid (4.16 g) was obtained. This yellow solid was dissolved in ethyl acetate (100 mL), then, the solution was extracted with 1 M hydrochloric acid (70, 50 mL) twice, the aqueous layer was adjusted to pH 8 with sodium bicarbonate, then, the solution was extracted with ethyl acetate twice. The organic layer was washed with brine, dried over anhydrous magnesium sulfate, then, filtered, organic layer was evaporated in vacuo, then, the title compound (2.989, 17.4 mmol, 77%) was obtained as a yellow solid.

$^1$H-NMR Spectrum (Acetone-d$_6$) δ(ppm): 2.73 (3H, s), 7.07 (1H, dd, J=8.4, 4.4 Hz), 8.11 (1H, d, J=9.2 Hz), 8.27 (1H, dd, J=8.8, 2.0 Hz), 8.50-8.53 (1H, m), 8.70 (1H, m), 9.02 (1H, m).

Preparation Example 132

4-Benzyloxy-3-methoxymethoxy-benzonitrile

To a solution of 3,4-dihydroxy-benzonitrile (1.36 g, 10 mmol) and potassium tert-butoxide (1.5 g, 13 mmol) in dimethylsulfoxide (15 mL) was added benzyl chloride (1.5 mL, 13 mmol) under nitrogen atmosphere at room temperature, and the solution was stirred for 24 hours. Silica gel (100 mL) was added portionwise to the reaction solution for adsorption, a pale yellow oil of 4benzyloxy-3-hydroxy-benzonitrile (2.38 g) was obtained by silica gel column chromatography (hexane:ethyl acetate=7:3), in addition, this was purified by NH silica gel column chromatography (hexane:ethyl acetate=1:1, then ethyl acetate, then ethyl acetate:methanol=90:10, then 85:15), and 4-benzyloxy-3-hydroxy-benzonitrile (0.588 g, 2.61 mmol, 24.8%) was obtained as a pale yellow solid.

To a solution of the resulting 4-benzyloxy-3-hydroxy-benzonitrile (300 mg, 1.33 mmol) and potassium tert-butoxide (300 mg, 2.66 mmol) in dimethylsulfoxide (4 mL) was added chloromethyl methyl ether (0.204 mL, 2.66 mmol) portionwise under nitrogen atmosphere stirring on an ice bath, and the solution was stirred for 2 days. NH silica gel (25 mL) was added to the reaction solution, purification was carried out by NH silica gel column chromatography (hexane:ethyl acetate=7:3) then silica gel column chromatography (hexane:ethyl acetate=7:3), and the title compound (306 mg, 0.829 mmol, 85.3%) was obtained as a pale yellow solid.

$^1$H-NMR Spectrum (Acetone-d$_6$) δ(ppm): 3.46 (3H, s), 5.26 (2H, s), 5.27 (2H, s), 7.26 (1H, d, J=8.4 Hz), 7.36-7.44 (4H, m), 7.45 (1H, d, J=2.4 Hz), 7.50-7.53 (2H, m).

Preparation Example 133

3-(3-Methyl-2-butenyloxy)-benzonitrile

3-Hydroxybenzonitrile (1.19 g, 10 mmol) and 4-bromo-2-methyl-2-butene (1.66 g, 10 mmol) were dissolved in N,N- dimethylformamide (5 mL), potassium carbonate (1.66 g, 12 mmol) was added, and the solution was stirred at room temperature for 2 hours. Water (50 mL) was added to the reaction solution, which was then extracted with ethyl acetate (50 mL). The extract was washed, then, dried over anhydrous magnesium sulfate, and the solvent was evaporated in vacuo. The residue was purified by silica gel column chromatography (hexane:ethyl acetate=95:5), and the title compound (1.71 g, 10 mmol, 99.4%) was obtained as a colorless oil.

$^1$H-NMR Spectrum (CDCl$_3$) δ(ppm): 1.73 (3H, s), 1.78 (3H, s), 4.51 (2H, d, J=6.8 Hz), 5.48 (1H, t, J=6.8 Hz), 7.13 (1H, dd, J=2.4, 8.4 Hz), 7.15 (1H, d, J=2.4 Hz), 7.23 (1H, d, J=8.4 Hz), 7.28 (1H, t, J=8.4 Hz).

Preparation Example 134

3-(3-Methyl-2-butenyloxy)-benzylamine 3-(3-Methyl-2-butenyloxy)-benzonitrile described in Preparation Example 133 (1.71 g, 10 mmol) was dissolved in tetrahydrofuran (20 mL), lithium aluminum hydride (0.57 g, 15 mmol) was added under stirring at room temperature, the solution was heated to 70° C., then stirring continued for 2 hours. The reaction solution was cooled on an ice bath, then, water (0.6 mL), an aqueous solution of 15% sodium hydroxide (0.6 mL) and water (1.8 mL) were added in this order, then, the solid was filtered, and washed with tetrahydrofuran (20 mL). The filtrate and the washings were combined, and dried over anhydrous sodium sulfate. The solvent was evaporated in vacuo, and the title compound (1.50 g, 8.52 mmol, 85.2%) was obtained as a colorless oil.

$^1$H-NMR Spectrum (CDCl$_3$) δ(ppm): 1.73 (3H, s), 1.78 (3H, s), 4.51 (2H, d, J=6.8 Hz), 4.68 (2H, d, J=5.6 Hz), 5.48 (1H, t, J=6.8 Hz), 6.77 (1H, dd, J=2.4, 8.4 Hz), 6.83 (1H, d, J=2.4 Hz), 6.87 (1H, s), 7.23 (1H, t, J=8.4 Hz).

Preparation Example 135

(3-Cyanobenzyl)phosphonic acid diethyl ester

3-Cyanobenzyl bromide (9.8 g, 50 mmol) and triethylphosphite (9.97 g, 60 mmol) were stirred at 140° C. for 3 hours. The resulting residue was evaporated, the distillate which has 145° C./1 mmHg was collected, and the title compound (10 g, 39.5 mmol, 79.1%) was obtained as a colorless oil.

Preparation Example 136

3-(2-Methylpropenyl) benzonitrile

Sodium hydride (0.40 g, 10 mmol, 60% in oil) was suspended in tetrahydrofuran (5 mL), (3-cyanobenzyl)phosphonic acid diethyl ester obtained in Preparation Example 135 (2.53 g, 10 mmol) was added dropwise under stirring at room temperature. After stirring for 1 hour at 60° C., the solution was allowed to room temperature, acetone (0.92 g, 20 mmol) was added dropwise, and the solution was further stirred for 30 minutes at room temperature. Water (100 mL) was added to the reaction solution, which was then extracted with ethyl acetate (50 mL). The organic layer was washed with water, then, dried over anhydrous magnesium sulfate, and the solvent was evaporated in vacuo. The residue was purified by silica gel column chromatography (hexane:ethyl acetate=97: 3), and the title compound (0.44 g, 2.80 mmol, 28%) was obtained as a colorless oil.

$^1$H-NMR Spectrum (CDCl$_3$) δ(ppm): 1.85 (3H, s), 1.93 (3H, s), 6.23 (1H, s), 7.40-7.50 (4H, m).

Preparation Example 137

(3-(2-Methylpropenyl)-benzylamine)

3-(2-Methylpropenyl)benzonitrile described in Preparation Example 136 (0.44 g, 2.8 mmol) was dissolved in tetrahydrofuran (5 mL), lithium aluminum hydride (0.16 g, 4.2 mmol) was added under stirring at room temperature, the solution was heated to 70° C., followed by stirring for 2 hours. The reaction solution was cooled on an ice bath, then, water (0.16 mL), an aqueous solution of 15% sodium hydroxide (0.16 mL) and water (0.48 mL) were sequentially added, then, the solid was filtered, and washed with tetrahydrofuran (10 mL). The filtrate and the washings were combined, and dried over anhydrous sodium sulfate. The solvent was evaporated in vacuo, and the title compound (0.40 g, 2.48 mmol, 88.7%) was obtained as a colorless oil.

$^1$H-NMR Spectrum (CDCl$_3$) δ(ppm): 1.87 (3H, s), 1.90 (3H, s), 3.85 (2H, s), 6.27 (1H, s), 7.11-7.28 (4H, m).

Preparation Example 138

3-Cyclopentylydenemethylbenzonitrile

Potassium tert-butoxide (1.12 g, 10 mmol) was suspended in N,N-dimethylformamide (10 mL), and (3-cyanobenzyl) phosphonic acid diethyl ester (2.53 g, 10 mmol) was added dropwise under stirring at room temperature. The solution was stirred at room temperature for 1 hour, then, cyclopentanone (0.84 g, 10 mmol) was added, and the solution was stirred at room temperature for 2 hours. Water (100 mL) was added to the reaction solution, which was then extracted with ethyl acetate (50 mL). The organic layer was washed with water, then, dried over anhydrous magnesium sulfate, and the solvent was evaporated in vacuo. The residue was purified by silica gel column chromatography (hexane:ethyl acetate=97: 3), and the title compound (1.32 g, 7.21 mol, 72.3%) was obtained as a colorless oil.

$^1$H-NMR Spectrum (CDCl$_3$) δ(ppm) :1.65-1.79 (4H, m), 2.47-2.58 (4H, m), 6.33 (1H, s), 7.40-7.57 (4H, m).

Preparation Example 139

3-Cyclopentylydenemethyl-benzylamine

3-Cyclopentylydenemethylbenzonitrile described in Preparation Example 138 (1.32 g, 7.21 mmol) was dissolved in tetrahydrofuran (10 mL), lithium aluminum hydride (0.41 g, 10.8 mmol) was added under stirring at room temperature, the solution was heated to 70° C., followed by stirring for 2 hours. The reaction solution was cooled on an ice bath, then, water (0.41 mL), an aqueous solution of 15% sodium hydroxide (0.41 mL) and water (1.23 mL) were sequentially added, then, the solid was filtered, and washed with tetrahydrofuran (20 mL). The filtrate and the washings were combined, and dried over anhydrous sodium sulfate. The solvent was evaporated in vacuo, and the title compound (1.30 g, 6.95 mmol, 96.4%) was obtained as a colorless oil.

Preparation Example 140

(5-Bromothiophen-2-yl)methanol

5-Bromo-2-thiophene carboxy aldehyde (25 g, 131 mmol) was dissolved in a mixture solvent of ethanol-tetrahydrofuran (1:1) (200 mL), sodium borohydride (1.86 g, 49 mmol) was added in small amounts under ice-cold stirring, and stirring continued for 30 minutes. An aqueous solution of saturated ammonium chloride (20 mL) was added to the reaction solution, which was then stirred for 30 minutes. The reaction solution was extracted with ethyl acetate (100 mL), washed with water, dried over anhydrous magnesium sulfate, then, the solvent was evaporated in vacuo. The residue was purified by silica gel column chromatography (hexane:ethyl acetate=90:10), and the title compound (6.7 g, 34.7 mmol, 26.5%) was obtained as a colorless oil.

Preparation Example 141

2-Bromo-5-chloromethylthiophene (5-Bromothiophen-2-yl)methanol described in Preparation Example 140 (6.7 g, 34.7 mmol) was dissolved in diethyl ether (40 mL), 10 mL of concentrated hydrochloric acid was added thereto, and the solution was vigorously stirred at room temperature for 8 hours. An ice water (200 mL) was added to the reaction solution, an aqueous solution of sodium bicarbonate was further added for neutralization, then, the solution was extracted with ethyl acetate (100 mL). The organic layer was washed with water, dried over anhydrous magnesium sulfate, then, the solvent was evaporated in vacuo, and the title compound (7.3 g, 34.5 mmol, 99.4%) was obtained as a colorless oil.

Preparation Example 142

(5-Bromothiophen-2-ylmethyl)phosphonic acid diethyl ester

2-Bromo-5-chloromethylthiophene described in Preparation Example 141 (7.3 g, 34.5 mmol) and triethylphosphite (6.35 g, 38.2 mmol) were stirred at 140° C. for 3 hours. The resulting residue was purified by silica gel column chromatography (hexane:ethyl acetate=50:50), and the title compound (8.82 g, 31.2 mmol, 90.3%) was obtained as a reddish brown oil.
$^1$H-NMR Spectrum (CDCl$_3$) δ(ppm): 1.27-1.36 (6H, m), 3.25 (2H, d, J=24 Hz), 4.05-4.16 (4H, m), 6.72 (1H, d, J=3.6 Hz), 6.92 (1H, d, J=3.6 Hz).

Preparation Example 143

2-Bromo-5-(2-methylpropenyl)-thiophene (5-Bromothiophen-2-ylmethyl)phosphonic acid diethyl ester described in Preparation Example 142 (3.13 g, 10 mmol) was dissolved in tetrahydrofuran (20 mL), sodium hydride (0.40 g, 10 mmol, 60% in oil) was added to this solution under stirring at room temperature. The solution was stirred for 30 minutes at 60° C., then, acetone (1 g, 17.2 mmol) was added, and the solution was further stirred for 30 minutes. Water (100 mL) was added to the reaction solution, which was then extracted with hexane (50 mL), the organic layer was washed with water, dried over anhydrous magnesium sulfate, then, the solvent was evaporated in vacuo. The residue was purified by silica gel column chromatography (hexane), and the title compound (60 mg, 0.27 mmol, 2.7%) was obtained as a colorless oil.
$^1$H-NMR Spectrum (CDCl$_3$) δ(ppm): 1.90 (3H, s), 1.93 (3H, s), 6.27 (1H, s), 6.62 (1H, d, J=3.6 Hz), 6.93 (1H, d, J=3.6 Hz).

Preparation Example 144

5-(2-Methylpropenyl)-thiophene-2-carbonitrile

2-Bromo-5-(2-methylpropenyl)-thiophene described in Preparation Example 143 (60 mg, 0.27 mmol) was dissolved in N,N-dimethylformamide (1 mL), copper cyanide (62 mg, 0.69 mmol) was added at 160° C., and the solution was stirred for 2 hours. The reaction solution was cooled, then, concentrated aqueous ammonia (5 mL) was added, and the solution was extracted with diethyl ether (10 mL). The organic layer was washed, dried over anhydrous magnesium sulfate, then, the solvent was evaporated in vacuo. The residue was purified by silica gel column chromatography (hexane:ethyl acetate=95:5), and the title compound (15 mg, 0.092 mmol, 34%) was obtained as a colorless oil.
$^1$H-NMR Spectrum (CDCl$_3$) δ(ppm): 1.97 (3H, s), 2.00 (3H, s), 6.39 (1H, s), 6.85 (1H, d, J=4.0 Hz), 7.50 (1H, d, J=4.0 Hz).

Preparation Example 145

C-(5-(2-Methylpropenyl)-thiophen-2-yl)-methylamine 5-(2-Methylpropenyl)-thiophene-2-carbonitrile described in Preparation Example 144 (15 mg, 0.092 mmol) was dissolved in tetrahydrofuran (2 mL), lithium aluminum hydride (10 mg, 0.26 mmol) was added under stirring at room temperature, the solution was heated to 70° C., followed by stirring for 2 hours. The reaction solution was cooled on an ice bath, then, water (0.01 mL), an aqueous solution of 15% sodium hydroxide (0.01 mL) and water (0.03 mL) were sequentially added, then, the solid was filtered, and washed with tetrahydrofuran (5 mL). The filtrate and the washings were combined, and dried over anhydrous sodium sulfate. The solvent was evaporated in vacuo, and the title compound (14 mg, 0.083 mmol, 91.1%) was obtained as a colorless oil.
$^1$H-NMR Spectrum (CDCl$_3$) δ(ppm): 1.91 (3H, s), 1.96 (3H, s), 4.09 (2H, s), 6.33 (1H, s), 6.75 (1H, d, J=3.6 Hz), 6.95 (1H, d, J=3.6 Hz).

Preparation Example 146

3-Isobutylbenzylamine 3-(2-Methylpropenyl)-benzylamine described in Preparation Example 137 (100 mg, 0.621 mmol) was dissolved in ethanol (5 mL), 10% palladium-carbon (50% water wet, 20 mg) was added thereto, and the mixture was stirred for 2 hours at room temperature under hydrogen atmosphere. The catalyst was filtered, then, the solvent was evaporated, and the title compound (58 mg, 56.6%) was obtained as a colorless oil.
$^1$H-NMR Spectrum (CDCl$_3$) δ(ppm): 0.90 (6H, d, J=6.8 Hz), 1.87 (1H, dq, J=7.6, 6.8 Hz), 2.48 (2H, d, J=7.6 Hz), 3.84 (2H, s), 7.02-7.28 (4H, m).

Preparation Example 147

2-(2-cyclopropyl vinyl)thiophene

Potassium tert-butoxide (1.81 g, 16.2 mmol) was suspended in N,N-dimethylformamide (50 mL), thiophen-2-ylmethyl triphenylphosphonium chloride (6.38 g, 16.2 mmol) was added while stirring at room temperature under a nitrogen stream, and the mixture was stirred at room temperature for 30 minutes. Then, cyclopropanecarboxyaldehyde (1.13 g, 16.2 mmol) was added dropwise to the reaction solution, and the solution was stirred for 1 hour. Water (100 mL) was added to the reaction solution, which was then extracted with hexane (50 mL). The organic layer was passed through silica gel (10 g) for filtration, the filtrate was evaporated in vacuo, and the title compound (1.27 g, 8.47 mmol, 52.3%) was obtained as a colorless oil.

$^1$H-NMR Spectrum (CDCl$_3$) δ(ppm): 0.44-0.52 (2H, m), 0.76-0.84 (2H, m), 1.45-1.55 (1H, m), 5.60 (1H, dd, J=8.8, 15.6 Hz), 6.83 (1H, d, J=3.2 Hz), 6.92 (1H, dd, J=3.2, 5.2 Hz), 7.00 (1H, dd, J=3.2, 5.2 Hz), 7.05 (1H, J=5.2 Hz).

Preparation Example 148

5-(2-Cyclopropylvinyl)thiophene-2-carboxy aldehyde 2-(2-Cyclopropylvinyl)thiophene described in Preparation Example 147 (1.27 g, 8.47 mmol) was dissolved in anhydrous diethyl ether (20 mL), n-butyl lithium (2.47M hexane solution, 4.1 mL, 10.2 mmol) was added dropwise under stirring on an ice bath, and the solution was stirred for 30 minutes. The reaction solution was cooled on a dry ice-acetone bath, N,N-dimethylformamide (2 g, 27.4 mmol) was added thereto, and the solution was stirred as is for 30 minutes. Acetic acid (1 mL) and water (10 mL) were sequentially added to the reaction solution, which was then allowed to room temperature. The reaction solution was extracted with ethyl acetate (50 mL), then, the organic layer was washed with brine and dried over anhydrous magnesium sulfate. The solvent was evaporated in vacuo, the residue was purified by silica gel column chromatography (hexane:ethyl acetate=95:5), and the title compound (960 mg, 5.39 mmol, 63.7%) was obtained as a colorless oil.

$^1$H-NMR Spectrum (CDCl$_3$) δ(ppm): 0.57-0.63 (2H, m), 0.88-0.94 (2H, m), 1.53-1.60 (1H, m), 5.84 (1H, dd, J=9.2, 15.6 Hz), 6.59 (1H, d, J=15.6 Hz), 6.91 (1H, d, J=3.6 Hz), 7.59 (1H, d, J=3.6 Hz), 9.80 (1H, s).

Preparation Example 149

(5-(2-Cyclopropylvinyl)thiophen-2-yl)methanol 5-(2-Cyclopropylvinyl)thiophen-2-aldehyde described in Preparation Example 148 (960 mg, 5.39 mmol) was dissolved in a mixture solvent of tetrahydrofuran-ethanol (2:1) (30 mL), sodium borohydride (100 mg, 2.64 mmol) was added under stirring on an ice bath, and the solution was stirred for 30 minutes. Acetic acid (0.5 mL) and water (10 mL) were added sequentially to the reaction solution, which was then extracted with ethyl acetate (50 mL). The organic layer was washed with an aqueous solution of saturated sodium bicarbonate and brine, and dried over anhydrous magnesium sulfate. The solvent was evaporated in vacuo, and the title compound (930 mg, 5.19 mmol, 96.2%) was obtained as a colorless oil.

Preparation Example 150

2-(5-(2-cyclopropylvinyl)thiophen-2-ylmethyl)isoindol-1,3-dione (5-(2-Cyclopropylvinyl)thiophen-2-yl)methanol described in Preparation Example 149 (930 mg, 5.19 mmol), triphenylphosphine (2040 mg, 7.78 mmol) and phthalimide (1140 mg, 7.78 mmol) were dissolved in tetrahydrofuran (50 mL), azodicarboxylic acid dimethyl ester (1140 mg, 7.78 mmol) was added under stirring at room temperature, and the solution was stirred for 1 hour. Water (50 mL) was added to the reaction solution, which was then extracted with ethyl acetate (50 mL). The organic layer was washed with water, dried over anhydrous magnesium sulfate, and the solvent was evaporated in vacuo. The residue was purified by NH silica gel column chromatography (hexane:ethyl acetate=9:1), and the title compound (330 mg, 1.07 mmol, 20.6%) was obtained as a white solid.

$^1$H-NMR Spectrum (CDCl$_3$) δ(ppm): 0.44-0.48 (2H, m), 0.76-0.80 (2H, m), 1.42-1.50 (1H, m), 4.92 (2H, s), 5.52 (1H, dd, J=8.8, 15.6 Hz), 6.47 (1H, d, J=15.6 Hz), 6.62 (1H, d, J=3.6 Hz), 6.93 (1H, d, J=3.6 Hz), 7.67-7.73 (2H, m), 7.82-7.86 (2H, m).

Preparation Example 151

C-(5-(2-Cyclopropylvinyl)thiophen-2-yl)methylamine 2-(5-(2-Cyclopropylvinyl)thiophen-2-ylmethyl)isoindol-1,3-dione described in Preparation Example 150 (330 mg, 1.02 mmol) was dissolved in ethanol (50 mL), hydrazine monohydrate (500 mg, 10 mmol) was added thereto, and the solution was stirred under reflux for 2 hours. After cooling to room temperature, 2N sodium hydroxide solution (10 mL) and water (100 mL) were added to the reaction solution, which was then washed twice with hexane (50 mL). The organic layer was dried over anhydrous sodium sulfate, then, the solvent was evaporated in vacuo, and the title compound (180 mg, 1.01 mmol, 98.6%) was obtained as a colorless oil.

$^1$H-NMR Spectrum (CDCl$_3$) δ(ppm): 0.44-0.48 (2H, m), 0.76-0.80 (2H, m), 1.42-1.50 (1H, m), 3.96 (2H, s), 5.52 (1H, dd, J=8.8, 15.6 Hz), 6.52 (1H, d, J=15.6 Hz), 6.65 (1H, d, J=3.6 Hz), 6.71 (1H, d, J=3.6 Hz).

Preparation Example 152

C-(5-(2,2-Dicyclopropylvinyl)thiophen-2-yl)methylamine

The title compound was synthesized according to an analogous method to Preparation Example 147 to 151.

$^1$H-NMR Spectrum (CDCl$_3$) δ(ppm): 0.42-0.46 (2H, m), 0.61-0.66 (2H, m), 0.83-0.88 (4H, m), 1.16-1.23 (1H, m), 1.96-2.03 (1H, m), 3.96 (2H, s), 6.30 (1H, s), 6.85 (1H, d, J=3.2 Hz), 6.90 (1H, d, J=3.2 Hz).

Preparation Example 153

Methanesulfonic acid 2-fluoro-benzyl ester

To a solution of 2-fluorobenzyl alcohol (4.40 g, 34.9 mmol) in dichloromethane (40 mL) was added methanesulfonyl chloride (3.24 mL, 41.9 mmol) and triethylamine (5.84 mL, 41.9 mmol) on an ice bath, the solution was warmed to room temperature and stirred overnight. The reaction solution was diluted with dichloromethane, washed with an aqueous solution of 5% sodium bicarbonate, then, dried over anhydrous magnesium sulfate, the solvent was evaporated, and the title compound (4.62 g, 65%) was obtained as a brown oil. This was used in the next reaction without purification.

Preparation Example 154

4-(2-Fluorobenzyloxy)-benzylamine

The title compound (710 mg, 14%) was obtained as a yellow oil from p-cyanophenol (2.70 g, 22.7 mmol) and methanesulfonic acid 2-fluoro-benzyl ester described in Preparation Example 153 (4.63 g, 22.7 mmol) according to an analogous method to Preparation Example 6.

Preparation Example 155

4-(4-Fluorobenzyloxy)-benzylamine 4-(4-Fluorobenzyloxy)-benzonitrile (5.89 g, quantitatively) was obtained from p-cyanophenol (3.00 g, 25.2 mmol) and 4-fluorobenzyl bromide (4.76 g, 25.2 mmol) according to an analogous method to Preparation Example 6.

Next, the title compound (1.02 g, 67%) was obtained as a yellow solid from the resulting 4-(4-fluorobenzyloxy)-benzonitrile (1.5 g, 6.6 mmol) according to an analogous method to Preparation Example 6.

Preparation Example 156

5-(4-chloro-phenoxy)-thiophene-2-carbonitrile

The title compound (770 mg, 3.27 mmol, 65%) was obtained as a pale yellow oil from 5-nitrothiophene-2-carbonitrile (771 mg, 5 mmol) and 4-chlorophenol (643 mg, 5 mmol) according to an analogous method to Preparation Example 22.
$^1$H-NMR Spectrum (Acetone-$d_6$) δ(ppm): 6.72 (1H, d, J=4.4 Hz), 7.30-7.32 (2H, m), 7.50-7.52 (2H, m), 7.67 (1H, d, J=4.4 Hz)

Preparation Example 157

C-(5-(4-Chloro-phenoxy)-thiophen-2-yl)-methylamine

The title compound (307 mg, 1.28 mmol, 86%) was obtained as an orange oil from 5-(4-chloro-phenoxy)-thiophene-2-carbonitrile described in Preparation Example 156 (350 mg, 1.49 mmol) according to an analogous method to Preparation Example 23.
$^1$H-NMR Spectrum (DMSO-$d_6$) δ(ppm): 2.19 (2H, brs), 3.81-3.82 (2H, m), 6.53-6.54 (1H, m), 6.69-6.70 (1H, m), 7.10-7.13 (2H, m), 7.42-7.45 (2H, m).

Preparation Example 158

5-(2-Chloro-phenoxy)-thiophene-2-carbonitrile

The title compound (516 mg, 2.19 mmol, 44%) was obtained as a white solid from 5-nitrothiophene-2-carbonitrile (771 mg, 5 mmol) and 2-chlorophenol (643 mg, 5 mmol) according to an analogous method to Preparation Example 22.
$^1$H-NMR Spectrum (Acetone-$d_6$) δ(ppm): 6.63 (1H, d, J=4.0 Hz), 7.35-7.40 (1H, m), 7.42-7.50 (2H, m), 7.61-7.65 (2H, m).

Preparation Example 159

C-(5-(2-Chloro-phenoxy)-thiophen-2-yl)-methylamine

The title compound (305 mg, 1.27 mmol, 72%) was obtained as an orange oil from 5-(2-chloro-phenoxy)-thiophene-2-carbonitrile described in Preparation Example 158 (356 mg, 1.51 mmol) according to an analogous method to Preparation Example 23.
$^1$H-NMR Spectrum (DMSO-$d_6$) δ(ppm): 2.10 (2H, brs), 3.80 (2H, s), 6.48-6.50 (1H, m), 6.66-6.72 (1H, m), 7.15-7.23 (2H, m), 7.34-7.38 (1H, m), 7.56-7.59 (1H, m).

Preparation Example 160

5-(2-Fluoro-phenoxy)-thiophene-2-carbonitrile

The title compound (684 mg, 3.12 mmol, 77%) was obtained as a colorless oil from 5-nitrothiophene-2-carbonitrile (771 mg, 5 mmol) and 2-fluorophenol (673 mg, 6 mmol) according to an analogous method to Preparation Example 22.
$^1$H-NMR Spectrum (DMSO-$d_6$) δ(ppm): 6.76 (1H, d, J=4.4 Hz), 7.29-7.33 (1H, m), 7.35-7.41 (1H, m), 7.43-7.53 (2H, m), 7.79 (1H, d, J=4.4 Hz).

Preparation Example 161

C-(5-(2-Fluoro-phenoxy)-thiophen-2-yl)-methylamine

The title compound (298 mg, 1.33 mmol, 84%) was obtained as a brown oil from 5-(2-fluoro-phenoxy)-thiophene-2-carbonitrile described in Preparation Example 160 (350 mg, 1.60 mmol) according to an analogous method to Preparation Example 23.
$^1$H-NMR Spectrum (DMSO-$d_6$) δ(ppm): 3.79 (2H, s), 6.45-6.47 (1H, m), 6.64-6.70 (1H, m), 7.15-7.27 (3H, m), 7.34-7.41 (1H, m).

Preparation Example 162

3-Bromo-quinoline-6-carboxylic acid methyl ester

To a mixture of quinoline-6-carboxylic acid methyl ester (0.50 g, 2.7 mmol) and tetrahydrofuran (10 mL) was added 1,3-dibromo-5,5-dimethyl hydantoin (0.76 g, 2.7 mmol) on an ice bath, and the solution was stirred at 50° C. for 4 hours. Water, an aqueous solution of saturated sodium bicarbonate and ethyl acetate were added to the reaction solution, which was then partitioned, the organic layer was washed with brine, the solvent was then evaporated in vacuo. The residue was purified by silica gel column chromatography (hexane: ethyl acetate=4:1), and the title compound (69 mg, 0.26 mmol, 10%) was obtained as a white solid.
$^1$H-NMR Spectrum (CDCl$_3$) δ(ppm) 4.01 (3H, s), 8.13 (1H, d, J=8.8 Hz), 8.32 (1H, dd, J=2.0, 8.8 Hz), 8.42 (1H, d, J=2.4 Hz), 8.52 (1H, d, J=1.8 Hz), 9.00 (1H, d, J=2.4 Hz).

Preparation Example 163

3-Bromo-quinoline-6-carboxylic acid lithium salt

To a mixture of 3-bromo-quinoline-6-carboxylic acid methyl ester described in Preparation Example 162 (26 mg, 0.098 mmol) and tetrahydrofuran (2 mL) were added methanol (0.2 mL), lithium hydroxide monohydrate (4.1 mg, 0.098 mmol) and water (0.2 mL), and the solution was stirred overnight at room temperature. The solvent was evaporated in vacuo, and the title compound (27 mg) was obtained.

Preparation Example 164

Quinoline-carboxylic acid methyl ester N-oxide

To a mixture of quinoline-6-carboxylic acid methyl ester (4.7 g, 25 mmol) and chloroform (80 mL) was added 3-chloro-peroxyl benzoic acid (purity 65%, 8.6 g, 33 mmol) on an ice bath, and the solution was stirred at room temperature for 75 minutes. Water and an aqueous solution of 1N sodium hydroxide were added to the reaction solution, which was then partitioned, the organic layer was sequentially washed with an aqueous solution of saturated sodium thiosulfate and brine, and dried over anhydrous magnesium sulfate. The solvent was evaporated in vacuo, and the title compound (3.8 g, 19 mmol, 75%) was obtained as a pale yellow solid.

$^1$H-NMR Spectrum (CDCl$_3$) δ(ppm): 4.03 (3H, s), 7.38 (1H, dd, J=6.0, 8.4 Hz), 7.84 (1H, d, J=8.4 Hz), 8.34 (1H, dd, J=1.8, 9.2 Hz), 8.60 (1H, dd, J=0.9, 6.0 Hz), 8.63 (1H, d, J=1.8 Hz), 8.81 (1H, d, J=9.2 Hz).

Preparation Example 165

2-Chloro-quinoline-6-carboxylic acid methyl ester

Phosphorus oxychloride (10 mL) was added to quinoline-6-carboxylic acid methyl ester N-oxide (1.5 g, 7.6 mmol), and the solution was refluxed for 2 hours. The reaction solution was poured onto an ice, and warmed gradually to room temperature. Ethyl acetate was added to the reaction solution, which was then extracted, and sequentially washed with an aqueous solution of saturated sodium bicarbonate and brine. The solvent was evaporated in vacuo, the residue was purified by silica gel column chromatography (hexane:ethyl acetate=2:1), and the title compound (0.47 g, 2.1 mmol, 28%) was obtained as a white solid.

$^1$H-NMR Spectrum (CDCl$_3$) δ(ppm): 4.01 (3H, s), 7.47 (1H, dd, J=0.6, 8.6 Hz), 8.07 (1H, d, J=8.8 Hz), 8.22 (1H, d, J=8.6 Hz), 8.32-8.35 (1H, m), 8.59 (1H, s).

Preparation Example 166

2-Chloro-quinoline-6-carboxylic acid lithium salt

The title compound (54 mg) was obtained as a crude compound from 2-chloro-quinoline-6-carboxylic acid methyl ester described in Preparation Example 165 (40 mg, 0.18 mmol) according to an analogous method to Preparation Example 163.

Preparation Example 167

C-(5-(2-Chloro-phenoxy)-thiophen-2-yl)-methylamine

To a solution of lithium aluminum hydride (1.79 g, 47.1 mmol) in tetrahydrofuran was added aluminum chloride (7.54 g, 56.5 mmol) on an ice bath, which was then stirred for 10 minutes. To the suspension was 5-(2-chloro-phenoxy)-thiophene-2-carbonitrile described in Preparation Example 158 (2.22 g, 9.42 mmol) was added on an ice bath, and the solution was stirred for 1 hour. An aqueous ammonia was added to the reaction solution, then, anhydrous magnesium sulfate was added for drying, and the solution was filtered through Celite pad. The filtrate was concentrated in vacuo, the residue was purified by NH silica gel column chromatography (heptane/ethyl acetate=1/2), and the title compound (2.26 g, 9.42 mmol, 100%) was obtained as a light brown oil.

$^1$H-NMR Spectrum (DMSO-d$_6$) δ(ppm): 3.81 (2H, s), 6.56 (1H, d, J=3.6 Hz), 6.69 (1H, dd, J=1.2, 3.6 Hz), 7.05 (1H, dd, J=2.4, 8.4 Hz), 7.11 (1H, t, J=2.0 Hz), 7.19 (1H, dt, J=1.2, 8.0 Hz), 7.40 (1H, t, J=8.0 Hz).

Preparation Example 168

5-(4-Fluoro-phenoxy)-furan-2-carbaldehyde

To a solution of 4-fluorophenol (2.39 g, 21.3 mmol) in dimethylsulfoxide (20 mL) was added sodium hydride (785 mg, 19.6-23.6 mmol, 60-72% in oil), and the solution was stirred at room temperature for 20 minutes. Next, a solution of 5-nitro-furan-2-carbaldehyde (3 g, 21.3 mmol) in dimethylsulfoxide (10 mL) was added dropwise, the solution was then stirred for 2 hours at room temperature. The reaction mixture was poured into brine, and the mixture was extracted with ethyl acetate. The fractionated organic layer was dried over anhydrous magnesium sulfate, then concentrated, and the title compound (4.3 g, 20.8 mmol, 98%) was obtained.

$^1$H-NMR Spectrum (CDCl$_3$) δ(ppm): 5.23 (1H, d, J=4.0 Hz), 7.07-7.24 (5H, m), 9.40 (1H, s).

Preparation Example 169

C-(5-(4-Fluoro-phenoxy)-furan-2-yl)methylamine

A suspension of 5-(4-fluoro-phenoxy)-furan-2-carbaldehyde described in Preparation Example 168 (4.3 g, 20.9 mmol), Raney nickel (1.5 g) and 7N ammonia-methanol solution (40 mL) was stirred at room temperature for 15 hours under hydrogen atmosphere (1 atm). The reaction solution was filtered through Celite pad to remove the catalyst, and the filtrate was concentrated. The residue was dissolved in ethyl acetate, filtered by NH silica gel lined over a glass filter, and then, this filtrate was concentrated to obtain the title compound (3.5 g, 16.9 mmol, 81%).

$^1$H-NMR Spectrum (CDCl$_3$) δ(ppm): 3.55 (2H, s), 5.64 (1H, d, J=3.2 Hz), 6.13-6.16 (1H, m), 7.04-7.10 (2H, m), 7.17-7.24 (2H, m).

Preparation Example 170

4-(Pyridin-2-ylmethoxy)-benzonitrile

To a solution of 4-cyanophenol (5 g, 42 mmol) in N,N-dimethyl formamide (40 mL) were added potassium carbonate (17.4 g, 126 mmol) and 2-picolyl bromide hydrobromide (10.6 g, 42 mmol), and the solution was stirred at room temperature for 15 hours. The reaction solution was poured into brine, and the solution was extracted with ethyl acetate. The fractionated organic layer was dried over anhydrous magnesium sulfate, then, filtered by NH silica gel lined over a glass filter, and the filtrate was concentrated to obtain the title compound (4.7 g, 22.4 mmol, 53%).

$^1$H-NMR Spectrum (CDCl$_3$) δ(ppm): 5.25 (2H, s), 7.03-7.07 (2H, m), 7.25-7.29 (1H, m), 7.48 (1H, d, J=8.0 Hz), 7.57-7.61 (2H, m), 7.74 (1H, dt, J=1.6 Hz, 8.0 Hz), 8.61-8.63 (1H, m).

Preparation Example 171

4-(Pyridin-2-ylmethoxy)-benzylamine

To a solution of 4(pyridine-2-ylmethoxy)-benzonitrile described in Preparation Example 170 (1.2 g, 5.70 mmol) in tetrahydrofuran (30 mL) was added lithium aluminum hydride (0.22 g, 5.80 mmol), and the solution was stirred for 2 hours 30 minutes at room temperature. Ice water was added to the reaction solution, which was then stirred for 30 minutes. This mixture was filtered through Celite pad, and washed with ethyl acetate. The filtrate was partitioned, this organic layer was dried over anhydrous magnesium sulfate, then, concentrated, and the title compound (1.1 g, 5.13 mmol, 90%) was obtained.

$^1$H-NMR Spectrum (CDCl$_3$) δ(ppm): 3.81 (2H, s), 5.21 (2H, s), 6.94-6.98 (2H, m), 7.20-7.26 (3H, m), 7.52 (1H, d, J=7.8 Hz), 7.74 (1H, dt, J=1.6 Hz, 7.8 Hz), 8.59-8.62 (1H, m).

Preparation Example 172

4-(Pyridin-2-yloxymethyl)-benzylamine

To a solution of 2-bromopyridine (2.35 g, 15.0 mmol) and 4-(hydroxymethyl)benzonitrile (3.00 g, 22.5 mmol) in N,N-dimethylformamide (20 mL) was added sodium hydride (0.90 g, 22.5 mmol; 60% in oil), and the solution was stirred at 70° C. for 30 minutes. The reaction solution was allowed to room temperature, then, partitioned in ethyl acetate and water, the organic layer was washed with water, and then, dried over anhydrous magnesium sulfate. The solvent was evaporated, the residue was purified by NH silica gel column chromatography (hexane/ethyl acetate), and a white solid (581 mg, 18%) was obtained.

To a solution of the obtained white solid (100 mg, 0.476 mmol) in tetrahydrofuran (3 mL) was added lithium aluminum hydride (45 mg, 1.19 mmol), and the solution was stirred at room temperature for 1 hour. The reaction solution was partitioned in ethyl acetate and water, and the organic layer was dried over anhydrous magnesium sulfate. The solvent was evaporated, and the title compound (71 mg, 70%) was obtained as a colorless solid, which is a crudely purified product.

$^1$H-NMR Spectrum (DMSO-d$_6$) δ(ppm): 3.70 (2H, s), 5.31 (2H, s), 6.84-6.87 (1H, m), 6.97-7.00 (1H, m), 7.32 (2H, d, J=8.0 Hz), 7.37 (2H, d, J=8.0 Hz), 7.69-7.74 (1H, m), 8.16-8.18 (1H, m).

Preparation Example 173

5-Bromo-2,3-dihydro-benzofuran

To a solution of 2,3-dihydrobenzofuran (15.0 g, 125 mmol) in tetrahydrofuran (300 mL) was added N-bromosuccinimide (24.5 g, 138 mmol) at 0° C. The reaction solution was stirred at room temperature for 50 minutes, then, water was added, the solution was extracted with ethyl acetate, and the organic layer was washed with brine. Anhydrous magnesium sulfate was added to the organic layer for drying, which was then filtered, the filtrate was concentrated in vacuo, the residue was purified by NH silica gel column chromatography (hexane), and the title compound (24.0 g, 97%) was obtained as a colorless oily substance.

$^1$H-NMR Spectrum (DMSO-d$_6$) δ(ppm): 3.19 (2H, t, J=8.6 Hz), 4.54 (2H, t, J=8.6 Hz), 6.72 (1H, d, J=8.2 Hz), 7.22 (1H, dd, J=2.2, 8.4 Hz), 7.40 (1H, s).

Preparation Example 174

2,3-Dihydro-benzofuran-5carbaldehyde

To a solution of 5-bromo-2,3-dihydro-benzofuran described in Preparation Example 173 (15.0 g, 75.4 mmol) in tetrahydrofuran (300 mL) was added n-butyl lithium (31.2 mL, 82.9 mmol) at −78° C. The reaction solution was stirred for 85 minutes at −78° C., then, N,N-dimethytformamide (6.42 mL, 82.9 mmol) was added thereto, followed by stirring at room temperature for 1 hour. 1N Hydrochloric acid was added to the reaction solution, which was then extracted with ethyl acetate, and the organic layer was washed with brine. Anhydrous magnesium sulfate was added to the organic layer for drying, which was then filtered, the filtrate was concentrated in vacuo, the residue was purified by silica gel column chromatography (hexane/ethyl acetate=5/1), and the title compound (10.1 g, 90%) was obtained as a pale yellow oil.

$^1$H-NMR Spectrum (DMSO-d$_6$) δ(ppm): 3.26 (2H, t, J=8.6 Hz), 4.67 (2H, t, J=8.6 Hz), 6.96 (1H, d, J=7.9 Hz), 7.72 (1H, d, J=8.2 Hz), 7.77 (1H, s), 9.82 (1H, s).

Preparation Example 175

Benzofuran-5-carbaldehyde

To a solution of 2,3-dihydro-benzofuran-5-carbaldehyde described in Preparation Example 174 (6.00 g, 40.5 mmol) in toluene (120 mL) was added 2,3-dichloro-5,6-dicyano-1,4-benzoquinone (18.3 g, 81 mmol), and the solution was refluxed for 4 hours 30 minutes. The reaction solution was cooled to room temperature, water was added, the solution was extracted with ethyl acetate and tetrahydrofuran, and the organic layer was washed with brine. Anhydrous magnesium sulfate was added to the organic layer for drying, which was then filtered, the filtrate was concentrated in vacuo, the residue was purified by silica gel column chromatography (hexane/ethyl acetate=5/1), and the title compound (1.24 g, 21%) was obtained as a pale yellow oil.

$^1$H-NMR Spectrum (CDCl$_3$) δ(ppm): 6.91 (1H, dd, J=0.92, 2.2 Hz), 7.63 (1H, d, J=8.6 Hz), 7.74 (1H, d, J=2.4 Hz), 7.89 (1H, dd, J=1.7, 8.6 Hz), 8.16 (1H, s), 10.08 (1H, s).

Preparation Example 176

Benzofuran-5-yl-(5-bromo-thiophen-2-yl)-methanol

To a solution of 2,5-dibromothiophene (2.05 g, 8.48 mmol) in tetrahydrofuran (25 mL) was added n-butyl lithium (3.48 mL, 8.48 mmol) at −78° C., and the solution was stirred for 40 minutes. Then, benzofuran-5-carbaldehyde described in Preparation Example 175 (1.24 g, 8.48 mmol) was added to this reaction solution at −78° C., and the solution was stirred at room temperature for 75 minutes. Water was added to the reaction solution, which was then extracted with ethyl acetate, and the organic layer was washed with brine. Anhydrous magnesium sulfate was added to the organic layer for drying, which was then filtered, the filtrate was concentrated in vacuo, the residue was purified by NH silica gel column chromatography (heptane/ethyl acetate=3/1), and the title compound (2.11 g, 81%) was obtained as a light brown oil.

$^1$H-NMR Spectrum (DMSO-d$_6$) δ(ppm): 5.98 (1H, s), 6.40 (1H, d, J=2.9 Hz), 6.68 (1H, dd, J=0.92, 3.8 Hz), 6.96 (1H, dd, J=0.92, 2.2 Hz), 7.01 (1H, d, J=3.8 Hz), 7.34 (1H, dd, J=1.5, 8.4 Hz), 7.55 (1H, d, J=8.4 Hz), 7.68 (1H, s), 7.99 (1H, d, J=2.2 Hz).

Preparation Example 177

5-(Benzofuran-5-yl-hydroxy-methyl)-thiophene-2-carbonitrile

To a solution of benzofuran-5-yl-(5-bromo-thiophen-2-yl)-methanol described in Preparation Example 176 (755 mg, 2.44 mmol) in 1-methyl-2-pyrrolidinone (15 mL) were added zinc cyanide (344 mg, 2.93 mmol) and tetrakis(triphenylphosphine)palladium (282 mg, 0.244 mmol), and the mixture was stirred at 120° C. for 3 hours. The reaction mixture was cooled to room temperature, then, aqueous ammonia was added, and the solution was filtered through Celite pad. The mother liquor was extracted with ethyl acetate, and the organic layer was washed with brine. Anhydrous magnesium sulfate was added to the organic layer for drying, which was then filtered, the filtrate was concentrated in vacuo, the residue was purified by silica gel column chromatography (heptane/ethyl acetate=3/1), and the title compound (364 mg, 58%) was obtained as a pale yellow oil.

$^1$H-NMR Spectrum (DMSO-$d_6$) δ(ppm): 6.13 (1H, s), 6.73 (1H, s), 6.97 (1H, d, J=2.2 Hz), 6.99 (1H, d, J=3.8 Hz), 7.37 (1H, dd, J=1.5, 8.4 Hz), 7.58 (1H, d, J=8.6 Hz), 7.72 (1H, s), 7.78 (1H, d, J=3.8 Hz), 8.01 (1H, d, J=2.2 Hz).

Preparation Example 178

C-(5-Benzofuran-5-ylmethyl-thiophen-2-yl)-methylamine

To a solution of lithium aluminum hydride (488 mg, 12.9 mmol) in tetrahydrofuran (10 mL) was added aluminum chloride (1.72 g, 12.9 mmol) on an ice bath, and the solution was stirred for 10 minutes. 5-(Benzofuran-5-yl-hydroxy-methyl)-thiophene-2 carbonitrile described in Preparation Example 177 (364 mg, 1.43 mmol) was added to this suspension on an ice bath, and the solution was stirred for 3 hours. Aqueous ammonia was added to the reaction solution, then, anhydrous magnesium sulfate was added for drying, and the solution was filtered through Celite pad. The filtrate was concentrated in vacuo, the residue was purified by NH silica gel column chromatography (heptane/ethyl acetate=1/1), and the title compound (285 mg, 82%) was obtained as a light brown oil.

$^1$H-NMR Spectrum (DMSO-$d_6$) δ(ppm): 3.77 (2H, s), 4.15 (2H, s), 6.70 (2H, s), 6.91 (1H, d, J=2.2 Hz), 7.19 (1H, dd, J=1.7, 8.4 Hz), 7.50-7.52 (2H, m), 7.96 (1H, d, J=2.2 Hz).

Preparation Example 179

C-(6-Benzyloxypyridin-3-yl)-methylamine

To a solution of 2,5-dibromopyridine (5.0 g, 21.1 mmol) and benzyl alcohol (3.28 mL, 31.7 mmol) in N,N-dimethylformamide (50 mL) was added sodium hydride (1.27 g, 31.7 mmol; 60% in oil), and the solution was stirred at 70° C. for 2 hours. The reaction solution was allowed to room temperature, then, partitioned in ethyl acetate and water, the organic layer was washed with water, and then, dried over anhydrous magnesium sulfate. The solvent was evaporated, the residue was purified by silica gel column chromatography (hexane/ethyl acetate), and a colorless oil (4.60 g, 83%) was obtained.

To a solution of the resulting colorless oil (2.0 g, 7.60 mmol) in N,N-dimethylformamide (20 mL) were added zinc cyanide (1.78 g, 15.2 mmol) and tetrakis(triphenylphosphine) palladium (0) (878 mg, 0.760 mmol) under nitrogen atmosphere, and the solution was stirred at 140° C. for 4 hours. The reaction solution was allowed to room temperature, then, partitioned in ethyl acetate and water, the organic layer was washed with water, and then, dried over anhydrous magnesium sulfate. The solvent was evaporated, the residue was purified by silica gel column chromatography (hexane/ethyl acetate), and a pale yellow solid (1.15 g, 72%) was obtained.

To a solution of the pale yellow solid (100 mg, 0.476 mmol) in tetrahydrofuran (3 mL) was added lithium aluminum hydride (45 mg, 0.120 mmol), and the solution was stirred at room temperature for 1 hour. The reaction solution was partitioned in ethyl acetate and water, and the organic layer was dried over anhydrous magnesium sulfate. The solvent was evaporated, and the title compound (75 mg, 74%) was obtained as a yellow oil, which was a crudely purified product.

$^1$H-NMR Spectrum (CDCl$_3$) δ(ppm): 4.37-4.38 (2H, br d), 5.36 (2H, s), 6.83-6.87 (1H, m), 7.30-7.46 (4H, m), 7.74-7.76 (1H, m), 8.17 (1H, s), 8.80-8.83 (1H, m).

Preparation Example 180

C-(6-Benzyl-pyridin-3-yl)-methylamine

A solution of 2,5-dibromopyridine (10 g, 42.2 mmol) in diethyl ether (260 mL) was cooled to −78° C. under nitrogen atmosphere, and n-butyl lithium (17.8 mL, 46.4 mmol; 2.6M hexane solution) was added dropwise. This solution was stirred at −78° C. for 15 minutes, then, a solution of N,N-dimethylformamide (4.94 mL) in diethyl ether solution (10 mL) was added dropwise at −78° C. This solution was warmed to 0° C., and further stirred for 2 hours at this temperature. After the reaction was completed, this solution was partitioned in diethyl ether and water. The organic layer was separated, washed with water and dried over anhydrous magnesium sulfate. The solvent was evaporated, the residue was purified by silica gel column chromatography (hexane:ethyl acetate), and an aldehyde derivative (5.82 g, 74%) was obtained.

To a solution of the resulting aldehyde derivative (5.82 g, 31.3 mmol) in toluene (120 mL) were added ethyleneglycol (17.5 mL, 0.313 mol) and D-10-camphor-sulfonic acid (73 mg, 0.313 mmol), and the solution was refluxed for 7 hours. The reaction mixture was cooled to room temperature, then, washed with an aqueous solution of saturated sodium hydrogen carbonate and brine, and the organic layer was separated. The organic layer was dried over anhydrous magnesium sulfate, then, solvent was evaporated, the residue was purified by silica gel column chromatography (hexane:ethyl acetate), and an acetal (6.65 g, 93%) was obtained.

Next, to a suspension of zinc (1.53 g, 23.4 mmol) in tetrahydrofuran (120 mL) was added benzyl bromide (2.1 mL, 17.6 mmol) dropwise over 15 minutes, at 0° C., and the solution was stirred at this temperature for 4 hours. After 4 hours, bis(triphenylphosphine)nickel(II) chloride (1.58 g, 2.42 mmol) and a solution of the acetal (3.0 g, 13.1 mmol) in tetrahydrofuran (90 mL) were added to this suspension, and the solution was stirred at room temperature for 12 hours. After the reaction was completed, this suspension was partitioned in ethyl acetate and an aqueous solution of saturated ammonium chloride. The organic layer was separated, washed with water and brine, and then, dried over anhydrous magnesium sulfate. The solvent was evaporated, the residue was purified by silica gel column chromatography (hexane: ethyl acetate), and a 2-benzyl pyridine derivative (1.08 g, 34%) was obtained.

To a mixture solution of the resulting 2-benzyl pyridine derivative (1.08 g, 4.48 mmol) in methanol and tetrahydrofuran (5 mL:4 mL) was added 2N hydrochloric acid (5 mL), and the solution was stirred at room temperature for 2 hours. Furthermore, to this solution was added 5N hydrochloric acid (8 mL) was added in three times, the solution was stirred at room temperature for 24 hours, then, refluxed for 30 minutes. The reaction solution was cooled to room temperature, then, partitioned in ethyl acetate and an aqueous solution of saturated sodium bicarbonate. The organic layer was separated, washed with water, and then, dried over anhydrous magnesium sulfate. The solvent was evaporated, and a formyl derivative (950 mg, quantitatively) was obtained.

To a solution of the resulting formyl derivative (950 mg, 4.48 mmol) in methanol (25 mL) was added sodium borohydride (176 mg, 4.66 mmol), and the solution was stirred at room temperature for 1 hour. The reaction solution was partitioned in ethyl acetate and water. This organic layer was separated, washed with water and dried over anhydrous magnesium sulfate. The solvent was evaporated, and a benzyl alcohol derivative (810 mg, 91%) was obtained.

Methanesulfonyl chloride (0.37 mL, 4.83 mmol) and triethylamine (0.67 mL, 4.84 mL) were added to a solution of the resulting benzyl alcohol derivative (810 mg, 4.07 mmol) in dichloromethane (8 mL) that had been cooled to 0° C., and the solution was stirred at room temperature for 14 hours. The reaction mixture was partitioned in dichloromethane and an aqueous solution of saturated sodium bicarbonate. The organic layer was separated, washed with brine, and then, dried over anhydrous magnesium sulfate. The solvent was evaporated, and a methanesulfonate ester derivative (1.09 g, 97%) was obtained.

To a solution of the resulting methanesultonate ester derivative (1.09 g, 3.93 mmol) in N,N-dimethylformamide (10 mL) was added phthalimide potassium salt (757 mg, 4.09 mmol), and the solution was stirred for 2 hours under reflux. This reaction mixture was cooled to room temperature, and partitioned in ethyl acetate and water. This organic layer was separated, washed with water and brine, and then, dried over anhydrous magnesium sulfate. The solvent was evaporated, the residue was purified by silica gel column chromatography (hexane:ethyl acetate), and a phthalimide derivative (910 mg, 71%) was obtained.

Then, to a solution of the resulting phthalimide derivative (910 mg, 2.77 mmol) in ethanol (23 mL) was added hydrazine monohydrate (144 mg, 2.88 mmol), and the solution was stirred for 2 hours under reflux. The reaction mixture was cooled to room temperature, then, water was added to this mixture. This mixture was concentrated in vacuo until the liquid volume of this mixture became half. This concentrated solution was partitioned in ethyl acetate and water. This organic layer was separated, washed with 2N sodium hydroxide and water, and dried over anhydrous magnesium sulfate. The solvent was evaporated, and the title compound (360 mg, 66%) was obtained. This was used in the next reaction without further purification.

Preparation Example 181

2-Amino-methyl-5-phenoxy-pyridine

2-Cyano-5-phenoxy-pyridine (150 mg, 0.76 mmol) and lithium aluminum hydride (58 mg, 1.53 mmol) were suspended in tetrahydrofuran (5 mL) and diethyl ether (5 mL), and the solution was stirred for 10 minutes under reflux. The reaction solution was partitioned in water and ethyl acetate. The organic layer was separated, the solvent was evaporated, and the title compound (140 mg, brown oil) was obtained as a crude product.

$^1$H-NMR Spectrum (DMSO-$d_6$) δ(ppm): 3.80 (2H, s), 6.70-6.80 (2H, m), 7.00-7.12 (1H, m), 7.12-7.22 (2H, m), 7.40-7.50 (2H, m), 8.30 (1H, s).

Preparation Example 182

5-Benzyloxy-2-methyl-pyridine

To a solution of 3-hydroxy-6-methylpyridine (5.00 g, 45.8 mmol) in N,N-dimethylformamide (50 mL) was added sodium hydride (2.02 g, 50.4 mmol, 60% in oil) at 0° C., and the solution was stirred for 15 minutes at 0° C. Then, benzyl bromide (5.99 mL, 50.4 mmol) was added at 0° C., and the solution was stirred for 3.5 hours at room temperature. The reaction solution was partitioned in water and ethyl acetate. This organic layer was separated, washed with water and brine and dried over anhydrous magnesium sulfate. The organic layer was filtered, then, the solvent was evaporated in vacuo, the residue was purified by silica gel column chromatography (heptane/ethyl acetate=2/1), and the title compound (5.99 g, 66%) was obtained as a colorless oil.

$^1$H-NMR Spectrum (CDCl$_3$) δ(ppm): 2.49 (3H, s), 5.08 (2H, s), 7.05 (1H, d, J=8.6 Hz), 7.17 (1H, dd, J=2.9 Hz, 8.4 Hz), 7.31-7.44 (5H, m), 8.27 (1H, d, J=2.9 Hz).

Preparation Example 183

(5-Benzyloxy-pydridin-2-yl)-methanol

To a solution of 5-benzyloxy-2-methyl pyridine described in Preparation Example 182 (5.99 g, 30.1 mmol) in methylene chloride (100 mL) was added 3-chloroperoxylbenzoic acid (8.79 g, 33.1 mmol, 65%) at 0° C., and the solution was stirred at room temperature for 2 hours. An aqueous solution of saturated sodium bicarbonate was added to the reaction solution at 0° C., which was partitioned with methylene chloride. This organic layer was separated, washed with an aqueous solution of saturated sodium bicarbonate and brine, and dried over anhydrous magnesium sulfate. The organic layer was filtered, then, the solvent was evaporated in vacuo, and 5-benzyloxy-2-methyl-pyridine-1-oxide (7.71 g) was obtained as a crude product of a white solid. Next, acetic anhydride (77 mL) was added to 5-benzyloxy-2-methyl-pyridin-1-oxide (7.71 g), and the solution was stirred for 80 minutes at 120° C. This reaction mixture was cooled to room temperature, then, the solvent was evaporated in vacuo. Ethanol (50 mL) and an aqueous solution of 5N sodium hydroxide (7 mL) were added to the resulting residue, and the solution was stirred at room temperature for 50 minutes. The solvent was evaporated in vacuo, this residue was partitioned in brine and ethyl acetate. The organic layer was separated, washed with brine and dried over anhydrous magnesium sulfate. The organic layer was filtered, then, the solvent was evaporated in vacuo, the residue was purified by NH silica gel column chromatography (heptane/ethyl acetate=1/1), and the title compound (4.17 g, 54%) was obtained as a white solid.

$^1$H-NMR Spectrum (DMSO-$d_6$) δ(ppm): 4.46 (2H, d, J=5.9 Hz), 5.15 (2H, s), 5.26 (1H, t, J=5.9 Hz), 7.29-7.40 (4H, m), 7.42-7.45 (3H, m), 8.22 (1H, d, J=2.9 Hz).

Preparation Example 184

2-(5-Benzyloxy-pyridin-2-ylmethyl)-isoindol-1,3-dione

To a solution of (5-benzyloxy-pyridin-2-yl)-methanol described in Preparation Example 183 (2.00 g, 9.29 mmol) in tetrahydrofuran (40 mL) were added phthalimide (1.50 g, 10.2 mmol), triphenylphosphine (2.92 g, 11.1 mmol) and diethyl azodicarboxylate (5.08 mL, 11.1 mmol, 40% toluene solution) at 0° C., and the solution was stirred at room temperature for 2 hours. The reaction solution was partitioned in water and ethyl acetate. The organic layer was separated, washed with brine and dried over anhydrous magnesium sulfate. The organic layer was filtered, then, the solvent was evaporated in vacuo, the residue was purified by silica gel column chromatography (heptane/ethyl acetate=2/1), and the title compound (4.1 g, quantitatively) was obtained as a white solid.

$^1$H-NMR Spectrum (DMSO-d$_6$) δ(ppm): 4.84 (2H, s), 5.15 (2H, s), 7.31-7.45 (7H, m), 7.86-7.92 (4H, m), 8.20 (1H, d, J=2.9 Hz).

Preparation Example 185

C-(5-Benzyloxy-pyridin-2-yl)-methylamine 2-(5-Benzyloxy-pyridin-2-ylmethyl)-isoindol-1,3-dione described in Preparation Example 184 (4.10 g, 11.9 mmol) was dissolved in ethanol (40 mL) and tetrahydrofuran (40 mL). Hydrazine monohydrate (5.77 mL, 119 mmol) was added to this solution at room temperature, and the solution was stirred under reflux for 50 minutes. The reaction solution was partitioned in water and ethyl acetate. This organic layer was separated, washed with brine and dried over anhydrous magnesium sulfate. The organic layer was filtered, then, the solvent was evaporated in vacuo, the residue was purified by NH silica gel column chromatography (ethyl acetate), and the title compound (2.8 g, quantitatively) was obtained as a pale yellow solid.

$^1$H-NMR Spectrum (DMSO-d$_6$) δ(ppm): 3.70 (2H, s), 5.15 (2H, s), 7.30-7.45 (7H, m), 8.23 (1H, d, J=3.2 Hz).

Preparation Example 186

2-Methyl-5-phenoxymethyl-pyridine

Thionyl chloride (1 mL) was added to (6-methyl-pyridin-3-yl)-methanol (300 mg, 2.44 mmol) at 0° C., and the solution was stirred at room temperature for 20 minutes. The reaction solution was partitioned in an aqueous solution of saturated sodium bicarbonate and ethyl acetate. This organic layer was separated, washed with brine, and then, dried over anhydrous magnesium sulfate. The organic layer was filtered, then, the solvent was evaporated in vacuo. N,N-dimethylformamide (5 mL), phenol (230 mg, 2.44 mmol) and potassium carbonate (674 mg, 4.88 mmol) were added to this residue at room temperature. This reaction mixture was stirred at room temperature for 40 minutes, then, further stirred for at 60° C. 40 minutes. The reaction solution was partitioned in water and ethyl acetate. The organic layer was separated, washed with water and brine, and then, dried over anhydrous magnesium sulfate. The organic layer was filtered, then, the solvent was evaporated in vacuo, the residue was purified by silica gel column chromatography (heptane/ethyl acetate=2/1), and the title compound (323 mg, 66%) was obtained as a white solid.

$^1$H-NMR Spectrum (CDCl$_3$) δ(ppm): 2.58 (3H, s), 5.04 (2H, s), 6.96-7.00 (3H, m), 7.18 (1H, d, J=8.2 Hz), 7.30 (2H, t, J=8.8 Hz), 7.67 (1H, dd, J=2.0 Hz, 8.0 Hz), 8.56 (1H, s).

Preparation Example 187

(5-Phenoxymethyl-pyridin-2-yl)-methanol

To a solution of 2-methyl-5-phenoxymethyl-pyridine described in Preparation Example 186 (323 mg, 1.62 mmol) in methylene chloride was added 3-chloroperoxylbenzoic acid (473 mg, 1.78 mmol, 65%) at 0° C., and the solution was stirred at room temperature for 7 hours. An aqueous solution of saturated sodium bicarbonate was added to the reaction solution at 0° C., which was then partitioned with ethyl acetate. The organic layer was separated, washed with an aqueous solution of saturated sodium bicarbonate and brine, and then, dried over anhydrous magnesium sulfate. The organic layer was filtered, then, the solvent was evaporated in vacuo. Acetic anhydride (4 mL) was added to this residue, which was then stirred for 30 minutes at 120° C. This reaction solution was cooled to room temperature, then, the solvent was evaporated in vacuo. Ethanol (5 mL), and an aqueous solution of 5N sodium hydroxide (2 mL) were added to this residue, and the solution was stirred at room temperature for 45 minutes. This reaction solution was concentrated in vacuo, the residue was partitioned in water and ethyl acetate. The organic layer was separated, washed with brine, and then, dried over anhydrous magnesium sulfate. The organic layer was filtered, then, the solvent was evaporated in vacuo, the residue was purified by NH silica gel column chromatography (heptane/ethyl acetate=1/1), and the title compound (167 mg, 48%) was obtained as a white solid.

$^1$H-NMR Spectrum (CDCl$_3$) δ(ppm): 3.63 (1H, t, J=5.2 Hz), 4.78 (2H, d, J=4.8 Hz), 5.09 (2H, s), 6.97-7.02 (3H, m), 7.27-7.33 (3H, m), 7.78 (1H, dd, J=2.2 Hz, 8.0 Hz), 8.63 (1H, d, J=1.7 Hz).

Preparation Example 188

2-(5-Phenoxymethyl-pyridin-2-ylmethyl)-isoindol-1,3-dione

To a solution of (5-phenoxymethyl-pyridin-2-yl)-methanol described in Preparation Example 187 (167 mg, 0.776 mmol) in tetrahydrofuran (4 mL) were added phthalimide (126 mg, 0.856 mmol), triphenylphosphine (244 mg, 0.930 mmol) and diethyl azodicarboxylate (424 μL, 0.931 mmol, 40% toluene solution) at 0° C., and the solution was stirred at room temperature for 30 minutes. The reaction solution was partitioned with water and ethyl acetate. The organic layer was separated, washed with brine, and then, dried over anhydrous magnesium sulfate. The organic layer was filtered, then, the solvent was evaporated in vacuo, the residue was purified by silica gel column chromatography (heptane/ethyl acetate=1/1), and the title compound (383 mg, quantitatively) was obtained as a white solid.

$^1$H-NMR Spectrum (DMSO-d$_6$) δ(ppm): 4.92 (2H, s), 5.10 (2H, s), 6.94 (1H, t, J=7.3Hz), 7.00 (2H, dd, J=0.92 Hz, 8.8 Hz), 7.29 (2H, dd, J=7.2 Hz, 8.8 Hz), 7.44 (1H, d, J=7.9 Hz), 7.85 (1H, dd, J=2.0 Hz, 8.0 Hz), 7.87-7.94 (4H, m), 8.52 (1H, d, J=1.8 Hz).

Preparation Example 189

C-(5-Phenoxymethyl-pyridin-2-yl)-methylamine 2-(5-Phenoxymethyl-pyridin-2-ylmethyl)-isoindol-1,3-dione described in Preparation Example 188 (383 mg, 1.11 mmol) was dissolved in ethanol (3 mL) and tetrahydrofuran (3 mL). Hydrazine monohydrate (538 μL, 11.1 mmol) was added to this solution at room temperature, and the solution was stirred under reflux for 1 hour. The reaction solution was partitioned in water and ethyl acetate. The organic layer was separated, washed with brine, and then, dried over anhydrous magnesium sulfate. The organic layer was filtered, then, the solvent was evaporated in vacuo, the residue was purified by NH silica gel column chromatography (ethyl acetate/methanol=10/1), and the title compound (122 mg, 51%) was obtained as a colorless oil.

$^1$H-NMR Spectrum (CDCl$_3$) δ(ppm): 4.00 (2H, s), 5.07 (2H, s), 6.67-7.01 (3H, m), 7.29-7.33 (3H, m), 7.75 (1H, dd, J=2.4 Hz, 8.0 Hz), 8.63 (1H, d, J=1.6 Hz).

Preparation Example 190

4-(6-Fluoro-pyridin-2-yloxymethyl)-benzylamine

To a solution of 2,6-difluoropyridine (500 mg, 4.34 mmol) and 4-(hydroxymethyl)benzonitrile (867 mg, 6.51 mmol) in N,N-dimethylformamide (3 mL) was added sodium hydride (0.26 g, 6.51 mmol; 60% in oil), and the solution was stirred at 70° C. for 7 hours. The reaction solution was allowed to room temperature, then, partitioned in ethyl acetate and water, the organic layer was washed with water, and then, dried over anhydrous magnesium sulfate. The solvent was evaporated, the residue was purified by silica gel column chromatography (hexane/ethyl acetate), and a white solid (734 mg, 74%) was obtained.

To a solution of the resulting white solid (734 mg, 3.22 mmol) in tetrahydrofuran (5 mL) was added lithium aluminum hydride (244 mg, 6.44 mmol), and the solution was stirred at room temperature for 30 minutes. The reaction solution was partitioned in ethyl acetate and water, and the organic layer was dried over anhydrous magnesium sulfate. The solvent was evaporated, and the title compound (662 mg, 89%) was obtained as a crude product.

$^1$H-NMR Spectrum (DMSO-$d_6$) δ(ppm): 3.71 (2H, s), 5.27 (2H, s), 6.71-6.73 (1H, m), 6.79-6.81 (1H, m), 7.33-7.39 (4H, m), 7.86-7.90 (1H, m).

Preparation Example 191

4-(3-Chloro-benzyloxy)-benzylamine

To a solution of 4-cyanophenol (2.28 g, 19.1 mmol) and 3-chlorobenzyl bromide (2.2 mL, 16.8 mmol) in N,N-dimethylformamide (100 mL) was added potassium carbonate (5.88 g, 42.5 mmol), and the solution was stirred at 50° C. for 9 hours. The reaction mixture was partitioned in ethyl acetate and water. This organic layer was separated, washed with 2N sodium hydroxide, water and then brine, and dried over anhydrous magnesium sulfate. The solvent was evaporated, and a crude product (4.20 g, quantitatively) was obtained.

To a suspension of aluminum chloride in tetrahydrofuran (40 mL) was added lithium aluminum hydride (4.70 g, 35.2 mmol) while cooling on a water bath. A solution of the crude product (1.15 g, 4.71 mmol) in tetrahydrofuran (10 mL) was added to this suspension, which was then stirred at 0-1° C. for 50 minutes. Concentrated aqueous ammonia (8 mL) was added to the reaction mixture, ultrasound was applied, concentrated aqueous ammonia (8 mL) was further added, and the solution was stirred for 1 hour at room temperature. This mixture was filtered through Celite pad, and this filtrate was separated. This filtrate was partitioned in tetrahydrofuran, ethyl acetate and water. This organic layer was separated, washed with water and brine, and dried over anhydrous sodium sulfate and anhydrous magnesium sulfate. The solvent was evaporated, and the title compound (1.15 g, 99%) was obtained.

$^1$H-NMR Spectrum (CDCl$_3$) δ(ppm): 3.03 (2H, brs), 3.64 (2H, s), 5.11 (2H, s), 6.94 (2H, d, J=8.0 Hz), 7.24 (2H, d, J=8.0 Hz), 7.37-7.45 (3H, m), 7.50 (1H, s).

Preparation Example 192

4-(3-Methoxy-benzyloxy)-benzylamine

To a solution of 4-cyanophenol (3.31 g, 27.8 mmol) and 3-methoxybenzyl bromide (3.7 mL, 26.4 mmol) in N,N-dimethylformamide (100 mL) was added potassium carbonate (8.50 g, 61.5 mmol), and the solution was stirred at 50° C. for 5 hours. The reaction mixture was partitioned in diethyl ether and water. This organic layer was separated, washed with 2N sodium hydroxide, water and brine, and dried over anhydrous magnesium sulfate. The solvent was evaporated, and a crude product (6.52 g, 98%) was obtained.

To a solution of the resulting crude product (3.75 g, 15.7 mmol) in tetrahydrofuran (80 mL) was added lithium aluminum hydride (596 mg, 15.7 mmol), and the solution was stirred at room temperature for 23 hours. Sodium fluoride (6.6 g) was added to the reaction mixture solution at room temperature, which was then cooled with an ice water bath, then, a mixture solution of water (2 mL) and tetrahydrofuran (18 mL) was added, followed by stirring. This mixture solution was filtered through Celite pad, and what was on Celite was washed with tetrahydrofuran and ethyl acetate. This filtrate was separated, the solvent was evaporated to obtain the title compound (3.84 g, quantitatively) as a crude product.

$^1$H-NMR Spectrum (CDCl$_3$) δ(ppm): 3.33 (2H, brs), 3.63 (2H, s), 3.76 (3H, s), 5.06 (2H, s), 6.87-6.90 (2H, d, J=8.4 Hz), 6.93 (2H, d, J=8.4 Hz), 7.00-7.01 (2H, m), 7.23 (2H, d, J=8.4 Hz), 7.28-7.32 (1H, m).

Preparation Example 193

4-(4-Methyl-pyridin-2-yloxymethyl)-benzylamine

To a solution of 2-fluoro-4-methylpyridine (500 mg, 4.50 mmol) and 4-(hydroxymethyl)benzonitrile (899 mg, 6.75 mmol) in N,N-dimethylformamide (3 mL) was added sodium hydride (0.27 g, 6.75 mmol; 60% in oil), and the solution was stirred at 70° C. for 1 hour. The reaction solution was allowed to room temperature, then, partitioned in ethyl acetate and water, the organic layer was washed with water, and then, dried over anhydrous magnesium sulfate. The solvent was evaporated, the residue was purified by silica gel column chromatography (hexane/ethyl acetate), and a white solid (833 mg, 83%) was obtained.

To a solution of the resulting white solid (200 mg, 0.891 mmol) in tetrahydrofuran (3 mL) was lithium aluminum hydride (68 mg, 1.78 mmol), and the solution was stirred at room temperature for 1 hour. The reaction solution was partitioned in ethyl acetate and water, and the organic layer was dried over anhydrous magnesium sulfate. The solvent was evaporated, and the title compound (181 mg, 89%) was obtained as a crude product.

$^1$H-NMR Spectrum (DMSO-$d_6$) δ(ppm): 2.77 (3H, s), 3.69 (2H, s), 5.29 (2H, s), 6.68 (1H, s), 6.82 (1H, d, J=4.4 Hz), 7.30-7.39 (4H, m), 8.02 (1H, d, J=5.6 Hz).

Preparation Example 194

4-(5-Methyl-pyridin-2-yloxyethyl)-benzylamine

To a solution of 2-fluoro-5-methylpyridine (1.0 g, 9.0 mmol) and 4-(hydroxymethyl)benzonitrile (1.8 g, 13.5 mmol) in N,N-dimethylformamide (5 mL) was added sodium hydride (0.54 mg, 13.5 mmol; 60% in oil), and the solution was stirred for 30 minutes at 70° C. The reaction solution was allowed to room temperature, then, partitioned in ethyl acetate and water, the organic layer was washed with water, and then, dried over anhydrous magnesium sulfate. The solvent was evaporated, the residue was purified by silica gel column chromatography (hexane/ethyl acetate), and a white solid (1.46 g, 72%) was obtained.

To a solution of the resulting white solid (500 mg, 2.23 mmol) in tetrahydrofuran (5 mL) was added lithium aluminum hydride (169 mg, 4.46 mmol), and the solution was stirred at room temperature for 30 minutes. The reaction solution was partitioned in ethyl acetate and water, and the organic layer was dried over anhydrous magnesium sulfate. The solvent was evaporated, and the title compound (457 mg, 90%) was obtained as a crude product.

$^1$H-NMR Spectrum (DMSO-$d_6$) δ(ppm): 2.20 (3H, s), 3.69 (2H, s), 5.27 (2H, s), 6.76 (1H, d, J=8.4 Hz), 7.30-7.39 (4H, m), 7.54 (1H, d, J=7.2 Hz), 7.97 (1H, s).

Preparation Example 195

1-Bromo-4-(2-propoxy-ethyl)-benzene

To a mixture of sodium hydride (66%, 360 mg, 15 mmol) and tetrahydrofuran (10 mL) was added 2-(4-bromophenyl)ethanol (1.5 g, 7.5 mmol) on an ice bath, the solution was stirred at room temperature for 1 hour. 1-Iodopropane (1.5 mL, 15 mmol) and N,N-dimethylformamide (10 mL) were added to the reaction solution on an ice bath, and the solution was stirred overnight at 45° C. The reaction solution was partitioned with water (100 mL) and heptane (200 mL). The organic layer was separated, and washed with brine. this solvent was evaporated in vacuo, the residue was purified by silica gel column chromatography (heptane:ethyl acetate=30: 1), and the title compound (0.80 g, 3.3 mmol, 44%) was obtained as a colorless oil.

$^1$H-NMR Spectrum (CDCl$_3$) δ(ppm): 0.88-0.92 (3H, m), 1.55-1.61 (2H, m), 2.83 (2H, t, J=7.0 Hz), 3.36-3.40 (2H, m), 3.60 (2H, dt, J=1.5, 7.0 Hz), 7.10 (2H, d, J=8.1 Hz), 7.40 (2H, d, J=8.2 Hz).

Preparation Example 196

4-(2-Propoxy-ethyl)-benzonitrile

1-Bromo-4-(2-propoxy-ethyl)-benzene described in Preparation Example 195 (790 mg, 3.2 mmol), zinc cyanide (380 mg, 3.2 mmol) and tetrakis(triphenylphosphine)palladium (190 mg, 0.16 mmol) were added to N-methylpyrrolidinone (10 mL), and this mixture was stirred at 125° C. for 4 hours. This reaction mixture was allowed to cool, and water (50 mL) and ethyl acetate (50 mL) were added thereto. This mixture solution was filtered through Celite pad. The organic layer was separated, then, washed with water (3 times) and brine, and then, concentrated in vacuo. The residue was purified by silica gel column chromatography (heptane:ethyl acetate=8:1), and the title compound (120 mg, 0.62 mmol, 19%) was obtained as a colorless oil.

$^1$H-NMR Spectrum (CDCl$_3$) δ(ppm): 0.89 (3H, t, J=7.3 Hz), 1.57 (2H, tq, J=7.3, 7.3 Hz), 2.93 (2H, t, J=6.6 Hz), 3.38 (2H, t, J=6.7 Hz), 3.64 (2H, t, J=6.6 Hz), 7.34 (2H, d, J=8.1 Hz), 7.58 (2H, d, J=8.2 Hz).

Preparation Example 197

4-(2-Propoxy-ethyl)-benzylamine

To a mixture of lithium aluminum hydride (120 mg, 2.5 mmol) and tetrahydrofuran (3 mL) was added 4-(2-propoxyethyl)-benzonitrile described in Preparation Example 196 (120 mg, 0.62 mmol), the solution was stirred overnight at room temperature. The reaction solution was cooled to 0° C., tetrahydrofuran (30 mL), water (0.12 mL), an aqueous solution of 5N sodium hydroxide (0.12 mL) and water (0.36 mL) were sequentially added dropwise. After stirring for 1 hour at room temperature, this reaction mixture was filtered through a filter paper. This filtrate was concentrated in vacuao, the residue was filtered using NH-silica gel, and the title compound (123 mg, 0.64 mmol, 103%) was obtained as a colorless oil.

$^1$H-NMR Spectrum (CDCl$_3$) δ(ppm): 0.91 (3H, t, J=7.4 Hz), 1.55-1.62 (2H, m), 2.88 (2H, t, J=7.3 Hz), 3.40 (2H, t, J=6.7 Hz), 3.63 (2H, t, J=7.2 Hz), 3.84 (2H, s), 7.20 (2H, d, J=8.1 Hz), 7.23 (2H, d, J=8.2 Hz).

Example A-1

2,6Diamino-N-(5-(4-fluoro-phenoxy)-furan-2-ylmethyl)-nicotinamide 2,6-Diamino-nicotinic acid described in Preparation Example A-15 (0.15 g, 0.98 mmol), triethylamine (0.41 mL, 2.94 mmol) and benzotriazol-1-yloxytris(dimethylamino)phosphonium hexafluorophosphate (0.65 g, 1.47 mmol) were dissolved in N,N-dimethylformamide (5 mL), and the solution was stirred at room temperature for 10 minutes. Then, a solution of C-(5-(4-fluoro-phenoxy)-furan-2-yl)methylamine described in Preparation Example 169 (304 mg, 1.47 mmol) in N,N-dimethylformamide (1 mL) was added thereto, followed by stirring at room temperature for 14 hours 50 minutes. After the reaction was completed, reaction solution was poured into brine, the solution was extracted with ethyl acetate, the fractionated organic layer was dried over anhydrous magnesium sulfate and then concentrated. The obtained residue was subjected to silica gel column chromatography, eluted with solvent (ethyl acetate), and the title compound (0.12 g, 0.35 mmol, 36%) was obtained.

$^1$H-NMR Spectrum (DMSO-$d_6$) δ(ppm): 4.28 (2H, d, J=5.2 Hz), 5.64-5.69 (2H, m), 6.10 (2H, br s), 6.22 (1H, d, J=3.2 Hz), 6.96 (2H, br s), 7.08-7.14 (2H, m), 7.19-7.26 (2H, m), 7.63 (1H, d, J=8.8 Hz), 8.22 (1H, t, J=5.2 Hz)

Example A-2

2,6-Diamino-N-(5-benzofuran-2-ylmethyl-furan-2-ylmethyl)-nicotinamide $^1$H-NMR Spectrum (CDCl$_3$) δ(ppm): 4.18 (2H, s), 4.31 (2H, d, J=5.6 Hz), 5.65 (1H, dd, J=1.2, J=8.4 Hz), 6.08 (2H, brs), 6.13-6.20 (2H, m), 6.65 (1H, s), 6.95 (2H, brs), 7.18-7.28 (2H, m), 7.48-7.53 (1H, m), 7.55 (1H, dd, J=0.8, J=5.6 Hz), 7.63 (1H, d, J=8.4 Hz), 8.23 (1H, t, J=5.6 Hz).

Example A-3

2-Amino-N-(5-(4-chloro-phenoxy)-furan-2-ylmethyl)nicotinamide

The title compound (55 mg, 0.160 mmol, 72.9%) was obtained as a brown oil from 2-aminonicotinic acid (34 mg, 0.24 mmol) and C-(5-(4-chlorophenoxy)furan-2-yl)methylamine described in Preparation Example 47 (50 mg, 0.22 mmol) according to an analogous method to Example Q-6.

$^1$H-NMR Spectrum (DMSO-$d_6$) δ(ppm): 4.33 (2H, d, J=5.6 Hz), 5.73-5.77 (1H, m), 6.29 (1H, d, J=3.2 Hz), 6.54-6.58 (1H, m), 7.00-7.10 (4H, m), 7.38-7.45 (2H, m), 7.88 (1H, d, J=7.6 Hz), 8.03-8.07 (1H, m), 8.85 (1H, t, J=5.6 Hz).

Example A-4

2-Amino-N-(5-(3-chloro-benzyl)-furan-2-ylmethyl)-nicotinamide

The title compound (110 mg, 0.322 mmol, 89.4%) was obtained as a white solid from 2-aminonicotinic acid (55 mg, 0.39 mmol) and C-(5-(3-chloro-benzyl)-furan-2-yl)-methylamine described in Preparation Example 56 (80 mg, 0.36 mmol) according to an analogous method to Example Q-6.

$^1$H-NMR Spectrum (DMSO-d$_6$) δ(ppm): 3.94 (2H, s), 4.34 (2H, d, J=5.6 Hz), 6.05 (1H, d, J=3.2 Hz), 6.15 (1H, d, J=3.2 Hz), 6.54 (1H, dd, J=4.0, 8.0 Hz), 7.03 (2H, brs), 7.16-7.20 (1H, m), 7.24-7.35 (3H, m), 7.87 (1H, dd, J=1.6, 8.0 Hz), 8.05 (1H, dd, J=1.6, 4.0 Hz), 8.48 (1H, t, J=5.6 Hz).

Example A-5

2-Amino-N-(5-benzyl-furan-2-ylmethyl)-nicotinamide

The title compound (118 mg, 0.384 mmol, 24%) was obtained from C-(5-benzyl-furan-2-yl)-methylamine (360 mg, 1.92 mmol) prepared from 5-benzyl-furan-2-carbaldehyde according to an analogous method to Example Q-1, and 2-aminonicotinic acid (221 mg, 1.60 mmol) according to an analogous method to Example H-1.

$^1$H-NMR Spectrum (DMSO-d$_6$) δ(ppm): 3.91 (2H, s), 4.34 (2H, d, J=6.0 Hz), 6.00 (1H, d, J=2.8 Hz), 6.14 (1H, d, J=2.8 Hz), 6.54 (1H, dd, J=4.8, 7.6 Hz), 7.04 (2H, brs), 7.13-7.32 (5H, m), 7.87 (1H, dd, J=1.6, 7.6 Hz), 8.05 (1H, d, J=1.6, 4.8 Hz), 8.84 (1H, t, J=6.0 Hz).

Example A-6

2-Amino-N-(5-(3-fluoro-benzyl)-furan-2-ylmethyl)-nicotinamide

The title compound (252 mg, 0.775 mmol, 65%) was obtained from 2-aminonicotinic acid (164 mg, 1.19 mmol) and C-(5-(3-fluoro-benzyl)-furan-2-yl)-methylamine described in Preparation Example 84 (269 mg, 1.31 mmol) according to an analogous method to Example H-1.

$^1$H-NMR Spectrum (DMSO-d$_6$) δ(ppm): 3.95 (2H, s), 4.34 (2H, d, J=5.6 Hz), 6.04 (1H, d, J=3.2 Hz), 6.15 (1H, d, J=3.2 Hz), 6.54 (1H, dd, J=4.8, 7.6 Hz), 6.97-7.12 (5H, m), 7.28-7.36 (1H, m), 7.87 (1H, dd, J=2.0, 7.6 Hz), 8.04 (1H, dd, J=2.0, 4.8 Hz), 8.84 (1H, t, J=5.6 Hz).

Example A-7

2-Amino-N-(5-phenylaminomethyl-furan-2-ylmethyl)-nicotinamide

The title compound (49 mg, 0.15 mmol, 90%) was obtained as a white solid from (5-aminomethyl-furan-2-ylmethyl)-phenyl-amine described in Preparation Example 104 (34 mg, 0.17 mmol) and 2-amino-nicotinic acid (26 mg, 0.19 mmol) according to an analogous method to Example A-26.

$^1$H-NMR Spectrum (DMSO-d$_6$) δ(ppm): 4.19 (2H, d, J=6.0 Hz), 4.39 (2H, d, J=5.5 Hz), 6.02 (1H, t, J=6.0 Hz), 6.19 (2H, dd, J=3.1, 11 Hz), 6.52 (1H, t, J=7.3 Hz), 6.57 (1H, dd, J=4.8, 7.7 Hz), 6.62 (2H, d, J=7.7 Hz), 7.03-7.07 (4H, m), 7.91 (1H, dd, J=1.7, 7.7 Hz), 8.07 (1H, dd, J=1.7, 4.8 Hz), 8.88 (1H, t, J=5.5 Hz).

Example A-8

2-Amino-N-(5-(2-phenylamino-ethyl)-furan-2-ylmethyl)-nicotinamide

The title compound (29 mg, 86 μmol, 89%) was obtained as a white solid from 2-(5-aminomethyl-furan-2-yl)-ethyl)-phenylamine described in Preparation Example 107 (21 mg, 97 μmol) and 2-amino-nicotinic acid (16 mg, 0.12 mmol) according to an analogous method to Example A-26.

$^1$H-NMR Spectrum (DMSO-d$_6$) δ(ppm): 2.83 (2H, t, J=7.3 Hz), 3.26 (2H, m), 4.38 (2H, d, J=5.5 Hz), 5.61 (1H, t, J=5.7 Hz), 6.12 (1H, d, J=3.1 Hz), 6.17 (1H, d, J=3.1 Hz), 6.52 (1H, t, J=7.3 Hz), 6.54-6.59 (3H, m), 7.04-7.08 (4H, m), 7.92 (1H, dd, J=1.8, 7.7 Hz), 8.07 (1H, dd, J=1.8, 4.8 Hz), 8.87 (1H, t, J=5.7 Hz).

Example A-9

6-Amino-N-(5-(3-fluoro-benzyl)-furan-2-ylmethyl)-nicotinamide

The title compound (265 mg, 0.814 mmol, 63%) was obtained from 6-aminonicotinic acid (180 mg, 1.30 mmol) and C-(5-(3-fluoro-benzyl)-furan-2-yl)-methylamine described in Preparation Example 84 (293 mg, 1.43 mmol) according to an analogous method to Example H-1.

$^1$H-NMR Spectrum (DMSO-d$_6$) δ(ppm): 3.95 (2H, s), 4.33 (2H, d, J=5.6 Hz), 6.03 (1H, d, J=3.2 Hz), 6.12 (1H, d, J=3.2 Hz), 6.38 (1H, d, J=8.8 Hz), 6.45 (2H, brs), 7.00-7.09 (3H, m), 7.28-7.36 (1H, m), 7.78 (1H, dd, J=2.4, 8.4 Hz), 8.43 (1H, d, J=2.4 Hz), 8.56 (1H, t, J=5.6 Hz).

Example A-10

2,6-Diamino-N-(4-benzyloxy-benzyl)-nicotinamide 2,6-Diamino-nicotinic acid described in Preparation Example A-15 (0.6 g, 3.92 mmol), triethylamine (1.64 mL, 11.8 mmol) and benzotriazole-1-yloxy tris(dimethylamino) phosphonium hexafluorophosphate (2.6 g, 5.9 mmol) were dissolved in N,N-dimethylformamide (200 mL), 4-benzyloxy-benzylamine described in Preparation Example 1 (1.25 g, 5.9 mmol) was added thereto, and the solution was stirred at room temperature for 16 hours. After the reaction was completed, the reaction solution was poured into brine, and the solution was extracted with ethyl acetate. The organic layer was dried over anhydrous magnesium sulfate, then concentrated, the obtained residue was purified by NH silica gel column chromatography (ethyl acetate:hexane=2:1, then ethyl acetate), the resulting solid was washed with solvent (chloroform:ethyl acetate=2:1), and the title compound (0.37 g, 1.1 mmol, 27%) was obtained.

$^1$H-NMR Spectrum (DMSO-d$_6$) δ(ppm): 4.29 (2H, d, J=6.0 Hz), 5.07 (2H, s), 5.66 (1H, d, J=8.4 Hz), 6.06 (2H, br s), 6.91-6.97 (4H, m), 7.19 (2H, d, J=8.8 Hz), 7.29-7.45 (5H, m), 7.65 (1H, d, J=8.4 Hz), 8.27 (1H, t, J=6.0 Hz).

Example A-11

2,6-Diamino-N-(4-(2-fluoro-benzyloxy)-benzyl)-nicotinamide 2,6-Diamino-nicotinic acid described in Preparation Example A-15 (200 mg, 1.3 mmol), triethylamine (0.54 mL, 3.87 mmol) and benzotriazol-1-yloxytris(dimethylamino) phosphonium hexafluorophosphate (862 mg, 1.95 mmol) were added to N,N-dimethylformamide (20 mL), and the solution was stirred at room temperature for 20 minutes. Next, 4 (2-fluoro-benzyloxy)-benzylamine described in Preparation Example 154 (453 mg, 1.96 mmol) was added thereto, and the solution was stirred at room temperature for 14 hours. After the reaction was completed, the reaction solution was poured into brine, the solution was extracted with ethyl acetate, the fractionated organic layer was dried over anhydrous magnesium sulfate and then concentrated. The obtained residue was subjected to silica gel column chromatography, eluted with solvent (ethyl acetate) and the title compound (147 mg, 0.40 mmol, 31%) was obtained.

$^1$H-NMR Spectrum (DMSO-d$_6$) δ(ppm): 4.30 (2H, d, J=6.0 Hz), 5.11 (2H, s), 5.67 (1H, d, J=8.8 Hz), 6.06 (2H, br s), 6.89-7.02 (4H, m), 7.16-7.28 (4H, m), 7.37-7.44 (1H, m), 7.51-7.56 (1H, m), 7.66 (1H, d, J=8.8 Hz), 8.28 (1H, t, J=6.0 Hz).

Example A-12

2,6-Diamino-N-(4-(pyridin-2-ylmethoxy)-benzyl)-nicotinamide $^1$H-NMR Spectrum (DMSO-d$_6$) δ(ppm): 4.29 (2H, d, J=6.0 Hz), 5.15 (2H, s), 5.66 (1H, d, J=8.8 Hz), 6.06 (2H, br s), 6.91-6.98 (4H, m), 7.17-7.23 (2H, m), 7.31-7.35 (1H, m), 7.49 (1H, d, J=7.6 Hz), 7.65 (1H, d, J=8.8 Hz), 7.82 (1H, dt, J=2.0, 7.6 Hz), 8.28 (1H, t, J=6.0 Hz), 8.55-8.58 (1H, m).

Example A-13

2,6-Diamino-N-(4-phenoxymethyl-benzyl)-nicotinamide $^1$H-NMR Spectrum (CDCl$_3$) δ(ppm): 4.51 (2H, brs), 4.57 (2H, d, J=5.6 Hz), 5.06 (2H, s), 5.77 (1H, d, J=8.4 Hz), 6.04 (1H, brs), 6.45 (2H, brs), 6.96-6.98 (3H, m), 7.28-7.31 (3H, m), 7.34-7.43 (4H, m).

Example A-14

2,6-Diamino-N-(4-(thiophen-3-ylmethoxy)-benzyl)-nicotinamide $^1$H-NMR Spectrum (DMSO-d$_6$) δ(ppm): 4.28 (2H, d, J=6.0 Hz), 5.04 (2H, s), 5.65 (1H, d, J=8.4 Hz), 6.05 (2H, br s), 6.89-6.99 (4H, m), 7.13-7.21 (3H, m), 7.51-7.55 (2H, m), 7.64 (1H, d, J=8.4 Hz), 8.26 (1H, t, J=6.0 Hz).

Example A-15

2-amino-N-(4-(2-nitro benzyloxy)-benzyl)-nicotinamide

To a solution of sodium 4-(((2-aminopyridin-3-carbonyl)-amino)-methyl)-phenolate described in Preparation Example A+-1 (100 mg, 0.377 mmol) in N,N-dimethylformamide (2.5 mL) was added O-Nitrobenzyl chloride (65 mg, 0.379 mmol), and the solution was stirred at room temperature for 2 hours. Ethyl acetate and water were added to the reaction solution, which was then partitioned, the organic layer was washed with water and dried over anhydrous magnesium sulfate. The residue was purified by silica gel column chromatography (hexane:ethyl acetate), and the title compound (51 mg, 37%) was obtained as a white solid.

$^1$H-NMR Spectrum (CDCl$_3$) δ(ppm): 4.55 (2H, d, J=5.6 Hz), 5.50 (2H, s), 6.23 (1H, brs), 6.39 (2H, brs), 6.57-6.60 (1H, m), 6.98 (2H, d, J=8.6 Hz), 7.30 (2H, d, J=8.6 Hz), 7.50-7.52 (1H, m), 7.58-7.60 (1H, m), 7.67-7.71 (1H, m), 7.87-7.89 (1H, m), 8.15-8.18 (2H, m).

Example A-16

2-Amino-N-(4-(2-amino-benzyloxy)-benzyl)-nicotinamide

2-Amino-N-(4-(2-nitrobenzyloxy)-benzyl)-nicotinamide described in Example A-15 was dissolved in a mixture solvent of ethanol-tetrahydrofuran-water (3:1:1.5), iron powder (4 mg) and ammonium chloride (85 mg) were added thereto, and the solution was stirred overnight under reflux. In addition, iron powder (10 mg) and ammonium chloride (20 mg) were added, and the solution was stirred under reflux for 2 hours. The reaction solution was allowed to room temperature, filtered through Celite pad to remove insoluble matter, and the filtrate was concentrated in vacuo. The residue was purified by NH silica gel chromatography (hexane:ethyl acetate), and the title compound (9 mg, 98%) was obtained as a pale brown solid.

$^1$H-NMR Spectrum (CDCl$_3$) δ(ppm): 4.53 (2H, d, J=5.6 Hz), 5.04 (2H, s), 6.24 (1H, brs), 6.51 (2H, brs), 6.57-6.60 (1H, m), 6.72-6.79 (2H, m), 6.99 (2H, d, J=8.4 Hz), 7.16-7.20 (2H, m), 7.28 (2H, d, J=8.4 Hz), 7.58-7.60 (1H, m), 8.13-8.14 (1H, m).

Example A-17

2-Amino-N-(4-benzyloxy-benzyl)-nicotinamide

The title compound (257 mg, 0.771 mmol, 72%) was obtained from 2-aminonicotinic acid (148 mg, 1.07 mmol) and 4-benzyloxy-benzylamine described in Preparation Example 1 (251 mg, 1.18 mmol) according to an analogous method to Example H-1.

$^1$H-NMR Spectrum (DMSO-d$_6$) δ(ppm): 4.34 (2H, d, J=6.0 Hz), 5.06 (2H, s), 6.55 (1H, dd, J=4.8, 7.6 Hz), 6.94 (2H, d, J=8.0 Hz), 7.03 (2H, brs), 7.20 (2H, d, J=8.0 Hz), 7.29 (1H, t, J=6.4 Hz), 7.36 (2H, dd, J=6.4, 6.8 Hz), 7.41 (2H, d, J=6.8 Hz), 7.90 (1H, d, J=7.6 Hz), 8.05 (1H, d, J=4.8 Hz), 8.88 (1H, t, J=6.0 Hz).

Example A-18

2-Amino-N-(3-phenoxy-benzyl)-nicotinamide

The title compound (87 mg, 0.27 mmol, 26%) was obtained from 2-aminonicotinic acid (144 mg, 1.04 mmol) and 3-phenoxy-benzylamine described in Preparation Example 4 (228 mg, 1.15 mmol) according to an analogous method to Example H-1.

$^1$H-NMR Spectrum (DMSO-d$_6$) δ(ppm): 4.40 (2H, d, J=5.6 Hz), 6.56 (1H, dd, J=4.8, 7.6 Hz), 6.85 (1H, dd, J=1.2, 8.0Hz), 6.92-7.05 (5H, m), 7.06 (1H, d, J=7.6 Hz), 7.11 (1H, dd, J=7.6, 8.0 Hz), 7.29-7.40 (3H, m), 7.89 (1H, dd, J=2.0, 7.6 Hz), 8.06 (1H, dd, J=2.0, 4.8 Hz), 8.96 (1H, t, J=5.6 Hz).

Example A-19

2-Amino-N-(4-(3-fluoro-benzyloxy)-benzyl)-nicotinamide

The title compound (172 mg, 0.489 mmol, 40%) was obtained from 2-aminonicotinic acid (170 mg, 1.23 mmol) and 4-(3-fluoro-benzyloxy)-benzylamine described in Preparation Example 6 (312 mg, 1.35 mmol) according to an analogous method to Example H-1.

$^1$H-NMR Spectrum (DMSO-d$_6$) δ(ppm): 4.35 (2H, d, J=6.0 Hz), 5.10 (2H, s), 6.45-6.60 (1H, m), 6.85-7.46 (10H, m), 7.85-7.92 (1H, m), 8.03-8.07 (1H, m), 8.75-8.92 (1H, m).

Example A-20

2-Amino-N-(4-(2-fluoro-benzyloxy)-benzyl)-nicotinamide

The title compound (67 mg, 0.19 mmol, 45%) was obtained from 2-aminonicotinic acid (58 mg, 0.42 mmol) and 4-(2-fluoro-benzyloxy)-benzylamine described in Preparation Example 154 (117 mg, 0.506 mmol) according to an analogous method to Example H-1 (with the proviso that only the reaction temperature was changed to 60° C.).

$^1$H-NMR Spectrum (DMSO-d$_6$) δ(ppm): 4.34 (2H, d, J=6.0 Hz), 5.10 (2H, s), 6.56 (1H, dd, J=4.8, 7.6 Hz), 6.90-7.00 (2H, m), 7.04 (2H, brs), 7.15-7.28 (4H, m), 7.35-7.44 (1H, m), 7.50-7.58 (1H, m), 7.90 (1H, dd, J=1.2, 7.6 Hz), 8.05 (1H, dd, J=1.2, 4.8 Hz), 8.86-8.95 (1H, m).

Example A-21

2-Amino-N-(4-(4-fluoro-benzyloxy)-benzyl)-nicotinamide

The title compound (187 mg, 0.532 mmol, 96%) was obtained from 2-aminonicotinic acid (77 mg, 0.56 mmol) and 4-(4fluoro-benzyloxy)-benzylamine described in Preparation Example 155 (155 mg, 0.670 mmol) according to an analogous method to Example H-1 (with the proviso that only the reaction temperature was changed to 60° C.).

$^1$H-NMR Spectrum (DMSO-d$_6$) δ(ppm): 4.34 (2H, d, J=5.6 Hz), 5.04 (2H, s), 6.56 (1H, dd, J=5.2, 8.0 Hz), 6.94 (2H, d, J=8.4 Hz), 7.03 (2H, brs), 7.12-7.25 (4H, m), 7.46 (2H, dd, J=6.0, 8.4 Hz), 7.90 (1H, d, J=8.0 Hz), 8.05 (1H, d, J=5.2 Hz), 8.88 (1H, t, J=5.6 Hz).

Example A-22

2-Amino-N-(4-benzyloxy-benzyl)-thionicotinamide

A mixture of 2-amino-N-(4-benzyloxy-benzyl)-nicotinamide described in Example A-17 (220 mg, 0.67 mmol), 2,4-bis(4-methoxyphenyl)-1,3-dithia-2,4-diphosphetane-2,4-disulphide (Lawesson's reagent) (670 mg, 1.7 mmol) and toluene (8 mL) was stirred at 80° C. for 15 minutes, then, refluxed for 45 minutes. After cooling, the precipitate was filtered, and the filtrate was evaporated in vacuo. Purification was carried out by NH silica gel column chromatography (ethyl acetate), and the title compound (28 mg, 0.080 mmol, 12%) was obtained as a pale yellow oil.

$^1$H-NMR Spectrum (CDCl$_3$) δ(ppm): 4.87 (2H, d, J=4.9 Hz), 5.08 (2H, s), 5.88 (2H, brs), 6.62 (1H, dd, J=4.9, 7.5 Hz), 6.98 (2H, d, J=8.6 Hz), 7.30 (2H, d, J=8.6 Hz), 7.32-7.44 (6H, m), 7.71 (1H, brs), 8.07 (1H, dd, J=1.7, 4.9 Hz).

Example A-23

2-Amino-N-(3-(2-butynyloxy)benzyl)-nicotinamide

Trifluoroacetic acid salt of the title compound (10 mg, 0.024 mmol, 49%) was obtained from 2-amino-N-(3-hydroxybenzyl)-nicotinamide described in Preparation Example A+-17 (12 mg, 0.050 mmol) and 1-bromo-2-butyne (6.6 mg, 0.050 mmol) according to an analogous method to Example E-43.

MS m/e (ESI) 296.3 (MH$^+$)

Example A-24

2-Amino-N-(4-benzylaminobenzyl)-6-chloro-nicotinamide

To a solution of (4-aminomethylphenyl)-benzylamine described in Preparation Example 19 (369 mg, 1.74 mmol) and 2-amino-6-chloro-nicotinic acid (300 mg, 1.74 mmol) in N,N-dimethylformamide (10 mL) were added benzotriazol-1-yloxytris(dimethylamino)phosphonium hexafluorophosphate (924 mg, 2.09 mmol) and triethylamine (0.49 mL, 3.48 mmol), and the solution was stirred overnight at room temperature. Ethyl acetate and water were added to the reaction solution, which was then partitioned, the organic layer was washed with water, and then, dried over anhydrous magnesium sulfate. The solvent was evaporated, the residue was purified by silica gel column chromatography (hexane:ethyl acetate), and the title compound (310 mg, 49%) was obtained as a pale yellow solid.

$^1$H-NMR Spectrum (CDCl$_3$) δ(ppm): 4.32-4.34 (3H, m), 4.45 (2H, d, J=5.6 Hz), 6.07 (1H, brs), 6.54-6.63 (5H, m), 7.03 (1H, dd, J=2.4, J=8.4 Hz), 7.14 (2H, d, J=8.4 Hz), 7.35-7.36 (4H, m), 7.48 (1H, d, J=8.0 Hz).

Example A-25

2-Amino-6-chloro-N-(4-phenylamino-benzyl)-nicotinamide

To a solution of (4-aminomethyl-phenyl)-phenylamine described in Preparation Example 20 (345 mg, 1.74 mmol) and 2-amino-6-chloro-nicotinic acid (300 mg, 1.74 mmol) in N,N-dimethylformamide (10 mL) were benzotriazol-1-yloxytris(dimethylamino)phosphonium hexafluorophosphate (924 mg, 2.09 mmol) and triethylamine (0.49 mL, 3.48 mmol), and the solution was stirred overnight at room temperature. Ethyl acetate and water were added to the reaction solution, which was then partitioned, the organic layer was washed with water, and then, dried over anhydrous magnesium sulfate. The solvent was evaporated, the residue was purified by silica gel column chromatography (hexane:ethyl acetate), and the title compound (360 mg, 59%) was obtained as a pale yellow solid.

$^1$H-NMR Spectrum (CDCl$_3$) δ(ppm): 4.51 (2H, d, J=5.2 Hz), 5.74 (1H, s), 6.16 (1H, brs), 6.57 (1H, d, J=8.0 Hz), 6.58 (2H, s), 6.94-6.97 (1H, m), 7.04-7.09 (4H, m), 7.21-7.30 (4H, m), 7.52 (1H, d, J=8.0 Hz).

Example A-26

2-Amino-6-chloro-N-(4-phenylaminomethyl-benzyl)-nicotinamide

To a solution of (4-aminomethyl-benzyl)-phenylamine described in Preparation Example 21 (369 mg, 1.74 mmol) and 2-amino-6-chloro-nicotinic acid (300 mg, 1.74 mmol) in N,N-dimethylformamide (10 mL) were added benzotriazol-1-yloxytris(dimethylamino)phosphonium hexafluorophosphate (924 mg, 2.09 mmol) and triethylamine (0.49 mL, 3.48 mmol), and the solution was stirred overnight at room temperature. Ethyl acetate and water were added to the reaction solution, which was then partitioned, the organic layer was washed with water, and then, dried over anhydrous magnesium sulfate. The solvent was evaporated, the residue was purified by silica gel column chromatography (hexane:ethyl acetate), and the title compound (479 mg, 75%) was obtained as a pale yellow solid.

$^1$H-NMR Spectrum (CDCl$_3$) δ(ppm): 4.08 (1H, brs), 4.31 (2H, s), 4.57 (2H, d, J=5.6 Hz), 6.21 (1H, brs), 6.57 (1H, d, J=8.0 Hz), 6.58 (2H, s), 6.61-6.63 (2H, m), 6.70-6.74 (1H, m), 7.15-7.19 (2H, m), 7.30 (2H, d, J=8.0 Hz), 7.37 (2H, d, J=8.0 Hz), 7.51 (1H, d, J=8.0 Hz).

Example A-27

2-Amino-6-chloro-N-(4-benzyloxy-benzyl)-nicotinamide

2-Amino-6chloro-nicotinic acid described in Preparation Example A-1 (220 mg, 1.4 mmol), triethylamine (0.47 mL, 3.37 mmol) and benzotriazol-1-yloxytris(dimethylamino) phosphonium hexafluorophosphate (764 mg, 1.73 mmol) were dissolved in N,N-dimethylformamide (3 mL), 4-benzyloxy-benzylamine described in Preparation Example 1 (399 mg, 1.87 mmol) was added thereto, followed by stirring at room temperature for 17 hours 30 minutes. After the reaction was completed, the reaction solution was poured into brine, which was then extracted with ethyl acetate. The organic layer was dried over anhydrous magnesium sulfate, then concentrated, the obtained residue was purified by silica gel column chromatography (ethyl acetate:hexane=1:1), and the title compound (115 mg, 0.31 mmol, 22%) was obtained.

$^1$H-NMR Spectrum (DMSO-$d_6$) δ(ppm): 4.35 (2H, d, J=6.0 Hz), 5.08 (2H, s), 6.63 (1H, d, J=8.0 Hz), 6.94-6.98 (2H, m), 7.23 (2H, d, J=8.4 Hz), 7.29-7.45 (5H, m), 7.52 (2H, brs), 7.97 (1H, d, J=8.0 Hz), 8.96 (1H, t, J=6.0 Hz).

Example A-28

2-Amino-N-(4-benzyloxy-benzyl)-6-cyclopropylamino-nicotinamide

2-Amino-6-chloro-N-(4-benzyloxy-benzyl)-nicotinamide described in Example A-27 (80 mg, 0.22 mmol) was dissolved in tetrahydrofuran (3 mL), cyclopropylamine (0.3 mL, 4.3 mmol) was added thereto, and the solution was heated in a sealed tube for 16 hours (oil bath temperature: 140° C.). The reaction solution was allowed to room temperature, the solution was concentrated, the obtained residue was purified by NH silica gel column chromatography (ethyl acetate:hexane=2:1), and the title compound (12 mg, 0.031 mmol, 14%) was obtained.

$^1$H-NMR Spectrum (CDCl$_3$) δ(ppm): 0.52-0.58 (2H, m), 0.74-0.81 (2H, m), 2.47-2.56 (1H, m), 4.45 (2H, d, J=5.2 Hz), 5.07 (2H, s), 5.02 (1H, brs), 5.96-6.01 (1H, m), 6.04 (1H, d, J=8.4 Hz), 6.39 (2H, brs), 6.95 (2H, d, J=8.8 Hz), 7.23-7.45 (8H, m).

Example A-29

2-Amino-N-(4-benzyloxy-benzyl)-6-ethoxy-nicotinamide

Sodium hydride (70 mg, 1.7 mmol, 60% in oil), catalytic amount of copper(I) iodide, 2-amino-6-chloronicotinic acid described in Preparation Example A-4 (30 mg, 0.17 mmol) were added sequentially to ethanol (0.5 mL), the solution was stirred at 110° C. for 3 hours, then, stirred overnight at 80° C. After cooling to room temperature, water, diethyl ether and an aqueous solution of 29% ammonia were added to the reaction solution, which was then partitioned, and the aqueous layer was neutralized with citric acid. Dichloromethane was added to the aqueous layer, the organic layer was partitioned, washed with brine, then, the solvent was evaporated in vacuo. Trifluoroacetic acid salt of the title compound (3.4 mg, 0.0069 mmol, 14%) was obtained from a portion (10 mg) of the residue (35 mg) and 4-benzyloxybenzylamine (10 mg, 0.047 mmol) according to an analogous method to Example Q-6.

MS m/e (ESI) 378.5 (MH$^+$)

Example A-30

(6-amino-5-(4-benzyloxy-benzylcarbamoyl)-pyridin-2-ylamino)-acetic acid

Glycine (935 mg, 12.5 mmol) and 1,8-diazabicyclo[5,4,0]undec-7-ene (1.86 mL, 12.5 mmol) were added to 2-amino-N-(4-benzyloxy-benzyl)-6-chloro-nicotinamide described in Preparation Example A+-18 (454 mg, 1.25 mmol) under nitrogen atmosphere, and the solution was stirred for 6 hours at 130° C. Dimethylsulfoxide (35 mL) was added to the reaction mixture, which was then filtered with polytetrafluoroethylene membrane filter (Whatman Inc), the filtrate was purified by reverse phase high performance liquid chromatography (acetonitrile-water mobile phase (containing 0.1% trifluoroacetic acid) was used), and the title compound (287 mg, 0.551 mmol, 44%) was obtained.

MS m/e (ESI) 406.91 (MH$^+$)

$^1$H-NMR Spectrum (DMSO-$d_6$) δ(ppm): 3.82-4.00 (2H, m), 4.29 (2H, d, J=6.0 Hz), 5.06 (2H, s), 5.77-5.88 (1H, m), 6.93 (2H, d, J=8.8 Hz), 7.18 (2H, d, J=8.8 Hz), 7.28-7.42 (5H, m), 7.68-7.80 (1H, m).

Example A-31

2-Amino-6-methoxymethyl-N-(4-(pyridin-2-ylmethoxy)-benzyl)-nicotinamide

To a solution of 2-amino-6-methoxymethyl-nicotinic acid described in Preparation Example A-11 (100 mg, 0.55 mmol) and 4-(pyridin-2-ylmethoxy)-benzylamine described in Preparation Example 171 (170 mg, 0.82 mmol) in N,N-dimethylformamide (5 mL) were added benzotriazol-1-yloxytris(dimethylamino)phosphonium hexafluorophosphate (290 mg, 0.66 mmol) and triethylamine (0.23 mL, 1.7 mmol), and the solution was stirred overnight at room temperature. Ethyl acetate and water were added to the reaction solution for extraction, the organic layer was washed with brine, then, the solvent was evaporated in vacuo. The residue was purified by silica gel column chromatography (heptane:ethyl acetate=1:2), and the title compound (150 mg, 0.40 mmol, 73%) was obtained as a colorless solid.

$^1$H-NMR Spectrum (DMSO-$d_6$) δ(ppm): 3.32 (3H, s), 4.27 (2H, s), 4.33 (2H, d, J=5.9 Hz), 5.14 (2H, s), 6.58 (1H, d, J=7.9 Hz), 6.96 (2H, d, J=8.6 Hz), 7.10 (2H, br s), 7.22 (2H, d, J=8.6 Hz), 7.31 (1H, ddd, J=7.5, 4.8, 1.1 Hz), 7.47 (1H, d, J=7.9 Hz), 7.80 (1H, td, J=7.6, 1.8 Hz), 7.94 (1H, d, J=8.1 Hz), 8.54-8.56 (1H, m), 8.87 (1H, t, J=5.9 Hz).

Example A-32

2-Amino-N-(4-(4-fluoro-benzyloxy)-benzyl)-6-methoxymethyl-nicotinamide

To a solution of 2-amino-6-methoxymethyl-nicotinic acid described in Preparation Example A-11 (10 mg, 0.055 mmol) and 4-(4-fluoro-benzyloxy)-benzylamine described in Preparation Example 155 (19 mg, 0.082 mmol) in N,N-dimethylformamide (1 mL) were added benzotriazol-1-yloxytris(dimethylamino)phosphonium hexafluorophosphate (29 mg, 0.066 mmol) and triethylamine (0.022 mL, 0.16 mmol), and the solution was stirred overnight at room temperature. Water was added to the reaction solution, the precipitated solid was filtered, and the title compound (13 mg, 0.033 mmol, 60%) was obtained as a colorless solid.

$^1$H-NMR Spectrum (DMSO-$d_6$) δ(ppm): 3.32 (3H, s), 4.27 (2H, s), 4.33 (2H, d, J=5.9 Hz), 5.04 (2H, s), 6.58 (1H, d, J=7.9 Hz), 6.94 (2H, d, J=8.8 Hz), 7.09 (2H, br s), 7.16-7.22 (4H, m), 7.46 (2H, dd, J=8.7, 5.6 Hz), 7.93 (1H, d, J=8.1 Hz), 8.85-8.88 (1H, m).

Example A-33

2-Amino-N-(4-benzyloxy-benzyl)-6-methoxymethyl-nicotinamide

MS m/e (ESI) 378 (MH$^+$)

Example A-34

2-Amino-6-methoxymethyl-N-(4-(pyridin-2-yloxymethyl)-benzyl)-nicotinamide $^1$H-NMR Spectrum (CDCl$_3$) δ(ppm): 3.46 (3H, s), 4.40 (2H, s), 4.60 (2H, d, J=5.6 Hz), 5.38 (2H, s), 6.25 (1H, brs), 6.40 (2H, brs), 6.68-6.70 (1H, m), 6.77-6.81 (1H, m), 6.87-6.91 (1H, m), 7.35-7.37 (2H, m), 7.46-7.48 (2H, m), 7.57-7.61 (2H, m), 8.16-8.18 (1H, m).

Example A-35

2-Amino-N-(4-(3-fluoro-benzyloxy)-benzyl)-6-methoxymethyl-nicotinamide

MS m/e (ESI) 396 (MH$^+$)

Example A-36

2-Amino-N-(4-benzyloxy-benzyl)-6-(3-methoxypropoxy)-nicotinamide

Trifluoroacetic acid salt of the title compound (0.65 mg, 0.0012 mmol, 2.4%) was obtained from 2-amino-6-chloronicotinic acid described in Preparation Example A-4 (8.6 mg, 0.050 mmol) and 3-methoxypropanol (0.5 mL) according to an analogous method to Example A-29.

MS m/e (ESI) 422.5 (MH$^+$)

Example A-37

2-Amino-N-(4-benzyloxy-benzyl)-6-methyl-nicotinamide

Trifluoroacetic acid salt of the title compound (0.38 mg, 0.00082 mmol, 4.6%) was obtained from 2-amino-N-(4-benzyloxy-benzyl)-6-chloro-nicotinamide described in Preparation Example A+-18 (6.5 mg, 0.018 mmol) and methylmagnesium bromide (0.93M tetrahydrofuran solution, 0.12 mL, 0.11 mmol) according to an analogous method to Example E-40.

MS m/e (ESI) 348.5 (MH$^+$)

Example A-38

2-Amino-N-(4-benzyloxy-benzyl)-6-propoxy-nicotinamide

Trifluoroacetic acid salt of the title compound (1.5 mg, 0.0030 mmol, 5.9%) was obtained from 2-amino-6-chloronicotinic acid described in Preparation Example A-4 (8.6 mg, 0.050 mmol) and propanol (0.5 mL) according to an analogous method to Example A-29.

MS m/e (ESI) 406.6 (MH$^+$)

Example A-39

6-Amino-N-(4-benzyloxybenzyl)-nicotinamide

Trifluoroacetic acid salt of the title compound (7.1 mg, 0.016 mmol, 32%) was obtained from 4-benzyloxybenzylamine described in Preparation Example 1 (11 mg, 0.050 mmol) and 6-aminonicotinic acid (6.9 mg, 0.050 mmol) according to an analogous method to Example Q-6.

MS m/e (ESI) 334.3 (MH$^+$)

Example A-40

6-Amino-N-(3-phenoxybenzyl)-nicotinamide

Trifluoroacetic acid salt of the title compound (16 mg, 0.037 mmol, 74%) was obtained from 3-phenoxybenzylamine described in Preparation Example 4 (10 mg, 0.050 mmol) and 6-aminonicotinic acid (6.9 mg, 0.050 mmol) according to an analogous method to Example Q-6.

MS m/e (ESI) 320.2 (MH$^+$)

Example A-41

6-Chloro-N-(3-phenoxy-benzyl)-nicotinamide

The title compound (240 mg, 0.71 mmol, 61%) was obtained as a white solid from 3-phenoxy-benzylamine described in Preparation Example 4 (230 mg, 1.1 mmol) and 6-chloronicotinic acid (180 mg, 1.1 mmol) according to an analogous method to Example Q-6.

$^1$H-NMR Spectrum (CDCl$_3$) δ(ppm): 4.63 (2H, d, J=5.7 Hz), 6.42 (1H, brs), 6.94 (1H, dd, J=1.8, 8.1 Hz), 6.98-7.03 (3H, m), 7.08 (1H, d, J=7.5 Hz), 7.11-7.15 (1H, m), 7.30-7.37 (3H, m), 7.41-7.43 (1H, m), 8.09 (1H, dd, J=2.6, 8.2 Hz), 8.74 (1H, d, J=2.2 Hz).

Example A-42

N-(4-Benzyloxy-benzyl)-6-methylamino-nicotinamide

The title compound (71 mg, 0.19 mmol, 88%) was obtained as a white solid from N-(4-benzyloxy-benzyl)-6-(ethoxymethyl-amino)-nicotinamide described in Preparation Example A+-8 (90 mg, 0.22 mmol) according to an analogous method to Example A-163.

$^1$H-NMR Spectrum (CDCl$_3$) δ(ppm): 2.96 (3H, s), 4.56 (2H, d, J=5.5 Hz), 5.07 (2H, s), 6.12 (1H, brs), 6.38 (1H, d, J=8.8 Hz), 6.96 (2H, d, J=8.8 Hz), 7.22-7.34 (4H, m), 7.36-7.44 (3H, m), 7.89 (1H, dd, J=2.4, 8.6 Hz), 8.50 (1H, d, J=2.4 Hz).

Example A-43

N-(4benzyloxybenzyl)-nicotinamide

The title compound (8.5 mg, 0.027 mmol, 33%) was obtained as a white solid from 4-benzyloxybenzylamine described in Preparation Example 1 (26 mg, 0.12 mmol) and nicotinic acid (10 mg, 0.081 mmol) according to an analogous method to Example Q-6.

$^1$H-NMR Spectrum (CDCl$_3$) δ(ppm): 4.59 (2H, d, J=5.5 Hz), 5.07 (2H, s), 6.41 (1H, brs), 6.97 (2H, d, J=8.6 Hz), 7.29 (2H, d, J=8.6 Hz), 7.32-7.44 (6H, m), 8.11-8.14 (1H, m), 8.71 (1H, dd, J=1.5, 4.8 Hz), 8.96 (1H, d, J=1.8 Hz).

Example A-44

2-Amino-N-(4-benzyloxy-3-hydroxy-benzyl)-nicotinamide

To a solution of 4-benzyloxy-3-methoxymethoxy-benzonitrile obtained in Preparation Example 132 (100 mg, 0.371 mmol) in tetrahydrofuran (5 mL) was added lithium aluminum hydride (75 mg, 1.98 mmol) portionwise under nitrogen atmosphere on an ice bath, the solution was stirred for 24 hours. In addition, lithium aluminum hydride (75 mg, 1.98 mmol) was added portionwise on an ice bath, then, the solution was stirred at 50-60° C. for 3 hours. Ethyl acetate (10 mL) and methanol (5 mL) were added little by little to the reaction solution on an ice bath, then, NH silica gel (50 mL) was added, and a pale yellow oily residue (73 mg) was obtained by NH silica gel column chromatography (hexane: ethyl acetate=7:3). This residue was purified again by NH silica gel column chromatography (hexane:ethyl acetate=7:3), and 4-benzyloxy-3-methoxymethoxy-benzylamine (30 mg, 0.11 mmol, 30%) was obtained as a pale yellow oil.

Next, a solution of 2-amino-nicotinic acid (16 mg, 0.116 mmol), 4-benzyloxy-3-methoxymethoxy-benzylamine (15 mg, 0.0549 mmol), benzotriazol-1-yl-tris(dimethylamino) phosphonium hexafluorophosphate (55 mg, 0.124 mmol) and triethylamine (0.08 mL, 0.574 mmol) in dimethylsulfoxide (4 mL) was stirred under nitrogen atmosphere at room temperature for 24 hours. Water (100 mL) and brine (50 mL) were added to the reaction solution, which was then extracted with ethyl acetate (100 mL) twice, and washed with water twice. The organic layer was dried over anhydrous magnesium sulfate, which was then filtered, the filtrate was evaporated in vacuo, and 2-amino-N-(4-benzyloxy-3-methoxymethoxy-benzyl)-nicotinamide was obtained as a pale yellow oil. This was purified by NH silica gel column chromatography (hexane:ethyl acetate=1:1, then hexane:ethyl acetate=3:7), and 2-amino-N-(4-benzyloxy-3-methoxymethoxy-benzyl)-nicotinamide) (9.4 mg, 0.0239 mmol, 43.5%) was obtained as a pale yellow oil. A solution of the resulting 2-amino-N-(4-benzyloxy-3-methoxymethoxy-benzyl)-nicotinamide (7.8 mg, 0.0198 mmol) and 2M hydrochloric acid (2 mL) in methanol (3 mL) was stirred for 21 hour at room temperature. Sodium bicarbonate (600 mg, 7.14 mmol) was added to the reaction mixture to basify it, which was then filtered, evaporation in vacuo was carried out, then, the obtained residue was purified by thin layer NH silica gel chromatography (methanol:ethyl acetate=5:95), and the title compound (2.0 mg, 0.0057 mmol, 29%) was obtained as a white solid.

MS m/e (ESI) 350 (MH$^+$)

Example A-45

2-Amino-N-(6-benzyloxypyridin-3-ylmethyl)-6-methoxymethyl-nicotinamide $^1$H-NMR Spectrum (CDCl$_3$) δ(ppm): 3.45 (3H, s), 4.39 (2H, s), 4.53 (2H, d, J=5.6 Hz), 5.38 (2H, s), 6.23 (1H, brs), 6.39 (2H, brs), 6.69-6.71 (1H, m), 6.80-6.82 (1H, m), 7.30-7.33 (1H, m), 7.36-7.40 (2H, m), 7.57-7.59 (2H, m), 7.60-7.63 (2H, m), 8.15-8.15 (1H, m).

Example A-46

2,6-Diamino-N-(1-(3-fluoro-benzyl)-1H-pyrrol-3-ylmethyl)-nicotinamide

The title compound (6.2 mg, 0.018 mmol, 5.5%) was obtained from 2,6-diamino-nicotinic acid ethyl ester described in Preparation Example A-14 (60 mg, 0.33 mmol) and C-(1-(3-fluoro-benzyl)-1H-pyrrol-3-yl)-methylamine described in Preparation Example 59 (159 mg, 0.78 mmol) according to an analogous method to Example A-54.

$^1$H-NMR Spectrum (CDCl$_3$) δ(ppm): 4.40 (2H, d, J=4.8 Hz), 4.53 (2H, brs), 5.01 (2H, s), 5.76 (1H, d, J=8.4 Hz), 5.84-5.89 (1H, m), 6.17 (1H, t, J=2.0 Hz), 6.48 (2H, brs), 6.62-6.67 (2H, m), 6.78-6.82 (1H, m), 6.91-6.93 (1H, m), 6.98 (1H, dt, J=2.4, 8.4 Hz), 7.27-7.33 (1H, m), 7.36 (1H, d, J=8.4 Hz).

Example A-47

2-Amino-N-(1-(3-fluoro-benzyl)-1H-pyrrol-3-ylmethyl)nicotinamide

The title compound (106 mg, 0.327 mmol, 66.7%) was obtained as a white solid from C-(1-(3-fluoro-benzyl)-1H-pyrrol-3-yl)methylamine described in Preparation Example 59 (100 mg, 0.49 mmol) and 2-aminonicotinic acid (68 mg, 0.49 mmol) according to an analogous method to Example Q-6.

$^1$H-NMR Spectrum (DMSO-d$_6$) δ(ppm): 4.22 (2H, d, J=5.6 Hz), 5.03 (2H, s), 5.97-6.01 (1H, m), 6.50-6.55 (1H, m), 6.73 (2H, s), 6.95-7.10 (5H, m), 7.32-7.38 (1H, m), 7.83-7.88 (1H, m), 8.00-8.05 (1H, m), 8.63 (1H, t, J=5.6 Hz).

Example A-48

2-Amino-N-(1-(3-fluoro-benzyl)-1H-pyrrol-3-ylmethyl)-6-methylamino-nicotinamide

2-Amino-6-chloro-N-(1-(3-fluoro-benzyl)-1H-pyrrol-3-ylmethyl)-nicotinamide described in Preparation Example A+-5 (50 mg, 0.14 mmol) was dissolved in a mixture solution of dimethylsulfoxide (1 mL) and N,N-diisopropylethylamine (0.5 mL), methylamine (2.0 M tetrahydrofuran solution) (1 mL, 2 mmol) was added thereto, and the solution was heated in a sealed tube for 15 hours (oil bath temperature: 135° C.). The reaction mixture was allowed to room temperature, poured into brine, and the solution was extracted with ethyl acetate. The organic layer was dried over anhydrous magnesium sulfate then concentrated, the obtained residue was purified by NH silica gel column chromatography (ethyl acetate), and the title compound (7.3 mg, 0.021 mmol, 15%) was obtained.

$^1$H-NMR Spectrum (CDCl$_3$) δ(ppm): 2.88 (3H, d, J=5.2 Hz), 4.40 (2H, d, J=5.2 Hz), 4.58-4.66 (1H, m), 5.01 (2H, s), 5.66 (1H, J=8.8 Hz), 5.81-5.87 (1H, m), 6.17 (1H, t, J=2.4 Hz), 6.45 (2H, brs), 6.63 (1H, t, J=2.4 Hz), 6.66 (1H, brs), 6.78-6.83 (1H, m), 6.92 (1H, br d, J=7.2 Hz), 6.97 (1H, dt, J=2.4, 8.4 Hz), 7.27-7.33 (1H, m), 7.36 (1H, d, J=8.8 Hz).

Example A-49

N-(1-(3-Fluoro-benzyl)-1H-pyrrol-3-ylmethyl)-6-methyl-nicotinamide

The title compound (61 mg, 0.18 mmol, 65.1%) was obtained as a colorless oil from C-(1-(3-fluoro-benzyl)-1H-pyrrol-3-yl)methylamine described in Preparation Example 59 (60 mg, 0.29 mmol) and 6-methylnicotinic acid (40 mg, 0.29 mmol) according to an analogous method to Example Q-6.

$^1$H-NMR Spectrum (DMSO-d$_6$) δ(ppm): 2.48 (3H, s), 4.27 (2H, d, 5.6 Hz), 5.03 (2H, s), 5.99-6.02 (1H, m), 6.74-6.78 (2H, m), 6.96-7.10 (3H, m), 7.28-7.38 (2H, m), 8.06 (1H, dd, J=2.4, 8.0 Hz), 8.80 (1H, t, J=5.6 Hz), 8.87 (1H, d, J=2.4 Hz).

Example A-50

2-Amino-N-(2-phenoxy-thiazol-5-ylmethyl)-nicotinamide

The title compound (13.5 mg, 41 μmol, 87%) was obtained as a white solid from C-(2-phenoxy-thiazol-5-yl)-methylamine described in Preparation Example 117 (9.8 mg, 48 µmol) and 2-amino-nicotinic acid (7.9 mg, 58 µmol) according to an analogous method to Example A-26.

$^1$H-NMR Spectrum (DMSO-d$_6$) δ(ppm): 4.44 (2H, d, J=5.7 Hz), 6.55 (1H, dd, J=4.8, 7.7 Hz), 7.05 (2H, s), 7.18 (1H, s), 7.27-7.31 (3H, m), 7.45 (2H, t, J=8.2 Hz), 7.84 (1H, d, J=7.5 Hz), 8.06 (1H, d, J=4.6 Hz), 9.05 (1H, t, J=6.0 Hz).

Example A-51

2-((furan-2-ylmethyl)-amino)-N-(5-phenoxy-thiophen-2-ylmethyl)-nicotinamide

The title compound (2.29 mg, 0.0044 mmol, 4.4%) was obtained as a trifluoroacetic acid salt from 2-chloro-N-(5-phenoxy-thiophen-2-ylmethyl)-nicotinamide described in Preparation Example A+-7 (35 mg, 0.10 mmol) and furfurylamine (16 µl, 0.18 mmol) according to an analogous method to Example A-133.

MS m/e (ESI) 406.15 (MH$^+$)

Example A-52

4-((3-((5-Phenoxy-thiophen-2-ylmethyl)-carbamoyl)-pyridin-2-yl) amino)-methyl) benzoic acid The title compound (2.75 mg, 0.0048 mmol, 4.8%) was obtained as a trifluoroacetic acid salt from 2-chloro-N-(5-phenoxy-thiophen-2-ylmethyl)-nicotinamide described in Preparation Example A+-7 (36 mg, 0.10 mmol) and 4-(aminomethyl)benzoic acid (16 mg, 0.11 mmol) according to an analogous method to Example A-133.

MS m/e (ESI) 460.17 (MH$^+$)
$^1$H-NMR Spectrum (DMSO-d$_6$) δ(ppm): 4.50 (2H, d, J=6.0 Hz), 4.71 (2H, d, J=4.8 Hz), 6.51 (1H, d, J=3.6 Hz), 6.63 (1H, dd, J=4.8, 8.0 Hz), 6.79 (1H, d, J=3.6 Hz), 7.09 (2H, d, J=8.0 Hz), 7.09-7.19 (1H, m), 7.32-7.47 (4H, m), 7.87 (2H, d, J=7.6 Hz), 7.98 (1H, dd, J=0.8, 8.0 Hz), 8.13 (1H, dd, J=0.8, 4.8 Hz), 8.87 (1H, brs), 9.16-9.24 (1H, m).

Example A-53

2,6-Diamino-N-(5-(4-fluoro-phenoxy)-thiophen-2-ylmethyl)-nicotinamide

The title compound (180 mg, 0.50 mmol, 38.6%) was obtained as a white solid from C-(5-(4-fluoro-phenoxy)-thiophen-2-yl)-methylamine described in Preparation Example 28 (290 mg, 1.3 mmol) and 2,6-diaminonicotinic acid described in Preparation Example A-15 (200 mg, 1.3 mmol) according to an analogous method to Example Q-6.

$^1$H-NMR Spectrum (DMSO-d$_6$) δ(ppm): 4.40 (2H, d, J=5.6 Hz), 5.64-5.68 (1H, m), 6.10 (2H, s), 6.45-6.49 (1H, m), 6.70-6.74 (1H, m), 6.95 (2H, s), 7.10-7.18 (2H, m), 7.18-7.26 (2H, m), 7.60 (1H, d, J=8.0 Hz), 8.40 (1H, t, J=5.6 Hz).

Example A-54

2,6-diamino-N-(5-phenoxy-thiophene-2-ylmethyl)-nicotinamide

To a solution of 2,6-diamino-nicotinic acid ethyl ester described in Preparation Example A-14 (18 mg, 0.1 mmol) in ethanol (10 mL) was added 1N sodium hydroxide aqueous solution (5 mL), and the solution was stirred for 1 hour 10 minutes under reflux. After cooling the reaction solution, the solution was neutralized with 1N hydrochloric acid and concentrated. The resulting crude product was suspended in N,N-dimethylformamide (3 mL), triethylamine (0.02 mL, 0.15 mmol), benzotriazol-1-yloxytris(dimethylamino)phosphonium hexafluorophosphate (65 mg, 0.15 mmol) and C-(5-phenoxy-thiophen-2-yl)-methylamine described in Preparation Example 26 (30 mg, 0.15 mmol) were added thereto, followed by stirring at room temperature for 19 hours 40 minutes. After the reaction was completed, reaction solution was poured into brine, and the solution was extracted with ethyl acetate. The organic layer was dried over anhydrous magnesium sulfate then concentrated, the obtained residue was purified by NH silica gel column chromatography (ethyl acetate), and the title compound (8.7 mg, 0.025mol, 25%) was obtained.

$^1$H-NMR Spectrum (CDCl$_3$) δ(ppm): 4.58-4.61 (2H, m), 4.62 (2H, brs), 5.75 (1H, d, J=8.4 Hz), 6.21-6.27 (1H, m), 6.36-6.38 (1H, m), 6.45 (2H, brs), 6.69-6.72 (1H, m), 7.06-7.12 (3H, m), 7.28-7.34 (2H, m), 7.39 (1H, d, J=8.4 Hz).

Example A-55

2,6-Diamino-N-(5-benzyl-thiophen-2-ylmethyl)-nicotinamide

To a solution of 2,6-diaminonicotinic acid described in Preparation Example A-15 (173 mg, 1.13 mmol) in dimethylsulfoxide (15 mL) were added 1-ethyl-3-(3-dimethylaminopropyl)carbodiimide hydrochloride (433 mg, 2.26 mmol), 1-hydroxybenzotriazole (346 mg, 2.26 mmol) and C-(5-benzyl-thiophen-2-yl)-methylamine described in Preparation Example 42 (230 mg, 1.13 mmol), and the solution was stirred at room temperature fro 16 hours 30 minutes. The reaction solution was poured into brine, the solution was extracted with ethyl acetate, the organic layer was dried over anhydrous magnesium sulfate and then concentrated. The obtained residue was subjected to NH silica gel column chromatography, eluted with solvent (ethyl acetate) and the title compound (114 mg, 0.34 mmol, 30%) was obtained.

$^1$H-NMR Spectrum (CDCl$_3$) δ(ppm): 4.00 (2H, s), 4.53 (2H, d, J=5.6 Hz), 4.70 (2H, br s), 5.69 (1H, d, J=8.4 Hz), 6.39 (2H, br s), 6.55 (1H, d, J=3.2 Hz), 6.67-6.95 (2H, m), 7.09-7.25 (5H, m), 7.38 (1H, d, J=8.4 Hz).

Example A-56

2,6-Diamino-N-(5-benzyloxy-thiophen-2-ylmethyl)-nicotinamide

To a solution of 2,6-diaminonicotinic acid described in Preparation Example A-15 (109 mg, 0.71 mmol) in dimethylsulfoxide (10 mL) were added 1-ethyl-3-(3-dimethylaminopropyl)carbodiimide hydrochloride (272 mg, 1.42 mmol), 1-hydroxybenzotriazole (217 mg, 1.42 mmol) and C-(5-benzyloxy-thiophen-2-yl)methylamine described in Example E-76 (156 mg, 0.71 mmol), and the solution was stirred at room temperature for 14 hours. The reaction solution was poured into brine, extracted with ethyl acetate, the fractionated organic layer was dried over anhydrous magnesium sulfate and then concentrated. The obtained residue was subjected to NH silica gel column chromatography, eluted with solvent (ethyl acetate) and the title compound (157 mg, 0.44 mmol, 62%) was obtained.

$^1$H-NMR Spectrum (CDCl$_3$) δ(ppm): 4.53 (2H, d, J=5.2 Hz), 4.69 (2H. br s), 5.03 (2H, s), 5.76 (1H, d, J=8.8 Hz), 6.08 (1H, d, J=4.0 Hz), 6.46 (3H. br), 6.59 (1H, d, J=4.0 Hz), 7.31-7.44 (6H, m).

Example A-57

2,6-Diamino-(5-(3-fluoro-phenoxy)-thiophen-2-ylmethyl)-nicotinamide $^1$H-NMR Spectrum (CDCl3) δ(ppm): 4.42 (2H, d, J=6.0 Hz), 5.66 (1H, d, J=8.4 Hz), 6.11 (2H, brs), 6.55-6.59 (1H, m), 6.75 (1H, d, J=4.0 Hz), 6.90-7.02 (5H, m), 7.38-7.45 (1H, m), 7.60 (1H, d, J=8.4 Hz), 8.42 (1H, t, J=6.0 Hz).

Example A-58

2,6-Diamino-N-(5-benzofuran-2-ylmethyl-thiophen-2-ylmethyl)-nicotinamide $^1$H-NMR Spectrum (CDCl$_3$) δ(ppm): 4.29 (2H, s), 4.43 (2H, d, J=6.0 Hz), 5.64 (1H, d, J=8.4 Hz), 6.09 (2H, brs), 6.66 (1H, d, J=0.8 Hz), 6.92 (2H, s), 6.94 (2H, brs), 7.17-7.26 (2H, m), 7.47-7.64 (3H, m), 8.37 (1H, t, J=6.0 Hz).

Example A-59

2,6-Diamino-N-(5-benzo[b]thiophen-2-ylmethyl-thiophen-2-ylmethyl)-nicotinamide $^1$H-NMR Spectrum (CDCl$_3$) δ(ppm): 4.39 (2H, s), 4.44 (2H, d, J=5.6 Hz), 5.64 (1H, d, J=8.4 Hz), 6.09 (2H, brs), 6.78-6.84 (2H, m), 6.95 (2H, brs), 7.23-7.36 (3H. m), 7.59 (1H, d, J=8.4 Hz), 7.74 (1H, dd, J=0.8, J=6.0 Hz), 7.85 (1H, dd, J=0.8, J=6.0 Hz), 8.38 (1H, t, J=5.6 Hz).

Example A-60

N-(5-(3-Fluorophenoxy)thiophen-2-ylmethyl)-2,6-dimethylnicotinamide

The title compound (56 mg, 0.157 mmol, 47.6%) was obtained as a light brown solid from 2,6-dimethylnicotinic acid (50 mg, 0.33 mmol) and C-(5-(3-fluorophenoxy)thiophen-2-yl)methylamine described in Preparation Example 23 (66 mg, 0.297 mmol) according to an analogous method to Example Q-6.

$^1$H-NMR Spectrum (DMSO-d$_6$) δ(ppm): 2.44 (3H, s), 2.46 (3H, s), 4.51 (2H, d, J=5.6 Hz, 6.59-6.62 (1H, m), 6.80-6.84 (1H, m), 6.90-7.03 (3H, m), 7.12 (1H, d, J=8.0 Hz), 7.40-7.47 (1H, m), 7.60 (1H, d, J=8.0 Hz), 9.00 (1H, t, J=5.6 Hz).

Example A-61

2-Acetylamino-N-(5-phenoxy-thiophen-2-ylmethyl)-nicotinamide

To a mixture of 2-amino-N-(5-phenoxy-thiophen-2-ylmethyl)-nicotinamide described in Example A-67 (50 mg, 0.15 mmol), acetonitrile (5 mL) and tetrahydrofuran (2 mL) was added nitronium tetrafluoroborate (0.50M sulfolane solution, 0.46 mL, 0.23 mmol) on an ice bath, and the solution was stirred overnight at room temperature. Water, ethyl acetate, tetrahydrofuran and an aqueous solution of saturated sodium bicarbonate were added to the reaction solution for extraction, washed with brine, then, the solvent was evaporated in vacuo. The residue was purified by silica gel column chromatography (methanol:ethyl acetate=1:30), and the title compound (1.3 mg, 0.0035 mmol, 2.3%) was obtained as a white solid.

$^1$H-NMR Spectrum (CDCl$_3$) δ(ppm): 2.31 (3H, s), 4.67 (2H, d, J=5.5 Hz), 6.40 (1H, d, J=3.9 Hz), 6.60 (1H, brs), 6.77 (1H, d, J=3.7 Hz), 7.05 (1H, dd, J=4.9, 7.8 Hz), 7.08-7.14 (3H, m), 7.32-7.36 (2H, m), 7.84 (1H, brs), 8.51 (1H, brs).

Example A-62

2-Amino-N-(5-(3-cyano-phenoxy)-thiophen-2-ylmethyl)-nicotinamide

To a solution of C-(5-(3-bromophenoxy)-thiophen-2-yl)-methylamine described in Preparation Example 17 (366 mg, 1.29 mmol) and 2-aminopyridine-3-carboxylic acid (178 mg, 1.29 mmol) in tetrahydrofuran (5 mL) were added benzotriazol-1-yloxytris(dimethylamino)phosphonium hexafluorophosphate (685 mg, 1.55 mmol) and triethylamine (0.36 mL, 2.58 mmol), and the solution was stirred overnight at room temperature. Ethyl acetate and water were added to the reaction solution, which was then partitioned, the organic layer was washed with water, and then, dried over anhydrous magnesium sulfate. The solvent was evaporated, the residue was purified by NH silica gel column chromatography (hexane:ethyl acetate), and a mixture of 2-amino-N-(5-(3-bromophenoxy)-thiophen-2-ylmethyl)-nicotinamide and debrominated compound (344 mg, 66%) was obtained as a yellow solid.

Next, to a solution of a mixture of 2-amino-N-(5-(3-bromophenoxy)-thiophen-2-ylmethyl)-nicotinamide and debrominated compound (100 mg, 0.247 mmol) in N,N-dimethylformamide (3.0 mL) were added zinc cyanide (58 mg, 0.495 mmol) and tetrakis(triphenylphosphine)palladium(0) (285 mg, 0.247 mmol) under nitrogen atmosphere, and the solution was stirred at 140° C. from 3 hours and a half. The reaction solution was allowed to room temperature, ethyl acetate and water were added to the reaction solution, which was then partitioned, the organic layer was washed with water and dried over anhydrous magnesium sulfate. The solvent was evaporated, then, the residue was purified by NH silica gel column chromatography (hexane:ethyl acetate), and the title compound (9 mg, 10%) was obtained as a pale yellow oil.

$^1$H-NMR Spectrum (CDCl$_3$) δ(ppm): 4.69 (2H, d, J=6.0 Hz), 6.36 (2H, brs), 6.41 (1H, brs), 6.47-6.48 (1H, m), 6.59-6.62 (1H, m), 6.79-6.80 (1H, m), 7.31-7.34 (2H, m) 7.37-7.44 (2H, m), 7.61-7.63 (1H, m), 8.17-8.19 (1H, m).

Example A-64

2-Amino-N-(5-m-tolyloxy-thiophen-2-ylmethyl)-nicotinamide

The title compound (126 mg, 0.37 mmol, 80.8%) was obtained as a brown oil from 2-aminonicotinic acid (69 mg, 0.51 mmol) and C-(5-m-tolyloxy-thiophen-2-yl)-methylamine described in Preparation Example 30 (100 mg, 0.46 mmol) according to an analogous method to Example Q-6.

$^1$H-NMR Spectrum (DMSO-d$_6$) δ(ppm): 2.26 (3H, s), 4.46 (2H, d, J=5.6 Hz), 6.46 (1H, d, J=3.6 Hz), 6.55 (1H, dd, J=4.8, 8.0 Hz), 6.74 (1H, d, J=3.6 Hz), 6.84-6.96 (3H, m) 7.04 (2H, s), 7.22 (1H, dd, J=8.0, 8.0 Hz), 7.86 (1H, dd, J=1.6, 8.0 Hz), 8.05 (1H, dd, J=1.6, 4.8 Hz), 9.02 (1H, t, J=5.6 Hz).

Example A-65

2-Amino-N-(5-p-tolyloxy-thiophen-2-ylmethyl)nicotinamide

The title compound (72 mg, 0.212 mmol, 57.4%) was obtained as a light brown solid from 2-aminonicotinic acid (55 mg, 0.41 mmol) and C-(5-p-tolyloxythiophen-2-yl)methylamine described in Preparation Example 32 (80 mg, 0.37 mmol) according to an analogous method to Example Q-6.

$^1$H-NMR Spectrum (DMSO-$d_6$) δ(ppm): 2.24 (3H, s), 4.44 (2H, d, J=5.6 Hz), 6.40-6.44 (1H, m), 6.53-6.58 (1H, m), 6.72 (1H, d, J=3.6 Hz), 6.95-7.00 (2H, m), 7.04 (2H, s), 7.12-7.18 (2H, m), 7.85 (1H, d, J=7.6 Hz), 8.03-8.08 (1H, m), 9.01 (1H, t, J=5.6 Hz).

Example A-66

2-amino-4-(5-(3-chloro-benzyl)thiophene-2-ylmethyl)-nicotinamide

The title compound (63 mg, 0.176 mmol, 51.9%) was obtained as a white solid from 2-aminonicotinic acid (51 mg, 0.37 mmol) and G(5-(3-chloro-benzyl)thiophen-2-yl)-methylamine described in Preparation Example 45 (80 mg, 0.34 mmol) according to an analogous method to Example Q-6.

$^1$H-NMR Spectrum (DMSO-$d_6$) δ(ppm): 4.06 (2H, s), 4.47 (2H, d, J=5.6 Hz), 6.54 (1 H, dd, J=4.8, 7.6 Hz), 6.72 (1H, d, J=3.6 Hz), 6.80 (1H, d, J=3.6 Hz), 7.05 (2H, brs), 7.18-7.34 (4H, m), 7.84 (1H, dd, J=1.6, 7.6 Hz), 8.04 (1H, dd, J=1.6, 4.8 Hz), 8.98 (1H, t, J=5.6 Hz).

Example A-67

2-Amino-N-(5-phenoxy-thiophen-2-ylmethyl)-nicotinamide

The title compound (148 mg, 0.455 mmol, 73%) was obtained from 2-aminonicotinic acid (87 mg, 0.63 mmol) and C-(5-phenoxy-thiophen-2-yl)methylamine described in Preparation Example 24 (1.43 mg, 0.697 mmol) according to an analogous method to Example H-1.

$^1$H-NMR Spectrum (DMSO-$d_6$) δ(ppm): 4.46 (2H, d, J=5.6 Hz), 6.49 (1H, d, J=4.0 Hz), 6.55 (1H, dd, J=4.8, 7.6 Hz), 6.76 (1H, d, J=4.0 Hz), 7.00-7.17 (5H, m), 7.32-7.40 (2H, m), 7.87 (1H, dd, J=1.6, 7.6 Hz), 8.06 (1H, dd, J=1.6, 4.8 Hz), 9.00-9.09 (1H, m).

Example A-68

2-Amino-N-(5-(3-fluoro-phenoxy)-thiophen-2-ylmethyl)-nicotinamide

The title compound (112 mg, 0.326 mmol, 75%) was obtained from 2-aminonicotinic acid (60 mg, 0.43 mmol) and C-(5-(3-fluoro-phenoxy)-thiophen-2-yl)methylamine described in Preparation Example 23 (106 mg, 0.475 mmol) according to an analogous method to Example H-1.

$^1$H-NMR Spectrum (DMSO-$d_6$) δ(ppm): 4.48 (2H, d, J=5.2 Hz), 6.52-6.59 (2H, m), 6.79 (1H, d, J=2.8 Hz), 6.87-7.00 (3H, m), 7.06 (2H, brs), 7.34-7.45 (1H, m), 7.87 (1H dd, J=2.0, 7.6 Hz), 8.06 (1H, dd, J=2.0, 4.8 Hz), 9.05 (1H, t, J=5.2 Hz).

Example A-69

2-Amino-N-(5-(4fluoro-phenoxy)-thiophen-2-ylmethyl)-nicotinamide

The title compound (174 mg, 0.507 mmol, 65%) was obtained from 2-aminonicotinic acid (107 mg, 0.777 mmol) and C-(5-(4-fluoro-phenoxy)-thiophen-2-yl)methylamine described in Preparation Example 28 (191 mg, 0.856 mmol) according to an analogous method to Example H-1.

$^1$H-NMR Spectrum (DMSO-$d_6$) δ(ppm): 4.45 (2H, d, J=6.0 Hz), 6.46 (1H, d, J=4.0 Hz), 6.55 (1H, dd, J=4.8, 7.6 Hz), 6.74 (1H, d, J=4.0 Hz), 6.85-7.25 (6H, m), 7.86 (1H, d, J=7.6 Hz), 8.05 (1H, d, J=4.8 Hz), 8.96-9.08 (1H, m).

Example A-70

2-Amino-N-(5-benzyl-thiophen-2-ylmethyl)-nicotinamide

The title compound (67 mg, 0.21 mmol, 92%) was obtained from 2-aminonicotinic acid (31 mg, 0.224 mmol) and C-(5-benzyl-thiophen-2-yl)-methylamine described in Preparation Example 42 (50 mg, 0.245 mmol) according to an analogous method to Example H-1.

$^1$H-NMR Spectrum (DMSO-$d_6$) δ(ppm): 4.04 (2H, s), 4.46 (2H, d, J=5.2 Hz), 6.54 (1H, dd, J=4.8, 8.0 Hz), 6.69 (1H, d, J=3.6 Hz), 6.78 (1H, d, J=3.6 Hz), 7.05 (2H, brs), 7.15-7.30 (5H, m), 7.85 (1H, dd, J=2.0, 8.0 Hz), 8.04 (1H, d, J=2.0, 4.8 Hz), 8.98 (1H, t, J=5.2 Hz).

Example A-71

2-Amino-N-(5-(3-fluoro-benzyl)-thiophen-2-ylmethyl)-nicotinamide

The title compound (13 mg, 0.038 mmol, 19%) was obtained from 2-aminonicotinic acid (28 mg, 0.205 mmol) and C-(5-(3-fluoro-benzyl)-thiophen-2-yl)-methylamine obtained by the method described in Example A-146 (50 mg, 0.226 mmol) according to an analogous method to Example H-1.

$^1$H-NMR Spectrum (DMSO-$d_6$) δ(ppm): 4.07 (2H, s), 4.40-4.53 (2H, m), 6.50-6.58 (1H, m), 6.71 (1H, d, J=3.2 Hz), 6.79 (1H, d, J=3.2 Hz), 6.94-7.09 (5H, m), 7.22-7.37 (1H, m), 7.84 (1H, dd, J=1.6, 8.0 Hz), 8.03-8.06 (1H, m), 8.92-9.03 (1H, m).

Example A-72

2-Amino-N-(4-phenoxy-thiophen-2-ylmethyl)-nicotinamide

The title compound (108 mg, 0.331 mmol, 74%) was obtained as a white solid from C-(4-phenoxy-thiophen-2-yl)-methylamine described in Preparation Example 111 (92 mg, 0.45 mmol) and 2-amino-nicotnic acid (68 mg, 0.49 mmol) according to an analogous method to Example A-26.

$^1$H-NMR Spectrum (CDCl$_3$) δ(ppm): 4.70 (2H, d, J=5.7 Hz), 6.35 (3H, brs), 6.48 (1H, d, J=1.7 Hz), 6.60 (1H, dd, J=4.9, 7.7 Hz), 6.82 (1H, d, J=1.6 Hz), 7.05 (2H, dd, J=1.1, 8.6 Hz), 7.11 (1H, tt, J=1.1, 7.7 Hz), 7.34 (2H, t, J=8.6 Hz), 7.61 (1H, dd, J=1.7, 7.7 Hz), 8.18 (1H, dd, J=1.8, 4.8 Hz).

Example A-73

2-Amino-N-(5-(3-chloro-phenoxy)-thiophen-2-ylmethyl)-nicotinamide

C-(5-(3-Chloro-phenoxy)-thiophen-2-yl)-methylamine (1.02g, 4.25 mmol, 98%) was obtained as an oil from 5-(3-chloro-phenoxy)-thiophene-2-carbonitrile described in Preparation Example 121 (1.02 g, 4.32 mmol) according to an analogous method to Example E-24. Then, title compound (12.1 mg) was obtained from the resulting C-(5-(3-chlorophenoxy)-thiophen-2-yl)-methylamine (30 mg, 0.13 mmol) and 2-amino-nicotinic acid (17 mg, 0.13 mmol). Trifluoroacetic acid salt of the title compound (12.1 mg) was obtained by reverse phase high performance liquid chromatography (acetonitrile-water mobile phase (containing 0.1% trifluoroacetic acid) was used).
MS m/e (ESI): 360.3(MH$^+$)

Example A-74

2-Amino-N-(5-(2-fluoro-benzyl)-thiophen-2-ylmethyl)nicotinamide

The title compound was obtained from C-(5-(2-fluoro-benzyl)thiophen-2-yl)-methylamine described in Preparation Example 126 (30 mg, 0.14 mmol) and 2-amino-nicotinic acid (21 mg, 0.15 mmol) according to an analogous method to Example A-26. Trifluoroacetic acid salt of the title compound (16.2 mg) was obtained by reverse phase high performance liquid chromatography (acetonitrile-water mobile phase (containing 0.1% trifluoroacetic acid) was used).
MS m/e (ESI) 342.34(MH$^+$)

Example A-75

2-Amino-N-(5-(4-chloro-phenoxy)-thiophen-2-ylmethyl)-nicotinamide

A solution of 2-amino-nicotinic acid (21 mg, 0.15 mmol), C-(5-(4-chloro-phenoxy)-thiophen-2-yl)-methylamine described in Preparation Example 157 (36 mg, 0.15 mmol), benzotriazol-1-yl-tris(dimethylamino)phosphonium hexafluorophosphate (86 mg, 0.195 mmol) and triethylamine (0.065 mL, 0.45 mmol) in dimethylsulfoxide (1 mL) was stirred under nitrogen atmosphere for 17 hours at room temperature. This reaction solution was purified by reverse phase high performance liquid chromatography (acetonitrile-water mobile phase (containing 0.1% trifluoroacetic acid) was used), and trifluoroacetic acid salt of the title compound (17.7 mg, 0.037 mmol, 24.9%) was obtained as a pale yellow solid.
MS m/e (ESI) 360(MH$^+$)

Example A-76

2-Amino(5-(2-chloro-phenoxy)-thiophen-2-ylmethyl)-nicotinamide

Trifluoroacetic acid salt of the title compound (31.1 mg, 0.07 mmol, 43.7%) was obtained as a light brown oil from 2-amino-nicotnic acid (21 mg, 0.15 mmol) and C-(5-(2-chloro-phenoxy)-thiophen-2-yl)-methylamine described in Preparation Example 159 (36 mg, 0.15 mmol) according to an analogous method to Example A-75.
MS m/e (ESI) 360(MH$^+$)

Example A-77

2-Amino-N-(5-(2,2-dicyclopropylvinyl)thiophen-2-ylmethyl)nicotinamide

The title compound (25 mg, 0.0742 mol, 53.8%) was obtained as a white solid from 2-aminonicotinic acid (19 mg, 0.138 mmol) and C-(5-(2,2-dicyclopropylvinyl)thiophen-2-yl)methylamine described in Preparation Example 152 (30 mg, 0.138 mmol) according to an analogous method to Example A-149.
$^1$H-NMR Spectrum (CDCl$_3$) δ(ppm): 0.42-0.46 (2H, m), 0.61-0.66 (2H, m), 0.83-0.88 (4H, m), 1.16-1.23 (1H, m), 1.96-2.03 (1H, m), 4.73 (2H, d, J=5.6 Hz), 6.27 (1H, s), 6.34 (3H, s), 6.58 (1H, dd, J=4.8, 7.6 Hz), 6.84 (1H, d, J=3.2 Hz), 6.92 (1H, d, J=3.2 Hz), 7.57 (1H, dd, J=1.6, 7.6 Hz), 8.16 (1H, dd, J=1.6, 4.8 Hz).

Example A-78

2-Amino-5-chloro-N-(5-phenoxy-thiophen-2-ylmethyl)-nicotinamide

Trifluoroacetic acid salt of the title compound (1.7 mg, 0.0036 mmol, 5.6%) was obtained as a by-product from Example A-171.
MS m/e (ESI) 360.1 (MH$^+$)

Example A-79

2-Amino-5-methyl-N-(5-phenoxy-thiophen-2-ylmethyl)-nicotinamide

The title compound was obtained from 2-amino-5-iodine-N-(5-phenoxy-thiophen-2-ylmethyl)-nicotinamide described in Preparation Example A+-16 (10 mg, 22 μmol) according to an analogous method to Example A-170. Trifluoroacetic acid salt of the title compound was obtained by reverse phase high performance liquid chromatography (acetonitrile-water mobile phase (containing 0.1% trifluoroacetic acid) was used).
MS m/e (ESI) 340.12(MH$^+$)

Example A-80

2-Amino-6-(1-pentynyl)-N-(5-phenoxy-thiophen-2-ylmethyl)-nicotinamide

Trifluoroacetic acid salt of the title compound (0.70 mg, 0.00014 mmol, 3.3%) was obtained from 2-amino-6-chloro-N-(5-phenoxy-thiophen-2-ylmethyl)-nicotinamide described in Example A-101 (15 mg, 0.042 mmol) and 1-pentyne (3.4 mg, 0.050 mmol) according to an analogous method to Example A-91.
MS m/e (ESI) 392.2 (MH$^+$)

Example A-81

2-Amino-N-(5-phenoxy-thiophen-2-ylmethyl)-6-(3-[1,2,3]-triazol-2-yl-propylamino)-nicotinamide The title compound (14.96 mg, 0.027 mmol, 9.2%) was obtained from 2-amino-6-chloro-N-(5-phenoxy-thiophen-2-ylmethyl)-nicotinamide described in Example A-101 (105 mg, 0.292 mmol) and 3-[1,2,3]triazol-2-yl-propylamine (279 mg, 2.21 mmol) according to an analogous method to Example A-126.
MS m/e(ESI) 450.38(MH$^+$)

Example A-82

2-Amino-6-(furfurylamino)-N-(5-phenoxy-thiophen-2-ylmethyl)-nicotinamide

2-Amino-6-chloro-N-(5-phenoxy-thiophen-2-ylmethyl)-nicotinamide described in Example A-101 (180 mg, 0.5 mmol) was dissolved in a mixture solution of dimethylsulfoxide (2 mL) and diisopropylethylamine (1 mL), furfurylamine (0.663 mL, 7.5 mmol) was added, and the solution was heated in a sealed tube for 13 hours 30 minutes (oil bath temperature: 135° C.). The reaction mixture was allowed to room temperature, poured into brine, and the solution was extracted with ethyl acetate. The organic layer was dried over anhydrous magnesium sulfate, then concentrated, the obtained residue was purified by NH silica gel column chromatography (ethyl acetate:hexane=2:1), and the title compound (144 mg, 0.34 mmol, 68%) was obtained.

$^1$H-NMR Spectrum (CDCl$_3$) δ(ppm): 4.50 (2H, d, J=5.6 Hz), 4.61 (2H, dd, J=0.8, 5.6 Hz), 4.87-4.94 (1H, m), 5.74 (1H, d, J=8.8 Hz), 6.04 (1H, t, J=5.2 Hz), 6.22 (1H, dd, J=0.8, 3.2 Hz), 6.31 (1H, dd, J=2.0, 3.2 Hz), 6.38 (1H, d, J=3.6 Hz), 6.45 (2H, brs), 6.69-6.72 (1H, m), 7.06-7.12 (3H, m), 7.297.38 (4H, m).

Example A-83

2-Amino-N-(5-phenoxy-thiophen-2-ylmethyl)-6-(2-pyridin-2-yl-ethylamino)-nicotinamide 2-Amino-6-chloro-N-(5-phenoxy-thiophen-2-ylmethyl)-nicotinamide described in Example A-101 (20 mg, 37 μmol) and 2-pyridin-2-yl-ethyl amine (66 μl, 0.56 mmol) were dissolved in a mixture solvent of dimethylsulfoxide (1 mL) and N,N-diisopropylethylamine (0.5 mL), and the solution was stirred at 130° C. for 17 hours. The reaction solution was cooled to room temperature, water and ethyl acetate were added, the organic layer was partitioned, washed with water and brine, and dried over anhydrous magnesium sulfate. The solvent was evaporated in vacuo, the residue was purified by reverse phase high performance liquid chromatography (acetonitrile-water mobile phase (containing 0.1% trifluoroacetic acid) was used), and the title compound (17.7 mg) was obtained as a trifluoroacetic acid salt.

MS m/e (ESI) 446.05(MH$^+$)

Example A-84

2-Amino-N-(5-phenoxy-thiophen-2-ylmethyl)-6-(tetrahydrofuran-2-ylmethoxy)-nicotinamide Trifluoroacetic acid salt of the title compound (16 mg, 0.030 mmol, 31%) was obtained from 2-amino-6-chloronicotinic acid described in Preparation Example A-4 (17 mg, 0.096 mmol), tetrahydrofuran-2-ylmethanol (0.5 mL) and C-(5-phenoxy-thiophen-2-yl)-methylamine (20 mg, 0.097 mmol) according to an analogous method to Example A-29.

MS m/e (ESI) 426.2 (MH$^+$)

Example A-85

2-Amino-N-(5-phenoxy-thiophen-2-ylmethyl)-6-(2-(R)-(−)-tetrahydrofurfurylamino)-nicotinamide 2-Amino-6-chloro-N-(5-phenoxy-thiophen-2-ylmethyl)-nicotinamide described in Example A-101 (30 mg, 0.083 mmol) was dissolved in a mixture solution of dimethylsulfoxide (1 mL) and diisopropylethylamine (0.5 mL), (R)-(−)-tetrahydrofurfuryl amine (0.086 mL, 0.83 mmol) was added thereto, followed by heating in a sealed tube for 22 hours 30 minutes (oil bath temperature: 130° C.). The reaction mixture was allowed to room temperature, poured into brine, and the solution was extracted with ethyl acetate. The organic layer was dried over anhydrous magnesium sulfate, then concentrated, the obtained residue was purified by silica gel column chromatography (ethyl acetate:hexane=1:1), and the title compound (22 mg, 0.052 mmol, 62%) was obtained.

$^1$H-NMR Spectrum (CDCl$_3$) δ(ppm): 1.56-1.67 (1H, m), 1.86-2.04 (3H, m), 3.23-3.31 (1H, m), 3.54-3.62 (1H, m), 3.73-3.80 (1H, m), 3.84-3.91 (1H, m), 4.02-4.09 (1H, m), 4.61 (2H, d, J=5.6 Hz), 4.91-5.02 (1H, m), 5.71 (1H, d, J=8.8 Hz), 5.98-6.04 (1H, m), 6.38 (1H, d, J=3.6 Hz), 6.46 (2H, brs), 6.71 (1H, d, J=3.6 Hz), 7.06-7.12 (3H, m), 7.29-7.37 (3H, m).

Example A-86

2-Amino-N-(5-phenoxy-thiophen-2-ylmethyl)-6-thiazol-2-yl-nicotinamide

To a solution of 2-amino-6-chloro-N-(5-phenoxy-thiophen-2-ylmethyl)-nicotinamide described in Example A-101 (101 mg, 0.281 mmol) in xylene (7 mL) were added 2-tributylstanyl thiazole (137 mg, 0.365 mmol) and tetrakis (triphenylphosphine)palladium(0) (81 mg, 0.070 mmol) under nitrogen atmosphere, and the solution was stirred for 12 hours at 120° C. The reaction mixture was concentrated, the obtained residue was purified by silica gel chromatography (toluene-ethyl acetate), then, the obtained residue was washed by hexane-ethyl acetate (20:1), and the title compound (22 mg, 0.054 mmol, 19%) was obtained.

$^1$H-NMR Spectrum (DMSO-d$_6$) δ(ppm): 4.50 (2H, d, J=6.0 Hz), 6.50 (1H, d, J=3.6 Hz), 6.78 (1H, d, J=3.6 Hz), 7.00-7.18 (3H, m), 7.22-7.50 (5H, m), 7.85 (1H, d, J=2.8 Hz, 7.97 (1H, d, J=2.8 Hz), 8.05 (1H, d, J=8.4 Hz), 9.12-9.22 (1H, m).

Example A-87

2-Amino-6-(3-methyl-2-butenyl)-N-(5-phenoxy-thiophen-2-ylmethyl)-nicotinamide

Trifluoroacetic acid salt of the title compound (0.71 mg, 0.0014 mmol, 1.7%) was obtained from 2-amino-6-chloro-N-(5-phenoxy-thiophen-2-ylmethyl)-nicotinamide described in Example A-101 (30 mg, 0.083 mmol) and tributyl(3-methyl-2-butenyl)tin (0.084 mL, 0.25 mmol) according to an analogous method to Example A-29, followed by purifying by reverse phase high performance liquid chromatography (acetonitrile-water mobile phase (containing 0.1% trifluoroacetic acid) was used).

MS m/e (ESI) 394.2 (MH$^+$)

Example A-88

2-Amino-6-(3-dimethylamino-1-propynyl)-N-(5-phenoxy-thiophen-2-ylmethyl)-nicotinamide Trifluoroacetic acid salt of the title compound (1.00 mg, 0.00019 mmol, 4.6%) was obtained from 2-amino-6-chloro-N-(5-phenoxy-thiophen-2-ylmethyl)-nicotinamide described in Example A-101 (15 mg, 0.042 mmol) and 1-dimethylamino-2-propyl (4.2 mg, 0.050 mmol) according to an analogous method to Example A-91.

MS m/e (ESI) 407.2 (MH$^+$)

Example A-89

2-Amino-(3-fluoro-benzylamino)-N-(5-phenoxy-thiophen-2-ylmethyl)-nicotinamide

The title compound (20.6 mg, 0.0365 mmol, 43%) was obtained from 2-amino-6-chloro-N-(5-phenoxy-thiophen-2-ylmethyl)-nicotinamide described in Example A-101 (30 mg, 0.085 mmol) and 3-fluorobenzylamine (146 μl, 1.28 mmol) according to an analogous method to Example A-94.

MS m/e (ESI) 449.50(MH$^+$)

Example A-90

2-Amino-6-(3-methoxy-1-(Z)-propenyl)-N-(5-phenoxy-thiophen-2-ylmethyl)-nicotinamide To a mixture of 2-amino-6 (3methoxy-1-propynyl)-N-(5-phenoxy-thiophen-2-yl methyl)-nicotinamide described in Example A-91 (11 mg, 0.028 mmol) and tetrahydrofuran (1 mL) were added quinoline (5.4 mg, 0.042 mmol) and Linear catalyst (5.0 mg), and the mixture was stirred under hydrogen atmosphere at room temperature for 15 minutes. The interior of the reaction system was exchanged with nitrogen, then, filtration was carried out through Celite pad, and the solvent was evaporated in vacuo. The residue was filtered by NH silica gel, then, purified by reverse phase high performance liquid chromatography (acetonitrile-water mobile phase (containing 0.1% trifluoroacetic acid) was used), and trifluoroacetic acid salt of the title compound (4.4 mg, 0.0086 mmol, 31%) was obtained.
MS m/e (ESI) 396.5 (MH$^+$)

Example A-91

2-Amino-6-(3-methoxy-1-propynyl)-N-(5-phenoxy-thiophen-2-ylmethyl)-nicotinamide

A mixture of 2-aminochloro-N-(5-phenoxy-thiophen-2-ylmethyl)-nicotinamide described in Example A-101 (15 mg, 0.042 mmol), methylpropargyl ether (3.5 mg, 0.050 mmol), diisopropylethylamine (0.023 mL, 0.13 mmol), pyridine (0.011 mL, 0.13 mmol), catalytic amount of copper(I) iodide, tetrakis(triphenylphosphine)palladium(0) (9.6 mg, 0.0083 mmol) and N-methylpyrrolidinone (1 mL) was stirred for 4 hours at 120° C. After cooling, water and dichloromethane were added to the reaction solution for extraction, and the organic layer was filtered through a membrane filter. The solvent was evaporated in vacuo, then, the residue was purified by reverse phase high performance liquid chromatography (acetonitrile-water mobile phase (containing 0.1% trifluoroacetic acid) was used), trifluoroacetic acid salt of the title compound (1.5 mg, 0.00030 mmol, 7.2%) was obtained.
MS m/e (ESI) 394.2 (MH$^+$)

Example A-92

2-Amino(2-(4-amino-phenylamine)-ethylamino)-N-(5-phenoxy-thiophen-2-ylmethyl)-nicotinamide 2-Amino-6-(2-(4-nitro-phenylamino)-ethylamino)-N-(5-phenoxy-thiophen-2-yl methyl)-nicotinamide described in Preparation Example A±13 (17 mg, 28 µmol), iron powder (7.7 mg, 138 µmol) and ammonium chloride (4.41 mg, 83 µmol) were suspended in a mixture solvent of ethanol (1 mL) and water (250 µl), and the solution was stirred at 90° C. for 8 hours. The reaction suspension was cooled to room temperature, then, filtered through Celite pad, water was added to the filtrate, which was then extracted with ethyl acetate, the organic layer was washed with brine and dried over anhydrous magnesium sulfate. The solvent was evaporated in vacuo, the residue was purified by NH silica gel column chromatography (ethyl acetate:methanol=10:1), and the title compound (10 mg, 21 µmol, 77%) was obtained as a white solid.
$^1$H-NMR Spectrum (CDCl$_3$) δ(ppm): 2.80 (3H, brs), 3.28 (2H, t, J=5.7 Hz), 3.53 (2H, q, J=5.7 Hz), 4.60 (2H, d, J=4.9 Hz), 4.91 (1H, t, J=5.7 Hz), 5.68 (1H, d, J=8.6 Hz), 6.07 (1H, t, J=5.3 Hz), 6.38 (1H, d, J=3.7 Hz), 6.46 (2H, s), 6.52 (2H, d, J=8.8 Hz), 6.60 (2H, d, J=8.8 Hz), 6.71 (1H, d, J=3.7 Hz), 7.08-7.12 (3H, m), 7.29-7.34 (3H, m).

Example A-93

2-Amino-N-(5-phenoxy-thiophen-2-ylmethyl)-6-(2-(4sulfamoyl-phenylamino)-ethylamino)-nicotinamide MS m/e (ESI) 539.47 (MH$^+$)

Example A-94

2-Amino-6-(4-chloro-benzylamino)-N-(5phenoxy-thiophen-2-ylmethyl)-nicotinamide

To a solution of 2-amino-6-chloro-N-(5-phenoxy-thiophen-2-ylmethyl)-nicotinamide described in Example A-101 (35 mg, 0.10 mmol) in dimethylsulfoxide (1mL) were added 4-chlorobenzylamine (234 µl, 1.92 mmol) and N,N-diisopropylethylamine (1.0 mL, 5.74 mmol), and the solution was stirred at 140° C. for 2.5 days. Ethanolamine (116 µl, 1.92 mmol) and N,N-diisopropylethylamine (1.0 mL, 5.74 mmol) were added to the reaction mixture, which was then further stirred at 140° C. for 2.5 days. Water was added to the reaction mixture, which was then extracted with ethyl acetate, the organic layer was sequentially washed with water and brine, dried over anhydrous sodium sulfate, and then, concentrated in vacuo. The obtained residue was purified by reverse phase high performance liquid chromatography (acetonitrile-water mobile phase (containing 0.1% trifluoroacetic acid) was used), and the title compound (13.8 mg, 0.024 mmol, 24%) was obtained as a trifluoroacetic acid salt.
MS m/e (ESI) 465.07(MH$^+$)

Example A-95

2-Amino-6-(4-fluoro-benzylamino)-N-(5-phenoxy-thiophen-2-ylmethyl)-nicotinamide

The title compound (10.6 mg, 0.0188 mmol, 16%) was obtained as a trifluoroacetic acid salt from 2-amino-chloro-N-(5-phenoxy-thiophen-2-ylmethyl)-nicotinamide described in Example A-101 (41 mg, 0.12 mmol) and 4-fluorobenzylamine (200 µl, 1.75 mmol) according to an analogous method to Example A-94.
MS m/e (ESI) 449.56(MH$^+$)

Example A-96

2-Amino-6-(4-methoxy-benzylamino)-N-(5-phenoxy-thiophen-2-ylmethyl)-nicotinamide The title compound (19.4 mg, 0.034 mmol, 37%) was obtained as a trifluoroacetic acid salt from 2-amino-6-chloro-N-(5-phenoxy-thiophen-2-ylmethyl)-nicotinamide described in Example A-101 (32 mg, 0.091 mmol) and 4-methoxybenzylamine (238 µl, 1.82 mmol) according to an analogous method to Example A-126.
MS m/e (ESI) 461.21 (MH$^+$)

Example A-97

2-Amino-N-(5-phenoxy-thiophen-2-ylmethyl)-6-(4-trifluoromethyl-benzylamino)-nicotinamide The title compound (15.0 mg, 0.024 mmol, 16%) was obtained from 2-amino-6-chloro-N-(5-phenoxy-thiophen-2- ylmethyl)-nicotinamide described in Example A-101 (54 mg, 0.15 mmol) and 4-(trifluoromethyl)benzylamine (330 μl, 2.45 mmol) according to an analogous method to Example A-126.

MS m/e(ESI) 499.10 (MH$^+$)

Example A-98

6-Acetyl-2-amino-N-(5-phenoxy-thiophen-2-ylmethyl)-nicotinamide

To a mixture of 2-amino-6 (1-ethoxy vinyl)-N-(5-phenoxy-thiophene-2-ylmethyl)-nicotinamide described in Preparation Example A+-14 (2.0 mg, 0.0051 mmol) and acetone (2 mL) were added water (1 mL) and concentrated sulfuric acid (0.2 mL), and the solution was stirred at room temperature for 3 hours. The reaction solution was neutralized with an aqueous solution of saturated sodium bicarbonate, and ethyl acetate was added for extraction. The organic layer was washed with brine, the solvent was then evaporated in vacuo, the residue was purified by silica gel column chromatography (hexane:ethyl acetate=2:1), and the title compound (1.0 mg, 0.0027 mmol, 53%) was obtained as a white solid.

$^1$H-NMR Spectrum (CDCl$_3$) δ(ppm): 2.62 (3H, s), 4.66 (2H, d, J=5.7 Hz), 6.39-6.40 (4H, m), 6.75 (1H, d, J=3.9 Hz), 7.08-7.13 (3H, m), 7.29-7.35 (3H, m), 7.71 (1H, d, J=7.9 Hz).

Example A-99

(6-Amino-5-((5-phenoxy-thiophen-2-ylmethyl)-carbamoyl)-pyridin-2-ylamino)-acetic acid Glycine (610 mg, 8.13 mmol) and 1,8-diazabicyclo[5,4,0]undec-7-ene (405 μl, 2.71 mmol) were added to 2-amino-6-chloro-N-(5-phenoxy-thiophen-2-ylmethyl)-nicotinamide described in Example A-101 (195 mg, 0.542 mmol) under nitrogen atmosphere, and the solution was stirred at 190° C. for 4 hours. Dimethylsulfoxide (5 mL) was added to the reaction mixture, which was then filtered with a polytetrafluoroethylene membrane filter (Whatman Inc), the filtrate was purified by reverse phase high performance liquid chromatography (acetonitrile-water mobile phase (containing 0.1% trifluoroacetic acid) was used), title compound (55.36 mg, 0.108 mmol, 20%) was obtained.

MS m/e(ESI) 399.30(MH$^+$)

Example A-100

2-amino-6-(1-(Z)-hydroxyamino-ethyl)-N-(5-phenoxy-thiophen-2-ylmethyl)-nicotinamide To a mixture of 6-acetyl-2-amino-N-(5-phenoxy-thiophen-2-ylmethyl)-nicotinamide described in Example A-98 (9.0 mg, 0.024 mmol), ethanol (1 mL) and water (0.5 mL) were added hydroxylamine hydrochloride (2.6 mg, 0.037 mmol) and sodium acetate (3.0 mg, 0.037 mmol), and the solution was stirred under reflux for 6 hours. After cooling the reaction solution, water and ethyl acetate were added for extraction. The solvent was evaporated in vacuo, the residue was purified by NH silica gel column chromatography (methanol:ethyl acetate=1:50), and the title compound (8.3 mg, 0.022 mmol, 90%) was obtained as a white solid.

$^1$H-NMR Spectrum (CDCl$_3$) δ(ppm): 2.28 (3H, s), 4.65 (2H, d, J=5.7 Hz), 6.36 (1H, brs), 6.39 (1H, d, J=3.9 Hz), 6.49 (2H, brs), 6.74 (1H, d, J=3.8 Hz), 7.06-7.13 (4H, m), 7.31-7.34 (2H, m), 7.58 (1H, d, J=8.1 Hz).

Example A-101

2-Amino-6-chloro-N-(5-phenoxy-thiophen-2-ylmethyl)-nicotinamide

2-Amino-6-chloro-nicotinic acid described in Preparation Example A-1 (400 mg, 2.31 mmol) was dissolved in N,N-dimethylformamide (10 mL), triethylamine (0.78 mL, 5.6 mmol), benzotriazol-1-yloxytris(dimethylamino)phosphonium hexafluorophosphate (1.23 g, 2.8 mmol) and C-(5-phenoxy-thiophen-2-yl)-methylamine described in Preparation Example 26 (572 mg, 2.8 mmol) were added, and the solution was stirred for 13 hours 30 minutes at room temperature. After the reaction was completed, the reaction solution was poured into brine, which was then extracted with ethyl acetate. The organic layer was dried over anhydrous magnesium sulfate, then concentrated, the obtained residue was purified by silica gel column chromatography (ethyl acetate:hexane=1:1), and the title compound (380 mg, 1.05 mmol, 46%) was obtained.

$^1$H-NMR Spectrum (DMSO-d$_6$) δ(ppm) 4.47 (2H, d, J=6.0 Hz), 6.50 (1H, d, J=4.0 Hz), 6.64 (1H, d, J=8.0 Hz), 6.78 (1H, d, J=4.0 Hz), 7.07-7.17 (3H, m), 7.36-7.41 (2H, m), 7.53 (2H, brs), 7.93 (1H, d, J=8.0 Hz), 9.11 (1H, t, J=6.0 Hz).

Example A-102

2-Amino-6-cyclopropyl-N-(5-phenoxy-thiophen-2-ylmethyl)-nicotinamide

To a mixture of 2-amino-N-(5-phenoxy-thiophen-2-ylmethyl)-6-vinyl-nicotinamide described in Example A-168 (6.0 mg, 0.017 mmol) and toluene (0.5 mL) were added diiodine methane (0.0055 mL, 0.068 mmol) and diethyl zinc (1.1M toluene solution, 0.046 mL, 0.051 mmol) on an ice bath, and the solution was stirred at room temperature for 30 minutes. Water, ethyl acetate and an aqueous solution of 29% ammonia were added to the reaction solution for extraction, the organic layer was then washed with brine. The organic layer was evaporated in vacuo, then, residue was purified by reverse phase high performance liquid chromatography (acetonitrile-water mobile phase (containing 0.1% trifluoroacetic acid) was used), and trifluoroacetic acid salt of the title compound (0.40 mg, 0.00083 mmol, 4.9%) was obtained.

MS m/e (ESI) 366.1 (MH$^+$)

Example A-103

2-Amino-cyclopropylamino-N-(5-phenoxy-thiophen-2-ylmethyl)-nicotinamide

2-Amino-6-chloro-N-(5-phenoxy-thiophen-2-ylmethyl)-nicotinamide described in Example A-101 (30 mg, 0.083 mmol) was dissolved in a mixture solution of dimethylsulfoxide (1 mL) and N,N-diisopropylethylamine (0.5 mL), cyclopropylamine (0.058 mL, 0.84 mmol) was added thereto, followed by heating in a sealed tube for 15 hours 30 minutes (oil bath temperature: 130° C.). The reaction mixture was allowed to room temperature, poured into brine, which was then extracted with ethyl acetate. The organic layer was dried over anhydrous magnesium sulfate, then concentrated, the obtained residue was purified by NH silica gel column chromatography (ethyl acetate:hexane=2:1), and the title compound (15 mg, 0.039 mmol, 47.5%) was obtained.

$^1$H-NMR Spectrum (CDCl$_3$) δ(ppm): 0.52-0.57 (2H, m), 0.74-0.80 (2H, m), 2.47-2.54 (1H, m), 4.62 (2H, d, J=5.6 Hz), 5.09 (1H, brs), 6.06 (1H, d, J=8.4 Hz), 6.08-6.14 (1H, m), 6.34-6.42 (3H, m), 6.72 (1H, d, J=3.6 Hz), 7.06-7.13 (3H, m), 7.29-7.35 (2H, m), 7.45 (1H, d, J=8.4 Hz).

Example A-104

2-Amino-6-(cylopropylmethyl-amino)-N-(5-phenoxy-thiophen-2-ylmethyl)-nicotinamide MS m/e (ESI) 395.22 (MH$^+$)

Example A-105

2-Amino-6-(2-ethoxy-ethylamino)-N-(5-phenoxy-thiophen-2-ylmethyl)-nicotinamide

2-Amino-6-chloro-N-(5-phenoxy-thiophen-2-ylmethyl)-nicotinamide described in Example A-101 (100 mg, 0.28 mmol) was dissolved in a mixture solution of dimethylsulfoxide (2 mL) and N,N-diisopropylethylamine (1 mL), 2-ethoxyethylamine (0.051 mL, 0.49 mmol) was added thereto, followed by heating in a sealed tube for 32 hours 40 minutes (oil bath temperature: 130° C.). The reaction mixture was allowed to room temperature, poured into brine, and the solution was extracted with ethyl acetate. The organic layer was dried over anhydrous magnesium sulfate, then concentrated, the obtained residue was purified by NH silica gel column chromatography (ethyl acetate:hexane=2:1), and the title compound (37 mg, 0.09 mmol, 32%) was obtained.

$^1$H-NMR Spectrum (DMSO-d$_6$) δ(ppm): 1.11 (3H, t, J=7.2 Hz), 3.35-3.47 (6H, m), 4.41 (2H, d, J=6.0 Hz), 5.72 (1H, d, J=8.8 Hz), 6.48 (1H, d, J=3.6 Hz), 6.67-6.77 (2H, m), 7.05 (2H, brs), 7.05-7.16 (3H, m), 7.35-7.41 (2H, m), 7.59 (1H, d, J=8.8 Hz), 9.39 (1H, t, J=6.0 Hz).

Example A-106

2-Amino-6-ethylamino-N-(5-phenoxy-thiophen-2-ylmethyl)-nicotinamide

2-Amino-6-chloro-N-(5-phenoxy-thiophen-2-ylmethyl)-nicotinamide described in Example A-101 (200 mg, 0.56 mmol) was dissolved in a mixture solution of dimethylsulfoxide (1 mL) and N,N-diisopropylethylamine (0.5 mL), ethylamine (2M tetrahydrofuran solution) (2 mL, 4 mmol) was added thereto, followed by heating in a sealed tube for 17 hours (oil bath temperature: 135° C.). The reaction mixture was allowed to room temperature, poured into brine, and the solution was extracted with ethyl acetate. The organic layer was dried over anhydrous magnesium sulfate, then concentrated, the obtained residue was purified by NH silica gel column chromatography (ethyl acetate:hexane=2:1), and the title compound (117 mg, 0.32 mmol, 57%) was obtained.

$^1$H-NMR Spectrum (CDCl$_3$) δ(ppm): 1.21 (3H, t, J=7.2 Hz), 3.24-3.32 (2H, m), 4.56-4.63 (3H, m), 5.67 (1H, d, J=8.8 Hz), 6.06-6.11 (1H, m), 6.37 (1H, d, J=4.0 Hz), 6.42 (2H, brs), 6.71 (1H, d, J=4.0 Hz), 7.06-7.12 (3H, m), 7.29-7.34 (2H, m), 7.37 (1H, J=8.8 Hz).

Example A-107

(±)-2-(6-Amino-5-((5-phenoxy-thiophen-2-ylmethyl)-carbamoyl)-pyridin-2-ylamino)-(R)-3-hydroxy-butyric acid Trifluoroacetic acid salt of the title compound (12 mg, 0.022 mmol, 26%) was obtained from 2-amino-6-chloro-N-(5-phenoxy-thiophen-2-ylmethyl)-nicotinamide described in Example A-101 (30 mg, 0.083 mmol) and (L)-threonine (99 mg, 0.83 mmol) according to an analogous method to Example A-99.

MS m/e (ESI) 443.1 (MH$^+$)

Example A-108

(±)-2-(6-Amino-5-((5-phenoxy-thiophen-2-ylmethyl)-carbamoyl)-pyridin-2-ylamino)-3-phenyl-propionic acid Trifluoroacetic acid salt of the title compound (11 mg, 0.019 mmol, 23%) was obtained from 2-amino-6-chloro-N-(5-phenoxy-thiophen-2-ylmethyl)-nicotinamide described in Example A-101 (30 mg, 0.083 mmol) and (±)-phenylalanine (140 mg, 0.83 mmol) according to an analogous method to Example A-99, trifluoroacetic acid salt of the title compound (11 mg, 0.019 mmol, 23%) was obtained.

MS m/e (ESI) 489.1 (MH$^+$)

Example A-109

(±)-2-(6-Amino-5-((5-phenoxy-thiophen-2-ylmethyl)-carbamoyl)-pyridin-2-ylamino)4methyl-pentanoic acid Trifluoroacetic acid salt of the title compound (6.8 mg, 0.012 mmol, 14%) was obtained from 2-amino-6-chloro-N-(5-phenoxy-thiophen-2-ylmethyl)-nicotinamide described in Example A-101 (30 mg, 0.083 mmol) and (D)-leucine (110 mg, 0.83 mmol) according to an analogous method to Example A-99.

MS m/e (ESI) 455.2 (MH$^+$)

Example A-110

(±)-2-(6-Amino-5-((5-phenoxy-thiophen-2-ylmethyl)-carbamoyl)-pyridin-2-ylamino)-3-methoxy-propionic acid Trifluoroacetic acid salt of the title compound (5.5 mg, 0.0099 mmol, 12%) was obtained from 2-amino-6-chloro-N-(5-phenoxy-thiophen-2-ylmethyl)-nicotinamide described in Example A-101 (30 mg, 0.083 mmol) and (±)-O-methylserine (99 mg, 0.83 mmol) according to an analogous method to Example A-99.

MS m/e (ESI) 443.1 (MH$^+$)

Example A-111

(±)-2-(6-Amino-5-((5-phenoxy-thiophene-2-ylmethyl)-carbamoyl)-pyridin-2-ylamino)-pentanedioic acid Trifluoroacetic acid salt of the title compound (1.7 mg, 0.0029 mmol, 3.5%) was obtained from 2-amino-6-chloro-N-(5-phenoxy-thiophen-2-ylmethyl)-nicotinamide described in Example A-101 (30 mg, 0.083 mmol) and (±)-glutamic acid (122 mg, 0.83 mmol) according to an analogous method to Example A-99.

MS m/e (ESI) 471.4 (MH$^+$)

Example A-112

2-Amino-6-(2-hydroxyethoxy)-N-(5-phenoxy-thiophen-2-ylmethyl)-nicotinamide

Sodium hydride (3.1 mg, 0.078 mmol, 60% in oil), catalytic amount of copper(I) iodide, 2-amino-6-chloro-N-(5- phenoxy-thiophen-2-ylmethyl)-nicotinamide described in Example A-102 (4.0 mg, 0.011 mmol) were added sequentially to ethyleneglycol (0.7 mL), and the solution was stirred at 65° C. for 2 hours. After further stirring at 90° C., the solution was allowed to cool to room temperature. Water, dichloromethane and an aqueous solution of saturated ammonium chloride were added to the reaction solution for extraction, which was then washed with brine, then, the solvent was evaporated in vacuo. The residue was purified by reverse phase high performance liquid chromatography (acetonitrile-water mobile phase (containing 0.1% trifluoroacetic acid) was used), and trifluoroacetic acid salt of the title compound (0.26 mg, 0.00052 mmol, 4.7%) was obtained.
MS m/e (ESI) 386.2 (MH$^+$)

Example A-113

2-Amino-6-(2-hydroxy-ethylamino)-N-(5-phenoxy-thiophen-2-ylmethyl)-nicotinamide

2-Amino-6-chloro-N-(5-phenoxy-thiophen-2-ylmethyl)-nicotinamide described in Example A-101 (170 mg, 0.47 mmol) was dissolved in a mixture solution of dimethylsulfoxide (2 mL) and diisopropylethylamine (1 mL), ethanolamine (0.428 mL, 7.1 mmol) was added thereto, followed by heating in a sealed tube for 15 hours 20 minutes (oil bath temperature: 135° C.). The reaction mixture was allowed to room temperature, poured into brine, and the solution was extracted with ethyl acetate. The organic layer was dried over anhydrous magnesium sulfate, then concentrated, the obtained residue was purified by NH silica gel column chromatography (ethyl acetate:hexane=2:1), and the title compound (138 mg, 0.36 mmol, 76%) was obtained.
$^1$H-NMR Spectrum (DMSO-d$_6$) δ(ppm): 3.24-3.31 (2H, m), 3.44-3.51 (2H, m), 4.39 (2H, d, J=5.6 Hz), 4.68 (1H, t, J=5.2 Hz), 5.70 (1H, d, J=8.4 Hz), 6.46 (1H, d, J=4.0 Hz), 6.66 (1H, brs), 6.70 (1H, d, J=4.0 Hz), 7.02 (2H, brs), 7.04-7.14 (3H, m), 7.34-7.39 (2H, m), 7.57 (1H, d, J=8.4 Hz), 8.37 (1H, t, J=5.6 Hz).

Example A-114

2-Amino-6-hydroxymethyl-N-(5-phenoxy-thiophen-2-ylmethyl)-nicotinamide

To a mixture of 2-amino-N-(5-phenoxy-thiophen-2-ylmethyl)-6-tributylstanyl-nicotinamide described in Preparation Example A+-15 (98 mg, 0.16 mmol) in tetrahydrofuran (1.5 mL) was added n-butyl lithium (2.4M hexane solution, 0.32 mL, 0.80 mmol) dropwise at −78° C., and the solution was stirred for 1 hour 40 minutes at the same temperature. N,N-dimethylformamide (0.037 mL, 0.48 mmol) was added at the same temperature, the solution was stirred from 35 minutes, then, a solution of sodium borocyanide (50 mg, 0.80 mmol) in tetrahydrofuran (1 mL) was added dropwise at the same temperature, and the solution was stirred at −3° C. for 1 hour. The reaction solution was cooled to −78° C., acetic acid (0.091 mL, 1.6 mmol) was added, and the solution was warmed gradually to 0° C. Water, ethyl acetate and tetrahydrofuran were added to the reaction solution for extraction, which was then washed with brine, then, the solvent was evaporated in vacuo. The residue was purified by silica gel column chromatography (methanol:ethyl acetate=1:50), and the title compound (19 mg, 0.053 mmol, 33%) was obtained as a pale yellow oil.
$^1$H-NMR Spectrum (CDCl$_3$) δ(ppm): 4.58 (2H, s), 4.64 (2H, d, J=5.5 Hz), 6.38 (1H, d, J=3.7 Hz), 6.43 (1H, brs), 6.48-6.50 (3H, m), 6.74 (1H, d, J=3.7 Hz), 7.08-7.13 (3H, m), 7.30-7.34 (2H, m), 7.59 (1H, d, J=7.9 Hz).

Example A-115

2-Amino-6-isopropoxy-N-(5-phenoxy-thiophen-2-ylmethyl)-nicotinamide

Trifluoroacetic acid salt of the title compound (4.3 mg, 0.0086 mmol, 9.0%) was obtained from 2-amino-6-chloronicotinic acid described in Preparation Example A-4 (17 mg, 0.096 mmol), isopropanol (0.5 mL) and G(5-phenoxy-thiophen-2-yl)-methylamine (20 mg, 0.097 mmol) according to an analogous method to Example A-29.
MS m/e (ESI) 384.2 (MH$^+$)

Example A-116

2-Amino-6-methoxy-N-(5-phenoxy-thiophen-2-ylmethyl)-nicotinamide 2,5-Diamino-N-(5-phenoxy-thiophen-2-ylmethyl)-nicotinamide described in Preparation Example A+-10 (27 mg, 59 μmol), sodium nitrite (4.1 mg, 59 μmol) and sulfuric acid (several drops) were dissolved in methanol (5 mL), and the solution was stirred for 30 minutes under reflux. An aqueous solution of saturated sodium bicarbonate was added to the reaction solution at 0° C., which was then extracted with ethyl acetate, and the organic layer was washed with brine. The solvent was evaporated in vacuo, the residue was purified by reverse phase high performance liquid chromatography (acetonitrile-water mobile phase (containing 0.1% trifluoroacetic acid) was used), then, further by NH silica gel column chromatography (hexane:ethyl acetate=5:1), and the title compound (0.7 mg) was obtained as a white solid.
MS m/e (ESI) 356.32(MH$^+$).
$^1$H-NMR Spectrum (CDCl$_3$) δ(ppm): 3.87 (3H, s), 4.63 (2H, d, J=5.7 Hz), 6.01 (1H, d, J=8.6 Hz), 6.11 (1H, brs), 6.39 (1H, d, J=3.8 Hz), 6.51 (1H, brs), 6.73 (1H, d, J=3.3 Hz), 7.08-7.12 (3H, m), 7.22-7.26 (1H, m), 7.32 (2H, t, J=8.6 Hz), 7.50 (1H, t, J=8.8 Hz).

Example A-117

2-Amino-N-(5-benzofuran-5-ylmethyl-thiophen-2-ylmethyl)-6-methoxymethyl-nicotinamide MS m/e (ESI) 407.85 (MH$^+$)

Example A-118

2-Amino-N-(5-benzo[1,3]dioxol-5-ylmethyl-thiophen-2-ylmethyl)6-methoxymethyl-nicotinamide $^1$H-NMR Spectrum (CDCl$_3$) δ(ppm): 3.33 (3H, s), 3.96 (2H, s), 4.28 (2H, s), 4.47 (2H, d, J=6.0 Hz), 5.96 (2H, d, J=1.2 Hz), 6.59 (1H, d, J=8.0 Hz), 6.68-6.74 (2H, m), 6.77-6.84 (3H, m), 7.12 (2H, brs), 7.90 (1H, d, J=8.0 Hz), 8.97 (1H, t, J=6.0 Hz).

Example A-119

2-Amino-6-methoxymethyl-N-(5-phenoxy-thiophen-2-ylmethyl)-nicotinamide $^1$H-NMR Spectrum (CDCl$_3$) δ(ppm): 3.46 (3H, s), 4.41 (2H, s), 4.64-4.66 (2H, m), 6.32 (1H, brs), 6.39 (1H, d, J=3.8

Hz), 6.47 (2H, br s), 6.71 (1H, d, J=7.9 Hz), 6.74 (1H, d, J=3.8 Hz), 7.08-7.13 (3H, m), 7.31-7.35 (2H, m), 7.62 (1H, d, J=7.9 Hz).

Example A-120

2-Amino-N-(4-benzylamino-benzyl)-6-methoxymethyl-nicotinamide

MS m/e (ESI) 377 (MH$^+$)

Example A-121

2-Amino-N-(5-benzyl-thiophen-2-ylmethyl)-6-methoxymethyl-nicotinamide $^1$H-NMR Spectrum (CDCl$_3$) δ(ppm): 3.44 (3H, s), 4.09 (2H, s), 4.38 (2H, s), 4.66 (2H, d, J=5.2 Hz), 6.25-6.34 (1H, m), 6.38 (2H, br s), 6.65 (1H, d, J=3.6 Hz), 6.67 (1H, d, J=8.0 Hz), 6.82 (1H, d, J=3.6 Hz), 7.20-7.27 (3H, m), 7.27-7.34 (2H, m), 7.57 (1H, d, J=8.0 Hz).

Example A-122

2-Amino-N-(5-(3-chloro-phenoxy)-thiophen-2-ylmethyl)-6-methoxymethyl-nicotinamide MS m/e (ESI) 404 (MH$^+$)

Example A-123

2-Amino-N-(5-(3-fluoro-phenoxy)-thiophen-2-ylmethyl)-6-methoxymethyl-nicotinamide MS m/e (ESI) 388 (MH$^+$)

Example A-124

2-Amino-6-(3-methoxy-propyl)-N-(5-phenoxy-thiophen-2-ylmethyl)-nicotinamide

To a mixture of 2-amino-6-(3-methoxy-1-(Z)-propenyl)-N-(5-phenoxy-thiophen-2-ylmethyl)-nicotinamide described in Example A-90 (3.0 mg, 0.0059 mmol) and tetrahydrofuran (1 mL) were added triethylamine (3.6 mg, 0.036 mmol) and 10% palladium-carbon (50% water wet, 5 mg), and the solution was stirred under hydrogen atmosphere at room temperature for 15 minutes. The interior of the reaction system was exchanged with nitrogen, then, filtration was carried out through Celite pad, the solvent was evaporated in vacuo. The residue was purified by reverse phase high performance liquid chromatography (acetonitrile-water mobile phase (containing 0.1% trifluoroacetic acid) was used), and trifluoroacetic acid salt of the title compound (0.48 mg, 0.00094 mmol, 16%) was obtained.
MS m/e (ESI) 398.3 (MH$^+$)

Example A-125

2-Amino-6-methylamino-N-(5phenoxy-thiophen-2-ylmethyl)-nicotinamide

2-Amino-6-chloro-N-(5-phenoxy-thiophen-2-ylmethyl)-nicotinamide described in Example A-101 (200 mg, 0.56 mmol) was dissolved in a mixture solution of dimethylsulfoxide (1 mL) and diisopropylethylamine (0.5 mL), methylamine (2M tetrahydrofuran solution) (2 mL, 4 mmol) was added thereto, followed by heating in a sealed tube for 14 hours (oil bath temperature: 135° C.). The reaction mixture was allowed to room temperature, poured into brine, and the solution was extracted with ethyl acetate. The organic layer was dried over anhydrous magnesium sulfate, then concentrated, the obtained residue was purified by NH silica gel column chromatography (ethyl acetate:hexane=2:1), and the title compound (144 mg, 0.41 mmol, 73%) was obtained.
$^1$H-NMR Spectrum (CDCl$_3$) δ(ppm): 2.89 (3H, d, J=5.2 Hz), 4.61 (2H, d, J=5.6 Hz), 4.64-4.71 (1H, m), 5.69 (1H, d, J=8.4 Hz), 6.03-6.09 (1H, m), 6.38 (1H, d, J=4.0 Hz), 6.44 (2H, brs), 6.71 (1H, d, J=4.0 Hz), 7.06-7.12 (3H, m), 7.29-7.35 (2H, m), 7.39 (1H, d, J=8.4 Hz).

Example A-126

2-Amino-6-benzylamino-N-(5-phenoxy-thiophen-2-ylmethyl)-nicotinamide

To a solution of 2-amino-6-chloro-N-(5-phenoxy-thiophen-2-ylmethyl)-nicotinamide described in Example A-101 (110 mg, 0.31 mmol) in dimethylsulfoxide (1 mL) were added benzylamine (1.8 mL, 16.5 mmol) and N,N-diisopropylethylamine (0.5 mL, 2.94 mmol), and the solution was stirred for 17 hours at 135° C. Water was added to the reaction mixture, which was then extracted with ethyl acetate, the organic layer was sequentially washed with water and brine, dried over anhydrous sodium sulfate, and then, concentrated in vacuo. The obtained residue was purified by reverse phase high performance liquid chromatography (acetonitrile-water mobile phase (containing 0.1% trifluoroacetic acid) was used), and the title compound (23.4 mg, 0.0429 mmol, 14%) was obtained as a trifluoroacetic acid salt.
MS m/e(ESI) 431.27(MH$^+$)

Example A-127

2-Amino-N-(5-phenoxy-thiophen-2-ylmethyl)-6-propoxy-nicotinamide

Trifluoroacetic acid salt of the title compound (5.3 mg, 0.011 mmol, 11%) was obtained from 2-amino-6-chloronicotinic acid described in Preparation Example A-4 (17 mg, 0.096 mmol), propanol (0.5 mL) and C-(5-phenoxy-thiophen-2-yl)-methylamine (20 mg, 0.097 mmol) according to an analogous method to Example A-29.
MS m/e (ESI) 384.1 (MH$^+$)

Example A-128

2-Amino-N-(5-phenoxy-thiophen-2-ylmethyl)-6-propylamino-nicotinamide

2-Amino-6-chloro-N-(5-phenoxy-thiophen-2-ylmethyl)-nicotinamide described in Example A-101 (200 mg, 0.56 mmol) was dissolved in a mixture solution of dimethylsulfoxide (2 mL) and N,N-diisopropylethylamine (1 mL), propylamine (0.685 mL, 8.3 mmol) was added thereto, followed by heating in a sealed tube for 13 hours (oil bath temperature: 135° C.). The reaction mixture was allowed to room temperature, poured into brine, which was then extracted with ethyl acetate. The organic layer was dried over anhydrous magnesium sulfate, then concentrated, the obtained residue was purified by NH silica gel column chromatography (ethyl acetate:hexane=2:1), and the title compound (89 mg, 0.23 mmol, 42%) was obtained.

$^1$H-NMR Spectrum (CDCl$_3$) δ(ppm): 0.96 (3H, t, J=7.6 Hz), 1.54-1.64 (2H, m), 3.16-3.22 (2H, m), 4.59 (2H, d, J=5.6 Hz), 4.69 (1H, t, J=5.2 Hz), 5.67 (1H, d, J=8.8 Hz), 6.16 (1H, t, J=5.6 Hz), 6.36 (1H, d, J=3.6 Hz), 6.42 (2H, brs), 6.69 (1H, d, J=3.6 Hz), 7.067.12 (3H, m), 7.29-7.35 (2H, m), 7.37 (1H, J=8.8 Hz).

Example A-129

2-Amino-N-(5-phenoxy-thiophen-2-ylmethyl)-((pyrazin-2-ylmethyl)-amino)-nicotinamide MS m/e (ESI) 433.15(MH$^+$)
$^1$H-NMR Spectrum (DMSO-d$_6$) δ(ppm): 4.33 (2H, d, J=5.6 Hz), 4.68 (2H, s), 5.99 (1H, d, J=8.4 Hz), 6.48 (1H, d, J=3.6 Hz), 6.73 (1H, d, J=3.6 Hz), 7.06-7.15 (3H, m) 7.34-7.39 (2H, m), 7.82-7.94 (1H, m), 8.55 (1H, d, J=2.4 Hz), 8.60 (1H, dd, J=2.4, 1.2 Hz), 8.67 (1H, d, J=1.2 Hz), 8.69-8.79 (1H, m).

Example A-130

2-Amino-N-(5-phenoxy-thiophen-2-ylmethyl)-6-((pyridin-2-ylmethyl)-amino)-nicotinamide MS m/e (ESI) 432.17 (MH$^+$)

Example A-131

3-(3-(5-Phenoxy-thiophen-2-ylmethyl)-carbamoyl)-pyridin-2-ylamino)-propionic acid To a solution of 2-chloro-N-(5-phenoxy-thiophen-2-ylmethyl)-nicotinamide described in Preparation Example A+-7 (51 mg, 0.15 mmol) in dimethylsulfoxide (2 mL) were added tert-butyl 3-aminopropanoate hydrochloride (32 mg, 0.178 mmol) and triethylamine (27 µl, 0.192 mmol), and the solution was stirred for 2.5 hours at 120° C. Potassium carbonate (49 mg, 0.36 mmol) was added to the reaction mixture, which was then stirred for 20 hours 120° C. Water was added to the reaction mixture, which was then extracted with ethyl acetate and concentrated. To a solution of the resulting residue in dichloromethane (1 mL) was added trifluoroacetic acid (500 µl, 6.49 mmol), and the solution was stirred for 2.5 hours at room temperature. The reaction mixture was concentrated, and the obtained residue was purified by reverse phase high performance liquid chromatography (acetonitrile-water mobile phase (containing 0.1% trifluoroacetic acid) was used), and the title compound (3.44 mg, 0.0067 mmol, 4.5%) was obtained as a trifluoroacetic acid salt.
MS m/e(ESI) 398.52(MH$^+$)

Example A-132

2-Chloro-N-(5-(3-fluorophenoxy)thiophen-2-ylmethyl)-6-methylnicotinamide

The title compound (330 mg, 0.877 mmol, 65.0%) was obtained as a white solid from 2-chloro-6-methylnicotinic acid (230 mg, 1.35 mmol) and C-(5-(3-fluorophenoxy)thiophen-2-yl)methylamine described in Preparation Example 23 (300 mg, 1.35 mmol) according to an analogous method to Example Q-6.
$^1$H-NMR Spectrum (DMSO-d$_6$) δ(ppm): 2.47 (3H, s), 4.52 (2H, d, J=5.6 Hz), 6.60-6.63 (1H, m), 6.84 (1H, d, J=4.0 Hz), 6.92-7.04 (3H, m), 7.32-7.35 (1H, m), 7.40-7.47 (1H, m), 7.77 (1H, d, J=7.2 Hz), 9.15 (1H, t, J=5.6 Hz).

Example A-133

2-(Cyclopropylmethyl-amino)-N-(5-phenoxy-thiophen-2-ylmethyl)-nicotinamide

To a solution of 2-chloro-N-(5-phenoxy-thiophen-2-ylmethyl)-nicotinamide described in Preparation Example A+-7 (64 mg, 0.186 mmol) in dimethylsulfoxide (1 mL) was added (aminomethyl)cyclopropane (48 µl, 0.56 mmol), and the solution was stirred for 14 hours at 120° C. The reaction mixture was purified by reverse phase high performance liquid chromatography (acetonitrile-water mobile phase (containing 0.1% trifluoroacetic acid) was used), and the title compound (15.6 mg, 0.0316 mmol, 17%) was obtained as a trifluoroacetic acid salt.
MS m/e(ESI) 380.43(MH$^+$)

Example A-134

2-(2-Methoxy-ethylamino)-N-(5-phenoxy-thiophen-2-ylmethyl -nicotinamide

To a solution of 2-chloro-N-(5-phenoxy-thiophen-2-ylmethyl)-nicotinamide described in Preparation Example A+-7 (16 mg, 0.046 mmol) in 1-methyl-2-pyrrolidone (2 mL) were added 2-methoxyethylamine (6 µl, 0.07 mmol) and sodium hydride (4 mg, 0.092 mmol, 60% in oil), and the solution was stirred for 8 hours at 110° C. An aqueous solution of saturated ammonium chloride was added to the reaction mixture, which was then extracted with ethyl acetate, and concentrated. The obtained residue was purified by reverse phase high performance liquid chromatography (acetonitrile-water mobile phase (containing 0.1% trifluoroacetic acid) was used), and the title compound (0.67 mg, 0.0013 mmol, 2.8%) was obtained as a trifluoroacetic acid salt.
MS m/e(ESI) 384.16(MH$^+$)

Example A-135

2-Methyl-N-(5-phenoxy-thiophen-2-ylmethyl)-nicotinamide

The title compound (40 mg, 0.123 mmol, 42.4%) was obtained as a light brown solid from 2-methylnicotinic acid (40 mg, 0.29 mmol) and C-(5-phenoxy-thiophen-2-yl)-methylamine described in Preparation Example 26 (60 mg, 0.29 mmol) according to an analogous technique to Example Q-6.
$^1$H-NMR Spectrum (DMSO-d$_6$) δ(ppm): 2.47 (3H, s), 4.49 (2H, d, J=5.6 Hz), 6.50-6.63 (1H, m), 6.77-6.80 (1H, m), 7.06-7.16 (3H, m), 7.23-7.28 (1H, m), 7.35-7.40 (2H, m), 7.66-7.70 (1H, m), 8.48 (1H, dd, J=1.6, 4.8 Hz), 9.05 (1H, t, J=5.6 Hz).

Example A-136

2-Methylamino-N-(5-phenoxy-thiophen-2-ylmethyl)-nicotinamide

To a solution of 2-(ethoxymethyl-amino)-N-(5-phenoxy-thiophene-2-ylmethyl)-nicotinamide described in Preparation Example A+-6 (148 mg, 0.385 mmol) in dimethylsulfoxide (3 mL) was added sodium borohydride (44 mg, 1.15 mmol), and the solution was stirred for 30 minutes at 100° C., followed by stirring for 20 minutes at 110° C. Furthermore, sodium borohydride (35 mg, 0.925 mmol) was added thereto, followed by stirring for 20 minutes at 110° C. Water was added to the reaction mixture, which was then extracted with ethyl acetate, the organic layer was sequentially washed with water and brine, dried over anhydrous sodium sulfate, and then, concentrated in vacuo. The obtained residue was purified by silica gel chromatography (hexane-ethyl acetate), and the title compound (86 mg, 0.26 mmol, 67%) was obtained.

$^1$H-NMR Spectrum (DMSO-d$_6$) δ(ppm): 2.87 (3H, d, J=4.8 Hz), 4.46 (2H, d, J=5.6 Hz), 6.48 (1H, d, J=3.6 Hz), 6.53 (1H, dd, J=4.8, 7.6 Hz), 6.76 (1H, d, J=3.6 Hz), 7.00-7.18 (3H, m), 7.30-7.41 (2H, m), 7.88 (1H, dd, J=2.0, 7.6 Hz), 8.10-8.25 (2H, m), 9.07 (1H, t, J=5.6 Hz).

Example A-137

6-Amino-N-(5-(3-fluorophenoxy)thiophen-2-ylm-ethyl)nicotinamide

The title compound (20 mg, 0.058 mmol, 21.6%) was obtained as a white solid from 6-amino-nicotinic acid (37 mg, 0.27 mmol) and C-(5-(3-fluorophenoxy)thiophen-2-yl)methylamine described in Preparation Example 23 (60 mg, 0.27 mmol) according to an analogous method to Example Q-6.

$^1$H-NMR Spectrum (DMSO-d$_6$) δ(ppm): 4.56 (2H, d, 6.0 Hz), 6.39 (1H, d, J=8.8 Hz), 6.48 (2H, brs), 6.56 (1H, d, J=3.6 Hz), 6.76 (1H, d, J=3.6 Hz), 6.88-7.00 (3H, m), 7.39 (1H, ddd, J=8.0, 8.0, 8.0), 7.79 (1H, dd, J=2.0, 8.8 Hz), 8.43 (1H, d, J=2.0 Hz), 8.77 (1H, t, J=6.0 Hz).

Example A-138

6Amino-N-(5-phenoxy thiophen-2-ylmethyl)-nicotinamide

To a solution of C-(5-phenoxythiophen-2-yl)methylamine described in Preparation Example 24 (170 mg, 0.83 mmol) and 6-aminonicotinic acid (130 mg, 0.91 mmol) in N,N-dimethylformamide (10 mL) were added benzotriazol-1-yl-tris(dimethylamino)phosphonium hexafluorophosphate (400 mg, 0.91 mmol) and triethylamine (0.3 mL, 2.2 mmol), and the solution was stirred for 35 minutes at 60° C. Water and ethyl acetate were added to the reaction solution, which was then partitioned, the organic layer was washed with water twice, NH silica gel was added to the organic layer, the solvent was evaporated in vacuo for adsorption, purification was carried out by NH silica gel column chromatography (ethyl acetate, then ethyl acetate:methanol=50:1), and the title compound (130 mg, 0.40 mmol, 48.2%) was obtained as a solid.

$^1$H-NMR Spectrum (DMSO-d$_6$) δ(ppm): 4.45 (2H, d, 5.2 Hz), 6.39 (1H, d, J=8.8 Hz), 6.43-6.54 (3H, m), 6.70-6.77 (1H, m), 7.20-7.16 (3H, m), 7.31-7.41 (2H, m), 7.78 (1H, d, J=8.8 Hz), 8.43 (1H, s), 8.76 (1H, d, J=5.2 Hz).

Example A-139

6-Amino-N-(5-(4fluoro-phenoxy)-thiophen-2-ylm-ethyl)-nicotinamide

To a solution of C-(5-(4-fluorophenoxy)thiophen-2-yl) methylamine described in Preparation Example 28 (500 mg, 2.24 mmol) and 6-aminonicotinic acid (340 mg, 2.46 mmol) in N,N-dimethylformamide (10 mL) were added benzotria-zol-1-yl-tris(dimethylamino)phosphonium hexafluorophos-phate (1.1 g, 2.46 mmol) and triethylamine (0.6 mL, 4.48 mmol), and the solution was stirred for 30 minutes at 60° C. Water and ethyl acetate were added to the reaction solution, which was then partitioned, and the organic layer was washed with water three times. The organic layer was passed through a glass filter lined with NH silica gel and silica gel (1:1), and eluted with a mixture solvent of ethyl acetate and methanol (20:1). The solvent was evaporated in vacuo, ethyl acetate and hexane were added to the residue, the generated solid was collected by filtration, and the title compound (560 mg, 1.63 mmol, 72.8%) was obtained as a slightly yellow solid.

$^1$H-NMR Spectrum (DMSO-d$_6$) δ(ppm): 4.44 (2H, d, J=5.2 Hz), 6.39 (1H, d, J=8.8 Hz), 6.44-6.50 (3H, m), 6.72 (1H, d, J=2.4 Hz), 7.09-7.16 (2H, m), 7.16-7.24 (2H, m), 7.78 (1H, d, J=8.8 Hz), 8.42 (1H, s), 8.74 (1H, t, J=5.2 Hz).

Example A-140

6-Amino-N-(5-(4-chloro-phenoxy)-thiophen-2-ylm-ethyl)-nicotinamide

The title compound (32 mg, 0.089 mmol, 30.7%) was obtained as a white solid from C-(5-(4chlorophenoxy) thiophen-2-yl)methylamine obtained according to an analogous method to Example E-66 (70 mg, 0.29 mmol) and 6-aminonicotinic acid (40 mg, 0.29 mmol).

$^1$H-NMR Spectrum (DMSO-d$_6$) δ(ppm): 4.45 (2H, d, 5.2 Hz), 6.39 (1H, d, J=8.4 Hz), 6.48 (2H, s), 6.51 (1H, d, J=3.6 Hz), 6.74 (1H, d, J=3.6 Hz), 7.04-7.14 (2H, m), 7.36-7.46 (2H, m), 7.78 (1H, d, J=8.4 Hz), 8.43 (1H, s), 8.76 (1H, t, J=5.2 Hz).

Example A-141

6-Amino-N-(5-m-tolyloxy-thiophen-2-ylmethyl) nicotinamide

The title compound (243 mg, 0.717 mmol, 52.7%) was obtained as a light brown solid from C-(5-m-tolylox-ythiophen-2-yl)methylamine described in Preparation Example 30 (300 mg, 1.36 mmol) and 6-aminonicotinic acid (210 mg, 1.52 mmol) according to an analogous method to Example Q-6.

$^1$H-NMR Spectrum (DMSO-d$_6$) δ(ppm): 2.26 (3H, s), 4.44 (2H, d, J=5.6 Hz), 6.39 (1H, d, J=8.8 Hz), 6.42-6.52 (3H, m), 6.70-6.74 (1H, m), 6.84-6.95 (3H, m), 7.22 (1H, dd, J=8.0, 8.0 Hz), 7.78 (1H, dd, J=2.4, 8.8 Hz), 8.43 (1H, d, J=2.4 Hz), 8.74 (1H, t, J=5.6 Hz).

Example A-142

6-Amino-N-(5-p-tolyloxy-thiophene-2-ylmethyl)-nicotinamide

The title compound (265 mg, 0.78 mmol, 52.1%) was obtained as a light brown solid from 6-aminonicotinic acid (210 mg, 1.50 mmol) and C-(5-p-tolyloxy-thiophen-2-yl)-methylamine described in Preparation Example 32 (300 mg, 1.37 mmol) according to an analogous method to Example Q-6.

$^1$H-NMR Spectrum (DMSO-d$_6$) δ(ppm): 2.24 (3H, s), 4.43 (2H, d, J=5.6 Hz), 6.38 (1H, d, J=8.8 Hz), 6.41 (1H, d, J=3.6 Hz), 6.47 (2H, s), 6.70 (1H, d, J=3.6 Hz), 6.94-7.00 (2H, m), 7.13-7.19 (2H, m), 7.78 (1H, dd, J=2.4, 8.8 Hz), 8.42 (1H, d, J=2.4 Hz), 8.73 (1H, t, J=5.6 Hz).

Example A-143

6Amino-N-(5-(4fluoro-benzyl)-thiophen-2-ylm-ethyl)-nicotinamide

The title compound (46 mg, 0.13 mmol, 81.2%) was obtained as a white solid from C-(5-(4-fluoro-benzyl)-thiophen-2-yl)-methylamine described in Preparation Example 38 (35 mg, 0.16 mmol) and 6-aminonicotinic acid (24 mg, 0.17 mmol) according to an analogous method to Example Q-6.
$^1$H-NMR Spectrum (DMSO-$d_6$) δ(ppm): 4.03 (2H, s), 4.45 (2H, d, J=5.6 Hz), 6.38 (1H, d, J=8.8 Hz), 6.45 (2H, s), 6.67 (1H, d, J=3.6 Hz), 6.76 (1H, d, J=3.6 Hz), 7.04-7.14 (2H, m), 7.20-7.30 (2H, m), 7.77 (1H, dd, J=2.4, 8.8 Hz), 8.41 (1H, d, J=2.4 Hz), 8.69 (1H, t, J=5.6 Hz).

Example A-144

6-Amino-N-(5-benzyl-thiophen-2-ylmethyl)-nicoti-namide

The title compound (27 mg, 0.082 mmol, 31.0%) was obtained as a white solid from 6-aminonicotinic acid (37 mg, 0.27 mmol) and C-(5-benzyl-thiophen-2-yl)-methylamine described in Preparation Example 42 (54 mg, 0.27 mmol) according to an analogous technique to Example Q-6.
$^1$H-NMR Spectrum (DMSO-$d_6$) δ(ppm): 4.03 (2H, s), 4.44 (2H, d, J=5.2 Hz), 6.37 (1H, d, J=8.8 Hz), 6.45 (2H, s), 6.67 (1H, d, J=3.2 Hz), 6.75 (1H, d, J=3.2 Hz), 7.15-7.30 (5H, m), 7.76 (1H, dd, J=2.0, 8.8 Hz), 8.41 (1H, d, J=2.0 Hz), 8.68 (1H, t, J=5.2 Hz).

Example A-145

6-Amino-N-(5-(3-chloro-benzyl)-thiophen-2-ylm-ethyl)-nicotinamide

The title compound (42 mg, 0.12 mmol, 56.0%) was obtained as a white solid from C-(5-(3-chloro-benzyl-2-yl) methylamine described in Preparation Example 45 (50 mg, 0.21 mmol) and 6-aminonicotinic acid (32 mg, 0.23 mmol) according to an analogous method to Example Q-6.
$^1$H-NMR Spectrum (DMSO-$d_6$) δ(ppm): 4.05 (2H, s), 4.45 (2H, d, J=5.6 Hz), 6.38 (1H, d, J=8.8 Hz), 6.45 (2H, s), 6.71 (1H, d, J=3.2 Hz), 6.76 (1H, d, J=3.2 Hz), 7.16-7.34 (4H, m), 7.77 (1H, d, J=8.8 Hz), 8.41 (1H, s), 8.70 (1H, t, J=5.6 Hz).

Example A-146

6-Amino-N-(5-(3-fluoro-benzyl)-thiophen-2-ylm-ethyl)-nicotinamide

To a solution of 5-(3-fluoro-benzyl)-thiophene-2-carbal-dehyde described in Preparation Example 53 (485 mg, 2.2 mmol) in 7N ammonia/methanol (30 mL) was added Raney nickel (1 g), and the solution was stirred under hydrogen atmosphere at room temperature for 16 hours. The reaction solution was filtered through Celite pad to remove the catalyst, then, the organic layer was concentrated in vacuo, the residue was purified by NH silica gel column chromatography (hexane, then hexane:ethyl acetate=4:1), and C-(5-(3-fluoro-benzyl-2-yl)-methylamine (290 mg, 1.3 mmol, 59.6%) was obtained as a brown oil. Using the resulting C-(5-(3-fluoro-benzyl-2-yl)-methylamine (50 mg, 0.226 mmol) and 6-aminonicotinic acid (34 mg, 0.248 mmol) according to an analogous technique to Example Q-6, the title compound (44 mg, 0.129 mmol, 57.1%) was obtained as a white solid.
$^1$H-NMR Spectrum (DMSO-$d_6$) δ(ppm): 4.06 (2H, s), 4.45 (2H, d, J=5.6 Hz), 6.38 (1H, d, J=8.8 Hz), 6.45 (2H, s), 6.70 (1H, d, J=2.0 Hz), 6.77 (1H, d, J=2.0 Hz), 6.96-7.10 (3H, m), 7.28-7.36 (1H, m), 7.77 (1H, dd, J=2.0, 8.8 Hz), 8.41 (1H, d, J=2.0 Hz), 8.70 (1H, t, J=5.6 Hz).

Example A-147

6-Amino-N-(5-(3-chloro-phenoxy)-thiophen-2-ylm-ethyl)-nicotinamide

The title compound (8.21 mg) was obtained from C-(5-(3-chloro-phenoxy)-thiophen-2-yl)-methylamine described in Example A-73 (30 mg, 0.13 mmol) and 6-amino-nicotinic acid (17 mg, 0.13 mmol) according to an analogous method to Example E-24, the title compound (8.21 mg) was obtained. Trifluoroacetic acid salt of the tile compound was obtained by reverse phase high performance liquid chromatography (acetonitrile-water mobile phase (containing 0.1% trifluoroacetic acid) was used).
MS m/e (ESI) 360.3(MH$^+$)

Example A-148

6-Amino-N-(5-(2-fluoro-phenoxy)-thiophen-2-ylm-ethyl)-nicotinamide

Trifluoroacetic acid salt of the title compound (26.6 mg) was obtained as a pale yellow oil from 6-amino-nicotinic acid (21 mg, 0.15 mmol) and C-(5-(2-fluoro-phenoxy)-thiophen-2-yl)-methylamine described in Preparation Example 161 (33.5 mg, 0.15 mmol) according to an analogous method to Example A-75. Then, the title compound (7.8 mg, 0.023 mmol, 15.1%) was obtained as a pale yellow solid by purifying again by thin layer NH silica gel chromatography (ethyl acetate).
MS m/e (ESI) 344(MH$^+$)

Example A-149

6-Amino-N-(5-(2-cyclopropylvinyl)thiophen-2-ylm-ethyl)nicotinamide

6-Aminonicotinic acid (35 mg, 0.251 mmol), C-(5-(2-cyclopropylvinyl)thiophen-2-yl)methylamine described in Preparation Example 151 (45 mg, 0.251 mmol), benzotriazol-1-yl-tris(dimethylamino)phosphonium hexafluorophosphate (133 mg, 0.301 mmol) and triethylamine (0.042 mL, 0.301 mmol) were dissolved in N,N-dimethylformamide (3 mL), and the solution was stirred at room temperature for 3 hours. Water (10 mL) was added to the reaction solution, which was then extracted with ethyl acetate (30 mL). The organic layer was washed, dried over anhydrous magnesium sulfate, then, the solvent was evaporated in vacuo, the obtained residue was purified by NH silica gel column chromatography (hexane:ethyl acetate=3:1), and the title compound (50 mg, 0.167 mmol, 66.6%) was obtained as a white solid.
$^1$H-NMR Spectrum (CDCl$_3$) δ(ppm): 0.44-0.52 (2H, m), 0.76-0.84 (2H, m), 1.45-1.55 (1H, m), 4.70 (2H, d, J=5.6 Hz), 4.76 (2H, s), 5.53 (1H, dd, J=8.8, 15.6 Hz), 6.21 (1H, d, J=5.6 Hz), 6.49 (1H, d, J=8.8 Hz), 6.52 (1H, d, J=15.6 Hz), 6.66

(1H, d J=3.6 Hz), 6.83 (1H, d, J=3.6 Hz), 7.88 (1H, dd, J=2.4, 8.8 Hz), 8.48 (1H, d, J=2.4 Hz).

Example A-150

6-Amino-N-(5-(4-fluoro-phenoxy)-thiophen-2-ylmethyl)-nicotinamide $^1$H-NMR Spectrum (CDCl$_3$) δ(ppm): 4.44 (2H, d, J=5.2 Hz), 6.39 (1H, d, J=8.8 Hz), 6.43-6.52 (3H, m), 6.72 (1H, d, J=2.4 Hz), 7.09-7.16 (2H, m), 7.16-7.24 (2H, m), 7.78 (1H, dd, J=2.4, 8.8 Hz), 8.42 (1H, s), 8.74 (1H, t, J=5.2 Hz).

Example A-151

6Amino-N-(5-(3-cyano-phenoxy)-thiophen-2-ylmethyl)-nicotinamide $^1$H-NMR Spectrum (CDCl$_3$) δ(ppm): 4.68 (2H, d, J=5.6 Hz), 4.78 (2H, s), 6.27 (1H, brs), 6.38-6.40 (1H, m), 6.49-6.52 (1H, m), 6.74-6.75 (1H, m), 7.08-7.10 (2H, m), 7.30-7.33 (2H, m), 7.88-7.91 (1H, m), 8.48-8.49 (1H, m).

Example A-152

N-(5-Benzyl-thiophen-2-ylmethyl)-6-(carbonylmethyl-amino)-nicotinamide

5N Hydrochloric acid (1.5 mL) and ethanol (10 mL) were added to (5-((5-benzyl-thiophen-2-ylmethyl)-carbamoyl)-pyridin-2-yl)-carbamoyl methyl-carbamic acid tert-butyl ester described in Preparation Example A+-4 (23 mg, 0.047 mmol), and the solution was stirred for 10 minutes at 80° C. An aqueous solution of sodium bicarbonate and ethyl acetate were added to the reaction solution, which was then partitioned, the organic layer was washed with water twice and dried over anhydrous magnesium sulfate. The solvent was evaporated, and the title compound (12 mg, 0.031 mmol, 67.1%) was obtained as a brown oily substance.

$^1$H-NMR Spectrum (DMSO-d$_6$) δ(ppm): 4.00-4.07 (4H, m), 4.46 (2H, d, J=5.6 Hz), 6.55 (1H, d, J=8.8 Hz), 6.66-6.69 (1H, m), 6.76 (1H, d, J=3.6 Hz), 7.15-7.30 (5H, m), 7.46 (1H, t, J=6.0 Hz), 7.80 (1H, dd, J=2.4, 8.8 Hz), 8.44 (1H, d, J=2.4 Hz), 8.74 (1H, t, J=5.6 Hz).

Example A-153

6-(Ethoxymethyl-amino)-N-(5-phenoxy-thiophen-2-ylmethyl)-nicotinamide

To a solution of 6-amino-N-(5-phenoxy-thiophen-2-ylmethyl)-nicotinamide described in Example A-138 (600 mg, 1.8 mmol) in ethanol (40 mL) were added 5,5-dimethylimidazo phospho-2,4-dione (260 mg, 2.0 mmol) and 37% formaldehyde aqueous solution (3 mL), and the solution was stirred under reflux for 30 minutes. Water and ethyl acetate were added to the reaction solution, which was then partitioned, and the organic layer was washed with water twice. NH silica gel was added to the organic layer, the solvent was evaporated in vacuo for adsorption, purification was carried out by NH silica gel column chromatography (ethyl acetate), and the title compound (457 mg, 1.19 mmol, 66.1%) was obtained as a white solid.

$^1$H-NMR Spectrum (DMSO-d$_6$) δ(ppm): 1.05 (3H, t, J=7.2 Hz), 3.42 (2H, q, J=7.2 Hz), 4.47 (2H, d, J=5.6 Hz), 4.73 (2H, d, J=6.8 Hz), 6.44-6.50 (1H, m), 6.55 (1H, d, J=8.8 Hz), 6.74 (1H, d, J=3.6 Hz), 7.03-7.15 (3H, m), 7.30-7.40 (2H, m), 7.83-7.92 (2H, m), 8.53 (1H, d, J=2.0 Hz), 8.85 (1H, t, J=5.6 Hz).

Example A-154

6-(Ethoxymethyl-amino)-N -(5-(4-fluoro-phenoxy)-thiophen-2-ylmethyl)-nicotinamide The title compound (120 mg, 0.30 mmol, 51.7%) was obtained as a white solid from (6-amino-N-(5-(4-fluoro-phenoxy)-thiophen-2-ylmethyl)-nicotinamide described in Example A-139 (200 mg, 0.58 mmol) according to an analogous method to Example A-153.

$^1$H-NMR Spectrum (DMSO-d$_6$) δ(ppm): 1.03-1.10 (3H, m), 3.40-3.46 (2H, m), 4.46 (2H, d, J=5.6 Hz), 4.73 (2H, d, J=6.8 Hz), 6.44-6.49 (1H, m), 6.55 (1H, d, J=8.8 Hz), 6.73 (1H, d, J=2.8 Hz), 7.08-7.16 (2H, m), 7.16-7.24 (2H, m), 7.83-7.90 (2H, m), 8.52 (1H, s), 8.84 (1H, t, J=5.6 Hz).

Example A-155

6-(Ethoxymethyl-amino)-N-(5-m-tolyloxy-thiophen-2-ylmethyl)-nicotinamide

The title compound (84 mg, 2.05 mmol, 31.5%) was obtained as a white solid from 6-amino-N-(5-m-tolyloxy-thiophen-2-ylmethyl)-nicotinamide described in Example A-141 (220 mg, 0.65 mmol) according to an analogous method to Example A-153.

$^1$H-NMR Spectrum (DMSO-d$_6$) δ(ppm): 1.03-1.10 (3H, m), 2.25 (3H, s), 3.40-3.46 (2H, m), 4.46 (2H, d, J=5.6 Hz), 4.73 (2H, d, J=6.8 Hz), 6.44-6.47 (1H, m), 6.54 (1H, d, J=8.8 Hz), 6.73 (1H, d, J=4.0 Hz), 6.83-6.96 (3H, m), 7.22 (1H, dd, J=8.0, 8.0 Hz), 7.84-7.91 (2H, m), 8.52 (1H, d, J=2.4 Hz), 8.84 (1H, t, J=5.6 Hz).

Example A-156

N-(5-(3-Fluoro-phenoxy)-thiophen-2-ylmethyl)-6-(2-methoxy-ethylamino)-nicotinamide To a solution of (5-((5-(3-fluoro-phenoxy)-thiophen-2-ylmethyl)-carbamoyl)-pyridin-2-yl)-carbamic acid tert-butyl ester described in Preparation Example A+−2 (100 mg, 0.227 mmol) and methoxyethyl bromide (38 mg, 0.272 mmol) in dimethylsulfoxide (5 mL) was added sodium hydride (11 mg, 0.272 mmol, 60% in oil), and the solution was stirred at room temperature for 1 hour. 5N Hydrochloric acid was added to the reaction solution, which was then stirred for 5 minutes at 80° C. Water and ethyl acetate were added to the reaction solution, which was then partitioned, the organic layer was washed with water twice, then, silica gel was added, the solvent was evaporated in vacuo for adsorption, purification was carried out by silica gel column chromatography (hexane:ethyl acetate=1:1, then ethyl acetate), and the title compound (39 mg, 0.097 mmol, 42.8%) was obtained as a white solid.

$^1$H-NMR Spectrum (DMSO-d$_6$) δ(ppm): 3.24 (3H, s), 3.41-3.46 (4H, m), 4.47 (2H, d, J=5.6 Hz), 6.48 (1H, d, J=9.2 Hz), 6.54-6.58 (1H, m), 6.76 (1H, d, J=2.8Hz), 6.88-7.00 (3H, m), 7.12 (1H, s), 7.36-7.44 (1H, m), 7.77 (1H, d, J=9.2 Hz), 8.48 (1H, s), 8.77 (1H, t, J=5.6 Hz).

Example A-157

6-Methoxymethyl-N-(5-phenoxy-thiophen-2-ylmethyl)-nicotinamide

The title compound (56 mg, 0.158 mmol, 43.9%) was obtained as a light brown solid from 6-methoxymethylnicotinic acid (60 mg, 0.36 mmol) and C-(5-phenoxy-thiophen-2-yl)methylamine described in Preparation Example 26 (64 mg, 0.36 mmol) according to an analogous technique to Example Q-6.

$^1$H-NMR Spectrum (DMSO-d$_6$) δ(ppm): 3.38 (3H, s), 4.53-4.57 (4H, m), 6.52 (1H, d, J=3.6 Hz), 6.81 (1H, d, J=3.6 Hz), 7.07-7.17 (3H, m), 7.35-7.42 (2H, m), 7.50 (1H, d, J=8.0 Hz), 8.22 (1H, dd, J=2.0, 8.0 Hz), 8.95 (1H, d, J=2.0 Hz), 9.31 (1H, t, J=5.6 Hz).

Example A-158

N-(5-(3-Chloro-benzyl)-thiophen-2-ylmethyl)-6-(methoxymethyl-amino)-nicotinamide To a solution of 6-amino-N-(5-(3-chloro-benzyl)-thiophen-2-ylmethyl)-nicotinamide described in Example A-145 (110 mg, 0.3 mmol) in methanol (10 mL) were added 5,5-dimethylimidazo phospho-2,4-dione (43 mg, 0.33 mmol) and an aqueous solution of 37% formaldehyde (0.5 mL), and the solution was stirred under reflux for 2 hours. NH silica gel was added to the reaction solution, the solvent was evaporated in vacuo for adsorption, purification was carried out by NH silica gel column chromatography (hexane:ethyl acetate=1:1, then ethyl acetate), and the title compound (65 mg, 0.16 mmol, 54%) was obtained as a slightly yellow solid.

$^1$H-NMR Spectrum (DMSO-d$_6$) δ(ppm): 3.16 (3H, s), 4.06 (2H, s), 4.48 (2H, d, J=6.0 Hz), 4.68 (2H, d, J=6.8 Hz), 6.54 (1H, d, J=8.4 Hz), 6.69-6.73 (1H, m), 6.76-6.80 (1H, m), 7.17-7.34 (4H, m), 7.84-7.92 (2H, m), 8.51 (1H, s), 8.81 (1H, t, J=6.0 Hz).

Example A-159

N-(5-benzylthiophen-2-ylmethyl)-6-(methoxymethyl-amino)-nicotinamide

To a solution of 6-amino-N-(5-benzylthiophen-2-ylmethyl)-nicotinamide described in Example A-144 (210 mg, 0.65 mmol) and 5,5-dimethylimidazo phospho-2,4-dione (92 mg, 0.71 mmol) in methanol (15 mL) was added an aqueous solution of 37% formaldehyde (2.5 mL) under reflux in three time, and the solution was stirred for 1 hour. NH silica gel was added to the reaction solution, the solvent was evaporated in vacuo for adsorption, purification was carried out by NH silica gel column chromatography (hexane:ethyl acetate=1:1, then ethyl acetate), and the title compound (210 mg, 0.57 mmol, 87.6%) was obtained as a white solid.

$^1$H-NMR Spectrum (DMSO-d$_6$) δ(ppm): 3.14-3.18 (3H, m), 4.03 (2H, s), 4.47 (2H, d, J=4.8 Hz), 4.68 (2H, d, J=7.2 Hz), 6.54 (1H, d, J=8.8 Hz), 6.68 (1H, s), 6.76 (1H, s), 7.14-7.30 (5H, m), 7.84-7.92 (2H, m), 8.51 (1H, s), 8.79 (1H, t, J=4.8 Hz).

Example A-160

N-(5-(3-Fluorophenoxy)thiophen-2-ylmethyl)-6-methylnicotinamide

The title compound (53 mg, 0.154 mmol, 43.0%) was obtained as a white solid from 6-methylnicotinic acid (49 mg, 0.36 mmol) and C-(5-(3-fluorophenoxy)thiophen-2-yl)methylamine described in Preparation Example 23 (100 mg, 0.36 mmol) according to an analogous method to Example Q-6.

$^1$H-NMR Spectrum (DMSO-d$_6$) δ(ppm): 2.51 (3H, s), 4.55 (2H, d, J=6.4 Hz), 6.58-6.61 (1H, m), 6.82-6.85 (1H, m), 6.92-7.03 (3H, m), 7.34-7.46 (2H, m), 8.10 (1H, dd, J=2.0, 8.0 Hz), 8.90 (1H, d, J=2.0 Hz), 9.25 (1H, t, J=5.6 Hz).

Example A-161

6-Methyl-N-(5-phenoxy-thiophen-2-ylmethyl)-nicotinamide

The title compound (31 mg, 0.095 mmol, 32.9%) was obtained as a white solid from 6-methylnicotinic acid (40 mg, 0.29 mmol) and C-(5-phenoxy-thiophen-2-yl)-methylamine described in Preparation Example 26 (49 mg, 0.24 mmol) according to an analogous method to Example Q-6.

$^1$H-NMR Spectrum (DMSO-d$_6$) δ(ppm): 2.49 (3H, s), 4.51 (2H, d, J=5.6 Hz), 6.49 (1H, d, J=4.0 Hz), 6.78 (1H, d, J=4.0 Hz), 7.05-7.15 (3H, m), 7.32-7.40 (3H, m), 8.07 (1H, dd, J=2.0, 8.0 Hz), 8.87 (1H, d, J=2.0 Hz), 9.21 (1H, t, J=5.6 Hz).

Example A-162

N-(5-(3-Chloro-benzyl)-thiophen-2-ylmethyl)-6-methyl-nicotinamide

The title compound (32 mg, 0.089 mmol, 26.4%) was obtained as a white solid from C-(5-(3-chloro-benzyl-2-yl)-methylamine described in Preparation Example 45 (80 mg, 0.34 mmol) and 6-methylnicotinic acid (46 mg, 0.34 mmol) according to an analogous method to Example Q-6.

$^1$H-NMR Spectrum (DMSO-d$_6$) δ(ppm): 2.50 (3H, s), 4.08 (2H, s), 4.54 (2H, d, 5.6 Hz), 6.75 (1H, d, J=3.6 Hz), 6.84 (1H, d, J=3.6 Hz), 7.20-7.36 (5H, m), 8.08 (1H, dd, J=2.0, 8.0 Hz), 8.88 (1H, d, J=2.0 Hz), 9.18 (1H, t, J=5.6 Hz).

Example A-163

6-Methylamino-N-(5-phenoxy-thiophen-2-ylmethyl)-nicotinamide

To a solution of 6-(ethoxymethyl-amino)-N-(5-phenoxy-thiophen-2-ylmethyl)-nicotinamide described in Example A-153 (427 mg, 0.92 mmol) in dimethylsulfoxide (5 mL) was added sodium borohydride (100 mg, 2.7 mmol), and the solution was stirred for 15 minutes at 100° C. Water and ethyl acetate were added to the reaction solution, which was then partitioned, and the organic layer was washed with water three times. Silica gel was added to the organic layer, the solvent was evaporated in vacuo for adsorption, and purified by silica gel column chromatography (ethyl acetate). The solvent was evaporated in vacuo, hexane, diethyl ether and ethyl acetate were added to the residue for solidification, and the title compound (150 mg, 0.44 mmol, 48.1%) was obtained as a white solid.

$^1$H-NMR Spectrum (DMSO-d$_6$) δ(ppm): 2.78 (3H, d, J=4.8 Hz), 4.46 (2H, d, J=5.6 Hz), 6.40 (1H, d, J=8.8 Hz), 6.47 (1H, d, J=3.6 Hz), 6.73 (1H, d, J=3.6 Hz), 6.98-7.15 (4H, m), 7.32-7.40 (2H, m), 7.79 (1H, dd, J=2.0, 8.8 Hz), 8.50 (1H, d, J=2.0 Hz), 8.75 (1H, t, J=5.6 Hz).

Example A-164

N-(5-(4-Fluoro-phenoxy)-thiophen-2-ylmethyl)-6-methylamino-nicotinamide

The title compound (1.20 mg, 0.30 mmol, 51.7%) was obtained as a white solid from 6-(ethoxymethyl-amino)-N-(5 (4-fluoro-phenoxy)-thiophen-2-ylmethyl)-nicotinamide described in Example A-154 according to an analogous method to Example A-163.

$^1$H-NMR Spectrum (DMSO-$d_6$) δ(ppm): 2.76-2.81 (3H, m), 4.45 (2H, d, J=5.6 Hz), 6.40 (1H, d, J=8.4 Hz), 6.44-6.48 (1H, m), 6.70-6.75 (1H, m), 6.98-7.06 (1H, m), 7.08-7.24 (4H, m), 7.79 (1H, d, J=8.4 Hz), 8.50 (1H, s), 8.75 (1H, t, J=5.6 Hz).

Example A-165

N-(5-(3-Fluoro-phenoxy)-thiophen-2-ylmethyl)-6-methylamino-nicotinamide

Ethanol (20 mL) and 5N hydrochloric acid (0.8 mL) were added to (5-((5-(3-fluoro-phenoxy)-thiophen-2-ylmethyl) carbamoyl)pyridin-2-yl)methyl-carbamic acid tert-butyl ester described in Preparation Example A+-3 (87 mg, 0.19 mmol), and the solution was stirred for 25 minutes at 80° C. An aqueous solution of sodium bicarbonate and ethyl acetate were added to the reaction solution, which was then partitioned, the organic layer was washed with water twice, washed with brine, and the organic layer was dried over anhydrous magnesium sulfate. The solvent was evaporated, and the title compound (58 mg, 0.162 mmol, 85.5%) was obtained as a white solid.

$^1$H-NMR Spectrum (DMSO-$d_6$) δ(ppm): 2.78 (3H, d, J=4.8 Hz), 4.47 (2H, d, J=5.6 Hz), 6.40 (1H, d, J=8.0 Hz), 6.55 (1H, d, J=3.6 Hz), 6.76 (1H, d, J=3.6 Hz), 6.86-7.06 (4H, m), 7.36-7.44 (1H, m), 7.79 (1H, dd, J=2.0, 8.0 Hz), 8.50 (1H, d, J=2.0 Hz), 8.77 (1H, t, J=5.6 Hz).

Example A-166

N-(5-Benzyl-thiophen-2-ylmethyl)-6-methylamino-nicotinamide

To a solution of N-(5-benzyl-thiophen-2-ylmethyl)-6-(methoxymethyl-amino)-nicotinamide described in Example A-159 (183 mg, 0.52 mmol) in dimethylsulfoxide (3 mL) was added sodium borohydride (120 mg, 3.12 mmol), and the solution was stirred at 140° C. for 5 hours. Water and ethyl acetate were added to the reaction solution, which was then partitioned, and the organic layer was washed with water twice. Silica gel was added to the organic layer, the solvent was evaporated in vacuo for adsorption, purification was carried out by silica gel column chromatography (ethyl acetate, then ethyl acetate:methanol=10:1), and the title compound (68 mg, 0.20 mmol, 38.8%) was obtained as a green solid.

$^1$H-NMR Spectrum (DMSO-$d_6$) δ(ppm): 2.77 (3H, d, J=4.8 Hz), 4.03 (2H, s), 4.46 (2H, d, J=5.6 Hz), 6.39 (1H, d, J=8.8 Hz), 6.68 (1H, d, J=3.6 Hz), 6.76 (1H, d, J=3.6 Hz), 6.96-7.04 (1H, m), 7.15-7.32 (5H, m), 7.77 (1H, dd, J=2.0, 8.8 Hz), 8.49 (1H, d, J=2.0 Hz), 8.70 (1H, t, J=5.6 Hz).

Example A-167

6-Methylamino-N-(5-m-tolyloxy-thiophen-2-ylmethyl)-nicotinamide

To a solution of 6-(ethoxymethyl-amino)-N-(5-m-tolyloxy-thiophen-2-ylmethyl)-nicotinamide described in Example A-155 (70 mg, 0.17 mmol) in dimethylsulfoxide (5 mL) was added sodium borohydride (20 mg, 0.51 mmol), and the solution was stirred for 20 minutes at 120° C. Water and ethyl acetate were added to the reaction solution, which was then partitioned, the organic layer was washed with brine once. The organic layer was passed through a glass filter lined with NH silica gel, and eluted thoroughly with ethyl acetate. The solvent was evaporated in vacuo, and the title compound (53 mg, 0.15 mmol, 88.2%) was obtained as a light brown solid.

$^1$H-NMR Spectrum (DMSO-$d_6$) δ(ppm): 2.25 (3H, s), 2.77 (3H, d, J=4.4 Hz), 4.45 (2H, d, J=5.6 Hz), 6.40 (1H, d, J=8.8 Hz), 6.45 (1H, d, J=3.6 Hz), 6.72 (1H, d, J=3.6 Hz), 6.83-6.96 (3H, m), 7.02 (1H, q, J=4.4 Hz), 7.22 (1H, dd, J=8.0, 8.0 Hz), 7.78 (1H, dd, J=2.4, 8.8 Hz), 8.50 (1H, d, J=2.4 Hz), 8.75 (1H, t, J=5.6 Hz).

Example A-168

2-Amino-N-(5-phenoxy-thiophen-2-ylmethyl)-6-vinyl-nicotinamide

To a mixture of 2-amino-6-chloro-N-(5-phenoxy-thiophen-2-ylmethyl)-nicotinamide described in Example A-101 (30 mg, 0.083 mmol), tetrakis(triphenylphosphine) palladium(0) (19 mg, 0.017 mmol) and xylene (1.5 mL) was added vinyl(tri-butyl)tin (0.073 mL, 0.25 mmol), and the solution was stirred at 130° C. for 3 hours. After cooling, water and ethyl acetate were added to the reaction solution for extraction, which was then washed with brine. The solvent was evaporated in vacuo, then, the residue was purified by NH silica gel column chromatography (hexane:ethyl acetate=2: 1), and the title compound (19 mg, 0.054 mmol, 65%) was obtained as a white solid.

$^1$H-NMR Spectrum (CDCl$_3$) δ(ppm): 4.65 (2H, d, J=5.5 Hz), 5.49 (1H, dd, J=1.4, 10.7 Hz), 6.22 (1H, dd, J=1.4, 17.3 Hz), 6.27 (1H, brs), 6.36 (2H, brs), 6.39 (1H, d, J=3.8 Hz), 6.60-6.67 (2H, m), 6.74 (1H, d, J=3.7 Hz), 7.08-7.13 (3H, m), 7.30-7.35 (2H, m), 7.56 (1H, d, J=8.1 Hz).

Example A-169

2-Amino-N-(5-bromo-4-phenoxy-thiophen-2-ylmethyl)-nicotinamide

The title compound was obtained from C-(5-bromo-4-phenoxy-thiophen-2-yl)-methylamine described in Preparation Example 129 (500 mg, 1.76 mmol) and 2-amino-nicotinic acid (267 mg, 1.94 mmol) according to an analogous method to Example A-26. Trifluoroacetic acid salt of the title compound was obtained by reverse phase high performance liquid chromatography (acetonitrile-water mobile phase (containing 0.1% trifluoroacetic acid) was used).

MS m/e (ESI) 405.94 (MH$^+$)

Example A-170

2-Amino-N-(5-methyl-4-phenoxy-thiophen-2-ylmethyl)-nicotinamide

To a mixture of 2-amino-N-(5-bromo-4-phenoxy-thiophen-2-ylmethyl)-nicotinamide described in Example A-169 (30 mg, 0.074 mmol), dichloro(1,1'-bis(diphenylphosphino)ferrocene)nickel(II) (10 mg, 0.015 mmol) and tetrahydrofuran (1 mL) was added methylmagnesium bromide (638 μl, 0.592 mmol) at room temperature, the solution was stirred for 2 hours at room temperature, and was further stirred for 2 hours at 50° C. After cooling, water and ethyl acetate were added for extraction, and the solution was washed with brine, then, the solvent was evaporated in vacuo. The residue was purified by reverse phase high performance liquid chromatography (acetonitrile-water mobile phase (containing 0.1% trifluoroacetic acid) was used), and the title compound was obtained as a trifluoroacetic acid salt.

MS m/e (ESI) 340.09 (MH$^+$)

Example A-171

2-Amino-N-(4-chloro-5-phenoxy-thiophen-2-ylmethyl)-nicotinamide

To a mixture of 2-amino-N-(5-phenoxy-thiophen-2-ylmethyl)-nicotinamide described in Example A-67 (21 mg, 0.064 mmol) and N,N-dimethylformamide (1 mL) was added N-chlorosuccinimide (13 mg, 0.096 mmol), and the solution was stirred overnight at room temperature. The reaction solution was purified by reverse phase high performance liquid chromatography (acetonitrile-water mobile phase (containing 0.1% trifluoroacetic acid) was used), and trifluoroacetic acid salt of the title compound (7.4 mg, 0.016 mmol, 24%) was obtained.

MS m/e (ESI) 360.1 (MH$^+$)

Example A-172

2-Amino-5-chloro-N-(4-chloro-5-phenoxy-thiophen-2-ylmethyl)-nicotinamide

Trifluoroacetic acid salt of the title compound (1.5 mg, 0.0030 mmol, 4.6%) was obtained as a by-product of Example A-171.

MS m/e (ESI) 394.0 (MH$^+$)

Example A-173

2.6-Diamino-N-(4-(3-chloro-benzyloxy)-benzyl)-nicotinamide

MS m/e (ESI) 383.246 (MH$^+$)

Example A-174

2,6-Diamino-N-(5-benzyloxy-pyridin-2-ylmethyl)-nicotinamide $^1$H-NMR Spectrum (DMSO-d$_6$) δ(ppm): 4.39 (2H, d, J=5.9 Hz), 5.16 (2H, s), 5.68 (1H, d, J=8.6 Hz), 6.09 (2H, s), 6.94 (2H, s), 7.20 (1H, d, J=8.8 Hz), 7.31-7.46 (6H, m), 7.69 (1H, d, J=8.6 Hz), 8.25 (1H, d, J=2.9 Hz), 8.35 (1H, t, J=5.9 Hz).

Example A-175

2.6-Diamino-N-(5-phenoxymethyl-pyridin-2-ylmethyl)-nicotinamide $^1$H-NMR Spectrum (CDCl$_3$) δ(ppm): 4.64 (2H, s), 4.68 (2H, d, J=4.9 Hz), 5.07 (2H, s), 5.80 (1H, d, J=8.4 Hz), 6.50 (2H, s), 6.96-7.01 (3H, m), 7.26-7.35 (4H, m), 7.56 (1H, d, J=8.4 Hz), 7.76 (1H, dd, J=2.2 Hz, 8.0 Hz), 8.61 (1H, d, J=1.7 Hz).

Example A-176

2-Amino-6-(2-cyano-ethyl)-N-(4-(6-fluoro-pyridin-2-yloxymethyl)-benzyl)-nicotinamide $^1$H-NMR Spectrum (CDCl$_3$) δ(ppm): 2.78 (2H, t, J=7.2 Hz), 2.94 (2H, t, J=7.2 Hz), 4.60 (2H, d, J=5.6 Hz), 5.33 (2H, s), 6.24 (1H, brs), 6.39 (2H, brs), 6.47-6.48 (1H, m), 6.49-6.50 (1H, m), 6.64-6.67 (1H, m), 7.35 (2H, d, J=8.4 Hz), 7.46 (2H, d, J=8.4 Hz), 7.53 (1H, d, J=8.0 Hz), 7.66 (1H, q, J=8.0 Hz).

Example A-177

2-Amino-6-(2-fluoro-ethyl)-N-(5-phenoxy-thiophen-2-ylmethyl)-nicotinamide $^1$H-NMR Spectrum (DMSO-d$_6$) δ(ppm): 2.93 (2H, td, J=6.0, 25.6 Hz), 4.47 (2H, d, J=5.6 Hz), 4.75 (2H, td, J=6.0, 47.2 Hz), 6.50 (1H, d, J=4.0 Hz), 6.53 (1H, d, J=8.0 Hz), 6.77 (1H, d, J=4.0 Hz), 7.07-7.18 (5H, m), 7.38 (2H, t, J=8.0 Hz), 7.85 (1H, d, J=8.0 Hz), 8.99 (1H, t, J=5.6 Hz).

Example A-178

2-Amino-6-ethoxymethyl-N-(4-(pyridin-2-yloxymethyl)-benzyl)-nicotinamide $^1$H-NMR Spectrum (CDCl$_3$) δ(ppm): 1.27 (3H, t, J=7.0 Hz), 3.60 (2H, q, J=7.2 Hz), 4.44 (2H, s), 4.60 (2H, d, 5.6 Hz), 5.38 (2H, s), 6.24 (1H, brs), 6.38 (2H, brs), 6.73 (1H, d, J=8.0 Hz), 6.80 (1H, dd, J=0.8, 7.6 Hz), 6.88-6.91 (1H, m), 7.36 (2H, d, J=8.0 Hz), 7.46 (2H, d, J=8.0 Hz), 7.56-7.61 (2H, m), 8.17-8.18 (1H, m).

Example A-179

2-Amino-N-(5-isopropoxy methyl-thiophen-2-ylmethyl)-6-methoxymethyl-nicotinamide MS m/e (ESI) 350 (MH$^+$)

Example A-180

2-Amino-N-(4-(3-methoxy-benzyloxy)-benzyl)-6-methoxymethyl-nicotinamide

MS m/e (ESI) 408.27 (MH$^+$)

$^1$H-NMR Spectrum (CD$_3$OD) δ(ppm): 3.50 (3H, s), 3.77 (3H, s), 4.48 (2H, d, J=4 Hz), 4.57 (2H, s), 5.04 (2H, s), 6.84-6.88 (2H, m), 6.94-6.98 (4H, m), 7.23-7.29 (3H, m), 8.27-8.29 (1H, m).

Example A-181

2-Amino-N-(4-(3-chloro-benzyloxy)-benzyl)-6-methoxymethyl-nicotinamide

MS m/e (ESI) 412.26(MH$^+$)

Example A-182

2-Amino-N-(4-butoxymethyl-benzyl)-6-methoxymethyl-nicotinamide

MS m/e (ESI) 358 (MH+)

Example A-183

2-Amino-6-methoxymethyl-N-(4-propoxymethyl-benzyl)-nicotinamide

MS m/e (ESI) 344 (MH+)

Example A-184

2-Amino-N-(3-cyclopropylmethoxy-benzyl)-6-methoxymethyl-nicotinamide

MS m/e (ESI) 342 (MH+)

Example A-185

2-Amino-N-(4-(6-fluoro-pyridin-2-yloxymethyl)-benzyl)-6-methoxymethyl-nicotinamide $^1$H-NMR Spectrum (CDCl$_3$) δ(ppm): 3.46 (3H, s), 4.40 (2H, s), 4.61 (2H, d, J=5.6 Hz), 5.33 (2H, s), 6.26 (1H, brs), 6.40 (2H, s), 6.49 (1H, dd, J=2.4, 7.6 Hz), 6.66 (1H, dd J=1.1, 7.6 Hz), 6.70 (1H, d, J=8.0 Hz), 7.36 (2H, d, J=8.0 Hz), 7.46 (2H, d, J=8.0 Hz), 7.60 (1H, d, J=8.0 Hz), 7.66 (1H, dd, J=8.0, 8.0 Hz).

Example A-186

2-Amino-6-methoxymethyl-N-(4-(4-methyl-pyridin-2-yloxymethyl)-benzyl)-nicotinamide $^1$H-NMR Spectrum (CDCl$_3$) δ(ppm): 2.30 (3H, s), 3.45 (3H, s), 4.39 (2H, s), 4.60 (2H, d, J=5.6 Hz), 5.36 (2H, s), 6.25 (1H, brs), 6.40 (2H, brs), 6.62 (1H, s), 6.65 (1H, d, J=8.0 Hz), 6.72 (1H, d, J=5.2 Hz), 7.35 (2H, d, J=8.4 Hz), 7.45 (2H, d, J=8.4 Hz), 7.59 (1H, d, J=8.0 Hz), 8.02 (1H, d, J=5.2 Hz).

Example A-187

2-Amino-N-(4 (6-fluoro-pyridin-2-ylmethoxy)-benzyl)-6-methoxymethyl-nicotinamide $^1$H-NMR Spectrum (CDCl$_3$) δ(ppm) 3.45 (3H, s), 4.39 (2H, s), 4.53 (2H, d, J=5.6 Hz), 5.13 (2H, s), 6.22 (1H, brs), 6.39 (2H, brs), 6.69 (1H, d, J=7.6 Hz), 6.87 (1H, 8.4 Hz), 6.96 (2H, d, J=8.4 Hz), 7.28 (2H, d, J=8.4 Hz), 7.40-7.42 (1H, m), 7.58 (1H, d, J=8.0 Hz), 7.81 (1H, dd, J=8.0, 8.0 Hz).

Example A-188

2-Amino-N-(4-butoxy-benzyl)-6-methoxymethyl-nicotinamide

MS m/e (ESI) 344 (MH+)

Example A-189

2-Amino-N-(4-(2-ethoxy-ethyl)-benzyl) )-6-methoxymethyl-nicotinamide

MS m/e (ESI) 344 (MH+)

Example A-190

2-Amino-methoxymethyl-N-(4-(5-methyl-pyridin-2-yloxymethyl)-benzyl)-nicotinamide $^1$H-NMR Spectrum (CDCl$_3$) δ(ppm): 2.25 (3H, s), 3.45 (3H, s), 4.40 (2H, s), 4.60 (2H, d, J=5.6 Hz), 5.34 (2H, s), 6.24 (1H, brs), 6.40 (2H, brs), 6.69 (1H, d, J=8.0 Hz), 6.71 (1H, d, J=8.0 Hz), 7.35 (2H, d, J=8.0 Hz), 7.41 (1H, dd, J=2.4, 8.4 Hz), 7.46 (2H, d, J=8.0 Hz), 7,59 (1H, d, J=8.4 Hz), 7.96 (1H, s).

Example A-191

2-Amino-N-(6-benzyl-pyridin-3-ylmethyl)-6-methoxymethyl-nicotinamide $^1$H-NMR Spectrum (CDCl$_3$) δ(ppm): 3.45 (3H, s), 4.15 (2H, s), 4.39 (2H, s), 4.57 (2H, d, J=5.6 Hz), 6.32 (1H, brs), 6.38 (2H, brs), 6.69 (1H, d, J=8.0 Hz), 7.12 (1H, d, J=8.4 Hz), 7.20-7.32 (5H, m), 7.58 (7.61 (2H, m), 8.52 (1H, d, J=2.0 Hz).

Example A-192

2-Amino-6-methoxymethyl-N-(5-phenoxymethyl-pyridin-2-ylmethyl)-nicotinamide $^1$H-NMR Spectrum (CDCl$_3$) δ(ppm): 3.46 (3H, s), 4.41 (2H, s), 4.72 (2H, d, J=4.8 Hz), 5.09 (2H, s), 6.45 (2H, s), 6.74 (1H, d, J=7.9 Hz), 6.96-7.02 (3H, m), 7.29-7.36 (3H, m), 7.53 (1H, s), 7.79 (2H, d, J=7.9 Hz), 8.63 (1H, d, J=1.7 Hz).

Example A-193

2-Amino-6-methoxymethyl-N-(5-phenoxy-pyridin-2-ylmethyl)-nicotinamide $^1$H-NMR Spectrum (DMSO-d$_6$) δ(ppm): 3.34 (3H, s), 4.30 (2H, s), 4.52 (2H, d, J=6.0 Hz), 6.62 (1H, d, J=8.0 Hz), 7.02-7.07 (2H, m), 7.10-7.20 (3H, m), 7.33-7.46 (4H, m), 8.02 (1H, d, J=8.0 Hz), 8.31 (1H, d, J=2.8 Hz), 9.02 (1H, t, J=6.0 Hz).

Example A-194

2-Amino-6-methoxymethyl-N-(4-(2-propoxy-ethyl)-benzyl)-nicotinamide

MS m/e (ESI) 358 (MH+)

Example AA-1

3-Amino-pyrazine-2carboxylic acid (5-phenoxy-thiophen-2-ylmethyl)-amide $^1$H-NMR Spectrum (DMSO-d$_6$) δ(ppm): 4.47 (2H, d, J=6.4 Hz), 6.47 (1H, d, J=4.0 Hz), 6.74 (1H, d, J=4.0 Hz), 7.05-7.15 (3H, m), 7.24-7.40 (2H, m), 7.50 (2H, brs), 7.80 (1H, d, J=2.4 Hz), 8.18 (1H, d, J=2.4 Hz), 9.28 (1H, t, J=6.4 Hz).

Example AA-2

3.5-Diamino-pyrazine-2-carboxylic acid 4-(pyridin-2-yloxymethyl)-benzylamide $^1$H-NMR Spectrum (DMSO-d$_6$) δ(ppm): 4.38 (2H, d, J=6.4 Hz), 5.3 (2H, s), 6.67 (2H, s), 6.84 (1H, d, J=8.2 Hz), 6.98 (1H, t, J=7.2 Hz), 7.13 (1H, s), 7.28 (2H, d, J=8.1 Hz), 7.38 (2H, d, J=8.1 Hz), 7.71 (1H, dt, J=2.0 Hz, 7.8 Hz), 8.16 (1H, dd, J=2.0 Hz, 4.8 Hz), 8.54 (1H, t, J=6.4 Hz).

Example B-1

4-Amino-pyrimidine-5-carboxylic acid (5-phenoxy-thiophen-2-ylmethyl)-amide

The title compound (7 mg, 0.021 mmol, 4.4%) was obtained as a white solid from 4-amino-pyrimidine-5-carboxylic acid (68 mg, 0.49 mmol) and C-(5-phenoxy-thiophen-2-yl)-methylamine described in Preparation Example 26 (100 mg, 0.49 mmol) according to an analogous technique to Example Q-6.

$^1$H-NMR Spectrum (DMSO-d$_6$) δ(ppm): 4.47 (2H, d, J=5.2 Hz), 6.47-6.50 (1H, m), 6.76-6.78 (1H, m), 7.04-7.15 (3H, m), 7.34-7.40 (2H, m), 7.77 (2H, brs), 8.40 (1H, d, J=1.6 Hz), 8.59 (1H, d, J=1.6 Hz), 9.19 (1H, t, J=5.2 Hz).

Example B-2

4-Amino-2-propylamino-pyrimidine-5-carboxylic acid 4-(pyridin-2-yloxymethyl)-benzylamide $^1$H-NMR Spectrum (DMSO-d$_6$) δ(ppm): 0.86 (3H, t, J=7.2 Hz), 1.44-1.55 (2H, m), 3.14-3.24 (2H, m), 4.38 (2H, d, J=6.4 Hz), 5.32 (2H, s), 6.83-6.87 (1H, m), 6.96-7.01 (1H, m), 7.28 (2H, d, J=8.0 Hz), 7.38 (2H, d, J=8.0 Hz), 7.69-7.75 (1H, m), 8.15-8.19 (1H, m), 8.42 (1H, s), 8.60 (1H, brs).

Example C-1

(2-Amino-6,7-dihydro-5H-cyclopenta[b]pyridine-3-carboxylic acid (5-phenoxy-thiophen-2-ylmethyl)-amide 2-Amino-6,7-dihydro-5H-cyclopenta[b]pyridine-3carboxylic acid described in Preparation Example C-5 (100 mg, 0.56 mmol), triethylamine (0.188 mL, 1.35 mmol) and benzotriazol-1-yloxytris(dimethylamino)phosphonium hexafluorophosphate (298 mg, 0.67 mmol) were dissolved in N,N-dimethylformamide (3 mL), C-(5-phenoxy-thiophen-2-yl)-methylamine described in Preparation Example 26 (138 mg, 0.67 mmol) was added, followed by stirring for 15 hours 20 minutes at room temperature. After the reaction was completed, the reaction solution was poured into brine, and the solution was extracted with ethyl acetate. The organic layer was dried over anhydrous magnesium sulfate, then concentrated, the obtained residue was purified by silica gel column chromatography (ethyl acetate:hexane=1:1), and the title compound (77 mg, 0.21 mmol, 38%) was obtained.

$^1$H-NMR Spectrum (DMSO-d$_6$) δ(ppm): 1.95-2.03 (2H, m), 2.68-2.76 (4H, m), 4.46 (2H, d, J=5.6 Hz), 6.45 (1H, d, J=4.0 Hz), 6.76 (1H, d, J=4.0 Hz), 6.97 (2H, brs), 7.07-7.17 (3H, m), 7.36-7.41 (2H, m), 7.76 (1H, s), 8.88-8.93 (1H, m).

Example D-1

[1,5]Naphthylidine-2-carboxylic acid 3-phenoxybenzylamide

The title compound (14 mg, 76%) was obtained as a colorless oil from [1,5]naphthylidine-2-carboxylic acid described in Preparation Example D-1 (9 mg, 0.0517 mmol) and 3-phenoxybenzylamine described in Preparation Example 4 (6 mg, 0.0517 mmol) according to an analogous method to Example L-4.

$^1$H-NMR Spectrum (CDCl$_3$) δ(ppm): 4.73 (2H, d, J=6.0 Hz), 6.92-6.94 (1H, m), 7.01-7.03 (2H, m), 7.07-7.17 (3H, m), 7.26-7.36 (3H, m), 7.70 (1H, dd, J=4.4, 8.8 Hz), 8.39 (1H, dd, J=1.6, 8.8 Hz), 8.51 (1H, brs), 8.57 (2H, s), 9.06 (1H, dd, J=1.6, 4.4 Hz).

Example D-2

[1.5]Naphthylidine-2-carboxylic acid 4-benzyloxybenzylamide

The title compound (11 mg, 52%) was obtained as a white solid from [1,5]naphthylidine-2-carboxylic acid described in Preparation Example D-1 (10 mg, 0.0574 mmol) and 4-benzyloxybenzylamine described in Preparation Example 1 (12 mg, 0.0574 mmol) according to an analogous method to Example L-4.

$^1$H-NMR Spectrum (CDCl$_3$) δ(ppm): 4.68 (2H, d, J=6.4 Hz), 5.08 (2H, s), 6.97-6.99 (2H, m), 7.32-7.45 (7H, m), 7.69 (1H, dd, J=4.4, 8.8 Hz), 8.36-8.39 (1H, m), 8.43 (1H, brs), 8.54-8.60 (2H, m), 9.04-9.06 (1H, m).

Example D-3

[1,5]Naphthylidine-2-carboxylic acid 4-phenoxymethyl-benzylamide $^1$H-NMR Spectrum (CDCl$_3$) δ(ppm): 4.76 (2H, d, J=6 Hz), 5.07 (2H, s), 6.94-6.99 (3H, m), 7.27-7.31 (3H, m), 7.43-7.45 (4H, m), 7.68-7.71 (1H, m), 8.37-8.40 (1H, m), 8.50 (1H, brs), 8.55-8.60 (1H, m), 9.05-9.06 (1H, m).

Example D-4

[1,5]Naphthylidine-2-carboxylic acid (1-(3-fluoro-benzyl)-1H-pyrrol-3-ylmethyl)-amide To a solution of C-(1-(3-fluoro-benzyl)-1H-pyrrol-3-yl)-methylamine described in Preparation Example 59 (59 mg, 0.287 mmol) and [1,5]naphthylidine-2-carboxylic acid described in Preparation Example D-1 (50 mg, 0.287 mmol) in N,N-dimethylformamide (3 mL) were added benzotriazol-1-yloxytris(dimethylamino)phosphonium hexafluorophosphate (152 mg, 0.344 mmol) and triethylamine (80 μL, 0.574 mmol), and the solution was stirred overnight at room temperature. Ethyl acetate and water were added to the reaction solution, which was then partitioned, the organic layer was washed with water, and then, dried over anhydrous magnesium sulfate. The solvent was evaporated, the residue was purified by NH silica gel column chromatography (hexane: ethyl acetate), and the title compound (49 mg, 47%) was obtained as a pale yellow solid.

$^1$H-NMR Spectrum (CDCl$_3$) δ(ppm): 4.59 (2H, d, J=5.6 Hz), 5.03 (2H, s), 6.26-6.27 (1H, m), 6.66-6.67 (1H, m), 6.74-6.75 (1H, m), 6.81-6.84 (1H, m), 6.92-6.94 (1H, m), 6.96-7.01 (1H, m), 7.28-7.33 (1H, m), 7.67-7.70 (1H, m), 8.31 (1H, brs), 8.37-8.40 (1H, m), 8.53-8.59 (2H, m), 9.03-9.05 (1H, m).

Example D-5

[1,5]Naphthylidine-2-carboxylic acid (5-(3-fluorophenoxy)thiophen-2-ylmethyl)amide The title compound (66 mg, 0.17 mmol, 72.5%) was obtained as a brown oil from [1,5]-naphthylidine-2-carboxylic acid (42 mg, 0.24 mmol) and C-(5-(3-fluorophenoxy)thiophen-2-yl)methylamine described in Preparation Example 23 (54 mg, 0.24 mmol) according to an analogous method to Example Q-6.
$^1$H-NMR Spectrum (DMSO-$d_6$) δ(ppm): 4.61 (2H, d, J=6.4 Hz), 6.57 (1H, d, J=3.6 Hz), 6.83 (1H, d, J=3.6 Hz), 6.87-7.00 (3H, m), 7.36-7.42 (1H, m), 7.87 (1H, dd, J=4.0, 8.8 Hz), 8.37 (1H, d, J=8.8 Hz), 8.49 (1H, d, J=8.8 Hz), 8.59 (1H, d, J=8.8 Hz), 9.09 (1H, d, J=4.0 Hz), 9.58 (1H, t, J=6.4 Hz).

Example D-6

[1,5]Naphthylidine-2-carboxylic acid (5-phenoxy-thiophen-2-ylmethyl)-amide

The title compound (15 mg, 0.042 mmol, 17.3%) was obtained as a light brown solid from [1,5]-naphthylidine-2-carboxylic acid (42 mg, 0.24 mmol) and C-(5-phenoxy-thiophen-2-yl)methylamine described in Preparation Example 26 (49 mg, 0.24 mmol) according to an analogous technique to Example Q-6.
$^1$H-NMR Spectrum (DMSO-$d_6$) δ(ppm): 4.59 (2H, d, J=5.6 Hz), 6.49 (1H, d, J=3.6 Hz), 6.81 (1H, d, J=3.6 Hz), 7.03-7.14 (3H, m), 7.30-7.40 (2H, m), 7.88 (1H, dd, J=4.0, 8.8 Hz), 8.36 (1H, d, J=8.8 Hz), 8.48 (1H, d, J=8.8 Hz), 8.58 (1H, d, J=8.8 Hz), 9.09 (1H, d, J=4.0 Hz), 9.56 (1H, t, J=5.6 Hz).

Example D-7

[1,5]Naphthylidine-2-carboxylic acid (5-(4-fluorophenoxy)-thiophen-2-ylmethyl)-amide To a solution of [1,5]naphthylidine-2-carboxylic acid described in Preparation Example D-1 (20 mg, 0.115 mmol) and described in Preparation Example 28C-(5-(4-fluorophenoxy)thiophen-2-yl)methylamine) (51 mg, 0.23 mmol) in dimethylsulfoxide (9 mL) were added benzotriazol-1-yloxy-tris(dimethylamino)phosphonium hexafluorophosphate (102 mg, 0.23 mmol) and triethylamine (56 μL, 0.43 mmol), and the solution was stirred at 60° C. for 30 minutes. Ethyl acetate and water were added to the reaction solution, which was then partitioned, the organic layer was sequentially washed with an aqueous solution of saturated sodium bicarbonate, water and brine, and then, dried over anhydrous sodium sulfate. The solvent was evaporated, the residue was sequentially purified by silica gel column chromatography (hexane:ethyl acetate), silica gel column chromatography (dichloromethane:ethyl acetate), reverse phase high performance liquid chromatography (acetonitrile-water mobile phase (containing 0.1% trifluoroacetic acid) was used), and the title compound (8.6 mg, 0.017 mmol, 15%) was obtained.
MS m/e (ESI) 379.76(MH$^+$)
$^1$H-NMR Spectrum (CD$_3$OD) δ(ppm): 4.71 (2H, d, J=6.4 Hz), 6.38 (1H, d, J=4.0 Hz), 6.83 (1H, d, J=4.0 Hz), 7.02-7.09 (4H, m), 7.85 (1H, dd, J=4.0, 8.8 Hz), 8.46 (1H, d, J=8.8 Hz), 8.56-8.61 (2H, m), 9.04 (1H, dd, J=1.6, 4.0 Hz), 9.55-9.64 (1H, m).

Example D-8

[1,5]Naphthylidine-2-carboxylic acid (5-(3-chlorophenoxy)-thiophen-2-ylmethyl)-amide MS m/e (ESI) 396.28 (MH$^+$)

Example D-9

[1,5]Naphthylidine-2-carboxylic acid (5-benzofuran-2-ylmethyl-thiophen-2-ylmethyl)-amide MS m/e (ESI) 400.51 (MH$^+$)

Example D-10

[1,5]Naphthylidine-2-carboxylic acid 4-(6-fluoro-pyridin-2-yloxymethyl)-benzylamide $^1$H-NMR Spectrum (CDCl$_3$) δ(ppm): 4.75 (2H, d, J=6.0 Hz), 5.34 (2H, s), 6.47-6.49 (1H, m), 6.64-6.66 (1H, m), 7.43-7.48 (4H, m), 7.62-7.70 (2H, m), 8.36-8.39 (1H, m), brs), 8.55-8.60 (2H, m), 9.04-9.06 (1H, m).

Example E-1

Quinoline-6-carboxylic acid (5-benzyl-furan-2-yl)-amide

The title compound (200 mg, 5.8 mmol, 54.6%) was obtained as a slightly yellow solid from 5-benzylfuran-2-carbaldehyde described in Preparation Example 39 and 6-quinolinecarboxylic acid according to an analogous method to Example Q-1.
$^1$H-NMR Spectrum (DMSO-$d_6$) δ(ppm): 3.92 (2H, s), 4.45 (2H, d, J=5.6 Hz), 6.02 (1H, d, J=2.8 Hz), 6.20 (1H, d, J=2.8 Hz), 7.16-7.30 (5H, m), 7.59 (1H, dd, J=4.4, 8.0 Hz), 8.05 (1H, d, J=8.8 Hz), 8.16 (1H, dd, J=2.0, 8.8 Hz), 8.44 (1H, dd, J=1.6, 8.0 Hz), 8.50 (1H, d, J=2.0 Hz), 8.97 (1H, dd, J=1.6, 4.4 Hz), 9.16 (1H, t, J=5.6 Hz).

Example E-2

Quinoline-6-carboxylic acid (5-phenoxy-furan-2-ylmethyl)-amide

The title compound (68 mg, 0.197 mmol, 17.2%) was obtained as a white solid from quinoline-6-carboxylic acid (200 mg, 1.15 mmol) and C-(5-phenoxy-furan-2-yl)-methylamine described in Preparation Example 49 (200 mg, 1.12 mmol) according to an analogous method to Example Q-6.
$^1$H-NMR Spectrum (DMSO-$d_6$) δ(ppm): 4.45 (2H, d, J=5.6 Hz), 5.72 (1H, d, J=3.2 Hz), 6.34 (1H, d, J=3.2 Hz), 7.02-7.08 (2H, m), 7.11-7.17 (1H, m), 7.14-7.40 (2H, m), 7.60 (1H, dd, J=2.0, 8.0 Hz), 8.06 (1H, d, J=8.8 Hz), 8.16 (1H, d, J=8.8 Hz), 8.45 (1H, d, J=8.0 Hz), 8.51 (1H, s), 8.97 (1H, d, J=4.0 Hz), 9.18 (1H, t, J=5.6 Hz).

Example E-3

Quinoline-6-carboxylic acid (5-(3-fluoro-phenoxy)-furan-2-ylmethyl)-amide

To a solution of (5-(3-fluoro-phenoxy)-furan-2-yl)-methanol described in Preparation Example 51 (1.5 g, 7.2 mmol), phthalimide (1.1 g, 7.2 mmol) and triphenyl phosphine (1.9 g, 7.2 mmol) in tetrahydrofuran (10 mL) was added diethyl azodicarboxylate (3.5 g, 7.9 mmol) dropwise at 0° C., and the solution was stirred at room temperature for 30 minutes. Silica gel was added to the reaction solution, the solvent was evaporated in vacuo for adsorption, purification was carried out by silica gel column chromatography (hexane:ethyl acetate=2:1), and a white solid (700 mg) was obtained. Ethanol (10 mL) and hydrazine monohydrate (0.3 mL) were added to this solid (700 mg), and stirred for 15 minutes at 90° C. The solution was allowed to room temperature, the solid was removed by filtration, and a pale yellow oil (360 mg) containing C-(5-(3-fluoro-phenoxy)-furan-2-yl)-methylamine was obtained. The title compound (17 mg, 0.046 mmol, 2.7%) was obtained as a brown solid from this oil (360 mg) and quinoline-6-carboxylic acid (300 mg, 1.7 mmol) according to an analogous method to Example Q-6.

$^1$H-NMR Spectrum (DMSO-$d_6$) δ(ppm): 4.46 (2H, d, J=5.2 Hz), 5.83 (1H, d, J=3.2 Hz), 6.36 (1H, d, J=3.2 Hz), 6.87-7.03 (3H, m), 7.38-7.45 (1H, m), 7.60 (1H, d, J=4.0, 8.4 Hz), 8.06 (1H, d, J=8.8 Hz), 8.16 (1H, dd, J=2.0, 8.8 Hz), 8.45 (1H, dd, J=1.6, 8.4 Hz), 8.51 (1H, d, J=2.0 Hz), 8.97 (1H, dd, J=1.6, 4.0 Hz), 9.19 (1H, t, J=5.2 Hz).

Example E-4

Quinoline carboxylic acid (5-phenyl-furan-2-ylmethyl)-amide

To a solution of quinoline-6-carboxylic acid (5-bromo-furan-2-ylmethyl)-amide described in Preparation Example E+-2 (200 mg, 0.60 mmol) in 1,4-dioxane (5 mL) were added phenylboronic acid (150 mg, 1.2 mmol), tetrakis(triphenylphosphine)palladium(0) (55 mg, 0.047 mmol) and an aqueous solution of potassium carbonate (2 mol), and the solution was stirred at 110° C. for 2 hours. Water and ethyl acetate were added to the reaction solution, which was then partitioned, NH silica gel was added to the organic layer, the solvent was evaporated in vacuo for adsorption, purification was carried out by NH silica gel column chromatography (hexane:ethyl acetate=2:1), and the title compound (65 mg, 0.198 mmol, 33.0%) was obtained as a white solid.

$^1$H-NMR Spectrum (DMSO-$d_6$) δ(ppm): 4.59 (2H, d, J=6.0 Hz), 6.44 (1H, d, J=3.2 Hz), 6.88 (1H, d, J=3.2 Hz), 7.23-7.28 (1H, m), 7.37-7.42 (2H, m), 7.60 (1H, dd, J=4.0, 8.4 Hz), 7.64-7.70 (2H, m), 8.07 (1H, d, J=8.8 Hz), 8.20 (1H, dd, J=2.0, 8.8 Hz), 8.45-8.50 (1H, m), 8.55 (1H, d, J=2.0 Hz), 8.97 (1H, dd, J=1.6, 4.0 Hz), 9.26 (1H, t, J=6.0 Hz).

Example E-5

Quinoline-6-carboxylic acid (5-(2,4-difluoro-phenoxy)-furan-2-ylmethyl)-amide

The title compound (71 mg, 0.187 mmol, 18%) was obtained from quinoline-6-carboxylic acid (180 mg, 1.04 mmol) and C-(5-(2,4-difluoro-phenoxy)-furan-2-yl)-methylamine described in Preparation Example 77 (258 mg, 1.15 mmol) according to an analogous method to Example H-1.

$^1$H-NMR Spectrum (DMSO-$d_6$) δ(ppm): 4.44 (2H, d, J=5.6 Hz), 5.59 (1H, d, J=3.6 Hz), 6.31 (1H, d, J=3.6 Hz), 7.06-7.13 (1H, m), 7.27-7.34 (1H, m), 7.44-7.51 (1H, m), 7.59 (1H, dd, J=4.0, 8.8 Hz), 8.06 (1H, d, J=9.2 Hz), 8.16 (1H, dd, J=1.2, 8.8 Hz), 8.45 (1H, d, J=9.2 Hz), 8.51 (1H, s), 8.97 (1H, dd, J=1.2, 4.0 Hz), 9.19 (1H, t, J=5.6 Hz).

Example E-6

Quinoline-6-carboxylic acid (5-(2,5-difluoro-phenoxy)-furan-2-ylmethyl)-amide

The title compound (194 mg, 0.51 mmol, 32%) was obtained from quinoline-6-carboxylic acid (275 mg, 1.59 mmol) and C-(5-(2,5-difluoro-phenoxy)-furan-2-yl)-methylamine described in Preparation Example 79 (357 mg, 1.59 mmol) according to an analogous method to Example H-1.

$^1$H-NMR Spectrum (DMSO-$d_6$) δ(ppm): 4.46 (2H, d, J=5.2 Hz), 5.78 (1H, d, J=3.2 Hz), 6.35 (1H, d, J=3.2 Hz), 7.04-7.18 (2H, m), 7.42-7.50 (1H, m), 7.60 (1H, dd, J=4.0, 8.0 Hz), 8.06 (1H, d, J=8.8 Hz), 8.17 (1H, dd, J=1.2, 8.0 Hz), 8.45 (1H, d, J=8.8 Hz), 8.52 (1H, s), 8.97 (1H, dd, J=1.2, 4.0 Hz), 9.19 (1H, t, J=5.2 Hz).

Example E-7

Quinoline-6-carboxylic acid (5-(3-fluoro-benzyl)-furan-2-ylmethyl)-amide

Title compound (301 mg, 0.835 mmol, 80%) was obtained from quinoline-6-carboxylic acid (188 mg, 1.16 mmol) and C-(5-(3-fluoro-benzyl)-furan-2-yl)-methylamine described in Preparation Example 84 (279 mg, 1.36 mmol) according to an analogous method to Example H-1.

$^1$H-NMR Spectrum (DMSO-$d_6$) δ(ppm): 3.96 (2H, s), 4.46 (2H, d, J=5.6 Hz), 6.07 (1H, d, J=3.2 Hz), 6.21 (1H, d, J=3.2 Hz), 7.00-7.09 (3H, m), 7.28-7.35 (1H, m), 7.59 (1H, dd, J=4.4, 8.4 Hz), 8.05 (1H, d, J=8.8 Hz), 8.16 (1H, d, J=2.0, 8.4 Hz), 8.44 (1H, dd, J=1.2, 8.8 Hz), 8.50 (1H, d, J=1.2 Hz), 8.97 (1H, dd, J=2.0, 4.4 Hz), 9.17 (1H, t, J=5.6 Hz).

Example E-8

Quinoline-6-carboxylic acid 4-benzyloxybenzylamide

To a solution of 6-quinoline carboxylic acid (100 mg, 0.577 mmol) in tetrahydrofuran (50 mL) was added N,N'-dicyclohexylcarbodiimide (1.90 g, 11.7 mmol), and the solution was stirred at room temperature for 1 hour. Then, to this solution was added a solution of 4-benzyloxybenzylamine described in Preparation Example 1 (2.49 g, 11.7 mmol) in tetrahydrofuran (5 mL), and the solution was stirred overnight at room temperature. The solvent was evaporated, the residue was purified by NH silica gel column chromatography (hexane: ethyl acetate), and the title compound (4.31 g, quantitatively) was obtained as a white solid.

$^1$H-NMR Spectrum (CDCl$_3$) δ(ppm): 4.65 (2H, d, J=5.6 Hz), 5.08 (2H, s), 6.48 (1H, brs), 6.97-7.00 (2H, m), 7.31-7.35 (3H, m), 7.37-7.45 (4H, m), 7.47 (1H, dd, J=4.4, 8.4 Hz), 8.05 (1H, dd, J=2.0, 8.8 Hz), 8.15 (1H, d, J=8.8 Hz), 8.22-8.25 (1H, m), 8.32 (1H, d, J=2.0 Hz), 8.98-9.00 (1H, m).

Example E-9

Quinoline-6-carboxylic acid 3-benzyloxybenzylamide

The title compound (102 mg, 48%) was obtained as a colorless oil from 6-quinolinecarboxylic acid (100 mg, 0.58 mmol) and 3-benzyloxybenzylamine described in Preparation Example 2 (126 mg, 0.58 mmol) according to an analogous method to Example E-8.

¹H-NMR Spectrum (CDCl₃) δ(ppm): 4.69 (2H, d, J=5.6 Hz), 5.07 (2H, s), 6.57 (1H, brs), 6.92-6.95 (1H, m), 6.98-7.02 (2H, m), 7.27-7.32 (2H, m), 7.34-7.38 (2H, m), 7.41-7.43 (2H, m), 7.47 (1H, dd, J=4.4, 8.4 Hz), 8.05 (1H, dd, J=2.0, 8.8 Hz), 8.16 (1H, d, J=8.8 Hz), 8.22-8.25 (1H, m), 8.32 (1H, d, J=2.0 Hz), 8.98-9.00 (1H, m).

Example E-10

Quinoline-6-carboxylic acid 4-phenoxybenzylamide

The title compound (63 mg, 31%) was obtained as a colorless solid from 6-quinolinecarboxylic acid (100 mg, 0.58 mmol) and 4-phenoxybenzylamine described in Preparation Example 3 (115 mg, 0.58 mmol) according to an analogous method to Example E-8.
¹H-NMR Spectrum (CDCl₃) δ(ppm): 4.69 (2H, d, J=5.6 Hz), 6.59 (1H, brs), 7.00-7.03 (4H, m), 7.1-7.14 (1H, m), 7.32-7.38 (4H, m), 7.46-7.49 (1H, m), 8.05-8.08 (1H, m), 8.15-8.17 (1H, m), 8.23-8.25 (1H, m), 8.34 (1H, s), 8.98-900 (1H, m).

Example E-11

Quinoline-6-carboxylic acid 3-phenoxybenzylamide

The title compound (140 mg, 69%) was obtained as a colorless oil from 6quinolinecarboxylic acid (100 mg, 0.58 mmol) and 4-phenoxybenzylamine described in Preparation Example 3 (115 mg, 0.58 mmol) according to an analogous method to Example E-8.
¹H-NMR Spectrum (CDCl₃) δ(ppm): 4.69 (2H, d, J=6.0 Hz), 6.63 (1H, brs), 6.92-6.95 (1H, m), 7.01-7.05 (3H, m), 7.09-7.14 (2H, m), 7.30-7.36 (3H, m), 7.47 (1H, dd, J=4.0, 8.0 Hz), 8.05 (1H, dd, J=2.0, 8.8 Hz), 8.15 (1H, d, J=8.8 Hz), 8.21-8.24 (1H, m), 8.32 (1H, d, J=2.0 Hz), 8.98-8.99 (1H, m).

Example E-12

Quinoline-6-carboxylic acid 4-(pyridin-2-ylmethoxy)-benzylamide

To a solution of quinoline carboxylic acid 4-hydroxybenzylamide described in Preparation Example E+-1 (20 mg, 0.0719 mmol) and 2-chloromethyl-pyridine hydrochloride (12 mg, 0.0719 mmol) in N,N-dimethyl formamide (1.0 mL) was added potassium carbonate (298 mg, 2.16 mmol), and the solution was stirred at room temperature for 12 hours. Ethyl acetate and water were added to the reaction solution, which was then partitioned, and the organic layer was dried over anhydrous magnesium sulfate. The solvent was evaporated, the residue was purified by reverse phase high performance liquid chromatography (acetonitrile-water mobile phase (containing 0.1% trifluoroacetic acid) was used), and trifluoroacetic acid salt of the title compound was obtained.
MS m/e (ESI) 369.2 (MH⁺)
¹H-NMR Spectrum (CD₃OD) δ(ppm): 4.60 (2H, s), 5.37 (2H, s), 7.35 (2H, d, J=8.8 Hz), 7.40 (2H, d, J=8.8 Hz), 7.74-7.77 (1H, m), 7.82-7.85 (1H, m), 7.92-7.94 (1H, m), 8.18-8.20 (1H, m), 8.29-8.35 (2H, m), 8.59-8.60 (1H, m), 8.70-8.71 (1H, m), 8.79-8.81 (1H, m), 9.08-9.09 (1H, m).

Example E-13

Quinoline-6-carboxylic acid (biphenyl-3-ylmethyl)-amide

The title compound (20 mg, 21%) was obtained as a colorless oil from 6-quinolinecarboxylic acid (50 mg, 0.289 mmol) and C-biphenyl-3-yl-methylamine described in Preparation Example 5 (48 mg, 0.263 mmol) according to an analogous method to Example E-8.
¹H-NMR Spectrum (CDCl₃) δ(ppm): 4.79 (2H, d, J=5.6 Hz), 6.62 (1H, brs), 7.34-7.49 (6H, m), 7.55-7.62 (4H, m), 8.08 (1H, dd, J=2.0, 8.8 Hz), 8.16 (1H, d, J=8.8 Hz), 8.23-8.25 (1H, m), 8.35 (1H, d, J=2.0 Hz), 8.98-9.00 (1H, m).

Example E-14

Quinoline-6-carboxylic acid 4-(3-methyl-benzyloxy)-benzylamide

The title compound (2.5 mg, 18%) was obtained as a white solid from quinoline-carboxylic acid 4-hydroxybenzylamide obtained in Preparation Example E+-1 (10 mg, 0.0359 mmol) and 3-methylbenzyl chloride (5 mg, 0.0359 mmol) according to an analogous method to Example E-12.
¹H-NMR Spectrum (CDCl₃) δ(ppm): 2.38 (3H, s), 4.66 (2H, d, J=5.2 Hz), 5.04 (2H, s), 6.50 (1H, brs), 6.97-7.00 (2H, m), 7.14-7.16 (1H, m), 7.22-7.35 (5H, m), 7.46-7.50 (1H, m), 8.06 (1H, dd, J=2.0, 8.8 Hz), 8.17 (1H, d, J=8.8 Hz), 8.23-8.26 (1H, m), 8.33 (1H, d, J=2.0 Hz), 8.99-9.00 (1H, m).

Example E-15

Quinoline-6-carboxylic acid 3-(4-fluoro-phenoxy)-benzylamide

The title compound (28 mg, 25%) was obtained as a colorless oil from 6-quinolinecarboxylic acid (52 mg, 0.30 mmol) and 3-(4-fluorophenoxy)-benzylamine described in Preparation Example 8 (65 mg, 0.30 mmol) according to an analogous method to Example L-4.
¹H-NMR Spectrum (CDCl₃) δ(ppm): 4.70 (2H, d, J=5.6 Hz), 6.64 (1H, brs), 6.88-6.91 (1H, m), 6.99-7.06 (5H, m), 7.12-7.14 (1H, m), 7.31-7.35 (1H, m), 7.47-7.50 (1H, m), 8.04-8.07 (1H, m), 8.15-8.17 (1H, m), 8.23-8.25 (1H, m), 8.33 (1H, m), 9.00-9.01 (1H, m).

Example E-16

Quinoline-6-carboxylic acid 3-(4methoxy-phenoxy)-benzylamide

The title compound (28 mg, 25%) was obtained as a colorless oil from 6-quinolinecarboxylic acid (50 mg, 0.29 mmol) and 3-(4-methoxyphenoxy)benzylamine described in Preparation Example 9 (66 mg, 0.30 mmol) according to an analogous method to Example L-4.
¹H-NMR Spectrum (CDCl₃) δ(ppm): 3.79 (3H, s), 4.66 (2H, d, J=5.6 Hz), 6.55 (1H, brs), 6.84-6.89 (3H, m), 6.95-6.99 (3H, m), 7.057.07 (1H, m), 7.46 (2H, dd, J=4.4, 8.4 Hz), 8.03 (1H, dd, J=2.4, 8.8 Hz), 8.14 (1H, d, J=8.8 Hz), 8.21-8.23 (1H, m), 8.29 (1H, d, J=2.0 Hz), 8.98 (1H, dd, J=2.0, 4.4 Hz).

Example E-17

Quinoline-6-carboxylic acid 3-(3-trifluoromethyl-phenoxy)-benzylamide

The title compound (39 mg, 32%) was obtained as a colorless oil from 6-quinolinecarboxylic acid (50 mg, 0.29 mmol) and 3-(3-trifluoromethyl-phenoxy)-benzylamine described in Preparation Example 10 (77 mg, 0.29 mmol) according to an analogous method to Example L-4.

¹H-NMR Spectrum (CDCl₃) δ(ppm): 4.70 (2H, d, J=5.6 Hz), 6.68 (1H, brs), 6.93-6.95 (1H, m), 7.05-7.06 (1H, m), 7.14-7.25 (3H, m), 7.31-7.47 (4H, m), 8.04 (1H, dd, J=1.6, 8.8 Hz), 8.13 (1H, d, J=8.8 Hz), 8.20-8.2 (1H, m), 8.31 (1H, d, J=2.0 Hz), 8.97 (1H, dd, J=1.6, 4.4 Hz).

Example E-18

Quinoline-6-carboxylic acid 3-(3-fluoro-phenoxy)-benzylamide

The title compound (70 mg, 65%) was obtained as a colorless oil from 6-quinolinecarboxylic acid (50 mg, 0.29 mmol) and 3-(3-fluoro-phenoxy)-benzylamine described in Preparation Example 11 (63 mg, 0.29 mmol) according to an analogous method to Example L-4.
¹H-NMR Spectrum (CDCl₃) δ(ppm): 4.71 (2H, d, J=6.0 Hz), 6.63 (1H, brs), 6.69-6.73 (1H, m), 6.78-6.83 (2H, m), 6.96-6.98 (1H, m), 7.07 (1H, s), 7.18 (1H, d, J=7.6 Hz), 7.24-7.30 (1H, m), 7.34-7.38 (1H, m), 7.48 (1H, dd, J=4.4, 8.4 Hz), 8.06 (1H, dd, J=2.0, 8.8 Hz), 8.16 (1H, d, J=8.8 Hz), 8.23-8.25 (1H, m), 8.33 (1H, d, J=1.6 Hz), 8.99 (1H, dd, J=1.6, 4.4 Hz).

Example E-19

2-(3-Phenoxy-phenyl)-N-quinolin-6-yl-acetamide

The title compound (116 mg, 94%) was obtained as a colorless oil from 6-aminoquinoline (50 mg, 3.47 mmol) and 3-phenoxyphenylacetic acid (79 mg, 3.47 mmol) according to an analogous method to Example L-4.
¹H-NMR Spectrum (CDCl₃) δ(ppm): 3.77 (2H, s), 6.98-7.06 (4H, m), 7.10-7.16 (2H, m), 7.34-7.44 (6H, m), 8.01 (1H, d, J=8.8 Hz), 8.09-8.16 (1H, m), 8.32 (1H, d, J=2.0 Hz), 8.83 (1H, dd, J=1.6, 4.0 Hz).

Example E-20

Quinoline-6-carboxylic acid 4-(furan-2-ylmethoxy)-benzylamide

The title compound (0.7 mg, 4%) was obtained as a colorless oil from 6-quinolinecarboxylic acid (10 mg, 0.0577 mmol) and 4-(furan-2-ylmethoxy)-benzylamine described in Preparation Example 12 (12 mg, 0.0577 mmol) according to an analogous method to Example L-4.
¹H-NMR Spectrum (CDCl₃) δ(ppm): 4.66 (2H, d, J=5.6 Hz), 5.02 (2H, s), 6.48 (1H, brs), 6.99-7.02 (2H, m), 7.24-7.27 (2H, m), 7.35-7.36 (2H, m), 7.47-7.50 (2H, m), 8.05-8.08 (1H, m), 8.16-8.18 (1H, m), 8.24-8.27 (1H, m), 8.33 (1H, s), 9.00 (1H, s), Example E-21

Quinoline-6-carboxylic acid 4-(thiophen-2-ylmethoxy)-benzylamide

The title compound (11 mg, 53%) was obtained as a colorless solid from 6-quinolinecarboxylic acid (10 mg, 0.0577 mmol) and 4-(thiophen-2-ylmethoxy)-benzylamine described in Preparation Example 13 (13 mg, 0.0577 mmol) according to an analogous method to Example L-4.
¹H-NMR Spectrum (CDCl₃) δ(ppm): 4.65 (2H, d, J=5.6 Hz), 5.23 (2H, s), 6.60 (1H, brs), 6.97-7.03 (3H, m), 7.11-7.12 (1H, m), 7.32-7.34 (3H, m), 7.45-7.48 (1H, m), 8.05-8.07 (1H, m), 8.13-8.16 (1H, m), 8.21-8.23 (1H, m), 8.32 (1H, s), 8.97-8.99 (1H, m).

Example E-22

Quinoline-6-carboxylic acid 4-(thiophen-3-ylmethoxy)-benzylamide

The title compound (78 mg, 72%) was obtained as a white solid from 6quinolinecarboxylic acid (50 mg, 0.289 mmol) and 4-(thiophen-3-ylmethyl)-benzylamine described in Preparation Example 14 (63 mg, 0.289 mmol) according to an analogous method to Example L-4.
¹H-NMR Spectrum (CDCl₃) δ(ppm): 4.65 (2H, d, J=5.6 Hz), 5.08 (2H, s), 6.51 (1H, brs), 6.96-6.99 (2H, m), 7.14-7.16 (1H, m), 7.32-7.36 (4H, m), 7.46-7.49 (1H, m), 8.04-8.07 (1H, m), 8.15 (1H, d, J=8.8 Hz), 8.22-8.24 (1H, m), 8.32 (1H, d, J=2.0 Hz), 8.99 (1H, dd, J=2.0, 4.4 Hz).

Example E-23

Quinoline-6-carboxylic acid 4-((S)-1-phenyl-ethoxy)-benzylamide

The title compound (219 mg, 80%) was obtained as a colorless oil from 6-quinolinecarboxylic acid (123 mg, 0.712 mmol) and 4-((S)-1-phenyl-ethoxy)-benzylamine described in Preparation Example 15 (172 mg, 0.712 mmol) according to an analogous method to Example L-4.
¹H-NMR Spectrum (CDCl₃) δ(ppm): 1.64 (3H, d, J=6.4 Hz), 4.58 (2H, d, J=5.2 Hz), 5.31 (1H, q, J=6.4 Hz), 6.47 (1H, brs), 6.86 (2H, d, J=8.8 Hz), 7.22 (2H, d, J=8.8 Hz), 7.26-7.27 (2H, m), 7.32-7.39 (3H, m), 7.46 (1H, dd, J=4.0, 8.0 Hz), 8.03 (1H, dd, J=2.0, 8.8 Hz), 8.13 (1H, d, J=8.8 Hz), 8.22 (1H, d, J=8.0 Hz), 8.30 (1H, d, J=2.0 Hz), 8.97-8.98 (1H, m).

Example E-24

Quinoline-6-carboxylic acid 3-benzylamino-benzylamide

3-Benzylamino-benzonitrile described in Preparation Example 87 (57 mg, 0.27 mmol) was dissolved at 0° C. in tetrahydrofuran (0.5 mL), and lithium aluminum hydride (52 mg, 1.35 mmol) was added. After stirring overnight at room temperature, water (52 μl), an aqueous solution of 5N sodium hydroxide (52 μl) and water (156 μl) were sequentially added at 0° C. The reaction solution was filtered through Celite pad, then, the solvent was evaporated in vacuo, and (3-aminomethyl-phenyl)-benzyl-amine (62 mg, 0.29 mmol) was obtained as an oil.
(3-Aminomethyl-phenyl)-benzylamine (62 mg, 0.29 mmol), quinoline-6-carboxylic acid (52 mg, 0.30 mmol), benzotriazol-1-yl-tris(dimethylamino)phosphonium hexafluorophosphate (182 mg, 0.41 mmol) and triethylamine (114 μl, 0.81 mmol) were dissolved in N,N-dimethylformamide (0.5 mL), and the solution was stirred at room temperature for 2 hours. Water was added to the reaction solution, which was then extracted with ethyl acetate, the organic layer was washed with water and brine, and dried over anhydrous magnesium sulfate. The solvent was evaporated in vacuo, the residue was purified by NH silica gel column chromatography (hexane:ethyl acetate=1:1), and the title compound (73 mg, 0.198 mmol, 73%) was obtained as a white solid.
¹H-NMR Spectrum (DMSO-d₆) δ(ppm): 4.22 (2H, d, J=6.0 Hz), 4.39 (2H, d, J=6.0 Hz), 6.25 (1H, t, J=6.0 Hz), 6.40

(1H, dd, J=1.6, 7.7 Hz), 6.50 (1H, d, J=7.7 Hz), 6.60 (1H, s), 6.97 (1H, t, J=7.8 Hz), 7.14 (1H, t, J=7.3 Hz), 7.23 (2H, t, J=7.8 Hz), 7.30 (2H, d, J=7.1 Hz), 7.60 (1H, dd, J=4.4, 8.4 Hz), 8.07 (1H, d, J=8.8 Hz), 8.19 (1H, dd, J=2.0, 8.8 Hz), 8.45 (1H, d, J=7.6 Hz), 8.52 (1H, d, J=1.6 Hz), 8.97 (1H, dd, J=1.6, 4.4 Hz), 9.14 (1H, t, J=6.0 Hz).

Example E-25

Quinoline-6-carboxylic acid 4-phenylamino-benzylamide (4-Aminomethyl-phenyl)-phenylamine (98 mg, 0.494 mmol) was obtained as an oil from 4-phenylamino-benzonitrile described in Preparation Example 88 (110 mg, 0.566 mmol) according to an analogous method to Example E-24.

Then, the title compound (52 mg, 0.147 mmol, 26%) was obtained from the resulting (4-aminomethyl-phenyl)-phenylamine and quinoline-6-carboxylic acid (108 mg, 0.623 mmol).

$^1$H-NMR Spectrum (CDCl$_3$) δ(ppm): 4.66 (2H, d, J=5.5 Hz), 5.76 (1H, s), 6.50 (1H, brs), 6.96 (1H, t, J=7.4 Hz), 7.07-7.10 (4H, m), 7.29-7.32 (4H, m), 7.49 (1H, dd, J=4.2, 8.4 Hz), 8.08 (1H, dd, J=2.0, 8.6 Hz), 8.17 (1H, d, J=8.8 Hz), 8.25 (1H, d, J=7.5 Hz), 8.34 (1H, d, J=1.8 Hz), 9.00 (1H, dd, J=1.7, 4.2 Hz).

Example E-26

Quinoline-6-carboxylic acid 4-(benzyl-methyl-amino)-benzylamide

Quinoline-6-carboxylic acid 4-benzylamino-benzylamide described in Preparation Example E+-3 (30 mg, 82 μmol), formalin (9 μl, 115 μmol), triacetoxy sodium borohydride (25 mg, 115 μmol) and acetic acid (several drops) were suspended in tetrahydrofuran (1 mL), and the solution was stirred at room temperature for 4 hours. An aqueous solution of saturated sodium bicarbonate was added to the reaction suspension at 0° C., which was then extracted with ethyl acetate, the organic layer was washed with brine and dried over anhydrous magnesium sulfate. The solvent was evaporated in vacuo, purification was carried out using thin layer NH silica gel chromatography (hexane:ethyl acetate=1:1), and the title compound (11 mg, 28 μmol, 35%) was obtained as a white solid.

$^1$H-NMR Spectrum (CDCl$_3$) δ(ppm) 3.05 (3H, s), 4.55 (2H, s), 4.59 (2H, d, J=5.1 Hz), 6.38 (1H, brs), 6.74 (2H, d, J=8.8 Hz), 7.21-7.26 (4H, m), 7.32 (2H, t, J=7.2 Hz), 7.4 (1H, d, J=7.0 Hz), 7.47 (1H, dd, J=4.3, 8.2 Hz), 8.05 (1H, dd, J=2.0, 8.8 Hz), 8.14 (1H, d, J=8.8 Hz), 8.23 (1H, d, J=7.1 Hz), 8.30 (1H, d, J=1.7 Hz), 8.98 (1H, dd, J=1.7, 4.2 Hz).

Example E-27

Quinoline-6-carboxylic acid 3-phenylsulfanyl-benzylamide

The title compound (50 mg, 0.14 mmol, 75%) was obtained as a white solid from 3-phenylsulfanyl-benzylamine described in Preparation Example 95 (38 mg, 0.18 mmol) and quinoline-6-carboxylic acid (31 mg, 0.18 mmol) according to an analogous method to Example A-26.

$^1$H-NMR Spectrum (CDCl$_3$) δ(ppm): 4.67 (2H, d, J=5.7 Hz), 6.52 (1H, brs), 7.23-7.26 (3H, m), 7.31 (4H, t, J=7.4 Hz), 7.38 (2H, d, J=6.8 Hz), 7.49 (1H, dd, J=4.2, 8.4 Hz), 8.03 (1H, dd, J=1.8, 8.8 Hz), 8.16 (1H, d, J=8.8 Hz), 8.24 (1H, d, J=7.5 Hz), 8.31 (1H, d, J=1.8 Hz), 9.00 (1H, dd, J=1.7, 4.2 Hz).

Example E-28

Quinoline-6-carboxylic acid 4-benzylsulfanyl-benzylamide

The title compound (54 mg, 0.14 mmol, 38%) was obtained as a white solid from 4-benzylsulfanyl-benzylamine described in Preparation Example 101 (84 mg, 0.37 mmol) and quinoline-6-carboxylic acid (70 mg, 0.40 mmol) according to an analogous method to Example A-26.

$^1$H-NMR Spectrum (DMSO-d$_6$) δ(ppm): 4.20 (2H, s), 4.47 (2H, d, J=5.9 Hz), 7.18-7.34 (9H, m), 7.59 (1H, dd, J=4.2, 8.4 Hz), 8.07 (1H, d, J=9.0 Hz), 8.18 (1H, dd, J=2.0, 8.8 Hz), 8.45 (1H, d, J=7.9 Hz), 8.52 (1H, d, J=2.0 Hz), 8.97 (1H, dd, J=1.8, 4.2 Hz), 9.24 (1H, t, J=5.9 Hz).

Example E-29

Quinoline-6-carboxylic acid 3-(3-methylbutoxy)-benzylamide

To a mixture solution of quinoline-6-carboxylic acid 3-hydroxybenzylamide described in Preparation Example E+-4 (13 mg, 0.048 mmol) and N,N-dimethylformamide (0.5 mL) were added potassium carbonate (13 mg, 0.096 mmol) and 1-iodine-3-methylbutane (0.013 mL, 0.096 mmol), and the solution was stirred overnight at room temperature. Water and dichloromethane was added to the reaction solution for extraction, which was then washed with brine, then, the solvent was evaporated in vacuo. The residue was purified by silica gel column chromatography (ethyl acetate), and the title compound (12 mg, 0.033 mmol, 69%) was obtained as a colorless oil.

$^1$H-NMR Spectrum (CDCl$_3$) δ(ppm): 0.96 (6H, d, J=6.6 Hz), 1.65-1.70 (2H, m), 1.80-1.87 (1H, m), 3.99 (2H, t, J=6.7 Hz), 4.68 (2H, d, J=5.7 Hz), 6.56 (1H, brs), 6.84-6.87 (1H, m), 6.93-6.98 (2H, m), 7.26-7.31 (1H, m), 7.48 (1H, dd, J=4.2, 8.2 Hz), 8.07 (1H, dd, J=2.0, 8.8 Hz), 8.16 (1H, d, J=8.8 Hz), 8.23-8.25 (1H, m), 8.33 (1H, d, J=2.0 Hz), 8.99 (1H, dd, J=1.8, 4.2 Hz).

Example E-30

Quinoline-6-carboxylic acid (Z)-4-styryl-benzylamide

To a mixture of quinoline-6-carboxylic acid 4-phenylethenyl-benzylamide described in Preparation Example E+-5 (48 mg, 0.13 mmol), quinoline (26 mg, 0.20 mmol) and tetrahydrofuran (2 mL) was added Linear catalyst (5.0 mg), and the solution was stirred under hydrogen atmosphere at room temperature for 1 hour. The interior of the reaction system was changed to nitrogen atmosphere, then, filtration was carried out through Celite pad. The filtrate was evaporated in vacuo, the residue was purified by silica gel column chromatography (hexane:ethyl acetate=1:4), and the title compound (45 mg, 0.12 mmol, 92%) was obtained as a colorless oil.

$^1$H-NMR Spectrum (DMSO-d$_6$) δ(ppm): 4.57 (2H, d, J=6.0 Hz), 6.58-6.60 (2H, m), 7.16-7.27 (9H, m), 7.59 (1H, dd, J=4.2, 8.2 Hz), 8.06 (1H, d, J=8.8 Hz), 8.19 (1H, dd, J=2.0, 8.8 Hz), 8.45-8.47 (1H, m), 8.54 (1H, d, J=1.7 Hz), 8.97 (1H, dd, J=1.7, 4.2 Hz), 9.24 (1H, t, J=5.7 Hz).

Example E-31

Quinoline-6-carboxylic acid 4-phenylaminomethyl-benzylamide

The title compound (13.8 mg) was obtained according to an analogous method to Example E-26 using quinoline-6-carboxylic acid 4-formyl-benzylamide described in Preparation Example E+-6 (50 mg, 0.172 mmol) instead of formalin, and phenylamine (31 µl, 10.34 mmol) instead of quinoline-6-carboxylic acid 4-benzyl amino-benzylamide. Trifluoroacetic acid salt of the title compound was obtained by reverse phase high performance liquid chromatography (acetonitrile-water mobile phase (containing 0.1% trifluoroacetic acid) was used).

MS m/e (ESI) 368.5(MH$^+$)

Example E-32

Quinoline-6-carboxylic acid 4-((methyl-phenyl-amino)-methyl)-benzylamide

The title compound (4.25 mg) was obtained from quinoline-6-carboxylic acid 4-phenylaminomethyl-benzylamide described in Example E-31 (30 mg, 82 µmol) according to an analogous method to Example E-26. Trifluoroacetic acid salt of the title compound was obtained by reverse phase high performance liquid chromatography (acetonitrile-water mobile phase (containing 0.1% trifluoroacetic acid) was used).

MS m/e (ESI) 382.3 (MH$^+$)

Example E-33

Quinoline-6-carboxylic acid 3-(4-nitro phenoxy)-benzylamide

To a mixture solution of quinoline-6-carboxylic acid 3-hydroxybenzylamide described in Preparation Example E+-4 (3.0 mg, 0.011 mmol), copper(II) acetate (2.9 mg, 0.016 mmol), molecular sieves 4A (50 mg) and dichloromethane (2 mL) were added triethylamine (0.0077 mL, 0.055 mmol) and 4-nitrophenylboronic acid (1.8 mg, 0.011 mmol), and the solution was stirred in the presence of air at room temperature for 10 days. The reaction solution was filtered, then, water, ethyl acetate and an aqueous solution of 29% ammonia were added for extraction, the solution was washed with brine, then, the solvent was evaporated in vacuo. The residue was purified by reverse phase high performance liquid chromatography (acetonitrile-water mobile phase (containing 0.1% trifluoroacetic acid) was used), and trifluoroacetic acid salt of the title compound (1.14 mg, 0.0022 mmol, 20%) was obtained.

MS m/e (ESI) 400.2 (MH$^+$)

Example E-34

Quinoline-6-carboxylic acid 3-(4-methanesulfonyl phenoxy)-benzylamide

Trifluoroacetic acid salt of the title compound (0.21 mg, 0.00038 mmol, 3.5%) was obtained from quinoline-6-carboxylic acid 3-hydroxybenzylamide described in Preparation Example E+-4 (3.0 mg, 0.011 mmol) and 4-methanesulfonylphenylboronic acid (2.2 mg, 0.011 mmol) according to an analogous method to Example E-33.

MS m/e (ESI) 433.2 (MH$^+$)

Example E-35

4-(3-(((Quinoline-6-carbonyl)amino)methyl)phenoxy)benzoic acid methyl ester

Trifluoroacetic acid salt of the title compound (0.14 mg, 0.00027 mmol, 2.4%) was obtained from quinoline-6-carboxylic acid 3-hydroxybenzylamide described in Preparation Example E+-4 (3.0 mg, 0.011 mmol) and 4-methoxy-carbonyl phenylboronic acid (1.8 mg, 0.011 mmol) according to an analogous method to Example E-33.

MS m/e (ESI) 413.3 (MH$^+$)

Example E-36

Quinoline-6-carboxylic acid 3-(3-cyanophenoxy)-benzylamide

Trifluoroacetic acid salt of the title compound (0.25 mg, 0.00051 mmol, 4.6%) was obtained from quinoline-6-carboxylic acid 3-hydroxybenzylamide described in Preparation Example E+-4 (5.0 mg, 0.011 mmol) and 3-cyanophenylboronic acid (2.6 mg, 0.018 mmol) according to an analogous method to Example E-33.

MS m/e (ESI) 380.1 (MH$^+$)

Example E-37

Quinoline-6-carboxylic acid 3-(3-acetylphenoxy)-benzylamide

Trifluoroacetic acid salt of the title compound (0.17 mg, 0.00033 mmol, 3.0%) was obtained from quinoline-6-carboxylic acid 3-hydroxybenzylamide described in Preparation Example E+-4 (5.0 mg, 0.011 mmol) and 3-acetylphenylboronic acid (3.0 mg, 0.018 mmol) according to an analogous method to Example E-33.

MS m/e (ESI) 397.0 (MH$^+$)

Example E-38

Quinoline-6-carboxylic acid 3-(3-trifluoromethoxy phenoxy)-benzylamide

Trifluoroacetic acid salt of the title compound (0.15 mg, 0.00027 mmol, 2.5%) was obtained from quinoline-6-carboxylic acid 3-hydroxybenzylamide described in Preparation Example E+-4 (5.0 mg, 0.011 mmol) and 3-trifluoromethoxyphenylboronic acid (3.7 mg, 0.018 mmol) according to an analogous method to Example E-330.

MS m/e (ESI) 439.0 (MH$^+$)

Example E-39

Quinoline-6-carboxylic acid (3'-fluorobiphenyl-3-ylmethyl)-amide

To a mixture of quinoline-6-carboxylic acid 3-bromobenzylamide described in Preparation Example E+-8 (4.0 mg, 0.012 mmol), toluene (1 mL) and methanol (0.25 mL) were added an aqueous solution of 2M sodium carbonate (0.5 mL), tetrakis(triphenylphosphine)palladium(0) (1.4 mg, 0.0012 mmol) and 3-fluorophenylboronic acid (1.7 mg, 0.012 mmol), and the solution was stirred at 70° C. for 4 hours. After cooling, water, ethyl acetate and acetic acid were added for extraction, the solution was washed with brine, then, the solvent was evaporated in vacuo. The residue was purified by reverse phase high performance liquid chromatography (acetonitrile-water mobile phase (containing 0.1% trifluoroacetic acid) was used), and trifluoroacetic acid salt of the title compound (0.47 mg, 0.0010 mmol, 8.3%) was obtained.
MS m/e (ESI) 357.2 (MH$^+$)

Example E-40

Quinoline-6-carboxylic acid 3benzyl-benzylamide

To a mixture of quinoline-6-carboxylic acid 3-bromobenzylamide described in Preparation Example E+-8 (8.0 mg, 0.023 mmol), dichloro(1,1'-bis(diphenylphosphino)ferrocene)nickel(II) (3.2 mg, 0.0047 mmol) and tetrahydrofuran (1 mL) was added benzylmagnesium chloride (1.1M tetrahydrofuran solution, 0.088 mL, 0.094 mmol) at room temperature, and the solution was stirred for 30 minutes at 50° C. After cooling, water and ethyl acetate were added for extraction, the solution was washed with brine, the solvent was then evaporated in vacuo. The residue was purified by reverse phase high performance liquid chromatography (acetonitrile-water mobile phase (containing 0.1% trifluoroacetic acid) was used), and trifluoroacetic acid salt of the title compound (2.1 mg, 0.0045 mmol, 19%) was obtained.
MS m/e (ESI) 353.2 (MH$^+$)

Example E-41

Quinoline-6-carboxylic acid 4-benzyl-benzylamide

Trifluoroacetic acid salt of the title compound (1.5 mg, 0.0032 mmol, 14%) was obtained from quinoline-6carboxylic acid 4-bromobenzylamide described in Preparation Example E+-9 (8.0 mg, 0.023 mmol) according to an analogous method to Example E-40.
MS m/e (ESI) 353.3 (MH$^+$)

Example E-42

Quinoline-6-carboxylic acid 4-phenylethyl-benzylamide

Trifluoroacetic acid salt of the title compound (0.39 mg, 0.00081 mmol, 3.5%) was obtained from quinoline-6-carboxylic acid 4-bromobenzylamide described in Preparation Example E+-9 (8.0 mg, 0.023 mmol) and phenethylmagnesium chloride (1.0M tetrahydrofuran solution, 0.094 mL, 0.094 mmol) according to an analogous method to Example E-40.
MS m/e (ESI) 367.3 (MH$^+$)

Example E-43

Quinoline-6-carboxylic acid 3-cyclopropylmethoxy-benzylamide

To a mixture of quinoline-6-carboxylic acid 3-hydroxybenzylamide described in Preparation Example E+-4 (87 mg, 0.31 mmol) and tetrahydrofuran (2 mL) was added an aqueous solution of 1N sodium hydroxide (0.31 mL, 0.31 mmol), and the solvent was evaporated in vacuo. To a mixture of a portion (5.0 mg) of the residue (93 mg) and N,N-dimethylformamide (1 mL) were added cyclopropylmethyl bromide (2.7 mg, 0.020 mmol) and catalytic amount of sodium iodide at room temperature, followed by stirring for 3 hours at the same temperature. The reaction solution was purified by reverse phase high performance liquid chromatography (acetonitrile-water mobile phase (containing 0.1% trifluoroacetic acid) was used), and trifluoroacetic acid salt of the title compound (1.50 mg, 0.0034 mmol, 20%) was obtained.
MS m/e (ESI) 333.0 (MH$^+$)

Example E-44

N-(4-Benzyloxy-benzyl)-N'-methoxy-quinoline-6-carboxamidine

To a mixture of quinoline-6-carbothioic acid 4-benzyloxy-benzylamide described in Preparation Example E+-10 (57 mg, 0.15 mmol) and acetonitrile (3 mL) was added 2-(bromomethyl)naphthalene (200 mg, 0.94 mmol), which was then refluxed for 2 hours. After cooling, the solvent was evaporated in vacuo, and the residue was washed with diethyl ether three times. A mixture of a portion (29 mg) of the resulting crude product (57 mg), methoxyamine hydrochloride (2.9 mg, 0.035 mmol), an aqueous solution of 1N sodium hydroxide (0.035 mL, 0.035 mmol) and N-methylpyrrolidinone (1 mL) was stirred at room temperature for 25 minutes. The reaction solution was directly purified by reverse phase high performance liquid chromatography (acetonitrile-water mobile phase (containing 0.1% trifluoroacetic acid) was used), and ditrifluoroacetic acid salt of the title compound (1.9 mg, 0.0030 mmol, 6.4%) was obtained.
MS m/e (ESI) 398.5 (MH$^+$)

Example E-45

N-(4-Benzyloxy-benzyl)-N'-cyano-quinoline-6-carboxamidine

To a mixture of quinoline-6-carbothioic acid 4-benzyloxy-benzylamide described in Preparation Example E+-10 (57 mg, 0.15 mmol) and toluene (2 mL) was added benzyl bromide (0.089 mL, 0.74 mmol), which was then stirred under reflux for 90 minutes. After cooling, the solvent was evaporated in vacuo, and the residue was washed with diethyl ether twice. A mixture of a portion (16 mg) of the resulting crude product (72 mg), cyanamide (20 mg, 0.48 mmol) and N-methylpyrrolidinone (1 mL) was stirred for 2.5 hours at 120° C. After cooling, the reaction solution was filtered through a membrane filter, the filtrate was directly purified by reverse phase high performance liquid chromatography (acetonitrile-water mobile phase (containing 0.1% trifluoroacetic acid) was used), and trifluoroacetic acid salt of the title compound (0.76 mg, 0.0015 mmol, 4.5%) was obtained.
MS m/e (ESI) 393.5 (MH$^+$)

Example E-46

Quinoline-6-carboxylic acid 4-(3-chloro-benzyloxy)-benzylamide

Trifluoroacetic acid salt of the title compound was obtained from quinoline-6-carboxylic acid 4-hydroxybenzylamine described in Preparation Example E+-1 and 3-chlorobenzyl chloride according to an analogous method to Example E-12.
MS m/e (ESI) 403 (MH$^+$)

Example E-47

Quinoline-6-carboxylic acid 4-(3-fluoro-benzyloxy)-benzylamide

Trifluoroacetic acid salt of the title compound was obtained from quinoline-carboxylic acid 4-hydroxybenzylamine described in Preparation Example E+-1 and 3-fluorobenzyl bromide according to an analogous method to Example E-12.
MS m/e (ESI) 387 (MH+)

Example E-48

Quinoline-6-carboxylic acid 4-(benzo[1,3]dioxol-5-ylmethoxy)-benzylamide

Trifluoroacetic acid salt of the title compound was obtained from quinoline-6-carboxylic acid 4-hydroxybenzylamine described in Preparation Example E+-1 and methanesulfonic acid benzo[1,3]dioxol-5-ylmethyl ester according to an analogous method to Example E-12.
MS m/e (ESI) 413 (MH+)

Example E-49

6-Quinolinecarboxlic acid 3-(3-methyl-2-butenyloxy)-benzylamide

6-Quinolinecarboxylic acid (100 mg, 0.577 mmol), 3-(3-methyl-2-butenyloxy)-benzylamine described in Preparation Example 134 (112 mg, 0.635 mmol), benzotriazol-1-yl-tris(dimethylamino)phosphonium hexafluorophosphate (306 mg, 0.693 mmol) and triethylamine (0.12 mL, 0.87 mmol) were dissolved in tetrahydrofuran (5 mL), and the solution was stirred at room temperature for 3 hours. The solvent was evaporated in vacuo, the obtained residue was purified by NH silica gel column chromatography (hexane:ethyl acetate=4:1), and the title compound (153 mg, 80.1%) was obtained as a white solid.
$^1$H-NMR Spectrum (CDCl$_3$) δ(ppm): 1.73 (3H, s), 1.78 (3H, s), 4.51 (2H, d, J=6.8 Hz), 4.68 (2H, d, J=5.6 Hz), 5.48 (1H, t, J=6.8 Hz), 6.62 (1H, t, J=5.6 Hz), 6.87 (1H, dd, J=2.4, 8.4 Hz), 6.95 (1H, d, J=2.4 Hz), 6.96 (1H, d, J=8.4 Hz), 7.28 (1H, t, J=8.4 Hz), 7.47 (1H, dd, J=4.0, 8.0 Hz), 8.05 (1H, dd, J=2.0, 8.8 Hz), 8.13 (1H, d, J=8.8 Hz), 8.23 (1H, dd J=1.2, 8.0 Hz), 8.32 (1H, d, J=2.0 Hz), 8.97 (1H, dd, J=1.2, 4.0 Hz).

Example E-50

6-Quinolinecarboxylic acid 3-(2-methylpropenyl)-benzylamide

The title compound (150 mg, 0.475 mmol, 82.2%) was obtained as a white solid from 6-quinolinecarboxylic acid (100 mg, 0.577 mmol) and 3-(2-methyl-propenyl)-benzylamine described in Preparation Example 137 (93 mg, 0.577 mmol) according to an analogous method to Example E49.
$^1$H-NMR Spectrum (CDCl$_3$) δ(ppm): 1.87 (3H, s), 1.90 (3H, s), 4.70 (2H, d, J=5.6 Hz), 6.27 (1H, s), 6.62 (1H, t, J=5.6 Hz), 7.20-7.46 (4H, m), 7.47 (1H, dd, J=4.0, 8.0 Hz), 8.05 (1H, dd, J=2.0, 8.8 Hz), 8.13 (1H, d, J=8.8 Hz), 8.23 (1H, dd, J=1.2, 8.0 Hz), 8.32 (1H, d, J=2.0 Hz), 8,97 (1H, dd, J=1.2, 4.0 Hz).

Example E-51

6-Quinolinecarboxylic acid 3-cyclopentylydenemethylbenzylamide

The title compound (150 mg, 0.457 mol, 79.3%) was obtained as a white solid from 6-quinolinecarboxylic acid (100 mg, 0.577 mmol) and 3-cyclopentylydenemethyl-benzylamine described in Preparation Example 139 (108 mg, 0.577 mmol) according to an analogous method to Example E49.
$^1$H-NMR Spectrum (CDCl$_3$) δ(ppm): 1.65-1.79 (4H, m), 2.47-2.58 (4H, m), 4.70 (2H, d, J=5.6 Hz), 6.36 (1H,s), 6.54 (1H, t, J=5.6 Hz), 7.20-7.35 (4H, m), 7.47 (1H, dd, J=4.0, 8.0 Hz), 8.05 (1H, dd, J=2.0, 8.8 Hz), 8.13 (1H, d, J=8.8 Hz), 8.23 (1H, dd, J=1.2, 8.0 Hz), 8.32 (1H, d, J=2.0 Hz), 8.97 (1H, dd, J=1.2, 4.0 Hz).

Example E-52

6-Quinolinecarboxylic acid 3-isobubenzylamide

The title compound (75 mg, 0.236 mol, 66.2%) was obtained as a white solid from 6-quinolinecarboxylic acid (60 mg, 0.356 mmol) and 3-isobutylbenzylamine described in Preparation Example 146 (58 mg, 0.356 mmol) according to an analogous method to Example E-49.
$^1$H-NMR Spectrum (CDCl$_3$) δ(ppm): 0.90 (6H, d, J=6.8 Hz), 1.87 (1H, dq, J=7.6 Hz, 6.8 Hz), 2.48 (2H, d, J=7.6 Hz), 4.69 (2H, d, J=6.0 Hz), 6.52 (1H, t, J=6.0 Hz), 7.10-7.30 (4H, m), 7.47 (1H, dd, J=4.0, 8.0 Hz), 8.05 (1H, dd, J=2.0, 8.8 Hz), 8.13 (1H, d, J=8.8 Hz), 8.23 (1H, dd, J=1.2, 8.0 Hz), 8.32 (1H, d, J=2.0 Hz), 8.97 (1H, dd, J=1.2, 4.0 Hz).

Example E-53

Quinoline-6-carboxylic acid 4-benzyloxy-2-fluoro-benzalamide

To a mixture of lithium aluminum hydride (84 mg, 2.2 mmol) and tetrahydrofuran (2 mL) was added 4-benzyloxy-2-fluoro-benzonitrile described in Preparation Example 118 (100 mg, 0.44 mmol) on an ice bath, and the solution was stirred at room temperature for 1 hour. Water (0.084 mL), an aqueous solution of 5N sodium hydroxide (0.084 mL) and water (0.25 mL) were added sequentially on an ice bath, and the solution was stirred at room temperature for 90 minutes. The reaction solution was filtered through Celite pad, then, the solvent was evaporated in vacuo. The title compound (140 mg, 0.35 mmol, 90%) was obtained as a white solid from the obtained residue (91 mg) and quinoline-6-carboxylic acid (68 mg, 0.39 mmol) according to an analogous method to Example Q-6.
$^1$H-NMR Spectrum (CDCl$_3$) δ(ppm): 4.68 (2H, d, J=5.7 Hz), 5.05 (2H, s), 6.62 (1H,br s), 6.71-6.78 (2H, m), 7.34-7.43 (6H, m), 7.47 (1H, dd, J=4.3, 8.3 Hz), 8.04 (1H, dd, J=2.0, 8.8 Hz), 8.15 (1H, d, J=8.8 Hz), 8.23-8.25 (1H, m), 8.31 (1H, d, J=2.0 Hz), 8.98

Example E-54

Quinoline-6-carboxylic acid 4-benzyloxy-3-chloro-benzylamide

Trifluoroacetic acid salt of the title compound (29 mg, 0.057 mmol, 10%) was obtained from quinoline-6-carboxylic acid 4-benzyloxybenzylamide described in Example E-8 (200 mg, 0.54 mmol) according to an analogous method to Example A-171.
MS m/e (ESI) 403.1 (MH+)

Example E-55

Quinoline-6-carboxylic acid (4-phenoxy-pyridine-2-ylmethyl)-amide

The title compound (9 mg, 8%) was obtained as a colorless oil from 6-quinolinecarboxylic acid (52 mg, 0.30 mmol) and C-(4-phenoxy-pyridine-2-yl)-methylamine described in Preparation Example 7 (60 mg, 0.30 mmol) according to an analogous method to Example L-4.

$^1$H-NMR Spectrum (CDCl$_3$) δ(ppm): 4.74 (2H, d, J=4.4 Hz), 6.79 (1H, dd, J=2.4 Hz, 5.6 Hz), 6.88 (1H, d, J=2.4 Hz), 7.10-7.12 (2H, m), 7.43-7.49 (4H, m), 7.81 (1H, brs), 8.14-8.19 (2H, m), 8.26-8.28 (1H, m), 8.40-8.44 (2H, m), 8.99-9.0 (1H, m).

Example E-56

Quinoline-6-carboxylic acid (6-phenoxy-pyridin-2-ylmethyl)-benzylamide

The title compound (32 mg, 28%) was obtained as a colorless oil from 6-quinolinecarboxylic acid (56 mg, 0.325 mmol) and C-(6-phenoxy-pyridin-2-yl)-methylamine described in Preparation Example 16 (65 mg, 0.325 mmol) according to an analogous method to Example L-4.

$^1$H-NMR Spectrum (CDCl$_3$) δ(ppm): 4.73 (2H, d, J=4.4 Hz), 6.89-6.91 (1H, m), 7.04-7.06 (1H, m), 7.21-7.23 (2H, m), 7.30-7.34 (1H, m), 7.44-7.52 (3H, m), 7.64 (1H, brs), 7.65-7.68 (1H, m), 7.73-7.77 (1H, m), 8.11 (1H, d, J=8.4 Hz), 8.26 (1H, d, J=8.0 Hz), 8.32 (1H, d, J=1.6 Hz), 9.01-9.03 (1H, m).

Example E-57

Quinoline-6-carboxylic acid (1-benzyl-1H-pyrrol-3-ylmethyl)-amide

7N Ammonia/methanol (80 mL) and Raney nickel (2 g) were added to 1-benzyl-1H-pyrrole-3-carbaldehyde described in Preparation Example 57 (800 mg, 4.3 mmol), and the solution was stirred at room temperature for 22 hours under hydrogen atmosphere at ordinary pressure. The catalyst was removed by filtrating through Celite pad, then, the solvent was evaporated in vacuo and C-(1-benzyl-1H-pyrrolo-3-yl)methylamine was quantitatively obtained as a brown oil. The title compound (110 mg, 0.32 mmol, 24.8%) was obtained as a white solid from the resulting C-(1-benzyl-1H-pyrrolo-3-yl)methylamine (240 mg, 1.3 mmol) and 6-quinolinecarboxylic acid (180 mg, 1.04 mmol) according to an analogous method to Example Q-6.

$^1$H-NMR Spectrum (DMSO-d$_6$) δ(ppm): 4.32 (2H, d, 5.6 Hz), 5.02 (2H, s), 6.02 (1H, s), 6.74 (1H, s), 6.76 (1H, s), 6.18-7.34 (5H, m), 7.58 (1H, dd, J=4.0, 8.4 Hz), 8.03 (1H, d, J=8.8 Hz), 8.16 (1H, dd, J=2.0, 8.8 Hz), 8.43 (1H, dd, J=1.6, 8.4 Hz), 8.49 (1H, d, J=2.0 Hz), 8.97 (1H, t, J=5.6 Hz), 8.95 (1H, dd, J=1.6, 4.0 Hz).

Example E-58

Quinoline-6-carboxylic acid (1-benzo[1,3]dioxol-5-ylmethyl-1H-pyrrol-3-ylmethyl)-amide The title compound (30 mg, 0.077 mmol, 18.1%) was obtained as a white solid from C-(1-benzo[1,3]dioxol-5-yl-methyl-1H-pyrrol-3-yl)-methylamine described in Preparation Example 61 (100 mg, 0.43 mmol) and 6-quinolinecarboxylic acid (75 mg, 0.43 mmol) according to an analogous method to Example Q-6.

$^1$H-NMR Spectrum (DMSO-d$_6$) δ(ppm): 4.28-4.34 (2H, m), 4.90 (2H, s), 5.95 (2H, s), 6.00 (1H, s), 6.70-6.86 (5H, m), 7.55-7.60 (1H, m), 8.01-8.05 (1H, m), 8.14-8.20 (1H, m), 8.40-8.46 (1H, m), 8.48-8.51 (1H, m), 8.39-8.98 (2H, m).

Example E-59

Quinoline-6-carboxylic acid (1-phenylethyl-1H-pyrrol-3-ylmethyl)-amide

The title compound (108 mg, 0.304 mmol, 30.4%) was obtained as a slightly yellow solid from 1-phenylethyl-1H-pyrrole-3-carbaldehyde described in Preparation Example 62 and quinoline-6-carboxylic acid (173 mg, 1.0 mmol) according to an analogous method to Example E-57.

$^1$H-NMR Spectrum (DMSO-d$_6$) δ(ppm): 2.96 (2H, t, J=7.6 Hz), 4.03 (2H, t, J=7.6 Hz), 4.31 (2H, d, J=5.6 Hz), 5.96 (1H, s), 6.64 (1H, s), 6.73 (1H, s), 7.14-7.28 (1H, dd, J=4.0, 8.0 Hz), 8.04 (1H, d, J=8.8 Hz), 8.17 (1H, d, J=8.8 Hz), 8.43 (1H, d, J=8.0 Hz), 8.50 (1H, s), 8.90 (1H, t, J=5.6 Hz), 8.95-8.99 (1H, m).

Example E-60

Quinoline-6-carboxylic acid (1-benzyloxy-1H-pyrrol-3-ylmethyl)-amide

Diethyl azodicarboxylate (154 mg, 0.869 mmol) was added dropwise to a solution of (1-benzyloxy-1H-pyrrol-3-yl)-methanol described in Preparation Example 64 (168 mg, 0.828 mmol), phthalimide (130 mg, 0.869 mmol) and triphenylphosphine (230 mg, 0.869 mmol) in dichloromethane at 0° C., and then, the solution was stirred at room temperature for 8 minutes. NH silica gel was added to the reaction solution, the solvent was evaporated in vacuo for adsorption, purification was carried out by NH silica gel column chromatography (hexane:ethyl acetate=4:1), and a colorless oil (100 mg) was obtained. Ethanol (5 mL) and hydrazine monohydrate (0.1 mL) were added to this oil (100 mg), and the solution was stirred under reflux for 15 minutes. The reaction solution was allowed to room temperature, solid was eliminated by filtration, then, the solvent was evaporated, and an oil containing C-(1-benzyloxy-1H-pyrrol-3-yl)methylamine was obtained (80 mg). The title compound (31 mg, 0.086 mmol) was obtained as a colorless oil from this oil (80 mg) and quinoline-6-carboxylic acid according to an analogous method to Example Q-6.

$^1$H-NMR Spectrum (DMSO-d$_6$) δ(ppm): 4.28 (2H, d, J=5.6 Hz), 5.11 (2H, s), 5.86-5.89 (1H, m), 6.78-6.81 (1H, m), 6.88-6.91 (1H, m), 7.34-7.42 (5H, m), 7.59 (1H, dd, J=4.0, 8.0 Hz), 8.04 (1H, d, J=8.8 Hz), 8.16 (1H, d, J=8.8 Hz), 8.44 (1H, d, J=8.0 Hz), 8.49 (1H, s), 8.92-8.98 (2H, m).

Example E-61

Quinoline-6-carboxylic acid (1-phenyl-1H-pyrrol-3-ylmethyl)-amide

The title compound (136 mg, 0.415 mmol, 47.8%) was obtained as a white solid from C-(1-phenyl-1H-pyrrol-3-yl)-methylamine described in Preparation Example 74 (150 mg, 0.87 mmol) and quinoline-6-carboxylic acid (150 mg, 0.87 mmol) according to an analogous method to Example Q-6.

$^1$H-NMR Spectrum (DMSO-d$_6$) δ(ppm): 4.42 (2H, d, J=5.6 Hz), 6.28-6.31 (1H, m), 7.18-7.24 (1H, m), 7.29-7.35 (2H, m), 7.40-7.45 (2H, m), 7.50-7.65 (2H, m, 7.59 (1H, dd, J=4.0, 8.0 Hz), 8.05 (1H, d, J=8.8 Hz), 8.20 (1H, dd, J=2.0, 8.8 Hz), 8.43-8.48 (1H, m), 8.53 (1H, d, J=2.0 Hz), 8.96 (1H, dd, J=1.6, 4.0 Hz), 9.01 (1H, t, J=5.6 Hz).

Example E-62

Quinoline-6-carboxylic acid (2-benzyl-2H-tetrazol-5-ylmethyl)-amide

Sodium azide (260 mg, 4.0 mmol) and ammonium chloride (210 mg, 4.0 mmol) were suspended in a solution of quinoline-6-carboxylic acid cyanomethyl-amide described in Preparation Example E-1 (420 mg, 2.0 mmol) in N,N-dimethylformamide (15 mL), and the solution was stirred at 100° C. for 12 hours. Benzyl bromide (0.12 mL, 1.0 mmol) and potassium carbonate (400 mg, 3.0 mmol) were added to a solution having half the amount of the solution containing quinoline-6-carboxylic acid (2H-tetrazol-5-ylmethyl)amide obtained, which was then stirred for 20 minutes at 50° C. Water and ethyl acetate were added to the reaction solution, which was then partitioned, NH silica gel was added to the organic layer, and the solvent was evaporated in vacuo for adsorption, purification was carried out by NH silica gel column chromatography, and the title compound (20 mg, 0.058 mmol) was obtained as a white solid.
$^1$H-NMR Spectrum (DMSO-$d_6$) δ(ppm): 4.78 (2H, d, J=5.6 Hz), 5.92 (2H, s), 7.34-7.43 (5H, m), 7.62 (1H, dd, J=4.0, 8.4 Hz), 8.09 (1H, d, J=8.8 Hz), 8.19 (1H, dd, J=2.0, 8.8 Hz), 8.48 (1H, dd, J=1.2, 8.4 Hz), 8.54 (1H, d, J=2.0 Hz), 9.00 (1H, dd, J=1.2, 4.0 Hz), 9.44 (1H, t, J=5.6 Hz).

Example E-63

Quinoline-6-carboxylic acid (2-phenoxy-thiazol-5-ylmethyl)-amide

The title compound (17 mg, 46 μmol, 91%) was obtained as a white solid from C-(2-phenoxy-thiazol-5-yl)-methylamine described in Preparation Example 117 (10 mg, 50 μmol) and quinoline-6-carboxylic acid (11 mg, 60 μmol) according to an analogous method to Example A-26.
$^1$H-NMR Spectrum (DMSO-$d_6$) δ(ppm): 4.55 (2H, d, J=5.7 Hz), 7.23 (1H, s), 7.27-7.31 (3H, m), 7.45 (2H, dd, J=7.2, 8.8 Hz), 7.59 (1H, dd, J=4.2, 8.8 Hz), 8.06 (1H, d, J=8.8 Hz), 8.14 (1H, dd, J=1.8, 8.8 Hz), 8.46 (1H, d, J=7.1 Hz), 8.5 (1H, d, J=1.8 Hz), 8.97 (1H, dd, J=1.7, 4.2 Hz), 9.39 (1H, t, J=5.7 Hz).

Example E-64

Quinoline-6-carboxylic acid (5-(3-cyano-phenoxy)-thiophen-2-ylmethyl)-amide

To a solution of C-(5-(3-bromophenoxy)-thiophen-2-yl)-methylamine described in Preparation Example 17 (200 mg, 0.703 mmol) and 6-quinolinecarboxylic acid (123 mg, 0.703 mmol) in tetrahydrofuran (5 mL) were added benzotriazol-1-yloxytris(dimethylamino)phosphonium hexafluorophosphate (373 mg, 0.844 mmol) and triethylamine (0.2 mL, 1.41 mmol), and the solution was stirred at room temperature for 2 hours. Ethyl acetate and water were added to the reaction solution, which was then partitioned, the organic layer was washed with water, and then, dried over anhydrous magnesium sulfate. The solvent was evaporated, the residue was purified by NH silica gel column chromatography (hexane:ethyl acetate), and a mixture of quinoline-6-carboxylic acid (5-(3-bromophenoxy)-thiophene-2ylmethyl)-amide and debrominated compound (170 mg, 55%) was obtained as a colorless oil.
Next, to a solution of the mixture of quinoline-6-carboxylic acid (5-(3-bromophenoxy)-thiophene-2ylmethyl)-amide and debrominated compound (130 mg, 0.303 mmol) in N,N-dimethylformamide (5.0 mL) were added zinc cyanide (71 mg, 0.605 mmol) and tetrakis(triphenylphosphine)palladium(0) (70 mg, 0.061 mmol) under nitrogen atmosphere, the solution was stirred at 100° C. for 1 hour, and the solution was stirred at 140° C. for 3 hours. The reaction solution was allowed to room temperature, ethyl acetate and water were added to the reaction solution, which was then partitioned, the organic layer was washed with water and dried over anhydrous magnesium sulfate. The solvent was evaporated, then, the residue was purified by NH silica gel column chromatography (hexane:ethyl acetate), and title compound (25 mg, 21%) was obtained as a colorless oil.
$^1$H-NMR Spectrum (CDCl$_3$) δ(ppm): 4.80 (2H, d, J=5.2 Hz), 6.49 (1H, d, J=4.0 Hz), 6.68 (1H, brs), 6.85 (1H, d, J=3.6 Hz), 7.30-7.45 (4H, m), 7.48 (1H, dd, J=4.4, 8.4 Hz), 8.07 (1H, dd, J=2.0, 8.8 Hz), 8.17 (1H, d, J=8.8 Hz), 8.24-8.27 (1H, m), 8.35 (1H, d, J=2.0 Hz), 8.99-9.01 (1H, m).

Example E-65

Quinoline-6-carboxylic acid (5-(3-fluorophenoxy)thiophen-2-ylmethyl) amide

The title compound (100 mg, 0.265 mmol, 29.4%) was obtained as a reddish brown oil from C-(5-(3fluorophenoxy)thiophen-2-yl)methylamine described in Preparation Example 23 and 6-quinolinecarboxylic acid according to an analogous method to Example Q-6.
$^1$H-NMR Spectrum (DMSO-$d_6$) δ(ppm): 4.59 (2H, d, J=5.6 Hz), 6.59 (1H, d, J=3.6 Hz), 6.84 (1H, d, J=3.6 Hz), 6.90-7.7.02 (3H, m), 7.39 (1H, ddd, J=8.0, 8.0, 8.0 Hz), 7.60 (1H, dd, J=4.0, 8.0 Hz), 8.06 (1H, d, J=8.8 Hz), 8.16 (1H, dd, J=1.6, 8.8 Hz), 8.45 (1H, d, J=8.0 Hz), 8.51 (1H, s), 8.97 (1H, d, J=4.0 Hz), 9.37 (1H, t, J=5.6 Hz).

Example E-66

Quinoline-6-carboxylic acid (5-phenoxythiophen-2-ylmethyl)amide

Sodium hydride (3 g, 74 mmol, 60% in oil) was added to a solution of phenol (7 g, 74 mmol) in dimethylsulfoxide (40 mL), which was then stirred at room temperature for 10 minutes, and 5-nitrothiophene-2-carbaldehyde (10 g, 64 mmol) was further added, followed by stirring for 15 minutes. Water and ethyl acetate were added to the reaction solution, which was then partitioned, the organic layer was washed with an aqueous solution of 2N sodium hydroxide twice and with water three times, then, passed through a glass filter lined with silica gel, and eluted with ethyl acetate. The solvent was evaporated in vacuo, and a yellow oil containing 5-phenoxy thiophene-2-carbaldehyde was obtained (500 mg). This oil (500 mg) was dissolved in 7N ammonia/methanol solution (30 mL), Raney nickel (1.5 g) was added thereto, and the solution was stirred overnight under hydrogen atmosphere. Raney nickel was removed by filtering through Celite pad, then, the filtrate was concentrated in vacuo, the residue was purified by silica gel chromatography (ethyl acetate, then ethyl acetate:methanol=4:1) and a brown oil containing C-(5-phenoxythiophen-2-yl)methylamine was obtained (40 mg).
Then, to a solution of the obtained oil (40 mg, 0.195 mmol) and 6-quinolinecarboxylic acid (41 mg, 0.234 mmol) in N,N-dimethylformamide (5 mL) were added benzotriazol-1-yl-tris(dimethylamino)phosphonium hexafluorophosphate (100 mg, 0.234 mmol) and triethylamine (0.054 mL, 0.39 mmol), and the solution was stirred for 30 minutes at 60° C. Water and ethyl acetate were added to the reaction solution, which was then partitioned, the organic layer was washed with water twice, NH silica gel was added to this organic layer, the solvent was evaporated in vacuo for adsorption, and purification was carried out by NH silica gel column chromatography (hexane:ethyl acetate=3:1, then 1:1, then ethyl acetate). The solvent was evaporated in vacuo, then, the solid generated by adding diethyl ether to the residue was collected by filtration, and the title compound (40 mg, 0.111 mmol, 56.9%) was obtained as a pale yellow solid.

$^1$H-NMR Spectrum (DMSO-$d_6$) δ(ppm): 4.57 (2H, d, J=5.6 Hz), 6.51 (1H, d, J=3.6 Hz), 6.81 (1H, d, J=3.6 Hz), 7.06-7.15 (3H, m), 7.23-7.40 (2H, m), 7.59 (1H, dd, J=4.0, 8.0 Hz), 8.06 (1H, d, J=8.8 Hz), 8.16 (1H, dd, J=2.0, 8.8 Hz), 8.45 (1H, dd, J=1.6, J=8.0 Hz), 8.51 (1H, d, J=2.0 Hz), 8.97 (1H, dd, J=1.6, 4.0 Hz), 9.36 (1H, t, J=5.6 Hz).

Example E-67

Quinoline-6-carboxylic acid (5-(4-fluorophenoxy)thiophen-2-yl)methyl amide

The title compound (38 mg, 0.100 mmol, 27.8%) was obtained as a white solid from C-(5-(4-fluorophenoxy) thiophen-2-yl)methylamine described in Preparation Example 28 and 6-quinolinecarboxylic acid according to an analogous method to Example Q-6.

$^1$H-NMR Spectrum (DMSO-$d_6$) δ(ppm): 4.57 (2H, d, J=6.0 Hz), 6.49 (1H, d, J=3.6 Hz), 6.80 (1H, d, J=3.6 Hz), 7.10-7.17 (2H, m), 7.17-7.24 (2H, m), 7.59 (1H, dd, J=4.0, 8.0 Hz), 8.06 (1H, d, J=8.8 Hz), 8.16 (1H, dd, J=2.0, J=8.8 Hz), 8.45 (1H, dd, J=1.6, 8.0 Hz), 8.51 (1H, d, J=2.0 Hz), 8.97 (1H, dd, J=1.6, 4.0 Hz), 9.36 (1H, t, J=6.0 Hz).

Example E-68

Quinoline-6-carboxylic acid (5-(4-chloro-phenoxy)-thiophen-2-ylmethyl)-amide

The title compound (87 mg, 0.22 mmol, 76.1%) was obtained as a brown oil from the resulting C-(5-(4-chlorophenoxy)thiophen-2-yl)methylamine (70 mg, 0.29 mmol) and 6-quinolinecarboxylic acid (51 mg, 0.29 mmol) according to an analogous method to Example E46.

$^1$H-NMR Spectrum (DMSO-$d_6$) δ(ppm): 4.58 (2H, d, 5.6 Hz), 6.55 (1H, d, J=4.0 Hz), 6.83 (1H, d, J=4.0 Hz), 7.08-7.14 (2H, m), 7.38-7.45 (2H, m), 7.59 (1H, dd, J=4.4, 8.0 Hz), 8.06 (1H, d, J=8.8 Hz), 8.16 (1H, dd, J=2.0, 8.8 Hz), 8.46 (1H, dd, J=1.6, 8.0 Hz), 8.51 (1H, d, J=2.0 Hz), 8.97 (1H, dd, J=1.6, 4.4 Hz), 9.36 (1H, t, J=5.6 Hz).

Example E-69

Quinoline-6-carboxylic acid (4-(3-fluoro-phenoxy)-thiophen-2-ylmethyl)-amide

The title compound (24 mg, 0.063 mmol, 39.7%) was obtained as a white solid from C-(4 (3-fluorophenoxy) thiophen-2-yl)methylamine described in Preparation Example 35 (35 mg, 0.16 mmol) and 6-quinolinecarboxylic acid (33 mg, 0.19 mmol) according to an analogous method to Example Q-6.

$^1$H-NMR Spectrum (DMSO-$d_6$) δ(ppm): 4.63 (2H, d, J=6.0 Hz), 6.83-6.97 (5H, m), 7.38 (1H, ddd, J=8.0, 8.0, 8.0 Hz), 7.60 (1H, dd, J=4.4, 8.0 Hz), 8.07 (1H, d, J=8.8 Hz), 8.17 (1H, dd, J=2.0, 8.8 Hz), 8.47 (1H, dd, J=2.0, 8.0 Hz), 8.53 (1H, d, J=2.0 Hz), (1H, dd, J=2.0, 4.4 Hz), 9.39 (1H, t, J=6.0 Hz).

Example E-70

Quinoline-6-carboxylic acid (5-benzyl-thiophen-2-ylmethyl)-amide

The title compound (40 mg, 0.111 mmol, 41.3%) was obtained as a white solid from quinoline-6-carboxylic acid (46 mg, 0.27 mmol) and C-(5-benzyl-thiophen-2-yl)-methylamine described in Preparation Example 42 (54 mg, 0.27 mmol) according to an analogous method to Example Q-6.

$^1$H-NMR Spectrum (DMSO-$d_6$) δ(ppm) 4.04 (2H, s), 4.57 (2H, d, J=5.6 Hz), 6.71 (1H, d, J=3.6 Hz), 6.84 (1H, d, J=3.6 Hz), 7.14-7.30 (5H, m), 7.58 (1H, dd, J=4.0, 8.4 Hz), 8.04 (1H, d, J=8.8 Hz), 8.14 (1H, dd, J=2.0, 8.8 Hz), 8.44 (1H, dd, J=2.0, 8.4 Hz), 8.49 (1H, d, J=2.0 Hz), 8.96 (1H, dd, J=2.0, 4.0 Hz), 9.29 (1H, t, J=5.6 Hz).

Example E-71

Quinoline-6-carboxylic acid (5-(3-chlorobenzyl)-thiophen-2-ylmethyl)-amide

The title compound (73 mg, 0.18 mmol, 85.7%) was obtained as a white solid from C-(5-(3-chloro-benzyl)-2-yl)-methylamine described in Preparation Example 45 (50 mg, 0.21 mmol) and 6-quinolinecarboxylic acid (40 mg, 0.23 mmol) according to an analogous method to Example Q-6.

$^1$H-NMR Spectrum (DMSO-$d_6$) δ(ppm): 4.07 (2H, s), 4.58 (2H, d, J=5.2 Hz), 6.74 (1H, d, J=2.4 Hz), 6.84 (1H, d, J=2.4 Hz), 7.17-7.34 (4H, m), 7.59 (1H, dd, J=4.0, 8.4 Hz), 8.05 (1H, d, J=8.4 Hz), 8.14 (1H, d, J=8.4 Hz), 8.44 (1H, d, J=8.4 Hz), 8.49 (1H, s), 8.95 (1H, d, J=4.0 Hz), 9.30 (1H, t, J=5.2 Hz).

Example E-72

Quinoline-6-carboxylic acid (5-(3-fluoro-benzyl)-thiophen-2-ylmethyl)-amide

The title compound (75 mg, 0.199 mmol, 80.2%) was obtained as a light brown solid from quinoline-6-carboxylic acid (43 mg, 0.248 mmol) and 5-(3-fluoro-benzyl)-thiophene-2-carbaldehyde described in Preparation Example 53 (50 mg, 0.226 mmol) according to an analogous method to Example A-146.

$^1$H-NMR Spectrum (DMSO-$d_6$) δ(ppm): 4.08 (2H, s), 4.58 (2H, d, J=5.6 Hz), 6.74 (1H, d, J=3.2 Hz), 6.85 (1H, d, J=3.2 Hz), 6.98-7.10 (3H, m), 7.28-7.35 (1H, m), 7.59 (1H), dd, J=4.0, 8.0 Hz), 8.05 (1H, d, J=8.8 Hz), 8.15 (1H, dd, J=1.6, 8.8 Hz), 8.44 (1H, d, J=8.0 Hz), 8.49 (1H, d, J=1.6 Hz), 8.95-8.99 (1H, m), 9.30 (1H, t, J=5.6 Hz).

Example E-73

Quinoline-6-carboxylic acid (5-(5-methyl-thiophen-2-ylmethyl)-thiophen-2-ylmethyl)-amide To a solution of (5-(5-methyl-thiophen-2-ylmethyl)-thiophen-2-yl)-methanol described in Preparation Example 67 (640 mg, 2.86 mmol), phthalimide (420 mg, 2.86 mmol) and triphenylphosphine (750 mg, 2.86 mmol) in tetrahydrofuran (7 mL) was added diethyl azodicarboxylate (500 mg, 2.86 mmol) dropwise at 0° C., which was then stirred at room temperature for 15 minutes. Water and ethyl acetate were added to the reaction solution, which was then partitioned, silica gel was added, the solvent was concentrated in vacuo for adsorption, and purification was carried out by silica gel column chromatography (hexane:ethyl acetate=8:1). The solvent was evaporated in vacuo, a brown solid (360 mg, 1.02 mmol, 35.6%) was obtained.

Ethanol (5 mL) and hydrazine monohydrate (180 mg, 3.06 mmol) were added to the resulting solid (360 mg), and the solution was stirred for 20 minutes at 90° C. The solution was allowed to room temperature, the solid was eliminated by filtration, and a pale yellow oil containing C-5-(5-methyl-thiophen-2-ylmethyl)-thiophen-2-yl)-methylamine was obtained (200 mg, 0.896 mmol, 89.6%). The title compound (101 mg, 0.267 mmol, 29.8%) was obtained as a white solid from this oil (200 mg, 0.896 mmol) and quinoline-carboxylic acid (160 mg, 0.896 mmol) according to an analogous method to Example Q-6.

$^1$H-NMR Spectrum (DMSO-$d_6$) δ(ppm): 2.35 (3H, s), 4.20 (2H, s), 4.61 (2H, d, J=5.6 Hz), 6.58-6.62 (1H, m), 6.69 (1H, d, J=3.2 Hz), 6.75 (1H, d, J=3.2 Hz), 6.86 (1H, d, J=3.2 Hz), 7.61 (1H, dd, J=4.0, 8.4 Hz), 8.08 (1H, d, J=8.8 Hz), 8.18 (1H, dd, J=2.0, 8.8 Hz), 8.47 (1H, d, J=8.4 Hz), 8.52 (1H, d, J=2.0 Hz), 8.97-9.01 (1H, m), 9.34 (1H, t, J=5.6 Hz).

Example E-74

Quinoline-6-carboxylic acid (5-(5-methyl-furan-2-ylmethyl)-thiophen-2-ylmethyl)-amide The title compound (3.0 mg, 0.008 mmol) was obtained as a brown oil from (5-(5-methyl-furan-2-ylmethyl)-thiophen-2-yl)-methanol described in Preparation Example 70 (210 mg, 1.0 mmol) according to an analogous method to Example E-73.

$^1$H-NMR Spectrum (DMSO-$d_6$) δ(ppm): 2.18 (3H, s), 4.04 (2H, s), 4.61 (2H, d, J=5.6 Hz), 5.94 (1H, d, J=3.2 Hz), 6.03 (1H, d, J=3.2 Hz), 6.74 (1H, d, J=3.2 Hz), 6.87 (1H, d, J=3.2 Hz), 7.61 (1H, dd, J=4.0, 8.0 Hz), 8.07 (1H, d, J=8.4 Hz), 8.17 (1H, dd, J=1.6, 8.4 Hz), 8.47 (1H, dd, J=2.0, 4.0 Hz), 8.52 (1H, d, J=1.6 Hz), 8.98 (1H, dd, J=2.0, 4.0 Hz), 9.33 (1H, t, J=5.6 Hz).

Example E-75

Quinoline-6-carboxylic acid (5-benzofuran-2-ylmethyl-thiophen-2-ylmethyl)-amide

The title compound (55 mg, 0.13 mmol) was obtained as a white solid from (5-benzofuran-2-ylmethyl-thiophene)-methanol described in Preparation Example 72 according to an analogous method to Example E-73.

$^1$H-NMR Spectrum (DMSO-$d_6$) δ(ppm): 4.31 (2H, s), 4.62 (2H, d, J=5.6 Hz), 6.68 (1H, s), 6.85 (1H, d, J=3.6 Hz), 6.91 (1H, d, J=3.6 Hz), 7.16-7.26 (2H, m), 7.46-7.64 (3H, m), 8.07 (1H, d, J=8.8 Hz), 8.17 (1H, dd, J=2.0, 8.8 Hz), 8.44-8.48 (1H, m), 8.52 (1H, d, J=2.0 Hz), 8.96-9.00 (1H, m), 9.34 (1H, t, J=5.6 Hz).

Example E-76

Quinoline-6-carboxylic acid (5-benzyloxy-thiophen-2-ylmethyl)-amide

To a solution of 5-benzyloxy-thiophene-2-carbonitrile described in Preparation Example 81 (30 mg, 0.14 mmol) in tetrahydrofuran (3 mL) was added lithium aluminum hydride (21 mg, 0.557 mmol), which was then stirred for 1.5 hours at room temperature. Sodium fluoride (240 mg, 5.72 mmol) was added to the reaction mixture, which was stirred for 2 hours, then, on an ice bath, 10% hydrous tetrahydrofuran (2 mL) was added. The reaction mixture was filtered through Celite pad, the filtrate was concentrated and C-(5-benzyloxy-thiophen-2-yl)methylamine (32 mg, 0.147 mmol) was obtained as a crude product. The title compound (3 mg, 0.008 mmol, 5.4%) was obtained from this and quinoline-6-carboxylic acid (26 mg, 0.15 mmol) according to an analogous method to Example H-1.

$^1$H-NMR Spectrum (CDCl$_3$) δ(ppm) 4.74 (2H, d, J=4.4 Hz), 5.09 (2H, s), 6.15 (1H, d, J=4.0 Hz), 6.52-6.62 (1H, m), 6.71 (1H, d, J=4.0 Hz), 7.32-7.47 (5H, m), 7.50 (1H, dd, J=4.0, 8.4 Hz), 8.07 (1H, dd, J=2.0, 8.8 Hz), 8.18 (1H, d, J=8.8 Hz), 8.27 (1H, dd, J=1.6, 8.4 Hz), 8.34 (1H, d, J=2.0 Hz), 9.02 (1H, dd, J=1.6, 4.0 Hz).

Example E-77

Quinoline-6-carboxylic acid (5-(3-chloro-phenoxy)-thiophen-2-ylmethyl)-amide

The title compound (9.53 mg) was obtained from C-(5-(3-chloro-phenoxy)-thiophen-2-yl)-methylamine described in Example A-73 (30 mg, 0.13 mmol) and quinoline-6-carboxylic acid (22 mg, 0.13 mmol) according to an analogous method to Example E-24. Trifluoroacetic acid salt of the title compound was obtained by reverse phase high performance liquid chromatography (acetonitrile-water mobile phase (containing 0.1% trifluoroacetic acid) was used).

MS m/e (ESI) 395.35(MH$^+$)

Example E-78

6-Quinolinecarboxylic acid (5-(2-methylpropenyl)thiophen-2-ylmethyl) amide

The title compound (15 mg, 0.0466 mmol, 56.1%) was obtained as a white solid from 6-quinolinecarboxylic acid (15 mg, 0.083 mmol) and C-(5-(2-methylpropenyl)-thiophen-2-yl)-methylamine described in Preparation Example 145 (14 mg, 0.083 mmol) according to an analogous method to Example E-49.

$^1$H-NMR Spectrum (CDCl$_3$) δ(ppm): 1.91 (3H, s), 1.96 (3H, s), 4.83 (2H, d, J=5.2 Hz), 6.33 (1H, s), 6.62 (1H, t, J=5.2 Hz), 6.75 (1H, d, J=3.6 Hz), 6.96 (1H, d, J=3.6 Hz), 7.47 (1H, dd, J=4.0, 8.0 Hz), 8.05 (1H, dd, J=2.0, 8.8 Hz), 8.13 (1H, d, J=8.8 Hz), 8.23 (1H, dd, J=1.2, 8.0 Hz), 8.32 (1H, d, J=2.0 Hz), 8.97 (1H, dd, J=1.2, 4.0 Hz).

Example E-79

Quinoline-6-carboxylic acid (5-(2-fluoro-phenoxy-thiophen-2-ylmethyl)-amide $^1$H-NMR Spectrum (CDCl$_3$) δ(ppm): 4.55 (2H, d, J=6.0 Hz), 6.47 (1H, d, J=4.0 Hz), 6.78 (1H, d, J=3.6 Hz), 7.16-7.26 (3H, m), 7.32-7.39 (1H, m), 7.59 (1H, dd, J=4.0, J=8.0 Hz), 8.06 (1H, d, J=8.8 Hz), 8.15 (1H, dd, J=2.0, J=8.8 Hz), 8.45 (1H, d, J=8.0 Hz), 8.51 (1H, d, J=2.0 Hz), 8.95-8.98 (1H, m), 9.35 (1H, t, J=6.0 Hz).

Example E-80

Quinoline-6-carboxylic acid (5-pyridin-2-ylmethyl-thiophen-2-ylmethyl)-amide $^1$H-NMR Spectrum (CDCl$_3$) δ(ppm): 4.20 (2H, s), 4.60 (2H, d, J=5.6 Hz), 6.77 (1H, d, J=3.2 Hz), 6.86 (1H, d, J=3.2

Hz), 7.22 (1H, dd, J=5.2, J=7.6 Hz), 7.31 (1H, d, J=7.6 Hz), 7.61 (1H, dd, J=4.0, 8.0 Hz), 7.71 (1H, ddd, J=1.6, J=7.6, J=7.6 Hz), 8.07 (1H, d, J=8.0 Hz), 8.17 (1H, dd, J=2.0, J=8.0 Hz), 8.42-8.51 (2H, m), 8.52 (1H, d, J=2.0 Hz), 8.98 (1H, dd, J=1.2, J=4.0 Hz), 9.32 (1H, t, J=5.6 Hz).

Example E-81

Quinoline-6-carboxylic acid (5-benzo[1,3]dioxol-5-ylmethyl-thiophen-2-ylmethyl)-amide $^1$H-NMR Spectrum (CDCl$_3$) δ(ppm): 3.97 (2H, s), 4.59 (2H, d, J=6.0 Hz), 5.95 (2H, s), 6.69-6.75 (2H, m), 6.78-6.87 (3H, m), 7.61 (1H, dd, J=4.4, J=8.4 Hz), 8.07 (1H, d, J=8.8 Hz), 8.17 (1H, dd, J=2.0, J=8.8 Hz), 8.46 (1H, dd, J=1.6, J=8.4 Hz), 8.51 (1H, d, J=2.0 Hz), 8.98 (1H, dd, J=1.6, J=4.4 Hz), 9.31 (1H, t, J=6.0 Hz).

Example E-82

Quinoline-6-carboxylic acid (5-(3-hydroxy-phenoxy)-thiophen-2-ylmethyl)-amide

To a solution of C-(5-(3-benzyloxy-phenoxy)-thiophen-2-yl)-methylamine described in Preparation Example 18 (180 mg, 0.578 mmol) and 6-quinolinecarboxylic acid (100 mg, 0.578 mmol) in tetrahydrofuran (5 mL) were added benzotriazol-1-yloxytris(dimethylamino)phosphonium hexafluorophosphate (307 mg, 0.694 mmol) and triethylamine (0.16 mL, 1.16 mmol), and the solution was stirred overnight at room temperature. Ethyl acetate and water were added to the reaction solution, which was then partitioned, the organic layer was washed with water, and then, dried over anhydrous magnesium sulfate. The solvent was evaporated, the residue was purified by NH silica gel column chromatography (hexane: ethyl acetate), and quinoline-6-carboxylic acid (5-(3-benzyloxy-phenoxy)-thiophen-2-ylmethyl)-amide (73 mg, 27%) was obtained as a pale yellow solid.

Trifluoroacetic acid (1.0 mL) and thioanisole (100 µl) were added to the resulting quinoline-6-carboxylic acid (5-(3-benzyloxy-phenoxy)-thiophene-2-ylmethyl)-amide (73 mg, 0.156 mmol), and the solution was stirred for 30 minutes at room temperature. The reaction solution was neutralized with an aqueous solution of saturated sodium bicarbonate, then, extracted with ethyl acetate and dried over anhydrous magnesium sulfate. The solvent was evaporated, the residue was purified by NH silica gel column chromatography (ethyl acetate: methanol), and the title compound (47 mg, 80%) was obtained as a colorless solid.

$^1$H-NMR Spectrum (CDCl$_3$) δ(ppm): 4.73 (2H, d, J=5.6 Hz), 6.39 (1H, d, J=3.6 Hz), 6.59-6.62 (2H, m), 6.64-6.67 (1H, m), 6.74 (1H, d, J=3.6 Hz), 6.83 (1H, brs), 7.17 (1H, t, J=8.4 Hz), 7.49 (1H, dd, J=4.4, 8.4 Hz), 8.05 (1H, dd, J=2.0, 8.4 Hz), 8.14 (1H, d, J=8.4 Hz), 8.24-8.26 (1H, m), 8.33 (1H, d, J=2.0 Hz), 8.98-8.99 (1H, m).

Example F-1

Cinnoline-6-carboxylic acid 3-phenoxy-benzylamide

To a solution of cinnoline-6-carboxylic acid methyl ester described in Preparation Example F-4 (16 mg, 0.085 mmol) in ethanol (1 mL) was added an aqueous solution of 1N sodium hydroxide (0.7 mL), and the solution was stirred at room temperature for 2 hours. 1N Hydrochloric acid was added to the reaction mixture to adjust the pH to 4, toluene was added, and the solution was concentrated in vacuo. To a solution of the obtained residue in N,N-dimethylformamide (2 mL) were added 4-phenoxybenzylamine described in Preparation Example 3 (17 mg, 0.085 mmol), benzotriazol-1-yloxytris(dimethylamino)phosphonium hexafluorophosphate (48 mg, 0.108 mmol) and triethylamine (24 µl, 0.172 mmol), and the solution was stirred at room temperature for 14 hours. Water was added to the reaction mixture, which was extracted with ethyl acetate, the organic layer was washed with an aqueous solution of saturated sodium bicarbonate, and then concentrated. The residue was purified by reverse phase high performance liquid chromatography (acetonitrile-water mobile phase (containing 0.1% trifluoroacetic acid) was used), and the title compound (4.4 mg, 0.0093 mmol, 11%) was obtained as a trifluoroacetic acid salt.

MS m/e(ESI) 356.44 (MH$^+$)

Example G-1

Isoquinoline-6-carboxylic acid 3-phenoxybenzylamide

The title compound (3.4 mg, 33%) was obtained as a colorless oil from isoquinoline-6-carboxylic acid described in Preparation Example G-1 (5 mg, 0.0289 mmol) and 4-phenoxybenzylamine described in Preparation Example 3 (6 mg, 0.0289 mmol) according to an analogous method to Example L-4.

$^1$H-NMR Spectrum (CDCl$_3$) δ(ppm): 4.70 (2H, d, J=5.6 Hz), 6.57 (1H, brs), 6.94-6.96 (1H, m), 7.02-7.04 (3H, m), 7.11-7.15 (2H, m), 7.32-7.37 (3H, m) 7.72-7.74 (1H, m), 7.96-7.98 (1H, m), 8.05-8.07 (1H, m), 8.26 (1H, s), 8.61-8.62 (1H, m), 9.32-9.33 (1H, m).

Example H-1

Quinazoline carboxylic acid 3-phenoxybenzylamide

To a solution of quinazoline-6-carboxylic acid obtained in Preparation Example H-3 (9 mg, 0.052 mmol) in N,N-dimethylformamide (3 mL) were added 3-phenoxybenzylamine described in Preparation Example 4 (11 mg, 0.052 mmol), benzotriazol-1-yloxytris(dimethylamino)phosphonium hexafluorophosphate (28 mg, 0.062 mmol) and triethylamine (17 µl, 0.125 mmol), and the solution was stirred for 2 days at room temperature. Water was added to the reaction mixture, which was extracted with ethyl acetate, and concentrated. The residue was purified by NH silica gel column chromatography (hexane-ethyl acetate), and the title compound (11 mg, 0.031 mmol, 50%) was obtained.

$^1$H-NMR Spectrum (CD$_3$OD) δ(ppm): 4.62 (2H, s), 6.88 (1H, dd, J=8.0, 1.2 Hz), 6.98 (2H, dd, J=1.2, 8.0 Hz), 7.09 (1H, s), 7.07 (1H, dd, J=7.6, 8.0 Hz), 7.15 (1H, d, J=7.6 Hz), 7.297.35 (3H, m), 8.10 (1H, d, J=8.8 Hz), 8.40 (1H, dd, J=2.0, 8.8 Hz), 8.57 (1H, d, J=2.0 Hz), 9.32 (1H, s), 9.61 (1H, s).

Example I-1

Quinoxaline-6-carboxylic acid 3-phenoxybenzylamide

To a solution of quinoxaline-6-carboxylic acid described in Preparation Example I-1 (15 mg, 0.063 mmol) and 4-phenoxybenzylamine described in Preparation Example 3 (13 mg, 0.063 mmol) in N,N-dimethylformamide (2 mL) were added benzotriazol-1-yloxytris(pyrrolidino)phosphonium hexafluorophosphate (36 mg, 0.069 mmol) and triethylamine (19 µl, 0.14 mmol), which was then stirred at room temperature for 24 hours. The reaction mixture was concentrated, the residue was purified by reverse phase high performance liquid chromatography (acetonitrile-water mobile phase (containing 0.1% trifluoroacetic acid) was used), and the title compound (12 mg, 0.025 mmol, 40%) was obtained as a trifluoroacetic acid salt.

MS m/e(ESI) 356.37(MH$^+$)

Example J-1

[1,8]Naphthylidine-3-carboxylic acid 3-phenoxybenzylamide

Tetrahydrofuran (1 mL), methanol (0.1 mL) and water (0.1 mL) were added to [1,8]naphthylidine-3-carboxylic acid ethyl ester described in Preparation Example J-7 (8.1 mg, 0.040 mmol) and lithium hydroxide monohydrate (3.4 mg, 0.080 mmol), and the solution was stirred at 50° C. for 1 hour. The solvent was evaporated in vacuo, then, the obtained residue and 3-phenoxybenzylamine (5.0 mg, 0.025 mmol) were reacted according to an analogous method to Example Q-6, and trifluoroacetic acid salt of the title compound (3.7 mg, 0.0079 mmol, 20%) was obtained.

MS m/e (ESI) 356.3 (MH$^+$)

Example K-1

2-Methyl-benzoxazole-6-carboxylic acid 3-phenoxybenzylamide

The title compound (22 mg, 0.061 mmol, 72%) was obtained from 2-methyl-benzoxazole-6-carboxylic acid described in Preparation Example K-2 (15 mg, 0.085 mmol) and 4phenoxybenzylamine described in Preparation Example 3 (17 mg, 0.085 mmol) according to an analogous method to Example H-1.

$^1$H-NMR Spectrum (CD$_3$OD) δ(ppm): 2.66 (3H, s), 4.56 (2H, s), 6.80-7.15 (6H, m) 7.22-7.78 (3H, m), 7.62-7.68 (1H, m), 7.81-7.86 (1H, m), 8.00-8.04 (1H, m), 9.08 (1H, brs).

Example L-1

Benzothiazole-6-carboxylic acid (5-(3fluoro-benzyl)-furan-2-ylmethyl)-amide

The title compound (290 mg, 0.791 mmol, 76%) was obtained from benzothiazole-6-carboxylic acid (188 mg, 1.05 mmol) and C-(5-(3-fluoro-benzyl)-furan-2-yl)-methylamine described in Preparation Example 84 (236 mg, 1.15 mmol) according to an analogous method to Example H-1 (with the proviso that only the reaction temperature was changed to 60° C.).

$^1$H-NMR Spectrum (DMSO-d$_6$) δ(ppm): 3.96 (2H, s), 4.43 (2H, d, J=5.2 Hz), 6.06 (1H, d, J=3.2 Hz), 6.20 (1H, d, J=3.2 Hz), 7.00-7.09 (3H, m), 7.29-7.36 (1H, m), 7.99 (1H, dd, J=1.6, 8.4 Hz), 8.12 (1H, d, J=8.4 Hz), 8.64 (1H, d, J=1.6 Hz), 9.07 (1H, t, J=5.2 Hz), 9.51 (1H, s).

Example L-2

Benzothiazole-6-carboxylic acid 4-benzyloxybenzylamide

The title compound (41 mg, 47%) was obtained as a white solid from benzothiazole-6-carboxylic acid (42 mg, 0.234 mmol) and 4-benzyloxybenzylamine described in Preparation Example 1 (50 mg, 0.234 mmol) according to an analogous method to Example E-8.

$^1$H-NMR Spectrum (CDCl$_3$) δ(ppm): 4.62 (2H, d, J=5.2 Hz), 5.08 (2H, s), 6.40 (1H, brs), 6.98 (2H, d, J=8.8 Hz), 7.30-7.35 (3H, m), 7.37-7.45 (4H, m), 7.85-7.88 (1H, m), 8.16 (1H, d, J=8.4 Hz), 8.49 (1H, d, J=1.6 Hz), 9.11 (1H, s).

Example L-3

Benzothiazole-6-carboxylic acid 3-phenoxybenzylamide

To a solution of 3-phenoxybenzylamine described in Preparation Example 4 (33 mg, 0.167 mmol) and benzothiazole-6-carboxylic acid (30 mg, 0.167 mmol) in tetrahydrofuran (1 mL) were added benzotriazol-1-yloxytris(dimethylamino)phosphonium hexafluorophosphate (89 mg, 0.20 mmol) and triethylamine (28 µl, 0.20 mmol), and the solution was stirred at room temperature for 17 hours. The solvent was evaporated, the residue was purified by NH silica gel column chromatography (hexane:ethyl acetate), and the title compound (37 mg, 62%) was obtained as a colorless oil.

$^1$H-NMR Spectrum (CDCl$_3$) δ(ppm): 4.68 (2H, d, J=6.0 Hz), 6.50 (1H, brs), 6.94 (1H, dd, J=2.0, 8.0 Hz), 7.02-7.04 (3H, m), 7.11-7.15 (2H, m), 7.31-7.37 (3H, m), 7.88 (1H, dd, J=1.6, 8.8 Hz), 8.18 (1H, d, J=8.8 Hz), 8.49 (1H, d, J=1.6 Hz), 9.13 (1H, s).

Example L-4

Benzothiazole-6-carboxylic acid 4-(3-fluoro-benzyloxy)-benzylamide

To a solution of 4-(3-fluorobenzyloxy)-benzylamine described in Preparation Example 6 (129 mg, 0.558 mmol) and benzothiazole-6-carboxylic acid (100 mg, 0.558 mmol) in tetrahydrofuran (5 mL) were added benzotriazol-1-yloxytris(dimethylamino)phosphonium hexafluorophosphate (296 mg, 0.670 mmol) and triethylamine (93 µl, 0.670 mmol), and the solution was stirred overnight at room temperature. Ethyl acetate and water were added to the reaction solution, which was then partitioned, the organic layer was washed with water, and then, dried over anhydrous magnesium sulfate. The solvent was evaporated, the residue was purified by NH silica gel column chromatography (hexane:ethyl acetate), and the title compound (148 mg, 68%) was obtained as a white solid.

$^1$H-NMR Spectrum (CDCl$_3$) δ(ppm): 4.64 (2H, d, J=5.6 Hz), 5.08 (2H, s), 6.42 (1H, brs), 6.97 (2H, d, J=8.8 Hz), 7.02 (1H, td, J=2.8, 8.4 Hz), 7.15-7.21 (2H, m), 7.31-7.38 (3H, m), 7.88 (1H, dd, J=1.6 Hz, 8.4 Hz), 8.17 (1H, d, J=8.8 Hz), 8.50 (1H, d, J=1.6 Hz), s).

Example L-5

N-Benzothiazol-6-yl-2-(3-phenoxy-phenyl)-acetamide

The title compound (118 mg, 95%) was obtained as a colorless oil from 6-aminobenzothiazole (50 mg, 3.33 mmol) and 3-phenoxyphenylacetic acid (76 mg, 3.33 mmol) according to an analogous method to Example L-4.

$^1$H-NMR Spectrum (CDCl$_3$) δ(ppm): 3.75 (2H, s), 6.97-7.22 (6H, m), 7.31 (1H, brs), 7.34-7.40 (4H, m), 8.01 (1H, d, J=8.8 Hz), 8.50 (1H, d, J=2.0 Hz), 8.91 (1H, s).

Example L-6

Benzothiazole-6-carboxylic acid (5-(3-fluorophenoxythiophene-2-ylmethyl)amide

The title compound (100 mg, 0.26 mmol, 48.2%) was obtained as a white solid from benzotriazole-6-carboxylic acid (96 mg, 0.54 mmol) and C-(5-(3-fluorophenoxy)thiophen-2-yl)methylamine described in Preparation Example 23 (120 mg, 0.54 mmol) according to an analogous method to Example 0-6.

$^1$H-NMR Spectrum (DMSO-$d_6$) δ(ppm): 4.57 (2H, d, 5.6 Hz), 6.58 (1H, d, J=3.6 Hz), 6.83 (1H, d, J=3.6 Hz), 6.89-7.00 (3H, m), 7.39 (1H, ddd, J=8.0, 8.0, 8.0 Hz), 8.00 (1H, dd, J=1.6, 8.8 Hz), 8.14 (1H, d, J=8.8 Hz), 8.66 (1H, d, J=1.6 Hz), 9.27 (1H, t, J=5.6 Hz), 9.51 (1H, s).

Example L-7

Benzothiazole-6-carboxylic acid (5-phenoxythiophen-2-ylmethyl)-amide

The title compound (97 mg, 0.265 mmol, 54.0%) was obtained as a light brown solid from benzothiazole-6-carboxylic acid (87 mg, 0.49 mmol) and C-(5-phenoxy-thiophen-2-yl)-methylamine described in Preparation Example 26 (100 mg, 0.49 mmol) according to an analogous method to Example Q-6.

$^1$H-NMR Spectrum (DMSO-$d_6$) δ(ppm): 4.55 (2H, d, J=5.6 Hz), 6.49 (1H, d, J=3.6 Hz), 6.79 (1H, d, J=3.6 Hz), 7.05-7.15 (3H, m), 7.30-7.40 (2H, m), 7.99 (1H, dd, J=1.6, 8.8 Hz), 8.13 (1H, d, J=8.8 Hz), 8.66 (1H, d, J=1.6 Hz), 9.25 (1H, t, J=5.6 Hz), 9.51 (1H, s).

Example L-8

Benzothiazole-6-carboxylic acid (5-(3-chloro-benzyl)-thiophen-2-ylmethyl)-amide

The title compound (64 mg, 0.16 mmol, 47.2%) was obtained as a white solid from C-(5-(3-chloro-benzyl-2-yl)-methylamine described in Preparation Example 45 (80 mg, 0.34 mmol) and benzothiazole-6-carboxylic acid (66 mg, 0.37 mmol) according to an analogous method to Example Q-6.

$^1$H-NMR Spectrum (DMSO-$d_6$) δ(ppm): 4.06 (2H, s), 4.56 (2H, d, J=5.6 Hz), 6.74 (1H, d, J=3.6 Hz), 6.84 (1H, d, J=3.6 Hz), 7.18-7.34 (4H, m), 7.98 (1H, dd, J=2.0, 8.8 Hz), 8.12 (1H, d, J=8.8 Hz), 8.64 (1H, d, J=2.0 Hz), 9.21 (1H, t, J=5.6 Hz), 9.51 (1H, s).

Example L-9

Benzothiazole-6-carboxylic acid (5-(3-chloro-phenoxy)-thiophen-2-ylmethyl)amide

The title compound (7.28 mg) was obtained from C-(5-(3-chloro-phenoxy)-thiophen-2-yl)-methylamine described in Example A-73 (30 mg, 0.13 mmol) and benzothiazole-6-carboxylic acid (22 mg, 0.13 mmol) according to an analogous method to Example E-24. Trifluoroacetic acid salt of the title compound (7.28 mg) was obtained by reverse phase high performance liquid chromatography (acetonitrile-water mobile phase (containing 0.1% trifluoroacetic acid) was used).

MS m/e (ESI) 401.32(MH$^+$)

Example L-10

Benzothiazole-6-carboxylic acid (5-(2-fluoro-phenoxy)-thiophen-2-ylmethyl)-amide Trifluoroacetic acid salt of the title compound (10.7 mg, 0.021 mmol, 14.3%) was obtained as a brown oil from benzothiazole-6-carboxylic acid (27.4 mg, 0.15 mmol) and C-(5-(2-fluoro-phenoxy)-thiophen-2-yl)-methylamine described in Preparation Example 161 (33.5 mg, 0.15 mmol) according to an analogous method to Example A-75.

MS m/e (ESI) 385(MH$^+$)

Example L-11

Benzothiazole-6-carboxylic acid ((5-(3-cyano-phenoxy)-thiophen-2-ylmethyl)-amide To a solution of C-(5-(3-bromophenoxy)-thiophen-2-yl)-methylamine described in Preparation Example 17 (141 mg, 0.496 mmol) and benzothiazole-6-carboxylic acid (89 mg, 0.496 mmol) in tetrahydrofuran (5 mL) were added benzotriazol-1-yloxytris(dimethylamino)phosphonium hexafluorophosphate (263 mg, 0.595 mmol) and triethylamine (0.14 mL, 0.992 mmol), and the solution was stirred at room temperature for 3 hours. Ethyl acetate and water were added to the reaction solution, which was then partitioned, the organic layer was washed with water, and then, dried over anhydrous magnesium sulfate. The solvent was evaporated, the residue was purified by NH silica gel column chromatography (hexane:ethyl acetate), and a mixture of benzothiazole-6-carboxylic acid (5-(3-bromophenoxy)-thiophene-2-ylmethyl)-amide and debrominated compound (120 mg, 53%) was obtained as a yellow oil.

Next, to a solution of the mixture of benzothiazole-6-carboxylic acid (5-(3-bromophenoxy)-thiophene-2ylmethyl)-amide and debrominated compound (120 mg, 0.269 mmol) in N,N-dimethylformamide (3.0 mL) were added zinc cyanide (63 mg, 0.538 mmol) and tetrakis(triphenylphosphine)palladium(0) (62 mg, 0.054 mmol) under nitrogen atmosphere, which was then stirred at 140° C. for 14 hours, and the solution was stirred at 140° C. for 3 hours. The reaction solution was allowed to room temperature, ethyl acetate and water were added to the reaction solution, which was then partitioned, the organic layer was washed with water and dried over anhydrous magnesium sulfate. After removing the solvent, the residue was purified by NH silica gel column chromatography (hexane:ethyl acetate), and the title compound (6.2 mg, 6%) was obtained as a colorless oil.

$^1$H-NMR Spectrum (CDCl$_3$) δ(ppm): 4.78 (2H, d, J=6.0 Hz), 6.48 (1H, d, J=4.0 Hz), 6.57 (1H, brs), 6.83 (1H, d, J=4.0 Hz), 7.30 (1H, s), 7.32-7.35 (1H, m), 7.39-7.43 (2H, m), 7.90 (1H, dd, J=1.6, 8.8 Hz), 8.19 (1H, d, J=8.8 Hz), 8.51 (1H, d, J=1.6 Hz), 9.13 (1H, s).

Example M-1

Benzo[1,2 5]thiadiazole-5-carboxylic acid 3-phenoxybenzylamide

The title compound (43 mg, 71%) was obtained as a colorless solid from 2,1,3-benzothiadiazole-5-carboxylic acid (30 mg, 0.167 mmol) obtained by hydrolysis of benzo-2,1,3-thiadiazole-5-carboxylic acid methyl ester with sodium hydroxide and 4-phenoxybenzylamine described in Preparation Example 3 (33 mg, 0.167 mmol) according to an analogous method to Example L-4.

¹H-NMR Spectrum (CDCl₃) δ(ppm): 4.67 (2H, d, J=6.0 Hz), 6.65 (1H, brs), 6.94 (1H, dd, J=2.4 Hz, 8.4 Hz), 7.01-7.03 (3H, m), 7.10-7.14 (2H, m), 7.30-7.36 (3H, m), 8.01-8.07 (2H, m), 8.37 (1H, s).

Example O-1

2.3-Dihydro-1H-pyrrolo[2.3-b]pyridine-5-carboxylic acid (5-phenoxy-thiophen-2-ylmethyl)-amide The title compound (15 mg, 43 μmol, 47%) was obtained as a white solid from 2,3-dihydro-1H-pyrrolo[2,3-b]pyridine-5-carboxylic acid described in Preparation Example O-2 (15 mg, 91 μmol) and C-(5-phenoxy-thiophen-2-yl)-methylamine described in Preparation Example 26 (19 mg, 91 μmol) according to an analogous method to Example A-26.

¹H-NMR Spectrum (DMSO-d₆) δ(ppm): 2.99 (2H, t, J=9.0 Hz), 3.53 (2H, t, J=8.6 Hz), 4.46 (2H, d, J=6.0 Hz), 6.49 (1H, d, J=3.8 Hz), 6.74 (1H, d, J=3.7 Hz), 7.00 (1H, s), 7.09 (2H, d, J=8.6 Hz), 7.14 (1H, t, J=7.5 Hz), 7.38 (2H, t, J=7.5 Hz), 7.63 (1H, s), 8.25 (1H, s), 8.71-8.77 (1H, m).

Example P-1

Furo[2.3-b]pyridine-5-carboxylic acid (5-phenoxy-thiophen-2-ylmethyl)-amide Furo[2,3-b]pyridine-5-carboxylic acid (31 mg) was obtained as a lithium salt from furo[2,3-b]pyridine-5-carboxylic acid ethyl ester described in Preparation Example P-4 (33 mg, 0.17 mmol) according to an analogous method to Example T-2.

The title compound (28 mg, 80 μmol, 79%) was obtained as a white solid from the lithium salt (17 mg) of the resulting furo[2,3-b]pyridine-5-carboxylic acid (31 mg) and C-(5-phenoxy-thiophen-2-yl)-methylamine described in Preparation

Example 26

23 mg, 0.11 mmol

¹H-NMR Spectrum (DMSO-d₆) δ(ppm): 4.57 (2H, d, J=5.9 Hz), 6.52 (1H, d, J=3.8 Hz), 6.82 (1H, d, J=3.7 Hz), 7.09-7.17 (4H, m), 7.39 (2H, t, J=8.4 Hz), 8.21 (1H, d, J=2.6 Hz), 8.58 (1H, d, J=2.2 Hz), 8.79 (1H, d, J=2.2 Hz), 9.34 (1H, t, J=6.0 Hz).

Example Q-1

Imidazo[1,2-a]pyridine-6-carboxylic acid (5-benzyl-furan-2-ylmethyl)-amide

7N Ammonia/methanol(40 mL) and Raney nickel(3 g) were added to 5-benzyl-furan-2-carbaldehyde described in Preparation Example 39 (2.5 g, 13 mmol), and the solution was stirred for 22 hours under hydrogen atmosphere at room temperature. After removing the catalyst by filtering through Celite pad, the solvent was evaporated in vacuo and C-(5-benzyl-furan-2-yl)methylamine (1.6 g, 8.6 mmol, 65.8%) was obtained.

The title compound (150 mg, 0.45 mmol, 45.3%) was obtained as a white solid from the resulting C-(5-benzylfuran-2-yl)methylamine (200 mg, 1.07 mmol) and imidazo[1,2-a]pyridine-6-carboxylic acid (170 mg, 1.07 mmol) according to an analogous method to Example Q-6.

¹H-NMR Spectrum (DMSO-d6) δ(ppm): 3.92 (2H, s), 4.41 (2H, d, J=5.2 Hz), 6.01 (1H, d, J=2.4 Hz), 6.19 (1H, d, J=2.4 Hz), 7.16-7.30 (5H, m), 7.56-7.66 (3H, m), 8.03 (1H, s), 9.00 (1H, t, J=5.2 Hz), 9.10 (1H, s).

Example Q-2

Imidazo[1,2-a]pyridine-6-carboxylic acid (5-(3-fluoro-benzyl)-furan-2-ylmethyl)-amide The title compound (363 mg, 1.04 mmol, 90%) was obtained from imidazo[1,2-a]pyridine-carboxylic acid (188 mg, 1.16 mmol) and C-(5-(3-fluoro-benzyl)-furan-2-yl)-methylamine described in Preparation Example 84 (286 mg, 1.39 mmol) according to an analogous technique to Example H-1 (with the proviso that only the reaction temperature was changed to 60° C.).

¹H-NMR Spectrum (DMSO-d₆) δ(ppm): 3.97 (2H, s), 4.42 (2H, d, J=5.2 Hz), 6.07 (1H, d, J=3.2 Hz), 6.21 (1H, d, J=3.2 Hz), 7.00-7.08 (3H, m), 7.29-7.37 (1H, m), 7.56-7.66 (3H, m), 8.04 (1H, s), 9.01 (1H, t, J=5.2 Hz), 9.10 (1H, dd, J=1.2, 1.6 Hz).

Example Q-3

Imidazol[1,2-a]pyridine-6-carboxylic acid 4-benzyloxybenzylamide

The title compound (121 mg, 55%) was obtained as a white solid from imidazo[1,2-a]pyridine-6-carboxylic acid (100 mg, 0.617 mmol) and 4-benzyloxybenzylamine described in Preparation Example 1 (132 mg, 0.617 mmol) according to an analogous method to Example E-8.

¹H-NMR Spectrum (CDCl₃) δ(ppm): 4.59 (2H, d, J=5.6 Hz), 5.07 (2H, s), 6.44 (1H, brs), 6.96-6.98 (2H, m), 7.27-7.30 (3H, m), 7.33-7.44 (5H, m), 7.59-7.61 (1H, m), 7.65-7.66 (1H, m), 7.69-7.70 (1H, m), 8.83-8.84 (1H, m).

Example Q-4

Imidazo[1,2-a]pyridine-6-carboxylic acid 3-phenoxybenzylamide

The title compound (22 mg, 35%) was obtained as a colorless oil from imidazo[1,2-a]pyridine-6-carboxylic acid (30 mg, 0.185 mmol) and 4-phenoxybenzylamine described in Preparation Example 3 (37 mg, 0.185 mmol) according to an analogous method to Example L-3.

¹H-NMR Spectrum (CDCl₃) δ(ppm): 4.64 (2H, d, J=5.6 Hz), 6.60 (1H, brs), 6.92-6.94 (1H, m), 7.00-7.02 (3H, m), 7.08-7.14 (2H, m), 7.30-7.41 (4H, m), 7.59-7.61 (1H, m), 7.69 (1H, s), 7.69-7.70 (1H, m), 8.83 (1H, s).

Example Q-5

Imidazo[1,2-a]pyridine-6-carboxylic acid 4-(3-fluoro-benzyloxy)-benzylamide The title compound (64 mg, 45%) was obtained as a white solid from 4-(3-fluorobenzyloxy)-benzylamine described in Preparation Example 6 (87 mg, 0.376 mmol) and imidazo[1,2-a]pyridine-6-carboxylic acid (61 mg, 0.376 mmol) according to an analogous method to Example L-4.

¹H-NMR Spectrum (CDCl₃) δ(ppm): 4.60 (2H, d, J=5.6 Hz), 5.07 (2H, s), 6.44 (1H, brs), 6.96 (2H, d, J=8.8 Hz), 7.02

(1H, dt, J=2.4, 8.4 Hz), 7.15 (1H, d, J=9.6 Hz), 7.19 (1H, d, J=8.4 Hz), 7.30 (2H, d, J=8.4 Hz), 7.32-7.40 (2H, m), 7.61 (1H, d, J=9.6 Hz), 7.67 (1H, s), 7.70 (1H, s), 8.84 (1H, s).

Example Q-6

Imidazo[1,2-a]pyridine-6-carboxylic acid (5-(3-fluorophenoxy)thiophen-2-ylmethyl) amide To a solution of imidazol[1,2-a]pyridine-6-carboxylic acid (87 mg, 0.54 mmol) and C(5-(3-fluorophenoxy)thiophen-2-yl)methylamine described in Preparation Example 23 (120 mg, 0.54 mmol) in N,N-dimethylformamide (5 mL) were added benzotriazol-1-yl-tris(dimethylamino)phosphonium hexafluorophosphate (240 mg, 0.54 mmol) and triethylamine (0.15 mL, 1.08 mmol), and the solution was stirred for 40 minutes at 80° C. Water and ethyl acetate were added to the reaction solution, which was then partitioned, and the organic layer was washed with water twice. Silica gel was added to the organic layer, the solvent was evaporated in vacuo for adsorption, purification was carried out by silica gel column chromatography (hexane:ethyl acetate=1:1, then ethyl acetate), and the title compound (90 mg, 0.25 mmol, 45.4%) was obtained as a light brown oil.
$^1$H-NMR Spectrum (DMSO-$d_6$) δ(ppm): 4.55 (2H, d, J=5.6 Hz), 6.58 (1H, d, J=4.0 Hz), 6.83 (1H, d, J=4.0 Hz), 6.90-7.00 (3H, m), 7.40 (1H, ddd, J=8.0, 8.0, 8.0 Hz), 7.57-7.66 (3H, m), 8.04 (1H, s), 9.12 (1H, d, J=0.8 Hz), 9.20 (1H, t, J=5.6 Hz).

Example Q-7

Imidazo[1,2-a]pyridine-6-carboxylic acid (5-phenoxy-thiophen-2-ylmethyl)-amide

The title compound (160 mg, 0.458 mmol, 93.5%) was obtained as a light brown oil from imidazo[1,2-a]pyridine-6-carboxylic acid (80 mg, 0.49 mmol) and C-(5-phenoxythiophen-2-yl)methylamine described in Preparation Example 26 (100 mg, 0.49 mmol) according to an analogous method to Example Q-6.
$^1$H-NMR Spectrum (DMSO-$d_6$) δ(ppm): 4.53 (2H, d, J=5.6 Hz), 6.50 (1H, d, J=4.0 Hz), 6.79 (1H, d, J=4.0 Hz), 7.04-7.15 (3H, m), 7.32-7.40 (2H, m), 7.56-7.66 (3H, m), 8.03 (1H, s), 9.08-9.13 (1H, m), 9.19 (1H, t, J=5.6 Hz).

Example Q-8

Imidazo[1,2-a]pyridine-6-carboxylic acid (5-(3-chloro-phenoxy)-thiophen-2-ylmethyl)-amide To a solution of C-(5-(3-chloro-phenoxy)-thiophen-2-yl)-methylamine described in Preparation Example 167 (104 mg, 0.434 mmol) and imidazo[1,2-a]pyridine-6-carboxylic acid (77 mg, 0.477 mmol) in N,N-dimethylformamide (3 mL) were added benzotriazol-1-yloxy tris(dimethylamino)phosphonium hexafluorophosphate (250 mg, 0.564 mmol) and triethylamine (181 µL) at room temperature, and the solution was stirred at room temperature for 4 hours. Water was added to the reaction solution, which was then extracted with ethyl acetate, and the organic layer was washed with water and brine. Anhydrous magnesium sulfate was added to the organic layer for drying, filtration was carried out, then, the solvent was evaporated in vacuo, the residue was purified by NH silica gel column chromatography (ethyl acetate/methanol=40/1), and the title compound (149 mg, 89%) was obtained as a white solid.
$^1$H-NMR Spectrum (DMSO-$d_6$) δ(ppm): 4.55 (2H, d, J=5.3 Hz), 6.59 (1H, dd, J=1.1, 3.7 Hz), 6.83 (1H, d, J=3.7 Hz), 7.06 (1H, dd, J=1.1, 8.2 Hz), 7.13 (1H, s), 7.20 (1H, d, J=8.1 Hz), 7.40 (1H, t, 8.1 Hz), 7.58-7.64 (3H, m), 8.05 (1H, s), 9.12 (1H, s), 9.23 (1H, t, J=5.5 Hz).

Example R-1

1H-Pyrrolo[2,3-b]pyridine-5-carboxylic acid (5-phenoxy-thiophen-2-ylmethyl)-amide The title compound (22 mg, 63 µmol, 68%) was obtained from 1H-pyrrolo[2,3-b]pyridine-5-carboxylic acid described in Preparation Example R-7 (15 mg, 93 µmol) and C-(5-phenoxy-thiophen-2-yl)-methylamine described in Preparation Example 26 (19 mg, 93 µmol) according to an analogous method to Example A-26. Trifluoroacetic acid salt of the title compound was obtained by reverse phase high performance liquid chromatography (acetonitrile-water mobile phase (containing 0.1% trifluoroacetic acid) was used).
MS m/e (ESI) 350.26(MH$^+$)

Example R-2

6-Amino-1H-pyrrolo[2,3-b]pyridine-5-carboxylic acid (5-phenoxy-thiophen-2-ylmethyl)-amide To a solution of 6-amino-1H-pyrrolo[2,3-b]pyridine-5-carboxylic acid ethyl ester described in Preparation Example R-2 (95 mg, 0.46 mmol) in ethanol (10 mL) was added an aqueous solution of 1N sodium hydroxide (5 mL, 5 mmol), which was then heated for 3 hours in an oil bath at 98° C. After cooling the reaction solution, the reaction solution was concentrated until it reached ⅓ of its volume, neutralized with 1N hydrochloric acid, and further concentrated. The resulting crude product was suspended in N,N-dimethylformamide (5 mL), triethylamine (0.096 mL, 0.69 mmol), benzotriazol-1-yloxytris(dimethylamino)phosphonium hexafluorophosphate (153 mg, 0.35 mmol) and C-(5-phenoxy-thiophen-2-yl)-methylamine described in Preparation Example 26 (71 mg, 0.35 mmol) were added thereto, followed by stirring at room temperature for 15 hours. After the reaction was completed, the reaction solution was poured into brine, and extracted with ethyl acetate. The organic layer was dried over anhydrous magnesium sulfate, then concentrated, the obtained residue was purified by silica gel column chromatography (ethyl acetate:hexane=2:1), and the title compound (31 mg, 0.085 mmol, 18.5%) was obtained.
$^1$H-NMR Spectrum (DMSO-d6) δ(ppm): 4.49 (2H, d, J=5.6 Hz), 6.24 (1H, dd, J=2.0, 3.6 Hz), 6.50 (1H, d, J=4.0 Hz), 6.78 (1H, d, J=4.0 Hz), 6.80 (2H, brs), 7.04 (1H, dd, J=2.0, 3.2 Hz), 7.07-7.16 (3H, m), 7.35-7.41 (2H, m), 8.14 (1H, s), 8.91-8.95 (1H, m), 11.0 (1H, brs).

Example S-1

Pyrrolo[3,2-b]pyridine-1-carboxylic acid 3-phenoxy-benzylamide

1H-Pyrrolo[3,2-b]pyridine described in Preparation Example S-4 (44 mg, 0.37 mmol) was dissolved in N,N-dimethylformamide (3 mL), sodium hydride (18 mg, 0.45 mmol, 60% in oil) was added thereto, followed by stirring at room temperature for 30 minutes. Next, (4-phenoxy-benzyl)-carbamic acid phenyl ester described in Preparation Example 75 (143 mg, 0.45 mmol) was added, and the solution was stirred at room temperature for 2 hours. After the reaction was completed, the reaction solution was poured into brine, which was then extracted with ethyl acetate, and concentrated. The obtained residue was purified by silica gel column chromatography (ethyl acetate:hexane=1:1), and the title compound (11 mg, 0.032 mmol, 8.7%) was obtained.

$^1$H-NMR Spectrum (DMSO-d$_6$) δ(ppm): 4.16 (2H, d, J=6.0 Hz), 6.49 (1H, d, J=3.6 Hz), 6.56 (1H, dd, J=2.0, 8.0 Hz), 6.65-6.73 (3H, m), 6.77-6.85 (2H, m), 6.93 (1H, dd, J=4.4, 8.0 Hz), 7.01-7.06 (3H, m), 7.85 (1H, d, J=3.6 Hz), 8.10-8.17 (2H, m), 8.58 (1H, t, J=6.0 Hz).

Example T-1

6-Amino-thieno[2,3-b]pyridine-5-carboxylic acid (5-phenoxy-thiophen-2-ylmethyl)-amide The title compound (30 mg, 78 μmol, 76%) was obtained as a white solid from 6-amino-thieno[2,3-b]pyridine-5-carboxylic acid described in Preparation Example T-6 (20 mg, 0.10 mmol) and C-(5-phenoxy-thiophen-2-yl)-methylamine described in Preparation Example 26 (21 mg, 0.10 mmol) according to an analogous method to Example A-26.

MS m/e (ESI) 382.35(MH$^+$)

$^1$H-NMR Spectrum (DMSO-d6) δ(ppm): 4.52 (2H, d, J=6.0 Hz), 6.52 (1H, d, J=3.7 Hz), 6.81 (1H, d, J=3.7 Hz), 7.09-7.19 (6H, m), 7.33 (1H, dd, J=1.1, 5.9 Hz), 7.39 (2H, t, J=8.6 Hz), 8.34 (1H, s), 9.21 (1H, m).

Example T-2

Thieno[2,3-b]pyridine-5-carboxylic acid (5-phenoxy-thiophen-2-ylmethyl)-amide

Thieno[2,3-b]pyridine-5carboxylic acid methyl ester described in Preparation Example T-10 (4.0 mg, 21 μmol) and lithium hydroxide monohydrate (0.9 mg, 21 μmol) were dissolved in a mixture solvent of tetrahydrofuran (0.5 mL), methanol (50 μl) and water (50 μl), and the solution was heated under reflux for 1 hour. The reaction solution was cooled to room temperature, then, removal in vacuo was carried out, and thieno[2,3-b]pyridine-5-carboxylic acid was obtained as a lithium salt.

Then, the lithium salt of the resulting thieno[2,3-b]pyridine-5-carboxylic acid, C-(5-phenoxy-thiophen-2-yl)-methylamine described in Preparation Example 26 (4.7 mg, 23 μmol), benzotriazol-1-yl-tris(dimethylamino)phosphonium hexafluorophosphate (14 mg, 32 μmol) and triethylamine (9 μl, 63 μmol) were dissolved in N,N-dimethylformamide (0.5 mL), and the solution was stirred at room temperature for 2 hours. Water and ethyl acetate were added to the reaction solution, the organic layer was partitioned, and washed with brine. The solvent was evaporated in vacuo, the residue was purified by silica gel column chromatography (hexane:ethyl acetate=1:1), and the title compound (3.0 mg, 8.2 μmol, 40%) was obtained as a white solid.

$^1$H-NMR Spectrum (CDCl$_3$) δ(ppm): 4.75 (2H, d, J=5.2 Hz), 6.40 (1H, d, J=3.6 Hz), 6.77 (1H, s), 6.93 (1H, d, J=3.2 Hz), 7.08-7.12 (3H, m), 7.30-7.34 (3H, m), 7.62 (1H, d, J=6.4 Hz), 8.51 (1H, d, J=2.0 Hz), 8.92 (1H, d, J=2.0 Hz).

Example U-1

5-Amino-thieno[3,2-b]pyridine-6carboxylic acid (5-phenoxy-thiophen-2-ylmethyl)-amide The title compound (85 mg, 0.22 mmol, 87%) was obtained as a white solid from 5-amino-thieno[3,2-b]pyridine-6-carboxylic acid described in Preparation Example U-4 (50 mg, 0.26 mmol) and C-(5-phenoxy-thiophen-2-yl)-methylamine described in Preparation Example 26 (53 mg, 0.26 mmol) according to an analogous method to Example A-26.

$^1$H-NMR Spectrum (DMSO-d$_6$) δ(ppm): 4.52 (2H, d, J=5.7 Hz), 6.52 (1H, d, J=3.7 Hz), 6.82 (1H, d, J=3.8 Hz), 6.99 (2H, s), 7.10 (2H, d, J=7.5 Hz), 7.15 (1H, t, J=7.3 Hz), 7.18 (1H, d, J=5.5 Hz), 7.39 (2H, dd, J=7.3, 8.8 Hz), 8.08 (1H, d, J=5.5 Hz), 8.49 (1H, s), 9.17 (1H, t, J=5.5 Hz).

Example U-2

Thieno[3,2-b]pyridine-6-carboxylic acid (5-phenoxy-thiophen-2-yl methyl)-amide

The title compound (7 mg, 19 μmol, 89%) was obtained as a white solid from trifluoromethanesulfonic acid 6-((5-phenoxy-thiophen-2-ylmethyl)-carbamoyl)-thieno[3,2-b]pyridin-5-yl ester described in Preparation Example U+-2 (11 mg, 21 μmol) according to an analogous method to Preparation Example T-10.

$^1$H-NMR Spectrum (DMSO-d$_6$) δ(ppm): 4.57 (2H, d, J=5.7 Hz), 6.50 (1H, d, J=3.7 Hz), 6.81 (1H, d, J=3.7 Hz), 7.08 (2H, d, J=8.1 Hz), 7.12 (1H, t, J=7.5 Hz), 7.36 (2H, t, J=7.7 Hz), 7.62 (1H, d, J=5.7 Hz), 8.31 (1H, d, J=5.5 Hz), 8.90 (1H, s), 9.08 (1H, d, J=2.0 Hz), 9.32-9.38 (1H, m).

Example V-1

1H-Indole-5-carboxylic acid 3-phenoxybenzylamide

The title compound was obtained from 1H-indole-5-carboxylic acid and 4-phenoxybenzylamine described in Preparation Example 3 according to an analogous method to Example H-1.

MS m/e(ESI) 343.15(MH$^+$)

Example W-1

(4-Benzyloxy-phenyl)-quinolin-6-ylmethyl-amine

To a solution of lithium aluminum hydride (52 mg, 1.37 mmol) in tetrahydrofuran (10 mL) was added a solution of quinoline-6-carboxylic acid (4-benzyloxyphenyl)-amide described in Preparation Example Z+-2 (194 mg, 19%) in tetrahydrofuran, and the solution was stirred under reflux for 3 hours. The reaction solution was allowed to room temperature, an aqueous solution of saturated ammonium chloride was added thereto, the solution was extracted with ethyl acetate and dried over anhydrous magnesium sulfate. The solvent was evaporated, the residue was purified by NH silica gel column chromatography (hexane:ethyl acetate), and the title compound (62 mg, 33%) was obtained as a pale yellow solid.

$^1$H-NMR Spectrum (CDCl$_3$) δ(ppm): 3.97 (1H, brs), 4.49 (2H, s), 4.98 (2H, s), 6.61-6.64 (2H, m), 6.84-6.86 (2H, m), 7.30-7.42 (6H, m), 7.73 (1H, dd, J=1.6, 8.4 Hz), 7.80 (1H, s), 8.09 (1H, d, J=8.8 Hz), 8.12 (1H, d, J=8.4 Hz), 8.89-8.90 (1H, m).

Example W-2

(4-Benzyloxy-benzyl)-quinolin-6-yl-amine

To a solution of lithium aluminum hydride (58 mg, 1.54 mmol) in tetrahydrofuran (10 mL) was added a solution of 4-benzyloxy-N-quinolin-6-yl-benzamide described in Preparation Example Z+-3 (218 mg, 0.615 mmol) in tetrahydrofuran (1 mL), and the solution was stirred under reflux for 7 hours. The reaction solution was allowed to room temperature, an aqueous solution of saturated ammonium chloride was added, the solution was extracted with ethyl acetate and dried over anhydrous magnesium sulfate. The solvent was evaporated, the residue was purified by NH silica gel column chromatography (hexane: ethyl acetate), and the title compound (147 mg, 70%) was obtained as a yellow solid.

$^1$H-NMR Spectrum (CDCl$_3$) δ(ppm): 4.27 (1H, m), 4.36 (2H, d, J=4.8 Hz), 5.07 (2H, s), 6.73 (1H, d, J=2.4 Hz), 6.98 (2H, d, J=8.8 Hz), 7.12 (1H, dd, J=2.8, 9.2 Hz), 7.24-7.27 (1H, m), 7.31-7.45 (7H, m), 7.87-7.91 (2H, m), 8.61-8.62 (1H, m).

Example W-3

2-(3-Benzyloxy-phenyl)-1-quinolin-6-yl-ethanone

A mixture of 1-quinolin-6-yl-ethanone described in Preparation Example 131 (171 mg, 1 mmol), 1-benzyloxy-3-bromo-benzene (289 mg, 1 mmol), bis(dibenzylideneacetone)palladium (3 mg, 0.0052 mmol), 1,1'-bis(diphenylphosphino)ferrocene (5 mg, 0.009 mmol), potassium tert-butoxide (236 mg, 2.1 mmol) and tetrahydrofuran (15 mL) were stirred under nitrogen atmosphere for 7 hours at 70° C. Silica gel (80 mL) was added to the reaction solution at room temperature, filtration was carried out by silica gel column chromatography (hexane:ethyl acetate=4:6), the filtrate was concentrated in vacuo, and a residue of yellow oil (0.191 g) was obtained. This residue was purified by thin layer silica gel chromatography (hexane:ethyl acetate=1:10), and a yellow oily residue (98 mg) was obtained. In addition, the residue was purified by NH silica gel column chromatography (hexane:ethyl acetate=85:15), and the title compound (50 mg, 0.14 mmol, 14%) was obtained as a pale yellow oil.

$^1$H-NMR Spectrum (Acetone-d6) δ(ppm): 4.51 (2H, s), 5.10 (2H, s), 6.89-6.91 (1H, m), 6.96-6.98 (1H, m), 7.07 (1H, m), 7.25 (1H, t, J=4.4 Hz), 7.29-7.33 (1H, m), 7.35-7.39 (2H, m), 7.44-7.47 (2H, m), 7.61 (1H, dd, J=8.4, 4.4 Hz), 8.11 (1H, d, J=8.8 Hz), 8.31 (1H, dd, J=8.8, 2.0 Hz), 8.50-8.53 (1H, m), 8.81 (1H, d, J=2.0 Hz), 9.02 (1H, m).

Example W-4

2-(3-Phenoxy-phenyl)-1-quinolin-6yl-ethanone

According to an analogous method to Example W-3, 1-quinolin-6-yl-ethanone described in Preparation Example 131 (171 mg, 1 mmol), 1-phenoxy-3-bromobenzene (274 mg, 1.1 mmol), bis(dibenzylideneacetone)palladium (10 mg, 0.0187 mmol), 1,1'-bis(diphenylphosphino)ferrocene (12.5 mg, 0.0225 mmol), potassium tert-butoxide (236 mg, 2.1 mmol) and tetrahydrofuran (15 mL) were stirred at 70° C. for 6 hours under nitrogen atmosphere, and the title compound (64 mg, 0.189 mmol, 19%) was obtained as a pale yellow oily substance.

$^1$H-NMR Spectrum (Acetone-d$_6$) δ(ppm): 4.56 (2H, s), 6.88-6.91 (1H, m), 6.98-7.00 (2H, m), 7.06-7.16 (3H, m), 7.32-7.37 (3H, m), 7.62 (1H, dd, J=8.4, 4.4 Hz), 8.12 (1H, d, J=8.8 Hz), 8.31 (1H, dd, J=8.8, 2.0 Hz), 8.49-8.52 (1H, m), 8.81 (1H, d, J=2.0 Hz), 9.02 (1H, m).

Example W-5

6-(4-Benzyloxy-benzyloxy)-quinoline

To a solution of quinoline-6-ol (37 mg, 0.25 mmol), 1-benzyloxy-4-chloromethyl-benzene (70 mg, 0.30 mmol) in dimethylsulfoxide (2.5 mL) was added potassium tert-butoxide (43 mg, 0.38 mmol) under nitrogen atmosphere, and the solution was stirred for 13 hours at room temperature. This reaction solution was purified by thin layer silica gel chromatography (hexane:ethyl acetate=1:1), and the title compound (74 mg, 0.217 mmol, 86%) was obtained as a pale yellow solid.

$^1$H-NMR Spectrum (Acetone-d$_6$) δ(ppm): 5.16 (2H, s), 5.19 (2H, s), 7.05-7.09 (2H, m), 7.31-7.35 (1H, m), 7.38-7.46 (5H, m), 7.46-7.51 (4H, m), 7.95 (1H, d, J=8.8 Hz), 8.19 (1H, dd, J=8.4, 0.8 Hz), 8.74 (1H, dd, J=4.0, 1.6 Hz).

Example W-6

6-(3-Phenoxy-benzylsulfanyl)-quinoline

To a solution of (3-phenoxy-phenyl)-methanol (2.0 g, 10 mmol) in tetrahydrofuran (50 ml) was added potassium tert-butoxide (1.35 g, 12 mmol) under nitrogen atmosphere and an ice-cold stirring, then, 4-methyl-benzenesulfonyl chloride (2.48 g,13 mmol) was added, and the solution was stirred at room temperature for 21 hours. An aqueous solution of saturated ammonium chloride was added, the solution was extracted with ethyl acetate (200 ml), washed with brine (150 ml), dried over anhydrous magnesium sulfate, then, the solvent was evaporated, and a residue of pale yellow oil (3.97 g) was obtained. This residue was purified by silica gel column chromatography (hexane:ethyl acetate=4:1), and toluene-4-sulfonic acid 3-phenoxybenzyl ester (2.93 g, 8.27 mmol, 82%) was obtained as a white solid.

To a solution of dithiocarbonic acid O-ethyl ester S-quinolin-6-yl ester described in Preparation Example W-1 (50 mg, 0.201 mmol), toluene-4-sulfonic acid 3-phenoxybenzyl ester (110 mg, 0.313 mmol) and methanol (1 ml) in tetrahydrofuran (5 ml) was added potassium tert-butoxide (135 mg, 1.20 mmol) under nitrogen atmosphere, which was then stirred at room temperature for 24 hours. This reaction solution was purified by thin layer silica gel chromatography (hexane: ethyl acetate=1:1), and the title compound (39 mg, 0.114 mmol, 57%) was obtained as a yellow oil.

$^1$H-NMR Spectrum (Acetone-d6) δ(ppm):4.36 (2H, s), 6.85-6.90 (3H, m), 7.02-7.03 (1H, m), 7.07-7.11 (1H, m), 7.20-7.22 (1H, m), 7.27-7.34 (3H, m), 7.49 (1H, dd, J=8.4, 4.0 Hz), 7.69 (1H, dd, J=8.8, 2.0 Hz), 7.84-7.85 (1H, m), 7.94 (1H, d, J=8.8 Hz), 8.18-8.20 (1H, m), 8.84-8.85 (1H, m).

Example X-1

(4-tert-Butyl-benzyl)-quinazolin-4-yl-amine

To a solution of 4-chloro-quinazoline described in Preparation Example X-1 (8 mg, 0.049 mmol) in 1-methyl-2-pyrrolidone (0.5 mL) were added 4-tert-butyl-benzylamine (10 μl, 0.059 mmol) and N,N-diisopropylethylamine (17 μl, 0.098 mmol), and the solution was stirred for 5 hours at 160° C. The reaction mixture was directly purified by reverse phase high performance liquid chromatography (acetonitrile-water mobile phase (containing 0.1% trifluoroacetic acid) was used), and the title compound (16.5 mg, 0.041 mmol, 72%) was obtained as a trifluoroacetic acid salt.

MS m/e(ESI) 292.20(MH$^+$)

Example X-2

(4-Benzyloxy-benzyl)-quinazolin-4-yl-amine

The title compound (9.63 mg, 0.021 mmol, 38%) was obtained as a trifluoroacetic acid salt from 4-chloro-quinazoline described in Preparation Example X-1 (9 mg, 0.055 mmol) and 4-benzyloxy-benzylamine described in Preparation Example 1 (12 mg, 0.055 mmol) according to an analogous method to Example X-1.

MS m/e(ESI) 342.27(MH$^+$)

Example Y-1

N*4*-(4-Benzyloxy-benzyl)-pyrido[2,3-d]pyrimidine-2,4-diamine

To a mixture of 2-amino-N-(4-benzyloxy-benzyl)-thionicotinamide described in Example A-22 (30 mg, 0.083 mmol) and toluene (1 mL) was added benzyl bromide (0.044 mL, 0.37 mmol), and the solution was refluxed for 3 hours. After cooling, the solvent was evaporated in vacuo, and the residue was washed with diethyl ether twice. A mixture of a portion (13 mg) of the resulting crude product (33 mg), cyanamide (20 mg, 0.48 mmol) and N-methylpyrrolidinone (1 mL) was stirred for 2 hours at 120° C. After cooling, the reaction solution was directly purified by reverse phase high performance liquid chromatography (acetonitrile-water mobile phase (containing 0.1% trifluoroacetic acid) was used), and ditrifluoroacetic acid salt of the title compound (0.75 mg, 0.0013 mmol, 4.2%) was obtained.

MS m/e (ESI) 358.2 (MH$^+$)

Example Z-1

(4-Butyl-3-methyl-phenyl)-quinolin-6-yl-metanone

To a solution of (4butyl-3-methyl-phenyl)-quinoline-6-yl-methanol described in Preparation Example Z+-1 (152 mg, 0.50 mmol) in chloroform (1.0 mL) was added active manganese dioxide (510 mg, 5.0 mmol), and the solution was stirred at room temperature for 5 hours. Manganese dioxide was removed by filtering through Celite pad, the filtrate was concentrated, the residue was purified by silica gel column chromatography (hexane:ethyl acetate), and the title compound (56 mg, 37%) was obtained as a pale yellow oil.

$^1$H-NMR Spectrum (CDCl$_3$) δ(ppm): 0.98 (3H, t, J=7.2 Hz), 1.40-1.49 (2H, m), 1.58-1.66 (2H, m), 2.39 (3H, s), 2.70 (2H, t, J=8.0 Hz), 7.26-7.28 (1H, m), 7.48-7.51 (1H, m), 7.60-7.62 (1H, m), 7.67 (1H, s), 8.13-8.16 (1H, m), 8.20-8.22 (1H, m), 8.25-8.27 (2H, m), 9.03-9.04 (1H, m).

Example Z-2

Quinoline-6-carboxylic acid (3-benzyloxyphenyl)-amide

Thionyl chloride (2 mL) was added to 6-quinolinecarboxylic acid (100 mg, 0.577 mmol), and the solution was stirred for 2 hours under reflux. Then, the solution was allowed to cool to room temperature, and excess thionyl chloride was evaporated in vacuo. The obtained residue was dissolved in N,N-dimethylformamide (2 mL), 3-benzyloxyaniline (115 mg, 0.577 mmol), triethylamine (0.12 mL, 0.866 mmol) and dimethylaminopyridine (1 mg) were added, and the solution was stirred overnight at room temperature. Ethyl acetate and water were added to the reaction solution, which was then partitioned, the organic layer was washed with water and dried over anhydrous magnesium sulfate. The solvent was evaporated, the residue was purified by silica gel column chromatography (hexane:ethyl acetate=1:1), and the title compound (53 mg, 26%) was obtained as a white solid.

$^1$H-NMR Spectrum (CDCl$_3$) δ(ppm): 5.12 (2H, s), 6.80-6.83 (1H, m), 7.16-7.18 (1H, m), 7.27-7.35 (2H, m), 7.38-7.42 (2H, m), 7.45-7.47 (2H, m), 7.49-7.52 (1H, m), 7.58-7.59 (1H, m), 8.03 (1H, s), 8.13 (1H, dd, J=2.0, 8.8 Hz), 8.21 (1H, d, J=8.8 Hz), 8.25-8.28 (1H, m), 8.38 (1H, d, J=2.0 Hz), 9.01-9.03 (1H, m).

Example Z-3

3-Phenoxy-N-quinolin-6-yl-benzamide

To a solution of 6-aminoquinoline (250 mg, 1.04 mmol) in N,N-dimethylformamide (15 mL) were added 3-phenoxybenzoic acid (371 mg, 1.73 mmol), O-benzotriazol-1-yl-N,N,N',N'-tetramethyluronium hexafluorophosphate (722 mg, 1.90 mmol) and triethylamine (603 µl, 4.33 mmol), and the solution was stirred for 2 days at room temperature. Water was added to the reaction mixture, which was extracted with ethyl acetate, the organic layer was washed with water, an aqueous solution of saturated sodium bicarbonate and brine, dried over anhydrous magnesium sulfate, and then, concentrated in vacuo. The obtained residue was purified by silica gel column chromatography (hexane-ethyl acetate), and the title compound (328 mg, 0.964 mmol, 93%) was obtained.

$^1$H-NMR Spectrum (DMSO-d$_6$) δ(ppm): 7.08 (2H, d, J=8.4 Hz), 7.18 (1H, t, J=7.6 Hz), 7.24 (1H, d, J=8.0 Hz), 7.43 (2H, dd, J=7.6, 8.4 Hz), 7.48 (1H, dd, J=4.0, 8.4 Hz), 7.56 (1H, dd, J=7.6, 8.0 Hz), 7.63 (1H, s), 7.79 (1H, d, J=7.6 Hz), 7.94-8.15 (2H, m), 8.29 (1H, d, J=8.0 Hz), 8.50 (1H, s), 8.80 (1H, dd, J=2.0, 4.0 Hz), 10.6 (1H, s).

Example Z-4

1H-Indole-5-carboxylic acid (4-benzyloxy-phenyl)amide

The title compound was obtained from 1H-indole-5-carboxylic acid and 4-benzyloxy-phenylamine hydrochloride according to an analogous method to Example H-1

MS m/e(ESI) 343.30(MH$^+$)

The structural formulae of the compounds obtained in the above preparation examples and examples are shown in the following Table 1 to Table 51.

TABLE 1

Preparation Example A-1

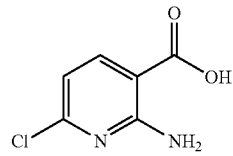

Preparation Example A-2

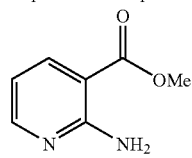

TABLE 1-continued

Preparation Example A-3
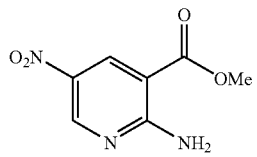

Preparation Example A-4
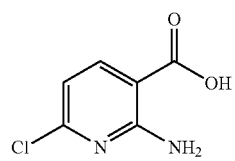

Preparation Example A-5
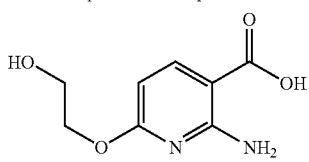

Preparation Example A-6
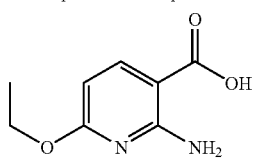

Preparation Example A-7
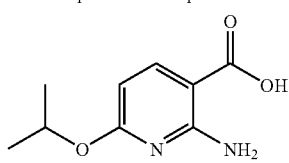

Preparation Example A-8
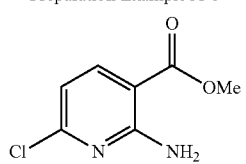

Preparation Example A-9
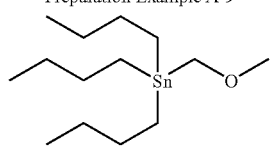

Preparation Example A-10
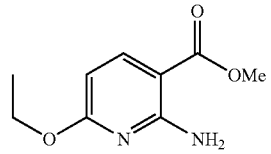

TABLE 1-continued

Preparation Example A-11
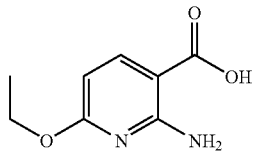

Preparation Example A-12
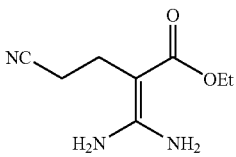

Preparation Example A-13
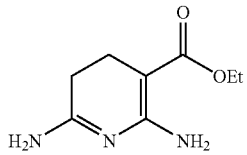

Preparation Example A-14
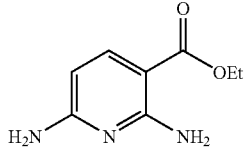

Preparation Example A-15
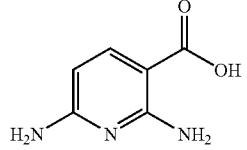

Preparation Example A-16
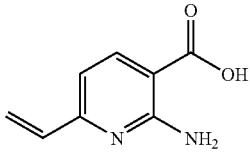

Preparation Example A-17
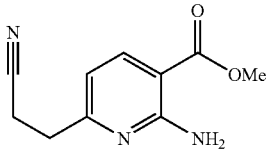

Preparation Example A-18
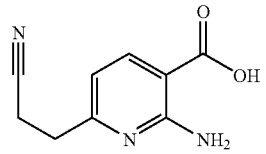

TABLE 2
Preparation Example A-19
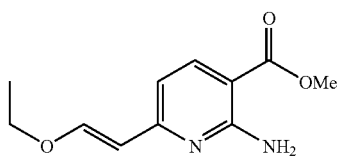
Preparation Example A-20
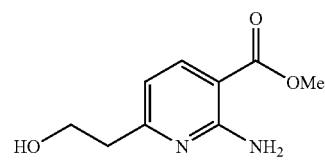
Preparation Example A-21
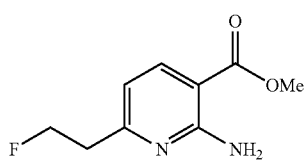
Preparation Example A-22
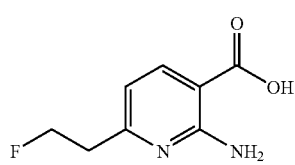
Preparation Example A-23
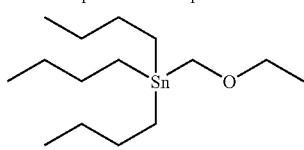
Preparation Example A-24
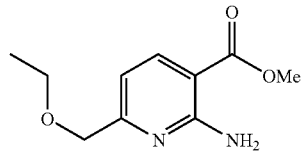
TABLE 2-continued
Preparation Example A-25
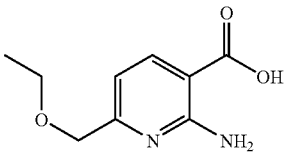
Preparation Example A-26
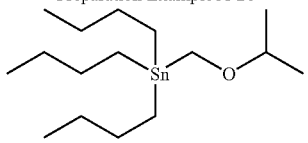
Preparation Example A-27
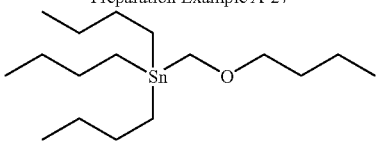
Preparation Example A-28
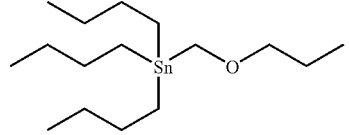
Preparation Example AA-1
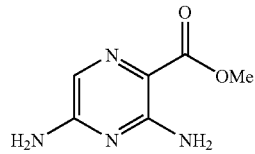
Preparation Example AA-2
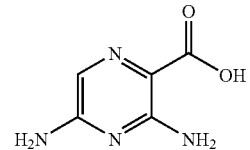
Preparation Example B-1
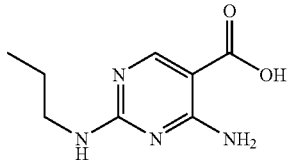
TABLE 3
Preparation Example A+-1
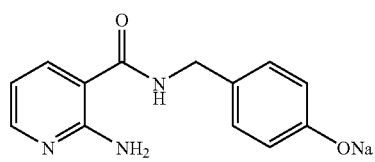

TABLE 3-continued
Preparation Example A+-2
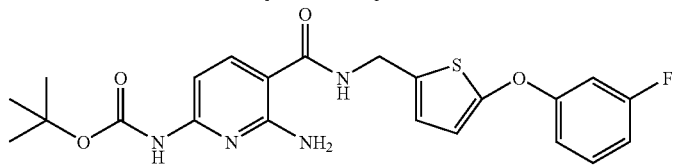
Preparation Example A+-3
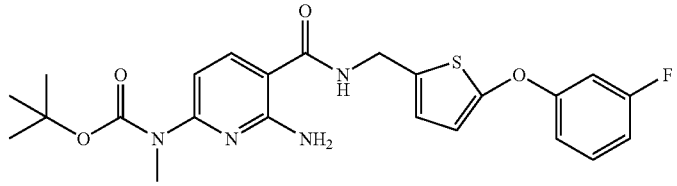
Preparation Example A+-4
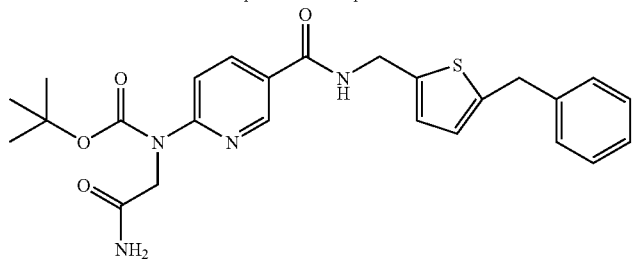
Preparation Example A+-5
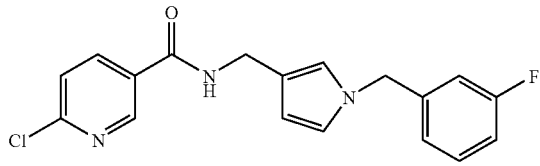
Preparation Example A+-6
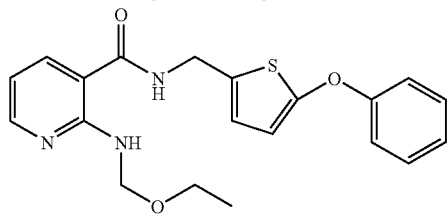
Preparation Example A+-7
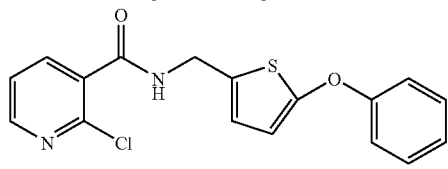
Preparation Example A+-8
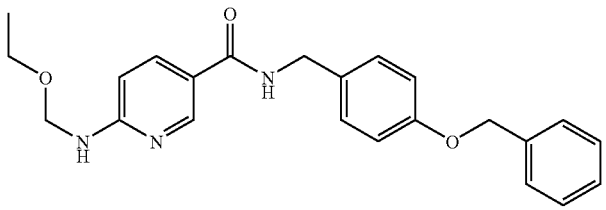

TABLE 3-continued
Preparation Example A+-9
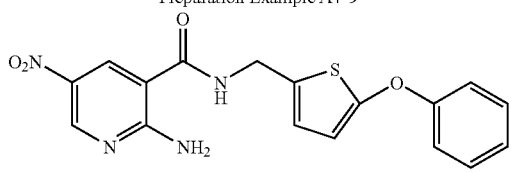
Preparation Example A+-10
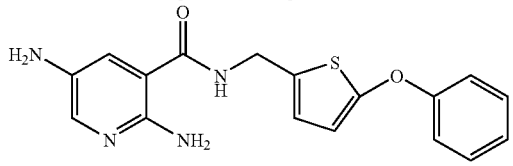
Preparation Example A+-11
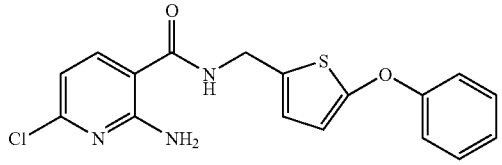
Preparation Example A+-12
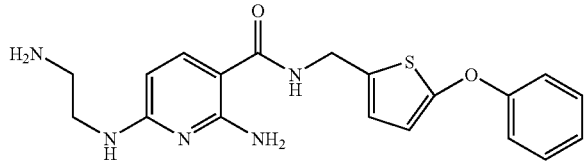
TABLE 4
Preparation Example A+-13
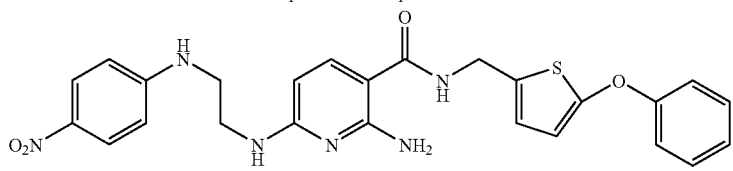
Preparation Example A+-14
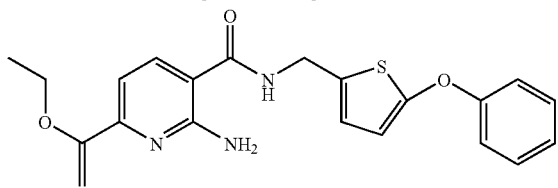
Preparation Example A+-15
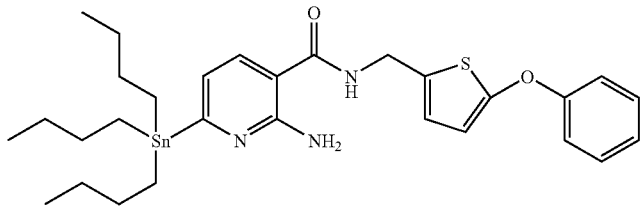

TABLE 4-continued
Preparation Example A+-16
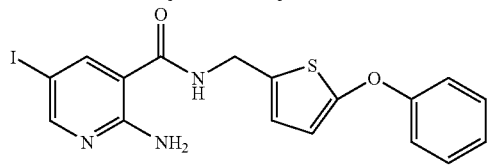
Preparation Example A+-17
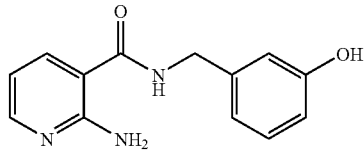
Preparation Example A+-18
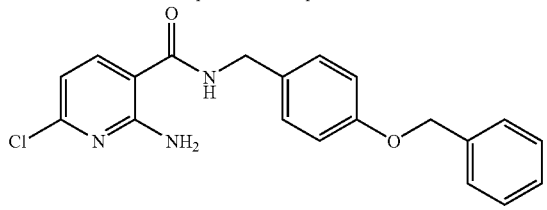
Preparation Example A+-19
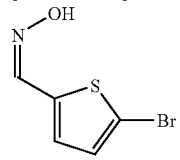
Preparation Example A+-20
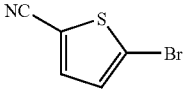
Preparation Example A+-21
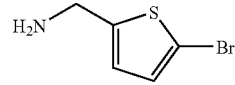
Preparation Example A+-22
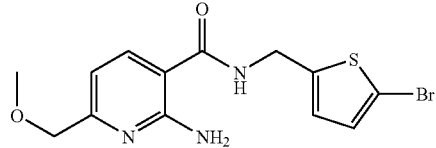
Preparation Example A+-23
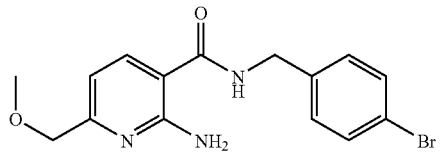
Preparation Example A+-24
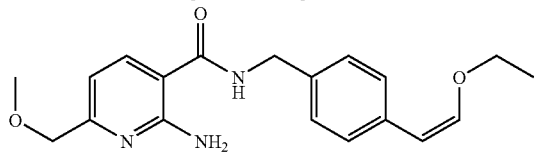

TABLE 4-continued
Preparation Example A+-25
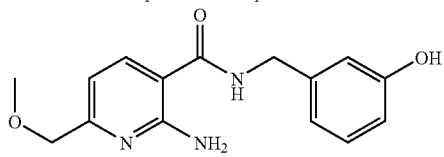
Preparation Example A+-26
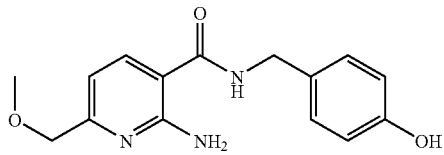
TABLE 5
Preparation Example C-1
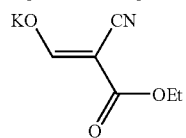
Preparation Example C-2
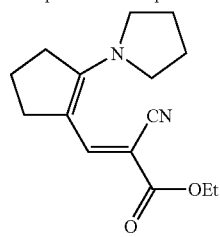
Preparation Example C-3
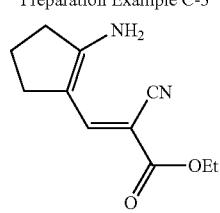
Preparation Example C-4
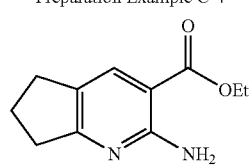
Preparation Example C-5
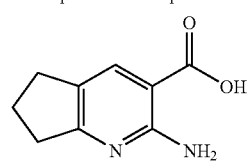
TABLE 5-continued
Preparation Example D-1
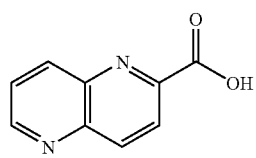
Preparation Example E-1
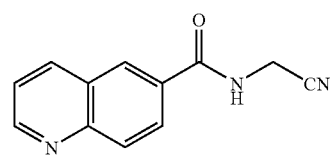
Preparation Example F-1
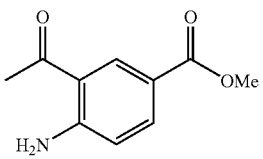
Preparation Example F-2
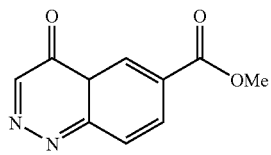
Preparation Example F-3
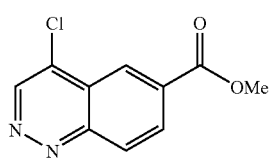

TABLE 5-continued

Preparation Example F-4
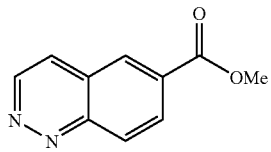

Preparation Example G-1
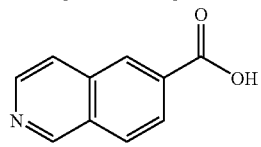

Preparation Example H-1
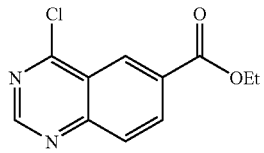

Preparation Example H-2
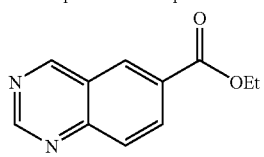

Preparation Example H-3
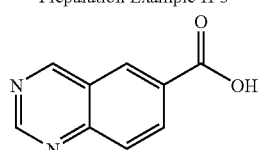

Preparation Example I-1
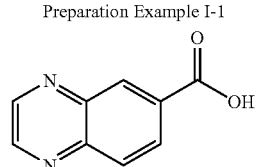

TABLE 6

Preparation Example E+-1
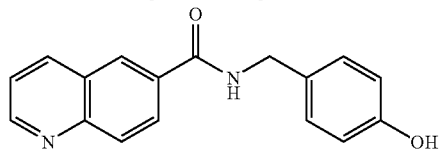

Preparation Example E+-2
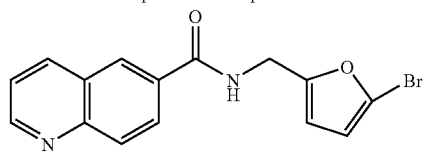

TABLE 6-continued

Preparation Example E+-3
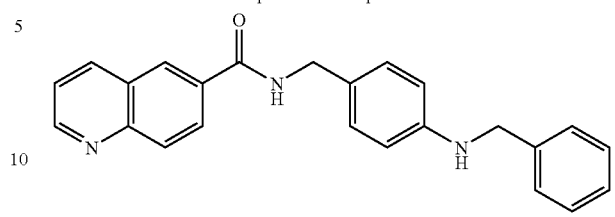

Preparation Example E+-4
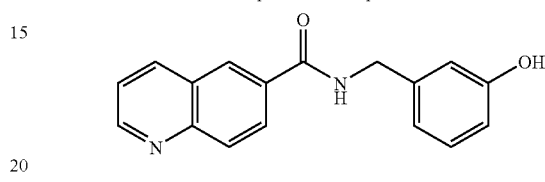

Preparation Example E+-5
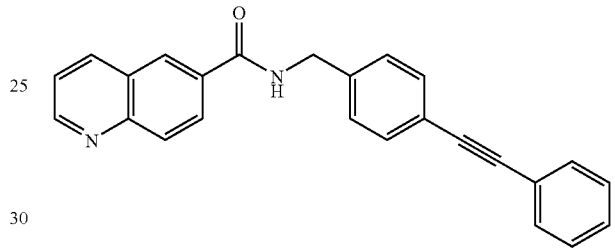

Preparation Example E+-6
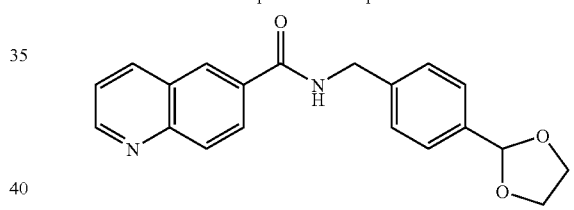

Preparation Example E+-7
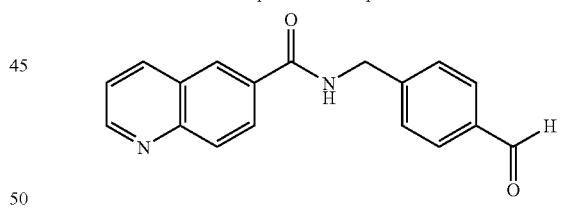

Preparation Example E+-8
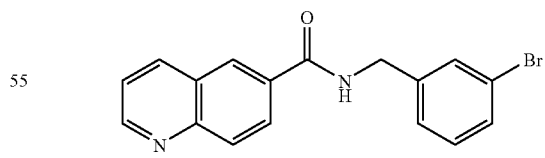

Preparation Example E+-9
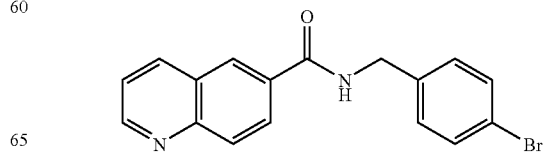

TABLE 6-continued

Preparation Example E+-10
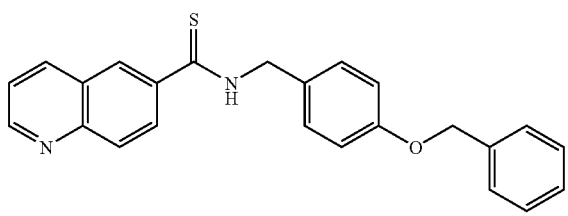

Preparation Example Q+-1
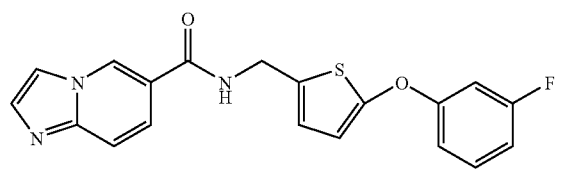

TABLE 7

Preparation Example J-1
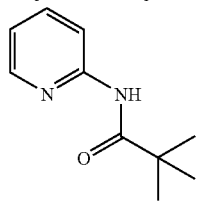

Preparation Example J-2
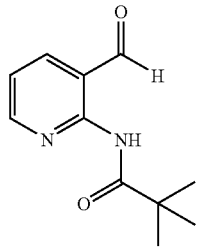

Preparation Example J-3
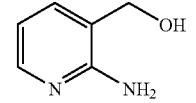

Preparation Example J-4
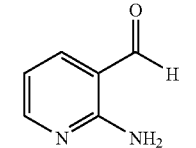

Preparation Example J-5
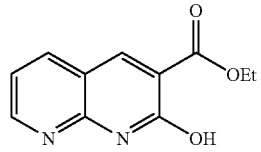

TABLE 7-continued

Preparation Example J-6
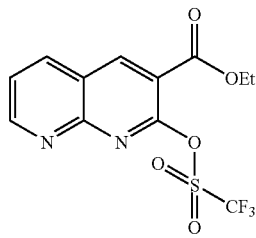

Preparation Example J-7
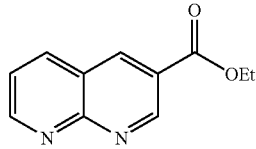

Preparation Example K-1
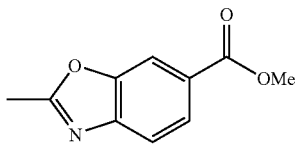

Preparation Example K-2
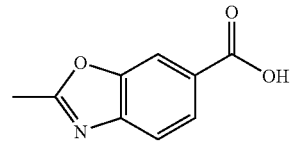

Preparation Example O-1
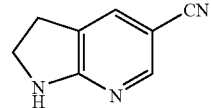

Preparation Example O-2
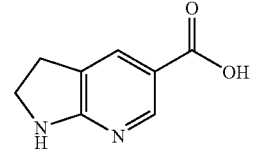

Preparation Example P-1
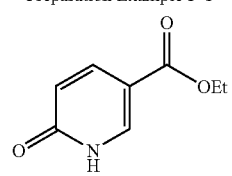

Preparation Example P-2
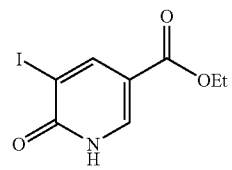

TABLE 7-continued

Preparation Example P-3
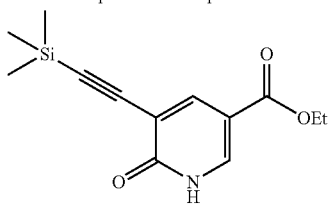

Preparation Example P-4
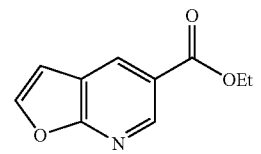

Preparation Example S-1
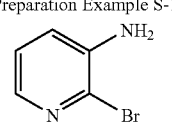

Preparation Example S-2
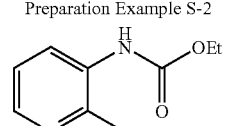

Preparation Example S-3
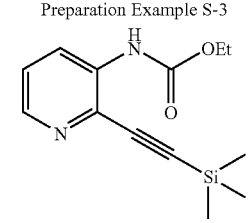

Preparation Example S-4
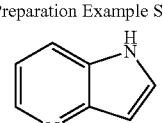

TABLE 8

Preparation Example R-1
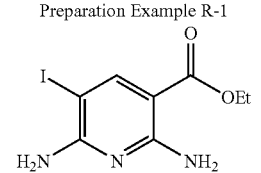

Preparation Example R-2
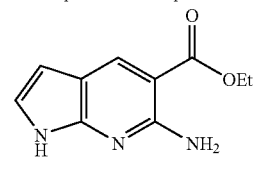

TABLE 8-continued

Preparation Example R-3
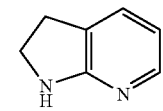

Preparation Example R-4
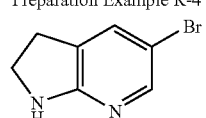

Preparation Example R-5
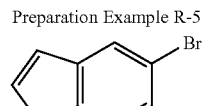

Preparation Example R-6
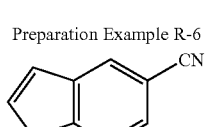

Preparation Example R-7
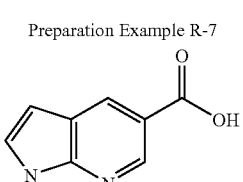

Preparation Example T-1
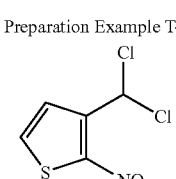

Preparation Example T-2
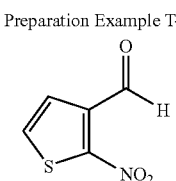

Preparation Example T-3
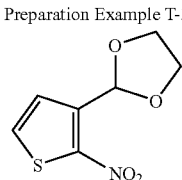

Preparation Example T-4
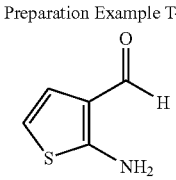

TABLE 8-continued

Preparation Example T-5
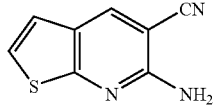

Preparation Example T-6
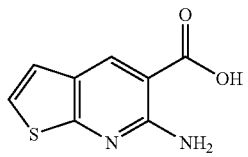

Preparation Example T-7
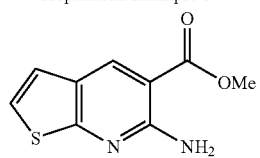

Preparation Example T-8
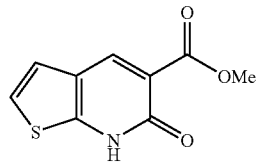

Preparation Example T-9
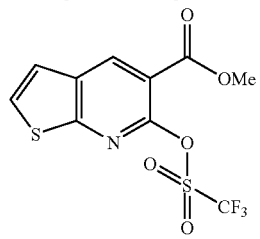

Preparation Example T-10
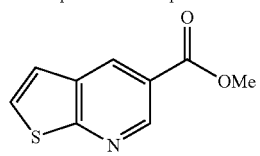

TABLE 9

Preparation Example U-1
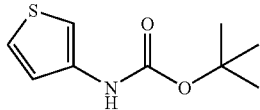

Preparation Example U-2
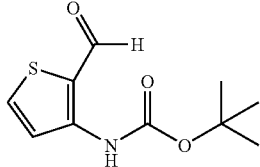

TABLE 9-continued

Preparation Example U-3
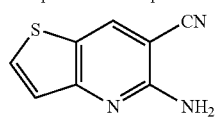

Preparation Example U-4
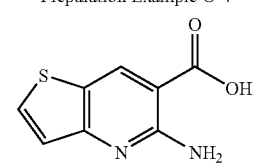

Preparation Example W-1
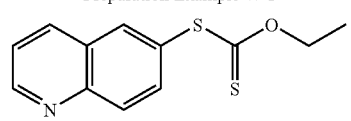

Preparation Example X-1
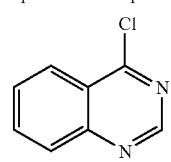

Preparation Example Z-1
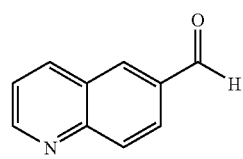

Preparation Example Z-2
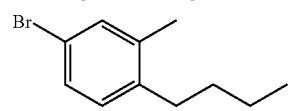

Preparation Example U+-1
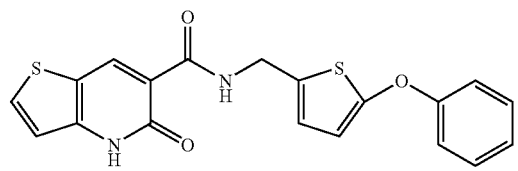

Preparation Example U+-2
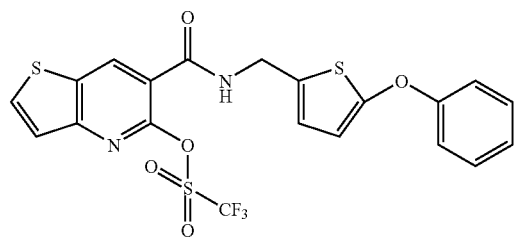

TABLE 9-continued

Preparation Example Z+-1
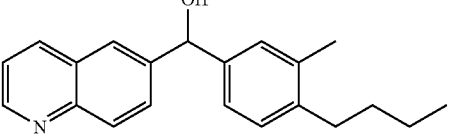

Preparation Example Z+-2
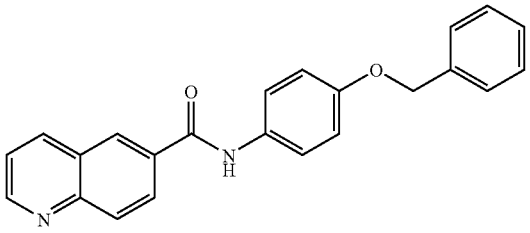

Preparation Example Z+-3
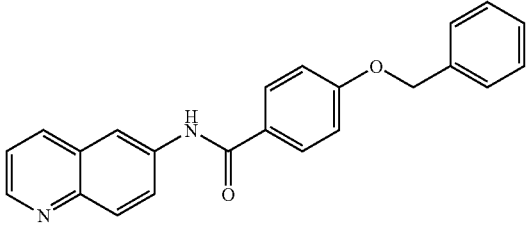

TABLE 10

Preparation Example 1
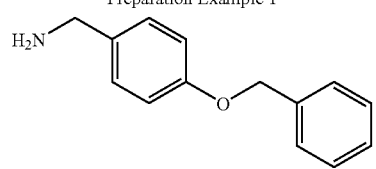

Preparation Example 2
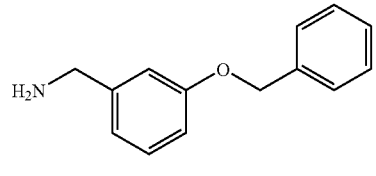

Preparation Example 3
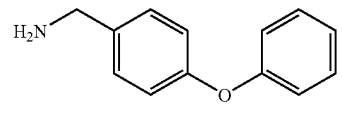

Preparation Example 4
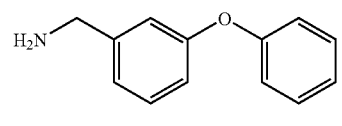

TABLE 10-continued

Preparation Example 5
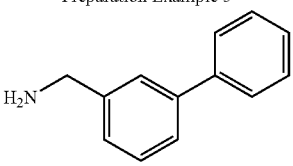

Preparation Example 6
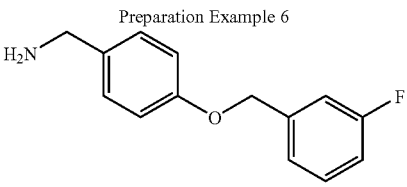

Preparation Example 7
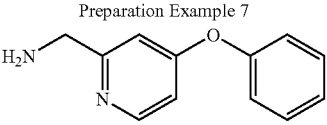

Preparation Example 8
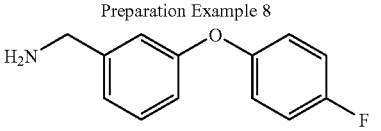

Preparation Example 9
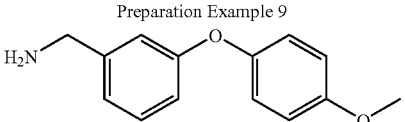

Preparation Example 10
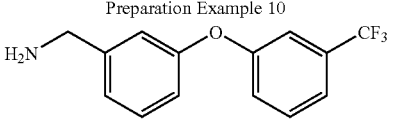

Preparation Example 11
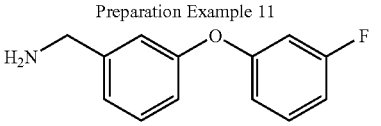

Preparation Example 12
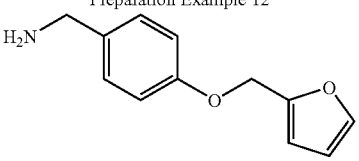

Preparation Example 13
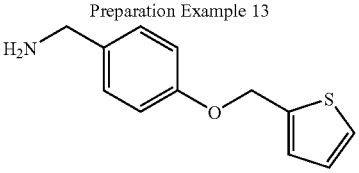

Preparation Example 14
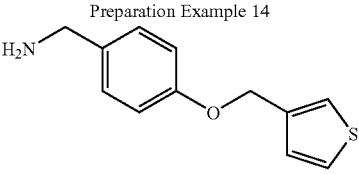

TABLE 10-continued

Preparation Example 15: H2N-CH2-C6H4-O-CH(CH3)-C6H5

Preparation Example 16: H2N-CH2-(pyridin-2-yl)-O-C6H5 (6-phenoxypyridin-2-yl)methanamine Preparation Example 17: H2N-CH2-(thiophen-2-yl)-O-C6H4-3-Br Preparation Example 18: H2N-CH2-(thiophen-2-yl)-O-C6H4-3-O-CH2-C6H5

TABLE 11

Preparation Example 19: H2N-CH2-C6H4-NH-CH2-C6H5

Preparation Example 20: H2N-CH2-C6H4-NH-C6H5

Preparation Example 21: H2N-CH2-C6H4-CH2-NH-C6H5

Preparation Example 22: NC-(thiophen-2-yl)-O-C6H4-3-F

Preparation Example 23: H2N-CH2-(thiophen-2-yl)-O-C6H4-3-F

TABLE 11-continued

Preparation Example 24: H2N-CH2-(thiophen-2-yl)-O-C6H5

Preparation Example 25: NC-(thiophen-2-yl)-O-C6H5

Preparation Example 26: H2N-CH2-(thiophen-2-yl)-O-C6H5

Preparation Example 27: NC-(thiophen-2-yl)-O-C6H4-4-F

Preparation Example 28: H2N-CH2-(thiophen-2-yl)-O-C6H4-4-F

Preparation Example 29: NC-(thiophen-2-yl)-O-C6H4-3-CH3

Preparation Example 30: H2N-CH2-(thiophen-2-yl)-O-C6H4-3-CH3

Preparation Example 31: NC-(thiophen-2-yl)-O-C6H4-4-CH3

Preparation Example 32: H2N-CH2-(thiophen-2-yl)-O-C6H4-4-CH3

Preparation Example 33: (1,3-dioxolan-2-yl)-(thiophen-2-yl)-O-C6H4-3-F

TABLE 11-continued

Preparation Example 34

Preparation Example 35

Preparation Example 36

TABLE 12

Preparation Example 37

Preparation Example 38

Preparation Example 39

Preparation Example 40

TABLE 12-continued

Preparation Example 41

Preparation Example 42

Preparation Example 43

Preparation Example 44

Preparation Example 45

Preparation Example 46

Preparation Example 47

Preparation Example 48

Preparation Example 49

TABLE 12-continued

Preparation Example 50: 5-(3-fluorophenoxy)furan-2-carbaldehyde

Preparation Example 51: (5-(3-fluorophenoxy)furan-2-yl)methanol

Preparation Example 52: 2-(5-(3-fluorobenzyl)thiophen-2-yl)-1,3-dioxolane

Preparation Example 53: 5-(3-fluorobenzyl)thiophene-2-carbaldehyde

Preparation Example 54: 2-(5-(3-chlorobenzyl)furan-2-yl)-1,3-dioxolane

TABLE 13

Preparation Example 55: 5-(3-chlorobenzyl)furan-2-carbaldehyde

Preparation Example 56: (5-(3-chlorobenzyl)furan-2-yl)methanamine

Preparation Example 57: 1-benzyl-1H-pyrrole-3-carbaldehyde

TABLE 13-continued

Preparation Example 58: 1-(3-fluorobenzyl)-1H-pyrrole-3-carbaldehyde

Preparation Example 59: (1-(3-fluorobenzyl)-1H-pyrrol-3-yl)methanamine

Preparation Example 60: 1-(benzo[d][1,3]dioxol-5-ylmethyl)-1H-pyrrole-3-carbaldehyde Preparation Example 61: (1-(benzo[d][1,3]dioxol-5-ylmethyl)-1H-pyrrol-3-yl)methanamine Preparation Example 62: 1-phenethyl-1H-pyrrole-3-carbaldehyde Preparation Example 63: 1-(benzyloxy)-1H-pyrrole-3-carbaldehyde Preparation Example 64: (1-(benzyloxy)-1H-pyrrol-3-yl)methanol Preparation Example 65: (5-(1,3-dioxolan-2-yl)thiophen-2-yl)(5-methylthiophen-2-yl)methanol Preparation Example 66: 5-((5-methylthiophen-2-yl)methyl)thiophene-2-carbaldehyde TABLE 13-continued Preparation Example 67
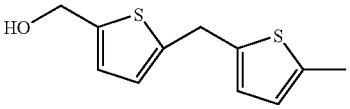

Preparation Example 68
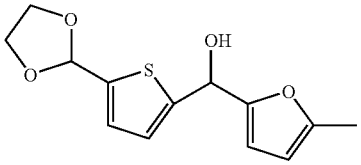

Preparation Example 69
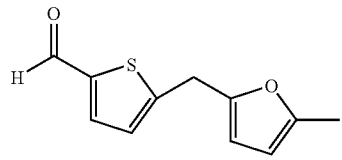

Preparation Example 70
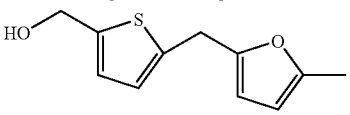

Preparation Example 71
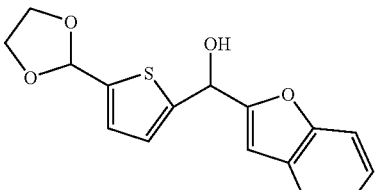

Preparation Example 72
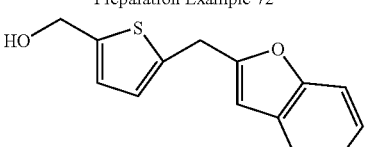

TABLE 14

Preparation Example 73
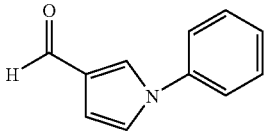

Preparation Example 74
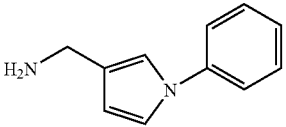

TABLE 14-continued

Preparation Example 75
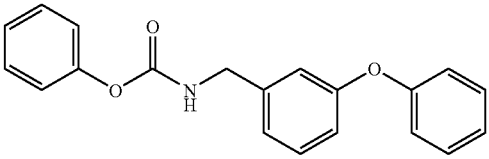

Preparation Example 76
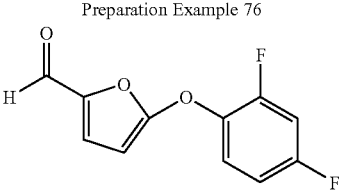

Preparation Example 77
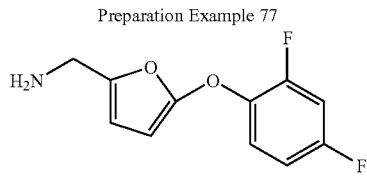

Preparation Example 78
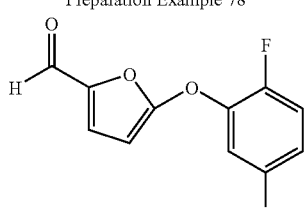

Preparation Example 79
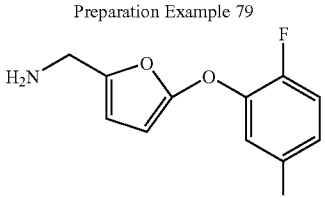

Preparation Example 80
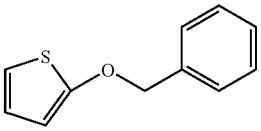

Preparation Example 81
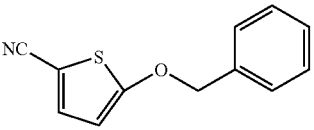

Preparation Example 82
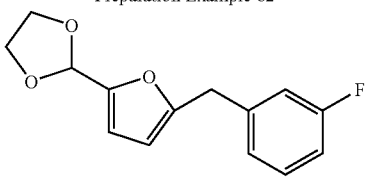

TABLE 14-continued
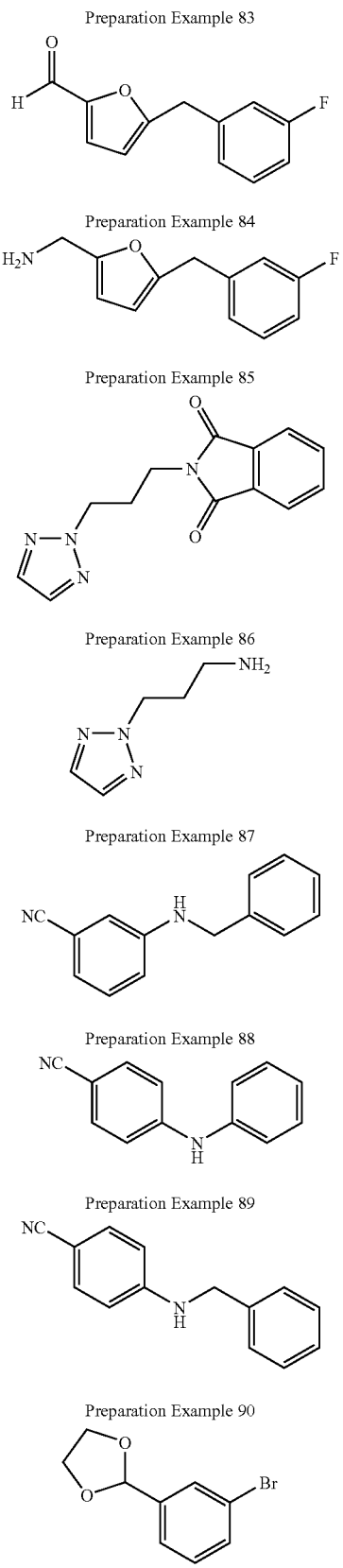
TABLE 15
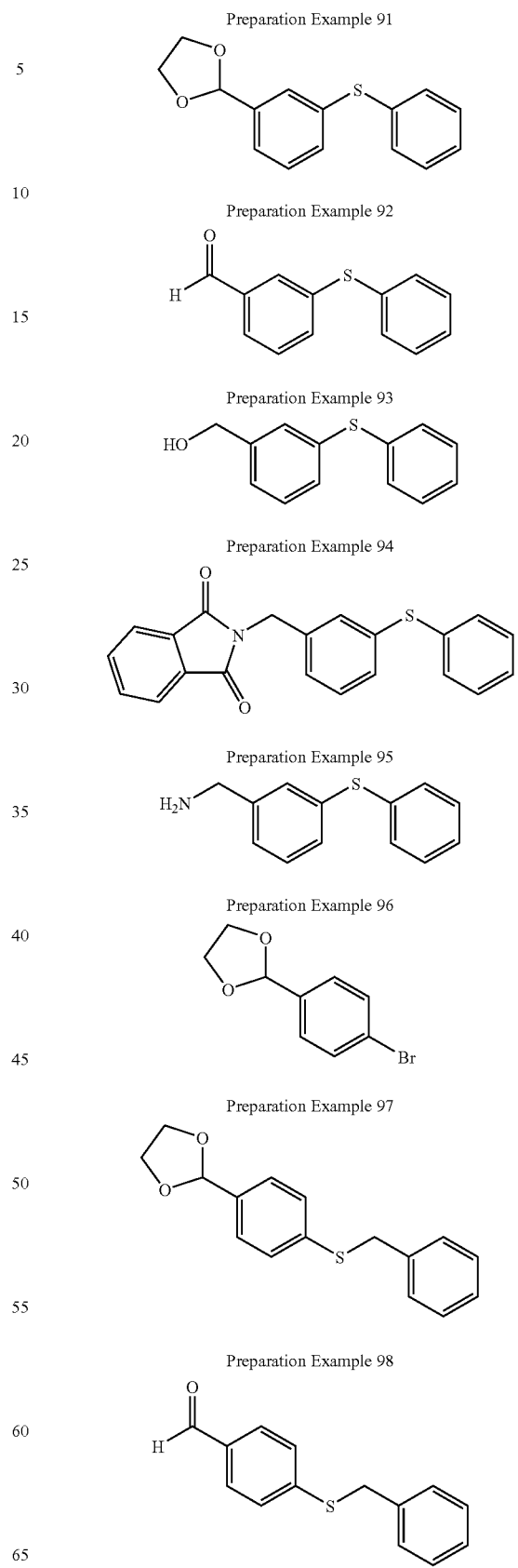

TABLE 15-continued
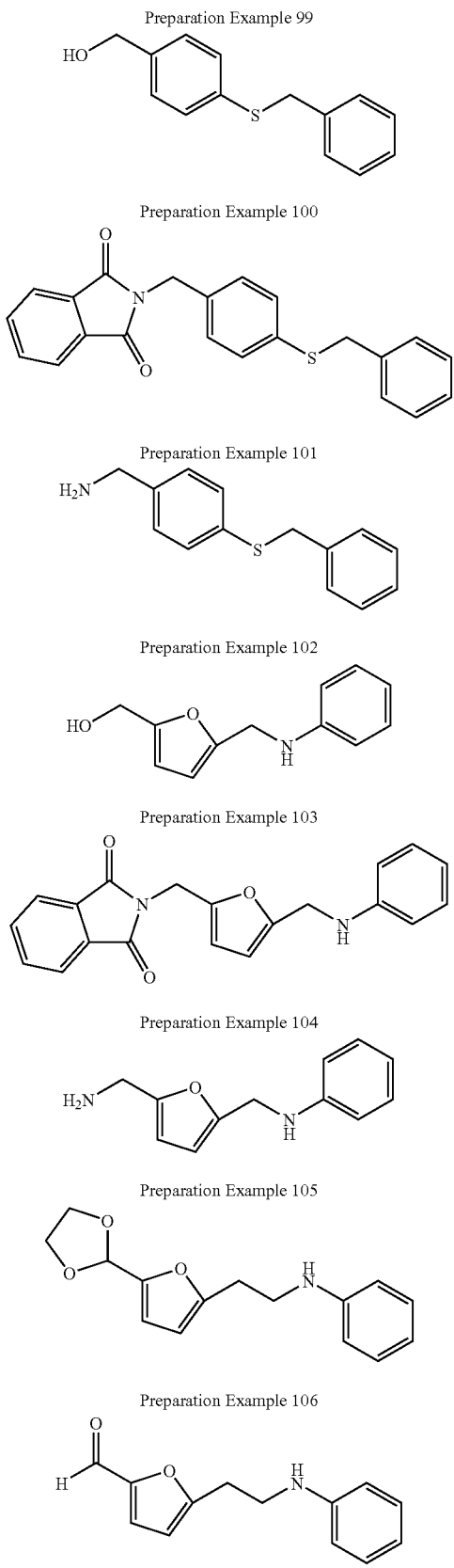
TABLE 15-continued
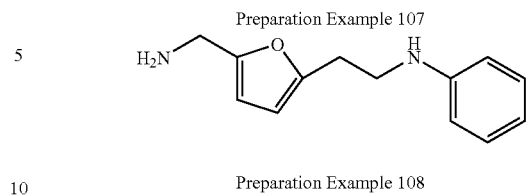
TABLE 16
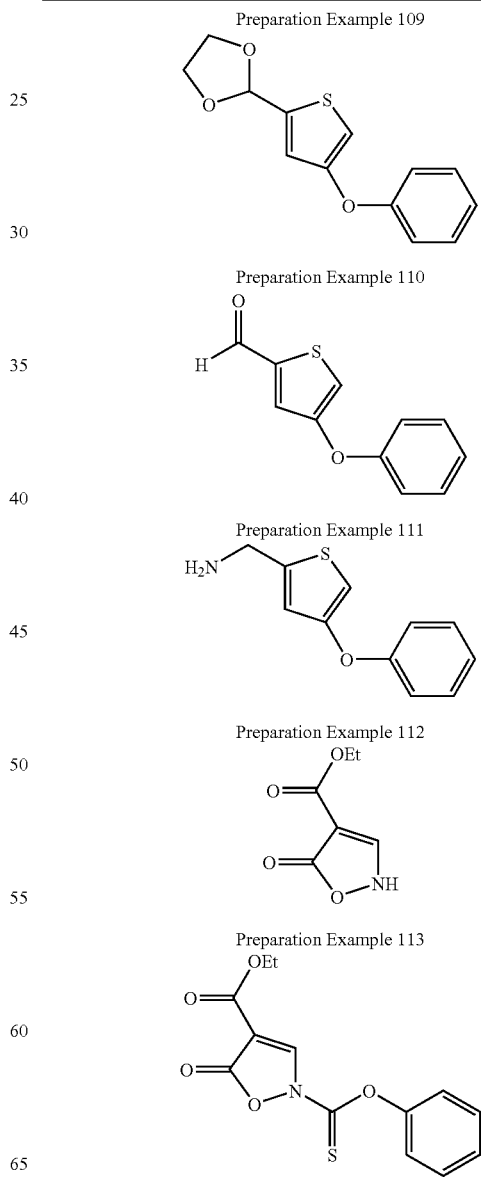

TABLE 16-continued
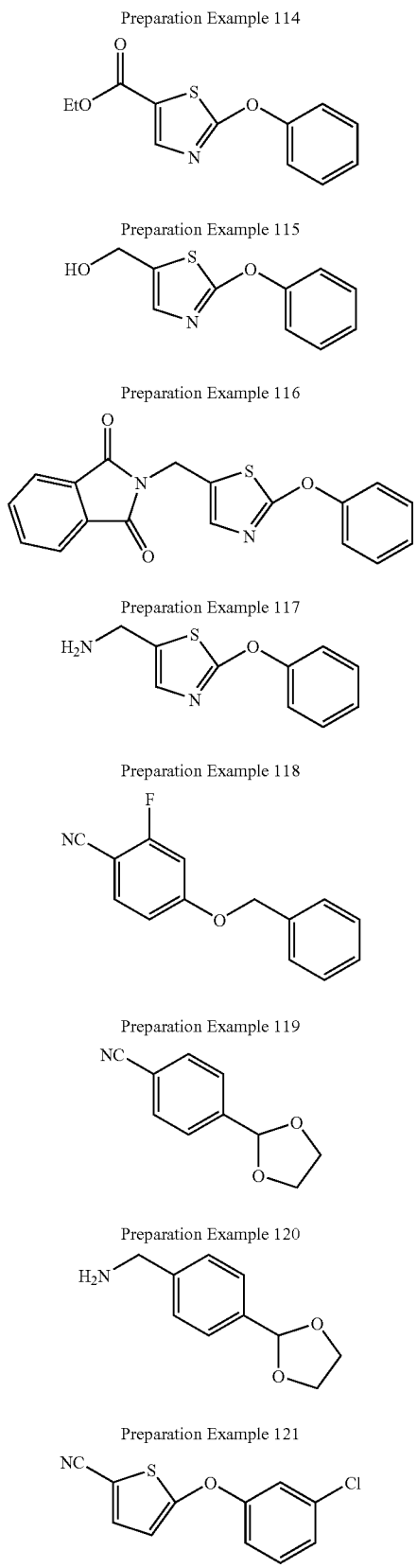
TABLE 16-continued
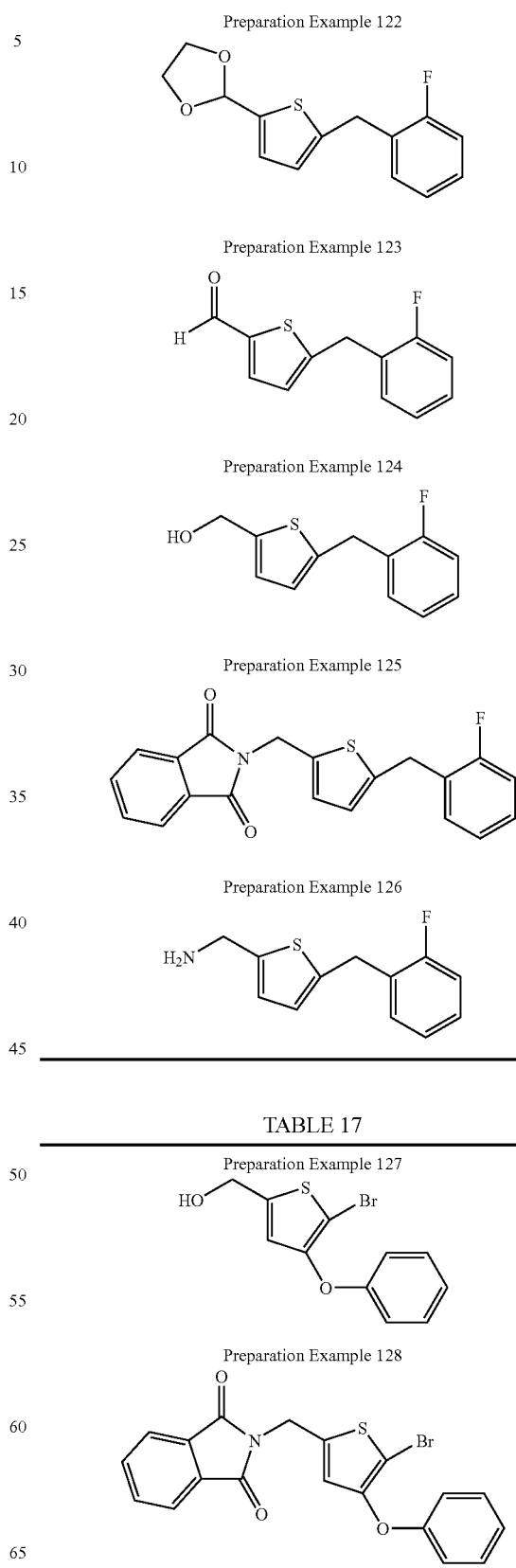
TABLE 17

TABLE 17-continued
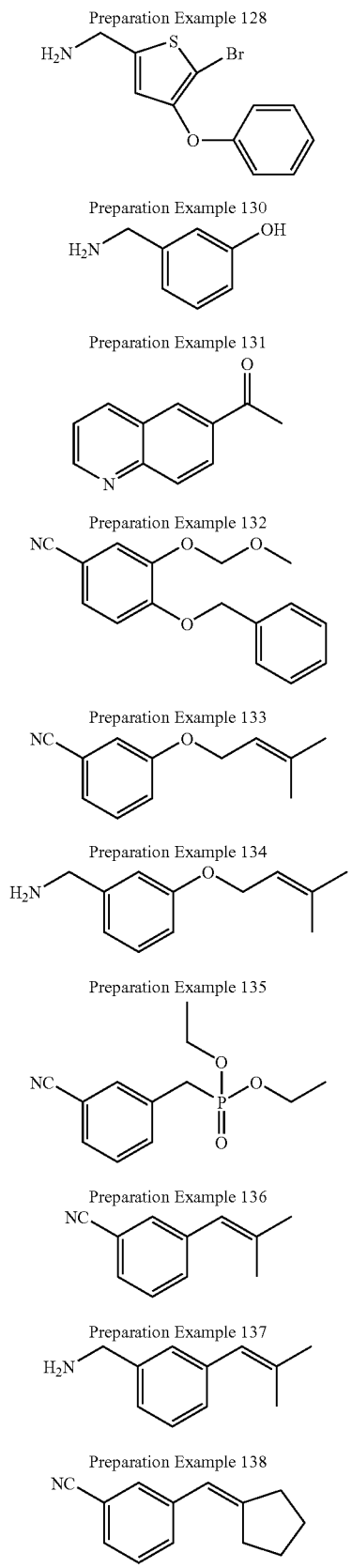
TABLE 17-continued
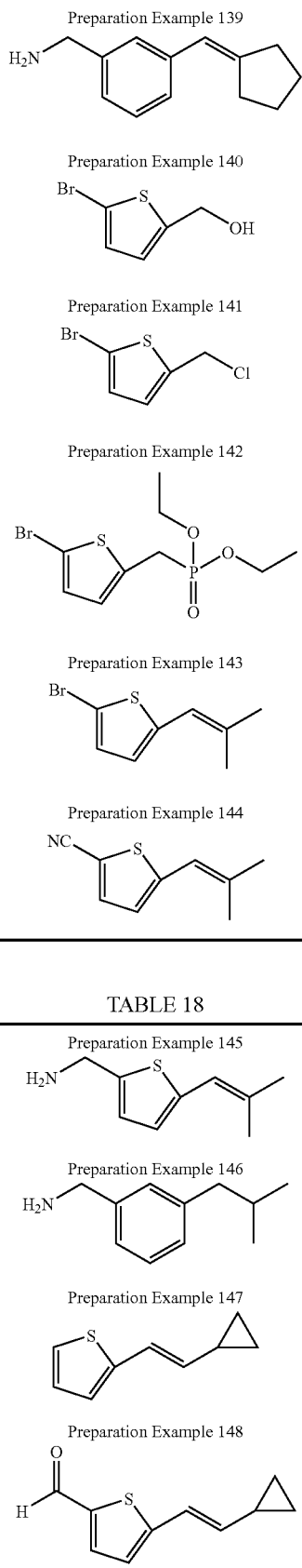
TABLE 18
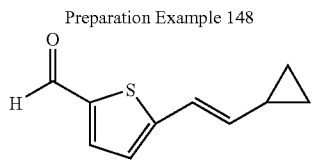

TABLE 18-continued

Preparation Example 149
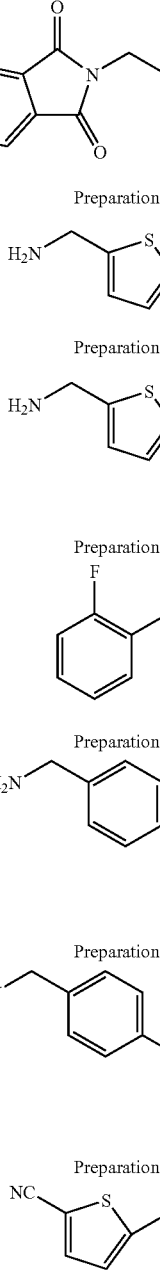

Preparation Example 150
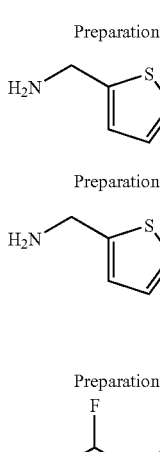

Preparation Example 151
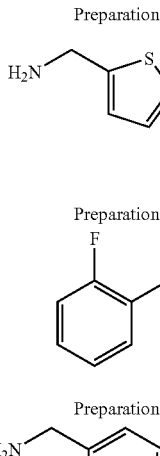

Preparation Example 152
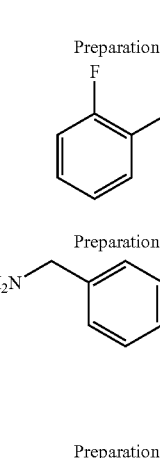

Preparation Example 153
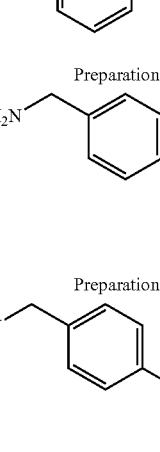

Preparation Example 154
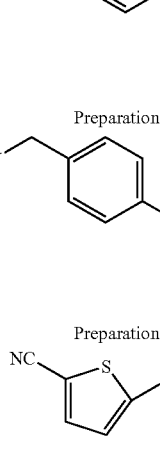

Preparation Example 155
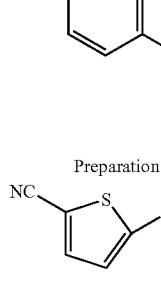

Preparation Example 156
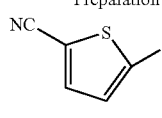

Preparation Example 157

TABLE 18-continued

Preparation Example 158

Preparation Example 159

Preparation Example 160

Preparation Example 161

Preparation Example 162

TABLE 19

Preparation Example 163

Preparation Example 164

Preparation Example 165

TABLE 19-continued

Preparation Example 166: 2-chloroquinoline-6-carboxylic acid lithium salt

Preparation Example 167: (5-(2-chlorophenoxy)thiophen-2-yl)methanamine

Preparation Example 168: 5-(4-fluorophenoxy)furan-2-carbaldehyde

Preparation Example 169: (5-(4-fluorophenoxy)furan-2-yl)methanamine

Preparation Example 170: 4-(pyridin-2-ylmethoxy)benzonitrile

Preparation Example 171: (4-(pyridin-2-ylmethoxy)phenyl)methanamine

Preparation Example 172: (4-((pyridin-2-yloxy)methyl)phenyl)methanamine

Preparation Example 173: 5-bromo-2,3-dihydrobenzofuran

Preparation Example 174: 2,3-dihydrobenzofuran-5-carbaldehyde

TABLE 19-continued

Preparation Example 175: benzofuran-5-carbaldehyde

Preparation Example 176: (5-bromothiophen-2-yl)(benzofuran-5-yl)methanol

Preparation Example 177: 5-(benzofuran-5-yl(hydroxy)methyl)thiophene-2-carbonitrile Preparation Example 178: (5-(benzofuran-5-ylmethyl)thiophen-2-yl)methanamine Preparation Example 179: (6-(benzyloxy)pyridin-3-yl)methanamine Preparation Example 180: (6-benzylpyridin-3-yl)methanamine Preparation Example 181: (5-phenoxypyridin-2-yl)methanamine

TABLE 20

Preparation Example 182: 2-methyl-5-(benzyloxy)pyridine

TABLE 20-continued
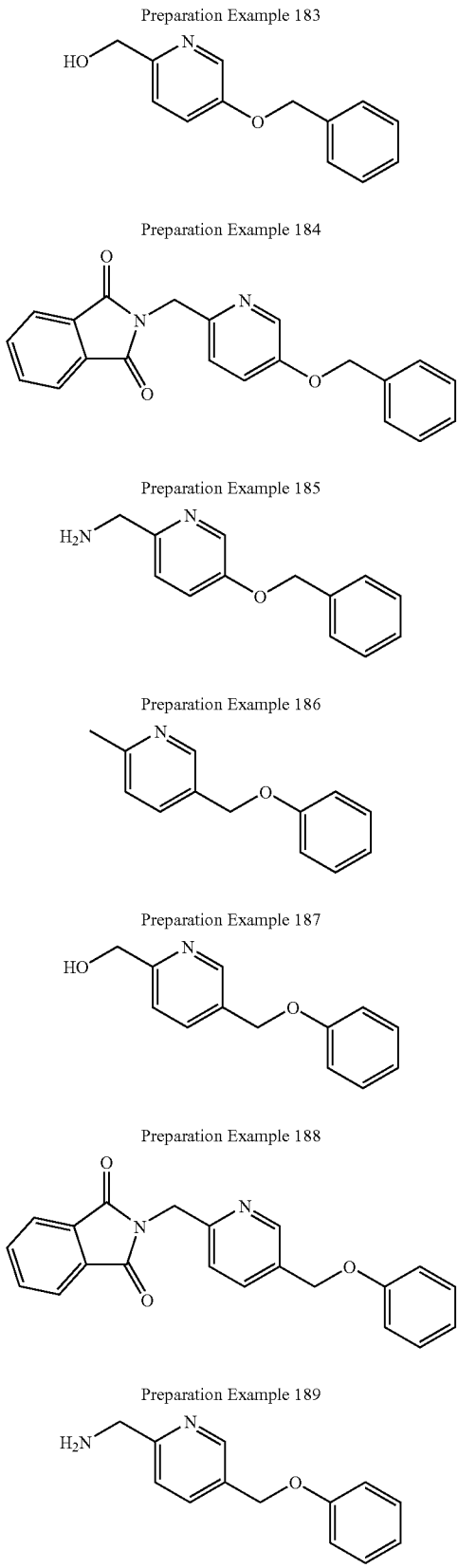
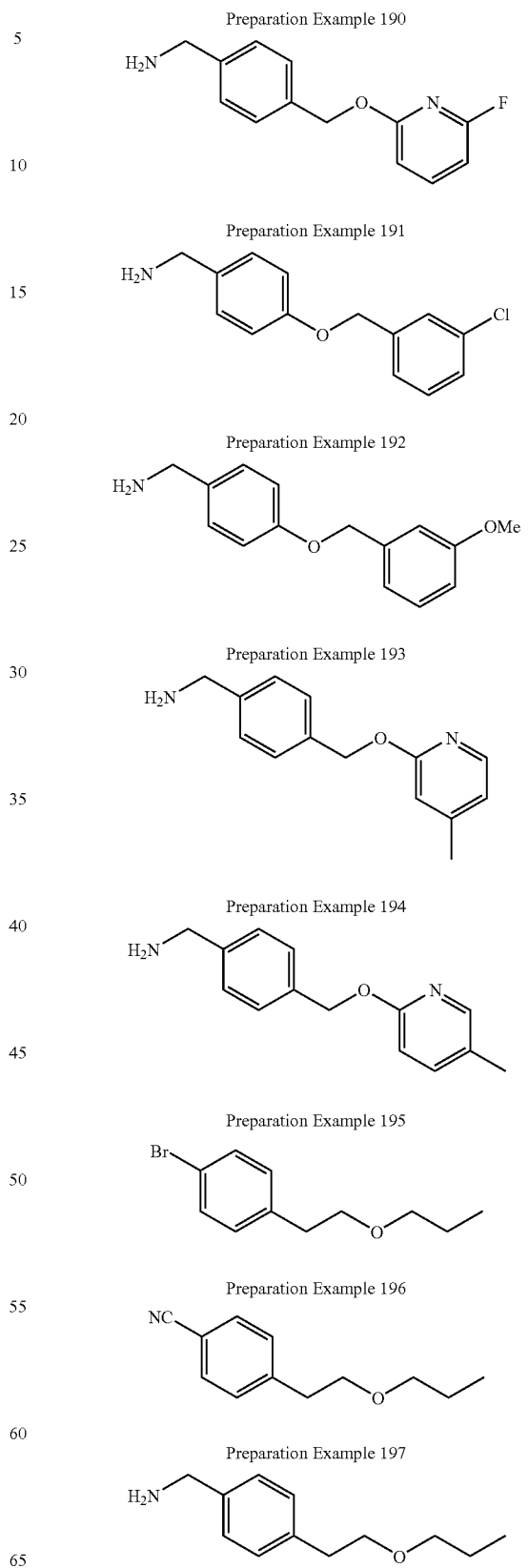

TABLE 21
Example A-1
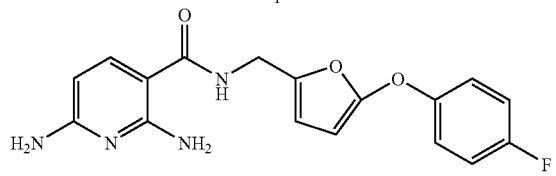
Example A-2
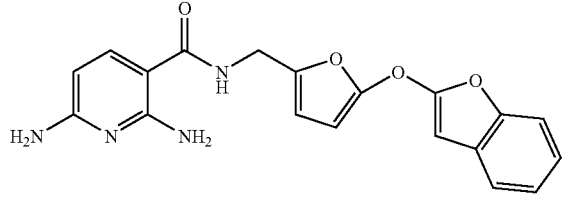
Example A-3
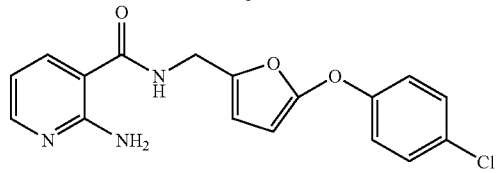
Example A-4
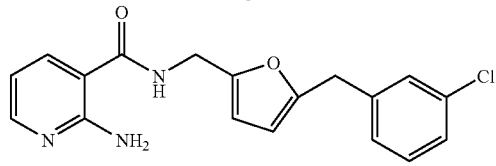
Example A-5
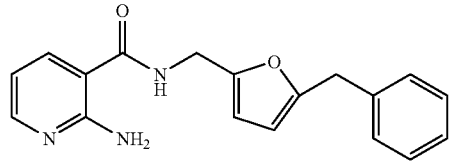
Example A-6
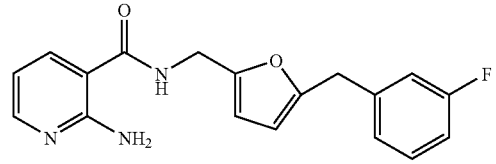
Example A-7
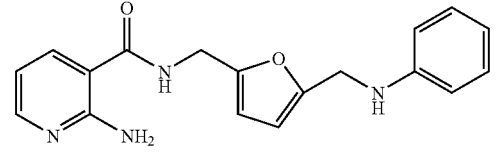
Example A-8
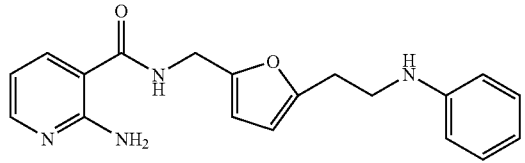
TABLE 21-continued
Example A-9
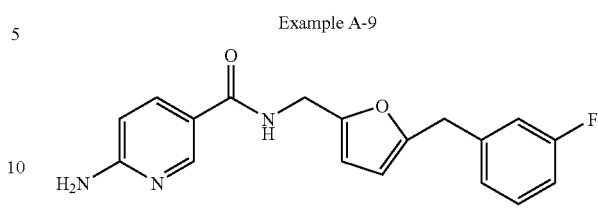
Example A-10
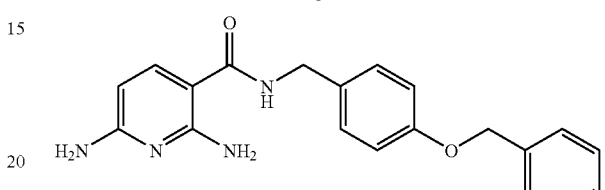
Example A-11
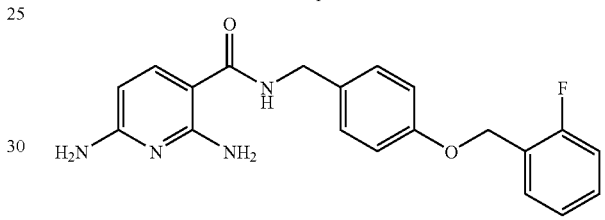
Example A-12
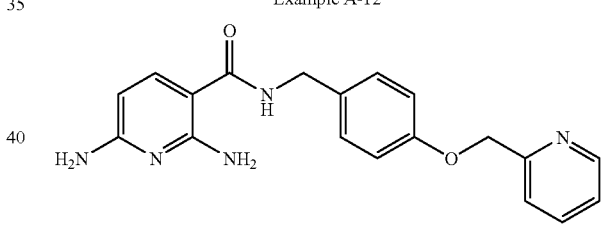
TABLE 22
Example A-13
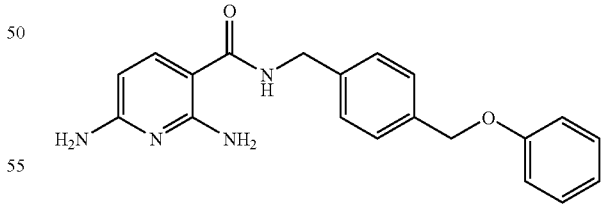
Example A-14
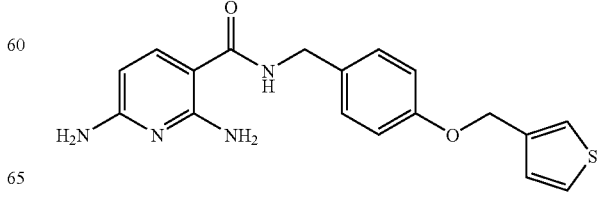

TABLE 22-continued
Example A-15
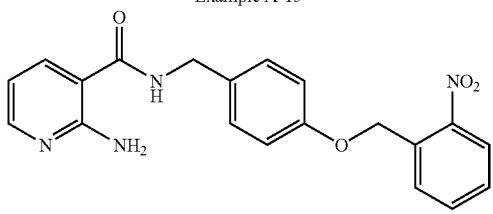
Example A-16
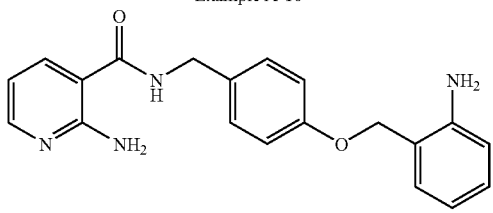
Example A-17
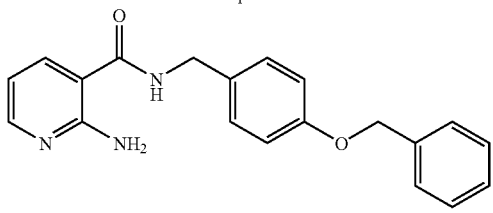
Example A-18
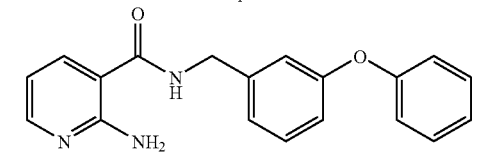
Example A-19
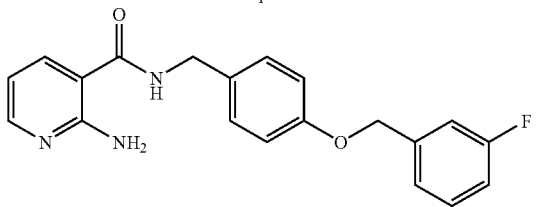
Example A-20
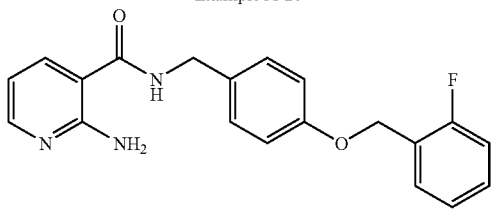
Example A-21
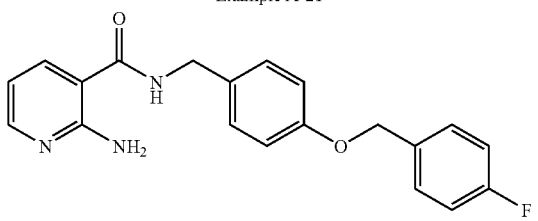
TABLE 22-continued
Example A-22
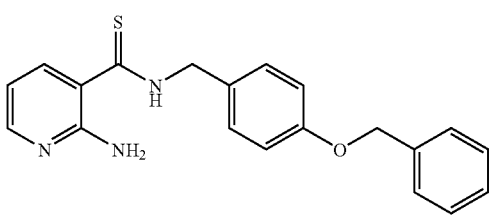
Example A-23
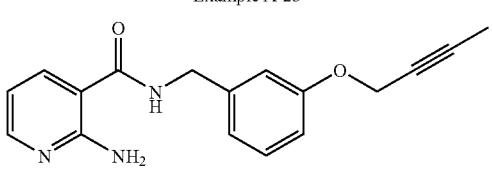
Example A-24
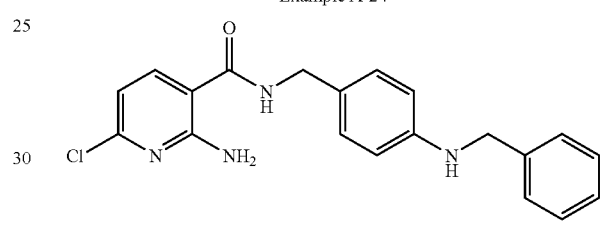
TABLE 23
Example A-25
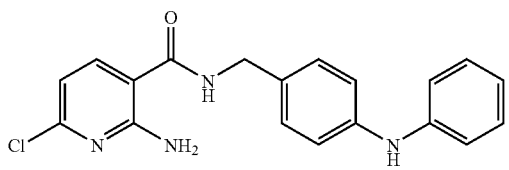
Example A-26
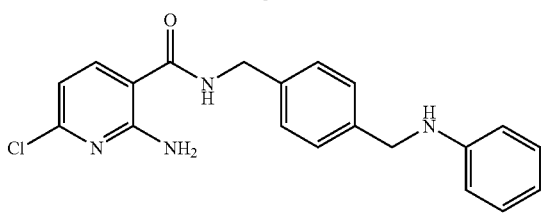
Example A-27
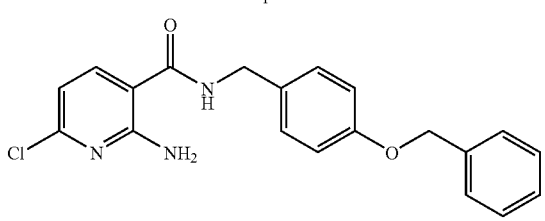

TABLE 23-continued
Example A-28
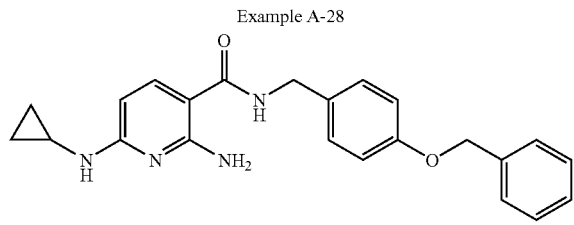
Example A-29
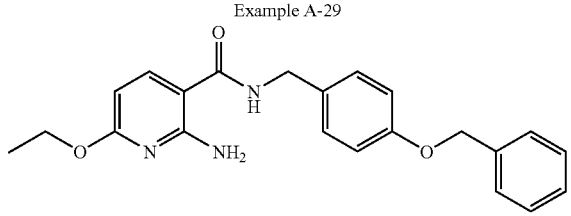
Example A-30
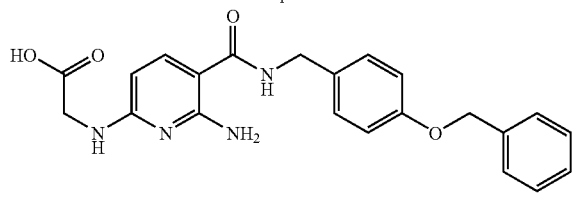
Example A-31
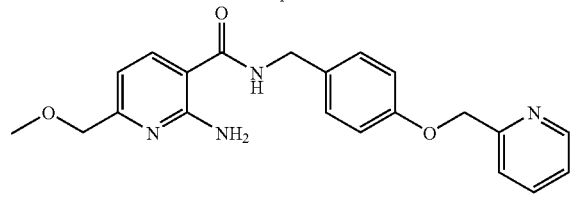
Example A-32
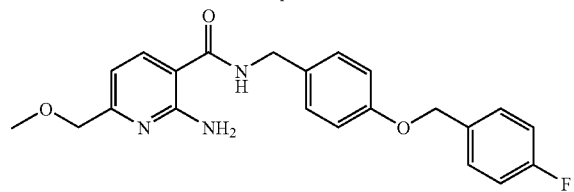
Example A-33
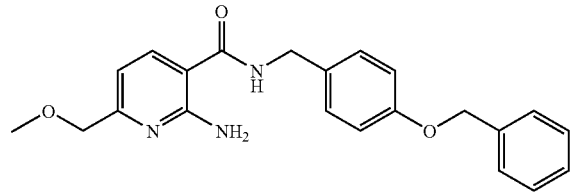
Example A-34
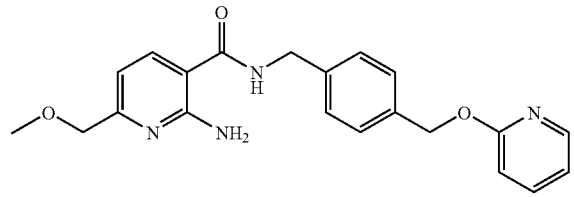
TABLE 23-continued
Example A-35
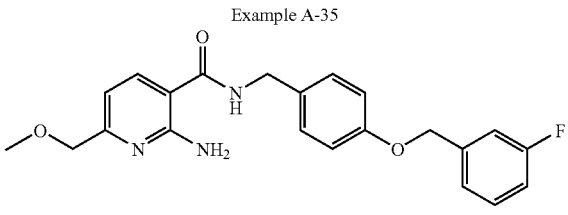
Example A-36
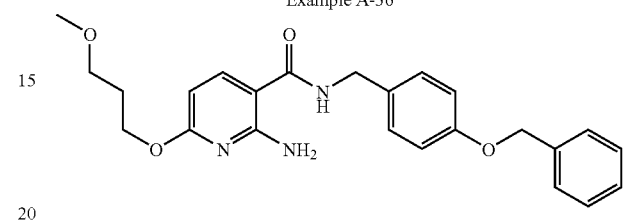
TABLE 24
Example A-37
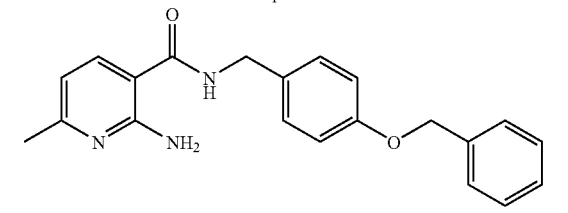
Example A-38
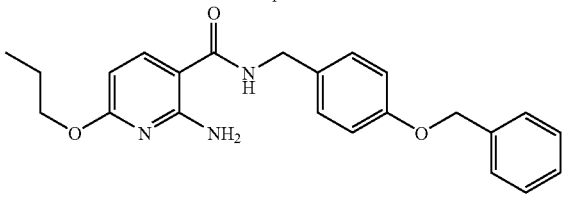
Example A-39
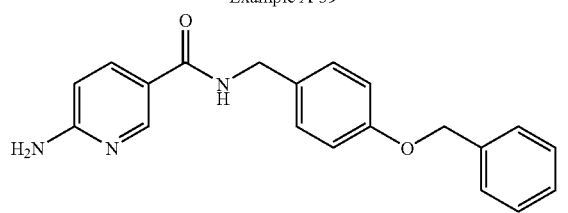
Example A-40
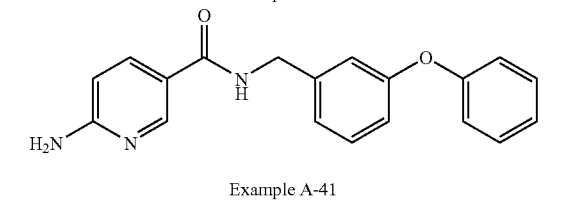
Example A-41
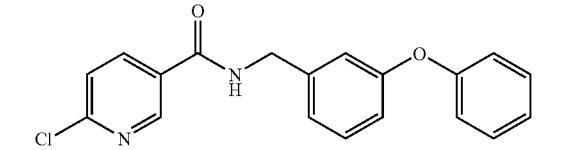

TABLE 24-continued
Example A-42
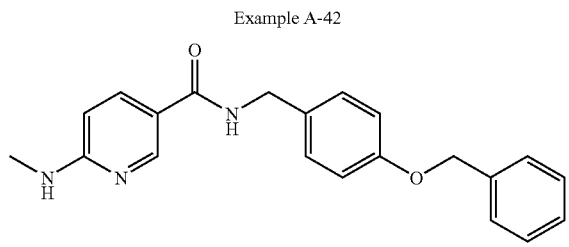
Example A-43
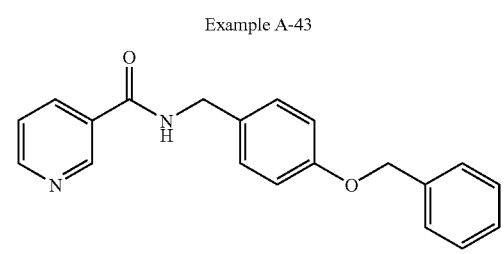
Example A-44
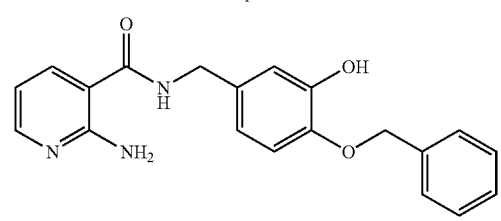
Example A-45
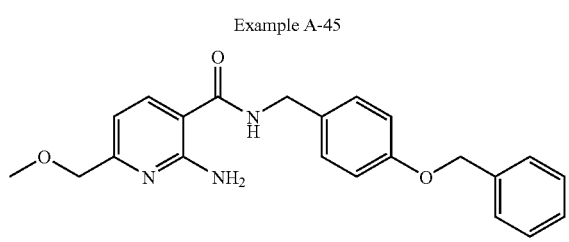
Example A-46
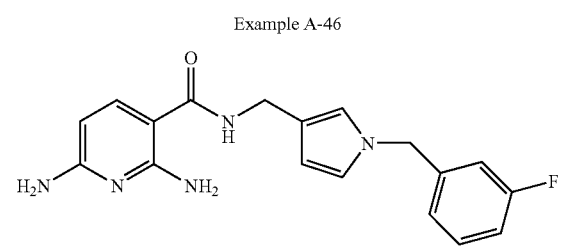
Example A-47
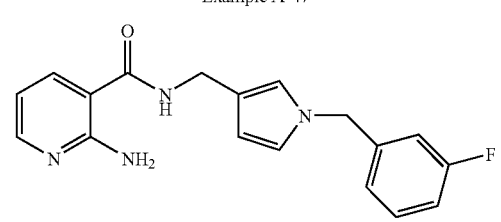
TABLE 24-continued
Example A-48
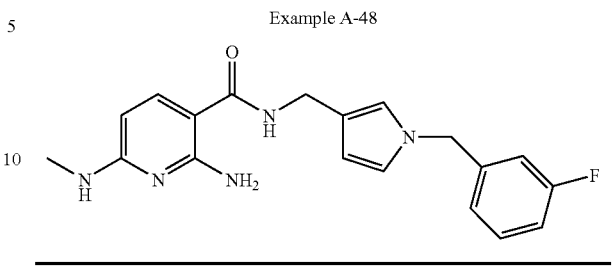
TABLE 25
Example A-49
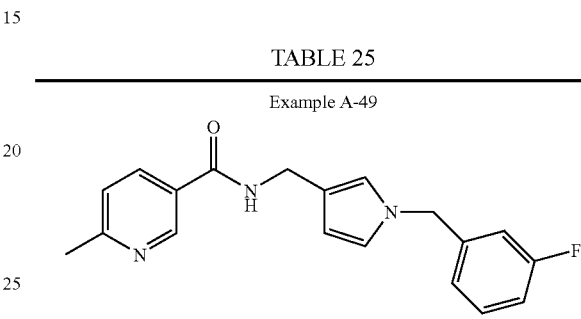
Example A-50
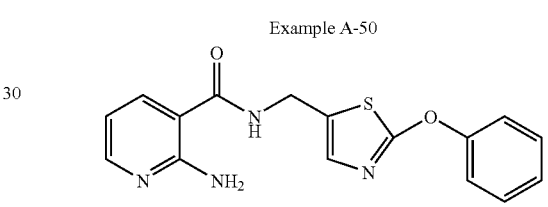
Example A-51
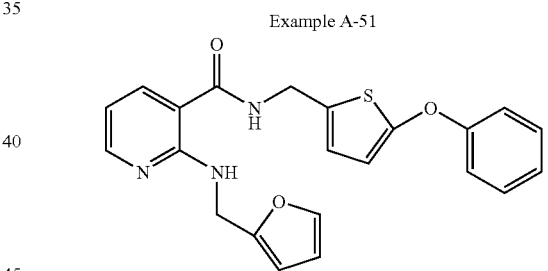
Example A-52
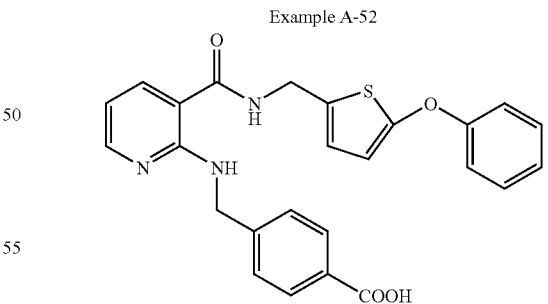
Example A-53
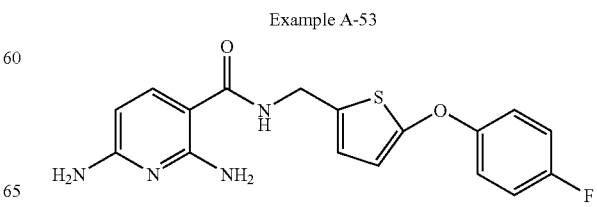

TABLE 25-continued
Example A-54
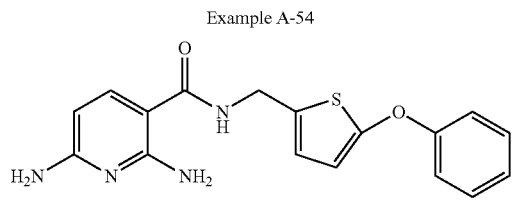
Example A-55
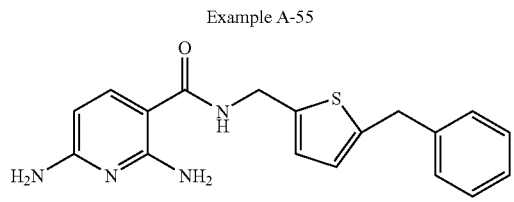
Example A-56
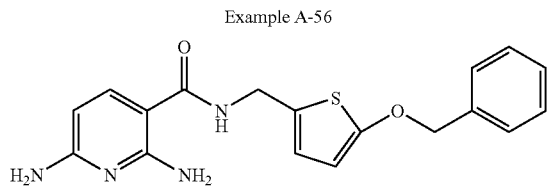
Example A-57
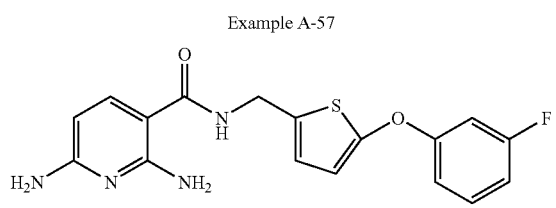
Example A-58
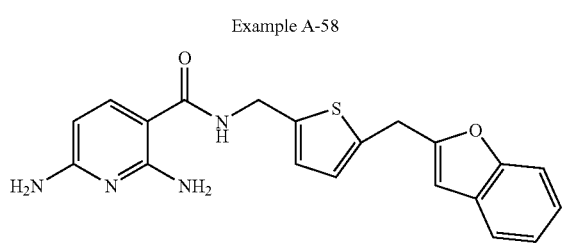
Example A-59
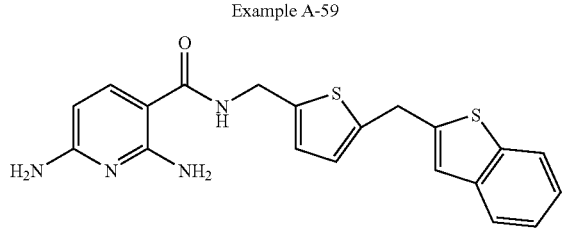
Example A-60
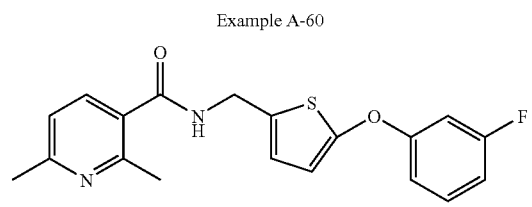
TABLE 26
Example A-61
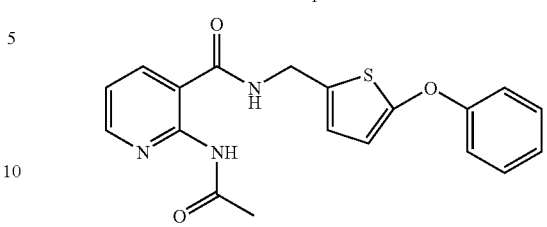
Example A-62
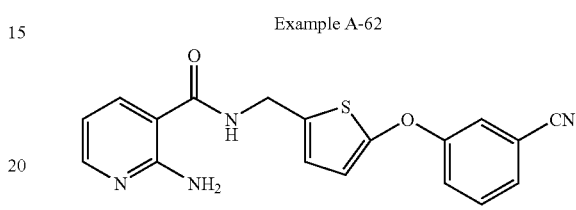
Example A-64
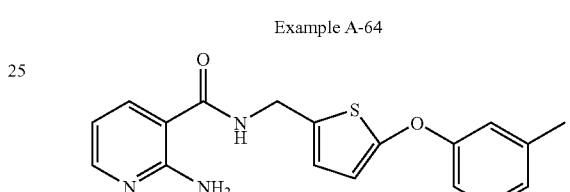
Example A-65
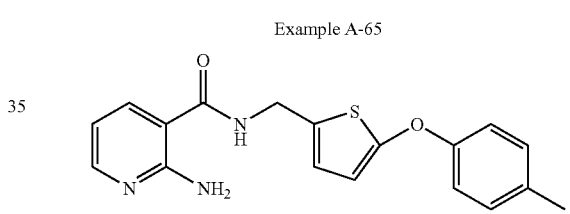
Example A-66
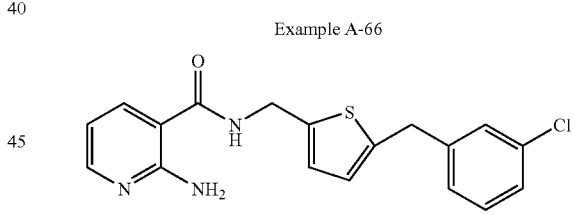
Example A-67
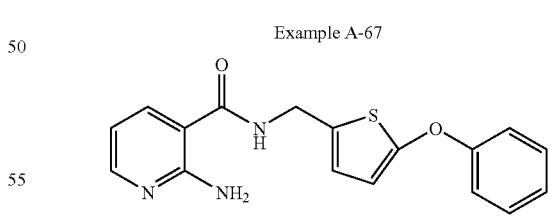
Example A-68
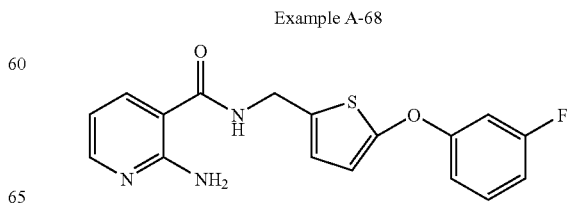

TABLE 26-continued
Example A-69
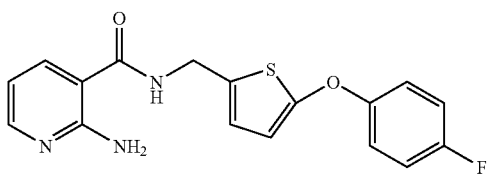
Example A-70
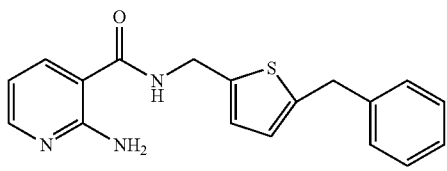
Example A-71
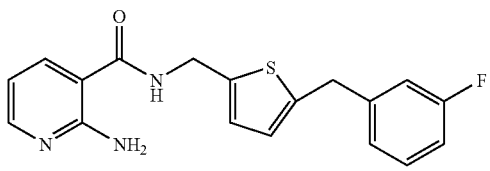
Example A-72
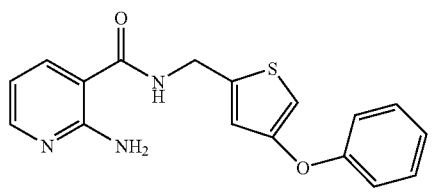
TABLE 27
Example A-73
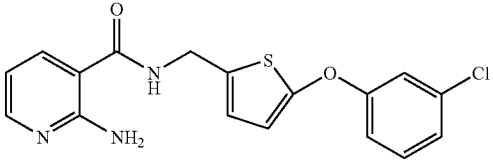
Example A-74
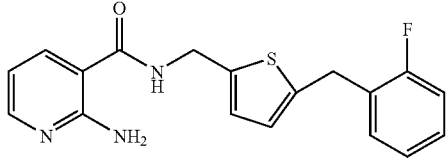
Example A-75
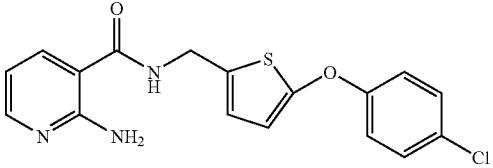
TABLE 27-continued
Example A-76
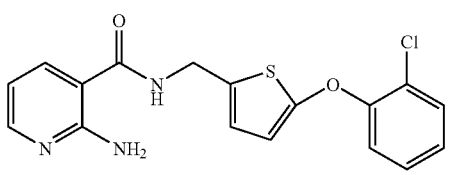
Example A-77
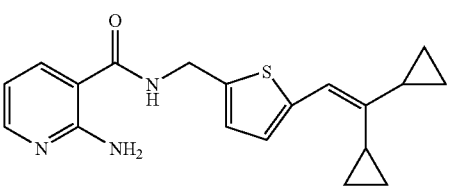
Example A-78
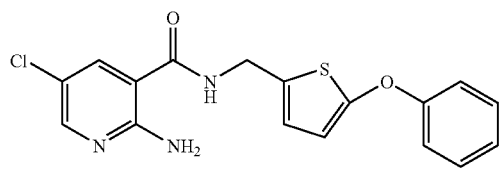
Example A-79
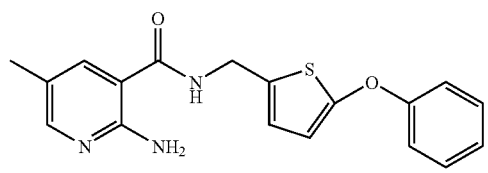
Example A-80
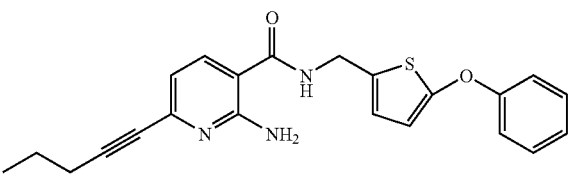
Example A-81
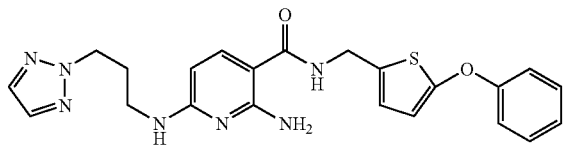
Example A-82
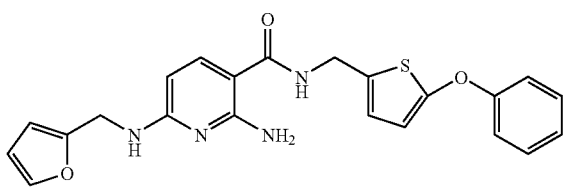

TABLE 27-continued
Example A-83
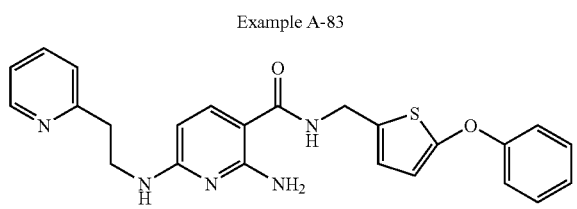
Example A-84
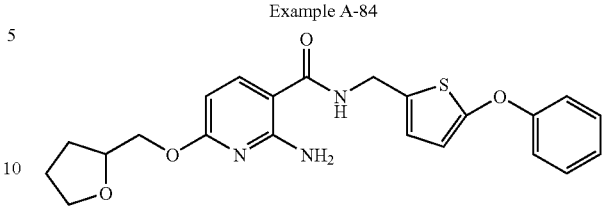
TABLE 28
Example A-85
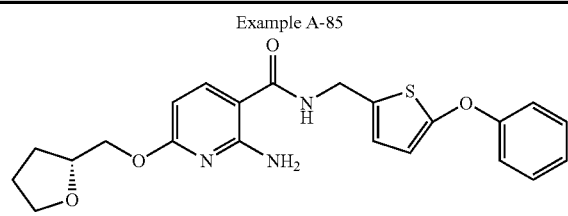
Example A-86
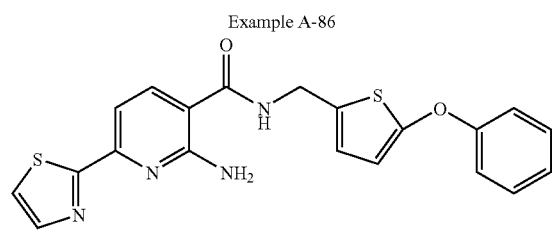
Example A-87
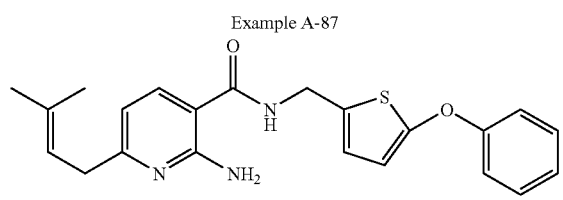
Example A-88
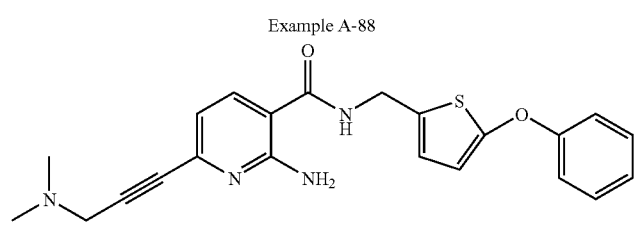
Example A-89
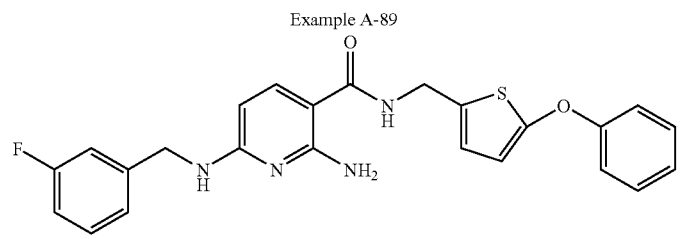
Example A-90
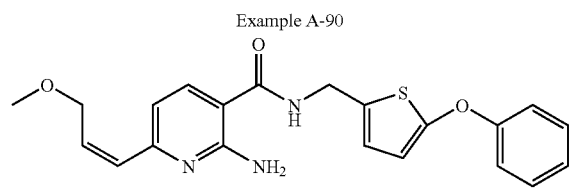

TABLE 28-continued
Example A-91
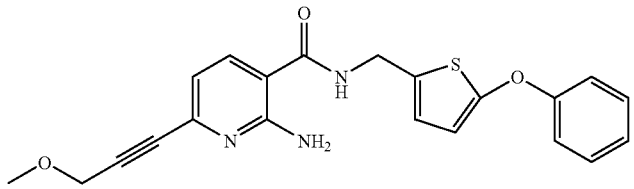
Example A-92
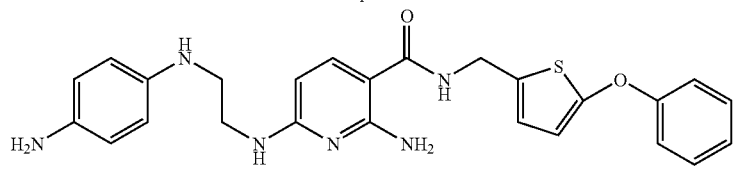
Example A-93
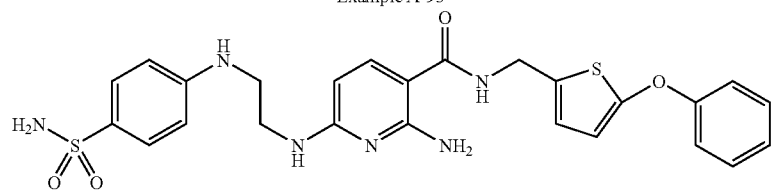
Example A-94
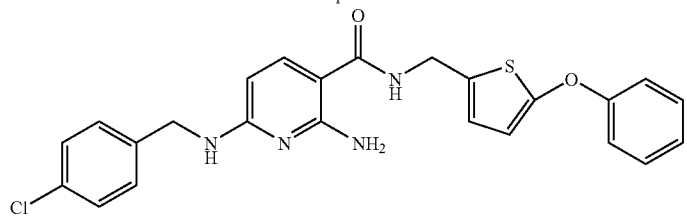
Example A-95
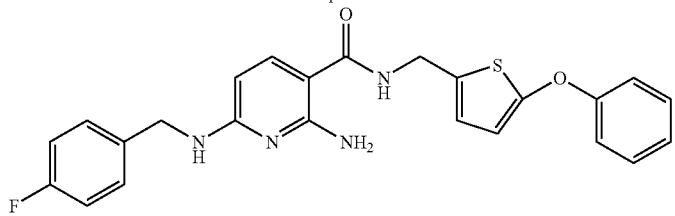
Example A-96
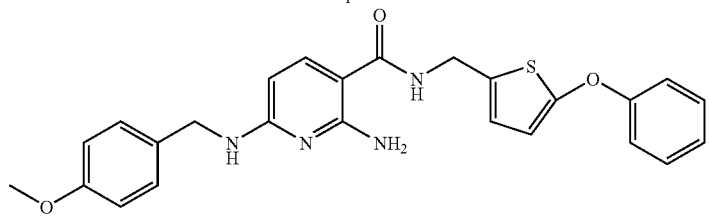

TABLE 29
Example A-97
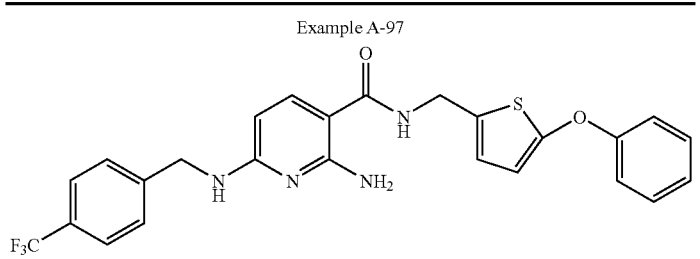
Example A-98
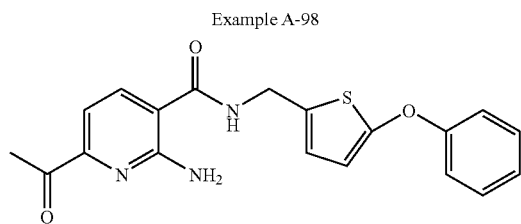
Example A-99
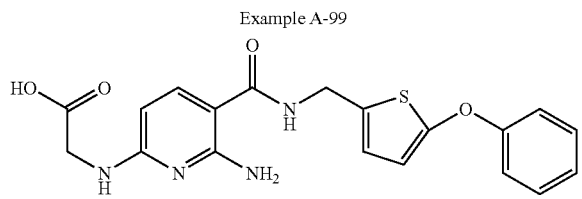
Example A-100
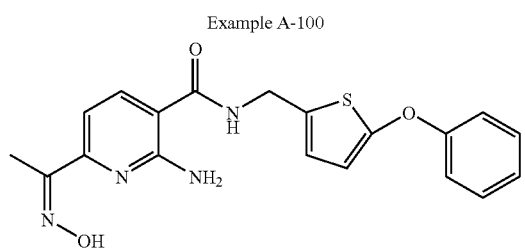
Example A-101
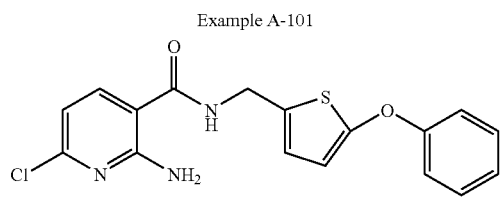
Example A-102
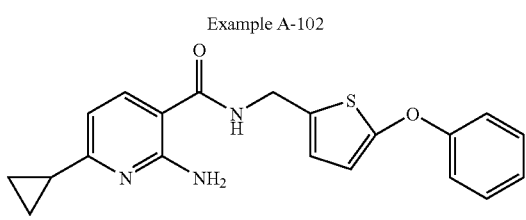
Example A-103
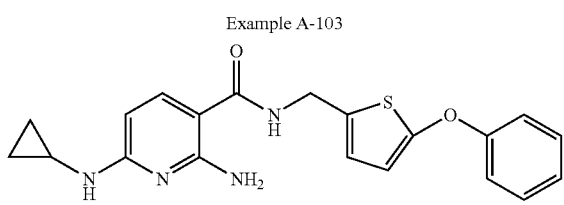

TABLE 29-continued
Example A-104
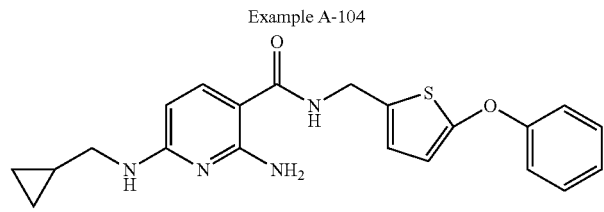
Example A-105
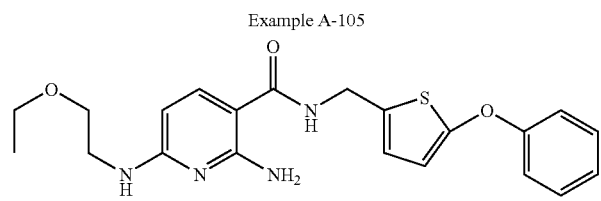
Example A-106
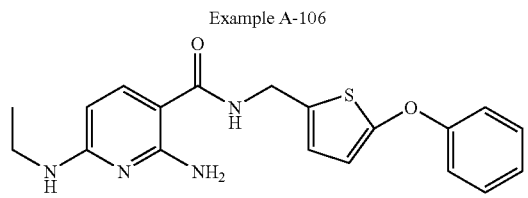
Example A-107
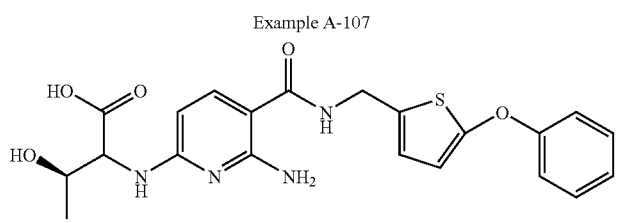
Example A-108
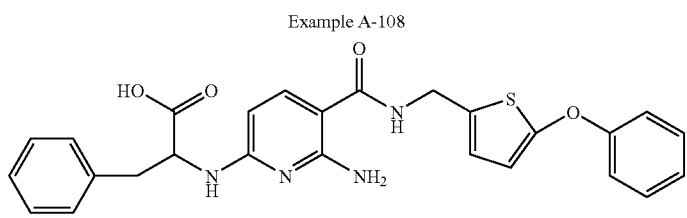
TABLE 30
Example A-109
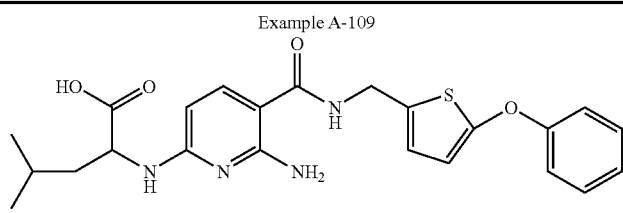
Example A-110
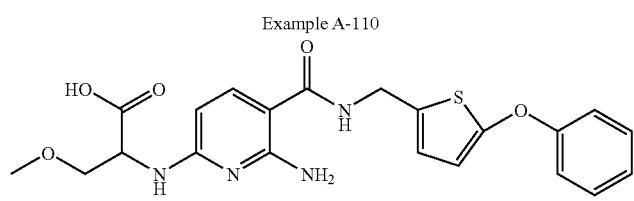

TABLE 30-continued
Example A-111
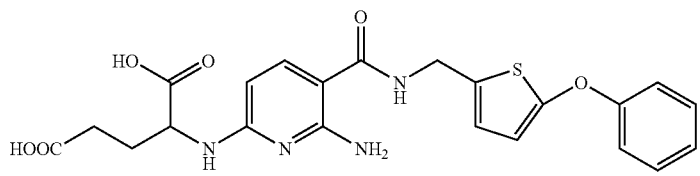
Example A-112
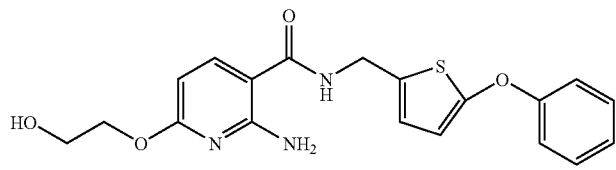
Example A-113
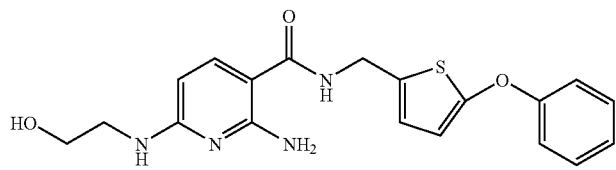
Example A-114
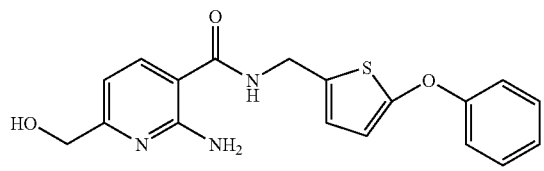
Example A-115
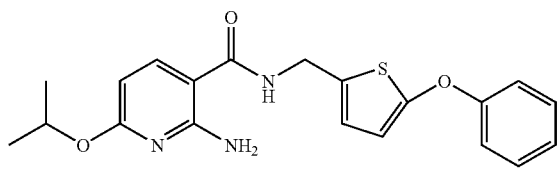
Example A-116
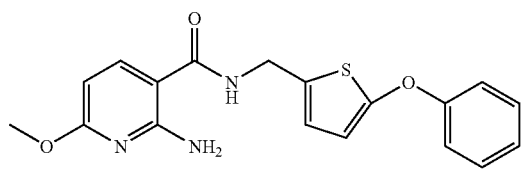
Example A-117
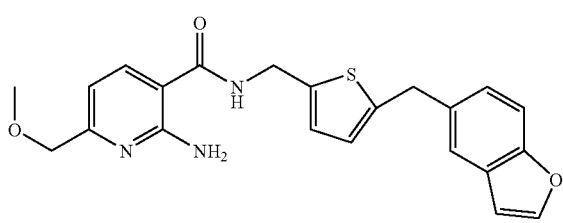

TABLE 30-continued
Example A-118
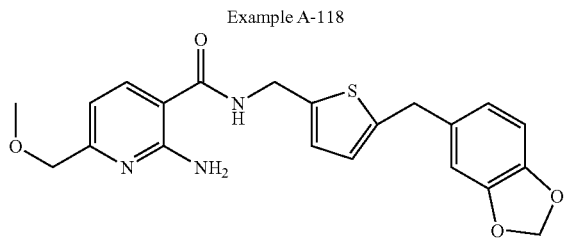
Example A-119
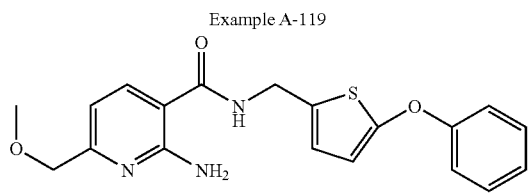
Example A-120
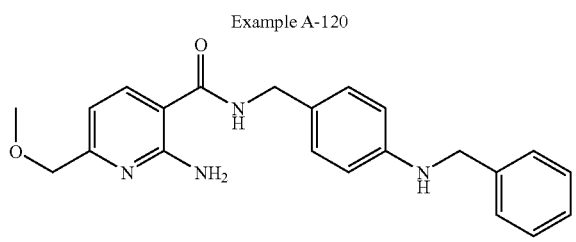
TABLE 31
Example A-121
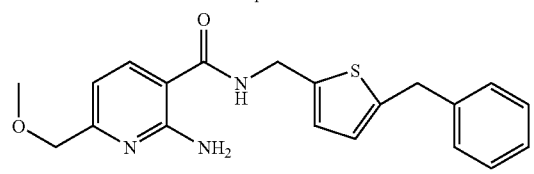
Example A-122
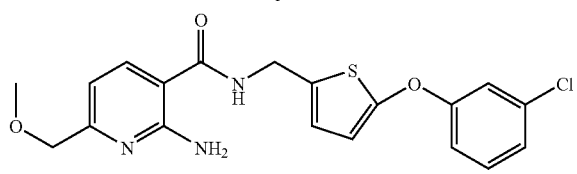
Example A-123
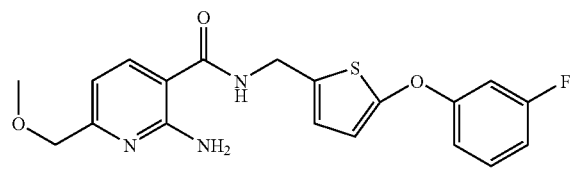
Example A-124
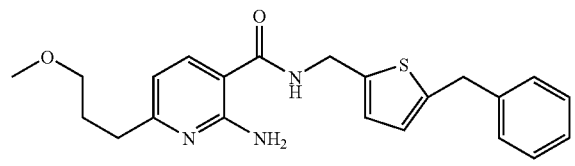
TABLE 31-continued
Example A-125
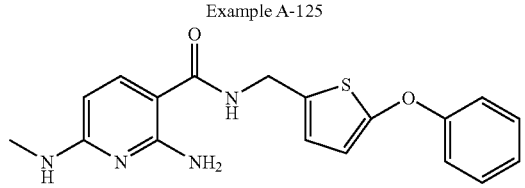
Example A-126
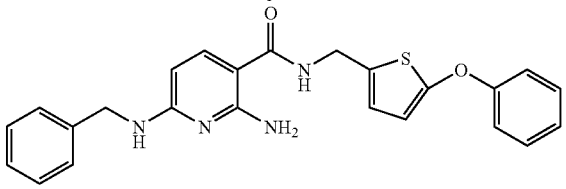
Example A-127
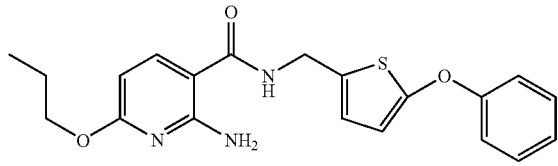
Example A-128
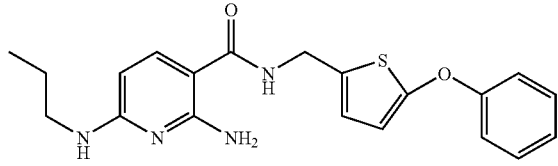

TABLE 31-continued
Example A-129
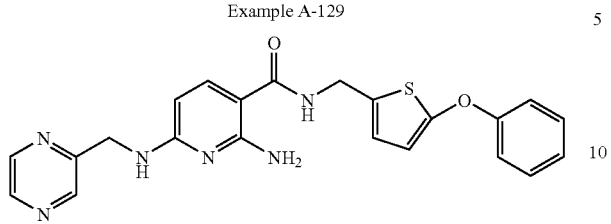
Example A-130
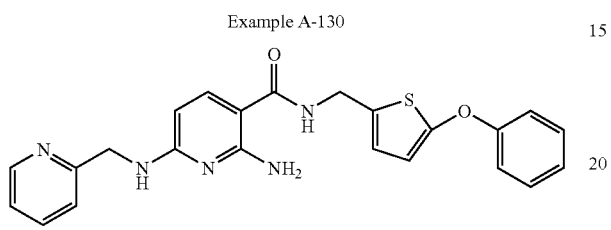
Example A-131
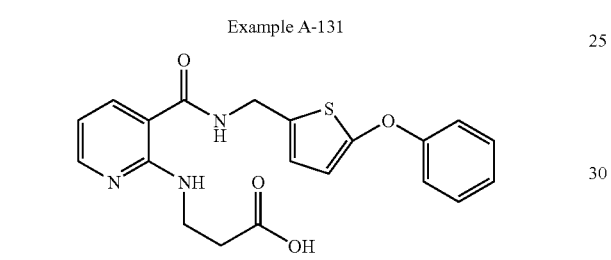
Example A-132
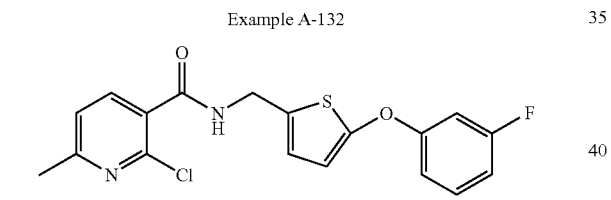
TABLE 32
Example A-133
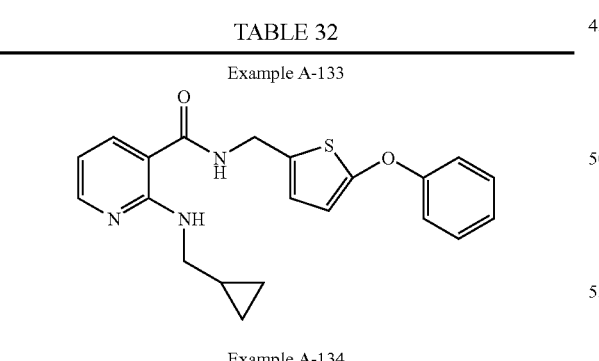
Example A-134
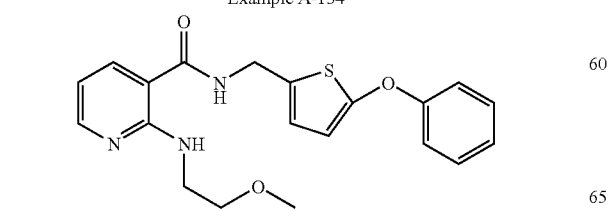
TABLE 32-continued
Example A-135
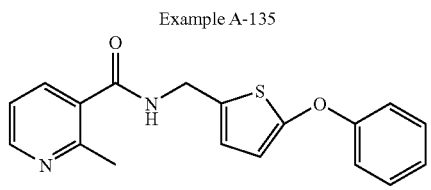
Example A-136
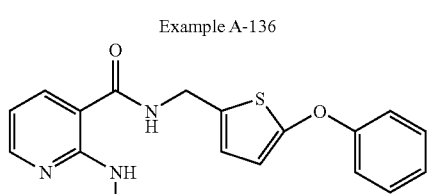
Example A-137
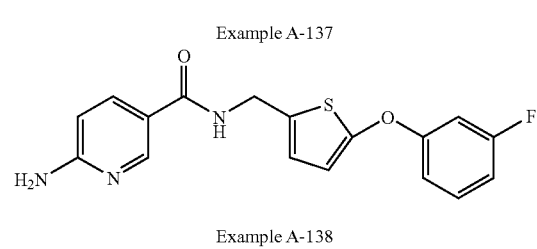
Example A-138
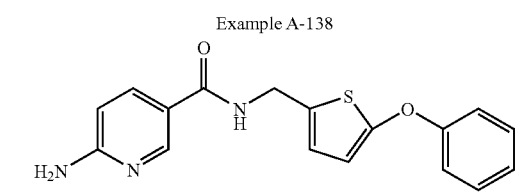
Example A-139
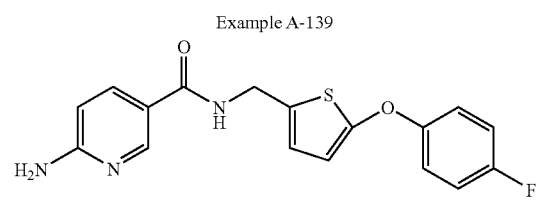
Example A-140
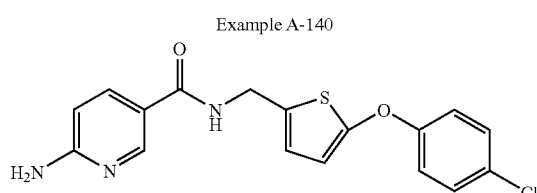
Example A-141
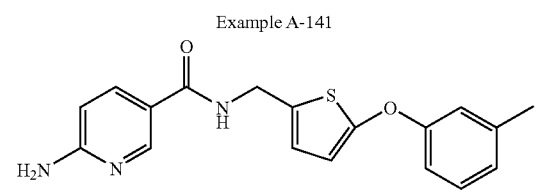
Example A-142
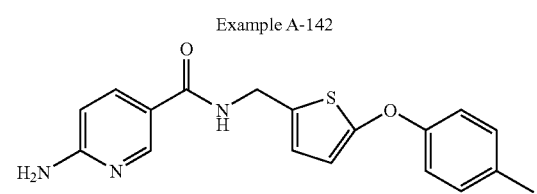

TABLE 32-continued
Example A-143
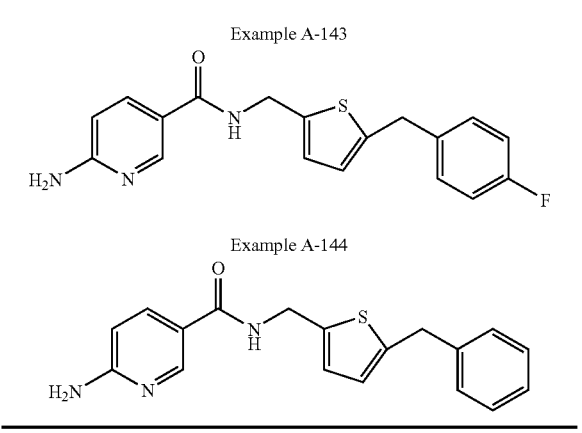
Example A-144
TABLE 33
Example A-145
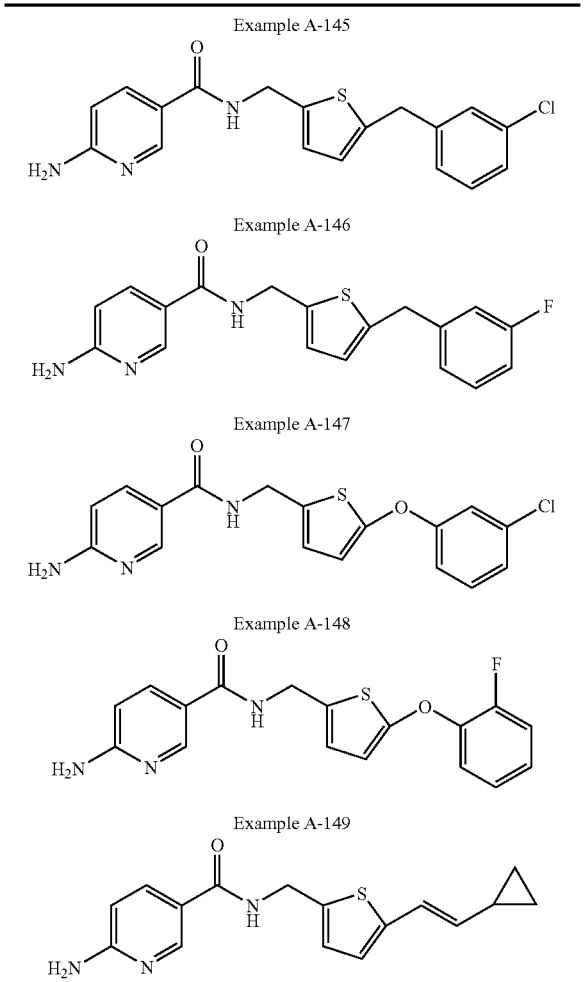
Example A-146
Example A-147
Example A-148
Example A-149
Example A-150
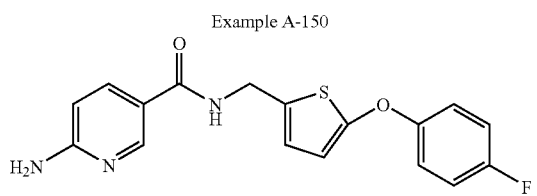
TABLE 33-continued
Example A-151
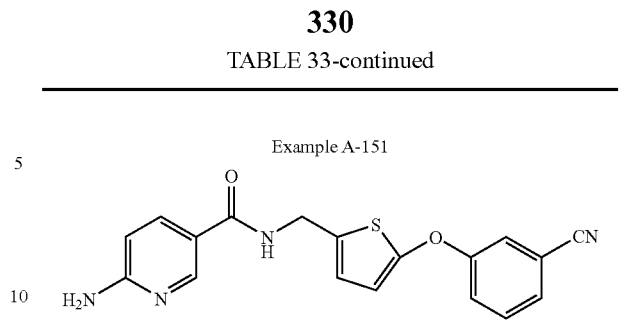
Example A-152
Example A-153
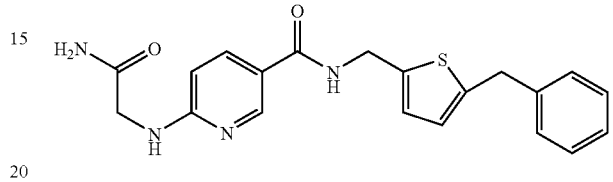
Example A-154
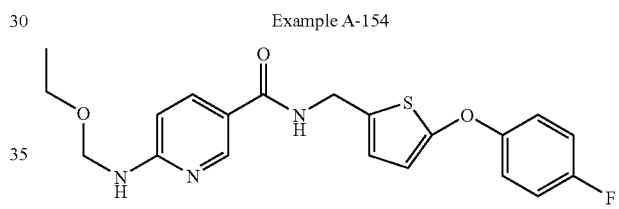
Example A-155
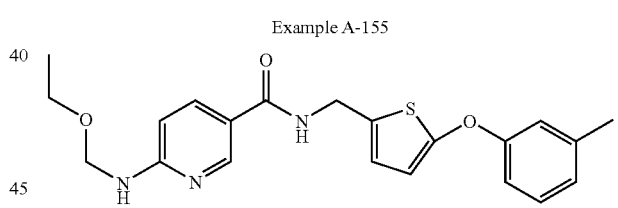
Example A-156
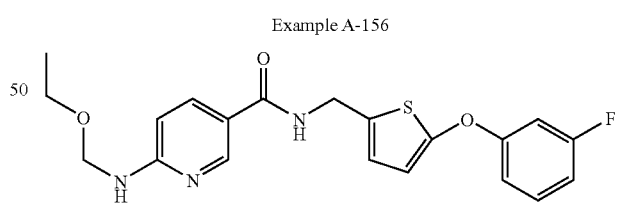
TABLE 34
Example A-157
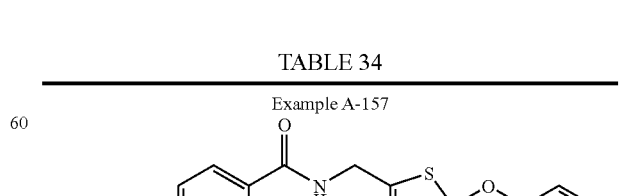

TABLE 34-continued
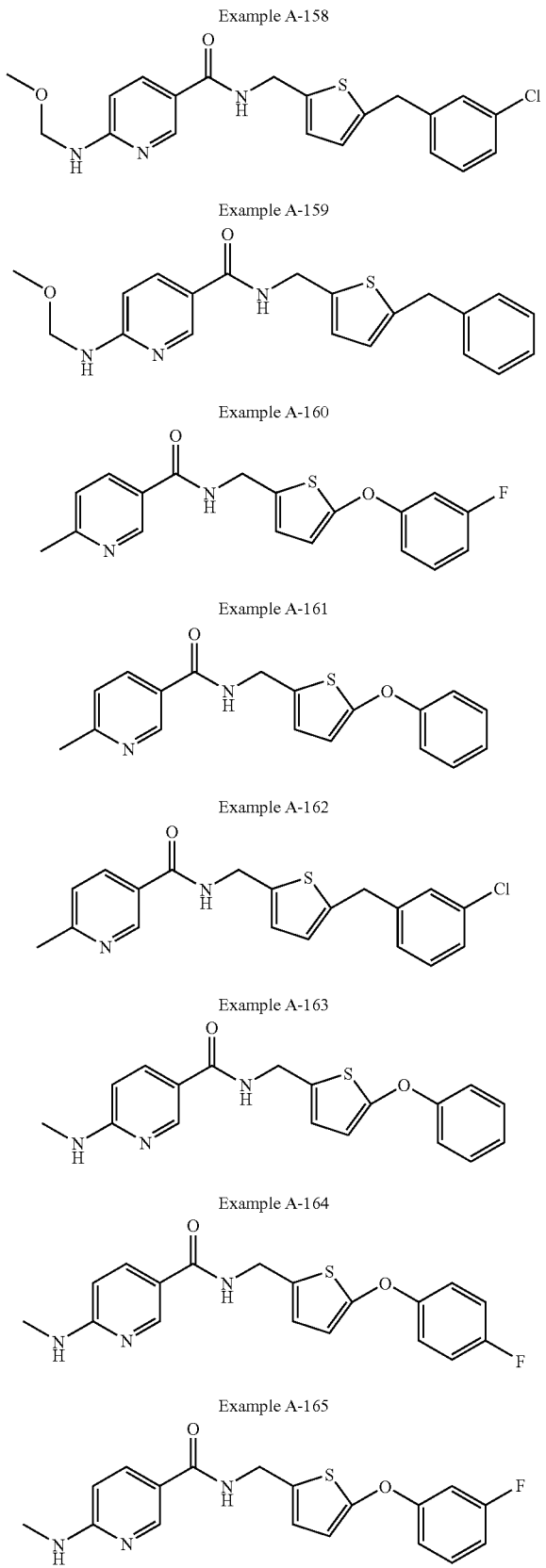
TABLE 34-continued
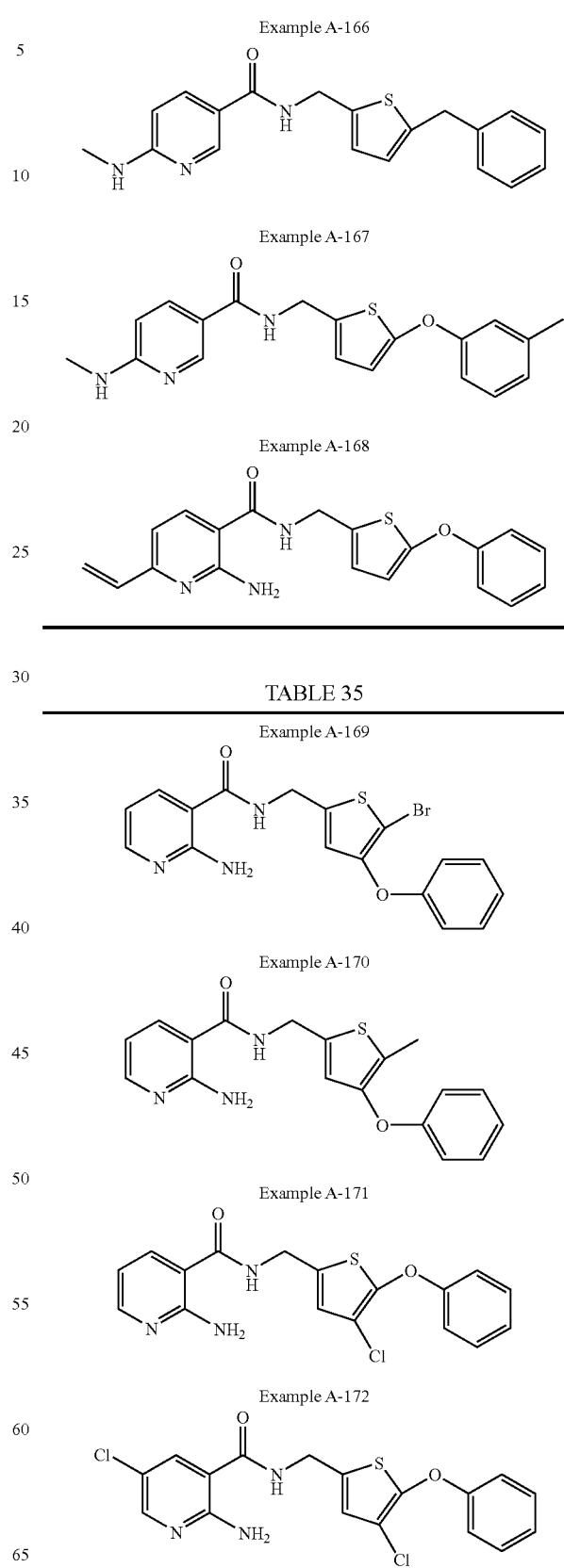
TABLE 35

TABLE 35-continued
Example A-173
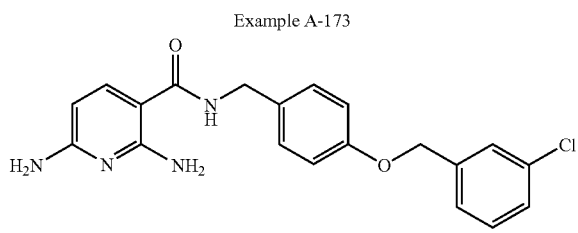
Example A-174
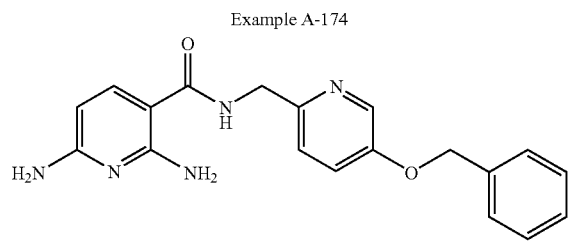
Example A-175
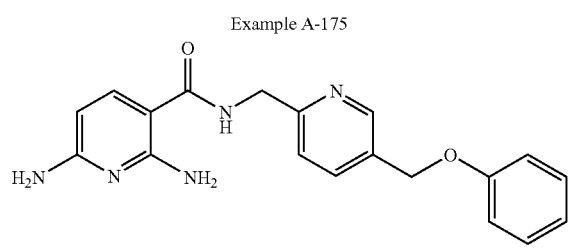
Example A-176
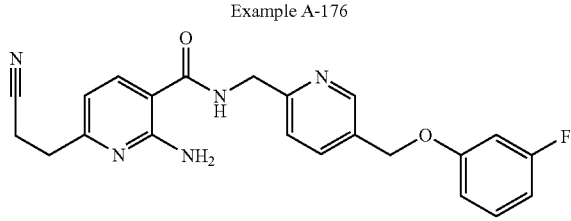
Example A-177
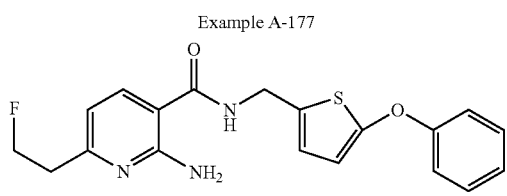
Example A-178
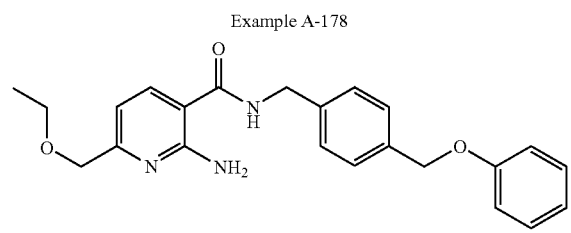
Example A-179
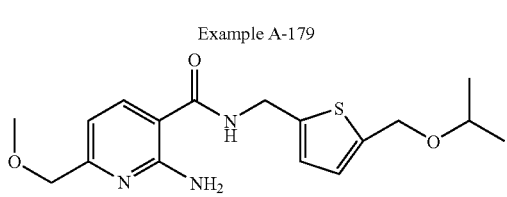
TABLE 35-continued
Example A-180
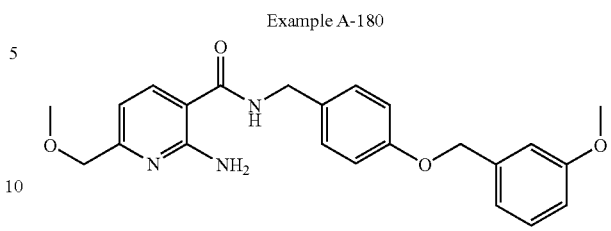
TABLE 36
Example A-181
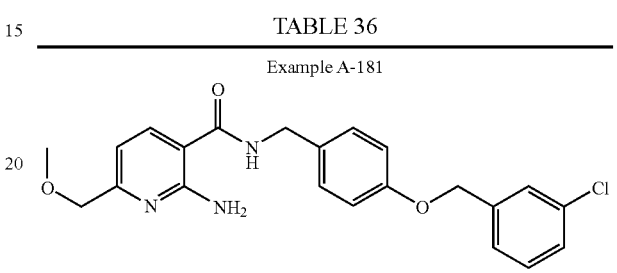
Example A-182
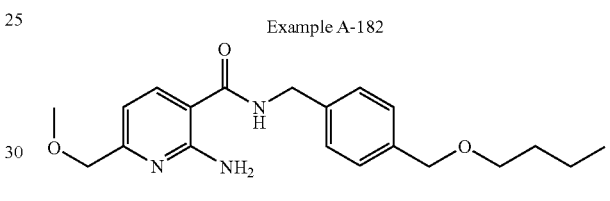
Example A-183
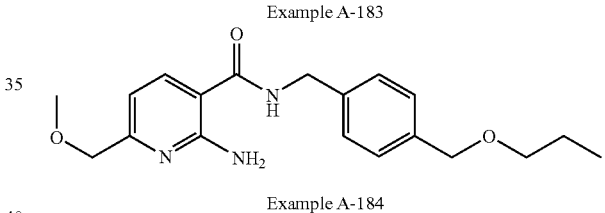
Example A-184
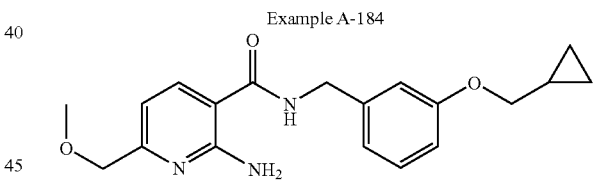
Example A-185
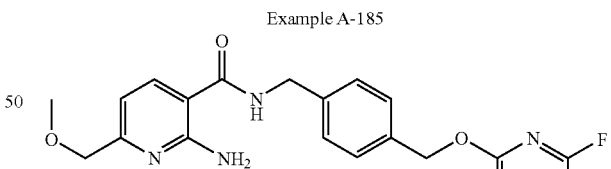
Example A-186
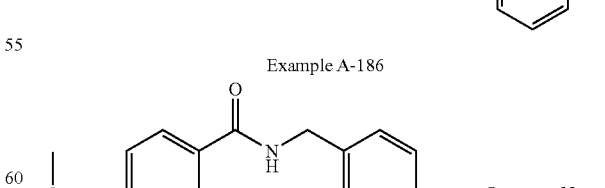

TABLE 36-continued
TABLE 37-continued
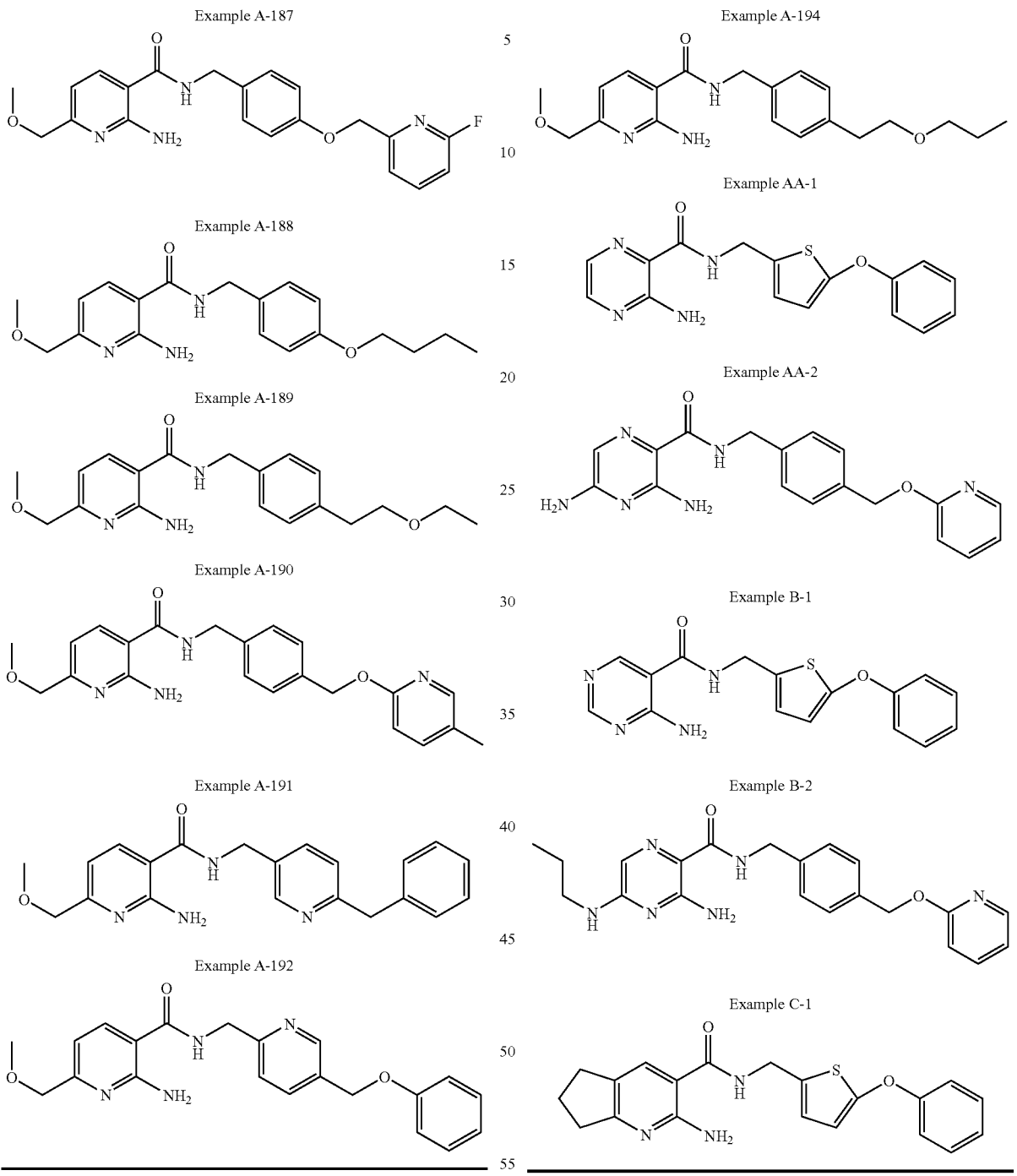
TABLE 37
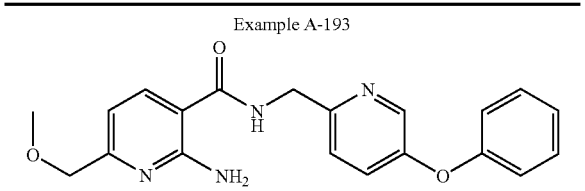
TABLE 38
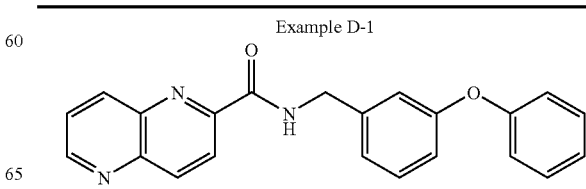

TABLE 38-continued
Example D-2
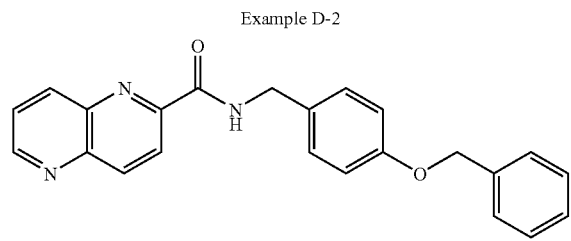
Example D-3
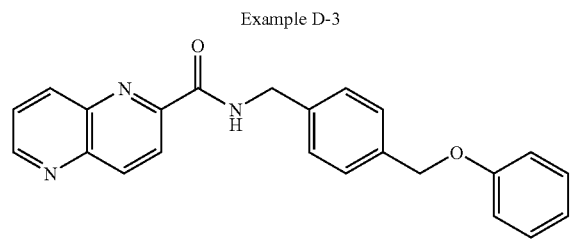
Example D-4
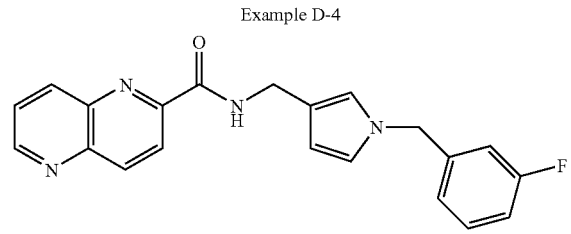
Example D-5
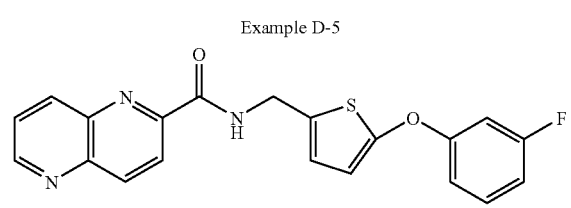
Example D-6
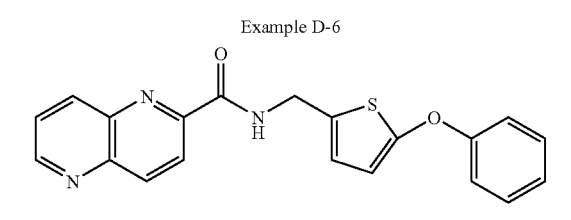
Example D-7
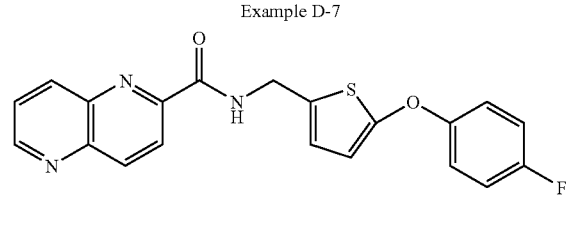
Example D-8
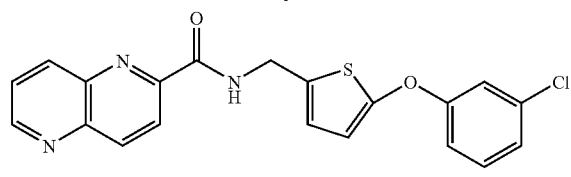
TABLE 38-continued
Example D-9
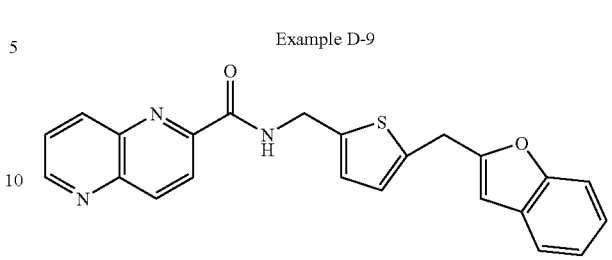
Example D-10
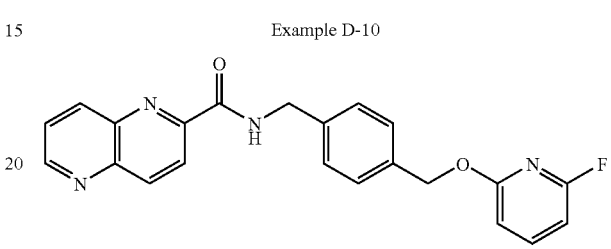
TABLE 39
Example E-1
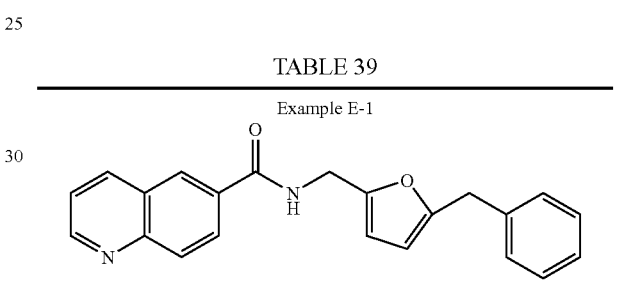
Example E-2
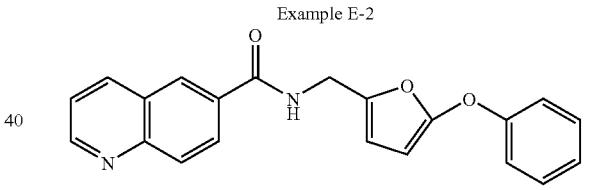
Example E-3
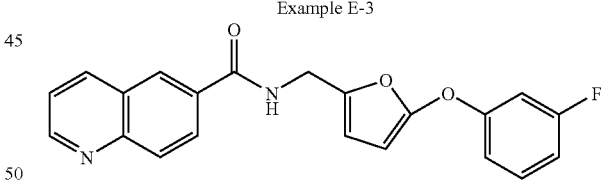
Example E-4
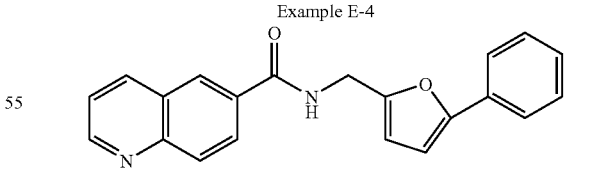
Example E-5
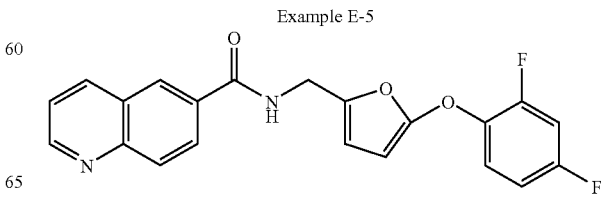

TABLE 39-continued
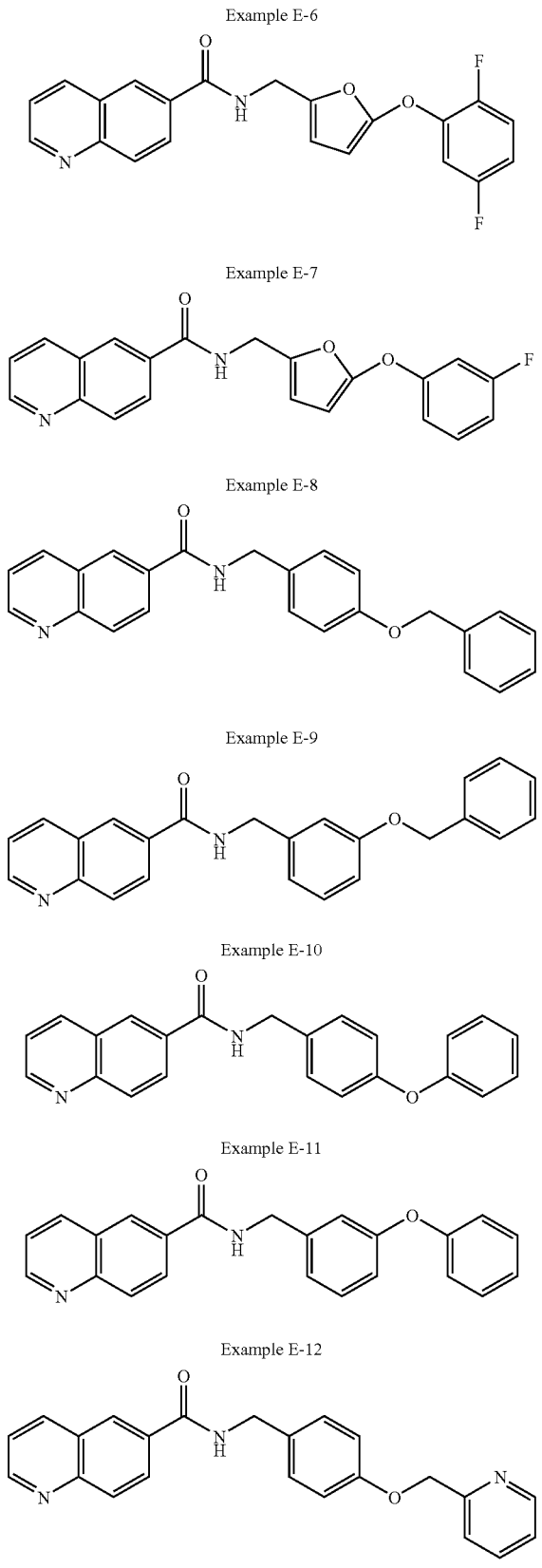
TABLE 40
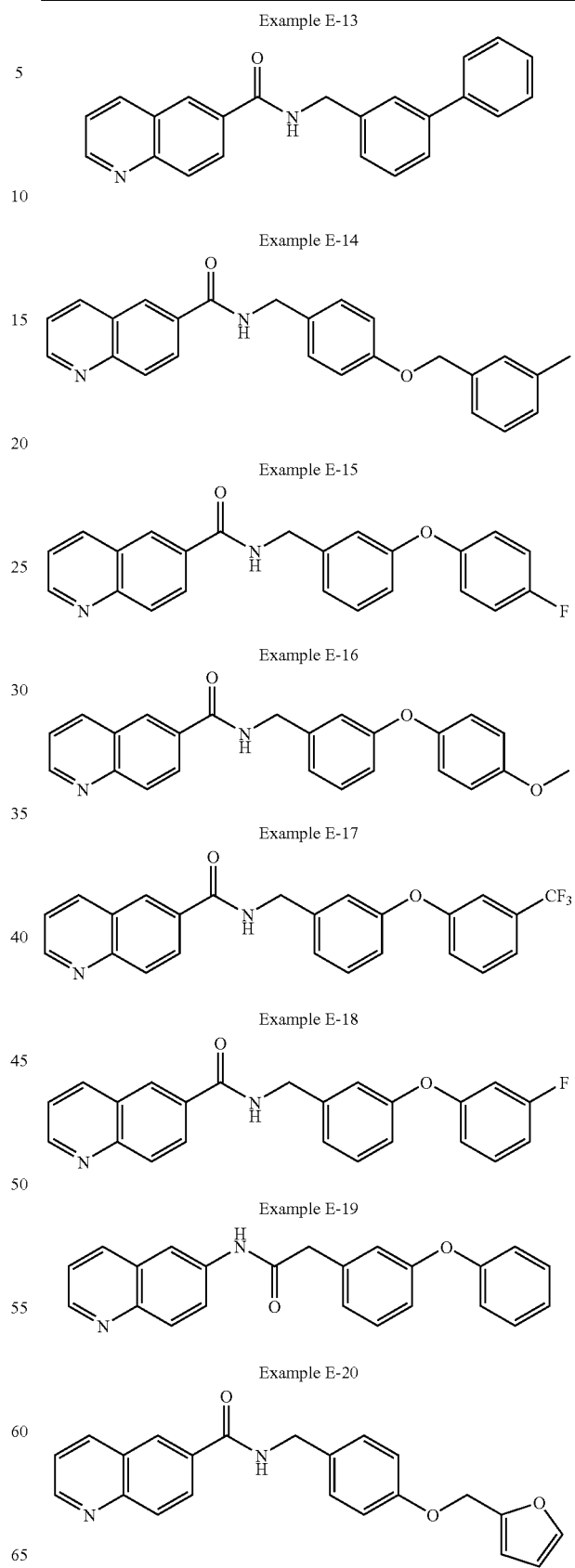

TABLE 40-continued
Example E-21
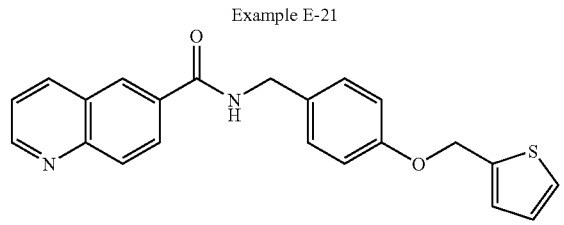
Example E-22
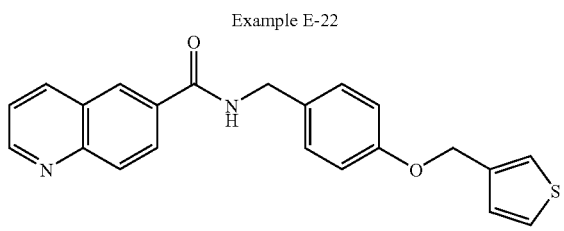
Example E-23
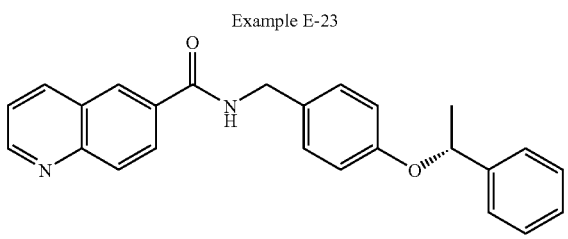
Example E-24
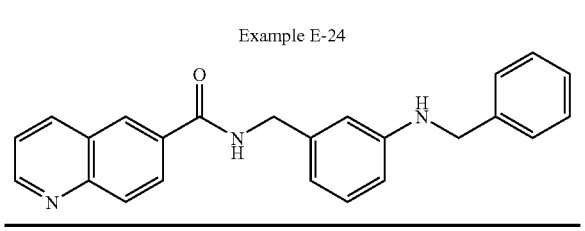
TABLE 41
Example E-25
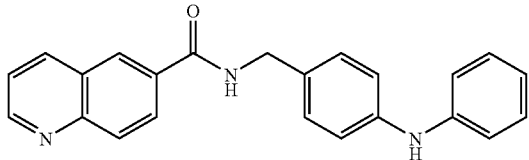
Example E-26
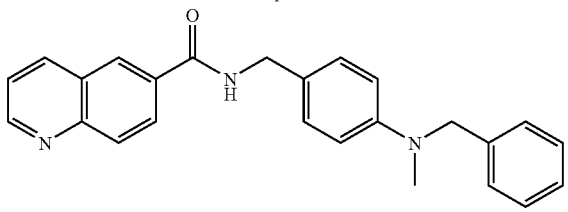
Example E-27
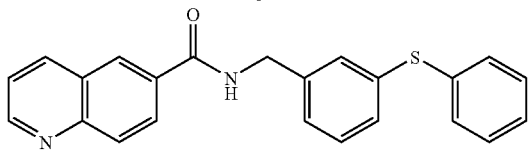
TABLE 41-continued
Example E-28
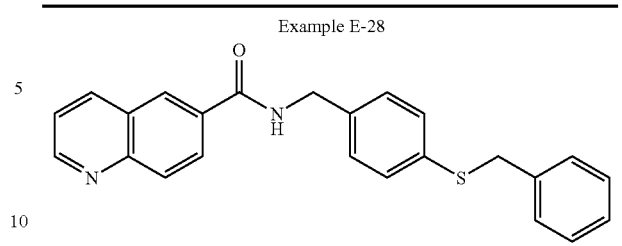
Example E-29
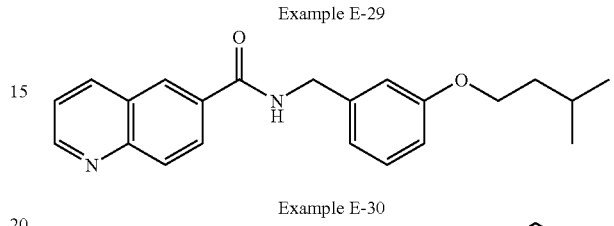
Example E-30
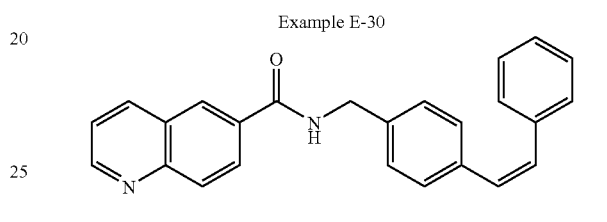
Example E-31
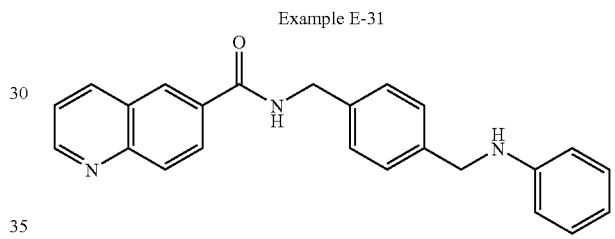
Example E-32
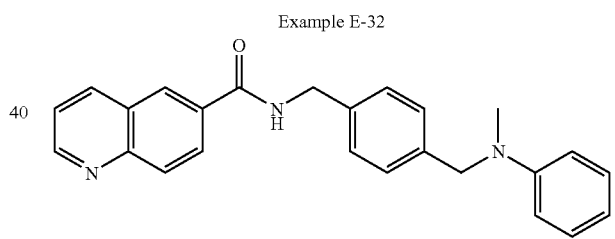
Example E-33
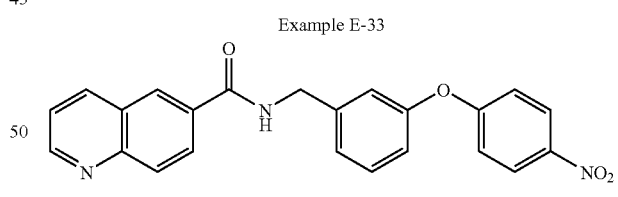
Example E-34
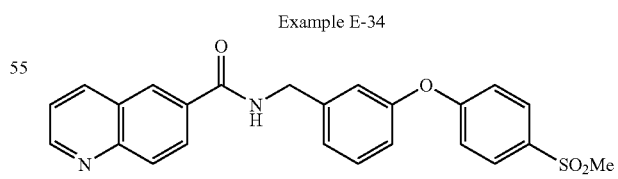
Example E-35
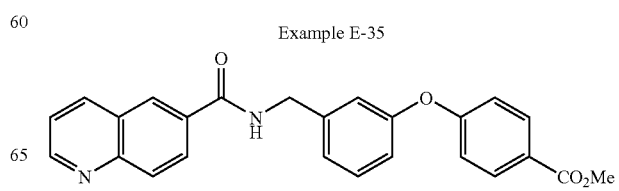

TABLE 41-continued
Example E-36
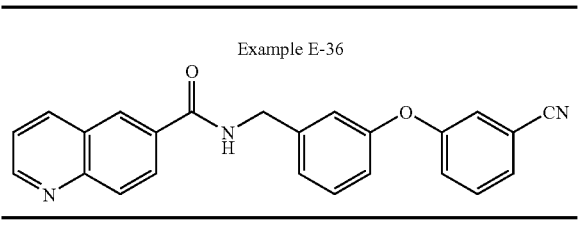
TABLE 42
Example E-37
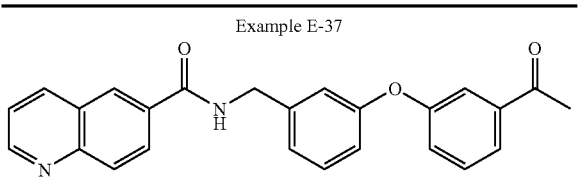
Example E-38
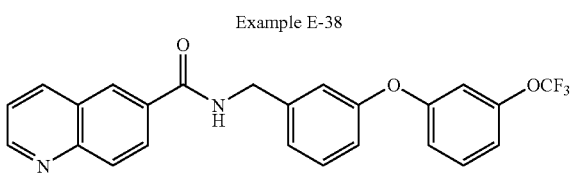
Example E-39
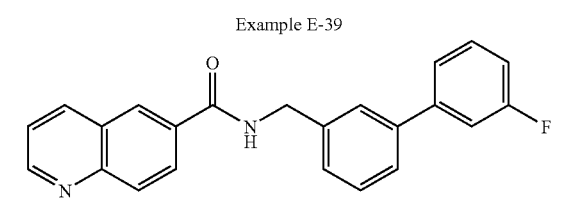
Example E-40
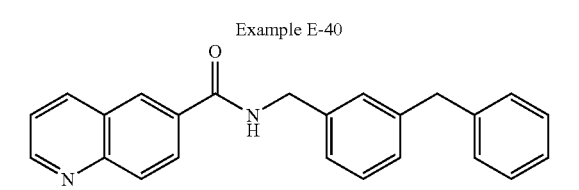
Example E-41
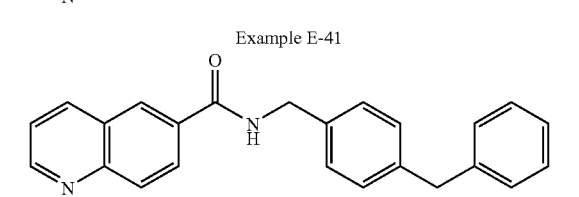
Example E-42
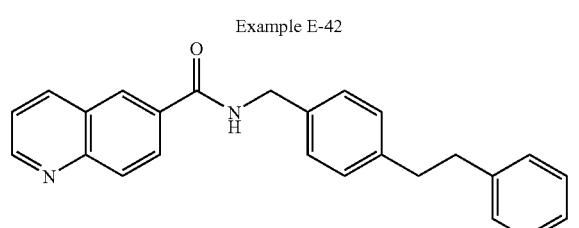
Example E-43
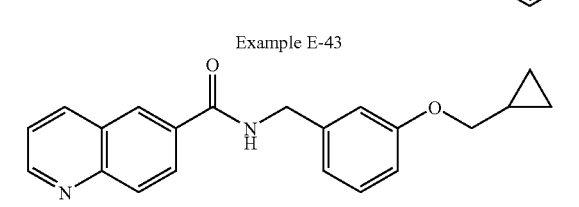
TABLE 42-continued
Example E-44
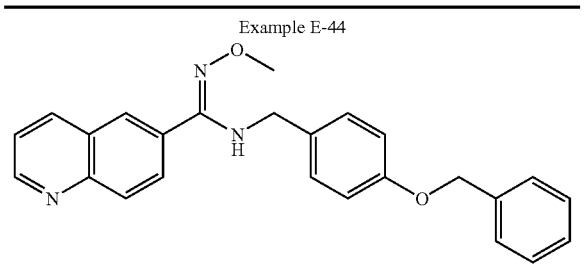
Example E-45
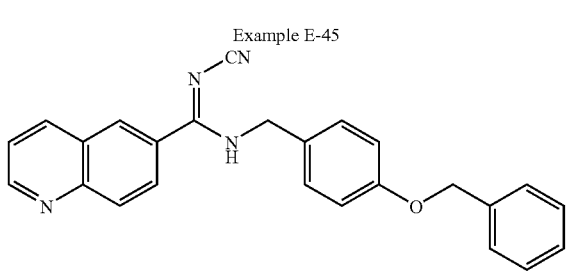
Example E-46
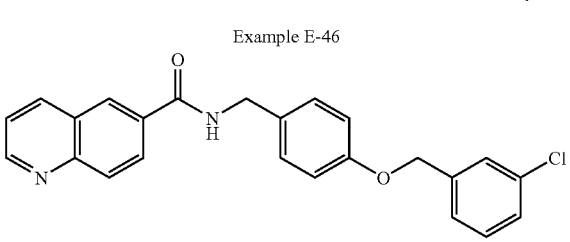
Example E-47
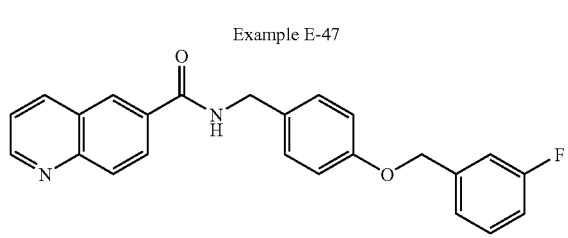
Example E-48
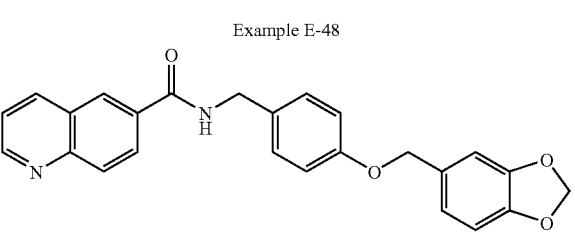
TABLE 43
Example E-49
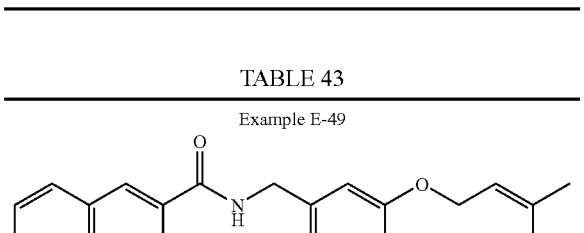
Example E-50
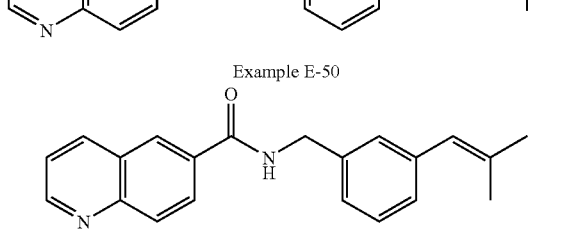

TABLE 43-continued
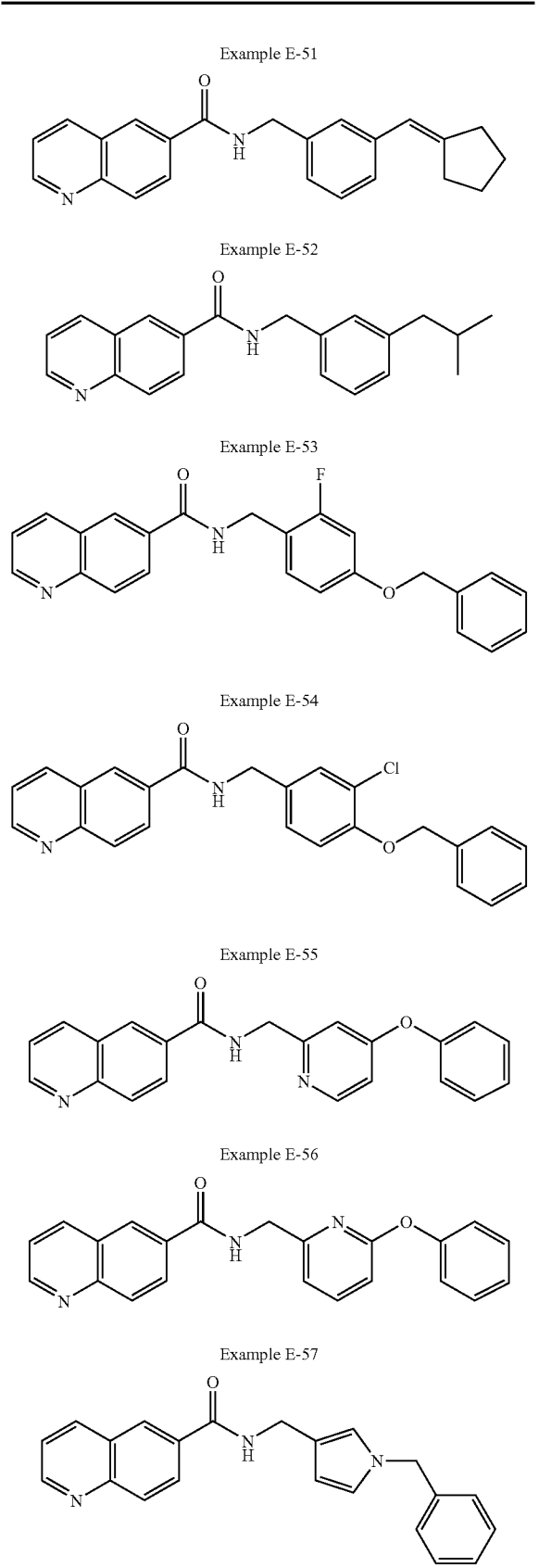
TABLE 43-continued
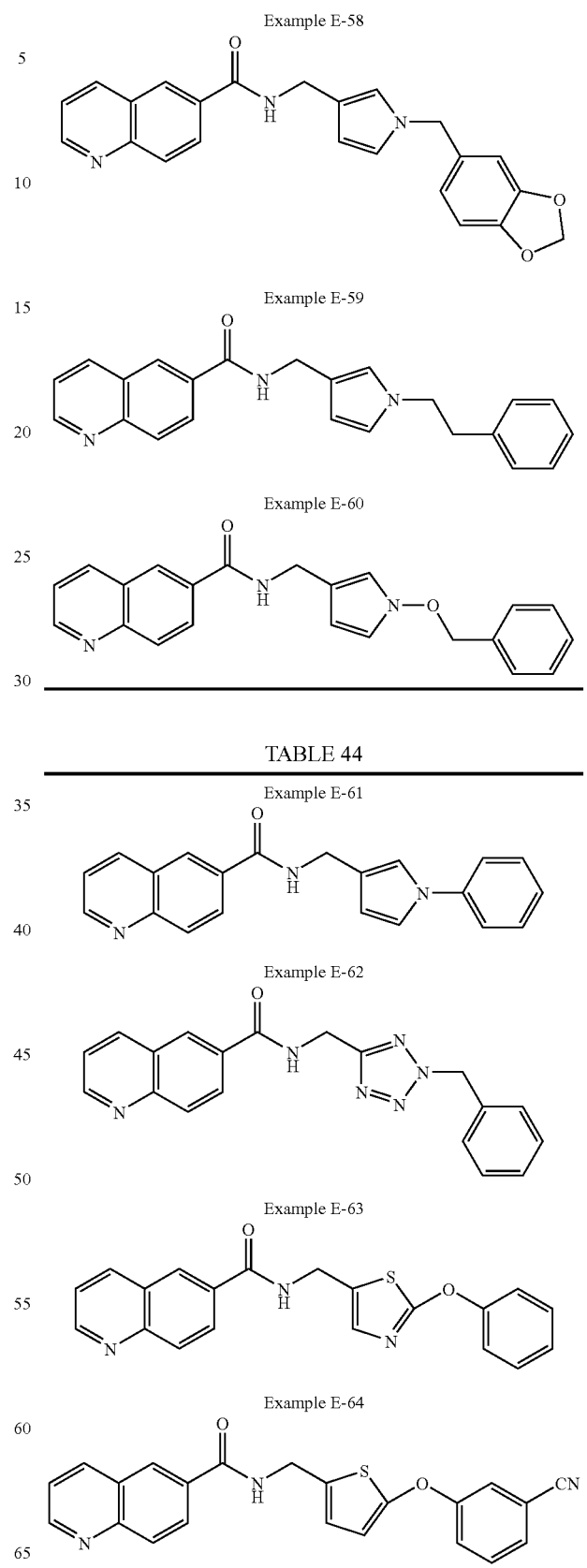

TABLE 44-continued
Example E-65
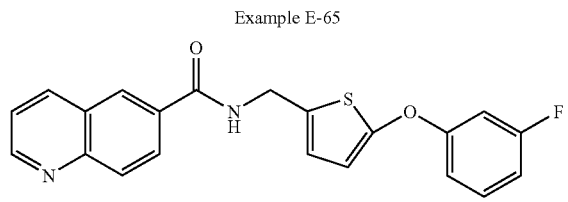
Example E-66
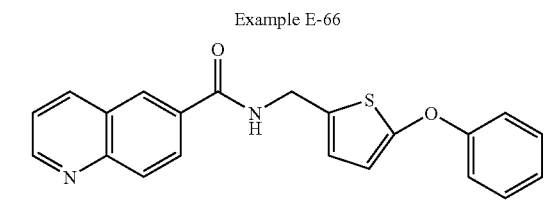
Example E-67
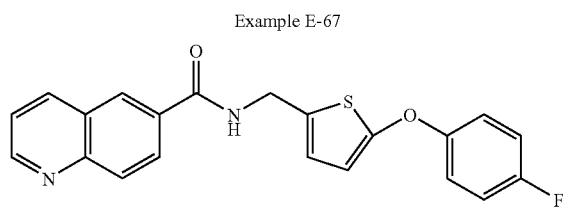
Example E-68
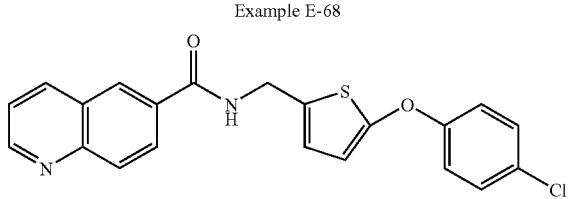
Example E-69
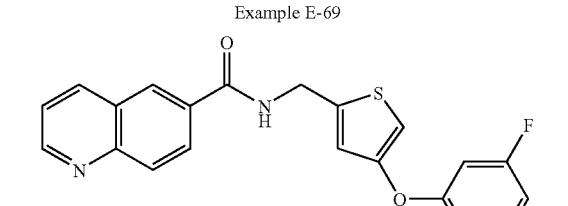
Example E-70
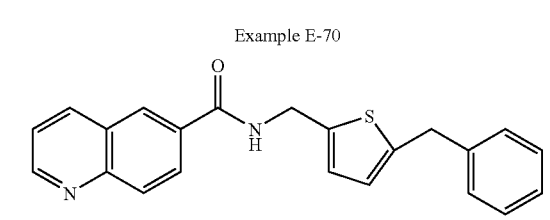
Example E-71
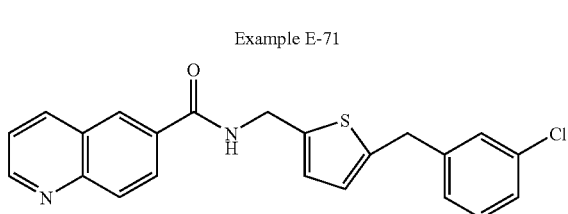
TABLE 44-continued
Example E-72
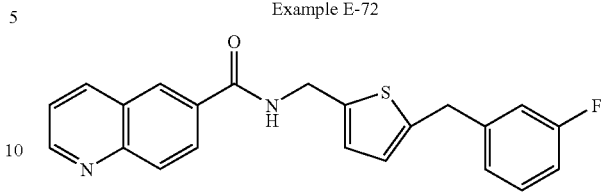
TABLE 45
Example E-73
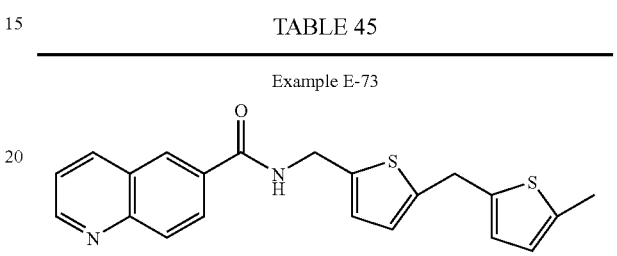
Example E-74
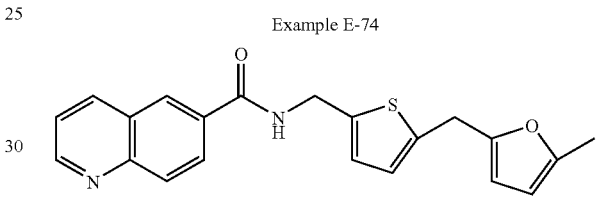
Example E-75
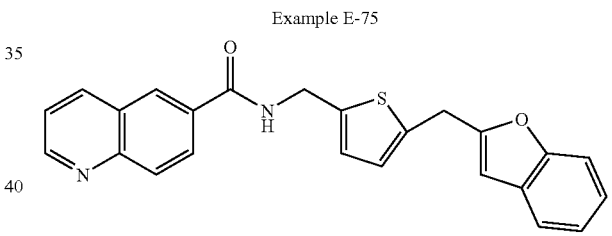
Example E-76
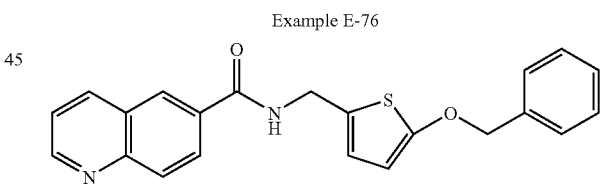
Example E-77
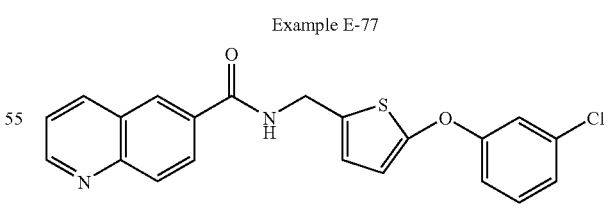
Example E-78
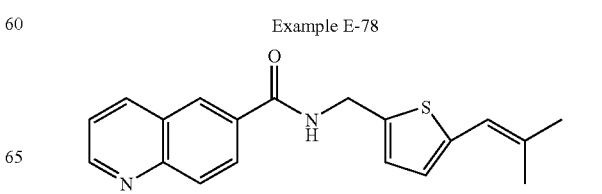

TABLE 45-continued
Example E-79
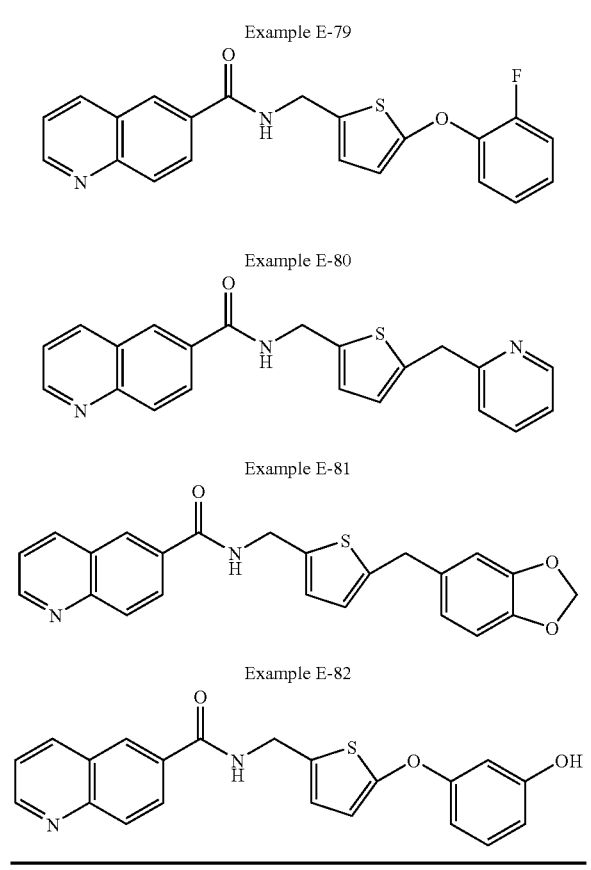
Example E-80
Example E-81
Example E-82
TABLE 46
Example F-1
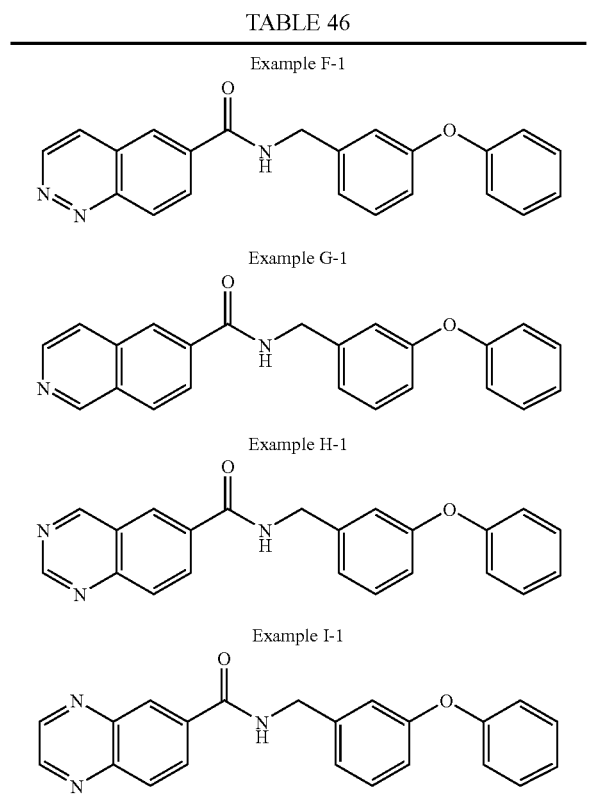
Example G-1
Example H-1
Example I-1
TABLE 46-continued
Example J-1
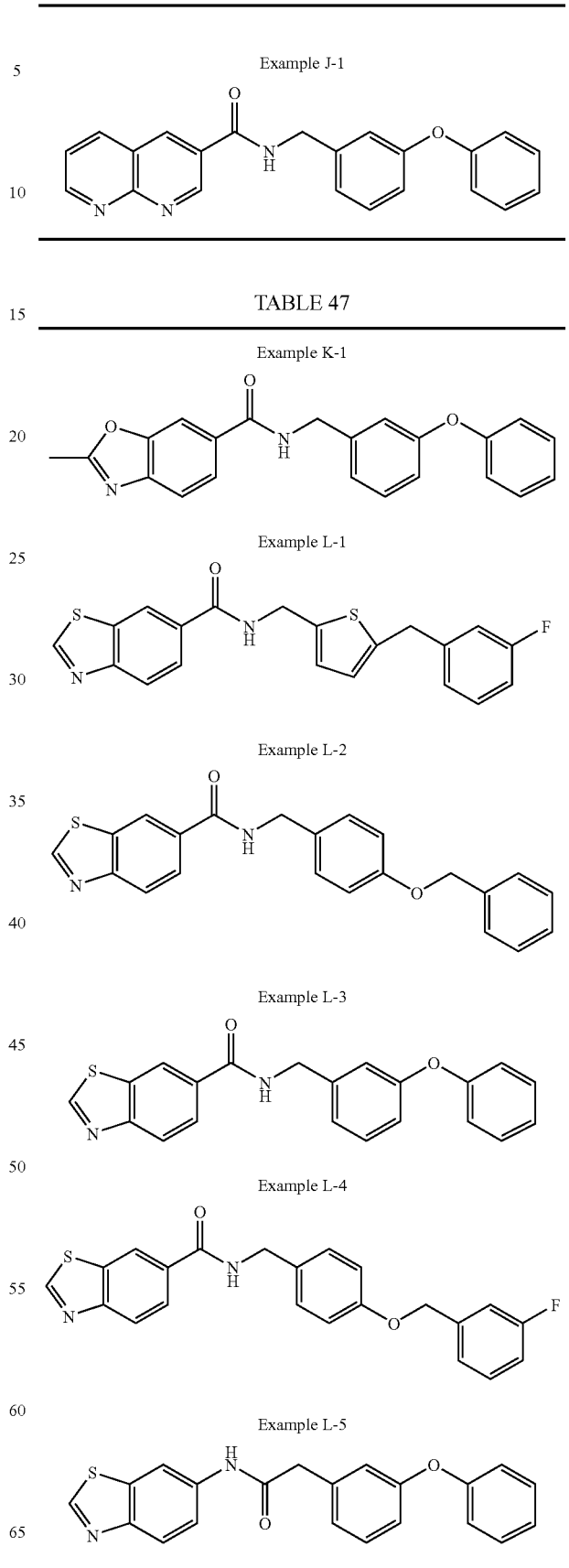
TABLE 47
Example K-1
Example L-1
Example L-2
Example L-3
Example L-4
Example L-5

TABLE 47-continued
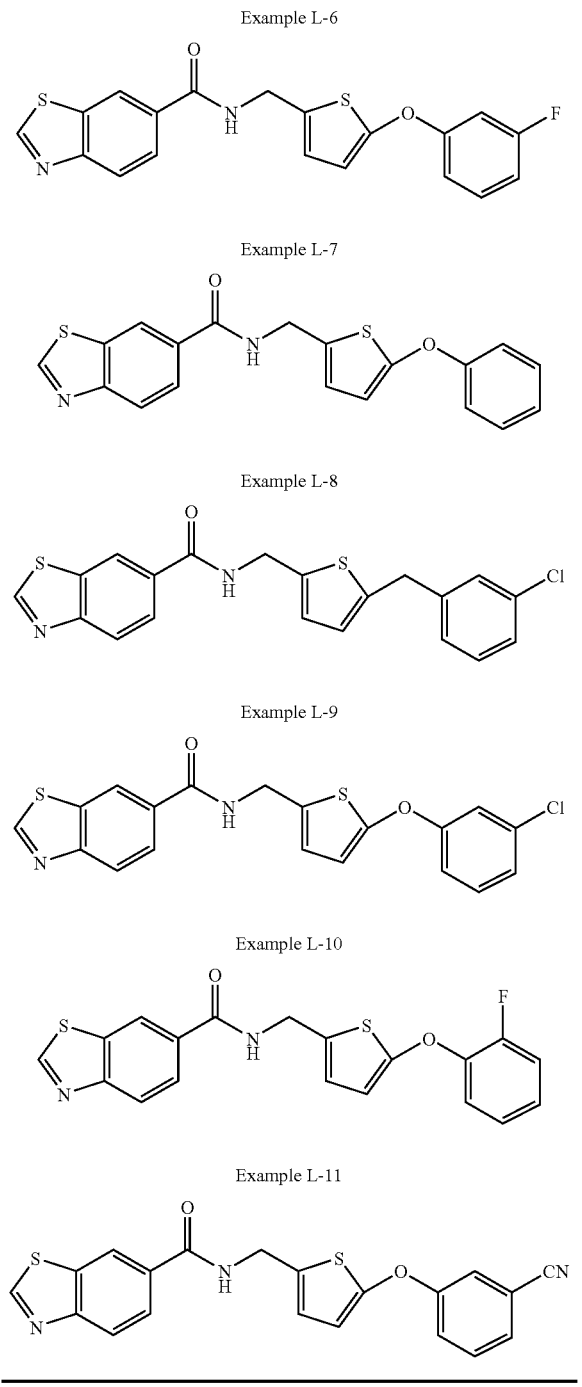
TABLE 48
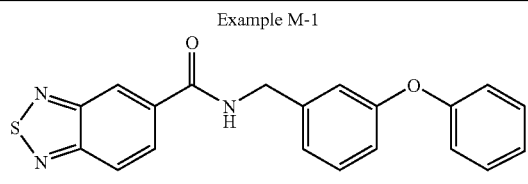
TABLE 48-continued
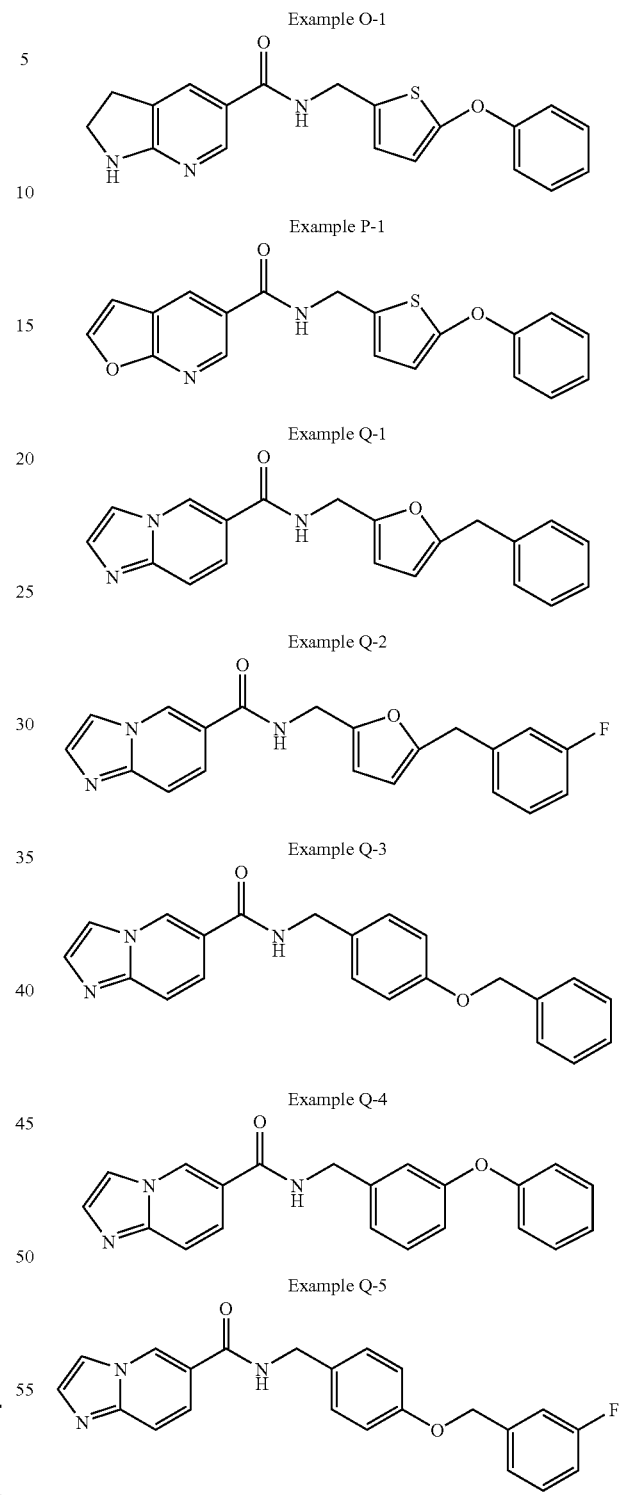
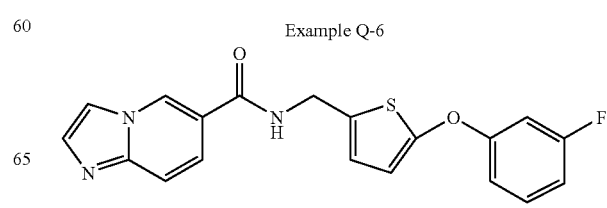

TABLE 48-continued
Example Q-7
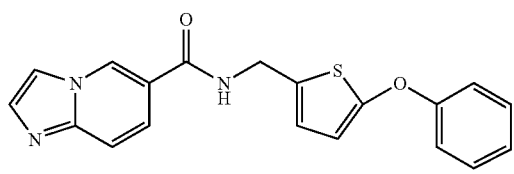
Example Q-8
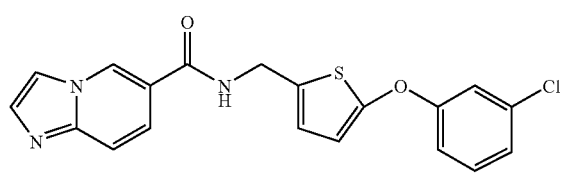
TABLE 49
Example R-1
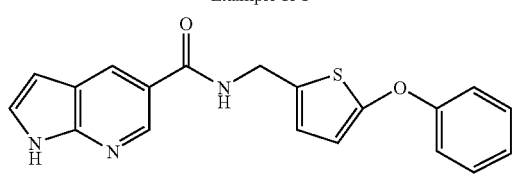
Example R-2
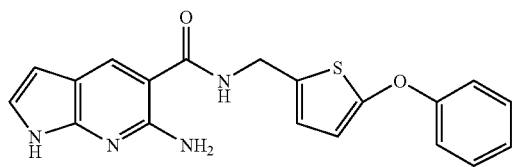
Example S-1
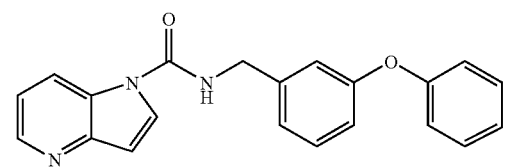
Example T-1
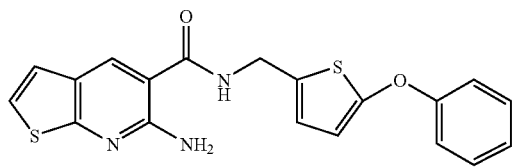
Example T-2
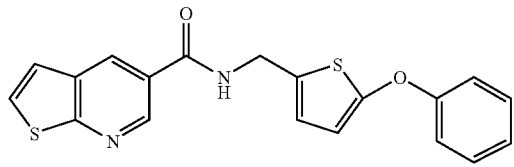
TABLE 49-continued
Example U-1
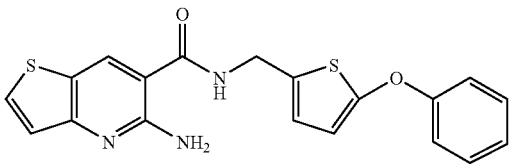
Example U-2
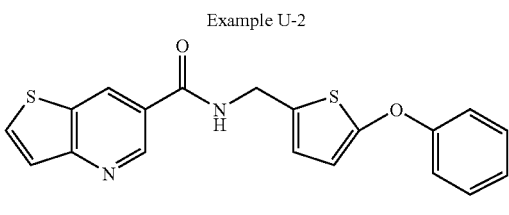
Example V-1
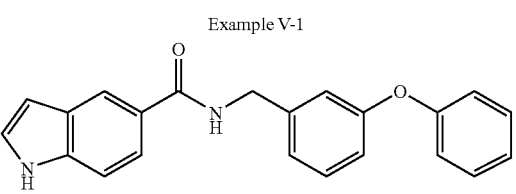
TABLE 50
Example W-1
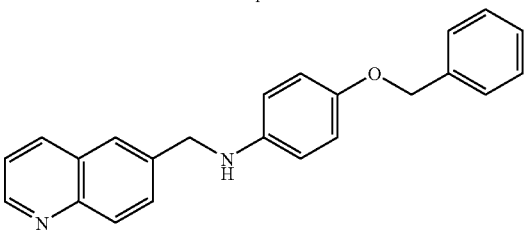
Example W-2
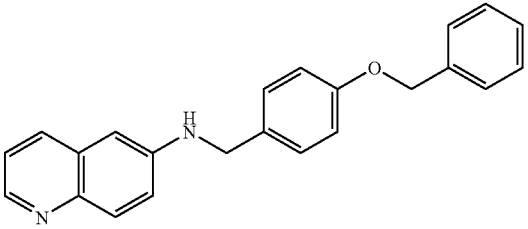
Example W-3
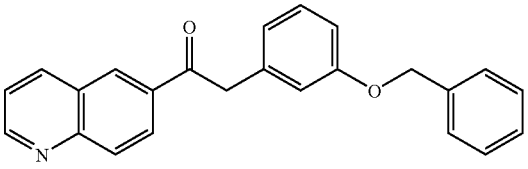
Example W-4
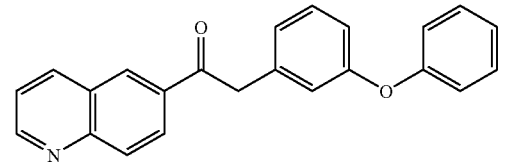

TABLE 50-continued

Example W-5

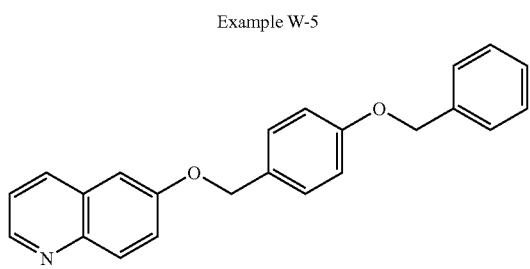

Example W-6

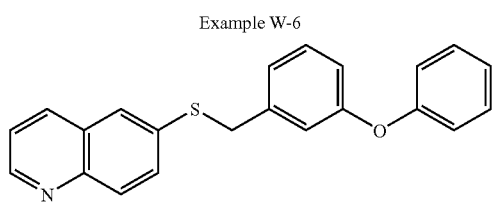

Example X-1

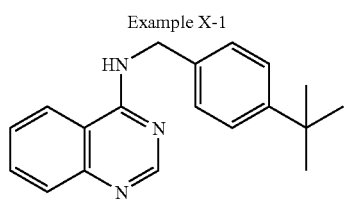

Example X-2

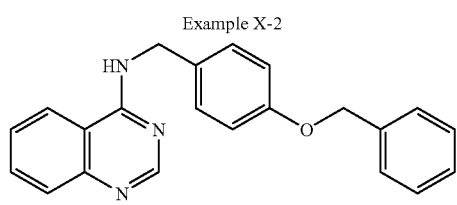

Example Y-1

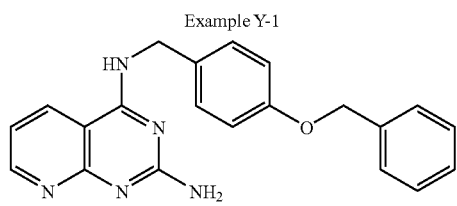

TABLE 51

Example Z-1

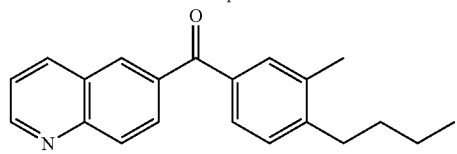

Example Z-2

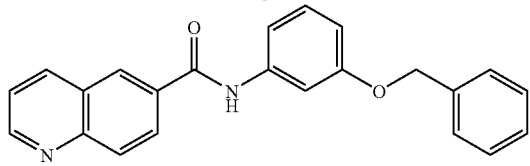

TABLE 51-continued

Example Z-3

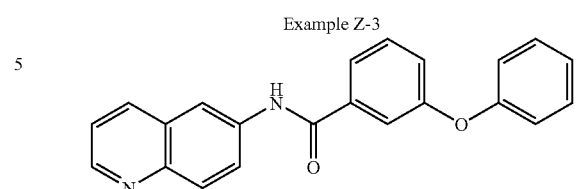

Example Z-4

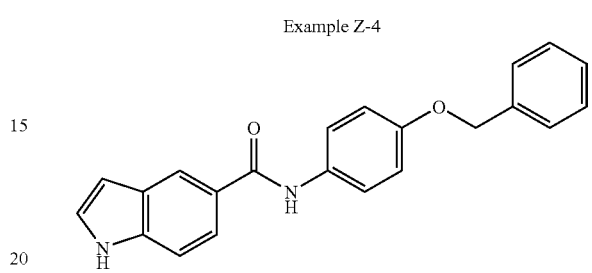

The heterocyclic compounds (I) according to the present invention, or salts, or hydrates thereof, demonstrate excellent inhibitory activity on the GPI-anchored protein transport process, anti-*Candida* activity, anti-*Aspergillus* activity. In addition, it is also excellent in terms of property, safety and metabolic stability, and is extremely useful as a preventive agent or therapeutic agent against fungal infection.

Pharmacological Test Example

In order to demonstrate the usefulness of the compounds (I) according to the present invention, 1. the inhibitory activity on the GPI-anchored protein transport process, 2. the anti-*Candida* activity and the anti-*Aspergillus* activity, 3. the activity in the experimental systemic *candida* infection model in mice, and 4. the activity in the experimental respiratory *aspergillus* infection model in mice, were measured for the antifungal activity of the compounds (I) according to the present invention.
1. Inhibitory Activity on the GPI-Anchored Protein Transport Process A reporter system that reflects the GPI-anchored protein transport process was constructed using cephalosporinase to which the CWP2 carboxyl-terminal sequence, which is known as the cell wall transport signal of a GPI-anchored protein (Van Der Vaat J M et al, J. Bacteriol., 177:3104-3110, 1995), was added. Then, using the constructed reporter system, the activity of the present invention compound that inhibits the transport process of the GPI-anchored protein was measured.

(1). Construction of the Reporter Gene

With pESH plasmid containing the ENO1 promoter, a secretion signal, and a lysozyme gene (Ichikawa K et al, Biosci. Biotech. Biochem., 57 (10), 1686-1690, 1993) as template and the oligonucleotides listed in SEQ ID NO. 1 and SEQ ID NO. 2 as primers, the DNA containing a promoter sequence-secretion signal portion was amplified by PCR, and this was subcloned into the BamHI-NotI site of pUC19 (a). In addition, with the *C. freundii* chromosomal DNA as template and the oligonucleotides listed in SEQ ID NO. 3 and SEQ ID NO. 4 as primers, the cephalosporinase gene was PCR-amplified, and this was subcloned into the NspV-XbaI site of pUC19 (b). Similarly, with the *S. cerevisiae* chromosomal DNA as template and the oligonucleotides listed in SEQ ID NO. 5 and SEQ ID NO. 6 as primers, the CWP2 gene was PCR-amplified, and this was subcloned into the XbaI-HindIII site of pUC19 (c). Furthermore, with pYES2 (INVITROGEN) as template and the oligonucleotides listed in SEQ ID NO. 7 and SEQ ID NO. 8 as primers, the CYC1 terminator was PCR-amplified, and this was subcloned into the NotI-KpnI site of pUC19 (d).

After producing the full length ENO1 promoter and secretion signal portion by inserting the BamHI-SalI fragment of pESH into the BamHI-SalI cleavage site of the plasmid into which (a) had been inserted, the cephalosporinase gene (b) excised with NspV-XbaI and the CWP2 gene (c) excised with XbaI-HindIII were inserted into the NspV-HindIII cleavage site. Next, pRCW63T was produced by excising with EcoRI-HindIII, inserting this fragment into the integration vector pRS306 (Sikorski R S et al, Genetics. 122 (1):19-27, 1989), and then inserting the CYC1 terminator (d) into the HindIII-KpnI cleavage site (2). Introduction of the Reporter Gene Into *S. cerevisiae*

The *S. cerevisiae* G2-10 strain was cultured by shaking in 10 ml of YPD culture medium at 30° C., and the cells were collected at the late logarithmic growth phase (2 to $5\times10^7$ cells/ml). After washing with sterilized water, pRCW63T produced in (1) was introduced by the lithium acetate method (described in the YEASTMAKER™ Yeast Transformation System User Manual) using the YEASTMAKER™ Yeast Transformation System (Clontech). pRCW63T in which the URA3 gene was cleaved with ApaI was used. After culturing in SD(Ura-) culture medium for 3 days at 30° C., the grown colonies were cultured in YPD culture medium.

When the localization of the cephalosporinase activity was confirmed; the activity was mainly localized in the cell wall, the C-terminal sequence of CWP2 was confirmed to function as a transport signal to the cell wall.

(3). Measurement By a Reporter System of the Inhibitory Activity on the GPI-anchored Protein Transport Process A screening of the compounds was performed using *S. cerevisiae* in which pRCW63T was introduced (*S. cerevisiae* CW63 strain).

After a standing culture in a YPD liquid culture medium for 48 hours at 30° C., 75 µl/well of a fungal suspension diluted 10-fold with YPD liquid culture medium (3 to $5\times10^5$ cells/ml) was used to inoculate a V-bottomed 96 well plate containing 25 µl/well of test compound dilute solution, and a standing culture was carried out for 48 hours at 30° C. The plate was centrifuged, then, 25 µl of supernatant was sampled into a 96 well flat-bottomed plate, the resulting solution serving as the culture medium supernatant fraction.

The precipitated cells were suspended, 75 µl/well of zymolyase (Seikagaku Kogyo) solution prepared with 2.4M sorbitol was added, and allowed to act for 1 hour at 30° C. The plate was centrifuged, then, 10 µl of supernatant was sampled in a 96 well flat-bottomed plate, 15 µl of phosphate buffer was added, the resulting solution serving as the cell wall fraction.

The pooled sample was added 200 µM of nitrocefin solution, after a predetermined time, the reaction was stopped with a citric acid buffer, then, the optical density at 490 nm was measured, to measure the cephalosporinase activity in the culture medium and the cell wall fraction. A compound that increases the cephalosporinase activity in the culture medium supernatant fraction, or decreases the cephalosporinase activity in the cell wall fraction, was considered as a compound that inhibits the transport process of GPI-anchored protein to the cell wall.

In addition, fungal growth in the presence of the test compound was visually determined.

2. Anti-*Candida* Activity and Anti-*Aspergillus* Activity (1). Preparation of Fungal Suspension For the *C. albicans* E81022 strain, a fungal suspension from a standing culture for 48 hours at 30° C. in a Sabouraud dextrose liquid culture medium (SDB) was diluted 10,000-fold with a 1.3-fold concentrated SDB to adjust to a fungal suspension of 1 to $2\times10^4$ cells/ml. For the *A. fumigatus* Tsukuba strain, –80° C. stored strain was diluted 1,000-fold with a 1.3-fold concentrated SDB to adjust to a fungal suspension of 2 to $3\times10^3$ cells/ml.

(2). Preparation of an Agent Dilution Plate

Using a U-bottomed 96 well plate, 8 samples/plate (A to H) of sample dilution solutions were prepared. On the $3^{rd}$ row of each plate was dispensed 240 µl of sterilized and distilled water, and on the $2^{nd}$ and $4^{th}$ to $12^{th}$ rows were dispensed 125 µl of 4% dimethylsulfoxide solution. Weighed sample was dissolved in dimethylsulfoxide to prepare a 2.5 to 20 mg/ml solution, 10 µl of this solution was then added to the $3^{rd}$ row of the prepared plate, and 10 steps of two-fold step dilutions (125 µl of solution+125 µl of 4% dimethylsulfoxide) were performed on the plate. This sample dilution solution was dispensed in the amount of 25 µl to a V-bottomed or flat-bottomed 96 well plate for MIC measurement to prepare a sample dilution plate.

(3). Inoculation of Fungal Suspension and Culture

The fungal suspension preprared in (1) was used in the amount of 75 µl/well to inoculate a V-bottomed or flat-bottomed 96 well plate containing 25 µl/well of test compound dilution solution prepared in (2), and a standing culture was carried out aerobically for 48 hours at 30 to 35° C.

(4). MIC Measurement

The minimum concentration that clearly inhibited fungal growth as compared to the control by visual inspection was determined as the minimum inhibitory concentration (MIC).

The following representative compounds prepared in the examples were measured for their inhibitory activity on the GPI-anchored protein transport process, anti-*candida* activity and anti-*aspergillus* activity by the measurement methods described in 1 and 2. As a result, as shown in Table 52 to Table 54, it was found that the compounds according to the present invention inhibited the GPI-anchored protein transport process, and have anti-*candida* activity and anti-*aspergillus* activity.

[Table 52]

TABLE 52

| Example Nos. | Reporter System Inhibitory Activity (µg/ml) |
|---|---|
| A-5 | 0.2 |
| A-8 | 3.13 |
| A-10 | 0.2 |
| A-22 | 0.2 |
| A-37 | 0.1 |
| A-39 | 0.78 |
| A-53 | 0.1 |
| A-54 | 0.2 |
| A-68 | 0.05 |
| A-70 | 0.025 |
| A-81 | 1.56 |
| A-82 | 0.2 |
| A-92 | 3.13 |
| A-98 | 0.2 |
| A-99 | 0.78 |
| A-101 | 0.1 |
| A-112 | 3.13 |
| A-116 | 0.39 |

TABLE 52-continued

| Example Nos. | Reporter System Inhibitory Activity (μg/ml) |
|---|---|
| A-124 | 1.56 |
| A-126 | 1.56 |
| A-131 | 0.39 |
| A-136 | 0.78 |
| A-137 | 0.78 |
| A-139 | 0.78 |
| A-170 | 0.39 |
| A-171 | 0.1 |
| B-1 | 3.13 |
| C-1 | 0.1 |
| D-2 | 0.39 |
| E-8 | 0.1 |
| E-11 | 0.2 |
| E-13 | 0.2 |
| E-19 | 0.2 |
| E-25 | 0.2 |
| E-43 | 0.1 |
| E-44 | 0.78 |
| E-45 | 0.78 |
| E-51 | 0.2 |
| E-53 | 0.2 |
| E-57 | 0.1 |
| E-64 | 0.39 |
| E-73 | 0.2 |
| E-65 | 0.1 |
| E-67 | 0.025 |
| E-69 | 0.2 |
| E-71 | 0.1 |
| F-1 | 1.56 |
| G-1 | 1.56 |
| H-1 | 1.56 |
| I-1 | 0.2 |
| K-1 | 0.39 |
| L-4 | 0.2 |
| L-7 | 0.1 |
| M-1 | 0.39 |
| Q-7 | 0.39 |
| R-1 | 0.2 |
| U-2 | 0.2 |
| V-1 | 0.78 |
| W-1 | 0.78 |
| W-2 | 0.39 |
| Y-1 | 0.2 |

[Table 53]

TABLE 53

| Example Nos. | Anti-*Candida* Activity (μg/ml) |
|---|---|
| A-5 | 0.2 |
| A-8 | 3.13 |
| A-10 | 0.78 |
| A-22 | 0.78 |
| A-37 | 0.39 |
| A-39 | 1.56 |
| A-53 | 0.39 |
| A-54 | 0.78 |
| A-68 | 0.05 |
| A-70 | 0.05 |
| A-81 | 3.13 |
| A-82 | 0.2 |
| A-92 | 3.13 |
| A-98 | 0.39 |
| A-99 | 3.13 |
| A-101 | 0.1 |
| A-112 | 3.13 |
| A-116 | 0.39 |
| A-124 | 1.56 |
| A-126 | 0.78 |
| A-131 | 1.56 |
| A-136 | 1.56 |
| A-137 | 1.56 |
| A-139 | 1.56 |
| A-170 | 0.78 |
| A-171 | 0.2 |
| B-1 | 3.13 |
| C-1 | 0.1 |
| D-2 | 0.78 |
| E-8 | 0.2 |
| E-11 | 0.39 |
| E-13 | 0.78 |
| E-19 | 0.78 |
| E-25 | 1.56 |
| E-43 | 0.39 |
| E-44 | 3.13 |
| E-45 | 3.13 |
| E-51 | 0.78 |
| E-53 | 1.56 |
| E-57 | 0.2 |
| E-64 | 0.2 |
| E-65 | 0.1 |
| E-67 | 0.39 |
| E-69 | 0.1 |
| E-71 | 0.2 |
| E-73 | 0.2 |
| F-1 | 3.13 |
| G-1 | 6.25 |
| I-1 | 0.78 |
| K-1 | 0.78 |
| L-4 | 0.2 |
| L-7 | 0.1 |
| M-1 | 1.56 |
| Q-7 | 0.39 |
| R-1 | 0.39 |
| U-2 | 0.78 |
| W-1 | 0.39 |
| W-2 | 1.56 |
| Y-1 | 0.78 |

[Table 54]

TABLE 54

| Example Nos. | Anti-*Aspergillus* Activity (μg/ml) |
|---|---|
| A-5 | 0.78 |
| A-8 | 6.25 |
| A-10 | 1.56 |
| A-22 | 3.13 |
| A-37 | 3.13 |
| A-39 | 1.56 |
| A-53 | 0.78 |
| A-54 | 1.56 |
| A-68 | 0.78 |
| A-70 | 0.78 |
| A-81 | 6.25 |
| A-82 | 1.56 |
| A-98 | 1.56 |
| A-99 | 6.25 |
| A-101 | 0.39 |
| A-112 | 6.25 |
| A-116 | 3.13 |
| A-126 | 6.25 |
| A-131 | 6.25 |
| A-139 | 1.56 |
| A-171 | 1.56 |
| B-1 | 6.25 |
| D-2 | 0.78 |
| E-8 | 0.2 |
| E-11 | 1.56 |

TABLE 54-continued

| Example Nos. | Anti-Aspergillus Activity (μg/ml) |
|---|---|
| E-13 | 1.56 |
| E-19 | 1.56 |
| E-45 | 3.13 |
| E-51 | 3.13 |
| E-53 | 3.13 |
| E-57 | 6.25 |
| E-64 | 6.25 |
| E-65 | 1.56 |
| E-67 | 0.78 |
| E-69 | 1.56 |
| E-71 | 1.56 |
| E-73 | 0.78 |
| I-1 | 1.56 |
| K-1 | 1.56 |
| L-4 | 0.2 |
| L-7 | 0.78 |
| M-1 | 1.56 |
| Q-7 | 6.25 |
| R-1 | 3.13 |
| U-2 | 3.13 |
| V-1 | 6.25 |
| W-1 | 0.78 |
| W-2 | 0.78 |
| Y-1 | 6.25 |

3. Experimental Systemic *Candida* Infection Model in Mice (1). Preparation of Fungal Inoculum A standing culture of *C. albicans* E81022 strain was carried out for 48 hours at 30° C. in Sabouraud dextrose agar medium (SDA), the recovered fungal cells were suspended in sterilized physiological saline. By counting the fungal number on a cytometry plate, the suspension was diluted to $2 \times 10^7$ cells/ml with sterilized physiological saline to serve as fungal inoculum.

(2). Infection

The fungal inoculum was used in the amounts of 0.2 ml to inoculate 4.5 to 5.5 week-old female ICR mice in the tail vein ($4 \times 10^6$ cells/mouse).

(3). Treatment

From 0.5 to 1 hour after fungal inoculation, 0.2 ml of agent solution (dissolved or suspended in sterilized physiological saline containing 6.5% dimethylsulfoxide and 3.5% Tween 80) was administered into the stomach using a peroral probe, 3 times every 4 hours. The agent concentration was 2.5 mg/kg, and the number of animals in one group was 5 animals.

(4). Determination of the Effect

The protective effect was determined by observing life/death until 14 days after infection and calculating the mean survival days.

As a result, as shown in Table 55, mice administered with the compounds according to the present invention survived for a long time as compared to the untreated group, and the compounds according to the present invention have been also found to demonstrate anti-*candida* activity in vivo.

[Table 55]

TABLE 55

| Example Nos. | Mean Survival Days (Days) |
|---|---|
| A-10 | 12.5 |
| A-53 | 13.4 |
| A-54 | 10.0 |
| A-68 | 10.6 |
| A-70 | 12.6 |
| A-137 | 12.8 |
| E-65 | 11.6 |
| R-1 | 10.4 |
| Non-Administered Group | 2.2~4.0 |

4. *Aspergillus* Respiratory Infection (1). Increasing Susceptibility of Mice to Infection In order to increase susceptibility of the mice to infection, 200 mg/kg of 5-fluorouracil was administered subcutaneously 6 days prior to infection.

(2). Test Strain

*A. fumigatus* Tsukuba strain was used.

(3). Prepration of Fungal Inoculum

A spore suspension of the infection strain was used to coat a potato dextrose agar medium (PDA), a standing culture was carried out for 4 to 7 days at 35° C., spore was then suspended in a sterilized physiological saline containing 0.05% Tween 80. By counting the pore count on a cytometry plate, the suspension was diluted to $6 \times 10^5$ cells/ml with sterilized physiological saline containing 0.05% Tween 80 to serve as fungal inoculum.

(4). Infection

Under ketalar anesthesia, 50 μl of fungal inoculum was used to inoculate 8 to 9 week-old female DBA/2N mice in the nose ($3 \times 10^4$ cells/mouse).

(5). Treatment

From 1 hour after fungal inoculation, 0.2 ml of agent solution (dissolved or suspended in sterilized physiological saline containing 6.5% DMSO and 3.5% Tween 80), was administered into the stomach using a peroral probe 3 times per day for 3 days. The agent dosage was from 20 or 40 mg/kg, and the number of animals in one group was 5 animals.

(6). Determination of the Effect

The protective effect was determined by observing life/death until 14 days after infection and calculating the mean survival days.

As a result, as shown in Table 56, mice administered with the compounds according to the present invention survived for a long time as compared to the untreated group, and the compounds according to the present invention have been also found to demonstrate anti-*aspergillus* activity in vivo.

[Table 56]

TABLE 56

| Example Nos. | Mean Survival Days (Days) |
|---|---|
| A-11 | 10.4 |
| A-31 | 11.2 |
| A-32 | 11.8 |
| A-55 | 12.6 |
| A-56 | 10.8 |
| D-4 | 10.8 |
| D-7 | 10.6 |
| Non-Administered Group | 4.0~4.2 |

INDUSTRIAL APPLICABILITY

The heterocyclic compounds (I) according to the present invention, or a salt or a hydrate thereof, 1) demonstrate effects against occurrence, development and persistence of infectious disease by inhibiting the expression of cell wall surface layer protein and inhibiting cell wall assembly, while at the same time, inhibiting adhesion of fungus onto the cells, preventing the pathogen from showing pathogenicity, in addition, 2) are also excellent in terms of property, safety and metabolic stability, and extremely useful as a preventive or therapeutic agent of fungal infection.

---

We claim:

1. A compound represented by the formula (I-a), or a salt thereof:

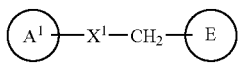

(I-a)

wherein $A^1$ represents a 3-pyridyl group;

$X^1$ represents a group represented by the formula —C(=$Y^1$)—NH—, wherein $Y^1$ represents an oxygen atom or a sulfur atom;

E represents a thienyl group;

with the proviso that $A^1$ optionally has 1 to 3 substituents selected from the following substituent groups a-1 and a-2, and that E has 1 or 2 substituents selected from the substituent groups a-1' and a-2';

<substituent group a-1> substituent group a-1 represents the group consisting of: a halogen atom, a hydroxyl group, a mercapto group, a cyano group, a carboxyl group, an amino group, a carbamoyl group, a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a $C_{3-8}$ cycloalkyl $C_{1-6}$ alkyl group, a $C_{3-8}$ cycloalkylidene $C_{1-6}$ alkyl group, a $C_{6-10}$ aryl $C_{1-6}$ alkyl group, a $C_{1-6}$ alkoxy group, a $C_{2-6}$ alkenyloxy group, a $C_{2-6}$ alkynyloxy group, a $C_{3-8}$ cycloalkoxy group, a $C_{3-8}$ cycloalkyl $C_{1-6}$ alkoxy group, a $C_{6-10}$ aryl $C_{1-6}$ alkoxy group, a $C_{1-6}$ alkylthio group, a $C_{2-6}$ alkenylthio group, a $C_{2-6}$ alkynylthio group, a $C_{3-8}$ cycloalkylthio group, a $C_{6-10}$ arylthio group, a $C_{3-8}$ cycloalkyl $C_{1-6}$ alkylthio group, a $C_{6-10}$ aryl $C_{1-6}$ alkylthio group, a mono-$C_{1-6}$ alkylamino group, a mono-$C_{2-6}$ alkenylamino group, a mono-$C_{2-6}$ alkynylamino group, a mono-$C_{3-8}$ cycloalkylamino group, a mono-$C_{6-10}$ arylamino group, a mono-$C_{3-8}$ cycloalkyl $C_{1-6}$ alkylamino group, a mono-$C_{6-10}$ aryl $C_{1-6}$ alkylamino group, a di-$C_{1-6}$ alkylamino group, a N—$C_{2-6}$ alkenyl-N—$C_{1-6}$ alkylamino group, a N—$C_{2-6}$ alkynyl-N—$C_{1-6}$ alkylamino group, a N—$C_{3-8}$ cycloalkyl-N—$C_{1-6}$ alkylamino group, a N—$C_{6-10}$ aryl-N—$C_{1-6}$ alkylamino group, a N—$C_{3-8}$ cycloalkyl $C_{1-6}$ alkyl-N—$C_{1-6}$ alkylamino group, a N—$C_{6-10}$ aryl $C_{1-6}$ alkyl-N—$C_{1-6}$ alkylamino group, a $C_{1-6}$ alkylcarbonyl group, a $C_{1-6}$ alkoxycarbonyl group, a $C_{1-6}$ alkylsulfonyl group, a group represented by the formula —C(=N—$R^{a1}$)$R^{a2}$ (wherein $R^{a1}$ represents a hydroxyl group or a $C_{1-6}$ alkoxy group; $R^{2a}$ represents a $C_{1-6}$ alkyl group), and a $C_{6-10}$ aryloxy $C_{1-6}$ group;

<substituent group a-2> substituent group a-2 represents the group consisting of: a $C_{1-6}$ alkyl group, a $C_{2-6}$ alkynyl group, a $C_{3-8}$ cycloalkyl group, a $C_{6-10}$ aryl group, a $C_{3-8}$ cycloalkyl $C_{1-6}$ alkyl group, a $C_{6-10}$ aryl $C_{1-6}$ alkyl group, a $C_{1-6}$ alkoxy group, a $C_{2-6}$ alkenyloxy group, a $C_{2-6}$ alkynyloxy group, a $C_{3-8}$ cycloalkoxy group, a $C_{3-8}$ cycloalkyl $C_{1-6}$ alkoxy group, a $C_{6-10}$ aryl $C_{1-6}$ alkoxy group, a $C_{1-6}$ alkylthio group, a $C_{2-6}$ alkenylthio group, a $C_{2-6}$ alkynylthio group, a $C_{3-8}$ cycloalkylthio group, a $C_{6-10}$ arylthio group, a $C_{3-8}$ cycloalkyl $C_{1-6}$,alkylthio group, a $C_{6-10}$ aryl $C_{1-6}$ alkylthio group, a mono-$C_{1-6}$ alkylamino group, a mono-$C_{2-6}$ alkenylamino group, a mono-$C_{2-6}$ alkynylamino group, a mono-$C_{3-8}$ cycloalkylamino group, a mono-$C_{6-10}$ arylamino group, a mono-$C_{3-8}$ cycloalkyl $C_{1-6}$ alkylamino group, a mono-$C_{6-10}$ aryl $C_{1-6}$ alkylamino group, a di-$C_{1-6}$ alkylamino group, a N—$C_{2-6}$ alkenyl-N—$C_{1-6}$ alkylamino group, a N—$C_{2-6}$ alkynyl-N—$C_{1-6}$ alkylamino group, a N—$C_{3-8}$ cycloalkyl-N—$C_{1-6}$ alkylamino group, a N—$C_{6-10}$ aryl-N—$C_{1-6}$ alkylamino group, a N—$C_{3-8}$ cycloalkyl $C_{1-6}$ alkyl-N—$C_{1-6}$ alkylamino group, a N—$C_{6-10}$ aryl $C_{1-6}$ alkyl-N—$C_{1-6}$ alkylamino group, and a $C_{6-10}$ aryloxy-$C_{1-6}$ alkyl group;

with the proviso that each group described in the substituent group a-2 has 1 to 3 substituents selected from the following substituent group b;

<substituent group b> substituent group b represents the group consisting of: a halogen atom, a hydroxyl group, a mercapto group, a cyano group, a carboxyl group, an amino group, a carbamoyl group, a nitro group, a $C_{1-6}$ alkyl group, a $C_{3-8}$ cycloalkyl group, a $C_{6-10}$ aryl group, a $C_{1-6}$ alkoxy group, a C$_{6-10}$ aryloxy group, a C$_{1-6}$ alkylcarbonyl group, a C$_{1-6}$ alkoxycarbonyl group, a C$_{1-6}$ alkylsulfonyl group, a trifluoromethyl group, a trifluoromethoxy group, a mono-C$_{1-6}$ alkylamino group, a di-C$_{1-6}$ alkylamino group, a mono-C$_{6-10}$ arylamino group which optionally has one amino group or aminosulfonyl group and a N—C$_{6-10}$ aryl C$_{1-6}$ alkyl-N—C$_{1-6}$ alkylamino group which optionally has one amino group;

<substituent group a-1'> substituent group a-1' represents the group consisting of: a halogen atom, a hydroxyl group, a mercapto group, a cyano group, a carboxyl group, an amino group, a carbamoyl group, a C$_{2-6}$ alkenyl group, a C$_{2-6}$ alkynyl group, a C$_{3-8}$ cycloalkyl group, a C$_{6-10}$ aryl group, a C$_{3-8}$ cycloalkyl C$_{1-6}$ alkyl group, a C$_{3-8}$ cycloalkylidene C$_{1-6}$ alkyl group, a C$_{6-10}$ aryl C$_{1-6}$ alkyl group, a C$_{1-6}$ alkoxy group, a C$_{2-6}$ alkenyloxy group, a C$_{2-6}$ alkenyloxy group, a C$_{3-8}$ cycloalkoxy group, a C$_{6-10}$ aryloxy group, a C$_{3-8}$ cycloalkyl C$_{1-6}$ alkoxy group, a C$_{6-10}$ aryl C$_{1-6}$ alkoxy group, a C$_{1-6}$ alkylthio group, a C$_{2-6}$ alkenylthio group, a C$_{2-6}$ alkynylthio group, a C$_{3-8}$ cycloalkylthio group, a C$_{6-10}$ arylthio group, a C$_{3-8}$ cycloalkyl C$_{1-6}$ alkylthio group, a C$_{6-10}$ aryl C$_{1-6}$ alkylthio group, a mono-C$_{1-6}$ alkylamino group, a mono-C$_{2-6}$ alkenylamino group, a mono-C$_{2-6}$ alkenylamino group, a mono-C$_{3-8}$ cycloalkylamino group, a mono-C$_{6-10}$ arylamino group, a mono-C$_{3-8}$ cycloalkyl C$_{1-6}$ alkylamino group, a mono-C$_{6-10}$ aryl C$_{1-6}$ alkylamino group, a di-C$_{1-6}$ alkylamino group, a N—C$_{2-6}$ alkenyl-N—C$_{1-6}$ alkylamino group, a N—C$_{2-6}$ alkynyl-N—C$_{1-6}$ alkylamino group, a N—C$_{3-8}$ cycloalkyl-N—C$_{1-6}$ alkylamino group, a N—C$_{6-10}$ aryl-N—C$_{1-6}$ alkylamino group, a N—C$_{3-8}$ cycloalkyl C$_{1-6}$ alkyl-N—C$_{1-6}$ alkylamino group, a N—C$_{6-10}$ aryl C$_{1-6}$ alkyl-N—C$_{1-6}$ alkylamino group, a C$_{1-6}$ alkylcarbonyl group, a C$_{1-6}$ alkoxycarbonyl group, a C$_{1-6}$ alkylsulfonyl group, a group represented by the formula —C(=N—R$^{a1}$)R$^{a2}$ (wherein R$^{a1}$ represents a hydroxyl group or a C$_{1-6}$ alkoxy group; R$^{a2}$ represents a C$_{1-6}$ alkyl group), and a C$_{6-10}$ aryloxy C$_{1-6}$ alkyl group;

<substituent group a-2'> substituent group a-2' represents the group consisting of: a C$_{2-6}$ alkenyl group, a C$_{2-6}$ alkynyl group, a C$_{3-8}$ cycloalkyl group, a C$_{6-10}$ aryl group, a C$_{3-8}$ cycloalkyl C$_{1-6}$ alkyl group, a C$_{6-10}$ aryl C$_{1-6}$ alkyl group, a C$_{1-6}$ alkoxy group, a C$_{2-6}$ alkenyloxy group, a C$_{2-6}$ alkynyloxy group, a C$_{3-8}$ cycloalkoxy group, a C$_{6-10}$ aryloxy group, a C$_{3-8}$ cycloalkyl C$_{1-6}$ alkoxy group, a C$_{6-10}$ aryl C$_{1-6}$ alkoxy group, a C$_{1-6}$ alkylthio group, a C$_{2-6}$ alkenylthio group, a C$_{2-6}$ alkenylthio group, a C$_{3-8}$ cycloalkylthio group, a C$_{6-10}$ arylthio group, a C$_{3-8}$ cycloalkyl C$_{1-6}$ alkylthio group, a C$_{6-10}$ aryl C$_{1-6}$ alkylthio group, a mono-C$_{1-6}$ alkylamino group, a mono-C$_{2-6}$ alkenylamino group, a mono-C$_{2-6}$ alkynylamino group, a mono-C$_{3-8}$ cycloalkylamino group, a mono-C$_{6-10}$ arylamino group, a mono-C$_{3-8}$ cycloalkyl C$_{1-6}$ alkylamino group, a mono-C$_{6-10}$ aryl C$_{1-6}$ alkylamino group, a di-C$_{1-6}$ alkylamino group, a N—C$_{2-6}$ alkenyl-N—C$_{1-6}$ alkylamino group, a N—C$_{2-6}$ alkynyl-N—C$_{1-6}$ alkylamino group, a N—C$_{3-8}$ cycloalkyl-N—C$_{1-6}$ alkylamino group, a N—C$_{6-10}$ aryl-N—C$_{1-6}$ alkylamino group, a N—C$_{3-8}$ cycloalkyl C$_{1-6}$ alkyl-N—C$_{1-6}$ alkylamino group, a N—C$_{6-10}$ aryl C$_{1-6}$ alkyl-N—C$_{1-6}$ alkylamino group, and a C$_{6-10}$ aryloxy-C$_{1-6}$ alkyl group;

with the proviso that each group described in the substituent group a-2' has 1 to 3 substituents selected from the following substituent group b;

<substituent group b> substituent group b represents the group consisting of: a halogen atom, a hydroxyl group, a mercapto group, a cyano group, a carboxyl group, an amino group, a carbamoyl group, a nitro group, a C$_{1-6}$ alkyl group, a C$_{3-8}$ cycloalkyl group, a C$_{6-10}$ aryl group, a C$_{1-6}$ alkoxy group, a C$_{6-10}$ aryloxy group, a C$_{1-6}$ alkylcarbonyl group, a C$_{1-6}$ alkoxycarbonyl group, a C$_{1-6}$ alkylsulfonyl group, a trifluoromethyl group, a trifluoromethoxy group, a mono-C$_{1-6}$ alkylamino group, a di-C$_{1-6}$ alkylamino group, a mono-C$_{6-10}$ arylamino group which optionally has one amino group or aminosulfonyl group and a N—C$_{6-10}$ aryl C$_{1-6}$ alkylamino group which optionally has one amino group;

with the proviso that the following is excluded:

a compound in which A$^1$ represents a group represented by the formula:

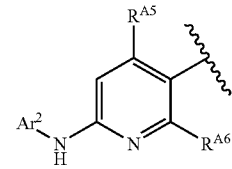

wherein R$^{A5}$ represents a hydrogen atom, a C$_{1-6}$ alkyl group or a trifluoromethyl group; R$^{A6}$ represents a hydrogen atom or a trifluoromethyl group; Ar$^2$ represents a phenyl group which optionally has a substituent; and X$^1$ represents a group represented by the formula —C(=O)—NH—.

2. The compound according to claim 1, or the salt thereof, wherein A$^1$ represents a 3-pyridyl group, with the proviso that A$^1$ optionally has 1 to 3 substituents selected from the substituent group a-1 defined above.

3. The compound according to claim 1, or the salt thereof, wherein A$^1$ represents a 3-pyridyl group, with the proviso that A$^1$ optionally has 1 to 3 substituents selected from the following substituent groups c-1 and c-2;

<substituent group c-1> substituent group c-1 represents the group consisting of: a halogen atom, an amino group, a C$_{1-6}$ alkyl group, a C$_{2-6}$ alkenyl group, a C$_{2-6}$ alkynyl group, a C$_{3-8}$ cycloalkyl group, a C$_{6-10}$ aryl group, a C$_{3-8}$ cycloalkyl C$_{1-6}$ alkyl group, a C$_{6-10}$ aryl C$_{1-6}$ alkyl group, a C$_{1-6}$ alkoxy group, a C$_{2-6}$ alkenyloxy group, a C$_{2-6}$ alkynyloxy group, a C$_{3-8}$ cycloalkyl C$_{1-6}$ alkoxy group, a C$_{6-10}$ aryl C$_{1-6}$ alkoxy group, a mono-C$_{1-6}$ alkylamino group, a mono-C$_{2-6}$ alkenylamino group, a mono-C$_{2-6}$ alkynylamino group, a mono-C$_{3-8}$ cycloalkylamino group, a mono-C$_{6-10}$ arylamino group, a mono-C$_{3-8}$ cycloalkyl C$_{1-6}$ alkylamino group, a mono-C$_{6-10}$ aryl C$_{1-6}$ alkylamino group, a C$_{1-6}$ alkylcarbonyl group and a group represented by the formula —C(=N—OH)R$^{a2}$, wherein R$^{a2}$ has the same meaning as defined above;

<substituent group c-2> substituent group c-2 represents the group consisting of: a C$_{1-6}$ alkyl group, a C$_{2-6}$ alkenyl group, a C$_{2-6}$ alkynyl group, a C$_{3-8}$ cycloalkyl group, a C$_{6-10}$ aryl group, a C$_{3-8}$ cycloalkyl C$_{1-6}$ alkyl group, a C$_{6-10}$ aryl C$_{1-6}$ alkyl group, a C$_{1-6}$ alkoxy group, a C$_{2-6}$ alkenyloxy group, a C$_{2-6}$ alkynyloxy group, a C$_{3-8}$ cycloalkyl C$_{1-6}$ alkoxy group, C$_{6-10}$ aryl C$_{1-6}$ alkoxy group, a mono-C$_{1-6}$ alkylamino group, a mono-$C_{2-6}$ alkenylamino group, a mono-$C_{2-6}$ alkynylamino group, a mono-$C_{3-8}$ cycloalkylamino group, a mono-$C_{6-10}$ arylamino group, a mono-$C_{3-8}$ cycloalkyl $C_{1-6}$ alkylamino group, and a mono-$C_{6-10}$ aryl $C_{1-6}$ alkylamino group;

with the proviso that each group described in substituent group c-2 has 1 to 3 substituents selected from the following substituent group d;

<substituent group d> substituent group d represents the group consisting of: a halogen atom, a hydroxyl group, a carboxyl group, an amino group, a carbamoyl group, a $C_{1-6}$ alkoxy group, a mono-$C_{1-6}$ alkylamino group, a di-$C_{1-6}$ alkylamino group, a mono-$C_{6-10}$ arylamino group that optionally having one amino group or aminosulfonyl group, a N—$C_{6-10}$ aryl $C_{1-6}$ alkyl-N—$C_{1-6}$ alkylamino group optionally having one amino group, a cyano group, a $C_{6-10}$ aryl group, and a $C_{1-6}$ alkoxycarbonyl group.

4. The compound according to claim 3, or the salt thereof, wherein $A^1$ represents a group represented by the formula:

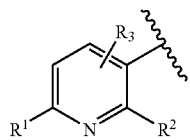

wherein $R^1$, $R^2$ and $R^3$ are the same as or different from each other and represent a substituent selected from the substituent groups c-1 and c-2 defined above.

5. The compound according to claim 3, or the salt thereof, wherein $A^1$ represents a group represented by the formula:

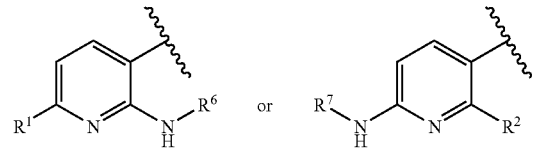

wherein $R^1$ and $R^2$ are the same as or different from each other and represent a substituent selected from the substituent groups c-1 and c-2 defined above; and $R^6$ and $R^7$ are the same or different from each other and represent a hydrogen atom, a $C_{1-6}$ alkyl group, a $C_{3-8}$ cycloalkyl group or a group represented by the formula —CHR$^8$—(CH$_2$)$_{n1}$—R$^9$, wherein $R^8$ represents a hydrogen atom, a carboxyl group or a $C_{1-6}$ alkoxycarbonyl group; $R^9$ represents a hydroxyl group, a carboxyl group, a carbamoyl group, a $C_{3-8}$ cycloalkyl group, a $C_{1-6}$ alkoxy group, a $C_{1-6}$ alkoxycarbonyl group, a mono-$C_{1-6}$ alkylamino group, a di-$C_{1-6}$ alkylamino group, a phenyl group optionally having 1 to 3 substituents selected from the substituent group d defined above, a mono-$C_{6-10}$ arylamino group optionally having one amino group or an N—$C_{6-10}$ aryl $C_{1-6}$ alkyl-N—$C_{1-6}$ alkylamino group optionally having one amino group; and n1 represents an integer from 0 to 3.

6. The compound according to claim 1, or the salt thereof, wherein $A^1$ represents a group represented by the formula:

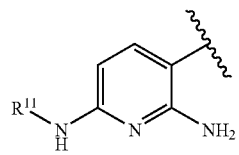

wherein $R^{11}$ represents a hydrogen atom or a group represented by the formula —CHR$^{12}$—(CH$_2$)$_{n2}$—R$^{13}$, wherein $R^{12}$ represents a hydrogen atom or a carboxyl group; $R^{13}$ represents a carboxyl group or a phenyl group optionally having 1 to 3 substituents selected from the substituent group d defined above; and n2 represents an integer from 0 to 3.

7. The compound according to claim 1, or the salt thereof, wherein $A^1$ represents a group represented by the formula:

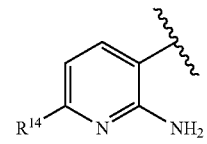

wherein $R^{14}$ represents a $C_{1-6}$ alkyl group having one $C_{1-6}$ alkoxy group.

8. A compound represented by the formula (I-a), or a salt thereof:

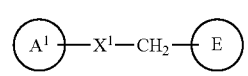

(I-a)

wherein $A^1$ represents a 3-pyridyl group, wherein optionally has 1 to 3 substituents selected from the following substituent groups c'-1 and c'-2;

<substituent group c'-1> substituent group c'-1 represents the group consisting of: an amino group, a $C_{1-6}$ alkyl group and a mono-$C_{1-6}$ alkylamino group; and <substituent group c'-2> substituent group c'-2 represents the group consisting of a $C_{1-6}$ alkyl group and a mono-$C_{1-6}$alkylamino group;

with the proviso that each group described in substituent group c'-2 has 1 to 3 substituents selected from the following substituent group d';

<substituent group d'> substituent group d' represents the group consisting of: a halogen atom, a hydroxyl group, a cyano group, a carboxyl group and a $C_{1-6}$ alkoxy group;

$X^1$ represents a group represented by the formula —C(=Y$^1$)—NH—;

$Y^1$ represents an oxygen atom or a sulfur atom;

wherein E represents a thienyl group, wherein E has 1 or 2 substituents selected from the following substituent groups e-1 and e-2;

<substituent group e-1> substituent group e-1 represents the group consisting of: a halogen atom, a hydroxyl group, a $C_{2-6}$ alkenyl group, a $C_{2-6}$ alkynyl group, a $C_{6-10}$ aryl group, a $C_{3-8}$ cycloalkyl $C_{1-6}$ alkyl group, a $C_{3-8}$ cycloalkylidene $C_{1-6}$ alkyl group, a $C_{6-10}$ aryl $C_{1-6}$ alkyl group, a $C_{1-6}$ alkoxy group, a $C_{2-6}$ alkenyloxy group, a $C_{2-6}$ alkynyloxy group, a C$_{6-10}$ aryloxy group, a C$_{3-8}$ cycloalkyl C$_{1-6}$ alkoxy group, a C$_{6-10}$ aryl C$_{1-6}$ alkoxy group, a C$_{6-10}$ arylthio group, a C$_{6-10}$ aryl C$_{1-6}$ alkylthio group, a mono-C$_{6-10}$ arylamino group, a mono-C$_{6-10}$ aryl C$_{1-6}$ alkylamino group, a N—C$_{6-10}$ aryl-N—C$_{1-6}$ alkylamino group, a N—C$_{6-10}$ aryl C$_{1-6}$ alkyl-N—C$_{1-6}$ alkylamino group, and a C$_{6-10}$ aryloxy C$_{1-6}$ alkyl group;

<substituent group e-2>
substituent group e-2 represents the group consisting of: a C$_{2-6}$ alkenyl group, a C$_{2-6}$ alkynyl group, a C$_{6-10}$ aryl group, a C$_{3-8}$ cycloalkyl C$_{1-6}$ alkyl group, a C$_{6-10}$ aryl C$_{1-6}$ alkyl group, a C$_{1-6}$ alkoxy group, a C$_{2-6}$ alkenyloxy group, a C$_{2-6}$ alkynyloxy group, a C$_{6-10}$ aryloxy group, a C$_{3-8}$ cycloalkyl C$_{1-6}$ alkoxy group, a C$_{6-10}$ aryl C$_{1-6}$ alkoxy group, a C$_{6-10}$ arylthio group, a C$_{6-10}$ aryl C$_{1-6}$ alkylthio group, a mono-C$_{6-10}$ arylamino group, a mono-C$_{6-10}$ aryl C$_{1-6}$ alkylamino group, a N—C$_{6-10}$ aryl-N—C$_{1-6}$ alkylamino group, a N—C$_{6-10}$ aryl C$_{1-6}$ alkyl-N—C$_{1-6}$ alkylamino group, and a C$_{6-10}$ aryloxy C$_{1-6}$ alkyl group;
with the proviso that each group described in substituent group e-2 has 1 to 3 substituents selected from the following substituent group f;

<substituent group f>
substituent group f represents the group consisting of: a halogen atom, a hydroxyl group, a cyano group, an amino group, a nitro group, a C$_{3-8}$ cycloalkyl group, a C$_{1-6}$ alkoxy group, a C$_{6-10}$ aryloxy group, a C$_{1-6}$ alkylcarbonyl group, a C$_{1-6}$ alkoxycarbonyl group, a C$_{1-6}$ alkylsulfonyl group, a mono-C$_{6-10}$ arylamino group, a trifluoromethyl group, a trifluoromethoxy group and a C$_{1-6}$ alkyl group.

9. The compound according to claim 8, or the salt thereof, wherein X$^1$ represents a group represented by the formula —C(=O)—NH—.

10. The compound according to claim 8, or the salt thereof, wherein E represents a thienyl group, wherein E has one substituent selected from the following substituent groups g-1 and g-2;

<substituent group g-1>
substituent group g-1 represents the group consisting of a C$_{3-8}$ cycloalkyl C$_{1-6}$ alkyl group, a phenyl C$_{1-6}$ alkyl group, a C$_{1-6}$ alkoxy group, a phenoxy group, a C$_{3-8}$ cycloalkyl C$_{1-6}$ alkoxy group, a phenyl C$_{1-6}$ alkoxy group, and a phenoxy C$_{1-6}$ alkyl group;

<substituent group g-2>
substituent group g-2 represents the group consisting of: a C$_{3-8}$ cycloalkyl C$_{1-6}$ alkyl group, a phenyl C$_{1-6}$ alkyl group, a C$_{1-6}$ alkoxy group, a phenoxy group, a C$_{3-8}$ cycloalkyl C$_{1-6}$ alkoxy group, a phenyl C$_{1-6}$ alkoxy group, and a phenoxy C$_{1-6}$ alkyl group;
with the proviso that each group described in substituent group g-2 has 1 to 3 substituents selected from the following substituent group h;

<substituent group h>
substituent group h represents the group consisting of: a halogen atom, a hydroxyl group, a cyano group and a C$_{1-6}$ alkyl group.

11. The compound according to claim 10, or the salt thereof, wherein E represents a 2-thienyl group, wherein E has one substituent selected from the substituent groups g-1 and g-2 defined above.

12. The compound according to claim 10, or the salt thereof, wherein X$^1$ represents a group represented by the formula —C(=O)—NH—, and A$^1$ represents a group represented by the formula:

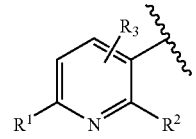

wherein R$^1$, R$^2$ and R$^3$ are the same as or different from each other and represent a substituent selected from the substituent c' 1 and c'-2;
with the proviso that each group described in substituent group c'-2 has 1 to 3 substituents selected from the substituent group d'; and
E represents a 2-thienyl group, wherein E has one substituent selected from the substituent group g-1 or g-2 defined above.

13. The compound according to claim 12, or the salt thereof, wherein A$^1$ represents a group represented by the formula:

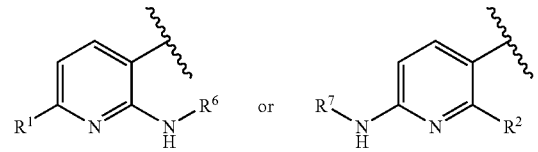

wherein R$^1$ and R$^2$ have the same meanings as defined above; and
R$^6$ and R$^7$ are the same or different from each other and represent a hydrogen atom, or a C$_{1-6}$ alkyl group which optionally has 1 to 3 substituents selected from the following substituent group d' below;

<substituent group d'>
substituent group d' represents the group consisting of: a halogen atom, a hydroxyl group, a cyano group, a carboxyl group and a C$_{1-6}$ alkoxy group.

14. The compound according to claim 12, or the salt thereof, wherein A$^1$ represents a group represented by the formula:

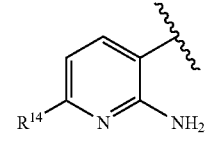

R$^{14}$ represents a C$_{1-6}$ alkyl group having one C$_{1-6}$ alkoxy group.

15. A pharmaceutical composition comprising the compound according to claim 1, or the salt thereof; and a pharmaceutically acceptable carrier.

16. A method for prevention or treatment of fungal infection comprising administering a pharmacologically effective amount of the compound according to claim 1, or the salt thereof.

17. A pharmaceutical composition comprising the compound according to claim 8, or the salt thereof; and a pharmaceutically acceptable carrier.

* * * * *